(12) United States Patent
Borns

(10) Patent No.: US 7,704,712 B2
(45) Date of Patent: Apr. 27, 2010

(54) DNA POLYMERASE FUSIONS AND USES THEREOF

(75) Inventor: Michael Borns, Escondido, CA (US)

(73) Assignee: Stratagene California, La Jolla, CA (US)

(*) Notice: Subject to any disclaimer, the term of this patent is extended or adjusted under 35 U.S.C. 154(b) by 482 days.

(21) Appl. No.: 10/805,650

(22) Filed: Mar. 19, 2004

(65) Prior Publication Data
US 2005/0048530 A1    Mar. 3, 2005

Related U.S. Application Data

(60) Provisional application No. 60/457,426, filed on Mar. 25, 2003.

(51) Int. Cl.
    *C12P 19/34* (2006.01)
(52) U.S. Cl. .................................................. 435/91.1
(58) Field of Classification Search ................. None
    See application file for complete search history.

(56) References Cited

U.S. PATENT DOCUMENTS

| 4,545,933 | A | * | 10/1985 | Ernster | ...................... 530/360 |
| 4,889,818 | A | | 12/1989 | Gelfand et al. | |
| 5,466,591 | A | | 11/1995 | Abramson et al. | .......... 435/194 |
| 5,541,311 | A | | 7/1996 | Dahlberg et al. | |
| 5,972,603 | A | | 10/1999 | Bedford et al. | ................ 435/6 |
| 0,119,461 | A1 | | 8/2002 | Chatterjee | ....................... 435/6 |
| 2003/0143577 | A1 | | 7/2003 | Hogrefe et al. | |
| 2003/0149257 | A1 | | 8/2003 | Sorge et al. | |
| 2004/0086890 | A1 | | 5/2004 | Sorge et al. | |

FOREIGN PATENT DOCUMENTS

| WO | WO 97/29209 | 2/1997 |
| WO | WO 01/61015 | 2/2001 |
| WO | WO 0111051 | 2/2001 |
| WO | WO 01/92501 A1 | 5/2001 |

OTHER PUBLICATIONS

Sanger et al., DNA sequencing with chain-terminating inhibitors, Dec. 1977, Biochemistry, Proc. Nati. Acad. Sci. USA, vol. 74, No. 12, pp. 5463-5467.*
Hugli et al., Determination of the Tryptophan Content of Proteins by Ion Exchange Chromatography of Alkaline Hydrolysates,Tihe Journal op Biology Chemistry, vol. 247, No. 9, Issue of May 10, 1972, pp. 2828-2834.*
Drazic et al., Kinetic and mechanistic study of hydroxyl ion electrosorption at the Pt(111) surface in alkaline media, Journal of Electroanalytical Chemistry 466 (1999) 155-164.*
Dietrich et al., PCR performance of the highly thermostable proof-reading B-type DNA polymerase from *Pyrococcus abyssi*, FEMS Microbiology Letters 217 (2002) 89-94.*

Barnes, "PCR amplification of up to 35-kb DNA with high fidelity and high yield from λ bacteriophage templates," *Proc. Nat'l. Acad. Sci. USA* 91:2216-2220 (1994).
Bedford et al., "The thioredoxin binding domain of bacteriophage T7 DNA polymerase confers processivity on *Escherichia coli* DNA polymerase I," *Proc. Nat'l Acad Sci. USA* 94:479-484 (1997).
Motz, M., et al., "Elucidation of an Archaeal Replication Protein Network to Generate Enhanced PCR Enzymes," *J. Biol. Chem.* 277(18):16179-16188 (May 3, 2002).
Pavlov et al., "Helix-hairpin-helix motifs confer salt resistance and processivity on chimeric DNA polymerases," *Proc. Natl. Acad. Sci. USA* 99:13510-13515 (2002).
International Search Report and Written Opinion of the International Searching Authority, or the Declaration for International Application No. PCT/US04/08875.
Motz, Michael et al., "Elucidation of an archaeal replication protein network to generate enhanced PCR enzymes." The Journal of Biological Chemistry, May 3, 2002, vol. 277, No. 18, pp. 16179-16188.
Pavlov, A.R. et al., "Helix-hairpin-helix motifs confer salt resistance and processivity on chimeric DNA polymerases" Proceedings of the National Academy of Sciences of USA, National Academy of Science, Wahsington, CD U.S. vol. 99, No. 21, Oct. 15, 2002, pp. 13510-13515.
Yates, Charles R. et al., "Molecular diagnosis of thiopurine S-methyltransferase deficiency: Genetic basis for azathioprine and mercaptopurine intolerance," Annals of Internal Medicine, vol. 126, No. 8, 1997, pp. 608-614.
Siegelman, M. et al., "Rapid, nonradioactive screening for mutations in exons 10, 11, and 16 of the RET protooncogene associated with inherited medullary thyroid carcinoma," Clinical Chemistry, Mar. 1997, vol. 43, No. 3, Mar. 1997, pp. 453-457.
Miettinen, PIJ. et al., "Impaired migration and delayed differentiation of pancreatic islet cells in mice lacking EGF-receptors," Development (Cambridge, England) Jun. 2000, vol. 127, No. 12, Jun. 2006, pp. 2617-2627.
Boehlke, et al., "PCR performance of the B-type DNA polymerase from the thermophilic euryarchaeon Thermococcus aggregans improved by mutuations in the Y-GG/A motif," Nucleic Acids Research, Oxford University Press, Surrey, GB, vol. 28, No. 20, Oct. 15, 2000, pp. 3910-3917.
Fogg, M.J. et al., "Structural basis for uracil recognitioin by archaeal family B DNA polymerases," Nature Structural Biology, New York, NY, US, vol. 9, No. 12, Dec. 2002, pp. 922-927.
Gardner, Andrew F. et al., "Determinanats of nucleotide sugar recognition in an archaeon DNA polymerase," Nucleic Acids Research, Oxford University Press, Surrey, GB, vol. 27, No. 12, Jun. 15, 1999, pp. 2545-2553.

* cited by examiner

*Primary Examiner*—Kenneth R. Horlick
*Assistant Examiner*—Mark Staples

(57) ABSTRACT

The present invention discloses methods of using DNA polymerase fusions at high pH in PCR, DNA sequencing and mutagenesis protocols.

29 Claims, 186 Drawing Sheets

900bp HαAT
1"/kb - 1" extension

FIGURE 10

Figure 10. Oligonucleotide Primers for QuikChange Mutagenesis

V93E#1

5'-gAACATCCCCAAgATgAACCCACTATTAgAgAAAAg-3' (SEQ ID NO: 5)

V93E#2

5'-CTTTTTCTCTAATAgTgggTTCATCTTggggATgTTC-3' (SEQ ID NO: 6)

V93R#1

5'-gAACATCCCCAAgATAgACCCACTATTAgAgAAAAg-3' (SEQ ID NO: 7)

V93R#2

5'-CTTTTTCTCTAATAgTgggTCTATCTTggggATgTTC-3' (SEQ ID NO: 8)

V93N#1

5'-gAACATCCCCAAgATAACCCCACTATTAgAgAAAAg-3' (SEQ ID NO: 9)

V93N#2

5'-CTTTTTCTCTAATAgTggggTTATCTTggggATgTTC-3' (SEQ ID NO: 10)

V93H#1

5'-gAACATCCCCAAgATCACCCCACTATTAgAgAAAAg-3' (SEQ ID NO: 11)

V93H#2

5'-CTTTTTCTCTAATAgTggggTgATCTTggggATgTTC-3' (SEQ ID NO: 12)

V93X (for saturation mutagenesis; obtained V93G and V93L mutants from library)

5'-(Phosphate)gAACATCCCCAAgATNNKCCCACTATTAgAgAAAAg-3' (SEQ ID NO: 13)

5'-gAACATCCCCAAgAT<u>AAA</u>CCCACTATTAgAg-3' (SEQ ID NO: 14)

V93K#2

5'-CTCTAATAgTgggTTTATCTTggggATgTTC-3' (SEQ ID NO: 15)

QCM#1     5'-(Phosphate)gAACATCCCCAAgATg<u>C</u>ACCCACTATTAgAgAAAAAg-(SEQ ID NO: 16)'

Alanine

QCM#2     5'-(Phosphate)gAACATCCCCAAgATgACCCCACTATTAgAgAAAAAg-3'(SEQ ID NO: 17)

Aspartic Acid

QCM#3     5'-(Phosphate)gAACATCCCCAAgATTgCCCCCACTATTAgAgAAAAAg-3' (SEQ ID NO: 18)

Cysteine

QCM#4     5'-(Phosphate)gAACATCCCCAAgATATACCCACTATTAgAgAAAAAg-3' (SEQ ID NO: 19)

Isoleucine

QCM#5     5'-(Phosphate)gAACATCCCCAAgATATgCCCACTATTAgAgAAAAAg-3' (SEQ ID NO: 20)

Methionine

QCM#6     5'-(Phosphate)gAACATCCCCAAgATTTCCCCACTATTAgAgAAAAAg-3' (SEQ ID NO: 21)

FIGURE 10 (CONT.)

Phenylalanine

QCM#7 5'-(Phosphate)gAACATCCCCAAgATCCTCCCACTATTAgAgAAAAAg-3' (SEQ ID NO: 22)

Proline

QCM#8 5'-(Phosphate)gAACATCCCCAAgATAgCCCCACTATTAgAgAAAAAg-3' (SEQ ID NO: 23)

Serine

QCM#9 5'-(Phosphate)gAACATCCCCAAgATACACCCACTATTAgAgAAAAAg- 3' (SEQ ID NO: 24)

Threonine

QCM#10 5'-(Phosphate)gAACATCCCCAAgATTACCCCACTATTAgAgAAAAAg-3' (SEQ ID NO: 25)

Tyrosine

QCM#11 5'-(Phosphate)gAACATCCCCAAgATTggCCCACTATTAgAgAAAAAg-3'

(SEQ ID NO: 26)

Tryptophan

FIGURE 11
a.)
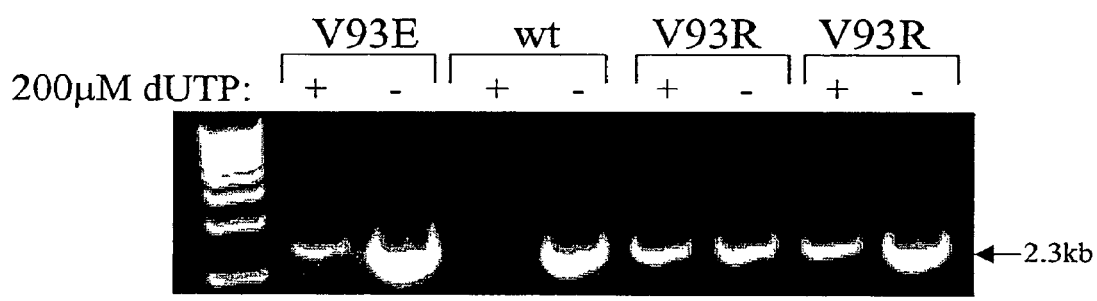
b.)
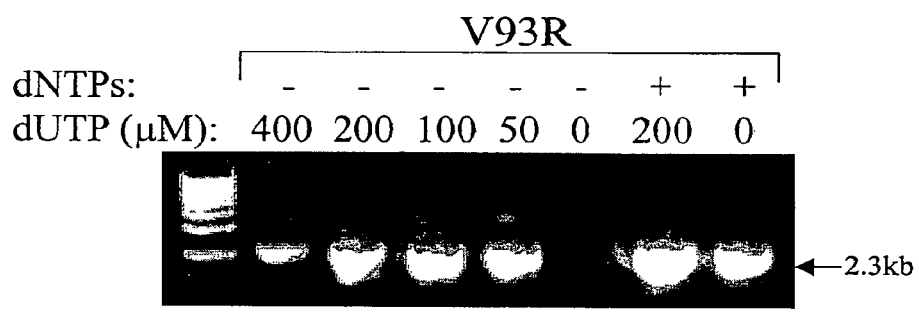

FIGURE 13A

PFU DNA POLYMERASE
V93R MUTANT: NNN = AGA, AGG, CGA, CGC, CGG, CGT (ALL POSSIBLE CODONS FOR ARGININE) (SEQ ID NO: 27)

V93E MUTANT: NNN = GAA, GAG (ALL CODONS FOR GLUTAMIC ACID) (SEQ ID NO: 28)

```
ATGATTTTAG ATGTGGATTA CATAACTGAA GAAGGAAAAC CTGTTATTAG GCTATTCAAA   60
AAAGAGAACG GAAAATTTAA GATAGAGCAT GATAGAACTT TTAGACCATA CATTTACGCT  120
CTTCTCAGGG ATGATTCAAA GATTGAAGAA GTTAAGAAAA TAACGGGGGA AAGGCATGGA  180
AAGATTGTGA GAATTGTTGA TGTAGAGAAG GTTGAGAAAA AGTTTCTCGG CAAGCCTATT  240
ACCGTGTGGA AACTTTATTT GGAACATCCC CAAGATNNNC CCACTATTAG AGAAAAAGTT  300
AGAGAACATC CAGCAGTTGT GGACATCTTC GAATACGATA TTCCATTTGC AAAGAGATAC  360
CTCATCGACA AAGGCCTAAT ACCAATGGAG GGGGAAGAAG AGCTAAAGAT TCTTGCCTTC  420
GATATAGAAA CCCTCTATCA CGAAGGAGAA GAGTTTGGAA AAGGCCCAAT TATAATGATT  480
AGTTATGCAG ATGAAAATGA AGCAAAGGTG ATTACTTGGA AAAACATAGA TCTTCCATAC  540
GTTGAGGTTG TATCAAGCGA GAGAGAGATG ATAAAGAGAT TTCTCAGGAT TATCAGGGAG  600
AAGGATCCTG ACATTATAGT TACTTATAAT GGAGACTCAT TCGCATTCCC ATATTTAGCG  660
AAAAGGGCAG AAAAACTTGG GATTAAATTA ACCATTGGAA GAGATGGAAG CGAGCCCAAG  720
ATGCAGAGAA TAGGCGATAT GACGGCTGTA GAAGTCAAGG GAAGAATACA TTTCGACTTG  780
TATCATGTAA TAACAAGGAC AATAAATCTC CCAACATACA CACTAGAGGC TGTATATGAA  840
GCAATTTTTG GAAAGCCAAA GGAGAAGGTA TACGCCGACG AGATAGCAAA AGCCTGGGAA  900
AGTGGAGAGA ACCTTGAGAG AGTTGCCAAA TACTCGATGG AAGATGCAAA GGCAACTTAT  960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG             2328
```

FIGURE 13A (CONT.)

PFU DNA POLYMERASE
G387P Mutant (CCN is the codon for Proline where N = C, G, A, or T)
V93R MUTANT: NNN = AGA, AGG, CGA, CGC, CGG, CGT (ALL POSSIBLE CODONS FOR ARGININE) (SEQ ID NO: 29)
V93E MUTANT: NNN = GAA, GAG (ALL CODONS FOR GLUTAMIC ACID) (SEQ ID NO: 30)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG     2328
```

PFU DNA POLYMERASE
D141A/E143A Mutant (GCN is the codon for alanine where N = C, G, A, or T)
V93R MUTANT: NNN = AGA, AGG, CGA, CGC, CGG, CGT (ALL POSSIBLE CODONS FOR ARGININE) (SEQ ID NO: 31)
V93E MUTANT: NNN = GAA, GAG (ALL CODONS FOR GLUTAMIC ACID) (SEQ ID NO: 32)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
```

FIGURE 13A (CONT.)

```
CTTCTCAGGG ATGATTCAAA GATTGAAGAA GTTAAGAAAA TAACGGGGGA AAGGCATGGA  180
AAGATTGTGA GAATTGTTGA TGTAGAGAAG GTTGAGAAAA AGTTTCTCGG CAAGCCTATT  240
ACCGTGTGGA AACTTTATTT GGAACATCCC CAAGATNNNC CCACTATTAG AGAAAAAGTT  300
AGAGAACATC CAGCAGTTGT GGACATCTTC GAATACGATA TTCCATTTGC AAAGAGATAC  360
CTCATCGACA AAGGCCTAAT ACCAATGGAG GGGGAAGAAG AGCTAAAGAT TCTTGCCTTC  420
GCNATAGCNA CCCTCTATCA CGAAGGAGAA GAGTTTGGAA AAGGCCCAAT TATAATGATT  480
AGTTATGCAG ATGAAAATGA AGCAAAGGTG ATTACTTGGA AAACATAGA  TCTTCCATAC  540
GTTGAGGTTG TATCAAGCGA GAGAGAGATG ATAAAGAGAT TTCTCAGGAT TATCAGGGAG  600
AAGGATCCTG ACATTATAGT TACTTATAAT GGAGACTCAT TCGCATTCCC ATATTTAGCG  660
AAAAGGGCAG AAAAACTTGG GATTAAATTA ACCATTGGAA GAGATGGAAG CGAGCCCAAG  720
ATGCAGAGAA TAGGCGATAT GACGGCTGTA GAAGTCAAGG GAAGAATACA TTTCGACTTG  780
TATCATGTAA TAACAAGGAC AATAAATCTC CCAACATACA CACTAGAGGC TGTATATGAA  840
GCAATTTTTG GAAAGCCAAA GGAGAAGGTA TACGCCGACG AGATAGCAAA AGCCTGGGAA  900
AGTGGAGAGA ACCTTGAGAG AGTTGCCAAA TACTCGATGG AAGATGCAAA GGCAACTTAT  960
GAACTCGGGA AGAATTCCT  TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGGTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG             2328
```

KOD DNA POLYMERASE
V93R MUTANT: NNN = AGA, AGG, CGA, CGC, CGG, CGT (ALL POSSIBLE CODONS FOR ARGININE) (SEQ ID NO: 33)
V93E MUTANT: NNN = GAA, GAG (ALL CODONS FOR GLUTAMIC ACID) (SEQ ID NO: 34)

```
ATGATCCTCG ACACTGACTA CATAACCGAG GATGGAAAGC TGTCATAAG  AATTTTCAAG   60
AAGGAAAACG GCGAGTTTAA GATTGAGTAC GACCGGACTT TTGAACCCTA CTTCTACGCC  120
CTCCTGAAGG ACGATTCTGC CATTGAGGAA GTCAAGAAGA TAACCGCCGA GAGGCACGGG  180
ACGGTTGTAA CGGTTAAGCG GGTTGAAAAG GTTCAGAAGA AGTTCCTCGG AGACCAGTT   240
GAGGTCTGGA AACTCTACTT TACTCATCCG CAGGACNNNC CAGCGATAAG GACAAGATA   300
CGAGAGCATC CAGCAGTTAT TGACATCTAC GAGTACGACA TACCCTTCGC CAAGCGCTAC  360
CTCATAGACA AGGGATTAGT GCCAATGGAA GGCGACGAGG AGCTGAAAAT GCTCGCCTTC  420
GACATTGAAA CTCTCTACCA TGAGGGCGAG GAGTTCGCCG AGGGGCCAAT CCTTATGATA  480
AGCTACGCCG ACGAGGAAGG GGCCAGGGTG ATAACTTGGA GAAACGTGGA TCTCCCCTAC  540
GTTGACGTCG TCTCGACGGA GAGGGAGATG ATAAAGCGCT TCCTCCGTGT TGTGAAGGAG  600
AAAGACCCGG ACGTTCTCAT AACCTACAAC GGCGACAACT TCGACTTCGC CTATCTGAAA  660
AAGCGCTGTG AAAAGCTCGG AATAAACTTC GCCCTCGGAA GGGATGGAAG CGAGCCGAAG  720
ATTCAGAGGA TGGGCGACAG GTTTGCCGTC GAAGTGAAGG GACGGATACA CTTCGATCTC  780
```

FIGURE 13A (CONT.)

```
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AGGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CTTGA 2325
```

Vent DNA POLYMERASE
V93R MUTANT: NNN = AGA, AGG, CGA, CGC, CGG, CGT (ALL POSSIBLE CODONS FOR ARGININE) (SEQ ID NO: 35)
V93E MUTANT: NNN = GAA, GAG (ALL CODONS FOR GLUTAMIC ACID) (SEQ ID NO: 36)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACNNNC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TGGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAGCAT GAAAAACTA GCCCAGTACT CAATGGAAGA TGCTAGGGCA 960
ACGTATGAGC TCGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
```

FIGURE 13A (CONT.)

```
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325

Deep Vent
V93R MUTANT: NNN = AGA, AGG, CGA, CGC, CGG, CGT (ALL POSSIBLE CODONS
FOR ARGININE) (SEQ ID NO: 37)
V93E MUTANT: NNN = GAA, GAG (ALL CODONS FOR GLUTAMIC ACID) (SEQ ID NO:
38)
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACNNNC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACTTCCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220
```

FIGURE 13A (CONT.)

```
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAGTAA                2328
```

JDF-3
V93R MUTANT: NNN = AGA, AGG, CGA, CGC, CGG, CGT (ALL POSSIBLE CODONS
FOR ARGININE) (SEQ ID NO: 39)
V93E MUTANT: NNN = GAA, GAG (ALL CODONS FOR GLUTAMIC ACID) (SEQ ID NO: 40)

```
ATGATCCTTGACGTTGATTACATCACCGAGAATGGAAAGCCCGTCATCAGGGTCTTCAAGAAGGAGAACGGCGAGTTCA
GGATTGAATACGACCGCGAGTTCGAGCCCTACTTCTACGCGCTCCTCAGGGACGACTCTGCCATCGAAGAAATCAAAAA
GATAACCGCGGAGAGGCACGGCAGGGTCGTTAAGGTTAAGCGCGCGGAGAAGGTGAAGAAAAAGTTCCTCGGCAGGTCT
GTGGAGGTCTGGGTCCTCTACTTCACGCACCCGCAGGACNNNCCGGCAATCCGCGACAAAATAAGGAAGCACCCCGCGG
TCATCGACATCTACGAGTACGACATACCCTTCGCCAAGCGCTACCTCATAGACAAGGGCCTAATCCCGATGGAAGGTGA
GGAAGAGCTTAAACTCATGTCCTTCGACATCGAGACGCTCTACCACGAGGGAGAAGAGTTTGGAACCGGGCCGATTCTG
ATGATAAGCTACGCCGATGAAAGCGAGGCGCGCGTGATAACCTGGAAGAAGATCGACCTTCCTTACGTTGAGGTTGTCT
CCACCGAGAAGGAGATGATTAAGCGCTTCTTGAGGGTCGTTAAGGAGAAGGACCCGGACGTGCTGATAACATACAACGG
CGACAACTTCGACTTCGCCTACCTGAAAAAGCGCTGTGAGAAGCTTGGCGTGAGCTTTACCCTCGGGAGGGACGGGAGC
GAGCCGAAGATACAGCGCATGGGGACAGGTTTGCGGTCGAGGTGAAGGGCAGGGTACACTTCGACCTTTATCCAGTCA
TAAGGCGCACCATAAACCTCCCGACCTACACCCTTGAGGCTGTATACGAGGCGGTTTTCGGCAAGCCCAAGGAGAAGGT
CTACGCCGAGGAGATAGCCACCGCCTGGGAGACCGGCGAGGGCTTGAGAGGGTCGCGCGCTACTCGATGGAGGACGCG
AGGGTTACCTACGAGCTTGGCAGGGAGTTCTTCCCGATGGAGGCCCAGCTTTCCAGGCTCATCGGCCAAGGCCTCTGGG
ACGTTTCCCGCTCCAGCACCGGCAACCTCGTCGAGTGGTTCCTCCTAAGGAAGGCCTACGAGAGGAACGAACTCGCTCC
CAACAAGCCCGACGAGAGGGAGCTGGCGAGGAGAAGGGGGGGCTACgcCGGTGGCTACGTCAAGGAGCCGGAGCGGGGA
CTGTGGGACAATATCGTGTATCTAGACTTTCGTAGTCTCTACCCTTCAATCATAATCACCCACAACGTCTCGCCAGATA
CGCTCAACCGCGAGGGGTGTAGGAGCTACGACGTTGCCCCCGAGGTCGGTCACAAGTTCTGCAAGGACTTCCCCGGCTT
CATTCCGAGCCTGCTCGGAAACCTGCTGGAGGAAAGGCAGAAGATAAAGAGGAAGATGAAGGCAACTCTCGACCCGCTG
GAGAAGAATCTCCTCGATTACAGGCAACGCGCCATCAAGATTCTCGCCAACAGCTACTACGGCTACTACGGCTATGCCA
GGGCAAGATGGTACTGCAGGGAGTGCGCCGAGAGCGTTACGGCATGGGGAAGGGAGTACATCGAAATGGTCATCAGAGA
GCTTGAGGAAAAGTTCGGTTTTAAAGTCCTCTATGCAGACACAGACGGTCTCCATGCCACCATTCTGGAGCGGACGCT
GAAACAGTCAAGAAAAGGCAATGGAGTTCTTAAACTATATCAATCCCAAACTGCCCGGCCTTCTCGAACTCGAATACG
AGGGCTTCTACGTCAGGGGCTTCTTCGTCACGAAGAAAAAGTACGCGGTCATCGACGAGGAGGGCAAGATAACCACGCG
CGGGCTTGAGATAGTCAGGCGCGACTGGAGCGAGATAGCGAAGGAGACGCAGGCGAGGGTTTTGGAGGCGATACTCAGG
CACGGTGACGTTGAAGAGGCCGTCAGAATTGTCAGGGAAGTCACCGAAAAGCTGAGCAAGTACGAGGTTCCGCCGGAGA
AGCTGGTTATCCACGAGCAGATAACGCGCGAGCTCAAGGACTACAAGGCCACCGGCCCGCACGTAGCCATAGCGAAgcG
TTTGGCCGCCAGAGGTGTTAAAATCCGGCCCGGAACTGTGATAAGCTACATCGTTCTGAAGGGCTCCGGAAGGATAGGC
GACAGGGCGATTCCCTTCGACGAGTTCGACCCGACGAAGCACAAGTACGATGCGGACTACTACATCGAGAACCAGGTTC
TGCCGGCAGTTGAGAGAATCCTCAGGGCCTTCGGCTACCGCAAGGAAGACCTGCGCTACCAGAAGACGAGGCAGGTCGG
GCTTGGCGCGTGGCTGAAGCCGAAGGGGAAGAAGAAGTGA
```

Figure 13B

>Pfu V93R (SEQ ID NO:41)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS //

>Pfu V93E (SEQ ID NO:42)
MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93R/G387P (SEQ ID NO:43)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93R/D141A/E143A (SEQ ID NO:44)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIGURE 13B (CONT.)

>Pfu V93E/G387P(SEQ ID NO:45)
MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>Pfu V93E/D141A/E143A(SEQ ID NO:46)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

>DEEP VENT V93R(SEQ ID NO:47)
MILDADYITEDGKPIIRIFKKENGEFKVEYDRNFRPYIYALLKDDSQIDEVRKITAERHGKIVRIIDAEKVRKKFLG
RPIEVWRLYFEHPQDRPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTQGLTAWL
NIKKK

>DEEP VENT V93E(SEQ ID NO:48)
MILDADYITEDGKPIIRIFKKENGEFKVEYDRNFRPYIYALLKDDSQIDEVRKITAERHGKIVRIIDAEKVRKKFLG
RPIEVWRLYFEHPQDEPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTQGLTAWL
NIKKK

>TGO V93R(SEQ ID NO:49)

FIGURE 13B (CONT.)

```
MILDTDYITEDGKPVIRIFKKENGEFKIDYDRNFEPYIYALLKDDSAIEDVKKITAERHGTTVRVVRAEKVKKKFLG
RPIEVWKLYFTHPQDRPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

>TGO V93E(SEQ ID NO:50)
MILDTDYITEDGKPVIRIFKKENGEFKIDYDRNFEPYIYALLKDDSAIEDVKKITAERHGTTVRVVRAEKVKKKFLG
RPIEVWKLYFTHPQDEPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

>KOD V93R(SEQ ID NO:51)
MILDTDYITEDGKPVIRIFKKENGEFKIEYDRTFEPYFYALLKDDSAIEEVKKITAERHGTVVTVKRVEKVQKKFLG
RPVEVWKLYFTHPQDRPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

>KOD V93E(SEQ ID NO:52)
MILDTDYITEDGKPVIRIFKKENGEFKIEYDRTFEPYFYALLKDDSAIEEVKKITAERHGTVVTVKRVEKVQKKFLG
RPVEVWKLYFTHPQDEPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT
```

FIGURE 13B (CONT.)

>VENT V93R(SEQ ID NO:53)
MILDTDYITKDGKPIIRIFKKENGEFKIELDPHFQPYIYALLKDDSAIEEIKAIKGERHGKTVRVLDAVKVRKKFLG
REVEVWKLIFEHPQDRPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

>VENT V93E(SEQ ID NO:54)
MILDTDYITKDGKPIIRIFKKENGEFKIELDPHFQPYIYALLKDDSAIEEIKAIKGERHGKTVRVLDAVKVRKKFLG
REVEVWKLIFEHPQDEPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

>JDF-3 V93R(SEQ ID NO:55)
MILDVDYITENGKPVIRVFKKENGEFRIEYDREFEPYFYALLRDDSAIEEIKKITAERHGRVVKVKRAEKVKKKFLGR
SVEVWVLYFTHPQDRPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

>JDF-3 V93E(SEQ ID NO:56)
MILDVDYITENGKPVIRVFKKENGEFRIEYDREFEPYFYALLRDDSAIEEIKKITAERHGRVVKVKRAEKVKKKFLGR
SVEVWVLYFTHPQDEPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

Figure 14

Tgo 93:
NNN = AGA, AGG, CGA, CGC, CGG, CGT (R)
(NUCLEOTIDE SEQUENCE: SEQ ID NO: 57; AMINO ACID SEQUENCE: SEQ ID NO: 58)

NNN = GAA, GAG (E)
(NUCLEOTIDE SEQUENCE: SEQ ID NO: 59; AMINO ACID SEQUENCE: SEQ ID NO: 60)

```
5'
atg atc ctc gat aca gac tac ata act gag gat gga aag ccc gtc atc      48
Met Ile Leu Asp Thr Asp Tyr Ile Thr Glu Asp Gly Lys Pro Val Ile
1               5                   10                  15 agg atc ttc aag aag gag aac ggc gag ttc aaa ata gac tac gac aga      96
Arg Ile Phe Lys Lys Glu Asn Gly Glu Phe Lys Ile Asp Tyr Asp Arg
                20                  25                  30 aac ttt gag cca tac atc tac gcg ctc ttg aag gac gac tct gcg att     144
Asn Phe Glu Pro Tyr Ile Tyr Ala Leu Leu Lys Asp Asp Ser Ala Ile
            35                  40                  45 gag gac gtc aag aag ata act gcc gag agg cac ggc act acc gtt agg     192
Glu Asp Val Lys Lys Ile Thr Ala Glu Arg His Gly Thr Thr Val Arg
50                  55                  60 gtt gtc agg gcc gag aaa gtg aag aag aag ttc cta ggc agg ccg ata     240
Val Val Arg Ala Glu Lys Val Lys Lys Lys Phe Leu Gly Arg Pro Ile
65                  70                  75                  80 gag gtc tgg aag ctc tac ttc act cac ccc cag gac nnn ccc gca atc     288
Glu Val Trp Lys Leu Tyr Phe Thr His Pro Gln Asp Xaa Pro Ala Ile
                85                  90                  95 agg gac aag ata aag gag cat cct gcc gtt gtg gac atc tac gag tac     336
Arg Asp Lys Ile Lys Glu His Pro Ala Val Val Asp Ile Tyr Glu Tyr
            100                 105                 110 gac atc ccc ttc gcg aag cgc tac ctc ata gac aaa ggc tta atc ccg     384
Asp Ile Pro Phe Ala Lys Arg Tyr Leu Ile Asp Lys Gly Leu Ile Pro
        115                 120                 125 atg gag ggc gac gag gaa ctt aag atg ctc gcc ttc gac atc gag acg     432
Met Glu Gly Asp Glu Glu Leu Lys Met Leu Ala Phe Asp Ile Glu Thr
    130                 135                 140 ctc tat cac gag ggc gag gag ttc gcc gaa ggg cct atc ctg atg ata     480
Leu Tyr His Glu Gly Glu Glu Phe Ala Glu Gly Pro Ile Leu Met Ile
145                 150                 155                 160 agc tac gcc gac gag gaa ggg gcg cgc gtt att acc tgg aag aat atc     528
Ser Tyr Ala Asp Glu Glu Gly Ala Arg Val Ile Thr Trp Lys Asn Ile
                165                 170                 175 gac ctt ccc tat gtc gac gtc gtt tcc acc gag aag gag atg ata aag     576
Asp Leu Pro Tyr Val Asp Val Val Ser Thr Glu Lys Glu Met Ile Lys
            180                 185                 190
```

FIGURE 14 (CONT.)

| | |
|---|---|
| cgc ttc ctc aag gtc gtc aag gaa aag gat ccc gac gtc ctc ata acc<br>Arg Phe Leu Lys Val Val Lys Glu Lys Asp Pro Asp Val Leu Ile Thr<br>              195                    200                    205 | 624 |
| tac aac ggc gac aac ttc gac ttc gcc tac ctc aag aag cgc tcc gag<br>Tyr Asn Gly Asp Asn Phe Asp Phe Ala Tyr Leu Lys Lys Arg Ser Glu<br>              210                    215                    220 | 672 |
| aag ctc gga gtc aag ttc atc ctc gga agg gaa ggg agc gag ccg aaa<br>Lys Leu Gly Val Lys Phe Ile Leu Gly Arg Glu Gly Ser Glu Pro Lys<br>225                    230                    235                    240 | 720 |
| atc cag cgc atg ggc gat cgc ttt gcg gtg gag gtc aag gga agg att<br>Ile Gln Arg Met Gly Asp Arg Phe Ala Val Glu Val Lys Gly Arg Ile<br>                    245                    250                    255 | 768 |
| cac ttc gac ctc tac ccc gtc att agg aga acg att aac ctc ccc act<br>His Phe Asp Leu Tyr Pro Val Ile Arg Arg Thr Ile Asn Leu Pro Thr<br>              260                    265                    270 | 816 |
| tac acc ctt gag gca gta tat gaa gcc atc ttt gga cag ccg aag gag<br>Tyr Thr Leu Glu Ala Val Tyr Glu Ala Ile Phe Gly Gln Pro Lys Glu<br>            275                    280                    285 | 864 |
| aag gtc tac gct gag gag ata gcg cag gcc tgg gaa acg ggc gag gga<br>Lys Val Tyr Ala Glu Glu Ile Ala Gln Ala Trp Glu Thr Gly Glu Gly<br>            290                    295                    300 | 912 |
| tta gaa agg gtg gcc cgc tac tcg atg gag gac gca aag gta acc tat<br>Leu Glu Arg Val Ala Arg Tyr Ser Met Glu Asp Ala Lys Val Thr Tyr<br>305                    310                    315                    320 | 960 |
| gaa ctc gga aaa gag ttc ttc cct atg gaa gcc cag ctc tcg cgc ctc<br>Glu Leu Gly Lys Glu Phe Phe Pro Met Glu Ala Gln Leu Ser Arg Leu<br>                    325                    330                    335 | 1008 |
| gta ggc cag agc ctc tgg gat gta tct cgc tcg agt acc gga aac ctc<br>Val Gly Gln Ser Leu Trp Asp Val Ser Arg Ser Ser Thr Gly Asn Leu<br>            340                    345                    350 | 1056 |
| gtc gag tgg ttt ttg ctg agg aag gcc tac gag agg aat gaa ctt gca<br>Val Glu Trp Phe Leu Leu Arg Lys Ala Tyr Glu Arg Asn Glu Leu Ala<br>            355                    360                    365 | 1104 |
| cca aac aag ccg gac gag agg gag ctg gca aga aga agg gag agc tac<br>Pro Asn Lys Pro Asp Glu Arg Glu Leu Ala Arg Arg Arg Glu Ser Tyr<br>            370                    375                    380 | 1152 |
| gcg ggt gga tac gtc aag gag ccc gaa agg gga ctg tgg gag aac atc<br>Ala Gly Gly Tyr Val Lys Glu Pro Glu Arg Gly Leu Trp Glu Asn Ile<br>385                    390                    395                    400 | 1200 |
| gtg tat ctg gac ttc cgc tcc ctg tat cct tcg ata ata atc acc cat<br>Val Tyr Leu Asp Phe Arg Ser Leu Tyr Pro Ser Ile Ile Ile Thr His<br>              405                    410                    415 | 1248 |
| aac gtc tcc cct gat aca ctc aac agg gag ggt tgt gag gag tac gac | 1296 |

FIGURE 14 (CONT.)

```
                Asn Val Ser Pro Asp Thr Leu Asn Arg Glu Gly Cys Glu Glu Tyr Asp
                            420             425             430 gtg gct cct cag gta ggc cat aag ttc tgc aag gac ttc ccc ggc ttc                1344
Val Ala Pro Gln Val Gly His Lys Phe Cys Lys Asp Phe Pro Gly Phe
        435             440             445 atc cca agc ctc ctc gga gac ctc ttg gag gag aga cag aag gta aag                1392
Ile Pro Ser Leu Leu Gly Asp Leu Leu Glu Glu Arg Gln Lys Val Lys
    450             455             460 aag aag atg aag gcc act ata gac cca atc gag aag aaa ctc ctc gat                1440
Lys Lys Met Lys Ala Thr Ile Asp Pro Ile Glu Lys Lys Leu Leu Asp
465             470             475             480 tac agg caa cga gca atc aaa atc ctt gct aat agc ttc tac ggt tac                1488
Tyr Arg Gln Arg Ala Ile Lys Ile Leu Ala Asn Ser Phe Tyr Gly Tyr
                485             490             495 tac ggc tat gca aag gcc cgc tgg tac tgc aag gag tgc gcc gag agc                1536
Tyr Gly Tyr Ala Lys Ala Arg Trp Tyr Cys Lys Glu Cys Ala Glu Ser
            500             505             510 gtt acc gct tgg ggc agg cag tac atc gag acc acg ata agg gaa ata                1584
Val Thr Ala Trp Gly Arg Gln Tyr Ile Glu Thr Thr Ile Arg Glu Ile
        515             520             525 gag gag aaa ttt ggc ttt aaa gtc ctc tac gcg gac aca gat gga ttt                1632
Glu Glu Lys Phe Gly Phe Lys Val Leu Tyr Ala Asp Thr Asp Gly Phe
    530             535             540 ttc gca aca ata cct gga gcg gac gcc gaa acc gtc aaa aag aag gca                1680
Phe Ala Thr Ile Pro Gly Ala Asp Ala Glu Thr Val Lys Lys Lys Ala
545             550             555             560 aag gag ttc ctg gac tac atc aac gcc aaa ctg ccc ggc ctg ctc gaa                1728
Lys Glu Phe Leu Asp Tyr Ile Asn Ala Lys Leu Pro Gly Leu Leu Glu
                565             570             575 ctc gaa tac gag ggc ttc tac aag cgc ggc ttc ttc gtg acg aag aag                1776
Leu Glu Tyr Glu Gly Phe Tyr Lys Arg Gly Phe Phe Val Thr Lys Lys
            580             585             590 aag tac gcg gtt ata gac gag gag gac aag ata acg acg cgc ggg ctt                1824
Lys Tyr Ala Val Ile Asp Glu Glu Asp Lys Ile Thr Thr Arg Gly Leu
        595             600             605 gaa ata gtt agg cgt gac tgg agc gag ata gcg aag gag acg cag gcg                1872
Glu Ile Val Arg Arg Asp Trp Ser Glu Ile Ala Lys Glu Thr Gln Ala
    610             615             620 agg gtt ctt gag gcg ata cta aag cac ggt gac gtt gaa gaa gcg gta                1920
Arg Val Leu Glu Ala Ile Leu Lys His Gly Asp Val Glu Glu Ala Val
625             630             635             640 agg att gtc aaa gag gtt acg gag aag ctg agc aag tac gag gtt cca                1968
Arg Ile Val Lys Glu Val Thr Glu Lys Leu Ser Lys Tyr Glu Val Pro
```

FIGURE 14 (CONT.)

```
                  645                    650                    655 ccg gag aag ctg gtc atc tac gag cag ata acc cgc gac ctg aag gac      2016
Pro Glu Lys Leu Val Ile Tyr Glu Gln Ile Thr Arg Asp Leu Lys Asp
            660                    665                    670 tac aag gcc acc ggg ccg cat gtg gct gtt gca aaa cgc ctc gcc gca      2064
Tyr Lys Ala Thr Gly Pro His Val Ala Val Ala Lys Arg Leu Ala Ala
            675                    680                    685 agg ggg ata aaa atc cgg ccc gga acg gtc ata agc tac atc gtg ctc      2112
Arg Gly Ile Lys Ile Arg Pro Gly Thr Val Ile Ser Tyr Ile Val Leu
            690                    695                    700 aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                    710                    715                    720 gac ccg gca aag cac aag tac gat gca gaa tac tac atc gag aac cag      2208
Asp Pro Ala Lys His Lys Tyr Asp Ala Glu Tyr Tyr Ile Glu Asn Gln
                    725                    730                    735 gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                    745                    750 gaa gat tta agg tat cag aaa acg cgg cag gtt ggc ttg ggg gcg tgg      2304
Glu Asp Leu Arg Tyr Gln Lys Thr Arg Gln Val Gly Leu Gly Ala Trp
            755                    760                    765 cta aaa cct aag aca tga                                              2322
Leu Lys Pro Lys Thr
```

Results: *Pfu* V93K and V93R mutants show significantly improved dUTP incorporation compared to wild type *Pfu*. In contrast, the *Pfu* V93W, V93Y, and V93M mutants show little-to-no improvement in dUTP incorporation.

Results: The *Pfu* V93D and V93R mutants show significantly improved dUTP incorporation compared to wild type *Pfu*.

Results: The *Pfu* V93N mutant shows a very small improvement in dUTP incorporation compared to wild type *Pfu*. In contrast, the *Pfu* V93G mutant shows little-to-no improvement.

Figure 16: Polymerase activity and Temperature optimum of Pfu N terminal truncation mutants

| Pfu clone # | Truncated after Pfu residue | Relative DNA polymerase activity | Temperature Optimum |
|---|---|---|---|
| 61 | H30 | Moderate | 65° |
| 72 | V66 | Similar to wild type | 70° |
| 81 | P128 | Low | Not tested |
| 92 | I158 | Low | Not tested |
| 3 | G125 | Similar to wild type | Not tested |
| 13/14 | K201 | low | 65° |

Figure 17A

Pyrococcus furiosus gene for archaeal histone (HMf-like)
(ACCESSION No: AB013081)
Nucleotide sequence (SEQ ID NO: 63)
Amino acid sequence (SEQ ID NO: 64)

```
  M   M   G   E   E   L   P   I   A   P   V   D   R   L   I   R   K   A   G    18
  ATG ATG GGA GAA GAA TTA CCA ATT GCC CCA GTT GAC AGA CTT ATA AGA AAG GCT GGT   54

A   Q   R   V   S   E   Q   A   A   K   A   V   L   A   E   H   L   E   E    36
  GCT CAG AGA GTT AGC GAG CAA GCA GCT AAG GTA CTT GCA GAG CAC CTT GAG GAA       108

K   A   I   E   I   A   K   K   A   V   D   L   A   K   H   A   G   R        54
  AAA GCT ATT GAG ATC GCA AAA AAG GCA GTA GAT CTT GCA AAG CAC GCA GGT AGA       162

K   T   V   K   V   E   D   I   K   L   A   I   K   S   *                     69
  AAG ACC GTT AAG GTC GAA GAC ATT AAG CTC GCA ATT AAG AGC TGA                    207
```

Figure 17B

(HMf-like)-Taq DNA polymerase fusion protein

Nucleotide sequence (SEQ ID NO: 65) // Nucleotide sequence (SEQ ID NO: 65)
Amino acid sequence (SEQ ID NO: 64) // Amino acid sequence (SEQ ID NO: 66)

```
  M   M   G   E   E   L   P   I   A   P   V   D   R   L   I   R   K   A   G    18
  ATG ATG GGA GAA GAA TTA CCA ATT GCC CCA GTT GAC AGA CTT ATA AGA AAG GCT GGT   54

A   Q   R   V   S   E   Q   A   A   K   A   V   L   A   E   H   L   E   E    36
  GCT CAG AGA GTT AGC GAG CAA GCA GCT AAG GTA CTT GCA GAG CAC CTT GAG GAA       108

K   A   I   E   I   A   K   K   A   V   D   L   A   K   H   A   G   R        54
  AAA GCT ATT GAG ATC GCA AAA AAG GCA GTA GAT CTT GCA AAG CAC GCA GGT AGA       162

K   T   V   K   V   E   D   I   K   L   A   I   K   S                         69
  AAG ACC GTT AAG GTC GAA GAC ATT AAG CTC GCA ATT AAG AGC
```

FIGURE 17B (CONT.)

```
        G   G   G
    //  GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   P   H   A   L   G   L   T   T
GAC GGC CAC CAC CTG GCC TAC CGC ACC TTC CAC GCC CTG GGC CTC ACC ACC

S   R   G   E   P   V   Q   A   V   Y   G   F   V   K   A   K   L   K
AGC CGG GGG GAG CCG GTG CAG GCG GTC TAC GGG TTC GTG AAG GCC CTC AAG

A   L   K   E   D   G   D   A   Y   G   I   V   K   A   D   P   A   P
GCC CTC AAG GAG GAC GGG GAC GCG GTG ATC GTG AAG GCG GAC TTT GAC GCC CCC

S   F   R   H   E   A   Y   L   A   Y   G   K   A   G   R   A   T   P
TCC TTC CGC CAC GAG GCC TAC CTC GCC TAC GGG AAG GCG GGC CGG GCC ACG CCA

E   D   F   P   R   Q   E   V   P   G   Y   E   A   D   R   V   L   G
GAG GAC TTT CCC CGG CAA GAG GTC CCG GGC TAC GAG GCG GAC CGG GTG CTG GGG

L   A   R   L   E   A   E   K   Y   G   Y   E   V   D   V   L   S   L
CTG GCG CGC CTC GAG GCG GAA AAG TAC GGC TAC GAG GTC GAC GTG CTG AGC CTG

A   K   K   A   E   K   L   W   E   K   Y   E   V   R   I   L   T   A   D   K
GCC AAG AAG GCG GAA AAG CTT TGG GAA AAG TAC GAG GTC CGC ATC CTC ACC GCC GAC AAA

D   L   Y   Q   L   L   T   G   D   E   N   L   H   P   D   G   Q   Y
GAC CTT TAC CAG CTC CTT TGG ACC GGG GAC GAG AAC CTT CAC CCC GAC GGG TAC

L   I   T   P   A   W   L   T   G   D   E   K   Y   G   L   R   P   W
CTC ATC ACC CCG GCC TGG CTT ACC GGG GAC GAG AAA TAC GGC CTG AGG CCC TGG

A   D   Y   R   A   L   T   G   D   E   S   D   N   L   R   P   D   V   K
GCC GAC TAC CGG GCC CTG ACC GGG GAC GAG TCC GAC AAC CTT CGG CCC GAC GTC AAG

G   I   G   E   K   T   A   R   K   L   E   W   L   E   G   S   L   E
GGC ATC GGG GAG AAG ACG GCG AGG AAG CTT CTG GAG TGG GAG GGG AGC CTG GAA
```

FIGURE 17B (CONT.)

| A GCC | L CTC | N AAC | L CTG | D GAC | R CGG | L CTG | K AAG | P CCC | A GCC | I ATC | R CGG | E GAG | K AAG | I ATC | L CTG |
| A GCC | H CAC | M ATG | D GAC | L CTG | K AAG | L CTG | S TCC | W TGG | D GAC | L CTG | A GCC | K AAG | V GTG | R CGC | T ACC | D GAC |
| L CTG | P CCC | L CTG | E GAG | V GTG | D GAC | F TTC | L CTC | A GCC | K AAA | R AGG | E GAG | P CCC | D GAC | R CGG | E GAG | R AGG | L CTT |
| R AGG | A GCC | F TTT | L CTG | E GAG | R AGG | L CTT | A GCC | L CTG | E GAG | F TTT | G GGC | E GAG | R AGG | E GAG | F TTC | G GGC | L CTT |
| L CTG | E GAA | S AGC | P CCC | K AAG | A GCC | L CTG | L CTG | S AGC | W TGG | P CCC | A GCC | P CCC | D GAT | P CCT | E GAA | L CTT | Y TAT | L CTT |
| F TTC | V GTG | G GGC | F TTT | V GTG | L CTT | S TCC | G GGC | R CGC | R CGG | V GTC | H CAC | R CGG | W TGG | M ATG | A GCC | P CCC | E GAG | K AAA | A GCC |
| L CTG | A GCC | A GCC | R AGG | G GGG | A GCC | E GAG | G GGC | G GGG | R CGG | R CGG | A GCC | P CCC | A GCC | R CGG | P CCC | E GAG | L CTT | L CTG | A GCC |
| L CTC | R CGG | D GAC | R CGG | E GAG | K AAG | A GCC | L CTG | P CCC | G GGC | L CTT | P CCC | D GAC | K AAA | D GAC | P CCC | V GTG | A GCC | R CGG | G GGC |
| A GCC | L CTG | R AGG | E GAG | G GGA | G GGC | L CTT | S TCC | N AAC | T ACC | T ACC | P CCC | E GAG | R CGG | E GAG | G GGC | A GCC | L CTC | R CTC | L CTC |
| Y TAC | L CTG | L CTG | D GAC | P CCT | S TCC | E GAG | E GAG | G GGG | A GCC | E GAG | G GGG | E GAG | A GCC | L CTG | M ATG | R CGG | L CTC | A GCC | H CAC |
| G GGG | E GAG | W TGG | T ACG | E GAG | R AGG | L CTT | E GAG | G GGG | L CTT | S TCC | A GCT | R AGG | L CTG | E GAG | A GCC | E GAG | M ATG |
| A GCC | N AAC | L CTG | W TGG | R AGG | P CCC | L CTT | S TCC | A GCG | R CGG | V GTC | L CTG | S TCC | A GCC | L CTG | H CAC | A GCC | T ACG | A GCC |
| E GAG | V GTG | E GAG | R AGG | P CCC | L CTT | Y TAT | A GCC | V GTC | L CTG | R CGG | A GCC | L CTG | S TCC | L CTG | M ATG | E GAG | V GTG | A GCC |
| R CGC | L CTG | D GAC | V GTG | Y TAT | L CTC | R AGG | A GCC | G GCC | T TAT | AGG | L CTC | TCC | TTG | CTG | CAC | M ATG | E GAG | V GTG | A GCC |

*(Note: sequence figure — codons with corresponding one-letter amino acid codes as reproduced from Figure 17B continued.)*

```
AAG GTG CGG GCC TGG ATT GAG AAG AGG AGG CTG GAG GAG GGC AGG AGG CGG GGG TAC
 K   V   R   A   W   I   E   K   R   R   L   E   E   G   R   R   R   G   Y

GTG GAG ACC CTC TTC GGC CGC CGC TAC GTG CCA GAC CTA GAG GCC CGG GTG
 V   E   T   L   F   G   R   R   Y   V   P   D   L   E   A   R   V

AAG AGC GTG CGG GAG GCG GCC GAG CGC ATG GCC TTC AAC ATG CCC GTC CAG GGC
 K   S   V   R   E   A   A   E   R   M   A   F   N   M   P   V   Q   G

ACC GCC GCC GAC CTC ATG AAG CTG GCT ATG GTG AAG CTC TTC CCC AGG CTG GAG
 T   A   A   D   L   M   K   L   A   M   V   K   L   F   P   R   L   E

GAA ATG GGG GCC AGG ATG CTC CTC CTT CAG GTC CAC GAC GAG CTG CTC GAG GCC
 E   M   G   A   R   M   L   L   Q   V   H   D   E   L   L   E   A

CCA AAA GAG AGG GCG GAG GCC GTG GCC CGG CTG GCC AAG GAG GTC ATG GAG GGG
 P   K   E   R   A   E   A   V   A   R   L   A   K   E   V   M   E   G

GTG TAT CCC CTG GCC GTG CCC CTG GAG GTG GAG GTG GGG ATA GGG GAG GAC TGG
 V   Y   P   L   A   V   P   L   E   V   E   V   G   I   G   E   D   W

CTC TCC GCC AAG GAG GGC ATT GAT GGC CGC GGC GGA CGC GGG CAT CAT CAT CAT
 L   S   A   K   E   G   I   D   G   R   G   G   R   G   H   H   H   H

CAT CAT TAA
 H   H   *
```

Figure 17C

Taq DNA polymerase- (HMf-like) fusion protein

Nucleotide sequence (SEQ ID NO: 65) /Nucleotide sequence (SEQ ID NO: 63)
Amino acid sequence (SEQ ID NO: 66) /Amino acid sequence (SEQ ID NO: 64)

```
 G   G   G
GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG
```

```
CTG CCC GAG GTG GAC TTC GCC AAA AGG CGG GAG CCC GAC CGG GAG AGG CTT
 R   A   E   L   F   D   R   A   F   E   K   R   R   E   P   D   R   E   L
 L   E   P   S   G   F   L   E   L   S   R   G   E   H   L   W   M   P   L
CTG GAA AGC TTT GGC CTT GAG CTG AGC GGG GGG CAC CTC ATG CCC CAC GAG TTC
 F   V   G   F   V   A   R   G   A   L   K   G   L   R   P   P   A   D
TTC GTG GGC TTT GTG GCC AGG GGG GCG CTG AAG GGC CTT CGG CCC CCG GCC GAT
 L   A   A   A   R   A   K   L   R   E   A   L   G   P   P   P   L   Y
CTG GCC GCC GCC CGG GCG AAG CTG AGG GAA GCG CTG GGC CTC CCC CCG CTT TAT
 L   R   K   D   L   R   E   A   G   L   G   L   P   T   T   R   G   Y
CTC AGG AAG GAC CTG AGG GAA GCG GGC CTT GGC CTC CCC ACC ACC CGG GGC TAT
 A   L   R   G   E   L   R   A   N   T   T   P   E   G   E   R   L   Y
GCC CTG AGG GGC GAA CTT CGG GCC AAC ACC ACC CCG GAG GGG GAG CGG CTC TAC
 Y   L   D   P   S   P   E   E   A   A   V   L   S   L   L   M   E   A
TAC CTC GAC CCT TCC CCT GAG GAG GCG GCC GTG CTT TCC CTT CTC ATG GAG GCC
 G   E   W   T   E   G   A   G   R   L   A   H   E   L   M   E   V   A
GGG GAG TGG ACG GAG GGG GCG GCG CTT GCC CAC GAG CTG ATG GAG GTG GCC GAG
 A   N   L   G   R   P   L   S   L   R   L   L   W   L   Y   R
GCC AAC CTG TGG GGG AGG CCC CTT TCC CTG AGG CTC CTT TGG CTT TAC CGG GTG
 E   V   E   D   V   A   Y   R   A   L   R   F   P   N   T   G   E   I
GAG GTG GAG GAC GTG GCC TAT CGT GCT AGG GCC TTT CCC AAC ACG GGG GAG ATC
 R   L   D   A   E   L   E   V   F   R   L   G   H   P   F   A   E   N
CGC CTG GAC GCC GAG CTC GAG GTC TTC CGC CTG GGC CAC CCC TTC GCC GAG AAC
 A   R   L   E   A   F   R   V   L   F   D   L   A   G   H   P   A   I
GCC CGC CTC GAG GCC GAG GTC TTC CGC CTG TTC GAC CTG GCC GGC CAC CCC GCC ATC
 S   R   D   Q   L   E   G   L   F   R   V   L   F   D   E   L   G   P   I
TCC CGG GAC CAG CAG CTG GAA GAG CTG TTC CGC GTC CTT TTT GAC GAG CTA GGG CTT CCC GCC ATC
```

FIGURE 17C (CONT.)

```
G   K   T   E   K   T   G   K   R   S   T   S   A   A   V   L   E   A
GGC AAG ACG GAG AAG ACC GGC AAG CGC TCC ACC AGC GCC GTC CTG GAG GCC

L   R   E   A   H   P   Y   I   V   E   K   H   I   P   R   E   L   T
CTC CGC GAG GCC CAC CCC ATC GTG GAG AAG ATC CTG GAG GAG CTC ACC

K   L   K   S   T   Y   I   D   P   L   Q   D   L   I   H   P   R   T
AAG CTG AAG AGC ACC TAC ATT GAC CCC TTG CAG GAC CTC ATC CAC CCC AGG ACG

G   R   L   H   T   R   F   N   Q   T   A   T   G   R   L   G   L   S
GGC CGC CTC CAC ACC CGC TTC AAC CAG ACG GCC ACG GGC AGG CTA AGT

S   D   P   N   L   Q   N   I   P   V   R   L   G   L   R   Q   R
AGC TCC GAT CCC AAC CTC CAG AAC ATC CCC GTC CGC CTA TTG GGG CTT CAG AGG

I   R   A   F   I   R   V   R   D   E   W   L   S   V   A   D   L   Y
ATC CGC GCC TTC ATC AGG GTG CGG GAC GAG TGG CTA TCC GTG GCC GAC CTG GAC TAT

S   Q   I   E   L   R   G   E   R   D   M   S   A   I   R   S   Q   I
AGC CAG ATA GAG CTC AGG GGG GAG CGG GAC ATG TCG GCC ATT TTG ATC CTG ATC

R   V   F   Q   E   E   A   V   R   E   M   D   T   A   R   R   Q   M
CGG GTC TTC CAG GAG GAG GCC GTG CGG GAG ATG GAC ACG GCC CGG CGG CAG ATG ATG TTC

G   V   P   R   E   A   V   G   M   D   D   P   L   S   A   A   K   T   I
GGC GTC CCC CGG GAG GCC GTG GGC ATG GAC GAC CCC CTG TCG GCC GCC AAG ACC ATC

N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

K   V   R   A   W   I   E   K   T   L   E   E   G   R   R   R   G   Y
AAG GTG CGG GCC TGG ATT GAG AAG ACC CTG GAG GAG GGC AGG CGG AGG GGG TAC

V   E   T   L   F   G   R   R   R   Y   V   P   D   L   E   A   R   V
GTG GAG ACC CTC TTC GGC CGC CGC CGC TAC GTC CCA GAC CTA GAG GCC CGG GTG

K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC
```

FIGURE 17C (CONT.)

```
T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

E   M   G   A   R   M   L   L   Q   V   H   D   L   E   L   V   E   A
GAA ATG GGG GCC AGG ATG CTC CTT CAG GTC CAC GAC GAG CTG GTC GAG GCC

P   K   E   R   A   E   A   V   A   R   L   A   A   K   E   V   M   E   G
CCA AAA GAG AGG GCG GAG GCC GTG GCC CGG CTG GCC GCC AAG GAG GTC ATG GAG GGG

V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

L   S   A   K   E   G   I   D   G   R   G   R   G   G   H   H   H   H
CTC TCC GCC AAG GAG GGC ATT GAT GGC CGC GGC GGA GGC CAT CAT CAT CAT

H   H                                                                    18
CAT CAT                                                                  54
//
//

M   M   G   E   L   P   I   A   P   V   D   R   L   I   R   K   A   G   36
ATG ATG GGA GAA TTA CCA ATT GCC CCA GTT GAC AGA CTT ATA AGA AAG GCT GGT  108

A   Q   R   V   S   E   Q   A   A   K   A   V   L   A   E   H   L   E
GCT CAG AGA GTT AGC GAG CAA GCA GCT AAG GTA CTT GCA GAG CAC CTT GAG GAA

K   A   I   E   I   A   K   K   A   K   A   V   D   L   A   K   H   A   G   R   54
AAA GCT ATT GAG ATC GCA AAA AAG GCA AAA GCA GTA GAT CTT GCA AAG CAC GCA GGT AGA 162

K   T   V   K   V   E   D   I   K   L   A   I   K   S   *                69
AAG ACC GTT AAG GTC GAA GAC ATT AAG CTC GCA ATT AAG AGC TGA
```

Figure 17D

Pfu DNA Polymerase (WT) -(HMf-like) fusion protein

Nucleotide sequence (SEQ ID NO: 61)   //Nucleotide sequence (SEQ ID NO: 63)

FIGURE 17D (CONT.)

```
cctgtcct gggtccacat atatgtctt actcgcctt atgaagaatc cccagtcgc
tctaacctgg gttatagtga caaatcttcc tccaccacg cccaagaagg ttatttctat
caacttcaca cctcccctat tttctctctt atgagatttt taagtatagt tatagagaag
gttttatact ccaaactgag ttagtagata tgtgggagc ataatgattt tagatgtgga
ttacataact gaagaaggaa aacctgttat taggctattc aaaaagaga acggaaaatt
taagatagag catgatagaa cttttagacc atacattac gctcttctca gggatgattc
aaagattgaa gaagttaaga aataacggg ggaaaggcat ggaaagattg tgagaattgt
tgatgtagag aaggttgaga aaaagtttct cggcaagcct attaccgtgt ggaaacttta
tttggaacat ccccaagatg ttccactat tagagaaaaa gttagagaac atccagcagt
tgtggacatc ttcgaatacg atattccatt tgcaaagaga tacctcatcg acaaaggcct
aataccaatg gaggggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gattctcag gattatcagg gagaaggatc ctgacattat
agttacttat aatggagact cattcgactt cccatattta gcgaaaaggg cagaaaaact
tggattaaa ttaaccattg gaagagatgg aagcgagccc aagatgcaga gaataggcga
tatgacggct gtagagtca agggaagaat acatttcgac ttgtatcatg taataacaag
gacaataaat ctccaacat acacactaga ggctgtatat gaagcaattt ttggaaagcc
aaaggagaag gtatacgccg acgagatagc aaaagcctgg gaaagtggag agaaccttga
gagagttgcc aatactcga tggaagatgc aaaggcaact tatgaactcg ggaaagaatt
```

FIGURE 17D (CONT.)

```
ccttccaatg gaaattcagc tttcaagatt agtggacaa cctttatggg atgtttcaag
gtcaagcaca gggaaccttg tagagtggtt cttacttagg aaagctacg aagaaacga
agtagctcca aacaagccaa gtgaagagga gtatccaaga aggctcaggg agagctacac
aggtggattc gttaaagagc cagaaaaggg gttgtgggaa aacatagtat acctagattt
tagagccta tatccctcga ttataattac ccacaatgtt tctccccgata ctctaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaatactc cttgactata gacaaaaagc
gataaaactc ttagcaaatt ctttctacgg atattatgc tatgcaaaag caagatggta
ctgtaaggag tgtgctgaga gcgttactgc ctgggggaaga aagtacatcg agttagtatg
gaaggagctc gaagaaaagt ttggatttaa agtccctac attgacactg atggtctcta
tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag aatacgatc ccaaaaagca
caagtatgac gcagaatatt acattgagaa ccaggtcctt ccagcggtac ttaggatatt
```

FIGURE 17D (CONT.)

```
ggagggattt ggatacagaa aggaagacct cagataccaa aagacaagac aagtcggcct
aacttcctgg cttaacatta aaaaatccta gaaaagcgat agatatcaac tttattctt
tctaaccttt ttctatgaaa gaagaactga gcaggaatta ccagttcttc cgttattta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taacttttac agaaataact gtctcaaatt atgcaaactc ttgacatttt tacttcatta
ccagggtaat gtttttaagt atgaaatttt tctttcatag aggagnnnn nngtcctctc
ctcgatttcc ttggttgtgc tccatatgat aagcttccaa agtgggtgtt cagacttta
gacactcaaa taccagacga caatggtgtg ctcactcaag cccatatgg gttgagaaaa
gtagaagcgg cactactcag atgcttcccc aggaatgagg ttgttgtagc tcntcccnga
aagattgaga tgttcttgg //

ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG GCT ATC GCA AAA AAG GCA GTA GAT CTT GCA CAC GCA GGT AGA   162
AAG ACC GTT AAG GTC GAA GTC AAG GAC ATT AAG CTC GCA ATT AAG AGC TGA
```

Figure 17E

(HMf-like) - Pfu DNA Polymerase (WT) fusion protein

Nucleotide sequence (SEQ ID NO: 63)  //Nucleotide sequence (SEQ ID NO: 61)

```
ATG ATG GGA GAA TTA CCA ATT GCC CCA GTT GAC AGA GTT GAC CTT ATA AGA AAG GCT GGT      54
GCT CAG AGA GTT AGC GAG CAA GCA GCT AAG GTA CTT GCA GAG CAC CTT GAG GAA             108
AAA GCT ATT GAG ATC GCA AAA AAG GCA GTA GAT CTT GCA AAG CAC CAC GCA GGT AGA         162
AAG ACC GTT AAG GTC GAA GAC GTT AAG CTC GCA ATT AAG AGC // cctgtgcct gggtccacat atatgttctt actcgcctt atgaagaatc cccagtcgc
tctaacctgg gttatagtga caaatcttcc tccaccacg cccaagaagg ttattctat
caactctaca cctcccctat tttctctctt atgagatttt taagtatagt tatagagaag
gttttatact ccaaactgag ttagtagata tgtggggagc ataatgattt tagatgtgga
ttacataact gaagaaggaa aacctgttat taggctattc aaaaaagaga acggaaaatt
taagatagag catgatagaa cttttagacc atacattac gctcttctca gggatgattc
aaagattgaa gaagttaaga aataacggg ggaaaggcat ggaaagattg tgagaattgt
tgatgtagag aaggttgaga aaaagtttct cggcaagcct attaccgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
aataccaatg gaggggaag aagagctaaa gattcttgcc ttcgatatag aaacccta
tcacgaagga gaagagttg gaaaaggccc aattataatg attagttatg cagatgaaaa
tgaagcaaag gtgattactt ggaaaaacat agatcttcca tacgttgagg ttgtatcaag
```

FIGURE 17E (CONT.)

```
tcgtggttta gagatagtta ggagagattg gagtgaaatt gcaaaagaaa ctcaagctag
agtttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca ataggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt
tctaacctt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa ttcgacgac gtagatcttt
tttgctccaa gcagagccgc tccaatggat aacaccctg ttcccgcacc caagtccgct
acaatttttt ccttgtatct cctaatgtat aagcaagcca aggagagta gatgctacct
ttccgggagt tttgtattgc tctagccaag gtttgggatt tttgaatcct ttaactctgg
aagtataat ttcaagctcc ttcttcttca tgacagatga aaaattgttt tgtctctttt
taactttac agaaataact gtctcaaatt atgcaactc ttgacatttt tacttcatta
```

FIGURE 17E (CONT.)

```
cgagagagag atgataaaga gatttcctcag gattatcagg gagaaggatc ctgacattat
agtacttat  aatggagact  cattcgactt  cccatattta  gcgaaaaggg  cagaaaaact
tggattaaa  ttaaccattg  gaagagatgg  aagcgagccc  aagatgcaga  gaataggcga
tatgacggct gtagaagtca  agggaagaat  acatttcgac  ttgtatcatg  taataacaag
gacaataaat ctcccaacat  acacactaga  ggctgtatat  gaagcaattt  ttggaaagcc
aaaggagaag gtatacgccg  acagagatagc aaaagcctgg  gaaagtggag  agaaccttga
gagagttgcc aaatactcga  tggaagatgc  aaaggcaact  tatgaactcg  ggaaagaatt
ccttccaatg gaaattcagc  tttcaagatt  agttggacaa  cctttatggg  atgtttcaag
gtcaagcaca gggaaccttg  tagagtggtt  cttacttagg  aaagcctacg  aaagaaacga
agtagctcca aacaagccaa  gtgaagagga  gtatcaaaga  aggctcaggg  agagctacac
aggtggattc gttaaagagc  cagaaaaggg  gttgtgggaa  aacatagtat  acctagattt
tagagcccta tatccctcga  ttataattac  ccacaatgtt  tctcccgata  ctctaaatct
tgagggatgc aagaactatg  atatcgctcc  tcaagtaggc  cacaagttct  gcaaggacat
ccctggtttt ataccaagtc  tcttgggaca  tttgttagag  gaaagacaaa  agattaagac
aaaaatgaag gaaactcaag  atcctataga  aaaaatactc  cttgactata  gacaaaaagc
gataaaactc ttagcaaatt  cttttctacgg atattatggc  tatgcaaaag  caagatggta
ctgtaaggag tgtgctgaga  gcgttactgc  ctggggaaga  aagtacatcg  agttagtatg
gaaggagctc gaagaaaagt  ttggatttaa  agtcctctac  attgacactg  atggtctcta
tgcaactatc ccaggaggag  aaagtgagga  aataaagaaa  aaggcttag   aatttgtaaa
atacataaat tcaaagctcc  ctggactgct  agagcttgaa  tatgaaggt   tttataagag
gggattcttc gttacgaaga  agaggtatgc  agtaatagat  gaagaaggaa  aagtcattac
```

FIGURE 17E (CONT.)

```
ccagggtaat gtttttaagt atgaaatttt tctttcatag aggaggnnnn nngtcctctc
ctcgattcc ttggttgtgc tccatatgat aagcttccaa agtgggtgtt cagactttta
gacactcaaa taccagacga caatggtgtg ctcactcaag ccccatatgg gttgagaaaa
gtagaagcgg cactactcag atgcttcccc aggaatgagg ttgttgtagc tcntcccnga
aagattgaga tgttcctgg  //  TGA
```

Figure 17F

(HMf-like) - PFU DNA POLYMERASE (V93 R OR E) fusion protein

Nucleotide sequence (SEQ ID NO: 63)   // Nucleotide sequence (SEQ ID NO: 27)
Nucleotide sequence (SEQ ID NO: 63)   //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG GCT GCA AAA AAG GCA GTA GAT CTT GCA AAG CAC GCA GGT AGA   162
AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA  60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGAA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAAACATC CAGCAGTTGT GGACATCTTC GAATACGATA TTCCATTTGC AAAGAGATAC 360
CTCATCGACA AAGGCCTAAT ACCAATGGAG GGGAAGAAG AGTTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGATTCCC ATATTTAGCG 660
AAAAGGGCAG AAAAACTTGG GATTAAATTA ACCATTGGAA GAGATGGAAG CGAGCCCAAG 720
```

FIGURE 17F (CONT.)

```
ATGCAGAGAA TAGGCGATAT GACGGCTGTA GAAGTCAAGG GAAGAATACA TTTCGACTTG  780
TATCATGTAA TAACAAGGAC AATAAATCTC CCAACATACA CACTAGAGGC TGTATATGAA  840
GCAATTTTTG GAAAGCCAAA GGAGAAGTTA TACGCCGACG AGATAGCAAA AGCCTGGGAA  900
AGTGGAGAGA ACCTTGAGAC AGTTGCCAAA TACTCGATGG AAGATGCAAA GGCAACTTAT  960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AGCTCCAAGT AAGAGGAGTA TCAAAGAAGG 1140
CTCAGGGAGA GCTACACAGG TGGATTCGTT AAAGAGCCAG AAAAGGGGTT GTGGAAAAAC 1200
ATAGTATACC TAGATTTTAG AGCCCTATAT CCCTGGATTA TAATTACCCA CAATGTTTCT 1260
CCCGATACTC TAAATCTTGA GGGATGCAAG AACTAGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAGACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAGAAACTC AAGCTAGAGT TTTGGAGACA ATACTAAAAC ACGGAGATGT TGAAGAAGCT 1920
GTGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT AAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAG 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //          2328
// TGA
```

Figure 17G

PFU DNA POLYMERASE (V93 R OR E)-(HMf-like) fusion protein

Nucleotide sequence (SEQ ID NO: 27) // Nucleotide sequence (SEQ ID NO: 63)
Nucleotide sequence (SEQ ID NO: 28) // Nucleotide sequence (SEQ ID NO: 63)

FIGURE 17G (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
```

FIGURE 17G (CONT.)

```
GCGGTACTTA GGATATTGGA GGGATTGGA TACAGAAAGG AAGACCTCAG ATACCAAAAG 2280
ACAAGACAAG TCGGCCTAAC TTCCTGGCTT AACATTAAAA AATCC //            2328

ATG ATG GGA GAA TTA CCA ATT GCC CCA GTT GAC CTT ATA AGA AAG GCT GGT      54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC TGA
```

Figure 17H

PFU DNA POLYMERASE (G387P/V93R OR E)-(HMf-like) fusion protein

Nucleotide sequence (SEQ ID NO: 29) // Nucleotide sequence (SEQ ID NO: 63)
Nucleotide sequence (SEQ ID NO: 30) // Nucleotide sequence (SEQ ID NO: 63)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA   60
AAAGAGAACG GAAAATTTAA GATAGAGCAT GATAGAACTT TTAGACCATA CATTTACGCT  120
CTTCTCAGGG ATGATTCAAA GATTGAAGAA GTTAAGAAAA TAACGGGGGA AAGGCATGGA  180
AAGATTGTGA GAATTGTTGA TGTAGAGAAG GTTGAGAAAA AGTTTCTCGG CAAGCCTATT  240
ACCGTGTGGA AACTTTATTT GGAACATCCC CAAGATXXXC CCACTATTAG AGAAAAAGTT  300
AGAGAACATC CAGCAGTTGT GGACATCTTC GAATACGATA TTCCATTTGC AAAGAGATAC  360
CTCATCGACA AAGGCCTAAT ACCAATGGAG GGGAAGAAG AGCTAAAGAT TCTTGCCTTC  420
GATATAGAAA CCCTCTATCA CGAAGGAGAA GAGTTTGGAA AAGGCCCAAT TATAATGATT  480
AGTTATGCAG ATGAAAATGA AGCAAAGGTG ATTACTTGGA AAAACATAGA TCTTCCATAC  540
GTTGAGGTTG TATCAAGCGA GAGAGAGATG ATAAAGAGAT TTCTCAGGAT TATCAGGGAG  600
AAGGATCCTG ACATTATAGT TACTTATAAT GGAGACTCAT TCGATTCCCC ATATTAGCG  660
AAAAGGCCAG AAAAACTTGG GATTAAATTA ACCATTGGAA GAGATGGAAG CGAGCCCAAG  720
ATGCAGAGAA TAGGCGATAT GACGGCTGTA GAAGTCAAGG GAAGAATACA TTTCGACTTG  780
TATCATGTAA TAACAAGGAC AATAAATCTC CCAACATACA CACTAGAGGC TGTATATGAA  840
GCAATTTTTG GAAAGCCAAA GGAGAAGGTA TACGCCGACG AGATAGCAAA AGCCTGGGAA  900
AGTGGAGAGA ACCTTGAGAG AGTTGCCAAA TACTCGATGG AAGATGCAAA GGCAACTTAT  960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
```

FIGURE 17H (CONT.)

```
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GGGATTTGGA TACAGAAAGG AAGACCTCAG 2220
GCGGTACTTA GGATATTGGA TTCCTGGCTT TTCCTGGCTT AACATTAAAA AATCC // 2280
ACAAGACAAG TCGGCCTAAC                                            2328
```

Figure 17B:
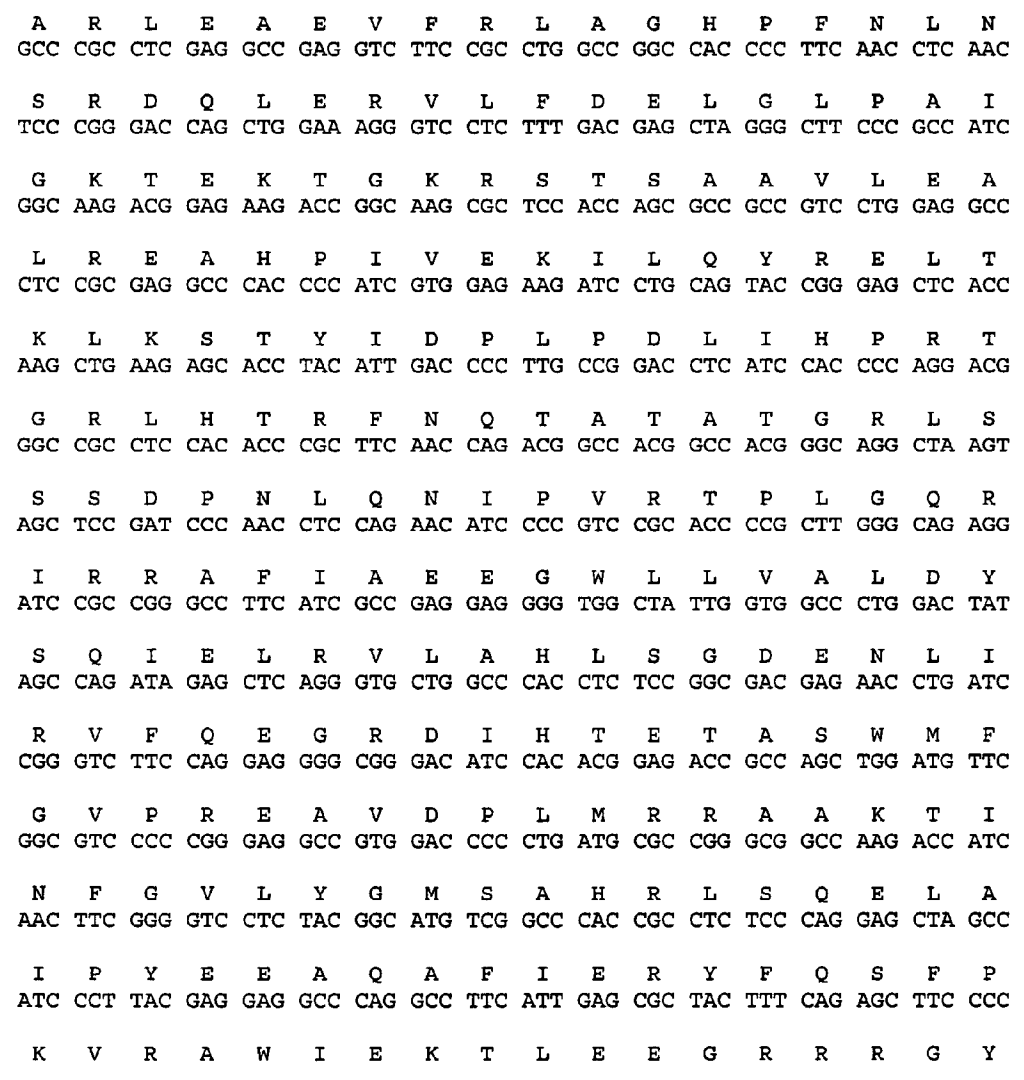
Figure 17C:
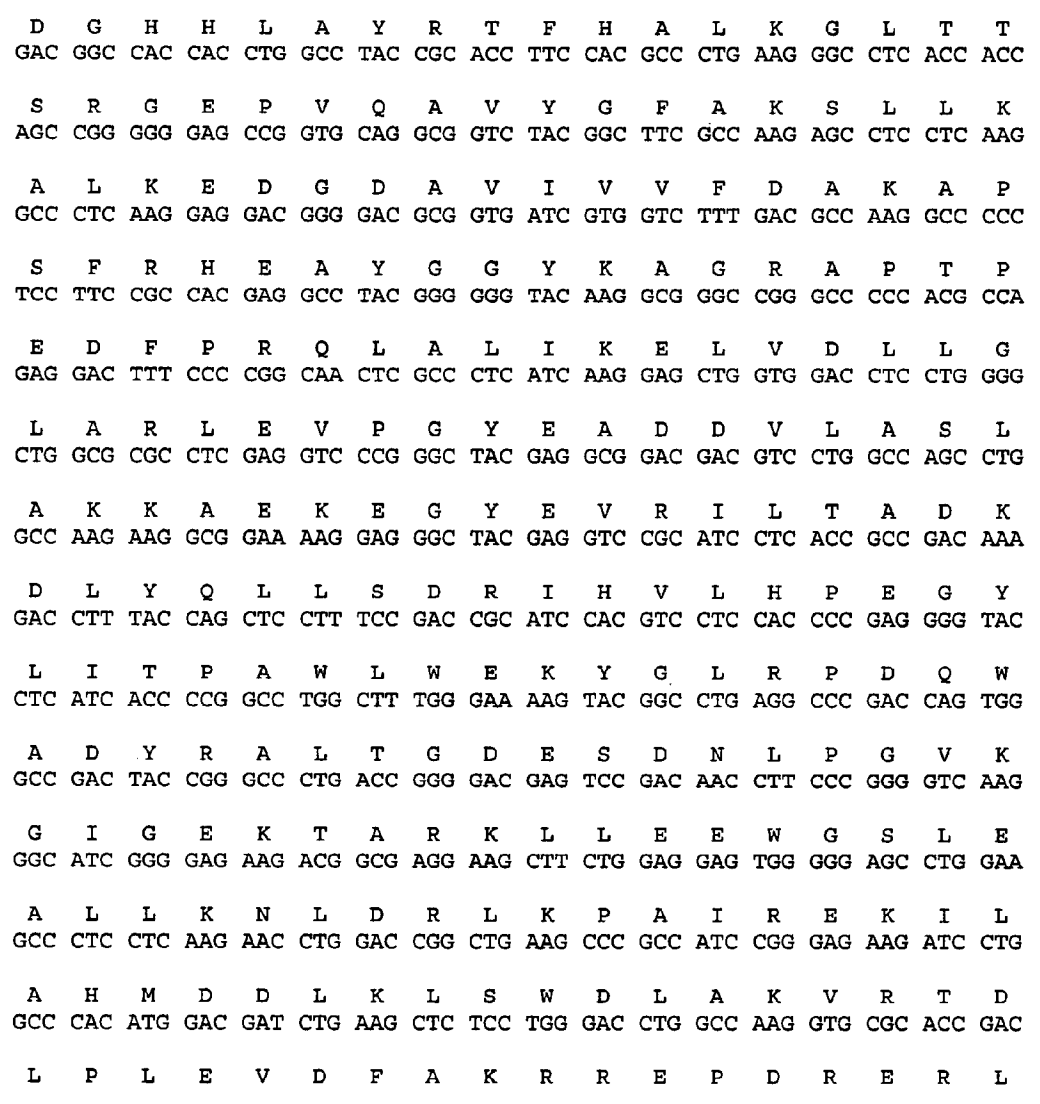
Figure 17U:
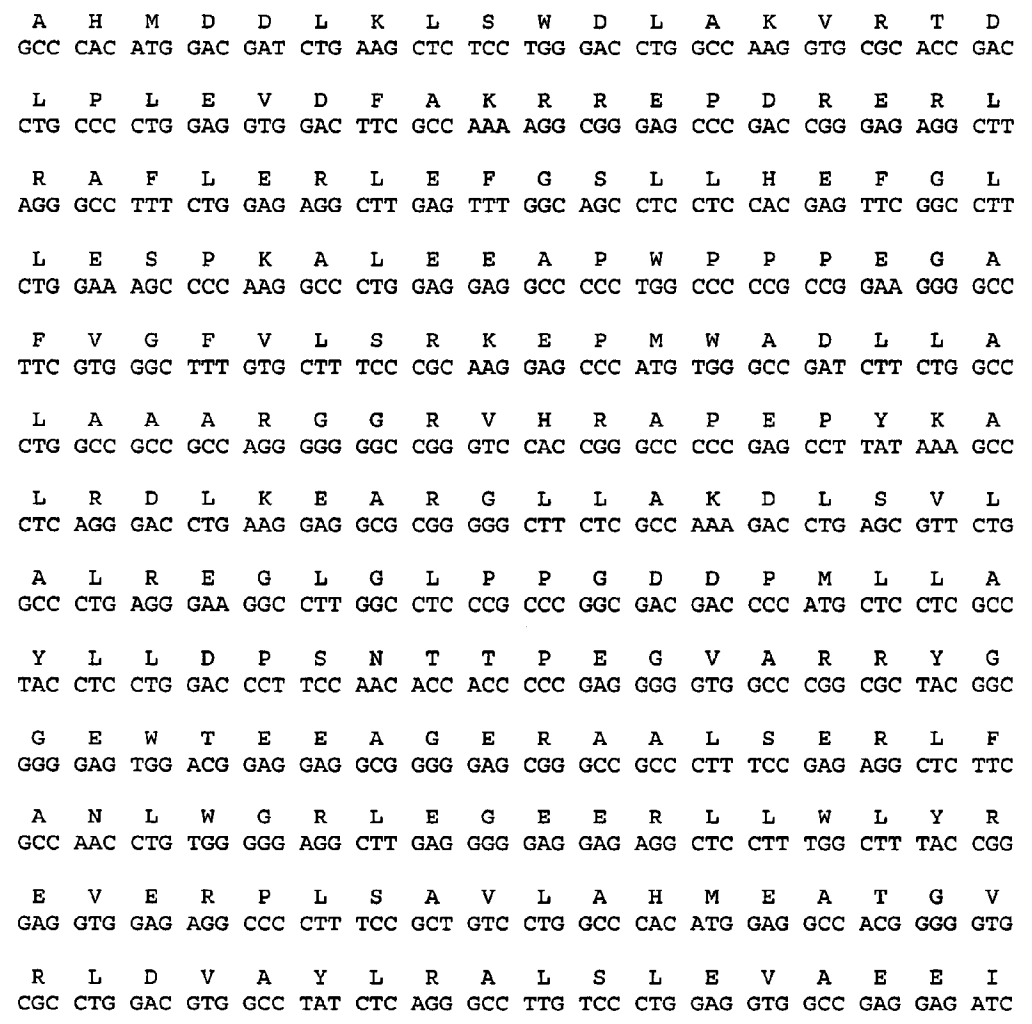
Figure 17:
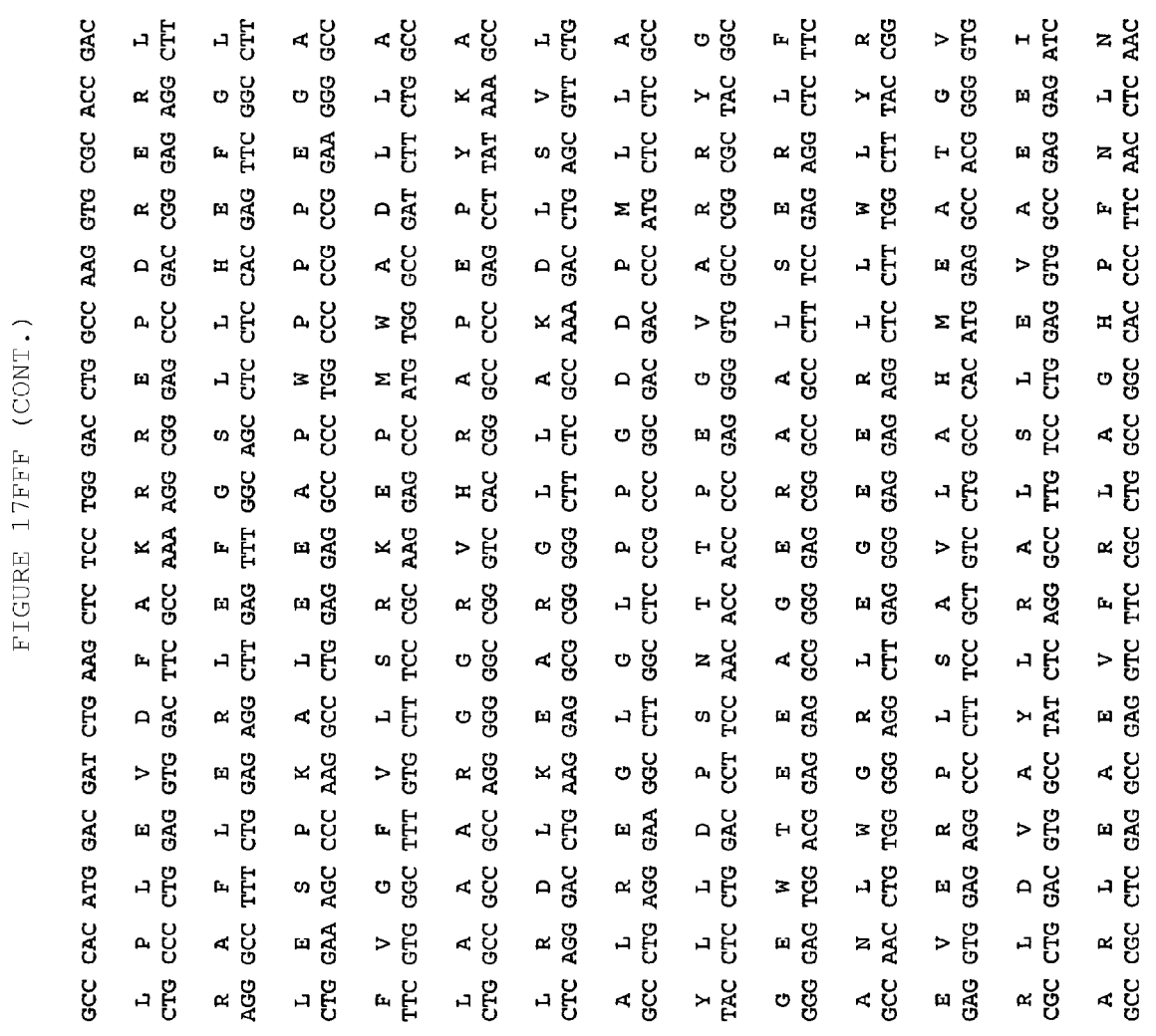

Figure 17I (HMf-like) - PFU DNA POLYMERASE (G387P/V93R OR E) fusion protein

Nucleotide sequence (SEQ ID NO: 63) // Nucleotide sequence (SEQ ID NO: 29)
Nucleotide sequence (SEQ ID NO: 63) // Nucleotide sequence (SEQ ID NO: 30)

```
ATG ATG GGA GAA TTA CCA ATT GCC CCA GTT GAC AGA CTT ATA AGA AAG GCT GGT
GCT CAG AGA GTT AGC GAG GAG CAA GCA GCT AAG GTA CTT GCA GAG CAC CTT GAG GAA   54
AAA GCT ATT GAG ATC GCA AAA AAG GCA GTA GAT CTT GCA AAG CAC AAG GCA GGT AGA  108
AAG ACC GTT AAG GTC GAA GAC ATT AAG CTC GCA ATT AAG AGC TGA                   162
```

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT       54
```

FIGURE 17I (CONT.)

```
GCT CAG AGA GTT AGC GAG CAA GCA GCT AAG GTA CTT GCA GAG CAC CTT GAG GAA   108
AAA GCT ATT GAG ATC GCA AAA GAC GTA GAT CTT GCA AAG CAC GCA GGT AGA
AAG ACC GTT AAG GTC GAA GAC ATT AAG CTC GCA ATT AAG AGC //                162

//ATGATTTTAG ATGTGGATTA CATAACTGAA GAAGGAAAAC CTGTTATTAG GCTATTCAAA   60
AAAGAGAACG GAAAATTTAA GATAGAGCAT GATAGACACTT TTAGACCATA CATTTACGCT   120
CTTCTCAGGG ATGATTCAAA GATTGAAGAA GTTAAGAAAA TAACGGGGGA AAGGCATGGA   180
AAGATTGTGA GAATTGTTGA TGTAGAGAAG GTTGAGAAAA AGTTTCTCGG CAAGCCTATT   240
ACCGTGTGA AACTTTATTT GGAACATCCC CAAGATXXXC CCACTATTAG AGAAAAAGTT   300
AGAGAACATC CAGCAGTTGT GGACATCTTC TTCCATTTGC AAAGAGATAC   360
CTCATCGACA AAGGCCTTAT ACCAATGGAA GCCATGGAAG AGCTAAAGAT TCTTGCCTTC   420
GATATAGAAA CCCTCTATCA CGAAGGAGAA GAGTTTGGAA AAGGCCCAAT TATAATGATT   480
AGTTATGCAG ATGAAAATGA AGCAAAGGTG ATTACTTGGA AAAACATAGA TCTTCCATAC   540
GTTGAGGTTG TATCAAGCGA GAGAGAGATG ATAAAGAGAT TTCTCAGGAT TATCAGGGAG   600
AAGGATCCTG ACATTATAGT TACTTATAAT GGAGACTTCAT TCGCATTCCC ATATTTAGCG   660
AAAAGGGCAG AAAAACTTGG GATTAAATTA ACCATTGGAA GAGATGAAG CGAGCCCAAG   720
ATGCAGAGAA TAGGCGATAT GACGGCTGTA GAAGTCAAGG GAAGAATACA TTTCGACTTG   780
TATCATGTAA TAACAAGGAC AATAAATCTC CCAACATACA CACTAGAGGC TGTATATGAA   840
GCAATTTTG GAAAGCCAAA GGAGAAGGTA TACCCGACG AGATAGCAAA AGCCTGGGAA   900
AGTGGAGAGA ACCTTGAGAG AGTTGCCAAA TACTCGATGG AAGATGCAAA GGCAACTTAT   960
GAACTCGGGA AAGAATTCCT TCCAATGAA ATTCAGCTTT CAAGATTAGT TGGACAACCT   1020
TTATGGATG TTTCAAGGTC AAGCTCCAAAC AACCTTGTAG AGTGGTTCTT ACTTAGGAAA   1080
GCCTACGAAA GAAACGAAGT AGCTCCAAAC AAGCCAAGTG AAGAGGAGTA TCAAAGAAGG   1140
CTCAGGGAGA GCTACACACC NGATTCGTT AAAGAGCCAG AAAAGGGGTT GTGGGAAAAC   1200
ATAGTATACC TAGATTTTAG AGCCCTATAT CCCTGATTA TAATTACCA CAATGTTTCT   1260
CCCGATACTC TAAATCTTGA GGGATGCAAG AACTATGATA TCGCTCCTCA AGTAGGCCAC   1320
AAGTTCTGCA AGGACATCCC TGGTTTTATA CCAAGTCTCT TGGGACATTT GTTAGAGGAA   1380
AGACAAAAGA TTAAGACAAA AATGAAGGAA ACTCAAGATC CTATAGAAA AATACTCCTT   1440
GACTATAGAC AAAAAGCGAT AAAACTTCTA GCAAATTCTT TCTACGATA TTATGCTAT   1500
GCAAAAGCAA GATGGTACTG TAAGGAGTGT GCTGAGAGCC TTACTGCCTG GGGAAGAAAG   1560
TACATCGAGT TAGTATGGAA GGAGCTCGAA GAAAAGTTTG GATTTAAAGT CCCTCTACATT   1620
GACACTGATG GTCTCTATGC AACTATCCCA GGAGGAGAAA GTGAGGAAAT AAGAAAAAG   1680
GCTCTAGAAT TTGTAAAATA CATAAATTCA AGCTCCCTG GACTGCTAGA GCTTGAATAT   1740
GAAGGGTTTT ATAAGAGGGG ATTCTTCGTT ACGAAGAAGA GGTATGCAGT AATAGATGAA   1800
AAAGAAACTC TCATTACTCG TGGTTTAGAG ATAGTTAGGA GAGATTGGAG TGAAATTGCA   1860
GTGAGAATAG AAGCTAGAGT TTTTGGAGACA ATACTAAAAC ACGGAGATGT TGAAGAAGCT   1920
CTCGAATAG TAAAAGAAGT AATACAAAG CTTGCCAATT ATGAAATTCC ACCAGAAGAAG   1980
CTCGCAATAT ATGAGAAACT AACCAAGACCA TTACATGAGT TAAGGCGAT AGGTCCTCAC   2040
GTAGCTGTTG CAAAGAAACT AGCTGCTAAA GGAGTAAAA TAAAGCCACA AGTGGTAATT   2100
GGATACATAG TACTTAGAGG CGATGGTCCA ATTAGCAATA GGGCAATTCT AGCTGAGGAA   2160
TACGATCCCA AAAAGCACACA GTATGACGCA GAATATTACA TGGAGAACCA GGTTCTTCCA   2220
```

FIGURE 17I (CONT.)

GCGGTACTTA GGATATTGGA GGGATTTGGA TACAGAAAGG AAGACCTCAG ATACCAAAAG  2280
ACAAGACAAG TCGGCCTAAC TTCCTGGCTT AACATTAAAA AATCC //TAG              2328

Figure 17J

(HMF-LIKE)-PFU DNA POLYMERASE (D141A/E143A/V93R OR E) fusion protein

Nucleotide sequence (SEQ ID NO: 63)  // Nucleotide sequence (SEQ ID NO: 31)
Nucleotide sequence (SEQ ID NO: 63)  // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT   54
GCT CAG AGA GTT AGC GAG CAA GCA GCT AAG GTA CTT GCA GAG CAC CTT GAG GAA  108
AAA GCT ATT GAG ATC GCA AAA GAC GTA GAT CTT GCA AAG CAC GCA GGT AGA      162
AAG ACC GTT AAG GTC GAA GAC ATT AAG CTC GCA ATT AAG AAG AGC //
//ATGATTTAG ATGTGGATTA CATAACTGAA GAAGGAAAAC CTGTTATTAG GCTATTCAAA       60
AAAGAGAACG GAAAATTTAA GATAGAGCAT GATAGAGAAA GTTAAGAAAA TAACGGGGGA CATTTACGCT CATTTACGCT  120
CTTCTCAGGG ATGATTCAAA GATTGAAGAA GTTAAGAAAA TAACGGGGGA AAGGCATGGA        180
AAGATTGTGA GAATTGTTGA TGTAGAGAAG GTTGAGAAAA AGTTTCTCGG CAAGCCTATT         240
ACCGTGTGGA AACTTTATTT GGAACATCCC CAAGATXXXC CCACTATTAG AGAAAAAGTT         300
AGAGAACATC CAGCAGTTGT GGACATCTTC GAATACGATA TTCCATTTGC AAAGAGATAC         360
CTCATCGACA AAGGCCTAAT ACCAATGGAG GGGGAAGAAG AGCTAAAGAT TCTTGCCTTC         420
AGTTATGCAG CCCTCTATCA CGAAGGAGAA GAGTTTGGAA AAGGCCAAT TATAATGATT         480
GTTGAGGTTG TATCAAGCGA AGCAAAGGTG ATAAGAGATT TCTTCCATAC TCTTCCATAC         540
AAGGATCCTG ACATTATAGT TACTTATAAT GGAGACTCAT TCGATTTCCC ATATTTAGCG         600
AAAAGGGCAG AAAAACTTGG GATTAAATTA ACCATTGGAA GAGATGGAAG CGAGCCCAAG         660
ATGCAGAGAA TAGGCGATAT GACGGCTGTA GAAGTCAAGG GAAGAATACA TTTCGACTTG         720
TATCATGTAA TAACAAGGAC AATAAATCTC CCAACATACA CACTAGAGGC TGTATATGAA         780
GCAATTTTTG GAAAGCCAAA GGAGAAGGTA TACGCCGACG AAGATGCAAA AGCCTGGGAA         840
AGTGGAGAGA ACCTTGAGAG AGTTGCCAAA TACTCCGATG AAGATGCAAA GGCCAACTTAT         900
GAACTCGGGA AAGAATTCCT TCCAATGGAA ATTCAGCTTT CAAGATTAGT TGGACAACCT        1020
```

FIGURE 17J (CONT.)

```
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GGT GGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAGAAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTGACAATA GGGCAATTCT AGCTGAGGAG 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //                2328
```

TGA

Figure 17K

<u>PFU DNA POLYMERASE (D141A/E143A/V93R OR E) - (HMF-LIKE) fusion protein</u>

Nucleotide sequence (SEQ ID NO: 31) // Nucleotide sequence (SEQ ID NO: 63)
Nucleotide sequence (SEQ ID NO: 32) // Nucleotide sequence (SEQ ID NO: 63)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA   60
AAAGAGAACG GAAAATTTAA GATAGAGCAT GATAGAACTT TTAGACCATA CATTTACGCT  120
CTTCTCAGGG ATGATTCAAA GATTGAAGAA GTTAAGAAAA TAACGGGGGA AAGGCATGGA  180
AAGATTGTGA GAATTGTTGA TGTAGAGAAG GTTGAGAAAG AGTTTCTCGG CAAGCCTATT  240
```

FIGURE 17K (CONT.)

```
ACCGTGTGGA AACTTTATTT GGAACATCCC CAAGATXXXC CCACTATTAG AGAAAAAGTT  300
AGAGAACATC CAGCAGTTGT GGACATCTTC GAATACGATA TTCCATTTGC AAAGAGATAC  360
CTCATCGACA AAGGCCTAAT ACCAATGGAA CGAAGGAGAG GGGGAAGAAG AGCTAAAGAT TCTTGCCTTC  420
GCNATAGCNA CCCTCTATCA CGAAGGAGAA GAGTTTGGAA AAGCCCAAT TATAATGATT  480
AGTTATGCAG ATGAAAATGA AGCAAAGGTG ATTACTTGGA AAAACATAGA TCTTCCATAC  540
GTTGAGGTTG TATCAAGCGA GAGAGAGATG ATAAAGAGAT TTCTCAGGAT TATCAGGGAG  600
AAGGATCCTG ACATTATAGT TACTTATAAT GGAGACTCAT TCGCATTCCC ATATTTAGCG  660
AAAAGGGCAG AAAAACTTGG GATTAAATTA ACCATTGGAA GAAGTCAAGG GAAGAATACA  720
ATGCAGAGAA TAGGCGATAT GACGGCTGTA GAAGTCAAGG GAAGAATACA TTTCGACTTG  780
TATCATGTAA TAACAAGGAC AATAAATCTC CCAACATACA CACTAGAGGC TGTATATGAA  840
GCAATTTTTG GAAAGCCAAA GGAGAAGGTA TACGCCGACG AGATAGCAAA AGCCTGGGAA  900
AGTGGAGAGA ACCTTGAGAG AGTTGCCAAA TACTCGATGG AAGATGCAAA GGCAACTTAT  960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GGTGGATTCGTT AAAGAGCCAG AAAAGGGGTT GTGGGAAAAC 1200
ATAGTATACC TAGATTTTAG AGCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCCTCTACATT 1620
GACACTGATG GTCTCTATGC AACTATCCCA GGAGGAGAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAGAAGT AATACAAAAG CTTGCCAATT ATGAAATTCC ACCAGAGAAG 1980
CTCGCAATAT ATGAGACAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //            2328

ATG ATG GGA GAA TTA CCA ATT GCC CCA GTT GAC AGA CTT ATA AGA AAG GCT GGT          54
GCT CAG AGA GTT AGC GAG CAA GCA GCT AAG GTA CTT GCA GAG CAC CTT GAG GAA         108
AAA GCT ATT GAG GCC ATC GCA AAA AAG GCA GTA GAT CTT GCA AAG CAC GCA GGT AGA     162
AAG ACC GTT AAG GTC GAA GAC ATT AAG CTC GCA ATT AAG AGC TGA
```

Figure 17L

KOD DNA POLYMERASE – (HMf-like) fusion protein

Nucleotide sequence (SEQ ID NO: 33)  // Nucleotide sequence (SEQ ID NO: 63)
Nucleotide sequence (SEQ ID NO: 34)  // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG    60
AAGGAAAACG GCGAGTTTAA GATTGAGTAC GACCGGACTT TTGAACCCTA CTTCTACGCC   120
CTCCTGAAGG ACGATTCTGC CATTGAGGAA GTCAAGAAGA TAACCGCCGA GAGGCACGGG   180
ACGGTTGTAA CGGTTAAGCG GGTTGAAAAG AGTTCCTCGG GAGACCAGTT               240
GAGGTCTGGA AACTCTACTT TACTCATCCG CAGGACXXXC CAGCGATAAG GGACAAGATA   300
CGAGAGCATC CAGCAGTTAT TGACATCTAC GAGTACGACA TACCCTTCGC CAAGCGCTAC   360
CTCATAGACA AGGGATTAGT GCCAATGGAA GGCGACGAGG AGCTGAAAAT GCTCGCCTTC   420
GACATTGAAA CTCTCTACCA TGAGGGCGAG GAGTTCGCCG AGGGGCCAAT CCTTATGATA   480
AGTACGCCCG ACGAGGAAGG GGCCAGGGTG ATAACTTGGA AGAACGTGGA TCTCCCCTAC   540
GTTGACGTCG TCTCGACGGA GAGGGAGATG ATAAAGCGCT TCCTCCGTGT TGTGAAGGAG   600
AAAGACCCGG ACGTTCTCAT AACCTACAAC GGCGACAACT TCGACTTCGC CTATCTGAAA   660
AAGCGCTGTG AAAAGCTCGG AATAAACTTC GCCCTCGGAA GGGATGGAAG CGAGCCGAAG   720
ATTCAGAGGA TGGGCGACAG GTTTGCCGTC GAAGTGAAGG GACGGATACA CTTCGATCTC   780
TATCCTGTGA TAAGACGGAC GATAAACCTG CCCACATACA CGCTTGAGGC CGTTTATGAA   840
GCCGTCTTCG GTCAGCCGAA GGAGAAGGTT TACGCTGAGG AATAACCAC AGCCTGGGAA   900
ACCGGCGAGA ACCTTGAGAG AGTCGCCCGC TACTCGATGG AAGATGCGAA GGTCACATAC   960
GAGCTTGGGA AGGAGTTCCT TCCGATGGAG TCCCAGCTTT CTCGCTTAAT CGGCCAGTCC  1020
CTCTGGGACG TCTCCCGCTC CAGCACTGGC AACCTCGTTG AGTGGTTCCT CCTCAGGAAG  1080
GCCTATGAGA GGAATGAGCT GGCCCCCGAAC AAGCCCGATG AAAAGGAGCT GGCCAGAAGA  1140
CGGCAGAGCT ATGAAGGAGG CTATGTAAAA GAGCCCGAGA AAGGGTTGTG GGAGAACATA  1200
GTGTACCTAG ATTTTAGATC CCTGTACCCC TCAATCATCA TCACCCACAA CGTCTCGCCG  1260
GATACGCTCA ACAGAAAGG ATGCAAGGAA TATGACGTTG CCCCACAGGT CGGCCACCGC  1320
TTCTGCAAGG ACTTCCCAGG ATTTATCCCG AGCCTGCTTG GAGACCTTCT AGAGGAGAGG  1380
CAGAAGATAA AGAAGAAGAT GAAGGCCACG ATTGACCCGA TCGAGAGGAA GCTCCTCGAT  1440
TACAGGCAGA GGGCCATCAA GATCCTGGCA AACAGCTACT ACGGTTACTA CGGCTATGCA  1500
AGGGCGCGCT GGTACTGCAA GGAGTGTGCA GAGAGCGTAA CGGCCTGGGG AAGGGAGTAC  1560
ATAACGATGA CCATCAAGGA GATAGAGGAA AAGTACGGCT TTAAGGTAAT CTACAGCGAC  1620
ACCGACGGAT TTTTTGCCAC AATACCTGGA GCCGATGCTG AAACCGTCAA AAAGAAGGCT  1680
```

FIGURE 17L (CONT.)

```
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT CGAGGTTCT TGAAGCTTTG CTAAAGACG GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGATA GGGCACGGG CGATACCGTT CGACGAGTTC 2160
GACCCGACGA AGCACAAGTA CGACGCCGAG TACTACATTG AGAACCAGGT TCTCCAGCC 2220
GTTGAGAGAA TTCTGAGAGC CTTCGGTTAC CGCAAGGAAG ACCTGCGCTA CCAGAGACG 2280
AGACAGGTTG GTTTGAGTGC TTGGCTGAAG CCGAAGGGAA CT 2325
//

ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC TGA
//
```

Figure 17M

(HMf-like) – KOD DNA POLYMERASE fusion protein

Nucleotide sequence (SEQ ID NO: 63) // Nucleotide sequence (SEQ ID NO: 33)
Nucleotide sequence (SEQ ID NO: 63) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //

ATGATCCTCG ACACTGACTA CATAACCGAG GATGGAAAGC CTGTCATAAG AATTTTCAAG      60
AAGGAAAACG GCGAGTTTAA GATTGAGTAC GACCGGACTT TTGAACCCTA CTTCTACGCC     120
CTCCTGAAGG ACGATTCTGC CATTGAGGAA GTCAAGAAGA TAACCGCCGA GAGGCACGGG     180
ACGGTTGTAA CGGTTAAGCG GGTTGAAAAG GTTCAGAAGA AGTTCCTCGG GAGACCAGTT     240
GAGGTCTGGA AACTCTACTT TACTCATCCG CAGGACXXXC CAGCGATAAG GGACAAGATA     300
CGAGAGCATC CAGCAGTTAT TGACATCTAC CAGTACGACA TACCCTTCGC CAAGCGCTAC     360
CTCATAGACA AGGGATTAGT GCCAATGGAA GGCGACGAGG AGCTGAAAAT GCTCGCCTTC     420
```

FIGURE 17M (CONT.)

```
GACATTGAAA CTCTCTTACCA TGAGGGCGAG GAGTTCGGCCG AGGGGCCAAT CCTTATGATA 480
AGTTACGCCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGAGCT GGCCAGAAGA 1140
CGGCGAGAGCT ATGAAGGAGG CTATGTAAAA GAGCCCGAGA GAGGTTGTG GGAGAACATA 1200
GTGTACTTAG ATTTTAGATC CCTGTACCCC TCAATCATCA TCACCCACA CGTCTCGCCG 1260
GATAACGCTCA ACAGAGAAGG ATGCAAGGAA TATGACGTTG CCCACAGTT CGGCCACCGC 1320
TTCTGCAAGG ACTTCCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCCGCGT GGTACTGCAA GGAGTGTGCA GAGAGCGTAA CGGCCTGGGG AAGGAGTAC 1560
ATAACGATGA CCATCAAGGA GATAGAGGAA AGTACGGCT TTAAGGTAAT CTACAGCGAC 1620
ACCGACGGAT TTTTGCCCAC AATACCTGGA GCCGATGCTG AACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GCAAGATAA CAACGCGCGG ACTTGAGATT GTGAGGCGTG ACTGGAGCGA GATAGCGAAA 1860
GAGAGCAGG CGAGGGTTCT TGAAGCTTTTG CTAAAGGACG GTGACGTCGA GAAGGCCGTG 1920
AGGATAGTCA AGAAGTTAC CGAAAAGCTG AGCAAGTACG AGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAATAC GCCGGAAC GGTGATAAGC 2100
TACATCGTGC TCAAGGGCTC TGGGAGATA GGGAGCCGAG CGATACCGT CGACGAGTTC 2160
GACCCGACGA AGCACAAGTA CGACGCCGAG TACTACATTG AGAACCAGT TCTCCCAGCC 2220
GTTGAGAGAA TTCTGAGAGC CTTCGGTTAC GCAAGGAAG ACCTGCCTA CCAAGAAGACG 2280
AGACAGGTTG GTTTGAGTGC TTGGCTGAAG CCGAAGGGAA CT //TAG 2325
```

Figure 17N (HMf-like)-Vent DNA POLYMERASE FUSION PROTEIN

Nucleotide sequence (SEQ ID NO: 63)  // Nucleotide sequence (SEQ ID NO: 35)
Nucleotide sequence (SEQ ID NO: 63)  // Nucleotide sequence (SEQ ID NO: 36)

FIGURE 17N (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT      54
GCT CAG AGA GTT AGC GAG CAA GCA GCT AAG GTA CTT GCA GAG CAC CTT GAG GAA     108
AAA GCT ATT GAG GCT GCA AAA AAG GCA GTA GAT CTT GCA GAG CAC CAC GGT AGA    162
AAG ACC GTT AAG GTC GAA GAC ATT AAG CTC GCA ATT AAG AGC //

ATGATACTGG ACACTGATTA CATAACAAAA GATGGCAAGC CTATAATCCG AATTTTTAAAG    60
AAAGAGAACG GGGAGTTTAA AATAGAACTT GACCCTCATT TTCAGCCCTA TATATATGCT   120
CTTCTCAAAG ATGACTCCGC TATTGAGGAG ATAAAGGCAA TAAAGGGCGA GAGACATGGA   180
AAAACTGTGA GAGTGCTCGA TGCAGTGAAA GTCAGGAAAA AATTTTTGGG AAGGAAGTT    240
GAAGTCTGGA AGCTCATTTT CGAGCATCCC CAAGACXXXC CAGCTATGCG GGGCAAAATA   300
AGGGAACATC CAGCTGTGGT TGACATTTAC TACCCTTTGC AAGCTTAAGCT CCTTGCCTTT   360
CTCATAGACA AGGGCTTGAT TCCCATGGAG GGAGACGAGG AGCTTAAGCT AATAATGATT   420
GATATTGAAA CGTTTTATCA TGAGGGAGAT GAATTTGGAA AGGGCGAGAT TTTGCCGTAT   480
AGTTATGCCG ATGAAGAAGA GGCCAGAGTA ATCACATGGA AAAATATCGA TTTGTTAAAGAA 540
GTCGATGTTG TGTCCAATGA AAGAGAAATG ATAAAGCGTT TTGTTCAAGT TGTTAAAGAA   600
AAAGACCCCG ATGTGATAAT AACTTACAAT GGGGACAATT TTGATTTGCC GTATCTCATA   660
AAACGGGCAG AAAAGTCGG AGTTCGGCTT GTCTTAGGAA GGGACAAAGA ACATCCCGAA   720
CCCAAGATTC AGAGGATGGG TGATAGTTTT GCTGTGAAA TCAAGGGTAG AATCCACTTT   780
GATCTTTTCC CAGTTGTGCG AAGGACGATA AACCCTCCAA CGTATACGCT TGAGGCAGTT   840
TATGAAGCAG TTTTAGGAAA ACCAAAAGC AAATTAGGAG GCCCAGTACT CAATGAAGA   900
TGGGAAACAG AAGAAAGCAT GAAAAAAACTA ATTCTTCCCC ATGGAAGCTG AGCTGGCAAA   960
ACGTATGAGC TCGGGAAGGA CGACGTCTC GAGATCAAGC ACCGGCACC TCGTGGAGTG GCTGATAGGT 1020
CAAAGTGTAT GGGACGTCTC GAGATCAAGC ACCGGCACC TCGTGGAGTG GCTGATAGGT 1020
AGGGTGGCAT ACGCGAGGAA TGAACTTGCA CCGAACAAAC CTGATGAGGA AGAGTATAAA 1080
CGGCGCTTAA GAACAACTTA CCTGGAGGA TATGTAAAAG AGCCAGAAAG AGTTTTGTGG 1140
GAAAATATCA TTTATTTGGA TTTCCGCAGT CTGTACCCTT CAATAATAGT TACTCACAAC 1200
GTATCCCCAG ATACCCTTGA AAAAGAGGGC TGTAAGAATT ACGATGTTGC TCCGATAGTA 1260
GGATATAGGT TCTGCAAGGA CTTTCCGGGC TTTATTCCCT CCATACTCGG GGACTTAATT 1320
GCAATGAGGC AAGATATAAA GAAGAAATAG AAATCCACAA TTGACCCGAT CGAAAAGAAA 1380
ATGCTCGATT ATAGGCAAAG GGCTATTAAA TTGCTTGCAA ACAGCTATTA CGGCTATATG 1440
GGGTATCCTA AGCCAAGATG GTACTCGAAG GAATGTCTG AAAGCGTTAC GCCATGGGGG 1500
AGACACTACA TAGAGATGAC GATAAGAGAA ATAGAGGAAA AGTTCGGCTT TAAGGTTCTT 1560
TATGCGGACA CTGACGGCTT TTATGCCACA AAAAGCCTGA ACTCATTAAA 1620
AAGAAGCCA AGGAATTCCT AAACTACATA AACTCCGGGG TTCCAGGTCT GCTTGAGCTT 1680
GAGTATGAGG GCTTTACTT GAGAGGATTC TTTGTTACAA AAAAGGCTA TGCAGTCATA 1740
GATGAAGAGG GCAGGATAAC AACAAGGGGC TTGAAGTAG TAAGGAGAGA TTGGAGTGAG 1800
                                                                      1860
```

FIGURE 17N (CONT.)

```
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GCAGATTACC AGGGATTTAA AGGACTACAA GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGATACA GAAAGGAGGA TTTAAGGTAT 2280
CAAAGCTCAA AACAAACCGG CTTAGATGCA TGGCTCAAGA GGTAG 2325
```

Figure 17O

Vent DNA POLYMERASE - (HMf-like) FUSION PROTEIN

Nucleotide sequence (SEQ ID NO: 35)    // Nucleotide sequence (SEQ ID NO: 63)
Nucleotide sequence (SEQ ID NO: 36)    // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGAAGTT 240
GAAGTCTGAA AGCTCATTTT CGAGCATCCC CAAGACXXXC CAGCTATGCG GGGCAAAATA 300
AGGGAACATC CAGCTGTGGT TGACATTTAC TGACTTTGGC TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG AAGAGAAATG TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG ACATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GAATTCTCCC CAATGGAAGA TGCTAGGGCA 960
ACGTATGAGC TCGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGAGTG GTATCTTTTA 1080
AGGGTGGCAT ACGCGAGGAA TGAACTTGCA CCGAACAAAC CTGATGAGGA AGAGTATAAA 1140
CGGCGCCTTAA GAACAACTTA CCTGGGAGGA TATGTAAAAG AGCCAGAAAA AGGTTTGTGG 1200
```

FIGURE 17O (CONT.)

```
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGATTTC TTTGTTACAA AAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTGTA AGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAGTGAA ACCGGGCACA 2100
ATAATAAGCT ATATCGTTCT CAAAGGAGAC GGAAAGATAA GCGATAGGGT ACTACATAGA 2160
ACAGAATACG ATCCTAGAAA ACACAAGTAC GATCCGGACT GAAAGGAGGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //
```

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA  162
AAG ACC GTT AAG GTC GAA GAC ATT AAG CTC GCA ATT AAG AGC TGA
```

Figure 17P

Deep Vent- (HMf-like) DNA polymerase fusion protein

Nucleotide sequence (SEQ ID NO: 37)    // Nucleotide sequence (SEQ ID NO: 63)
Nucleotide sequence (SEQ ID NO: 38)    // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
AAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG AGTTCCTGGG GAGGCCGATT GAGGCCGATT   240
GAGGTATGGA GGCTGTACTT TGAACACCCT CAGGACXXXC CCGAATAAAG GGATAAGATA   300
AGAGAGCATT CCGCAGTTAT TGACATCTTT GAGTACGACA TTCCGTTCGC GAAGAGGTAC   360
```

FIGURE 17P (CONT.)

```
CTAATAGACA AAGGCCTAAT TCCAATGGAA GGCGATGAAG AGCTCAAGTT GCTCGCATTT    420
GACATAGAAA CCCTCTATCA CGAAGGGGAG GAGTTCGCGA AGGGGCCCAT TATAATGATA    480
AGCTATGCTG ATGAGGAAGA AGCCAAAGTC ATAACGTGGA AAAAGATCGA TCTCCCGTAC    540
GTCGAGGTAG TTTCCAGCGA GAGGGAGATG ATAAAGCGGT TCCTCAAGGT GATAAGGGAG    600
AAAGATCCCG ATGTTATAAT TACCTACAAC GGCGATTCTT TCGACCTTCC CTATCTAGTT    660
AAGAGGGCCG AAAAGCTCGG GATAAAGCTA CCCCTGGGAA GGGACGGTAG TGAGCCAAAG    720
ATGCAGAGGC TTGGGATAT GACAGCGGTG GAGATAAAGG GAAGGATACA CTTTGACCTC    780
TACCACGTGA TTAGGAGAAC GATAAACCTC CCAACATACA CCCTCGAGGC AGTTTATGAG    840
GCAATCTTCG GAAAGCCAAA GGAGAAAGTT TACGCTCACG AGATAGCTGA GGCCTGGGAG    900
ACTGGAAAGG GACTGGAGAG AGTTGCAAAG TATTCAATGG AGATGCAAAA GGTAACGTAC    960
GAGCTCGGTA GGGAGTTCTT CCCAATGGAG GCCCAGCTTT CAAGGTTAGT CGGCCAGCCC   1020
CTGTGGGATG TTTCTAGGTC TTCAACTGGC AACTTGGTGG AGTGGTACCT CCTCAGGAAG   1080
GCCTACGAGA GGAATGAATT GGCTCCAAAC AAGCCGGATG AAGGGAAGTA CGAGAGAAGG   1140
CTAAGGGAGA GCTACGCTGG GGGATACGTT AAGGAGCCGG AGAAAGGGCT CTGGGAGGGG   1200
TTAGTTTCCC TAGATTTCAG GAGCCTGTAC CCCTCGATAA TAATCACCCA TAACGTCTCA   1260
CCGGATACGC TGAACAGGGA AGGGTGTAGG GAATACGATG TCGCCCCAGA GGTTGGGCAC   1320
AAGTTCTGCA AGGACTTCCC GGGGTTTATC CCCAGCCTGC TCAAGAGGTT ATTGGATGAA   1380
AGGCAAGAAA TAAAAGGAA GATGAAAGCT TCTAAAGACC CAATCGAGAA GAAGATGCTT   1440
GATTACAGGC AACGGGCAAT CAAAATCCTG GCAAACAGCT ATTATGGGTA TTATGGGTAC   1500
GCAAAAGCCC GTTGGTACTG TAAGGAGTGC GCAGAGAGCG TTACGGCCTG GGGGAGGAA   1560
TATATAGAGT TCGTAAGGAA GGAACTGGAG GAAAAGTTCG GGTTCAAAGT CTTATACATA   1620
GACACAGATG GACTCTACGC CACAATTCCT GGGGCAAAAC CCGAGGAGAT AAAGAAGAAA   1680
GCCCTAGAGT TCGTAGATTA TATAAACGCC AAGCTCCCAG GGCTGTTGGA GCTTGAGTAC   1740
GAGGGCTTCT ACGTGAGAGG GTTCTTCGTG ACGAAGAAGA AGTATGCGTT GATAGATGAG   1800
GAAGGAAGA TAATCACTAG GGGGCTTGAA ATAGTCAGGA GGGACTGGAG CGAAATAGCC   1860
AAAGAAACCC AAGCAAAAGT CCTAGAGGCT ATCCTAAAGC ATGGCAACGT TCCAGAAAAG   1920
GTAAAGATAG TTAAGGAGGT AACTGAAAAG CTGACCAAGT CTTCACGAGT ACAAGGCTAT   1980
CTAGTTATTT ACGAGCAGAT CACGAGGCCC CTTCACGAGT ACAAGGCTAT AGTCCGCAC   2040
GTTGCCGTGG CAAAAAGGTT AGCCGCTAGA GGAGTAAAGG TGAGGCCTGG CATGGTGATA   2100
GGGTACACTG TGCTGAGGGG GGATGGCCA ATAAGCAAGA GGGCTATCCT TGCAGAGGAG   2160
TTCGATCTCA GGAAGCATAA GTATGACGGT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAG //                2328
```

```
ATG ATG GGA GAA TTA CCA ATT GCC CCA GTT GAC AGA CTT ATA AGA AAG GCT GGT         54
GCT CAG AGA GTT AGC GAG CAA GCA GCT AAG GTA CTT GCA GAG CAC CTT GAG GAA        108
AAA GCT ATT GAG GTC GCA AAA AAG GCA GTA GAT CTT GCA AAG CAC AAG GCA AGA        162
AAG ACC GTT AAG GTT GAA GAC GTC GAA GCA ATT AAG CTC GCA ATT AAG AGC TGA
```

FIGURE 17Q

(HMflike) - Deep Vent DNA polymerase fusion protein

Nucleotide sequence (SEQ ID NO: 63)    // Nucleotide sequence (SEQ ID NO: 37)
Nucleotide sequence (SEQ ID NO: 63)    // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT      54
GCT CAG AGA GTT AGC GAG CAA GCA GCT AAG GTA CTT GCA GAG CAC CTT GAG GAA     108
AAA GCT ATT GAG GCA ATC GCA AAA AAG GCA GTA GAT CTT GCA AAG CAC GCA GGT AGA 162
AAG ACC GTT AAG GTC GAA GAC GTC GCA ATT AAG CTC GCA ATT AAG AGC TGA

ATGATACTTG ACGCTGACTA CATCACCGAG GATGGGAAGC CGATTATAAG GATTTTCAAG      60
AAAGAAAACG GCGAGTTTAA GGTTGAGTAC GACAGAAACT TTAGACCTTA CATTTACGCT     120
CTCCTCAAAG ATGACTCGCA GATTGATGAG GTTAGGAAGA TAACCGCCGA GAGGCATGGG     180
AAGATAGTGA GAATTATAGA TGCCGAAAAG GTAAGGAAGA AGTTCCTGGG GAGGCCGATT     240
GAGGTATGGA GGCTGTACTT TGAACACCCT CAGGACXXXC CCGCAATAAG GGATAAGATA     300
AGAGAGCATT CCGCAGTTAT TGACATCTTT GAGTACAAG TTCCGTTCGC GAAGAGGTAC     360
CTAATAGACA AAGGCCTAAT TCCAATGGAA GGCGATGAAG AGCTCAAGTT GCTCGCATTT     420
GACATAGAAA CCCTCTATCA CGAAGGGGAG GAGTTCGCGA AGGGCCCAT TATAATGATA     480
AGCTATGCTG ATGAGGAAGA AGCCAAAGTC ATAACGTGGA AAAAGATCGA TCTCCCGTAC     540
GTCGAGGTAG TTTCCAGCGA GAGGGAGATG ATAAAGCGGT TCCTCAAGGT GATAAGGGAG     600
AAAGATCCCG ATGTTATAAT TACCTACAAC GGCGATTCTT TCGACCTTCC CTATCTAGTT     660
AAGAGGGCCG AAAAGCTCGG GATAAAGCTA CCCCTGGGAA GGGACGGTAG TGAGCCAAAG     720
ATGCAGAGGC TTGGGGATAT GACAGCGGTG GAGGATACA CTTTGACCTC                780
TACCACGTGA TTAGGAGAAC GATAAACCTC CCAACATACA CCCTCGAGGC AGTTTATGAG     840
GCAATCTTCG GAAAGCCAAA GGAGAAAGTT TACGCTCACG AGATAGCTGA GGCCTGGGAG     900
ACTGGAAAGG GACTGGAGAG AGTTGCAAAG TATTCAATGG AGGATGCAAA GGTAACGTAC     960
GAGCTCGGTA GGGAGTTCTT CCCAATGGAG GCCCAGCTTT CAAGGTTAGT CGGCCAGCCC    1020
CTGTGGGATG TTTCTAGGTC TTCAACTGGC AACTTGGTGG AGTGGTACCT CCTCAGGAAG    1080
GCCTACGAGA GGAATGAATT GGCTCCAAAC AAGCCGGATG AGAGGAGTA CGAGAGAAGG    1140
CTAAGGGAGA GCTACGCTGG GGGATACGTT AAGGAGCCGG AGAAAGGGCT CTGGGAGGGG    1200
TTAGTTTCCC TAGATTTCAG GAGCCTGTAC CCCTCGATAA TAATCACCCA TAACGTCTCA    1260
CCGGATACGC TGAACAGGGA AGGGTGTAGG GAATACGATG TCGCCCCAGA GGTTGGGCAC    1320
AAGTTCTGCA AGGACTTCCC GGGGTTTATC CCAAGCCTGC TCAAGAGGTT ATTGGATGAA    1380
AGGCAAGAGA TAAAAGGAA GATGAAAGCT TCTAAAGACC GCAAACAGCT CAATCGAGAA    1440
GATTACAGGC AACGGGCAAT CAAAATCCTG GCAAACAGCT ATTATGGGTA TTATGGTTAC    1500
GCAAAAGCCC GTTGGTACTG TAAGGAGTGC GCAGAGAGCG TTACGGCCTG GGGGAGGGAA    1560
```

FIGURE 17Q (CONT.)

```
TATATAGAGT TCGTAAGGAA GGAACTGGAG GAAAAGTTCG GGTTCAAAGT CTTATACATA    1620
GACACAGATG GACTCTACGC CACAATTCCT GGGCAAAAC  CCGAGGAGAT AAAGAAGAAA    1680
GCCCTAGAGT TCGTAGATTA TATAAACGCC AAGCTCCCAG GGCTGTTGGA GCTTGAGTAC    1740
GAGGGCTTCT ACGTGAGAGG GTTCTTCGTG ACGAAGAAGA AGTATGCGTT GATAGATGAG    1800
AAGGGAAGA  TAATCACTAG GGGGCTTGAA ATAGTCAGGA GGGACTGGAG CGAAATAGCC    1860
AAAGAAACCC AAGCAAAAGT CCTAGAGGCT ATCCTAAAGC ATGGCAACGT TGAGGAGGCA    1920
GTAAAGATAG TTAAGGAGGT ACTGAAAAG  CTGAGCAAGT ACGAAATACC TCCAGAAAAG    1980
CTAGTTATTT ACGAGCAGAT CACGAGGCCC CTTCACGAGT ACAAGGCTAT AGGTCCGCAC    2040
GTTGCCGTGG CAAAAAGGTT AGCCGCTAGA GGAGTAAAGG TGAGGCCTGG CATGGTGATA    2100
GGGTACATAG TGCTGAGGGG AGCGGGCCA  ATAAGCAAGA GGGCTATCCT TGCAGAGGAG    2160
TTCGATCTCA GGAAGCATAA GTATGACGCT GAGTATTACA TAGAAAATCA GGTTTTACCT    2220
GCCGTTCTTA GAATATTAGA GGCCTTTGGG TACAGGAAAG AAGACCTCAG GTGGCAGAAG    2280
ACTAAACAGA CAGGTCTTAC GGCATGGCTT AACATCAAGA AGAAG TAA                2328
```

Figure 17R

JDF-3 – (HMf-like) fusion protein

Nucleotide sequence (SEQ ID NO: 39)  // Nucleotide sequence (SEQ ID NO: 63)
Nucleotide sequence (SEQ ID NO: 40)  // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTTGACGTTGATTACATCACCGAGAATGAAAGCCCGTCATCAGGGTCTTCAAGGGAGAGTCTTCAAGAAGGAGAACGGCGAGTTCGAGCCCTACTTCT
ACGGCGTCCTCAGGGACGACTCTGCCATCGAACGACTCTGAAGAAATCAAAAGATAACCGCGGAGAGCACGCAGGGTCGTTAAGGTTAAGCGCGGAGAAGTTCTCGG
CAGGTCGTGAGGTCGAGTTCTGGGCTCCTCATTCACCCGGACAAAATAAGGAGCACAAACTACGAGTACGACATACCC
TTCGCCAAGCGCTACCTCATAGACAAGGGCTTAAGTGAGGAAGCGGCGTCGATAAGCAGAGCTTAAACTCATGTCCTTCGACATCGAGCTCTACCGAGGGAGAAGAGTTGAA
CCGGGCCGATTCTGATGATAAGCTACGCCGCCATGAAAGCGAGGCCGGTGATAACATACAACGGCAACAACTTCGACTTCGCCTACCTTGAGGTGAAAAAGGCTGTGAGGGACAGGTTTGCG
GCGCTTCTTGAGGGTCGTTAAGGAGGACGGACGAGCGGGAGCGAGACGGAGGAGCAGGACTGTTTGGCAAGCCCAAGGAGAGTTCTTCCGAGGTCTTCCGATGGAGGAAGGATAGCCACAGGCTTTCCAGGCCCAACAAGGAACTCGCGTCGTAGTCTCGTAGTCTCTCCCGGCTTCATTCCGAGCTTCAAGGACTTACAGGCACGGCAATATCCTCCAAGGTTCATCGCGCCGGAGACTTCGAGAAGCAACGAACTCGCTCGTAGTCTCGTACCTTCGGCTTAGCCCTTCCGTTCAATTACGGATCG
GGTCGCGCGCTACTCGATGAGGAGCGGAGTTGGTCGTCGAGGCGGAGTACGACGTTGCCCCGAGGTGCCCCCGAGTTGCCCCCGAGTTGCCCCCGAGTTGCCCGGCTTGCCCGAGCGCGAGAGCCGGCGAGAGCGGAGAGCCCAAAGGCCTCCGAGGAGAAGGGGGGCT
ACgCGGTGGCTACGTCAAGGAGCGAGCGCGTCCAAGAGCTACGACGTTGCCCCGAGGTGCCCCCGAGTTGCCCCCGAGTTGCCCCCGAGTTGCCCCCGAGTTGCCCCCGAGTTGCCCCAATCATAATCACCCACAACGTCTCGCCAGATAC
GCTCAACCGGCTGAGGGGTAGGAGCGCTACGCACGTTGGTCGAGAAGAATCTCCTCGAGAAGATTCCAAGCTACGAGCTACGGCTACGGCTACGCCTACGCCCGCTTAAAGCTCC
CAGAAGATAAAGAAGAAGATGAAGGCAACTCTGCCGCAGGAGCGCTACGGAGCGTTACGGCAGCTTAACGACGAGAAAAGCAATGAGTTCTTAAACATTATCATCCAATCTCCAAACTGCCCCGGCCTTCTC
ATGCCAGGCAAGATGGTACTGCAGGAGCGTCCATGCCCATTCCTGCCTGAGGCGACGTTCGAGGCGACGTTACGCATGGGAAGAGCGTTACGCATGGGAAGAGCGTTACGCATGGGAAGAGCGTTACGAGAAAAAGCAATGAGTTCTTAAACATTATCATCCAAACTGCCCCGGCCTTCTC
CTATGCAGACACGAGCTCCATGCCAATTCCTGAGCGACGTCAAGAAAAGCAATGAGTCCTTAAACATTATCATCCAAACTGCCCCGGCCTTCTC
GAACTCGAATACGAGGGCTTCAGGGCGTCAGGGGCGACGAAGAAAAAAGTACGCGGTCATCGACGAGGAGGCAAGATAACCACGGCGTCCCGGCTTGAGATAGTCAGGCGCG
```

FIGURE 17R (CONT.)

ACTGGAGCGAGATAGCGAAGGAGACGCAGGCGAGGGTTTTGGAGGCACGGTGACTTCAGGCACGGTGAAGAGGCCGTCAGAATTGTCAGGGAAGTCACCGAAAAGCTGAGCAA
GTACGAGGTTCCGCCGGAGAAGCTGGTTATCCACGAGGAACTGTGATAAGCTACATCGTTCTGAAGGGCTCCGAAGGACTACAAGGCGAGCTTCAAGGCCACCGGCCAGAGGT
GTTAAATCCGGCCCGGAACCCGGAACTGTGATAAGCTACATCGTTCTGAAGGGCTCCGAAGGAGATAGGCGACAGGGCGATTCCTTCGACGAGTTCGACGAAGCACAAGTACGATG
CGGACTACTACATCGAGAACCAGGTTCGTGCCGGCAGTTGAGAGAATCCTTCGGGCCTTCGCCAAGGAAGAACTGCGCCTACCAGAGAGACGAGGCAGGTCGGGCTTGGCGC
GTGGCTGAAGCCGAAGGGGAAGAAGAAG//

ATG GGA GAA TTA CCA ATT GCC CCA GTT GAC AGA CTT ATA AGA AAG GCT GGT     54
GCT CAG AGA GTT GAG AGC GCA GCA AAA AAG GCA GTA CTT GCA GAG CAC CTT GAG GAA     108
AAA GCT ATT GAG ATC GCA AAA AAG GCA GTA GAT CTT GCA GCA CAC CAC GCA GGT AGA     162
AAG ACC GTT AAG GTC GAA GAC ATT AAG CTC GCA ATT AAG AGC TGA

Figure 17S (HMf-like) - JDP-3 fusion protein

Nucleotide sequence (SEQ ID NO: 63)   // Nucleotide sequence (SEQ ID NO: 39)
Nucleotide sequence (SEQ ID NO: 63)   // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATG ATG GGA GAA TTA CCA ATT GCC CCA GTT GAC AGA CTT ATA AGA AAG GCT GGT     54
GCT CAG AGA GTT GAG AGC GCA GCA AAA AAG GCA GTA CTT GCA GAG CAC CTT GAG GAA     108
AAA GCT ATT GAG ATC GCA AAA AAG GCA GTA GAT CTT GCA GCA CAC CAC GCA GGT AGA     162
AAG ACC GTT AAG GTC GAA GAC ATT AAG CTC GCA ATT AAG AGC //

ATGGATCCTTGACGTTGATTACATCACCGAGAATGGAAAGCCCGTCATCAGGGTCTTCAAGAAGGAGAACGGCGAGTTCAGGATTGAATACGACCGGAGTTCGAGCC
CTACTTCTACGCGTTCCTCAGGGACGACTCTGCCATGCAGTTCTGGAGTCTGTGAGGTCGCCATCAAAAGATAACCGCGAGGACGCACGGCAGGGTCGTTAAGGTTAAGCGCCGGAGAAGGTGA
AGAAAAGTTCCTGGCCAGGTCCAGGTCTGTGAGGTCGACATCCGGCAATCCGGACAAATAAGGAAGCACCCGGGTCATC
GACATCTACGAGTACGACATACCCTTCGCCAAGCGCTAACCGGCCTAATCCCGATGGAAGGTGAGGAAGAGCGCCGCTAATCCCGATGAAGCTACGCCGATGAATAAGCTACGCGATGATAAGCTCGTGGGAGTCGTTAAGGGTCGTTAAGGGTCGTTAACCAGCCTGGGATCGAGAATAACATACAACGGCACAGTTCTCGGT
CTTACGTTGAGTTGTCTCCACCGAGGAAGAGATGATTAAGCGCTTGGCGTGACCTGTGACCTTCGACCCTTATCCAGTCATAAGGCGCACCCAGTGTATACGAGGCGGTTTCGGCAAGC
GACTTCGACCTACCGGTGAAGGCGCTGTGACCTTGACCCTTATCCAGTCATAAGGCGCACAGTAGTTTATCCAGTCATAAGGCGCACAGTGTATACGAGGCGGTTTCGGCAAGC
CGAGGTGAAGGGCAGGTGACACTTCGACCGAGGATACAGCCCCAGTTCGAGAGGACCCGGTGCGCGTACTCCAGCACCGGACACGTTCCCGCTACTCAGAGG
CCAAGGAGAAGGTCTACGCCGAGGAGTACACTTCGACCGAGGATACAGCCCCAGTTCTCCAAGGCTCATCGCCAAGCCTGCTCCAAGCCCGACGAGGAGAAGGGGACGTGGCGAGGTCAAGGGTCTCCT
CTTTGGCAGCGCGGAGTTCTTCCCCGATGGAGGCCGACGAACGAACCTCGTCGCCTTTCAGATCTGTAGTTCGTAGTTCGTAGTCTCTACCCTCAATCATAATCACCCACAACGTCTCGCCAGATACGCTCAACCGCGAGGGGTGT
CCTAAGGAAGGCTACGGGGACAATATCGTGTATCTAGACTTTCGTAGTCTCTACCCTCAATCATAATCACCCACAACGTCTCGCCAGATACGCTCAACCGCGAGGGGTGT
AGCGGGGACTACGACGTTGCCCCGAGGTCGGTCACAAGTTCTGCAAGGACTTCATTCCGAAACCTGCTCGGAGGAAGGCAGAAGATAAA

FIGURE 17S (CONT.)

```
GAGGAAGATGAAGGCAACTCTCGACCCGCTGGAGAAGAATCTCCTCGATTACAGGCAACGCGCCATCAAGATTCTCGCCAACAGTACTACGGCTACTACGGCTATG
CCAGGGCAAGATGGTACTGCAGGGAGTGCGCCGAGAGCGTTACGGCATGGGAAGGGAGTACATCGAAATGGTCATCAGAGAGCTTGAGGAAAAGTTCGGTTTTAAA
GTCCTCTATGCAGACACAGACGGTCTCCATGCCACCATTCCTGAGCGGACGCTGAAACAGTCAATGGAGTTCTTAAACTATATCAATCCCAAACT
GCCCGGCCTTCTCGAACTCGAATACGAGGGCTTCTACGTCACGAGGGCTTCTTCGTCACGAAGAAAAGTACGCGGTCATCGACGAGGAGGCAAGATAACCACGCG
GGCTTGAGATAGTCAGGCGCGACTGAGCGAGTAGCCAGGCGAGATACGAGGTTTTGGAGGCACGTCAGGCACGTGACGTTGAAGAGGCCGTCAGAATT
GTCAGGGAAGTCACCGAAAAGCTGAGCAAGTAGAGGTTCCGCCGAGAGTTAAAAGCGCGAGCTCAAGACTACAAGGCCACCGGCC
GCACGTAGCCATAGCGAAgcGTTTGGCCCGACCCGACAAGCACACAAGTACGAAGAAGCTCCGGAAGGATAGGCACAGG
CGATTCCCTTCGACGAGTTCGACCCGACGAAGCACAAGTACGATGCGGACTACTACATCGAGAACCAGGTTCTGCCGGCAGTTGAGAGAATCCTCAGGGCCTTCGGC
TACCGCAAGGAAGACCTGCGCTACCAGAAGACGAGGCAGGTCGGGCTTGGCGCGTGGCTGA
```

Figure 17T

Pyrococcus furiosus DSM 3638, Archeael hostone (HMf-1) section 85 of 173 of the complete genome.
ACCESSION No: AE010210 REGION: complement (8333..9082)
/product="pcna sliding clamp (proliferating-cell nuclear antigen)"

Nucleotide sequence (SEQ ID NO: 67)
Amino acid sequence (SEQ ID NO: 68)

| | | | | | | | | | | | | | | | | | | | |
|---|---|---|---|---|---|---|---|---|---|---|---|---|---|---|---|---|---|---|---|
| M | P | F | E | I | V | F | E | G | A | K | E | F | A | Q | L | I | D | | 18 |
| ATG | CCA | TTT | GAA | ATC | GTA | TTT | GAA | GGT | GCA | AAA | GAG | TTT | GCC | CAA | CTT | ATA | GAC | | 54 |
| T | A | S | K | L | I | D | E | A | A | F | K | V | T | E | D | G | I | | 36 |
| ACC | GCA | AGT | AAG | TTA | ATA | GAT | GAG | GCC | GCG | TTT | AAA | GTT | ACA | GAA | GAT | GGG | ATA | | 108 |
| S | M | R | A | M | D | P | S | R | V | V | L | I | D | L | N | L | P | | 54 |
| AGC | ATG | AGG | GCC | ATG | GAT | CCA | AGT | AGA | GTT | GTC | ATT | GAC | CTG | AAT | CTC | CCG | | | 162 |
| S | S | I | F | S | K | Y | E | V | E | P | E | T | I | G | V | N | | | 72 |
| TCA | AGC | ATA | TTT | AGC | AAA | TAT | GAA | GTT | GAA | CCA | GAA | ACA | ATT | GGA | GTT | AAC | | | 216 |
| M | D | H | L | K | K | I | K | R | G | K | A | K | D | T | L | I | | | 90 |
| ATG | GAC | CAC | CTA | AAG | AAG | ATC | CTA | AAG | AGA | GGT | AAA | GCA | AAG | GAC | ACC | TTA | ATA | | 270 |
| L | K | G | E | E | E | N | F | L | E | D | V | E | M | E | V | D | L | P | 108 |
| CTC | AAG | GGA | GAG | GAA | GAA | AAC | TTC | TTA | GAG | GAT | GTA | GAA | ATG | GAG | GTT | GAC | CTC | CCA | 324 |
| R | T | F | R | V | P | L | I | I | Q | T | A | T | | | | | | | 126 |
| AGA | ACA | TTT | AGA | GTT | CCC | CTA | ATA | ATA | CAA | GGA | ACT | GCA | ACA | | | | | | 378 |
| E | L | P | F | T | A | K | V | V | L | G | E | V | L | K | D | A | | | 144 |
| GAA | CTT | CCA | TTC | ACT | GCA | AAG | GTT | GTA | CTT | GGA | GAA | GTC | CTA | AAA | GAT | GCT | | | 432 |
| V | K | D | A | S | L | V | S | D | S | I | K | F | I | A | R | E | N | | 162 |

FIGURE 17T (CONT.)

```
GTT AAA GAT GCC TCT CTA GTG AGT GAC AGC ATA AAA TTT ATT GCC AGG GAA AAT       486
 E   F   I   M   K   A   E   G   E   T   Q   E   V   E   I   K   L   T       180
GAA TTT ATA ATG AAG GCA GAG GGA GAA ACC CAG GAA GTT GAG ATA AAG CTA ACT       540
 L   E   D   E   G   L   L   D   I   E   V   Q   E   E   T   K   S   A       198
CTT GAA GAT GAG GGA TTA TTG GAC ATC GAG GTT CAA GAG GAG ACA AAG AGC GCA       594
 Y   G   V   S   Y   L   S   D   M   V   K   G   L   G   K   A   D   E       216
TAT GGA GTC AGC TAT CTC TCC GAC ATG GTT AAA GGA CTT GGA AAG GCC GAT GAA       648
 V   T   I   K   F   G   N   E   M   P   M   Q   M   E   Y   Y   I   R       234
GTT ACA ATA AAG TTT GGA AAT GAA ATG CCC ATG CAA ATG GAG TAT TAC ATT AGA       702
 D   E   G   R   L   T   F   L   A   P   R   V   E   *                       250
GAT GAA GGA AGA GGA AGA CTT ACA TTC CTA CTG GCT CCA AGA GTT GAA GAG TGA       750
```

Figure 17U

(PCNA)-Taq DNA polymerase fusion protein

Nucleotide sequence (SEQ ID NO: 67) // Nucleotide sequence (SEQ ID NO: 65)
Amino acid sequence (SEQ ID NO: 68) // Amino acid sequence (SEQ ID NO: 66)

```
 M   P   F   E   I   V   F   E   G   A   K   E   F   A   Q   L   I   D        18
ATG CCA TTT GAA ATC GTA TTT GAA GGT GCA AAA GAG TTT GCC CAA CTT ATA GAC        54
 T   A   S   K   L   I   D   E   A   A   F   K   V   T   E   D   G   I        36
ACC GCA AGT AAG CTA ATA GAT GAG GCC GCG TTT AAA GTT ACA GAA GAT GGG ATA       108
 S   M   R   A   M   D   P   S   R   V   V   L   I   D   L   N   L   P        54
AGC ATG AGG GCC ATG GAT CCA AGT AGA GTT GTC CTG ATT GAC CTA AAT CTC CCG       162
```

FIGURE 17U (CONT.)

```
     S   S   I   F   S   K   Y   V   V   E   P   E   T   I   G   V   N        72
     TCA AGC ATA TTT AGC AAA TAT GAA GTT GTT GAA CCA GAA ACA ATT GGA GTT AAC  216

M   D   H   L   K   K   I   E   L   K   R   G   K   A   K   D   T   I    90
     ATG GAC CAC CTA AAG AAG ATC CTA AAG AGA GGT AAA GCA AAG GAC ACC TTA ATA  270

L   K   K   G   E   E   N   F   L   E   I   T   I   Q   E   T   A   T   108
     CTC AAG AAA GGA GAG GAA AAC TTC TTA GAG ATA ACA ATT CAA AAG ACT GCA ACA  324

R   T   F   R   V   P   L   I   D   V   E   E   M   E   V   D   L   P   126
     AGA ACA TTT AGA GTT CCC CTA ATA GAT GTA GAA GAG ATG GAA GTT GAC CTC CCA  378

E   L   P   A   T   F   T   A   K   V   V   L   G   E   V   L   K   D   A  144
     GAA CTT CCA ACT GCA TTC ACT GCA AAG GTT GTA CTT GGA GAA GTC CTA AAA GAT GCT  432

V   K   D   A   S   L   V   S   D   S   I   K   F   I   A   R   E   N   162
     GTT AAA GAT GCC TCT CTA GTG AGT GAC AGC ATA AAA TTT ATT GCC AGG GAA AAT  486

E   F   I   M   K   A   E   G   D   E   T   Q   E   E   T   K   L   T   180
     GAA TTT ATA ATG AAG GCA GAG GGA GAC GAA ACC CAG GAG GAG ACA AAG CTA ACT  540

L   E   D   E   L   Y   L   S   D   I   E   V   Q   E   L   G   K   A   S   A  198
     CTT GAA GAT GAG TAT CTC TCC GAC ATC GAG GTT CAA GAG CTT GGA AAG GCC AGC GCA  594

Y   G   V   S   Y   L   F   G   N   E   M   P   M   Q   M   E   Y   Y   D   E   216
     TAT GGA GTC AGC TAT CTC TTT GGA AAT GAA ATG CCC ATG CAA ATG GAG TAT TAC GAT GAA  648

V   T   I   K   F   L   T   F   L   A   P   R   A   P   K   G   R   V   L   L   V  234
     GTT ACA ATA AAG TTT CTA ACA TTC CTA GCT CCA AGA GTT GAA GAG  702
     D   E   G   R   L   T   F   L   A   P   R   A   P   K   G   R   V   L   L   V   250
     GAT GAA GGA AGA AGA CTT ACA TTC CTA GCT CCA AGA GTT GAA GAG

G   G   E
     // GGC GGC GGT
     V   T   S   G   M   L   P   L   F   E   P   K   G   R   V   L   L   V
```

FIGURE 17U (CONT.)

```
    GTC ACT AGT GGG ATG CTG CCC TTT GAG CCC AAG GGC CGG GTC CTC CTG GTG
D   G   H   L   P   V   R   Y   A   T   F   H   A   L   K   G   L   T
GAC GGC CAC CTG CCG GTG TAC CGC ACC TTC CAC GCC CTG AAG GGC CTC ACC ACC

S   R   G   E   A   Q   V   G   Y   V   F   A   K   S   L   K
AGC CGG GGG GAG CCG CAG GTG TAC GGC GTC TTC GCC AAG AGC CTC CTC AAG

A   L   K   E   D   A   Y   D   A   V   I   V   F   D   A   K   A   P
GCC CTC AAG GAG GAC GCC TAC GAC GCG GTC ATC GTG TTT GAC GCC AAG GCC CCC

S   F   R   H   E   A   Y   G   G   Y   K   A   G   L   T   P
TCC TTC CGC CAC GAG GCC TAC GGG GGG TAC AAG GCG GGC CTG ACG CCA

E   D   F   P   R   Q   L   A   L   I   K   E   L   V   D   L   G
GAG GAC TTT CCC CGG CAA CTC GCC CTC ATC AAG GAG CTG GTG GAC CTC GGG

L   A   R   L   E   V   P   G   Y   E   A   D   D   V   L   A   S   L
CTG GCG CGC CTC GAG GTC CCG GGC TAC GAG GCG GAC GTC CTG GCC AGC CTG

A   K   K   A   E   K   E   G   Y   E   V   R   I   L   T   A   D   K
GCC AAG AAG GCG GAA GAG GGC TAC GAG GTC CGC ATC CTC ACC GCC GAC AAA

D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

A   D   Y   R   A   L   T   G   D   E   S   D   N   L   P   G   V   K
GCC GAC TAC CGG GCG GCC CTG ACC GGG GAC GAG TCC GAC AAC CTT CCC GGG GTC AAG

G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

L   L   K   N   L   D   R   L   K   P   A   I   R   E   K   I   L
CTC CTC AAG AAC CTG GAC CGG CTG AAG CCC GCC ATC CGG GAG AAG ATC CTG
```

```
A   E   A   V   F   R   L   A   G   H   P   F   N   L   N
GCC GAG GCC GTC TTC CGC CTG GCC GGC CAC CCC TTC AAC CTC AAC

S   R   D   Q   L   E   R   V   L   F   D   E   L   G   P   A   I
TCC CGG GAC CAG CTG GAA AGG GTC CTC TTT GAC GAG CTA GGG CCC GCC ATC

G   K   T   E   K   T   G   K   R   S   T   A   V   L   E   A
GGG AAG ACG GAG AAG ACC GGC AAG CGC TCC ACC AGC GCC GTC CTG GAG GCC

L   R   E   A   H   P   I   V   E   K   I   L   Q   Y   R   E   T
CTC CGC GAG GCC CAC CCC ATC GTG GAG AAG ATC CTG CAG TAC CGG GAG ACC

K   L   K   S   T   Y   I   D   P   L   P   D   L   I   H   P   T
AAG CTG AAG AGC ACC TAC ATT GAC CCC TTG CCG GAC CTC ATC CAC CCC ACG

G   R   L   H   T   R   F   N   Q   T   A   A   T   R   L   S
GGC CGC CTC CAC ACC CGC TTC AAC CAG ACG GCC GCC ACG AGG CTA AGT

S   D   P   N   I   Q   N   I   P   V   R   T   P   L   G   Q   R
AGC GAT CCC AAC ATC CAG AAC ATC CCC GTC CGC ACC CCG CTT GGG CAG AGG

I   R   R   A   F   I   A   E   E   G   W   L   L   V   A   D   Y
ATC CGC CGG GCC TTC ATC GCC GAG GAG GGG TGG CTA TTG GTG GCC GAC TAT

S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

G   V   P   R   E   A   V   D   P   L   M   R   R   A   A   K   T   I
GGC GTC CCC CGG GAG GCC GTG GAC CCC CTG ATG CGG CGG GCC GCG AAG ACC ATC

N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

```
ATC CCT TAC GAG GAG GCC CAG GCC TTC ATT GAG CGC TAC TTT CAG AGC TTC CCC
 I   P   Y   E   E   A   Q   A   F   I   E   R   Y   F   Q   S   F   P

K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

E   M   G   A   R   M   L   L   Q   V   H   D   E   L   V   L   E   A
GAA ATG GGC GCC AGG ATG CTC CTT CAG GTC CAC GAC GAG CTG GTC CTC GAG GCC

P   K   E   R   A   E   A   V   A   R   L   A   K   E   V   M   E   G
CCA AAA GAG AGG GCC GAG GCG GTG GCC CGG CTG GCC AAG GAG GTC ATG GAG GGG

V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

H   H   *
CAT CAT TAA
```

Figure 17V

<ins>Taq DNA polymerase- (PCNA) fusion protein</ins>

FIGURE 17V (CONT.)

Nucleotide sequence (SEQ ID NO: 65) //Nucleotide sequence (SEQ ID NO: 67)
Amino acid sequence (SEQ ID NO: 66) /Amino acid sequence (SEQ ID NO: 68)

```
  G   G   G
// GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   G   Y   F   A   K   S   L   L   K
AGC CGG GGG GAG CCG GTG CAG GCG GTG GGG TAC TTC GCC AAG AGC CTC CTC AAG

A   L   K   E   D   G   D   A   V   I   V   F   D   A   K   A   P   P
GCC CTC AAG GAG GAC GGG GAC GCG GTG ATC GTG TTT GAC GCC AAG GCC CCC CCC

S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

L   A   R   L   E   V   P   G   Y   E   A   D   D   V   L   A   S   L
CTG GCG CGC CTC GAG GTC CCG GGC TAC GAG GCG GAC GTC CTG GCC AGC CTG

A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG
```

FIGURE 17V (CONT.)

| | | | | | | | | | | | | | | |
|---|---|---|---|---|---|---|---|---|---|---|---|---|---|---|
| A GCC | D GAC | Y TAC | R CGG | A GCC | L CTG | T ACC | G GGG | D GAC | E GAG | S TCC | D GAC | N AAC | L CTT | P CCC | G GGG | V GTC | K AAG |
| G GGC | I ATC | G GGG | E GAG | E GAG | T ACG | A GCG | R AGG | R AGG | E GAG | L CTT | L CTG | E GAG | E GAG | W TGG | G GGG | S AGC | L CTG | E GAA |
| A GCC | L CTC | K AAG | N AAC | L CTG | D GAC | R CGG | K AAG | R CGG | A GCC | P CCC | K AAG | I ATC | R CGG | E GAG | K AAG | I ATC | L CTG |
| A GCC | H CAC | M ATG | D GAC | D GAT | L CTG | K AAG | L CTC | S TCC | W TGG | D GAC | K AAA | A GCC | L CTG | V GTG | R CGC | T ACC | D GAC |
| L CTG | P CCC | L CTG | E GAG | V GTG | D GAC | F TTC | A GCC | K AAA | R AGG | R CGG | E GAG | P CCC | L CTC | H CAC | P CCC | D GAC | R CGG | E G

FIGURE 17V (CONT.)

| A | N | L | W | G | R | L | E | E | E | R | L | L | W | L | Y | R |
|---|---|---|---|---|---|---|---|---|---|---|---|---|---|---|---|---|
| GCC | AAC | CTG | TGG | GGG | AGG | CTT | GAG | GAG | GAG | AGG | CTC | CTT | TGG | CTT | TAC | CGG |
| E | V | E | R | P | L | S | A | V | L | M | E | L | W | A | T | V |
| GAG | GTG | GAG | AGG | CCC | CTT | TCC | GCT | GTC | CTC | ATG | GAG | CTG | GCC | ACG | GGG | GTG |
| R | L | D | V | A | Y | L | R | A | L | E | V | M | E | V | A | E | I |
| CGC | CTG | GAC | GTG | GCC | TAT | CTC | AGG | GCC | CTG | GAG | GTG | ATG | GAG | GTG | GCC | GAG | ATC |
| A | R | L | E | A | E | V | F | R | L | L | A | S | V | A | E | N | L |
| GCC | CGC | CTC | GAG | GCC | GAG | GTC | TTC | CGC | CTG | CTG | GCC | TCC | GTG | GCC | GAG | AAC | CTC | AAC |
| S | R | D | Q | L | E | R | V | L | R | F | D | H | P | G | L | P | A | I |
| TCC | CGG | GAC | CAG | CTG | GAA | AGG | GTC | CTC | CGC | TTT | GAC | CAC | CCC | GGG | CTT | CCC | GCC | ATC |
| G | K | T | E | K | T | G | I | S | R | E | L | Q | V | R | Y | L | E | A |
| GGC | AAG | ACG | GAG | AAG | ACC | GGC | ATC | AGC | CGC | GAG | CTG | CAG | GTC | CGG | TAC | CTG | GAG | GCC |
| L | R | E | A | H | P | I | V | E | K | I | L | Q | D | L | H | I | L | T |
| CTC | CGC | GAG | GCC | CAC | CCC | ATC | GTG | GAG | AAG | ATC | CTG | CAG | GAC | CTC | CAC | ATC | CTC | ACC |
| K | L | K | S | T | Y | I | D | P | L | P | D | P | L | R | T | P | R | T |
| AAG | CTG | AAG | AGC | ACC | TAC | ATT | GAC | CCC | TTG | CCG | GAC | CCC | CTC | CGC | ACG | CCC | AGG | ACG |
| G | R | L | H | T | T | N | Q | N | F | A | T | V | R | T | P | L | G | S |
| GGC | CGC | CTC | CAC | ACC | ACC | AAC | CAG | AAC | TTC | GCC | ACG | GTC | CGC | ACC | CCG | CTT | GGG | AGT |
| S | D | P | N | F | A | E | E | G | W | L | S | L | T | P | V | A | L | R |
| AGC | GAT | CCC | AAC | TTC | GCC | GAG | GAG | GGG | TGG | CTA | TCC | CTC | ACC | CCG | GTC | GCC | CTT | AGG |
| I | R | A | F | I | A | E | E | L | A | H | L | S | G | D | V | A | L | Y |
| ATC | CGC | GCC | TTC | ATC | GCC | GAG | GAG | CTC | GCC | CAC | CTC | TCC | GGC | GAC | GTG | GCC | CTG | GAT |
| S | Q | I | E | L | R | V | L | A | H | L | T | G | D | E | N | L | I |
| AGC | CAG | ATA | GAG | CTC | AGG | GTG | CTG | GCC | CAC | CTC | ACG | GGC | GAC | GAG | AAC | CTG | ATC |
| R | V | F | Q | E | G | R | D | I | H | T | E | T | A | S | W | M | F |

FIGURE 17V (CONT.)

```
  R   G   V   F   Q   E   G   R   A   V   G   D   I   H   T   E   R   A   K   R   T   I
  CGG GGC GTC TTC CAG GAG GGG CGG GCC GTG GGC GAC ATC CAC ACG GAG ACC GCC AGC TGG ATG TTC

N   F   P   G   V   Y   L   E   A   V   G   M   S   A   R   L   M   R   A   K   T   I
  AAC TTC CCC GGG GTC TAC CTC GAG GCC GTG GGC ATG TCG GCC CGC CTC ATG CGG GCG GCC ACC ATC

I   P   Y   E   A   Q   I   E   A   F   T   F   Q   S   Q   E   L   A
  ATC CCT TAC GAG GCC CAG ATT GAG GCC TTC ACC TTT CAG AGC CAG GAG CTA GCC

K   V   R   A   W   I   E   R   R   K   Y   R   R   E   Q   Y   P   P
  AAG GTG CGG GCC TGG ATT GAG CGC CGC AAG TAC CGC CGC GAG CAG TAC CCC CCC

V   E   T   L   F   G   R   A   E   R   R   Y   V   P   D   L   G   G   G   R   Y
  GTG GAG ACC CTC TTC GGC GCG GAG CGC CGC TAC GTG CCA GAC CTA GGC GGG TAC

K   S   V   R   E   A   A   E   L   M   R   M   A   F   N   L   E   A   R   V
  AAG AGC GTG CGG GAG GCG GCC GAG CGC ATG CGC ATG GCC TTC AAC CTC GAG GCC CGG GTG

T   A   A   D   L   M   K   L   L   Q   V   K   L   F   P   P   R   L   E   G
  ACC GCC GCC GAC CTC ATG AAG CTG CTT CAG GTG AAG CTC TTC CCC AGG CTG GAG GGC

E   M   G   A   R   M   M   A   Q   V   H   D   E   L   V   R   E   V   M   E   A
  GAA ATG GGG GCC AGG ATG ATG GCT CAG GTC CAC GAC GAG CTG GTC CGG GAG GTC ATG GAG GCC

P   K   E   R   A   E   A   V   R   L   A   K   E   V   M   E   G
  CCA AAA GAG AGG GCG GAG GCC GTG CGG CTG GCC AAG GAG GTC ATG GAG GGG

V   Y   P   L   A   V   P   L   E   V   E   V   G   I   G   E   D   W
  GTG TAT CCC CTG GCC GTG CCC CTG GAG GTG GAG GTG GGG ATA GGG GAG GAC TGG

L   S   A   K   E   G   I   D   G   R   G   G   H   H   H   H   H
  CTC TCC GCC AAG GAG GAG ATT GAT GGC CGC GGC GGA GGC GGG CAT CAT CAT CAT CAT

H   H   //
  CAT CAT
```

FIGURE 17V (CONT.)

```
M   P   F   E   I   V   F   E   G   A   K   E   F   A   Q   L   I   D          18
ATG CCA TTT GAA ATC GTA TTT GAA GGT GCA AAA GAG TTT GCC CAA CTT ATA GAC        54

T   A   S   K   L   I   D   E   A   A   F   K   V   T   E   D   G   I         36
ACC GCA AGT AAG TTA ATA GAT GAG GCC GCG TTT AAA GTT ACA GAA GAT GGG ATA      108

S   M   R   A   M   D   P   S   R   V   V   E   F   I   D   L   P            54
AGC ATG AGG GCC ATG GAT CCA AGT AGA GTT GTT GAA TTT ATT GAC CTC CCG          162

S   S   I   F   S   K   Y   K   I   L   K   R   G   K   A   T   I   N       72
TCA AGC ATA TTT AGC AAA TAT AAG CTA AAG AGA GGT AAA GCA ATT GGA AAT ATA    216

M   D   H   L   K   K   K   I   B   N   F   L   E   T   Q   D   T   I       90
ATG GAC CAC CTA AAG AAG AAG ATC CTA GAG AAC TTC TTA GAG ACA CAA GAC ACA    270

L   K   K   G   E   E   V   P   A   K   V   L   B   E   M   H   A   P     108
CTC AAG AAA GGA GAA GAG CCC GCA GTT CTA GAT GTA GTT GAA GAG ATG GCA CCA    324

R   T   F   R   V   P   L   I   D   V   V   G   E   K   F   I   A   A     126
AGA ACA TTT AGA GTT CCC CTA ATA GAT GTA GTT GGA GAA AAA TTT ATT GCC CTC    378

E   L   P   F   T   A   K   V   V   S   D   E   G   E   V   L   D   A     144
GAA CTT CCA TTC ACT GCA AAG GTT GTT AGT GAC GAA GGA GAA GTT CTA GAT GCT    432

V   K   D   A   S   L   A   K   V   E   G   I   E   T   Q   K   L   N     162
GTT AAA GAT GCC TCT CTA GCA GCA AAG GTG GAG GGA ATA GAG ACC CAG AAG AAT    486

E   F   I   M   K   A   E   L   L   D   I   E   E   V   Q   E   L   T     180
GAA TTT ATA ATG AAG GCA GAG GAG TTA TTG GAC ATC GAG GAA GTT CAA GAG ACT    540

L   E   D   E   G   G   L   S   D   M   V   K   G   L   A   K   S   A     198
CTT GAA GAT GAG GGA GGA TTA TCC GAC ATG GTT AAA GGA CTT GAA ACA AAG GCA    594

Y   G   V   S   Y   L   F   V   D   M   V   K   G   L   G   K   A   D   E 216
TAT GGA GTC AGC TAT CTC TCC GAC ATG GTT AAA GGA CTT GGA AAG GCC GAT GAA    648
```

FIGURE 17V (CONT.)

```
V   T   I   K   F   G   N   E   M   P   M   Q   M   E   Y   Y   I   R
GTT ACA ATA AAG TTT GGA AAT GAA ATG CCC ATG CAA ATG GAG TAT TAC ATT AGA   234
                                                                          702

D   E   G   R   L   T   F   L   L   A   P   R   V   E   E   *
GAT GAA GGA AGA CTT ACA TTC CTA CTG GCT CCA AGA GTT GAA GAG TGA           250
```

Figure 17W

Pfu DNA Polymerase (WT) -(PCNA) fusion protein

Nucleotide sequence (SEQ ID NO: 61) // Nucleotide sequence (SEQ ID NO: 67)

```
ccctggtcct gggtccacat atatgtcctt actcgcctt atgaagaatc cccagtcgc
tctaacctgg gttatagtga caaatcttcc tccaccaccg cccaagaagg ttattctat
caactctaca cctccctat tttctctctt atgagatttt taagtatagt tatagagaag
gttttatact ccaaactgag ttagtagata tgtggggagc ataatgattt tagatgtgga
ttacataact gaagaaggaa aacctgttat taggctattc aaaaaagaga acggaaaatt
taagatagag catgatagaa ctttagacc atacatttac gtctcttctca gggatgattc
aaagattgaa gaagttaaga aaataacggg ggaaaggcat ggaaagattg tgagaattgt
tgatgtagag aaggttgaga aaagtttcct cggcaagcct attaccgtgt ggaaacttta
tttggaacat cccaagatg ttcccactat tagagaaaaa gttagagaac atccagcagt
tgtggacatc ttcgaatacg atattccatt tgcaaagaga tacctcatcg acaaaggcct
```

FIGURE 17W (CONT.)

```
aataccaatg gaggggggaag aagagctaaa gattcctgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagcaa gtgaagagga gtatcaaaga aggcttcaggg agagctacac
aggtggattc gttaaagagc cagaaaaggg gttgtgggaa aacatagtat acctagattt
tagagcccta tatccctcga ttataattac ccacaatgtt tctcccgata ctctcaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaactc ttagcaaatt ctttctacgg atattatggc tatgcaaaag caagatggta
```

FIGURE 17W (CONT.)

```
ctgtaaggag tgtgctgaga gcgttactgc ctggggaaga aagtacatcg agttagtatg
gaagagctc gaagaaaagt ttggatttaa agtcctctac attgacactg atggtctcta
tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagctgcca attatgaaat tccaccagag aagctcgcaa tatatgagca
gataacaaga ccattacatg agtataaggc gataggtcct cacgtagctg ttgcaaagaa
actagctgct aaaggagtta aataaaagcc aggaatggta attggataca tagtacttag
aggcgatggt ccaattagca ataggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac tttattctt
tctaacttt ttctatgaaa gaagaactga gcaggaatta ccagttcttc cgttatttta
tgggtaatta aaaaccatg ctcttgggag aatcttcgaa taaatccct aacttcaggc
tttgctaagt gaatagaata aacaacatca ctcacttcaa acgccttcgt tagaaatggt
ctatctgcat gcttcctgg ctcggaanng gaggattcat aacaacagta tcaacattct
cagagaattg agaaacatca gaaactttga cttctacaac atttctaact ttgcaactct
```

FIGURE 17W (CONT.)

```
tcaagattttt ctaaaagaat tttaacggcc tcctcgtcaa tttcgacgac gtagatcttt
tttgctccaa gcagagccgc tccaatggat aacaccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtcttttt
taactttac agaaataact gtctcaaatt atgacaactc ttgacatttt tacttcatta
ccagggtaat gttttttaagt atgaaatttt tctttcatag aggaggnnnn nngtcctctc
ctcgatttcc ttggttgtgc tccatatgat aagcttccaa agtgggtgtt cagactttta
gacactcaaa taccagacga caatggtgtg ctcactcaag cccatatgg gttgagaaaa
gtagaagcgg cactactcag atgcttcccc aggaatgagg ttgttgtagc tcntcccnga
aagatttgaga tgttcttgg //

ATG CCA TTT GAA ATC GTA TTT GAA GGT GCA AAA GAG TTT GCC CAA CTT ATA GAC      54
ACC GCA AGT AAG ATG GAT GAG GCG GTT TTT ACA GAA GAT GGG ATA           108
AGC ATG AGG GCC ATG GAT CCA AGT AGA GTT GTC CTG ATT GAC ACA ATT CTC CCG      162
TCA AGC ATA TTT AGC AAA TAT GAA ATC CTA AAG GTT AGA GGT ATA GAA ACA AAG GAC GTT ATA AAC      216
ATG GAC CAC GTC AAG GAG GAA AAC TTC ATA GAT GAG ATT GAA ACA ATT CAA GAA ACT GCA ACA      270
CTC AAG AAA GGA GAG GTT CCC CTA AAG GTT CTT GAA GTC CTA AAA GAT CTC CCA      324
AGA ACA TTT AGA TTC ACT GCA TTC GCC TCT CTA GTG GAG GGA GAA GAA TTT GCC AGG GAA AAT      378
GAA CTT AAA GAT GCC ATG GCA GAG TTA TTG GAC ATC GAG GTT CAA GAG CTA ACA AAG AGC GCA      432
GAA TTT ATA ATG GAT GGA TAT CTC TCC GAC ATG GTT AAA GGA CTT GGA AAG GCC GAT GAA      486
CTT GAA GAT GTC AGC AAG TTT GGA AAT GAA ATG CCC ATG CAA ATG GAG TAT TAC ATT AGA      540
TAT GGA GTC TAC TTT ACA ATA TTC CTA CTG GCT CCA AGA GTT GAA GAG TGA      594
GTT ACA ATA AAG GGA TAT TTT GGA AAT GAA ATG CCC ATG CAA ATG GAG TAT TAC ATT AGA      648
GAT GAA GGA AGA CTT ACA TTC CTA CTG GCT CCA AGA GTT GAA GAG TGA           702
```

Figure 17X

(PCNA) - Pfu DNA Polymerase (WT) fusion protein

Nucleotide sequence (SEQ ID NO: 67) // Nucleotide sequence (SEQ ID NO: 61)

```
ATG CCA TTT GAA ATC GTA TTT GAA GGT GCA AAA GAG TTT GCC CAA CTT ATA GAC    54
ACC GCA AGT TTA ATA GAT GAG AGT GCC GCG TTT AAA GTT ACA GAT AAT GGG ATA   108
AGC ATG AGG GCC ATG GAT CCA AGT AGA GTT GTT CTG ATT GAC CTA AAT CTC CCG   162
TCA GCT TTT AGC AAA TAT GAA GTT GAA CCA GAA ACA ACA AAG GGA GTT AAC       216
ATG GAC CAC CTA AAG GAG ATC CTA AAG AGA GGT ATA ACA ATT CAA GCA ACA       270
CTC AAG AAA GGA GAA GTT CCC CTA TTC ATA GAT GAG ATG ATG GAA CTC CCA       324
AGA ACA TTT AGA GTT ACT TCA AAG GTT GTA CTT CTT GGA GAA GTC CTA AAA GAT GCT   378
GAA CTT AAA GAT GCC TCT CTA GTG AGT GGA GAA ACC AGC ATT TAT ATT GCC AGG GAA AAT   432
GAA TTT ATA ATG GGA TTA TTG GAC ATC GAG GTT CAA GAG GAG ATA AAG CTA ACT   486
CTT GAA GAT GAG GGA TTA CTC TCC GAC ATG ATG AAA GGA CTT GGA ACA AAG AGC GCA   540
TAT GGA GTC AGC AAG TTT GGA AAT GAA ATG CCC ATG CAA ATG GAG AAG GCC GAT GAA   594
GTT ACA ATA AAG AGA AGA CTT ACA TTC CTA CTG GCT CCA AGA GTT GAA AGA      648
GAT GAA GGA AGA GTT GTT TAC TAT TAC AGA                                   702
```

```
ccctggtcct gggtccacat atatgttctt actcgcttt atgaagaatc cccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga ttacataact gaagaaggaa aactgttat taggctattc aaaaaagaga acggaaaatt
```

FIGURE 17X (CONT.)

```
taagatagag catgatagaa ctttagacc  atacatttac gctcttctca gggatgattc
aaagattgaa gaagttaaga aaataacggg ggaaggcat  ggaaagattg tgagaattgt
tgatgtgaga aaggttgaga aaaagtttct cgcaagcct  attaccgtgt ggaaacttta
tttggaacat ccccaagatg ttcccactat tagagaaaaa gttagagaac atccagcagt
tgtggcatc  ttcgaatacg atattccatt tgcaagaga  tacctcatcg acaaaggcct
aataccaatg gaggggaag  aagagctaaa gattcttgcc ttcgatatag aaaccctcta
tcacgaagga gaagagtttg gaaaggccc  attataatg  attagttatg cagatgaaaa
tgaagcaaag gtgattactt ggaaaacat  agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagaga  gtatcaaga  aggctcaggg agagctacac
aggtggattc gttaaagagc cagaaaaggg gttgtgggaa aacatagtat acctagatt
```

FIGURE 17X (CONT.)

```
tagagccta tatccctcga ttataattac ccacaatgtt tctcccgata ctctaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaaactc ttagcaaatt ctttctacgg atattatggc tatgcaaaag caagatggta
ctgtaaggag tgtgctgaga gcgttactgc ctggggaaga aagtacatcg agttagtatg
gaaggagctc gaagaaaagt ttgatttaa agtccctcac attgacactg atggtctcta
tgcaactatc ccaggaggag aaagtgagga aataaagaaa aaggctctag aatttgtaaa
atacataaat tcaaagctcc ctggactgct agagcttgaa tatgaaggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac tttattctt
```

FIGURE 17X (CONT.)

```
tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gctctcctgg ctcggaanng gaggattcat aacaacagta tcaacattct
cagagaattg agaaacatca gaaactttga cttctacaac atttctaact ttgcaactct
tcaagatttt ctaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taactttac agaaataact gtctcaaatt atgacaactc ttgacatttt tacttcatta
ccagggtaat gtttttaagt atgaaatttt tcttttcatag aggagnnnn nngtcctctc
ctcgatttcc ttggtgtgc tccatatgat aagcttccaa agtgggtgtt cagactttta
gacactcaaa taccagacga caatggtgtg ctcactcaag cccatatgg gttgagaaaa
gtagaagcgg cactactcag atgcttcccc aggaatgagg ttgttgtagc tcntcccnga
aagattgaga tgttcttgg // TGA
```

FIGURE 17Y

(PCNA) - PFU DNA POLYMERASE (V93 R OR E) fusion protein

Nucleotide sequence (SEQ ID NO: 67)   //Nucleotide sequence (SEQ ID NO: 27)
Nucleotide sequence (SEQ ID NO: 67)   //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC      54
ACC GCA AGT AGA TTA ATA GAT GAG GCC GCG TTT AAA GTT ACA GAA GAT GGG ATA     108
AGC ATG AGG GCC ATG ATG GAT CCA AGT AGA GTT GTT AGA ATT GAC CTA AAT CTC CCG 162
TCA AGC ATA TTT GAC AAA TAT GAA ATC CTA AAG AGA GGT ATA GAA ACA AAG GGA GTT AAC 216
ATG GAC CAC CTA AAG GAG GAA AAC TTC TTA AAG ATA GAT ACA ATT CAA GGA ACT GCA ACA 270
CTC AAG AAA TTT AGA GAA GTT CCC CTA ATA GAT GTA GAA GAG ATG GAA GTT GAC CTC CCA 324
AGA ACA TTT CCA TTC ACT GCA AAG GTT CTT AGT GTT CTT GGA GAA GTC CTA AAA GAT GCT 378
GTT AAA GAT GCC TCT CTA AAG GCA GAG GGA GAA ACC CAG ATA AAA TTT ATT GCC AGG GAA AAT 432
GAA TTT ATA ATG GAT GAT TTG TCC GAC ATC GAG GTT CAA GAG GTT GAG ATA AAG CTA ACT 486
CTT GAA GAT GGA GTC AGC TAT CTC TCC GAC TAT GAA CTT AAA GAA CTT GGA AAG GCC GAT 540
TAT GGA GTC AGC ATA AAG TTT GGA AAT GAA ATG GCC ATG ATG CAA AGA GTT CAA GAG GAA 594
GTT ACA ATA AAG AGA GGA CTT ACA TTC CTA CTG GCT CCA AGA GTT GAA GTT GAA GAG         648
GAT GAA CTT ACA TTC CTA CTG GCT CCA AGA GTT GAA GTT //                              702
```

```
ATGATTTTAG ATGTGGATTA CATAACTGAA GAAGGAAAAC CTGTTATTAG GCTATTACGCT    60
AAAGAACG GAAAATTTAA GATAGAGCAT GATAGAACTT TTAGACCATA CATTTACGCT      120
CTTCTCAGGG ATGATTCAAA GATTGAAGAA GTTAAGAAAA TAACGGGGGA AAGGCATGGA    180
AAGATTGTGA GAATTGTTGA TGTAGAGAAG GTTGAGAAAA AGTTTCTCGG CAAGCCTATT    240
ACCGTGTGA AACTTTATTT GGAACATCCC CAAGATCCCC CCACTATTAG AGAAAAAGTT    300
AGAGAACATC AAGCAGTTGT GGACATCTTC GGACATCGATA TTCCATTTGC AAAGAGATAC   360
CTCATCGACA AAGGCCTAAT ACCAATGGAG GGGAAGAAG AGCTAAAGAT TCTTGCCTTC     420
GATATAGAAA CCCCTCATCA CGAAGGAGAA GAGTTTGGAA AAGGCCCAAT TATAATGATT    480
AGTTATGCAG ATGAAAATGA AGCAAAGGTG ATTACTTGGA AAAACATAGA TCTTCCATAC    540
GTTGAGGTTG TATCAAGCGA GAGAGATG ATAAAGAGAT TTCTCAGGAT TATCAGGGAG      600
```

FIGURE 17Y (CONT.)

```
AAGGATCCTG ACATTATAGT TACTTATAAT GGAGACTCAT TCGCATTCCC ATATTAGCG   660
AAAAGGGCAG AAAAACTTGG GATTAAATTA ACCATTGGAA GAGATGGAAG CGAGCCCAAG   720
ATGCAGAGAA TAGGCGATAT GACGGCTGTA GAAGTCAAGG GAAGAATACA TTTCGACTTG   780
TATCATGTAA TAACAAGGAC AATAAATCTC CCAACATACA CACTAGAGGC TGTATATGAA   840
GCAATTTTTG GAAAGCCAAA GGAGAAGGTA TACGCCGACG AGATAGCAAA AGCCTGGAA    900
AGTGGAGAGA ACCTTGAGAG AGTTGCCAAA TACTCGATGG AAGATGCAAA GGCAACTTAT   960
GAACTCGGGA AAGAATTCCT TCCAATGGAA ATTCAGCTTT CAAGATTAGT TGGACAACCT  1020
TTATGGGATG TTTCAAGTC AAGCACAGGG AACCTTGTAG AGTGGTTCTT ACTTAGGAAA   1080
GCCTACGAAA GAAACGAAGT AGCTCCAAAC AAGCCAAGTG AAGAGGAGTA TCAAAGAAGG  1140
CTCAGGGAGA GCTACACAGG TGGATTCGTT AAAGAGCCAG AAAAGGGGTT GTGGGAAAAC  1200
ATAGTATACC TAGATTTTAG AGCCCTATAT CCCTCGATTA TAATTACCCA CAATGTTTCT  1260
CCCGATACTC TAAATCTTGA GGGATGCAAG AATATGATA TCGCTCCCTCA AGTAGGCCAC  1320
AAGTTCTGCA AGGACATCCC TGGTTTTATA CCAAGTCTCT TGGGACATTT GTTAGAGGAA  1380
AGACAAAAGA TTAAGACAAA AATGAAGGAA ACTCAAGATC CTATAGAAAA AATACTCCTT  1440
GACTATAGAC AAAAAGCGAT AAAACTCTTA GCAAATTCTT TCTACGGATA TTATGGCTAT  1500
GCAAAAGCAA GATGGTACTG TAAGGAGTGT GCTGAGAGCG TTACTGCCTG GGGAAGAAAG  1560
TACATCGAGT TAGTATGGAA GGAGCTCGAA GAAAAGTTTG GATTTAAAGT CCCTCTACAT  1620
GACACTGATG GTCTCTATGC AACTATCCCA GGAGAGGAAA GTGAGGAAAT AAAGAAAAAG  1680
GCTCTAGAAT TTGTAAAATA CATAAATTCA AAGCTCCCTG GACTGCTAGA GCTTGAATAT  1740
GAAGGTTTT ATAAGAGGGG ATTCTTCGTT ACGAAGAAGA GGTATGCAGT AATAGATGAA   1800
GGAGGAAAAG TCATTACTCG TGGTTTAGAG ATAGTTAGGA GAGATTGGAG TGAAATTGCA  1860
AAAGAAACTC AAGCTAGAGT TTTGGAGACA ATACTAAAAC ACGGAGATGT TGAAGAAGCT  1920
GTGAGAATAG TAAAAGAAGT AATACAAAAG CTTGCCAATT ATGAAATTCC ACCAGAGAAG  1980
CTCGCAATAT ATGAGCAGAT AACAAGACCA TTACATGAGT ATAAGGCGAT AGGTCCTCAC  2040
GTAGCTGTTG CAAAGAAACT AGCTGCTAAA GGAGTTAAAA TAAAGCCAGG AATGGTAATT  2100
GGATACATAG TACTTAGAGG CGATGGTCCA ATTAGCAATA GGGCAATTCT AGCTGAGGAA  2160
TACGATCCCA AAAAGCACAA GTATGACGCA GAATATTACA TGGAGAACCA GGTTCTTCCA  2220
GCGGTACTTA GGATATTGGA GGGATTTGGA TACAGAAAGG AAGACCTCAG ATACCAAAAG  2280
ACAAGACAAG TCGGCCTAAC TTCCTGGCTT AACATTAAAA AATCC //              2328
// TGA
```

Figure 17Z

PFU DNA POLYMERASE (V93 R OR E)-(PCNA) fusion protein

FIGURE 17Z (CONT.)

Nucleotide sequence (SEQ ID NO: 27) // Nucleotide sequence (SEQ ID NO: 67)
Nucleotide sequence (SEQ ID NO: 28) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
```

FIGURE 17Z (CONT.)

```
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACCAGACCA TTACATGAGT AAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //              2328
```

```
ATG CCA GCA AGT ATC GTA TTT GAA GGT GCA AAA GAG TTT GCC CAA CTT ATA GAC    54
ACC GCA AGT AGG GCC ATG AGC GAT AAA TAT AGC AGT GAA GTT GTC CTG ATT GGG ATA  108
AGC GAC ATA TTT AGC AAG GAG CTA AAG AAG GAA ATC TTA AAG AGA GTT GTT GAA ACA  162
TCA GAC CAC AAA GAG GAG AAC TTC ATA ATA GAT CCA AAG GGT AAA GCA ACA ATT CTC  216
ATG GAC AAA TTT AGA GAA GTT CCC CTA AAG GTT GTA GAG ATA GAG ACT GCA ACA     270
CTC AAG GAA ACA CTT AAA GAT GCC TCT CTA GTG GAG GGA ATG ATG CTT AAA GAT CCA  324
AGA ACA CTT AAA GAT GCC TCT CTA GTG GAG GGA AAA TTT ATT GCC AGG GAA AAT    378
GAA CTT AAA GAT ATA ATG AAG GCC TTA TTG TCC GAC ATC GAG GTT AAA ACA CTA ACT  432
GTT GAT GAT GAT GAT AAG GCA GGA TTA TTC TCC GAC ATC GAG GTT AAA ACA CTA ACT  486
CTT GAA GAT GTC AGC TAT TTT GGA AAT GAA GTT CAA CTT GGA CTT ATG AAG GCC GCA  540
TAT GGA GTC AGC TAT TTT GGA AAT GAA GTT CCC ATG GAG CTT GAG TAT GCC GAT GAA  594
GTT ACA ATA AAG AGA TTT GGA AAT GAA ATG ATG CAA AGA GTT TAC ATT AGA          648
GAT GAA GGA AGA CTT ACA TTC ACA CTG GCT CCA GTT GAA GTT GAG GAG TGA          702
```

Figure 17AA

PFU DNA POLYMERASE (G387P/V93R OR E) -(PCNA) fusion protein

Nucleotide sequence (SEQ ID NO: 29)   // Nucleotide sequence (SEQ ID NO: 67)
Nucleotide sequence (SEQ ID NO: 30)   // Nucleotide sequence (SEQ ID NO: 67)

FIGURE 17AA (CONT.)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
```

FIGURE 17AA (CONT.)

```
CTCGCAATAT ATGAGCAGAT AACAAGACCA TTACATGAGT ATAAGGCGAT AGTCCTCAC 2040
GTAGCTGTTG CAAAGAAACT AGCTGCTAAA GGAGTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //        2328

ATG CCA TTT GAA ATC GTA TTT GAA GGT GCA AAA GAG TTT GCC CAA CTT ATA GAC  54
ACC GCA AGT TTA ATA GAT CCA AGT GAG GCC GCG GTT GTC ATT ACA GAA GAT GGG ATA 108
AGC ATG AGG GCC ATG GAT AAA TAT AGC AGT AGA GTT GTT AGA GTT GAC CTA AAT CTC CCG 162
TCA AGC ATA TTT GCC ATA TTT GAA TAT CTA AAG AGA ATC CCA AAA ATT GGA GTT AAC 216
ATG GAC CAC AAA GAG GAA AAC TTC TTA AAG GAG GGT ATA GCA ATT CAA GCA ACA 270
CTC AAG ACA TTT AGA GTT CCC CTA AAG GTT CCC CTA TTC TTA GAT GTA GAA ATG GAA GTT CAA GGA CTC CCA 324
AGA ACA CTT CCA TTC ACT GCA TTC GCC TCT CTA GTG GAG GGA AGT GAC AGC ACC AGC ATA TTT GCC AGG GAA GAT GCT 378
GAA CTT AAA GAT GCC TCT CTA GTG GAG GGA AGT GAC AGC ACC AGC ATA TTT GCC AGG AAG CTA ACT 432
GTT TTT ATA ATG GAT GAG GGA TTA TTG GAC ATC GAG ATG ATG CAA GTT GAG GAG CTT GGA ACA AAG AGC GCA 486
GAA CTT GAA GAT GTC AGC TAT CTC TCC GAC GAG GTT AAA GGA CTT GGA AAG GCC GAT GAA 540
TAT GGA GTC AGC TAT CTC TCC GAC GAG GTT AAA GGA CTT GGA AAG GCC GAT GAA 594
GTT ACA ATA AAG TTT GGA AAT GAA ATG ATG CCC ATG GAG GAG TAT TAC ATT AGA 648
GAT GAA GGA AGA CTT ACA TTC CTA CTG GCT CCA AGA GTT GAA GAG TGA     702
```

Figure 17BB (PCNA) - PFU DNA POLYMERASE (G387P/V93R OR E) fusion protein

Nucleotide sequence (SEQ ID NO: 67) // Nucleotide sequence (SEQ ID NO: 29)
Nucleotide sequence (SEQ ID NO: 67) // Nucleotide sequence (SEQ ID NO: 30)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIGURE 17BB (CONT.)

```
ATG CCA TTT GAA ATC GTA TTT GAA GGT GCA AAA GAG TTT GCC CAA CTT ATA GAC      54
ACC GCA AGT AAG TTA ATA GAT GAT GAG GCC GCG TTT AAA GTT ACA GAA GAT GGG ATA  108
AGC ATG AGG GCC ATG GAT CCA AGT GAT AGA GTT GTC CTG ATT GAC CTA AAT CTC CCG  162
TCA AGC ATA TTT AGC AAA TAT GAA AAG GTT GTT GAA CCA GAA ACA ATT GGA GTT AAC  216
ATG GAC CAC CTA AAG AAG ATC CTA AAG AGA GGT AAA GCA ATT CAA GAC ACC TTA ATA  270
CTC AAG AAA GGA GAG GAA AAC TTC TTA GAG ATA GAA ATG CAA GGA GTT GAC CTC ACA  324
AGA ACA TTT AGA GTT CCC CTA ATA GAT GTT CTT GGA GAA GTC CTA AAA GAT GCT CCA  378
GAA CTT CCA TTC ACT GCA AAG GTT CTA GTG AGT GAC AGC ATA AAA TTT ATT GCC GAA AAT  432
GTT AAA GAT GCC TCT CTA AAG GCA GAG GAA ACC CAG GAA GTT GAG ATA AAG CTA ACT  486
GAA TTT ATA ATG GAT GAG GGA TTA TTG GAC ATC GAG GTT CAA GAG GAG ACA AAG GCA  540
CTT GAA GAT GAG AGC TAT CTC TCC GAC ATG ATG GGA CTT GGA GAG TAT TAC GCA GAA  594
TAT GGA GTC ACA ATA AAG TTT GGA AAT GAA ATG CAA GTC CAA AGA GAG TAT TAC AGA  648
GTT ACA ATA AAG AGA GGA CTT ACA TTC CTA CTG GCT CCA AGA GTT GAA GAG //       702

ATGATTTTAG ATGTGGATTA CATAACTGAA GAAGGAAAAC CTGTTATTAG GCTATTCAAA            60
AAAGAGAACG GAAAATTTAA GATAGAGCAT GATAGAACTT TTAGACCATA CATTTACGCT           120
CTTCTCAGGG ATGATTCAAA GATTGAAGAA GTTAAGAAAA TAACGGGGGA AAGGCATGGA           180
AAGATTGTGA GAATTGTTGA TGTAGAGAAG GTTGAGAAAA AGTTTCTCGG CAAGCCTATT           240
ACCGTGTGGA AACTTTATTT GGAACATCCC CAAGATXXXC CCACTATTAG AGAAAAAGTT           300
AGAGAACATC CAGCAGTTGT GGACATCTTC GAATACGATA TTCCATTTGC AAAGAGATAC           360
CTCATCGACA AAGGCCTAAT ACCAATGGAG GGGGAAGAAG AGCTAAAGAT TCTTGCCTTC           420
GATATAGAAA CCCTCTATCA CGAAGGAGAA GAGTTTGGAA AAGGCCCAAT TATAATGATT           480
AGTTATGCAG ATGAAAATGA AGCAAAGGTG ATTACTTGGA AAAACATAGA TCTTCCATAC           540
GTTGAGGTTG TATCAAGCGA GAGAGAGATG ATAAAGAGAT TTCTCAGGAT TATCAGGGAG           600
AAGGATCCTG ACATTATAGT TACTTATAAT GGAGACTCAT TCGCATTCCC ATATTTAGCG           660
AAAAGGGCAG AAAAACTTGG GATTAAATTA ACCATTGGAA GAGATGGAAG CGAGCCCAAG           720
ATGCAGAGAA TAGGCGATAT GACGGCTGTA GAAGTCAAGG GAAGAATACA TTTCGACTTG           780
TATCATGTAA TAACAAGGAC AATAAATCTC CCAACATACA CACTAGAGGC TGTATATGAA           840
GCAATTTTTG GAAAGCCAAA GGAGAAGGTA TACGCCGACG AGATAGCAAA AGCCTGGGAA           900
AGTGGAGAGA ACCTTGAGAG AGTTGCCAAA TACTCGATGG AAGATGCAAA GGCAACTTAT           960
GAACTCGGGA AAGAATTCCT TCCAATGGAA ATTCAGCTTT CAAGATTAGT TGGACAACCT          1020
TTATGGGATG TTTCAAGGTC AAGCACAGGG AACCTTGTAG AGTGGTTCTT ACTTAGGAAA          1080
GCCTACGAAA GAAACGAAGT AGCTCCAAAC AAGCCAAGTG AAGAGGAGTA TCAAAGAAGG          1140
CTCAGGGAGA GCTACACACC NGGATTCGTT AAAGAGCCAG AAAAGGGGTT GTGGGAAAAC          1200
ATAGTATACC TAGATTTTAG AGCCCTATAT CCCTCGATTA TAATTACCCA CAATGTTTCT          1260
CCCGATACTC TAAATCTTGA GGGATGCAAG AACTATGATA TCGCTCCTCA AGTAGGCCAC          1320
```

FIGURE 17BB (CONT.)

```
AAGTTCTGCA AGGACATCCC TGGTTTTATA CCAAGTCTCT TGGGACATTT GTTAGAGGAA  1380
AGACAAAGA  TTAAGACAAA  AATGAAGGAA  ACTCAAGATC  CTATAGAAAA  AATACTCCTT  1440
GACTATAGAC AAAAAGCGAT AAAACTCTTA GCAAATTCTT TCTACGATA  TTATGGCTAT  1500
GCAAAAGCAA GATGGTACTG TAAGGAGTGT GCTGAGAGCG TTACTGCCTG GGGAAGAAAG  1560
TACATCGAGT TAGTATGGAA GGAGCTCGAA GAAAAGTTTG GATTTAAAGT CCTCTACATT  1620
GACACTGATG GTCTCTATGC AACTATCCCA GGAGGAGAAA GTGAGGAAAT AAAGAAAAAG  1680
GCTCTAGAAT TTGTAAAATA CATAAAATTCA AAGCTCCCTG GACTGCTAGA GCTTGAATAT  1740
GAAGGGTTTT ATAAGAGGGG ATTCTTCGTT ACGAAGAAGA GGTATGCAGT AATAGATGAA  1800
GAAGGAAAAG TCATTACTCG TGGTTTAGAG ATAGTTAGGA GAGATTGGAG TGAAATTGCA  1860
AAAGAAACTC AAGCTAGAGT TTTTGGAGACA ATACTAAAAC ACGGAGATGT TGAAGAAGCT  1920
GTGAGAATAG TAAAAGAAGT AATACAAAAG CTTGCCAATT ATGAAATTCC ACCAGAGAAG  1980
CTCGCAATAT ATGAGCAGAT AACAAGACCA TTACATGAGT ATAAGGCGAT AGGTCCTCAC  2040
GTAGCTGTTG CAAAGAAACT AGCTGCTAAA GGAGTTAAAA TAAAGCCAGG AATGGTAATT  2100
GGATACATAG TACTTAGAGG CGATGGTCCA ATTAGCAATA GGGCAATTCT AGCTGAGGAA  2160
TACGATCCCA AAAAGCACAA GTATGACGCA GAATATTACA TGGAGAACCA GGTTCTTCCA  2220
GCGGTACTTA GGATATTGGA GGGATTTGGA TACAGAAAGG AAGACCTCAG ATACCAAAAG  2280
ACAAGACAAG TCGGCCTAAC TTCCTGGCTT AACATTAAAA AATCC //TAG            2328
```

Figure 17CC (PCNA)-PFU DNA POLYMERASE(D141A/E143A/V93R OR E) fusion protein

Nucleotide sequence (SEQ ID NO: 67)    // Nucleotide sequence (SEQ ID NO: 31)
Nucleotide sequence (SEQ ID NO: 67)    // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC      54
ACC GCA AGT AAG TTA ATA GAT GAG GCC GCG TTT AAA GTT ACA GAA GAT GGG ATA     108
AGC ATG AGG GCC ATG GAT CCA AGT GTC CTG ATT GAC CTA AAT GGA CTC CCG         162
TCA AGC ATA TTT AGC AAA TAT GAA AAA GTT GTT GAA CCA GAA ACA ATT GGA GTT AAC  216
```

FIGURE 17CC (CONT.)

```
ATG GAC CAC CTA AAG AAG ATC CTA AAG AGA GGT AAA GCA AAG GAC ACC TTA ATA    270
CTC AAG AAA GGA GAG GTT CCC CTA AAG GTT TTA GAG GTA GAG ATT CAA GGA ACT GCA ACA    324
AGA ACA TTT AGA TTC ACT GCA TTC GCC CTA AAG GTT CTT GGA GAA GTC GAC CTC CCA    378
GAA CTT AAA GAT GCC TCT CTA GTG GAG GGA GAA ATA AAA TTT ATT GCC AGG GAA GAT GCT    432
GTT TTT ATA ATG GAG GGA TTA TTG GAC ATC CAG GAA GTT CAA GAG GAG ATA AAG CTA ACT    486
CTT GAA GAT GTC AGC TAT CTC TCC GAC ATG ATG CTT AAA GGA CTT GGA AAG GCC GAT GCA    540
TAT GGA GTC AGC TAT CTC TCC GAC ATG ATG CTT AAA GGA CTT GGA AAG GCC GAT GAA    594
GTT ACA ATA AAG TTT GGA AAT GAA ATG CCC ATG CAA ATG GAG TAT TAC ATT AGA        648
GAT GAA GGA CTT ACA TTC CTA CTG GCT CCA AGA GTT GAA GAG //                    702

//ATGATTTTAG ATGTGGATTA CATAACTGAA GAAGGAAAAC CTGTTATTAG GCTATTCAAA    60
AAAGAGAACG GAAAATTTAA GATAGAGCAT GATAGACTT TTAGACCATA CATTTACGCT    120
CTTCTCAGGG ATGATTCAAA GATTGAAGAA GTTAAGAAAA TAACGGGGGA AAGGCATGGA    180
AAGATTGTGA GAATTGTTGA TGTAGAGAAG GTTGAGAAAA AGTTTCTCGG CAAGCCTATT    240
ACCGTGTGGA AACTTTATTT GGAACATCCC CAAGATXXXC CCACTATTAG AGAAAAAGTT    300
AGAGAACATC CAGCAGTTGT GGACATCTTC GAATACGATA TTCCATTTGC AAAGAGATAC    360
CTCATCGACA AAGGCCTAAT ACCAATGGAG GGGGAAGAAG AGCTAAAGAT TCTTGCCTTC    420
GCNATAGCNA CCCTCTATCA CGAAGGAGAA GAGTTTGGAA AAGCCCAAT TATAATGATT    480
AGTTATGCAG ATGAAAATGA AGCAAAGGTG ATTACTTGGA AAAACATAGA TCTTCCATAC    540
GTTGAGGTTG TATCAAGCGA GAGAGAGATG ATAAAGAGAT TTCTCAGGAT TATCAGGGAG    600
AAGGATCCTG ACATTATAGT TACTTATAAT GGAGACTCAT TCGCATTCCC ATATTAGCG    660
AAAGGGCAG AAAAACTTTGG GATTAAATTA ACCATTGGAA GAGATGGAAG CGAGCCCAAG    720
ATGCAGAGAA TAGGCGATAT GACGGCTGTA GAAGTCAAGG GAAGAATACA TTTCGACTTG    780
TATCATGTAA TAACAAGGAC AATAAATCTC CCAACATACA CACTAGAGGC TGTATATGAA    840
GCAATTTTTG GAAAGCCAAA GGAGAAGGTA TACGCCGACG AGATAGCAAA AGCCTGGGAA    900
AGTGGAGAGA ACCTTGAGAG AGTTGCCAAA TACTCGATGG AAGATGCAAA GGCAACTTAT    960
GAACTCGGGA AAGAATTCCT TCCAATGGAA ATTCAGCTTT CAAGATTAGT TGGACAACCT    1020
TTATGGGATG TTTCAAGGTC AAGCACAGGG AACCTTGTCA AGTGGTTCTT ACTTAGGAAA    1080
GCCTACGAGA GAAACGAAGT AGCTCCAAAC AAGCCAAGTG AAGAGGAGTA TCAAAGAAGG    1140
CTCAGGGAGA GCTACACA GTT_GGATTCGTT AAAGACCCAG AAAAGGGGTT GTGGGAAAAAC    1200
ATAGTATACC TAGATTTTAG AGCCCTATAT CCCTCGATTA TAATTACCCA CAATGTTTCT    1260
CCCGATACTC TAAATCTTGA GGGATGCAAG AACTATGATA TCGCTCCTCA AGTAGGCCAC    1320
AAGTTCTGCA AGGACATCCC TGGTTTTATA CCAAGTCTCT TGGGACATTT GTTAGAGGAA    1380
AGACAAAAGA TTAAGACAAA AATGAAGGAA ACTCAAGATC CTATAGAAAA AATACTCCTT    1440
GACTATAGAC AAAAAGCGAT AAAACTCTTA GCAAATTCTT TCTACGGATA TTATGGCTAT    1500
GCAAAAGCAA GATGGTACTG TAAGGAGTGT GCTGAGACGG TTACTGCCTG GGGAAGAAAG    1560
TACATCGAGT TAGTATGGAA GGAGCTCGAA GAAAAGTTTG GATTTAAAGT CCCTCTACATT    1620
```

FIGURE 17CC (CONT.)

```
GACACTGATG GTCTCTATGC AACTATCCCA GGAGGAGAAA GTGAGGAAAT AAAGAAAAAG 1680
GCTCTAGAAT TTGTAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATGA TAAAGAAGT AATACAAAAG CTTGCCAATT ATGAAATTCC ACCAGAGAAG 1980
CTTCCAATAT ATGAGACAGA T ACCAAGACCA TTACATGAGT ATAAGGCAGG AGTCCTCAC 2040
GTAGCTGTTG CAAAGAAACT AGCTGCTAAA GGAGTTAAAA TAAAGCCAGG AATGTAATT 2100
GGATACATAG TACTTAGAGG CGATGGTCTA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //           2328
TGA
```

Figure 17DD

PFU DNA POLYMERASE(D141A/E143A/V93R OR E) - (PCNA) fusion protein

Nucleotide sequence (SEQ ID NO: 31) // Nucleotide sequence (SEQ ID NO: 67)
Nucleotide sequence (SEQ ID NO: 32) // Nucleotide sequence (SEQ ID NO: 67)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA  60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATGTGG CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GAGGAGAA GAGTTTGGAA AAGGCCCAAT TATAATGATT 480
GCNATAGCNA CCCTCTATCA
```

FIGURE 17DD (CONT.)

```
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATATAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GTT GGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAGA TTAAGACAAA ATGAAGGAA ACTCAAGATC CTATAGAAAA AATACTCCTT 1440
GACTATAGAC AAAAAGCGAT AAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATGCGAGT TAGTAGTAGA GGAGCTCAGA GAAAAGTTTG GATTTAAAGT CCTCTACATT 1620
GACACTGATG GTCTCTATGC AACTATCCCA GGAGAGAGAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGAAAAG TCATTACTCG TGGTTTAGAG ATAGTTAGGA GAGATTGGAG TGAAGAAGCT 1860
AAAGAAACTC AAGCTAGAGT TAAAAGAAGT AATACAAAAG CTTGCCAATT ACGGAGATGT 1920
GTGAGAATAG ATGAGCAGAT AACAAGACCA TTACATGAGT ATAAGGCGAT AGTTCCTCAC 1980
CTCGCAATAT CAAAGAAACT AGCTGCTAAA GGAGTTAAAA TAAAGCCAGG AATGGTAATT 2040
GTAGCTGTTG TACTTAGAGG CGATGGTCCA ATTAGCAATA GGGCAATTCT AGCTGAGGAA 2100
GGATACATAG AAAAGCACAA GTATGACGCA GAATATTACA TGGAGAACCA GGTTCTTCCA 2160
TACGATCCCA AAAAGCACAA GTATGACGCA GAATATTACA TGGAGAACCA GGTTCTTCCA 2220
GCGTTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC // 2328

ATG CCA TTT GAA ATC GTA TTT GAA GGT GCA AAA GAG TTT GCC CAA GAA CTT ATA GAC     54
ACC GCA AGT AAG TTA ATA GAT GAT GAG GCC GCG TTT AAA GTT ACA GAA GAT GGG ATA    108
AGC ATG AGG GCC ATG GAT CCA AGT AGA GTT GTC CTG ATT GAC CTA AAT GAC CTC CCG    162
TCA AGC ATA TTT AGC ATG AAA TAT GAA GTT GTT GAA CCA GAA ACA ATT GGA GTT AAC    216
ATG GAC CAC CTA AAG GAC ATC CTA AAG AGA GGT AAA GCA AAG GAC ACC TTA ATA        270
CTC AAG AAA GGA GAG GAA AAC TTC TTA GAG ATA ACA ATT CAA GGA ACT GCA ACA        324
```

FIGURE 17DD (CONT.)

```
AGA ACA TTT AGA GTT CCC CTA ATA GAT GTA GAA GAG ATG GAA GTT GAC CTC CCA    378
GAA CTT CCA TTC ACT GCA AAG GTT GTA GTT GAC AGC GTT CTT GGA GAA GTC CTA AAA GAT GCT    432
GTT AAA GAT GCC TCT CTA GTG GAG GGA GAA AGC ATA AAA TTT ATT GCC AGG GAA AAT    486
GAA TTT ATA ATG AAG GCA GGA TTA TTG GAC ATC GAG GTT CAA GAA GTT GAG GAG ATA AAG CTA ACT    540
CTT GAA GAT GGT CAG TAT CTC TCC GAC ATG ATG GGA CTT AAA GGA CTT GGA AAG GCC AGC GAA    594
TAT GGA GTC AGC TAT TCT TGG GAA TTT GGA AAT GAA ATG CCC ATG CAA ATG GAG TAT TAC ATT AGA    648
GTT ACA ATA AAG AGA GGA CTT ACA TTC CTA CTG GCT CCA AGA GTT GAA GAG TGA    702
```

Figure 17EE

KOD DNA POLYMERASE – (PCNA) fusion protein

Nucleotide sequence (SEQ ID NO: 33)  // Nucleotide sequence (SEQ ID NO: 67)
Nucleotide sequence (SEQ ID NO: 34)  // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGAAAAGC CTGTCATAAG AATTTTCAAG      60
AAGGAAAACG GCGAGTTTAA GATTGAGTAC GACCGGACTT TTGAACCCTA CTTCTACGCC     120
CTCCTGAAGG ACGATTCTGC CATTGAGGAA GTCAAGAAGA TAACCGCCGA GAGGCACGGG     180
ACGGTTGTAA CGGTTAAGCG GGTTGAAAAG GTTCAGAAGA AGTTCCTCGG GAGACCAGTT     240
GAGGTCTGGA AACTCTACTT TACTCATCCG CAGGACXXXC CAGGATAAG  GGAACAAGATA   300
CGAGAGCATC CAGGAGTTAT TGACATCTAC GAGTACGACA TACCCTTCGC CAAGCGCTAC     360
CTCATAGACA AGGGATTAGT GCCAATGGAA GGCGACGAGG AGCTGAAAAT GCTCGCCTTC     420
GACATTGAAA CTCTCTACCA TGAGGGCGAG GAGTTCGCCG AGGGGCCAAT CCTTATGATA     480
AGCTACGCCG ACGAGGAAGG GGCCAGGGTG GAGGGAGATG ATAACCTTGA AGAACGTGGA     540
GTTGACGTCG TCTGCGACAG AGTTCTCAT  AACCTACACG GCGACAACT   TCTCCCCTAC    600
AAAGACCCGG ACGTTCTCAT AAAAAGCTCT GCCCTCGGAA GGCGACAACT TCGACTTCGC     660
AAGCGCTGTG AAAAGCTCGG AATAAACTTC GCCCTCGGAA GGGATGGAAAG CGAGCCGAAG     720
ATTCAGAGGA TGGGCGACAG GTTTGCCGTC GAAGTGAAGG GACGGATACA CTTCGATCTC     780
TATCCTGTGA TAAGACGGAC GATAAACCTG CCCACATACA CGCTTGAGGC CGTTTATGAA     840
GCCATTCTCG GTCAGCCGAA GGAGAAGGTT TACGCTGAGG AAATAACCAC AGCTCGGAA      900
ACCGGCGAGA ACCTTGAGAG AGTCGCCCGC TACTCGATGG AAGATGCGAA GGTCACATAC     960
```

FIGURE 17EE (CONT.)

```
GAGCTTGGGA AGGAGTTCCT TCCGATGGAG GCCCAGCTTT CTCGCTTAAT CGGCCAGTCC 1020
CTCGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA CAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG AGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGGCGTAA CGGCCTGGGG AAGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGACGTCGA GAAGGCCGTG 1860
GAGACGCAGG CGAGGGTTCT TGAAGCTTTG CTAAAGGACG AGTTCCGCC GGAGAAGCTG 1920
AGGATAGTCA AAGAAGTTAC CGAAAAGCTG AGCAAGTACG AGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT 2325
```

```
ATG CCA TTT GAA ATC GTA TTT GAA GGT GCA AAA GAG TTT GCC CAA CTT ATA GAC   54
ACC GCA AGT AGG TTA ATA GAT GAG GCC AGT AGA GTT GTC CTG ATT GAC TTA AAT CTC CCG  108
AGC ATG ATG AGG GCC ATG GAT AGA CCA AGT GAA GTT GAA CCA GAA ACA ATT GAC GTT AAC  162
TCA AGC ATA TTT AGC AAG ATC CTA AAG AGA GGT ATA AAG GCA ATT CAA GAC ACC TTA ATA  216
ATG GAC CAC TCA AAG GAG AAC TTC ATA GAT GTA GAG ATG GAA ACT CAA GGA CTC ACA  270
CTC AAG AAA TTT AGA GTT CCC CTA AAG GTT CTT GGA GAA GTC CTA AAA GAT GCT CCA  324
AGA ACA CTT CCA TTC ACT GCA TTC ACT GTG AGT GAC AGC ACC CAG GAA TTT ATT GCC AGG GAA AAT  378
GAA GTT AAA GAT GCC TCT CTA AAG GCA GAG GAA ACC CAG GTT AAA GAA GTT GAG ATA AAG CTA ACT  432
GAA TTT ATA ATG GCA GGA TTA CTC TTG GAC ATC GAG GTT AAA GGA CTT ATG AAG GCC GAT AGC GCA  486
CTT GAA GAT GAG AGC AGC TAT CTC TCC GAC ATG ATG ATG CCC ATG ACA AAG GAT TAC GAT GAT GAA  540
TAT GGA GTC ATA AAG TTT GGA AAT GAA TTC GGA CAA ATG ACA AAG TAT TAC ATT AGA  594
GTT ACA ATA AGG AGC TAT ACA TTC CTA CTG GCT CCA AGA GTT GAA GAG TGA  648
```

Figure 17FF

(PCNA) - KOD DNA POLYMERASE fusion protein

Nucleotide sequence (SEQ ID NO: 67) // Nucleotide sequence (SEQ ID NO: 33)
Nucleotide sequence (SEQ ID NO: 67) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC        54
ACC GCA AGT GAG AAG TTA ATA GAT GAT CCA AGT GCG TTT AAA GTT ACA GAA GAT GGG ATA       108
AGC ATG AGG GCC ATG GCG GAT CCA AGA AGA GTT AGG AAG GTT ACA GAA GAT GGG ATA       108
AGC ATG AGG GCC ATG GCG GAT CCA AGA AGA GTT AGG AAG GTT CTG ATT GAC AAT CTC CCG       162
TCA AGC ATA TTT AGC AAG TAT AAA ATC CTA AAG GTT GTT GAA CCA GAA ACA ATT GGA GTT AAC       216
ATG GAC CAC CTA AAG GAG GAA AAC TTC TTA GAG ATA GAG ATT CAA GGA ACT GCA ACA       270
CTC AAG GAA AAA TTT AGA GTT CCC CTA AAG GTT GTA GAA GAG ATG ATG GAC CTC CCA       324
AGA ACA TTT CCA GTT ACT GCA TTC ACT GTG TCT AGT GAC GAA GTC CTA AAA GAT GCT       378
GAA CTT AAA GAT GCC TCT CTA AAG GCA GAG GGA GAA ACC CAG AGC ATA TTT GCC AGG GAA AAT       432
GTT AAA TTT ATA ATG GAA GGA GAG TTA TTC CTC GAC TAT AAG ATA AAG CTA ACT       486
CTT GAA GAT GAG GTC AGC AGC TAT CTC TCC GAC CTG ATG ATG GAG GAG ACA AAG AGC GCA       540
TAT GGA GTC AGC AGT TAT CTC TCC GAC CTG ATG ATG GGA GAG AAG GCC GAT GAA       594
GTT ACA ATA AAG TTT GGA GAG AAT GAA ATG CCC ATG CAA ATG GAG TAT TAC ATT AGA       648
GAT GAA GGA AGA CTT ACA TTC CTA CTG CCA AGA GTT GAA GAG //                          702
```

```
ATGATCCCTCG ACACTGACTA CATAACCGAG GATGGAAAGC CTGTCATAAG AATTTTCAAG        60
AAGGAAAACG GCGAGTTTAA GATTGAGTAC GACCGGACTT TTGAACCCTA CTTCTACGCC       120
CTCCTGAAGG ACGATTCTGC CATTGAGGAA GTCAAGAAGA TAACCGCCGA GAGGCACGGG       180
ACGGTTGTAA CGGTTAAGCG GGTTGAAAAG GTTCAGAAGA AGTTCCTCGG GAGACCAGTT       240
GAGGTCTGGA AACTCTACTT TACTCATCCG CAGGACXXXC CAGGATAAG GGACAAGATA       300
CGAGAGCATC CAGCAGTTAT TGACATCTAC GAGTACGACA TACCCTTCGC CAAGCGCTAC       360
CTCATAGACA AGGGATTAGT GCCAATGGAA GGCGACGAGG AGCTGAAAAT GCTCGCCTTC       420
```

FIGURE 17FF (CONT.)

```
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT GGCGACAACT TCGACTTCGC CTATCTGAAA 660
AAGCGCTGTG AAAAGCTCGG AATAAACTTC GCCCTCGAA GGGATGGAAG CGAGCCGAAG 720
ATTCAGAGAGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTTCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG TACTACATTG AGAACCGTT CGACGAGTTC 2160
GACCCGACGA AGCACAAGTA CGACACGGAG TACTACATTG AGAACCAGGT TCTCCCAGCC 2220
GTTGAGAGAA TTCTGAGAGC CTTCGGTTAC CGGAAGGAAG ACCTGCGCTA CCAGAAGACG 2280
AGACAGGTTG GTTTGAGTGC TTGGCTGAAG CCGAAGGGAA CT //TAG 2325
```

FIGURE 17GG (PCNA)-Vent DNA POLYMERASE FUSION PROTEIN

Nucleotide sequence (SEQ ID NO: 67) // Nucleotide sequence (SEQ ID NO: 35)
Nucleotide sequence (SEQ ID NO: 67) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC   54
ACC GCA AGT TTA ATA GAT GAG CCA AGT GAA TTT AAA GTT ACA GAA GAT GGG ATA  108
AGC ATG AGG GCC ATG AGC AGT GAA AAA TAT GAC CTG ATT GAC CTA AAT CTC CCG  162
TCA AGC ATA TTT GAC AAA AAG AAG CTA GAA ATT GAA ACA AAG AAG GTT GTT AAC  216
ATG GAC CAC AAG GAG GAA GTT AAG AGA GGT ATA GCA ATT CAA GGA ACC TTA ATA  270
CTC AAG AAA GGA AGA GTT CCC CTA TTC ATA GAT GTA GAG ATG CAA CTC GCA ACA  324
AGA ACA TTT CCA TTC ACT GCA AAG GTT CTT CTT GGA GAA GTC GAC CTC AAA CCA  378
GAA CTT AAA GAT GCC TCT CTA GTG AGT GAC AGC ATA GTC ATT GCC AGG GAA AAT  432
GTT AAA GAT GCC TCT CTA GTG AGT GAC GAA ACC CAG GAA GTT ATT GAG AAG CTA ACT  486
GAA TTT ATA ATG AAG GCA TTA GGA GAA ATC GAG GTT CAA GAG GAG ACA AAG AGC GCA  540
CTT GAA GAT GAG GGA TTA TTG GAC ATG ATG GAG CTT AAA GGA CTT GGA AAG GCC GAT GAA  594
TAT GGA GTC AGC TAT CTC TCC GAC TAT TTT GGA CTT GGA AAG ATG CAA AAG GCC GAT GAA  648
GTT ACA ATA AAG TTT GGA AAT GAA ATG CCA GCT CTG CTA CTG CAA ATG GAG TAT TAC ATT AGA  702
GAT GAA GGA AGA CTT ACA TTC CTA CTG CTG GCT CTG AGA GTT GAA GAG //

ATGATACTGG ACACTGATTA CATAACAAAA GATGGCAAGC CTATAATCCG AATTTTTAAG    60
AAAGAGAACG GGGAGTTTAA AATAGAACTT GACCCTTCATT TTCAGCCCTA TATATATGCT  120
CTTCTCAAAG ATGACTCCGC TATTGAGGAG ATAAAGGCAA TAAAGGGCGA GAGACATGGA  180
AAAACTGTGA GAGTGCTCGA AGCTCATCTT TGCAGTGAAA AATTTTTGGG AAGGGAAGTT  240
GAAGTCTGGA AGCTCATTTT CGAGCATCCC CAAGCATGCG CAGCTATGCG GGGCAAAATA  300
AGGGAACATC CAGCTGTGGT TGACATTTAC TGACACAGACA TACCCTTTGC CAAGCGTTAT  360
CTCATAGACA AGGGCTTGAT TCCCATGGAG GGAGACGAGG AGCTTAAGCT CCTTGCTTT   420
GATATTGAAA CGTTTTATCA TGAGGAGAT GAATTTGGAA AGGGCGAGAT AATAATGATT  480
AGTTATGCCG ATGAAGAAGA GGCCAGAGTA ATCACATGGA AAAATATCGA TTTGCCGTAT  540
GTCGATGTTG TGTCCAATGA AAGAGAAATG ATAAAGCGTT TTGTTCAAGT TGTTAAAGAA  600
AAAGACCCCG ATGTGATAAT AACTTACAAT GGGGACAATT TTGATTTGCC GTATCTCATA  660
AAACGGGCAG AAAAGCTGGG AGTTCGGCTT GTCTTAGGAA GGGACAAAGA ACATCCCGAA  720
```

FIGURE 17GG (CONT.)

```
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGTTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TGTTATTCCT CCATACTCGG GGACTTAATT 1380
GCAATGAGGC AAGATATAAA GGCTATTAAA GAAGAAAATG ATGAAAAATG TTGACCCGAT CGAAAAGAAA 1440
ATGCTCGATT ATAGGCAAAG GGCTATTAAA TTGCTTGCAA ACAGCGTTAC CGGCTATATG 1500
GGGTATCCTA AGGCAAGATG GTACTCGAAG GAATGTGCTG AAAGCGTTAC CGGCTATATG 1500
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TGGAGTGAG 1860
ATAGCTAAGG GCAGGATAAC ACAAGGTTTTA GAGGCTATAC TTAAAGAGGG AAGTGTTGAA 1920
AAAGCTGTAG AGTTGTAG AGATGTTGTA GAGAAAATAG CAAAATACAG GGTTCCACTT 1980
GAAAAGCTTG TTATCCATGA GCAGATTACC AGGATTTAA AGGACTACAA AGCCATTGGC 2040
CCTCATGTCG CGATAGCAAA AGACTTGCC GCAAGAGGGA TAAAAGTGAA ACCGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGATACA GAAAGGAGGA TTTAAGGTAT 2280
CAAAGCTTCAA AACAAAACCGG CTTAGATGCA TGGCTCAAGA GGTAG 2325
```

Figure 17HH

Vent DNA POLYMERASE — (PCNA) FUSION PROTEIN

FIGURE 17HH (CONT.)

Nucleotide sequence (SEQ ID NO: 35) // Nucleotide sequence (SEQ ID NO: 67)
Nucleotide sequence (SEQ ID NO: 36) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
```

FIGURE 17HH (CONT.)

```
GATGAAGAGG GCAGGATAAC AACAAGGGC TTGGAAGTAG TAAGGAGAGA TTGGAGTGAG 1860
ATAGCTAAGG AGACTCAGGC AAAGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

ATG CCA TTT GAA ATC GTA TTT GAA GGT GCA AAA GAG TTT GCC CAA CTT ATA GAC   54
ACC GCA AGT AGG ATG GCC ATG GAT CCA AGT GAG GCG GTT GTT ACA GAA GAT AAT GGG ATA  108
AGC ATG AGG ATA TTT AGC GCC ATG AGC AAA TAT GAA AGT GAA CTG GTC ATT GAC ACA AAG CTC CCG  162
TCA AGC ATA TTT AAG ATA GAC AAG AAG GAA AAT CTA AAG ATC CTA AAG AGA GGT AAA GCA ATT GAC ACC GTT ATA  216
ATG GAC CAC CTA AAG GAG GAA TTC TTA GAG ATA GAT TTC CAA GGA ATG GAA CTC GCA ACA  270
CTC AAG ACA TTT AGA GTT CCC CTA AAG GTT CTT CTT GGA GTC CTA AAA GAT GCT  324
AGA ACA CTT CCA TTC ACT GCC TCT CTA GTG AGT GGA GAA AAA TTT ATT GCC AGG AAG AAT  378
GAA GTT AAA GAT GCC TCT CTA GTG AGT GGA GAA ATA CAG ACC GAG ATA AAG CTA ACT  432
GAA TTT ATA ATG AAG GGA TTA CTC TTG GAC ATC ATG GTT AAA GGA CTT AAA AGC GCA  486
CTT GAA GAT GAG AGC TAT CTC TCC GAC ATG ATG CCC ATG GGA CTT AAG GCC GAT GAA  540
TAT GGA GTC AGC TAT CTC TCC GAC AAT TTC ACA CTG GCT CAA ATG ATG CAA AGA GTT TAC ATT AGA  594
GTT ACA ATA AAG AGA GGA CTT ACA TTC GGA AAT TTC CTA CTG GCT CCA AGA GTT GAA GAG TGA  648
GAT GAA GGA AGA CTT ACA TTC GGA AAT TTC CTA CTG GCT CCA AGA GTT GAA GAG TGA  702
```

Figure 17II

Deep Vent- (PCNA) DNA polymerase fusion protein

FIGURE 17II (CONT.)

Nucleotide sequence (SEQ ID NO: 37) // Nucleotide sequence (SEQ ID NO: 67)
Nucleotide sequence (SEQ ID NO: 38) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
```

FIGURE 17II (CONT.)

```
AAGAAACCC AAGCAAAAGT CCTAGAGGCT ATCCTAAAGC ATGGCAACGT TGAGGAGGCA    1920
GTAAAGATAG TTAAGGAGGT AACTGAAAAG CTGAGCAAGT ACGAAATACC TCCAGAAAAG   1980
CTAGTTATTT ACGAGCAGAT CACGAGGCCC CTTCACGAGT ACAAGGCTAT AGGTCCGCAC   2040
GTTGCCGTGG CAAAAAGGTT AGCCGCTAGA GGAGTAAAGG TGAGGCCTGG CATGGTGATA   2100
GGGTACATAG TGCTGAGGGG AGACGGGCCA ATAAGCAAGA GGGCTATCCT TGCAGAGGAG   2160
TTCGATCTCA GGAAGCATAA GTATGACGCT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAG //                2328

ATG CCA TTT GAA ATC GTA TTT GAA GGT GCA AAA GAG TTT GCC CAA CTT ATA GAC    54
ACC GCA AGT AGG GCC ATG GAT CCA AGT GAT GAG AGT TTT AAA GTT ACA GAA GAT GGG ATA   108
AGC ATG AGG GCC ATG AGC ATA TTT GAC AAA TAT CCA AGT AGA GTT GTT AGA GTT GTC ATT GAC CTG ATT GAC ACA ATT GAC CTA AAT GGA CTC CCG   162
TCA AGC ATA TTT CTA AAG GAG ATC AAG GAG GAA AAC TTC TTA AAG GAG ATA AAG GCA ATT GAC ACC AAG GTT AAC    216
ATG GAC CAC AAA TTT CCA GTT CCC CTA AAG GTT ACT GCA TTC CTA GTG AGT GGA GAA ACC CAG GTT CAG GAG GAG ATG GAA TTT ATT GCC AGG GAA AAT    270
CTC AAG AAA GGA GAA GTT CCC CTA AAG GTT ACT GCA TTC CTA GTG AGT GGA GAA ACC CAG GTT CAG GAG GAG ATG GAA TTT ATT GCC AGG GAA AAT    324
AGA ACA TTT AGA TTC ACT GCC TCT CTA AAG GCA GGA GAA ATC GAG GTT AAA GGA CTT GGA ACA AAG AGC GCA    378
GAA CTT AAA GAT GCC TCT CTA GTG GAG GAC GAA ATC GAG GTT AAA GGA CTT GGA ACA AAG AGC GCA    432
GTT AAA GAT GCC TCT CTA GTG GAG GAC GAA ATC GAG GTT AAA GGA CTT GGA ACA AAG AGC GCA    486
GAA TTT ATA ATG AAG GCA TTA CTC TCC GAC ATG AGT GAA CAA ATG CAA ATG CCC ATG CAA ATG GAG TAT TAC ATT AGA    540
CTT GAA GAT GAG GGA TAT CTC TCC GAC ATG AGT GAA CAA ATG GAG CTT GGA CAA ATG GAG TAT TAC ATT AGA    594
TAT GGA GTC AGC AAG TTT GGA AAT GAA ATG CCC ATG CAA ATG GAG TAT TAC ATT AGA    648
GTT ACA ATA AAG TTT GGA AAT GAA ATG CCC ATG GCT CCA AGA GTT GAA GAG TGA    702
GAT GAA GGA AGA GTT ACA ATA AAG TTT GGA AAT GAA ATG CCC ATG GCT CCA AGA GTT GAA GAG TGA
```

Figure 17JJ (PCNA) - Deep Vent DNA polymerase fusion protein

Nucleotide sequence (SEQ ID NO: 67) // Nucleotide sequence (SEQ ID NO: 37)
Nucleotide sequence (SEQ ID NO: 67) // Nucleotide sequence (SEQ ID NO: 38)

FIGURE 17JJ (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC      54
ACC GCA AGT AAG TTA ATA GAT GAG GCC GCG TTT AAA GTT ACA GAA GAT GGG ATA     108
AGC ATG GCC ATG GAT CCA AGT AGA GTT GTT GAA CTG ATT GAC CTA AAT CTC CCG     162
TCA AGC ATA TTT AGC AAA TAT GAA GTT GTT GAA CCA GAA ACA ATT GGA GTT AAC     216
ATG GAC CAC CTA AAG GAG ATC CTA AAG AGA GGT AAA GCA AAT CAA GGA ACC TTA ATA 270
CTC AAG AAA GGA GAA AAC TTC ATA GAT GTA GAG ATA ACA ATT CAA GGA ACT GCA ACA 324
AGA ACA TTT AGA GTT CCC CTA AAG GTT CTA GTT CTT GGA GAA GTC CTA AAA GAT GCT 378
GAA CTT AAA GAT GCC TTC ACT GCA TCT CTA GTG AGT GAC GAA AGC ATA TTT GCC AGG GAA AAT 432
GTT ATA ATG AAG GCA GGA TTA AAG GGA TTA TTG GAC ATC GAG GTT CAA GAG GAG ATA AAG AAG CTA ACT 486
GAA TTT GAA GAT GAG AGC TAT CTC TCC GAC ATG GGA CTT GTT AAA GGA CTT GGA AAG GCC GAT GAA 540
CTT GAA GAT GAG AGC TAT CTC TCC GAC ATG GGA CTT GTT AAA GGA CTT GGA AAG GCC GAT GAA 594
TAT GGA GTC AGC TAT CTC TCC GAC ATG GAA ATG GGA TAT TTT GGA AAT GAA ATG GGA TAT TAC ATT AGA 648
GTT ACA ATA AAG AGA AGA CTT ACA TTC CTA CTG GCT AGA GTT GAA GAG //              702
GAT GAA GGA AGA AGA CTT ACA TTC CTA CTG GCT AGA GTT GAA GAG //
```

```
ATGATACTTG ACGCTGACTA CATCACCGAG GATGGGAAGC CGATTATAAG GATTTTCAAG              60
AAAGAAAACG GCGAGTTTAA GGTTGAGTAC GACAGAAACT TTAGACCTTA CATTTACGCT             120
CTCCTCAAAG ATGACTCGCA GATTGATGAG GTTAGGAAGA TAACCGCCGA GAGGCATGGG             180
AAGATAGTGA GAATTATAGA TGCCGAAAAG GTAAGGAAGA AGTTCCTGGG GAGGCCGATT             240
GAGGTATGGA GGCTGTACTT TGAACACCCT CAGGACXXXC TTCCGTTCGC GGATAAGATA             300
AGAGAGCATT CCGCAGTTAT TGACATCTTT GAGTACGACA AGCTCAAGTT GCTCGCATTT             360
CTAATAGACA AAGGCCTAAT TCCAATGGAA GGCGATGAAG AGGGCCCAT TATAATGATA              420
GACATAGAAA CCCTCTATCA CGAAGGGGAG GAGTTCGCGA AAAAGATCGA TCTCCCGTAC             480
AGCTATGCTG ATGAGGAAGA AGCCAAAGTC ATAAACGTGT TCCTCAAGGT GATAAGGGAG             540
GTCGAGGTAG TTTCCAGCGA GAGGGAGATG ATAAAGCGGT TCCTCAAGGT CTATCTAGTT             600
AAAGATCCCG ATGTTATAAT TACCTACAAC GGCGATTCTT TCGACCTTCC CTATCTAGTT             660
AAGAGGCCCG AAAAGCTCGG GATAAAGCTA CCCCTGGGAA GGGACGGTAG TGAGCCAAAG             720
ATGCAGAGGC TTGGGGATAT GACAGCGGTG GAAGGATACA CTTTGACCTC AGTTTATGAG             780
TACCACGTGA TTAGGAGAAC GATAAACCTC CCAACATACA CCCTCGAGGC AGTTTATGAG             840
GCAATCTTCG GAAAGCCAAA GGAGAAAGTT TACGCTCACG AGATAGCTAA GGCCTGGGAG             900
ACTGAGAGAG GACTGGAGAG AGTTGCAAAG TATTCAATGG AGGATGCAAA GGTAACGTAC             960
GAGCTCGGTA GGGAGTTCTT CCCAATGGAG GCCCAGCTTT CAAGGTTAGT CGGCCAGCCC            1020
```

FIGURE 17JJ (CONT.)

```
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAGA TAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGAA 1560
TATATAGAGT TCGTAAGGAA GGAACTGGAA GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGTT AGCCGCTAGA GGAGTAAAGG TGAGGCCTGG CATGGTGATA 2100
GGGTACATAG TGCTGAGGGG AGACGGGCCA ATAACAAGA GGGCTATCCT TGCAGAGGAG 2160
TTCGATCTCA GGAAGCATAA GTATGACGCT GAGTATTACA TAGAAAATCA GGTTTTACCT 2220
GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAG TAA              2328
```

Figure 17KK

JDF-3 – (PCNA) fusion protein

Nucleotide sequence (SEQ ID NO: 39) // Nucleotide sequence (SEQ ID NO: 67)
Nucleotide sequence (SEQ ID NO: 40) // Nucleotide sequence (SEQ ID NO: 67)

FIGURE 17KK (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTTGACGTTGATTACATCACCGAGAATGAAAGCC

FIGURE 17KK (CONT.)

```
GTT ACA ATA AAG TTT GGA AAT GAA ATG CCC ATG CAA ATG GAG TAT TAC ATT AGA
GAT GAA GGA AGA CTT ACA TTC CTA CTG GCT CCA AGA GTT GAA GAG TGA              702
```

Figure 17LL (PCNA) - JDF-3 fusion protein

Nucleotide sequence (SEQ ID NO: 67)  // Nucleotide sequence (SEQ ID NO: 39)
Nucleotide sequence (SEQ ID NO: 67)  // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC       54
ACC GCA AGT AAG TTA ATA GAT GAG GCC GCG TTT AAA GTT ACA GAA GAT CTC CCG      108
AGC ATG AGG GCC ATG GAT CCA AGT GTC CTG ATT GAC ACA AAG CTA AAT CTC AAC      162
TCA AGC ATA TTT AGC AAA TAT ATC GAA CCA GTT GTT GAA GCA ATT GAC ACC ATA      216
ATG GAC CAC AAA AAG GAG GAA AAC TTC CTA AAG AGA ATA GAG ATT CAA GGA GTT      270
CTC AAG ACA TTT AGA GTT CCC CTA AAG GTT TTA GAT GTA GAA ATG ACT GAC CTC CCA  324
AGA ACA CTT CCA TTC ACT GCA CTA GTG GAG GTT CTT GGA GAA GTC CTA AAA GAT GCT  378
GAA CTT AAA GAT GCC TCT CTT AAG GCA GGA GAA ACC CAG AGC TTT ATT GCC AGG GAA AAT 432
GAA TTT ATA ATG GAG GGA TTA TTG GAC ATC GAG GTT CAA GAG ATA AAG CTA ACT      486
CTT GAA GAT GAG AGC TAT CTC TCC GAC ATG GTT AAA GGA CTT GGA AAG GCC GAT GAA  540
TAT GGA GTC AGC TAT CTC TCC GAC ATG GTT AAA GGA CTT GGA AAG GCC GAT GAA      594
GTT ACA ATA AAG TTT GGA AAT GAA ATG CCC ATG CAA ATG GAG TAT TAC ATT AGA      648
GAT GAA GGA AGA CTT ACA TTC CTA CTG GCT CCA AGA GTT GAA GAG   //             702
```

```
ATGATCCTTGACGTTGATTACATCACCGAGAATGAAAGCCCGTCATCAGGGTCTTCAAGAAGGAAGAAGGAGAACGGCGAGTTCAGGATTGAATACGACCCGCGAGTTCGAGCC
CTACTTCTACGCGCTCCTCGGACGAGTCTGCCATCGAAGAAATCAAAAAGATAACCGGGAGGAGGCACGGCAGGTCGTTAAGGTTAAGCGGCGGAGAAGGTGA
AGAAAAGTTCCTCGGCAGGTCGTGAGGTCTGTGAGGTCGGAGCACXXXCCGGACAATCCGCAGGACXXXCCGACACCCGACAAATAAGGAAGCACCCGCGGTCATC
GACATCTACGAGTACGACATACCCTTCGCCAAGGACTACAGAAAGAAGACAAGGGCCTAATCCCGATGGAAGGTGAGGAAGAGCTTAAACTCATGTCCTTCGACATGA
[G]ACGCTCTACCACGAGGGAGAAGAGTTTGGAACCGGGCCGATTCTGATGATAAGCTACGCCGATGAATAAGCGAGGCGCGTGATAACCTGAATAACCTGGAAGAATCGACCTTC
```

FIGURE 17LL (CONT.)

CTTACGTTGAGGTTGTCTCCACCGAGAAGGAGATGATTAAGCGCTTCTTGAGGGTCGTTAAGGAGAAGGACCCGACGTGCTGATAACATACAACGGCGACAACTTC
GACTTCGCCTACCTGAAAAAGCGCTGTGAGAAGCGCTGGCGTGAGCTTTCGACCTTTATCGACTTCAGTCATAAGGCGCACCATAAACCTCCCGACCTACACCCTTGAGGCTGTATACGAGGCGGTTTTCGCAAGC
CGAGGTGAAGGGCAGGGTACACTTCGACCTTTATCGACTTCAGTCATAAGGCGCACCATAAACCTCCCGACCTACACCCTTGAGGCTGTATACGAGGCGGTTTTCGCAAGC
CCAAGGAGAAGGTCTACGCCGAGGAGATAGCCACCGCCCTGAGGGGCTTGAGAGGGTCGCGCGCTACTCGATGAGGACCGGAGGGTTACCTACGAG
CTTGGCAGGGAGTTCTTCCCGATGGAGGCCGAGCTCGTCATCGGCAAGGCCTCATCGGCGACGTTTCCCGCTCTCGGACGTTTCCCGACCACCGGCAACCTCGTCGAGTGGTTCCT
CCTAAGGAAGGCCTACGACGTGGGACAATATCGTGTATCTAGACTTCGTAGTCTCTAC[CCT]CAATCATAATCACCCACAACGTCTCGCCAGATACGCTCAACCGCGAGGGTGT
AGCGGGGACTGTGGGACAATATCGTGTATCTAGACTTCGTAGTCTCTAC[CCT]CAATCATAATCACCCACAACGTCTCGCCAGATACGCTCAACCGCGAGGGTGT
AGGAGCTACGACGTTGCCCCCGAGGTCGGTCACCCGCTGGAGAAGCAACTCTCGACCCGCTGGAGAAGAATCTCCTCGATTACAGGCAACG[GC]ATCAAGATTCTCGCCAACAGCTACTACGGCTACTACGGCTATG
GAGGAAGATGAAGGCAACTCTCGACCCGCTGGAGAAGAATCTCCTCGATTACAGGCAACG[GC]ATCAAGATTCTCGCCAACAGCTACTACGGCTACTACGGCTATG
CCAGGGCAAGATGGTACTGCAGGGAGTGCGCCAGAGACGGTCTCCATGCCACCATTCTCGGAGCGGACGCTGAAACAGTCAAGAAAAAGGCAATGGTCATCAGAGAGTTCTTAAACTATATCAATCCAAACT
GTCCTCTATGCAGACAGACGGTCTCCATGCCACCATTCTCGGAGCGGACGCTGAAACAGTCAAGAAAAAGGCAATGGTCATCAGAGAGTTCTTAAACTATATCAATCCAAACT
GCCCGGCCTTCTCGAACTCGAATACGAGGGCTTCTACGTCAGGGGCTTCTCGTCACGAAGAGAAGTACGCGGTCATCACGAGGAGGGCAAGATAACCACGCGCG
GGCTTGAGATAGTCAGGCGCGACTGGAGCGCAGTGAGGAGATAGCCAAGGAGATACGAGGTTCCGCCGAGAAGCTGTTATCCACGACGCAGATAACGGCGGAGCTCAAGGACTACAAGGCCACCGGCCG
GTCAGGGAAGTCACCGAAAAGCGAAgCGTTTGGCCCGACAAGCTGAGCAAGTTCCGCCGAGAAGCTGTTATCCACGACGCAGATAACGGCGGAGCTCAAGGACTACAAGGCCACCGGCCG
GCACGTAGCCATAGCGGAAgCGTTTGGCCCGACAAGCTGAGCAAGTTCCGCCGAGAAGCTGTTATCCACGACGCAGATAACGGCGGAGCTCAAGGACTACAAGGCCACCGGCCG
CGATTCCCTTCGACGAGTTCGACCCGACGAAGACACAAGTACGATGCGAACTACAAGGTTCTGCCGGCAGTTGAGAGAATCCTTGAGGGCCTTCGGC
TACCGCAAGGAAGACCTGCGCTACCAGAAGACGAGGCAGGTCGGGCTTGGCGCGTGGCTGA

Figure 17MM

Sac7d gene (ACCESSION No: M87569)

Nucleotide sequence (SEQ ID NO: 69)
Amino acid sequence (SEQ ID NO: 70)

```
  M   V   K   V   K   F   K   Y   K   G   E   E   K   E   V   D   T   S       18
 ATG GTG AAG GTA AAG TTC AAG TAT AAG GGT GAA GAG AAA GAA GTA GAC ACT TCA       54

K   I   K   K   V   W   R   V   G   K   M   V   S   F   T   Y   D   D       36
 AAG ATA AAG AAG GTT TGG AGA GTA GGC AAA ATG GTG TCC TTT ACC TAT GAC GAC      108

N   G   K   T   G   R   G   A   V   S   E   K   D   A   P   K   E   L       54
 AAT GGT AAG ACA GGT AGA GGA GCT GTA AGC GAG AAA GAT GCT CCA AAA GAA TTA      162

L   D   M   L   A   R   A   E   R   E   K   K   *                           67
 TTA GAC ATG TTA GCA AGA GCA GAA AGA GAG AAG AAA TAA                          201
```

Figure 17NN

Sac7d-Taq DNA polymerase fusion protein

Nucleotide sequence (SEQ ID NO: 69) // Nucleotide sequence (SEQ ID NO: 65)
Amino acid sequence (SEQ ID NO: 70) // Amino acid sequence (SEQ ID NO: 66)

```
  M   V   K   V   K   F   K   Y   K   G   E   E   K   E   V   D   T   S
 ATG GTG AAG GTA AAG TTC AAG TAT AAG GGT GAA GAG AAA GAA GTA GAC ACT TCA

K   I   K   K   V   W   R   V   G   K   M   V   S   F   T   Y   D   D
 AAG ATA AAG AAG GTT TGG AGA GTA GGC AAA ATG GTG TCC TTT ACC TAT GAC GAC

N   G   K   T   G   R   G   A   V   S   E   K   D   A   P   K   E   L
 AAT GGT AAG ACA GGT AGA GGA GCT GTA AGC GAG AAA GAT GCT CCA AAA GAA TTA
```

FIGURE 17NN (CONT.)

```
L   D   M   L   A   R   A   E   R   E   K   K  //
TTA GAC ATG TTA GCA AGA GCA GAA AGA GAG AAG AAA //

G       G
//  GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   Y   G   F   A   K   S   L   L   K
AGC CGG GGG GAG CCG GTG CAG GCG GTC TAC GGC TTT GCC AAG AGC CTC CTC AAG

A   L   K   E   D   G   D   A   G   L   A   I   K   D   A   K   A   P
GCC CTC AAG GAG GAC GGG GAC GCG GGG CTC GCC ATC AAG GAC GCC AAG GCC CCC

S   F   R   H   E   A   Y   L   Y   G   L   A   R   G   V   D   L   P
TCC TTC CGC CAC GAG GCC TAC CTC TAC GGG CTC GCC CGG GGC GTG GAC CTC CCC

E   D   F   P   R   Q   L   V   P   G   E   A   D   V   L   I   L   G
GAG GAC TTT CCC CGG CAA GTC CCG GGC GAG GCG GAC GTC CTG ATC CTG GGG

L   A   R   L   E   A   E   Y   Y   R   I   L   H   P   E   G   Y
CTG GCG CGC CTC GAG GCG GAG TAC TAC CGC ATC CTC CAC CCC GAG GGG TAC

A   K   K   A   K   L   L   S   D   R   H   V   L   H   P   E   G   Y
GCC AAG AAG GCG AAG CTC TTC TCC GAC CGC CAC GTC CTC CAC CCC GAG GGG TAC

D   L   Y   Q   L   L   W   E   K   Y   G   L   R   P   D   Q   W   K
GAC CTT TAC CAG CTC CTT TGG GAA AAG TAC GGC CTG AGG CCC GAC CAG TGG AAA

L   I   T   P   A   W   L   T   G   D   E   S   D   N   L   P   G   V
CTC ATC ACC CCG GCC TGG CTT ACT GGG GAT GAA TCA GAC AAT CTG CCC GGG GTG

```
G    I    G    E    T    A    R    K    L    E    W    G    S    L    E
GCC  GAC  TAC  CGG  GCC  CTG  ACC  GGG  GAC  GAG  TCC  GAC  AAC  CTT  CCC  GGG  GTC  AAG
A    L    L    K    N    L    D    R    L    K    P    A    I    R    E    K    I    L
GCC  CTC  CTC  AAG  AAC  CTG  GAC  CGG  CTG  AAG  CCC  GCC  ATC  CGG  GAG  AAG  ATC  CTG
A    H    M    D    D    L    K    L    S    W    D    L    A    K    V    R    T    D
GCC  CAC  ATG  GAC  GAT  CTG  AAG  CTC  TCC  TGG  GAC  CTG  GCC  AAG  GTG  CGC  ACC  GAC
L    P    L    E    V    D    F    A    K    R    R    E    P    D    R    E    R    L
CTG  CCC  CTG  GAG  GTG  GAC  TTC  GCC  AAA  AGG  CGG  GAG  CCC  GAC  CGG  GAG  AGG  CTT
R    A    F    L    E    R    L    E    F    G    S    L    H    P    L    G    L
AGG  GCC  TTT  CTG  GAG  AGG  CTT  GAG  TTT  GGC  AGC  CTC  CAC  CCC  CTC  GGC  CTT
L    E    S    P    K    A    L    E    E    E    A    P    W    P    P    E    G    A
CTG  GAA  AGC  CCC  AAG  GCC  CTG  GAG  GAG  GAG  GCC  CCC  TGG  CCC  CCG  GAA  GGG  GCC
F    V    G    F    V    L    S    R    K    E    M    P    W    A    D    P    L    A
TTC  GTG  GGC  TTT  GTG  CTT  TCC  CGC  AAG  GAG  ATG  CCC  TGG  GCC  GAT  CTT  CTG  GCC
L    A    A    A    R    G    G    R    G    R    A    P    E    P    Y    K    A
CTG  GCC  GCC  GCG  AGG  GGC  GGC  CGG  CGG  GCC  CCC  GAG  CCC  TAT  AAA  GCC
L    R    D    L    K    E    A    R    G    L    L    A    K    D    L    S    V    L
CTC  AGG  GAC  CTG  AAG  GAG  GCG  CGG  GGG  CTT  CTC  GCC  AAA  GAC  CTG  AGC  GTT  CTG
A    L    R    E    G    L    P    P    G    P    P    D    D    P    M    L    L    A
GCC  CTG  AGG  GAA  GGC  CTT  CCC  CCG  GGC  CCC  CCC  GAC  GAC  CCC  ATG  CTC  CTC  GCC
Y    L    D    P    S    N    T    T    P    E    G    V    A    R    R    Y    G
TAC  CTC  CTG  GAC  CCT  TCC  AAC  ACC  ACC  CCC  GAG  GGG  GTG  GCC  CGG  CGG  TAC  GGC
G    E    W    T    E    E    A    G    E    R    A    A    L    S    E    R    L    F
GGG  GAG  TGG  ACG  GAG  GAG  GCG  GGG  GAG  CGG  GCC  GCC  CTT  TCC  GAG  AGG  CTC  TTC
```

FIGURE 17NN (CONT.)

```
A   N   L   W   G   R   L   E   G   E   E   R   L   W   L   Y   R
GCC AAC CTG TGG GGG AGG CTT GAG GGG GAG GAG AGG CTC CTT TGG TAC CGG

E   V   E   R   P   L   Y   A   E   A   H   M   E   A   T   G   V
GAG GTG GAG AGG CCC CTT TAT GCC GAG GCC CAC ATG GAG GCC ACG GGG GTG

R   L   D   R   A   Y   A   E   L   S   A   L   B   V   A   E   I
CGC CTG GAC CGC GCT TAT GCC GAG CTG TCC GCC CTG GAG GTG GCC GAG ATC

A   R   L   E   A   R   L   R   A   G   L   A   A   E   V   A   N
GCC CGC CTC GAG GCC AGG CTC CGC GCC GGC CTG GCC GCC GAG GTG GCC AAC

S   R   D   Q   L   E   V   F   D   L   F   S   T   D   P   N   I
TCC CGG GAC CAG CTG GAA CTC TTT GAC CTA TTT TCC ACC GAC CCC AAC ATC

G   K   E   L   G   K   R   V   K   E   S   I   Q   L   E   B   A
GGC AAG GAG CTG GGC AAG CGC GTC AAG GAG TCC ATC CAG CTG GAG GAG GCC

L   H   P   A   I   V   E   V   L   Q   D   L   I   T   R   L   T
CTC CAC CCC GCC ATC GTG GAG GTG CTG CAG GAC CTC ATC ACG CGG CTC ACC

K   S   T   H   P   Y   I   D   P   L   T   A   T   P   R   T   T
AAG AGC ACC CAC CCC TAC ATC GAC CCG TTG ACG GCC ACC CCC AGG AGG ACG

G   H   T   R   F   N   F   Q   A   E   V   W   P   L   R   S   T
GGC CAC ACC CGC TTC AAC TTC CAG GCC GAG GTC TGG CCC CTT GGG CTA AGT

S   P   N   L   A   E   V   D   G   H   L   A   D   E   N   Q   R
AGC CCC AAC CTC GCC GAG GTG GAC GGC CAC CTC GCC GAC GAG AAC CAG AGG

I   A   F   T   T   R   L   H   I   A   V   L   A   E   L   D   Y
ATC GCC TTC ACC ACC CGC CTC CAC ATC GCC GTG CTA GCC GAG CTG GAC TAT

S   Q   L   I   R   R   L   S   G   A   H   L   S   T   A   N   L   I
AGC CAG CTC ATC CGC AGG CTC TCC GGC GCC CAC CTC TCC ACC GCC AAC CTG ATC

R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC
```

FIGURE 17NN (CONT.)

```
G    V    P    R    E    A    V    D    P    L    M    R    R    A    A    K    T    I
GGC  GTC  CCC  CGG  GAG  GCC  GTG  GAC  CCC  CTG  ATG  CGG  CGC  GCC  GCC  AAG  ACC  ATC

N    F    G    V    L    Y    G    M    S    A    H    R    L    S    Q    E    L    A
AAC  TTC  GGG  GTC  CTC  TAC  GGC  ATG  TCG  GCC  CAC  CGG  CTC  TCC  CAG  GAG  CTA  GCC

I    P    Y    E    E    A    Q    A    F    I    E    T    L    R    Q    S    F    P
ATC  CCT  TAC  GAG  GAG  GCC  CAG  GCC  TTC  ATT  GAG  ACC  CTG  CGC  CAG  AGC  TTC  CCC

K    V    R    A    W    I    E    K    R    R    E    G    R    R    R    A    G    Y
AAG  GTG  CGG  GCC  TGG  ATT  GAG  AAG  CGC  CGC  GAG  GGC  AGG  AGG  CGG  GCC  GGG  TAC

V    E    T    L    F    G    R    A    A    E    L    D    P    V    Q    A    R    V
GTG  GAG  ACC  CTC  TTC  GGC  CGG  GCG  GCC  GAG  CTA  GAC  CCA  GTG  CAG  GCC  CGG  GTG

K    S    V    R    E    A    L    M    R    Y    N    F    A    V    Q    P    Q    G
AAG  AGC  GTG  CGG  GAG  GCG  CTG  ATG  CGC  TAC  AAC  TTC  GCC  GTG  CAG  CCC  CAG  GGC

T    A    A    D    L    K    L    L    A    M    V    K    L    F    R    P    L    E
ACC  GCC  GCC  GAC  CTC  AAG  CTG  CTT  GCT  ATG  GTG  AAG  CTC  TTC  CGC  CCC  CTG  GAG

E    M    G    A    R    A    V    Q    H    D    E    L    D    E    L    V    E    A
GAA  ATG  GGG  GCC  AGG  GCG  GTG  CAG  CAC  GAC  GAG  CTG  GTC  GAG  CTC  GAG  GAG  GCC

P    K    R    E    R    A    V    A    R    L    A    K    E    V    M    E    G
CCA  AAA  GAG  AGG  GAG  GCG  GTG  GCC  CGG  CTG  GCC  AAG  GAG  GTC  ATG  GAG  GGG

V    Y    P    L    A    V    P    L    E    V    G    I    G    E    D    W
GTG  TAT  CCC  CTG  GCC  GTG  CCC  CTG  GAG  GTG  GGG  ATA  GGG  GAG  GAC  TGG

L    S    A    K    E    G    R    D    G    G    G    G    H    H    H    H
CTC  TCC  GCC  AAG  GAG  GGG  CGC  GAT  GGC  GGA  GGC  GGG  CAT  CAT  CAT  CAT

H    H    *
CAT  CAT  TAA
```

Figure 170O

Taq DNA polymerase- Sac7d fusion protein

Nucleotide sequence (SEQ ID NO: 65) //Nucleotide sequence (SEQ ID NO: 69)
Amino acid sequence (SEQ ID NO: 66) /Amino acid sequence (SEQ ID NO: 70)

```
              G   G   G
          // GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

A   L   K   E   D   G   D   A   V   I   V   F   D   A   K   A   P
GCC CTC AAG GAG GAC GGG GAC GCG GTG ATC GTG GTC TTT GAC GCC AAG GCC CCC

S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA
```

FIGURE 1700 (CONT.)

```
D    L    Y    Q    L    S    D    R    I    H    V    L    H    P    E    G    Y
GAC  CTT  TAC  CAG  CTC  TCC  GAC  CGC  ATC  CAC  GTC  CTC  CAC  CCC  GAG  GGG  TAC

L    I    T    P    A    W    L    T    G    K    Y    W    E    P    D    Q    W
CTC  ATC  ACC  CCG  GCC  TGG  CTT  ACC  GGG  AAG  TAC  TGG  GAA  CCC  GAC  CAG  TGG

A    D    Y    R    A    L    T    A    R    G    D    E    S    P    G    V    K
GCC  GAC  TAC  CGG  GCC  CTG  ACC  GCG  GGG  GAC  GAG  TCC  CCC  GGG  GTC  AAG

G    I    G    E    K    W    E    D    E    S    K    L    E
GGG  ATC  GGG  GAG  AAG  TGG  GAA  GAC  GAG  AGC  AAG  CTG  GAA

A    L    N    L    D    R    K    L    K    P    A    I    L
GCC  CTC  AAC  CTG  GAC  CGG  AAG  CTT  AAG  CCC  GCC  ATC  CTG

A    H    M    D    K    L    S    W    D    L    A    K    V    R    T    D
GCC  CAC  ATG  GAC  AAG  CTG  TCC  TGG  GAC  CTG  GCC  AAG  GTG  CGC  ACC  GAC

L    P    L    E    D    V    F    A    K    R    E    P    D    R    B    L
CTG  CCC  CTG  GAG  GAT  GTG  TTC  GCC  AAA  AGG  GAG  CCC  GAC  CGG  GAG  CTT

R    A    F    S    R    D    F    L    E    A    E    H    P    P    E    G    L
AGG  GCC  TTT  AGC  AGG  GAC  TTT  CTT  GAG  GCC  GAG  CAC  CCG  CCG  GAA  GGC  CTT

L    E    S    P    K    V    L    S    R    E    K    P    M    W    A    P    Y    K    A
CTG  GAA  AGC  CCC  AAG  GTG  CTT  TCC  CGC  GAG  AAG  CCC  ATG  TGG  GCC  CCT  TAT  AAA  GCC

F    V    G    F    A    R    G    R    R    V    H    R    A    P    E    D    L    S    V    L
TTC  GTG  GGC  TTT  GCC  GCG  GGG  CGG  CGG  GTC  CAC  CGG  GCC  CCC  GAG  GAT  CTG  AGC  GTT  CTG

L    A    A    R    G    G    E    A    P    H    R    L    L    A    D    P    M    L    A
CTG  GCC  GCC  AGG  GGG  GGC  GAG  GCC  CCC  CAC  CGG  CTC  CTC  GCC  GAC  CCC  ATG  CTC  GCC

L    R    D    L    K    E    R    G    R    R    G    P    L    L    E    G    D    D    P    L    A
CTC  AGG  GAC  CTG  AAG  GAG  CGG  GGG  CGG  CGG  GGG  CCT  CTT  CTC  GAG  GGG  GAC  GAC  CCC  CTG  GCC

A    L    R    E    G    L    G    L    P    P    G    D    D    P    M    L    L    A
GCC  CTG  AGG  GAA  GGC  CTT  GGC  CTC  CCG  CCC  GGC  GAC  GAC  CCC  ATG  CTC  CTC  GCC
```

FIGURE 1700 (CONT.)

```
Y   G   A   E   V   G   T   T   P   E   G   V   A   R   R   Y   G
TAC GGG GCC GAG GTG GGG ACC ACC CCC GAG GGG GTG GCC CGG CGC TAC GGC

L   E   N   V   L   E   E   R   P   G   A   L   E   L   R   L   F
CTC GAG AAC GTG CTG GAG GAG AGG CCC GGG GCG CTT GAG CTC AGG CTC TTC

D   T   L   E   P   G   A   V   L   G   A   L   S   E   A   R   L
GAC ACG CTG GAG CCT GGG GCG CTT CTT GGG GCC CTT TCC GAG GCC AGG CTT

P   E   W   E   R   A   V   L   E   R   E   M   L   V   L   Y   Y
CCT GAG TGG GAG AGG GCC GTC CTG GAG AGG GAG ATG CTT GTG CTC TAC TAC

S   E   G   R   P   Y   A   R   M   H   L   A   L   V   W   L   R
TCC GAG GGG AGG CCC TAT GCC CGC ATG CAC CTG GCC CTT GTC TGG CTC CGG

N   A   L   V   A   E   R   L   E   A   A   H   M   E   L   Y   V
AAC GCC CTG GTG GCC GAG AGG CTG GAG GCC GCC CAC ATG GAG CTC TAC GTG

T   G   S   E   B   G   A   R   A   S   L   D   E   V   P   A   I
ACC GGG TCC GAG GAG GGG GCC AGG GCT TCC CTG GAC GAG GTG CCC GCC ATC

T   E   E   R   B   A   A   H   M   L   A   H   L   E   A   R   N
ACC GAG GAG AGG GAG GCG GCG CAC ATG CTG GCC CAC CTG GAG GCC CGC AAC

P   B   G   R   V   L   S   R   V   L   A   L   G   E   L   E   L
CCC GAG GGG AGG GTG CTT TCC AGG GTC CTC GCC CTA GGG GAG CTC GAG CTC

E   S   D   E   B   L   E   F   R   V   L   D   A   A   Y   L   A
GAG TCC GAC GAG GAG CTG GAG TTC CGG GTC CTA GAC GCC GCC TAC GCC GCC

T   G   K   E   B   V   K   R   V   R   S   T   K   I   Q   L   T
ACG GGG AAG GAG GAG GTG AAG CGG GTC CGG AGC ACC AAG ATC CAG CTG ACC

H   A   E   P   L   I   V   I   P   D   L   P   H   R   H   P   T
CAC GCC GAG CCC CTT ATC GTG ATC CCC GAC CTC CCC CAC CGG CAC CCC ACC

S   H   S   T   Y   T   I   P   I   D   P   A   T   A   T   G   T
AGC CAC AGC ACC TAC ACC ATT CCC ATC GAC CCC GCC ACG GCC ACG GGC ACG

R   L   R   T   R   F   N   Q   N   H   P   V   R   H   G   R   S
CGC CTC CGC ACC CGC TTC AAC CAG AAC CAC CCC GTC CGC CAC GGC AGG CTA

D   P   N   D   P   N   H   Q   I   P   A   V   R   P   G   L   R
GAT CCC AAC GAT CCC AAC ATC CAG ATC CCG GCC GTC CGC ACC CCG CTT GGG CAG AGG

```
S    I    R    A    F    I    R    A    V    L    S    G    D    E    N    L    I
AGC  ATA  CGC  GCC  TTC  ATC  GCC  GAG  GGG  CTA  TTG  GTG  GCC  CTG  GAC  TAT
                                                                   N    L    I
                                                                   AAC  CTG  ATC

R    V    F    Q    E    L    V    R    G    E    G    W    S    T    A    W    M    F
CGG  GTC  TTC  CAG  GAG  CTC  GTG  AGG  GGG  GAG  GGG  TGG  TCC  ACC  GCC  TGG  ATG  TTC

G    V    P    R    E    A    V    D    R    A    V    H    I    H    T    E    A    K    T    I
GGC  GTC  CCC  CGG  GAG  GCC  GTG  GAC  CGG  GCG  GTG  CAC  ATC  CAC  ACG  GAG  GCC  AAG  ACC  ATC

N    F    G    V    L    Y    G    M    S    A    H    R    L    S    Q    E    L    A
AAC  TTC  GGG  GTC  CTC  TAC  GGC  ATG  TCG  GCC  CAC  CGC  CTC  TCC  CAG  GAG  CTA  GCC

I    P    Y    E    E    A    Q    A    F    I    E    R    Y    F    Q    S    F    P
ATC  CCT  TAC  GAG  GAG  GCC  CAG  GCC  TTC  ATT  GAG  CGC  TAC  TTT  CAG  AGC  TTC  CCC

K    V    R    A    W    I    E    K    R    R    E    E    G    R    R    R    G    Y
AAG  GTG  CGG  GCC  TGG  ATT  GAG  AAG  CGC  CGC  GAG  GAG  GGC  AGG  CGG  AGG  GGG  TAC

V    E    T    L    F    G    R    R    R    Y    V    P    D    L    E    A    R    V
GTG  GAG  ACC  CTC  TTC  GGC  CGC  CGC  CGC  TAC  GTG  CCA  GAC  CTA  GAG  GCC  CGG  GTG

K    S    V    R    E    A    A    E    R    M    A    F    N    M    P    V    Q    G
AAG  AGC  GTG  CGG  GAG  GCG  GCC  GAG  CGC  ATG  GCC  TTC  AAC  ATG  CCC  GTC  CAG  GGC

T    A    A    D    L    M    K    L    A    M    V    K    L    F    P    R    L    E
ACC  GCC  GCC  GAC  CTC  ATG  AAG  CTG  GCT  ATG  GTG  AAG  CTC  TTC  CCC  AGG  CTG  GAG

E    M    G    A    R    M    L    L    Q    V    H    D    E    L    V    L    E    A
GAA  ATG  GGG  GCC  AGG  ATG  CTG  CTT  CAG  GTC  CAC  GAC  GAG  CTG  GTC  CTC  GAG  GCC

P    K    E    R    A    E    A    V    A    R    L    A    K    E    V    M    E    G
CCA  AAA  GAG  AGG  GCG  GAG  GCC  GTG  GCC  CGG  CTG  GCC  AAG  GAG  GTC  ATG  GAG  GGG

V    Y    P    L    A    V    P    L    E    V    E    V    G    I    G    E    D    W
GTG  TAT  CCC  CTG  GCC  GTG  CCC  CTG  GAG  GTG  GAG  GTG  GGG  ATA  GGG  GAG  GAC  TGG
```

FIGURE 1700 (CONT.)

```
L   S   A   K   E   G   I   D   G   R   G   G   G   H   H   H   H   H   H
CTC TCC GCC AAG GAG GGC ATT GAT GGC CGC GGA GGG GGC CAT CAT CAT CAT CAT CAT

H   H   //
CAT CAT //

M   V   K   V   K   F   K   Y   K   G   E   E   K   E   V   D   T   S
ATG GTG AAG GTA AAG TTC AAG TAT AAG GGT GAA GAG AAA GAA GTA GAC ACT TCA

K   I   K   K   V   W   R   V   G   K   M   V   S   F   T   Y   D   D
AAG ATA AAG AAG GTT TGG AGA GTA GGC AAA ATG GTG TCC TTT ACC TAT GAC GAC

N   G   K   T   G   R   G   A   V   S   E   K   D   A   P   K   E   L
AAT GGT AAG ACA GGT AGA GGA GCT GTA AGC GAG AAA GAT GCT CCA AAA GAA TTA

L   D   M   L   A   R   A   E   R   E   K   K   //  *
TTA GAC ATG TTA GCA AGA GCA GAA AGA GAG AAG AAA //  TAG
```

Figure 17PP

Pfu DNA Polymerase (WT) -Sac7d fusion protein

Nucleotide sequence (SEQ ID NO: 61) // Nucleotide sequence (SEQ ID NO: 69)

```
//
cctggtcct  gggtccacat  atatgttctt  actcgccttt  atgaagaatc  cccagtcgc
tctaacctgg gttatagtga caaatcttcc tccaccaccg cccaagaagg ttatttctat
caactctaca cctcccctat tttctctctt atgagatttt taagtatagt tatagagaag
gttttatact ccaaactgag ttagtagata tgtggggagc ataatgattt tagatgtgga
```

FIGURE 17PP (CONT.)

```
ttacataact gaagaaggaa aacctgttat taggctattc aaaaaagaga acggaaaatt
taagatagaa catgatagaa cttttagacc atacattac gctcttctca gggatgattc
aaagattgaa gaagttaaga aataacggg ggaaaggcat ggaaagattg tgagaattgt
tgatgtagag aaggttgaga aaaagtttct cggcaagcct attaccgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
aataccaatg gagggggaag aagagctaaa gattccttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gattctcag gattatcag gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acattcgac ttgtatcatg taataacaag
gacaataaat ctcccaacat acacactaga ggctgtatat gaagcaattt ttggaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
```

FIGURE 17PP (CONT.)

```
aggtggattc gttaaagagc cagaaaaggg gttgtgggaa aacatagtat acctagattt
tagagcccta tatccctcga ttataattac ccacaatgtt tctcccgata ctctaaatct
tgagggatgc aagaactatg atatcgctcc tcaagtaggc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaaactc ttagcaaatt ctttctacgg atattatggc tatgcaaaag caagatggta
ctgtaaggag tgtgctgaga gcgttactgc ctggggaaga aagtacatcg agttagtatg
gaaggagctc gaagaaaagt ttggatttaa agtcctctac attgacactg atggtctcta
tgcaactatc ccaggaggag aaagtgagga aataaagaaa aaggctctag aatttgtaaa
atacataaat tcaaagctcc ctggactgct agagcttgaa tatgaaggt tttataagag
gggattcttc gttacgaaga agagtatgc agtaatagat gaagaaggaa aagtcattac
tcgtggttta gagatagtta ggagagattg gagtgaaatt gcaaaagaaa ctcaagctag
agtttttggag acaatactaa aacacgaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca ataggcaat acattgagaa tctagctgag gaatacgatc ccaaaagca
caagtatgac gcagaatatt acattgagaa ccaggttctt ccagcggtac ttaggatatt
ggagggatt ggatacagaa aggaagacct cagataccaa aagacaagac aagtcggcct
```

FIGURE 17PP (CONT.)

```
aacttcctgg cttaacatta aaaaatccta gaaaagcgat agatatcaac ttttattctt
tctaaccttt ttctatgaaa gaagaactga gcaggaatta ccagttcttc cgttatttta
tgggtaatta aaaacccatg ctcttgggag aatctttcga taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacaccccctg ttcccgcacc caagtccgct
acaattttt cctgtatct cctaatgtat aagcaagcca aaggagagta gatgctacct
ttccgggagt tttgtattgc tctagccaag gttgggatt tttgaatcct ttaactctgg
aaagtataat ttcaagctcc ttcttcttca tgacagatga aaaattgttt tgtctctttt
taacttttac agaaataact gtctcaaatt atgacaactc ttgacatttt tacttcatta
ccagggtaat gtttttaagt atgaaatttt tctttcatag aggagnnnn nngtcctctc
ctcgatttcc ttggttgtgc tccatatgat aagcttccaa agtgggtgtt cagacttta
gacactcaaa taccagacga caatggtgtg ctcactcaag cccatatgg gttgagaaaa
gtagaagcgg cactactcag atgcttcccc aggaatgagg ttgttgtagc tcntcccnga
aagattgaga tgttcttgg //

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
```

FIGURE 17PP (CONT.)

TTA GAC ATG TTA GCA AGA GCA GAA AGA GAG AAG AAA //TGA

Figure 17QQ

Sac7d - Pfu DNA Polymerase (WT) fusion protein

Nucleotide sequence (SEQ ID NO: 69) // Nucleotide sequence (SEQ ID NO: 61)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //
//
   ccctggtcct gggtccacat atatgttctt actcgcttt atgaagaatc ccccagtcgc
   tctaacctgg gttatagtga caaatcttcc tccaccaccg cccaagaagg ttattctat
   caactctaca cctcccctat tttctctctt atgagattt taagtatagt tatagagaag
   gttttatact ccaaactgag ttagtagata tgtggggagc ataatgattt tagatgtgga
   ttacataact gaagaaggaa aacctgttat taggctattc aaaaaagaga acggaaaatt
   taagatagag catgatagaa ctttagacc atacatttac gctcttctca gggatgattc
   aaagattgaa gaagttaaga aaataacggg ggaaaggcat ggaaagattg tgagaattgt
   tgatgtagag aaggttgaga aaaagtttct cggcaagcct attaccgtgt ggaaacttta
   tttgaacat ccccaagatg ttcccactat tagagaaaaa gttagagaac atccagcagt
   tgtggacatc ttcgaatacg atattccatt tgcaaagaga tacctcatcg acaaaggcct
   aataccaatg gaggggaag aagagctaaa gattcttgcc ttcgatatag aaaccctcta
```

FIGURE 17QQ (CONT.)

```
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
aggtggattc gttaaagagc cagaaaaggg gttgtgggaa aacatagtat acctagattt
tagagcccta tatccctcga ttataattac ccacaatgtt tctcccgata ctctaaatct
tgagggatgc aagaactatg atatcgctcc tcaagtagcc cacaagttct gcaaggacat
ccctggtttt ataccaagtc tcttgggaca tttgttagag gaaagacaaa agattaagac
aaaaatgaag gaaactcaag atcctataga aaaaatactc cttgactata gacaaaaagc
gataaaactc ttagcaaatt ctttctacgg atattatggc tatgcaaaag caagatggta
ctgtaaggag tgtgctgaga gcgttactgc ctggggaaga aagtacatcg agttagtatg
```

FIGURE 17QQ (CONT.)

```
gaaggagctc gaagaaaagt ttggatttaa agtcctctac attgacactg atggtctcta
tgcaactatc ccaggaggag aaagtgagga aataaagaaa aagctctag aatttgtaaa
atacataaat tcaaagctcc ctggactgct agagcttgaa tatgaaggt tttataagag
gggattcttc gttacgaaga agaggtatgc agtaatagat gaagaaggaa aagtcattac
tcgtggttta gagatagtta ggagagattg gagtgaaatt gcaaaagaaa ctccaagctag
agtttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaaagc aggaatggta attggataca tagtacttag
aggcgatggt ccaattagca ataggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt
tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata acaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
```

FIGURE 17QQ (CONT.)

```
tttgctccaa gcagagccgc tccaatggat aacacccctg ttcccgcacc caagtccgct
acaattttt ccttgtatct cctaatgtat aagcaagcca aaggagagta gatgctacct
ttccgggagt tttgtattgc tctagccaag gtttgggatt tttgaatcct ttaacttctgg
aaagtataat ttcaagctcc ttcttcttca tgacagatga aaaattgttt tgtctctttt
taacttttac agaaataact gtctcaaatt atgacaactc ttgacatttt tacttcatta
ccagggtaat gtttttaagt atgaaatttt tctttcatag aggaggnnnn nngtcctctc
ctcgatttcc ttggttgtgc tccatatgat aagcttccaa agtgggtgtt cagacttta
gacactcaaa taccagacga caatggtgtg ctcactcaag ccccatatgg gttgagaaaa
gtagaagcgg cactactcag atgcttcccc aggaatgagg ttgttgtagc tcntcccnga
aagattgaga tgttcttgg  //  TGA
```

Figure 17RR

Sac7d - PFU DNA POLYMERASE (V93 R OR E) fusion protein

Nucleotide sequence (SEQ ID NO: 69)   // Nucleotide sequence (SEQ ID NO: 27)
Nucleotide sequence (SEQ ID NO: 69)   //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIGURE 17RR (CONT.)

```
ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA AGA GAG AAG AAA //
```

```
ATGATTTTAG ATGTGGATTA CATAACTGAA GAAGGAAAAC CTGTTATTAG GCTATTACAAA   60
AAAGAAACG  GAAAATTTAA GATAGAGCAT GATAGAACTT TTAGACCATA CATTTACGCT   120
CTTCTCAGGG ATGATTCAAA GATTGAAGAA GTTAAGAAAA TAACGGGGAA AAGGCATGGA   180
AAGATTGTGA GAATTGTTGA TGTAGAGAAG GTTGAGAGAA AGTTTCTCGG CAAGCCTATT   240
ACCGTGTGGA AACTTTATTT GGAACATCCC CAAGATXXXC CCACTATTAG AGAAAAAGTT   300
AGAGAACATC CAGCAGTTGT GGACATCTTC GAATACGATA TTCCATTTGC AAAGAGATAC   360
CTCATCGACA AAGGCCTAAT ACCAATGGAG GGGGAAGAAG AGCTAAAGAT TCTTGCCTTC   420
GATATAGAAA CCCTCTATCA CGAAGGAGAA GAGTTTGGAA AAGGCCCAAT TATAATGATT   480
AGTTATGCAG ATGAAAATGA AGCAAAGGTG ATTACTTGGA AAAACATAGA TCTTCCATAC   540
GTTGAGGTTG TATCAAGCGA GAGAGAGATG ATAAAGAGAT TTCTCAGGAT TATCAGGGAG   600
AAGGATCCTG ACATTATAGT TACTTATAAT GGAGACTCAT TCGCATTCCC ATATTTAGCG   660
AAAAGGGCAG AAAAACTTGG GATTAAATTA ACCATTGGAA GAGATGGAAG CGAGCCAAG   720
ATGCAGAGAA TAGGCGATAT GACGGTCGTA GAAGTCAAGG GAAGAATACA TTTCGACTTG   780
TATCATGTAA TAACAAGGAC AATAAAATCT CCAACATACA CACTAGAGGC TGTATATGAA   840
GCAATTTTTG GAAAGCCAAA GGAGAAGGTA TACGCCGACG AGATAGCAAA AGCCTGGGAA   900
AGTGGAGAGA ACCTTGAGAG AGTTGCCAAA TACTCCGATGG AAGATGCAAA GGCAACTTAT   960
GAACTCGGGA AAGAATTCCT TCCAATGGAA ATTCAGCTTT CAAGATTAGT TGGACAACCT  1020
TTATGGGATG TTTCAAGGTC AAGCACAGGG ACCTTGTAG AGTGGTTCTT ACTTAGGAAA  1080
GCCTACGAAA GAAACGAAGT AGCTCCAAAC AAGCCAAGTG AAGAGGAGTA TCAAAGAAGG  1140
CTAGGGAGA  GCTACACAGG TGGATTCGTT AAAGAGCCAG TTACTGCCTG GTGGGAAAAC  1200
ATAGTATACC TAGATTTTAG AGCCCTATAT CCCTCGATTA TAATTACCCA CAATGTTTCT  1260
CCCGATACTC TAAATCTTGA GGGATGCAAG AACTATGATA TCGCTCCTCA AGTAGGCCAC  1320
AAGTTCTGCA AGGACATCCC TGGTTTTATA CCAAGTCTCT TGGGACATTT GTTAGAGGAA  1380
AGACAAAAGA TTAAGACAAA AATGAAGGAA ACTCAAGATC CTATAGAAAA AATACTCCTT  1440
GACTATAGAC AAAAAGCGAT AAAACTCTTA GCAAATTCTT TCTACGGATA TTATGCTAT   1500
GCAAAAGCAA GATGGTACTG TAAGGAGTGT GCTGAGAGCG TTACTGCCTG GGAAGAAAG   1560
TACATCGAGT TAGTATGGAA GGACTCGAA GAAAAGTTTG GATTTAAAGT CCTCTACATT   1620
GACACTGATG GTCTCTATGC AACTATCCCA GGAGAAGAAA GTGAGGAAAT AAGAAAAAC   1680
GCTCTAGAAT TTGTAAAATA CATAAATTCA AGCTCCCTG GACTGCTAGA GCTTGAATAT   1740
GAAGGTTTT  ATAAGAGGGG ATTCTTTCGT ACGAAGAAGA GGTATGCAGT AATAGATGAA   1800
GAAGAAACTC AAGCTAGAGT TCATTACTCG TGGTTTAGAG ATAGTTAGGA GAGATTGGAG   1860
AAAGAAACTC AAGCTAGAGT TTGGAGACA  ATACAAAAAC ACGAGATGT  TGAAGAAGCT   1920
GTGAGAATAG TAAAGAAGT  AATACAAGAG CTTGCCAATT ATGAAATTCC ACCAGAGAAG   1980
```

FIGURE 17RR (CONT.)

```
CTCGCAATAT ATGAGCAGAT AACAAGACCA TTACATGAGT ATAAGGCCAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AGACCCTCAG ATACCAAAAG 2280
ACAAGACAAG TCGGCCTAAC TTCCTGGCTT AACATTAAAA AATCC //            2328
// TGA
```

Figure 17SS

PFU DNA POLYMERASE (V93 R OR E)-Sac7d fusion protein

Nucleotide sequence (SEQ ID NO: 27) // Nucleotide sequence (SEQ ID NO: 69)
Nucleotide sequence (SEQ ID NO: 28) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA  60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGAAGGAAG AGCTAAAGAT TCTTGCCTTC 420
GATATAGAAA CCCTCTATCA CGAAGGAGAA GAGTTTGGAA AAGCCCAAT TATAATGATT 480
AGTTATGCGA ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGATTTCCC ATATTTAGCG 660
AAAAGGGCAG ACATTTAATG GATTAAATTA ACCATTGGAA GAGATGGAAG CGAGCCCAAG 720
ATGCAGAGAA TAGGCGATAT GACGGCTGTA AGTCAAGG GAAGAATACA TTTCGACTTG 780
TATCATGTAA TAACAAGGAC AATAAAICTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AGAATTCCT TCCAATGGAA ATTCAGCTTT CAAGATTAGT TGGACAACCT 1020
```

FIGURE 17SS (CONT.)

```
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG CCCTCGATTA GTGGGAAAAC 1200
ATAGTATACC TAGATTTTAG AGCCCTATAT AACTATGATA TAATTACCCA CAATGTTTCT 1260
CCCGATACTC TAAATCTTGA GGGATGCAAG TGGTTTTATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATTACTCCTT 1440
GACTATAGAC AAAAAGCGAT AAAACTCTTA GCAAATTCTT TCTACGATA TTATGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT AACTATCCCA ACGGAGATGT TGAAGAAGCT ACCAGAGAAG 1920
GTGAGAATAG TAAAGAAGT CTTGCCAATT ATGAAATTCC AGGTCCTCAC AGTTCCTCAC 1980
CTCGCAATAT ATGAGACAGA CAAAGAAACT TTACATGAGT ATAAGGCGAT AATGGTAATT 2040
CTAGCTGTTG CAAAGAAACT TACTTAGAGG CGATGGTCCA GGAGTTAAAA TAAAGCAATA 2100
GGATACATAG TACTTAGAGG CGATGACGCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //                     2328

// ATG GTG AAG GTA AAG TTC AAG TAT AAG GGT GAA GAG AAA GAA GTA GAC ACT TCA
AAG ATA AAG AAG GTT TGG AGA GTA GGC AGA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG ATG TTA GCA AGA AGA GCA GAA AGA GAG AAG AAA // TGA
```

Figure 17TT

PFU DNA POLYMERASE (G387P/V93R OR E)-Sac7d fusion protein

Nucleotide sequence (SEQ ID NO: 29)   // Nucleotide sequence (SEQ ID NO: 69)
Nucleotide sequence (SEQ ID NO: 30)   // Nucleotide sequence (SEQ ID NO: 69)

FIGURE 17TT (CONT.)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA     60
AAAGAGAACG GAAAATTTAA GATAGAGCAT GATAGAACTT TTAGACCATA CATTTACGCT    120
CTTCTCAGGG ATGATTCAAA GATTGAAGAA GTTAAGAAAA TAACGGGGGA AAGGCATGGA    180
AAGATTGTGA GAATTGTTGA TGTAGAGAAG GTTGAGAAAA AGTTTCTCGG CAAGCCTATT    240
ACCGTGTGAA AACTTTATTT GGAACATCCC CCACTATTAG AGAAAAAGTT AGAAAAAGTT    300
AGAGAACATC CAGCAGTTGT GGACATCTTC GAATACGATA TTCCATTTGC AAAGAGATAC    360
CTCATCGACA AAGGCCTAAT ACCAATGGAG AGCTAAAGAT TCTTGCCTTC TATAATGATT    420
GATATAGAAA CCCTCTATCA CGAAGGAGAA GGGGAAGAAG AAGGCCCAAT TATAATGATT    480
AGTTATGCAG ATGAAAATGA AGCAAAGGTG ATTACTTGGA AAAACATAGA TCTTCCATAC    540
GTTGAGGTTG TATCAAGCGA GAGAGAGATG ATAAAAGATT TTCTCAGGAT TATCAGGGAG    600
AAGGATCCTG ACATTATAGT TACTTATAAT GGAGACTCAT TCGCATTCCC ATATTTAGCG    660
AAAAGGGCAG AAAAACTTGG GATTAAATTA ACCATTGGAA GAGATGGAAG CGAGCCCAAG    720
ATGCAGAGAA TAGGCGATAT GACGGCTGTA GAAGTCAAGG GAAGAATACA TTTCGACTTG    780
TATCATGTAA TAACAAGGAC AATAAATCTC CCAACATACA CACTAGAGGC TGTATATGAA    840
GCAATTTTTG GAAAGCCAAA GGAGAAGGTA TACGCCGACG AGATAGCAAA AGCCTGGGAA    900
AGTGGAGAGA ACCTTGAGAG AGTTGCCAAA TACTCGATGG AAGATGCAAA GGCAACTTAT    960
GAACTCGGGA AAGAATTCCT TCCAATGGAA ATTCAGCTTT CAAGATTAGT TGGACAACCT   1020
TTATGGGATG TTTCAAGGTC AAGCAGGAGG AACCTTGTAG AGTGGTTCTT ACTTAGGAAA   1080
GCCTACGAAA GAAACGAAGT AGCTCCAAAC AAGCCAAGTG AAGAGCCAG TCAAAGAAGG   1140
CTCAGGGAGA GCTACACACC NGGATTCGTT AAAGAGCCAG AAAAGGGGTT GTGGGAAAAC   1200
ATAGTATACC TAGATTTTAG AGCCCTATAT CCCTCGATTA TAATTACCCA CAATGTTTCT   1260
CCCGATACTC TAAATCTTGA GGGATGCAAG AACTAGTGTA TCGCTCCTCA AGTAGGCCAC   1320
AAGTTCTGCA AGGACATCCC TGGTTTTATA CCAAGTCTCT TGGGACATTT GTTAGAGGAA   1380
AGACAAAAGA TTAAGACAAA AATGAAGGAA ACTCAAGATC CTATAGAAAA AATACTCCTT   1440
GACTATAGAC AAAAAGCGAT AAAAACTCTTA GCAAATTCTT TCTACGGATA TTATGGCTAT   1500
GCAAAAGCAA GATGGTACTG TAAGGAGTGT GCTGAGAGCG TTACTGCCTG GGGAAGAAAG   1560
TACATCGAGT TAGTATGGAA GGAGCTCGAA AACTATCCCA GAAAAGTTTG GATTTAAAGT   1620
GACACTGATG GTCTCTATGC AACTATCCCA GGAGGAGAAA GTGAGGAAAT AAAGAAAAAG   1680
GCTCTAGAAT TTGTAAAATA CATAAATTCA AGCTCCCTG GACTGCTAGA GCTTGAATAT   1740
GAAGGGTTTT ATAAGAGGGG ATTCTTCGTT ACGAAGAAGA GGTATGCAGT AATAGATGAA   1800
GAAGGAAAAG TCATTACTCG TGGTTTAGAG ATAGTTAGGA GAGATTGGAG TGAAATTGCA   1860
AAAGAAACTC AAGCTAGAGT TTTGGAGACA ATACTAAAAC ACGGAGATGT TGAAGAAGCT   1920
GTGAGAATAG TAAAAGAAGT AATACAAAAG CTTGCCAATT ATGAAATTCC ACCAGAGAAG   1980
CTTCGCAATAT ATGAGCAGAT AACAAGACCA TTACATGAGT ATAAGGCGAT AGGTCCTCAC   2040
```

FIGURE 17TT (CONT.)

```
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //                 2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA AGA GCA GAA AGA GAG AAG AAA //       TGA
```

Figure 17UU

PFU DNA POLYMERASE (G387P/V93R OR E) -Sac7d fusion protein

Nucleotide sequence (SEQ ID NO: 29)    //Nucleotide sequence (SEQ ID NO: 69)
Nucleotide sequence (SEQ ID NO: 30)    //Nucleotide sequence (SEQ ID NO: 69)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA  60
AAAGAAACG GAAAATTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGAAGAAG AGCTAAAGAT TCTTGCCTTC 420
```

FIGURE 17UU (CONT.)

```
GATATAGAAA CCCTCTATCA CGAAGGAGAA GAGTTTGGAA AAGGCCCAAT TATAATGATT 480
AGTTATGCAG ATGAAAATGA AGCAAAGGTG AGCAAAGATG ATTACTTGGA TCTTCCATAC 540
GTTGAGGTTG TATCAAGCGA GAGAGAGATG ATAAAGAGAT AAAACATAGA TATCAGGGAG 600
AAGGATCCTG ACATTATAGT TACTTATAAT GGAGACTCAT TTCTCAGGAT ATATTTAGCG 660
AAAAGGGCAG AAAAACTTGG GATTAAATTA ACCATTGGAA TCGCATTCCC CGAGCCCAAG 720
ATGCAGAGAA TAGGCGATAT GACGGCTGTA GAAGTCAAGG GAGATGAAAG TTTCGACTTG 780
TATCATGTAA TAACAAGGAC AATAAATCTC CCAACATACA GAAGAATACA TGTATATGAA 840
GCAATTTTTG GAAAGCCAAA GGAGAAGGTA TACGCCGACG CACTAGAGGC AGCCTGGGAA 900
AGTGGAGAGA ACCTTGAGAG AGTTGCCAAA TACTGCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTTCTT AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGT TGGATTCGTT AAAGAGCCAG AAAAGGGGTT GTGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGCTTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ACGTAAAAAC ACGGAGATGT TGAAGAAGCT 1920
GTGAGAAGT AATACAAAAG CTTGCCAATT ATGAAATTCC ACCAGAGAAG 1980
CTCGCAATAT ATGAGCGAAT TTACATGAGT TTACATGAGT ATAAGGCGAT AGTTCCTCAC 2040
GTAGCTGTTG CAAAGAAACT AGCTGCTAAA GGAGTTAAAA TAAAGGCCAG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAAAAGG AAGACCTCAG ATACCAAAAG 2280
ACAAGACAAG TCGGCCTAAC TTCCTGGCTT AACATTAAAA AATCC //                2328

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAT GCT CCA AAA GAA GAA TTA
TTA GAC ATG TTA GCA AGA GCA GAA AGA GAG AAG AAA // TGA
```

Figure 17VV

SAC7D-PFU DNA POLYMERASE (D141A/E143A/V93R OR E) fusion protein

Nucleotide sequence (SEQ ID NO: 69)  // Nucleotide sequence (SEQ ID NO: 31)
Nucleotide sequence (SEQ ID NO: 69)  // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGA GGA GCT GTA AGC GAG AAA GAT GCT CCA AAA GAA TTA
   TTA GAC ATG ATG GCA GTA AGA GAA AGA GAG AAG AAA //

//ATGATTTTAG ATGTGGATTA CATAACTGAA GAAGGAAAAC CTGTTATTAG GCTATTCAAA    60
AAAGAGAACG GAAAATTTAA GATAGAGACA GTTAAGAGTT TTAACCATA CATTACGCT      120
CTTCTCAGGG ATGATTCAAA GATTGAAGAA GTTAAGAAAA TAACGGGGA AAGGCATGGA    180
AAGATTGTGA GAATTGTTGA TGTGAGAAGA GTTGAGAAAA AGTTCTCGG CAAGCCTATT    240
ACCGTGTGGA AACTTTATTT GGAACATCCC CAAGATXXXC CCACTATTAG AGAAAAAGTT   300
AGAACATC CAGCAGTTGT GGACATCTTC GAATACGATA TTCCATTTGC AAAGAGATAC     360
CTCATCGACA AAGGCCTAAT ACCAATGGAG GGGAAGAAG AGCTAAAGAT TCTTGCCTTC    420
GCNATAGCNA CCCTCTATCA CGAAGGAGAA GAGTTTGGAA AAGCCCAAT TATAATGATT    480
AGTTATGCAG ATGAAAATGA AGCAAAGGTG ATTACTTGGA AAACATAGA TCTTCCATAC    540
GTTGAGGTTG TATCAAGCGA GAGAGAATG ATAAAGAGAT TTCTCAGGAT TATCAGGGAG    600
AAGGATCCTG ACATTATAGT TACTTATAAT GGAGACTCAT TCGATTCCCC ATATTTAGCG   660
AAAAGGGCAG AAAAACTTGG GATTAAATTA ACCATTGGAA GAGATGGAAG CGAGCCAAG    720
ATGCAGAGAA TAGGCGATAT GACGGCTGTA GAAGTCAAGG GAAGAATACA TTTCGACTTG   780
TATCATGTAA TAACAAGGAC AATAAATCTC CCAACATACA CCTAGAGGC TGTATATGAA    840
GCAATTTTG GAAAGCCAAA GGAGAAGGTA TACGCCGACG AGATAGCAAA AGCCTGGGAA    900
AGTGGAGAGA ACCTTGAGAG AGTTGCCAAA TACTCGATGG AAGATGCAAA GGCAACTTAT   960
GAACTCGGGA AAGAATTCCT TCCAATGGAA ATTCAGCTTT CAAGATTAGT TGGACAACCT   1020
TTATGGGATG TTTCAAGGTC AAGCACAGGG AACCTTGTAG AGTGGTTCTT ACTTAGGAAA   1080
GCCTACGAAA GAAACGAAGT AGCTCCAAAC AAGCCAAGTG AAGAGGAGTA TCAAAGAAGG   1140
```

FIGURE 17VV (CONT.)

```
CTCAGGGAGA GCTACACAGT TGGATTCGTT AAAGAGCCAG AAAAGGGGTT GTGGAAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGCAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA ATTCTTCGTT ACGAAGAAGA AGCTCCCCTG GACTGCTAGA GCTTGAATAT 1740
GAAGGTTTT ATAAGAGGGG ATTCTTCGTT ACGAAGAAGA GGTATGCAGT AATAGATGAA 1800
GAAGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAGAAGT AATACAAAAG CTTGCCAATT ATGAAATTCC ACCAGAGAAG 1980
CTCGCAATAT ATGAGGAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACGAAAAGG AAGACCTCAG ATACCAAAAG 2280
ACAAGACAAG TCGGCCTAAC TTCCTGGCTT AACATTAAAA AATCC // 2328
```

TGA

Figure 17WW

KOD DNA POLYMERASE – Sac7d fusion protein

Nucleotide sequence (SEQ ID NO: 33) // Nucleotide sequence (SEQ ID NO: 69)
Nucleotide sequence (SEQ ID NO: 34) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG  60
AAGGAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGTTGTAA CGGTTAAGCG GTTCAGAAGA AGTTCCTCGG GAGACCAGTT 240
GAGGTCTGGA AACTCTACTT TACTCATCCG CAGGACXXXC CAGCGATAAG GGACAAGATA 300
```

FIGURE 17WW (CONT.)

```
CGAGAGCATC CAGCAGTTAT TGACATCTAC GAGTACGACA TACCCTTCGC CAAGCGCTAC    360
CTCATAGACA AGGGATTAGT GCCAATGGAA GGCGACGAGG AGCTGAAAAT GCTCGCCTTC    420
GACATTGAAA CTCTCTACCA TGAGGGCGAG GAGTTCGCCG AGGGGCCAAT CCTTATGATA    480
AGCTACGCCG ACGAGGAAGG GGCCAGGGTG ATAACTTGGA AGAACGTGGA TCTCCCCTAC    540
GTTGACGTCG TCTCGACGGA GAGGGAGATG ATAAAGCGCT TCCTCCGTGT TGTGAAGGAG    600
AAAGACCCGG ACGTTCTCAT AACCTACAAC GGCGACAACT TCGACTTCGC CTATCTGAAA    660
AAGCGCTGTG AAAAGCTCGG AATAAAACTTC GCCCTCGGAA GGGATGGAAG CGAGCCGAAG    720
ATTCAGAGGA TGGGCGACAG GTTTGCCGTC GAAGTGAAGG GACGGATACA CTTCGATCTC    780
TATCCTGTGA TAAGACGGAC GATAAACCTG CCCACATACA CGCTTGAGGC CGTTTATGAA    840
GCCGTCTTCG GTCAGCCGAA GGAGAAGGTT TACGCTGAGG AAATAACCAC AGCCTGGGAA    900
ACCGGCGAGA ACCTTGAGAG AGTCGCCCGC TACTCGATGG AAGATGCGAA GGTCACATAC    960
GAGCTTGGGA AGGAGTTCCT TCCGATGGAG GCCCAGCTTT CTCGCTTAAT CGGCCAGTCC   1020
CTCTGGGACG TCTCCCGCTC CAGCACTGGC AACCTCGTTG AGTGGTTCCT CCTCAGGAAG   1080
GCCTATGAGA GGAATGAGCT GGCCCCGAAC AAGCCCGATG AAAAGGAGCT GGCCAGAAGA   1140
CGGCAGAGCT ATGAAGGAGG CTATGTAAAA GAGCCCGAGA GAGGGTTGTG GGAGAACATA   1200
GTGTACCTAG ATTTTAGATC CCTGTACCCC TCAATCATCA TCACCCACAA CGTCTCGCCG   1260
GATACGCTCA ACAGAGAAGG ATGCAAGGAA TATGACGTTG CCCCACCAGT CGGCCACCGC   1320
TTCTGCAAGG ACTTCCCAGG ATTTATCCCG AGCCTGCTTG GGACACTTCCT AGAGGAGAGG   1380
CAGAAGATAA GAAGAAGAT GGGCCATCAA ATTGACCCGA TCGAGAGGA GCTCCTCGAT   1440
TACAGGCAGG GGGCCATCAA GATCCTGGCA AACAGCTACT ACGGTTACTA CGGCTATGCA   1500
AGGGCGCGCT GGTACTGCAA GGAGTGTGCA GGAGCGTGAA CGGCCTGGGG AAGGGAGTAC   1560
ATAACGATGA CCATCAAGGA GATAGAGGAA AAGTACGGCT TTAAGGTAAT CTACAGCGAC   1620
ACCGACGGAT TTTTTGCCAC AATACCTGGA GCCGATGCTG AAACCGTCAA AAGAAGGCT   1680
ATGGAGTTCC TCAAGTATAT CAACGCCAAA CTTCCGGGCG CGCTTGAGCT CGAGTACGAG   1740
GGCTTCTACA AACGCGGCTT CTTCGTCACG AAGAAGAAGT ATGCGGTGAT AGACGAGGAA   1800
GGCAAGATAA CAACGCGCGG ACTTGAGATT GTGAGGCGTG ACTGGAGCGA GATAGCGAAA   1860
GAGACGCAGG CGAGGGTTCT TGAAGCTTTG CTAAAGGACG GTGACGTCGA GAAGGCCGTG   1920
AGGATAGTCA AAGAAGTTAC CGAAAAGCTG AGCAAGTACG AGGTTCCGCC GGAGAAGCTG   1980
GTGATCCACG AGCAGATAAC GAGGGATTTA AAGGACTACA AGCCTGGAAC TCCCCACGTT   2040
GCCGTTGCCA AGAGGTTGGC CGCGAGAGGA GTCAAAATAC GCCGACAGGG GGTGATAAGC   2100
TACATCGTGC TCAAGGGCTC TGGGAGGATA GGCGACAGGG CGATACCGTT CGACGAGTTC   2160
GACCCGACGA AGCACAAGTA CGACGCCGAG TACTACATTG AGAACCAGGT TCTCCCAGCC   2220
GTTGAGAGAA TTCTGAGAGC CTTCGGTTAC CGCAAGGAAG ACCTGCGCTA CCAGAAGACG   2280
AGACAGGTTG GTTTGAGTGC TTGGCTGAAG CCGAAGGGAA CT 2325
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA GAG AGA AGA AAA //  TGA
```

Figure 17XX

Sac7d - KOD DNA POLYMERASE fusion protein

Nucleotide sequence (SEQ ID NO: 69) // Nucleotide sequence (SEQ ID NO: 33)
Nucleotide sequence (SEQ ID NO: 69) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA GAG AAG AAA //

//ATGGATCCTCG ACACTGACTA CATAACCGAG GATGGAAAGC CTGTCATAAG AATTTTCAAG   60
AAGGAAAACG GCGAGTTTAA GATTGAGTAC GACCGGACTT TTGAACCCTA CTTCTACGCC    120
CTCCTGAAGG ACGATTCTGC CATTGAGGAA GTCAAGAAGA TAACGCCCGA GAGGCACGGG    180
ACGGTTGTAA CGGTTAAGCG GGTTGAAAAG GTTCAGAAGA AGTTCCTCGG GAGACCAGTT    240
GAGGTCTGGA AACTCTACTT TACTCATCCG CAGGACXXXC CAGCGATAAG GGACAAGATA    300
CGAGAGCATC CAGCAGTTAT TGACATCTAC GAGTACGACA TACCCTTCGC CAAGCGCTAC    360
CTCATAGACA AGGGATTAGT GCCAATGGAA GGCGACGAGG AGCTGAAAAT GCTCGCCTTC    420
GACATTGAAA CTCTCTACCA TGAGGGCGAG GAGTTCGCCG AGGGGCCAAT CCTTATGATA    480
AGCTACGCCG ACGAGGAAGG GGCCAGGGTG ATAACTTGGA AGAACGTGGA TCTCCCCTAC    540
GTTGACGTCG TCTCGACGGA GAGGGAGATG ATAAAGCGCT TCCTCCGTGT TGTGAAGGAG    600
AAAGACCCGG ACGTTCTCAT AACCTACAAC GGGGACACTT TCGACTTCGC CTATCTGAAA    660
AAGCGCTGTG AAAAGCTCGG AATAAACTTC GCCCTCGGAA GGGATGGAAG CGAGCCGAAG    720
ATTCAGAGGA TGGGCGACAG GTTTGCCGTC GAAGTGAAGG GACGGATACA CTTCGATCTC    780
TATCCTGTGA TAAGACGGAC GATAAACCTG GGAGAAGGTT CCCACACTG CGTTTATGAA    840
GCCGGTCTTC GTCAGCCGAA GGAGAAGAGT AGCGGCCGGC AAATAACCAC AGCCTGGGAA    900
ACCGGCGAGA ACCTTGAGAG AGGAGTTCCT TCCGATGGAG GCCCAGCTTT CTCGCTTAAT    960
GAGCTTGGGA TCTCCCGCTC CAGCACTGGC AACCTCGTTG AGTGGTTCCT CCTCAGGAAG    1020
GCCTATGAGA GGAATGAGCT GGCCCCCGAAC AAGCCCGATG AAAAGGAGCT GGCCAGAAGA    1080
CGGCAGAGCT ATGAAGGAGG CTATGTAAAA GAGCCCGAGA GAGGGTTGTG GGAGAACATA    1200
GTGTACCTAG ATTTTAGATC CCTGTACCCC TCAATCATCA TCACCCACAA CGTCTCGCCG    1260
```

FIGURE 17XX (CONT.)

```
GATACGGTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGCGCGCT GGTACTGCAA GGAGTGTGCA GAGAGCGTAA CGGCCTGGGG AAGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAGAAAGGCT 1680
ATGGAGTTCC TCAAGTATAT CAACGCCCAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GAAGGCCGTG 1860
GAGACGCAGG CGAGGGTTCT TGAAGCTTTG CTAAAGGACG AGGTTCCGCC GGAGAAGCTG 1920
AGGATAGTCA AAGAAGTTAC CGAAAAGCTG AGCAAGTACG AAGGACTACA AGGTTGAAC 1980  
GTGATCCACG AGCAGATAAC GAGGGATTTA AAGGACTACA AGGTTCCGCC GGAGAAGCTG 2040
GCCGTTGCCA AGAGTTGGC CGCGAGAGGA GTCAAAATAC GCCCTGGAAC GGTGATAAGC 2100
TACATCGTGC TCAAGGGCTC TGGAGGGATA GGCGACAGGG CGATACCGTT CGACGAGTTC 2160
GACCCGACGA AGCACAAGTA CGACGCCGAG TACTACATTG AGAACCAGGT CCTCGCGCTA 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTAGGC CCGAAGGGAA CT //TAG 2325
```

Figure 17YY

Sac7d-Vent DNA POLYMERASE FUSION PROTEIN

Nucleotide sequence (SEQ ID NO: 69)   // Nucleotide sequence (SEQ ID NO: 35)
Nucleotide sequence (SEQ ID NO: 69)   // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA GCA GAT GCT CCA AAA GAA TTA
   TTA GAC ATG TTA GCA AGA GCA GAA GAG AAG AAA //

ATGATACTGG ACACTGATTA CATAACAAAA GATGGCAAGC CTATAATCCG AATTTTTAAG   60
AAAGAAACG GGGAGTTTAA AATAGAACTT GACCCTCATT TTCAGCCCTA TATATATGCT  120
CTTCTCAAAG ATGACTCCGC TATTGAGGAG ATAAAGGCAA TAAAGGGCGA GAGACATGGA  180
```

FIGURE 17YY (CONT.)

```
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCC AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTCCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
CGGGTGGCAT ACGCGAGGAA TGAACTTGCA CCGAACAAAC CTGATGAGGA AGAGTTTGTGG 1140
CGGCGCTTAA GAACAACTTA CCTGGGAGGA TATGTAAAAG AGCCAGAAAA ACTTCACAAC 1200
GAAAATATCA TTTATTTGGA TTTCCGCAGT CTGTACCCTT GTAAGAATT ACGATGTTGC TCCGATAGTA 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAAGATAAC AACAAGGGGC TTGAAGTAG TAAGGAGAGA TTGGAGTGAG 1860
ATAGCTAAGG AGACTCAGGC AAAGGTTTTA GAGGCTATAC TTAAAGAGGG AGTTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGATTTAA GAGACTACAA AGCCATTGGC 2040
CCTCATGTCG CGATAGCAAA AAGACTTGCC GCAAAGGAGC GGAAAGATAA GCGATAGGGT 2100
ATAATAAGCT ATATCGTTCT CAAAGGGGAG AAAGATAA GCGATAGGGT TAAAAGTGAA ACCGGGCACA 2160
ACAGAATACG ATCCTAGAAA ACACAAGTAC GATCCGGACT ACTACATAGA AATTTACTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

Figure 17ZZ

Vent DNA POLYMERASE - Sac7d FUSION PROTEIN

Nucleotide sequence (SEQ ID NO: 35)     // Nucleotide sequence (SEQ ID NO: 69)
Nucleotide sequence (SEQ ID NO: 36)     // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAAATCCG AATTTTTAAG    60
AAAGAGAACG GGGAGTTTAA AATAGAACTT GACCCTCATT TTCAGCCCTA TATATATGCT   120
CTTCTCAAAG ATGACTCCGC TATTGAGGAG ATAAAGGCAA TAAAGGGCGA GAGACATGGA   180
AAAACTGTGA GAGTGCTCGA TGCAGTGAAA GTCAGGGAAA AATTTTTGGG AAGGAAGTT    240
GAAGTCTGGA AGCTCATTTT CGAGCATCCC CAAGACXXXC CAGCTATGCG GGGCAAAATA   300
AGGGAACATC CAGCTGTGGT TGACATTTAC GAATATGACA TACCCTTTGC CAAGCGTTAT   360
CTCATAGACA AGGGCTTGAT TCCCATGGAG GGAGACGAGG AGCTTAAGCT CCTTGCCTTT   420
GATATTGAAA CGTTTTATCA TGAGGGAGAT GAATTTGGAA AGGGCGAGAT AATAATGATT   480
AGTTATGCCG ATGAAGAAGA GGCCAGAGTA ATCACATGGA AAAATATCGA TTTGCCGTAT   540
GTCGATGTTG TGTCCAATGA AAGAGAAATG ATAAAGCGTT TTGTTCAAGT TGTTAAAGAA   600
AAAGACCCCG ATGTGATAAT AACTTACAAT GGGGACAATT TTGATTTGCC GTATCTCATA   660
AAACGGGCAG AAAAGCTGGG AGTTCGGCTT GTCTTAGGAA GGGACAAAGA ACATCCCGAA   720
CCCAAGATTC AGAGGATGGG TGATAGTTTT GCTGTGGAAA TCAAGGGTAG AATCCACTTT   780
GATCTTTTCC CAGTTGTGCG AAGGACGATA AACCTCCCAA CGTATACGCT TGAGGCAGTT   840
TATGAAGCAG TTTTAGGAAA AACCAAAAGC AAATTAGGAG CAGAGGAAAT TGCCGCTATA   900
TGGGAAACAG AAGAAAGCAT GAAAAAACTA GCCCAGTACT CAATGGAAGA TGCTAGGGCA   960
ACGTATGAGC TCGGGAAGGA ATTCTTCCCC ATGGAAGCTG AGCTGGCAAA GCTGATAGGT  1020
CAAAGTGTAT GGGACGTCTC GAGATCAAGC ACCGGCAACC TCGTGGAGTG GTATCTTTTA  1080
AGGGTGGCAT ACGCGAGGAA TGAACTTGCA CCGAACAAAC CTGATGAGGA AGAGTATAAA  1140
CGGCGCTTAA ACGGAGGA TATGTAAAAG AGCCAGAAAA AGTTTGTGTG TACTCACAAC    1200
GAAAATATCA TTTATTTGGA TTTCCGCAGT CTGTACCCTT CAATAATAGT TCCGATAGTA  1260
GTATCCCAG ATACCCTTGA AAAAGAGGGC TGTAAGAATT ACGATGTTGC TCCGATAGTA   1320
GGATATAGGT TCTGCAAGGA CTTTCCGGGC TTTATTCCCT GTAAGAATT ACGATGTTGC   1320
GGATATAGGT TCTGCAAGGA CTTTCCGGGC TTTATTCCCT GTAAGAATT GGACTTAATT  1380
```

FIGURE 17ZZ (CONT.)

```
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGCCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGAAGTAG TAAGGAGAGA TTGGAGTGAG 1860
ATAGCTAAGG AGACTCAGGC AAAGGTTTTA GAGGCTATAC TTAAAGAGAGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AAGACTTGCC AGGGATTTAA AGGACTACAA AGCCATTGGC 2040
CCTCATGTCG CGATAGCAAA AAGACTTGCC CAAGGGAGCG GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGA TTTAAGGTAT 2280
CAAAGCTCAA AACAAACCGG CTTAGATGCA TGGCTCAAGA GG 2325 //

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA AGA GCA GAA AGA GAG AAG AAA // TGA
```

Figure 17AAA

Deep Vent- Sac7d DNA polymerase fusion protein

Nucleotide sequence (SEQ ID NO: 37)   // Nucleotide sequence (SEQ ID NO: 69)
Nucleotide sequence (SEQ ID NO: 38)   // Nucleotide sequence (SEQ ID NO: 69)

FIGURE 17AAA (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
```

FIGURE 17AAA (CONT.)

```
TTCGATCTCA GGAAGCATAA GTATGACGCT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAG //                2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA // TGA
```

Figure 17BBB

Sac7d - Deep Vent DNA polymerase fusion protein

Nucleotide sequence (SEQ ID NO: 69)    // Nucleotide sequence (SEQ ID NO: 37)
Nucleotide sequence (SEQ ID NO: 69)    // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA      60
AAG ATA AAG AAG GTT TGG AGA GTA GGC AAA ATG GTG TCC TTT ACC TAT GAC GAC        120
AAT GGT AAG ACA GGT AGA GGA GCT GTA AGC GAG AAA GAT GCT CCA AAA GAA TTA        180
TTA GAC ATG ATG TTA GCA AGA GAA GCA GAA AGA GAG AAG AAA //

//ATGATACTTG ACGCTGACTA CATCACCGAG GATGGGAAGC TTAGACCTTA CATTTACGCT              60
AAAGAAAACG GCGAGTTTAA GGTTGAGTAC GACAGAAACT TTAGACCTTA CATTTACGCT              120
CTCCTCAAAG ATGACTCGCA GATTGATGAG GTTAGGAAGA TAACCGCCGA GAGGCATGGG              180
AAGATAGTGA GAATTATAGA TGCCGAAAAG GTAAGGAAGA AGTTCCTGGG GAGGCCGATT              240
GAGGTATGGA GGCTGTACTT TGAACACCCT CAGGACXXXC CCGCAATAAG GGATAAGATA              300
AGAGAGCATT CCGCAGTTAT TGACATCTTT GAGTACGACA TTCCGTTCGC GAAGAGGTAC              360
CTAATAGACA AAGGCCTAAT TCCAATGGAA GGCGATGAAG AGCTCAAGTT GCTCGCATTT              420
GACATAGAAA CCCTCTATCA CGAAGGGGAG GAGTTCGCGA AGGGGCCCAT TATAATGATA              480
AGCTATGCTG ATGAGGAAGA AGCCAAAGTC ATAACGTGGA AAAAGATCGA TCTCCCGTAC              540
GTCGAGGTAG TTTCCAGCGA GAGGGAGATG ATAAAGCGGT TCCTCAAGGT GATAAGGGAG              600
AAAGATCCCG ATGTTATAAT TACCTACAAC GGCGATTCTT TCGACCTTCC CTATCTAGTT              660
AAGAGGGCCG AAAAGCTCGG GATAAAGCTA CCCCTGGGAA GGGACGGTAG TGAGCCAAAG              720
ATGCAGAGGC TTGGGGATAT GACAGCGGTG GAAGGATACA CTTTGACCTC                         780
TACCACGTGA TTAGGAGAAC GATAAACCTC CCAACATACA CCCTCGAGGC AGTTTATGAG              840
GCAATCTTCG GAAAGCCAAA GGAGAAAGTT TACGCTCACG AGATAGCTGA GGCCTGGGAG              900
ACTGGAAAGG GACTGGAGAG AGTTGCAAAG TATTCAATGG AGGATGCAAA GGTAACGTAC              960
GAGCTCGGTA GGGAGTTCTT CCCAATGGAG GCCCAGCTTT CAAGGTTAGT CGGCCAGCCC             1020
CGTGGGATG TTTCTAGGTC TTCAACTGGC AACTTGGTGG AGTGGTACCT CCTCAGGAAG              1080
GCCTACGAGA GGAATGAATT GGCTCCAAAC AAGCCGGATG AAGGGAGTA AGAGAGAAGG              1140
CTAAGGGAGA GCTACGCTGG GGGATACGTT AAGGAGCCGG AGAAAGGGCT CTGGAGGGG              1200
TTAGTTTCCC TAGATTTCAG GAGCCTGTAC CCCTCGATAA TAATCACCCA TAACGTCTCA             1260
CCGGATACGC TGAACAGGGA AGGGTGTAGG GAATACGATG TCGCCCCAGA GGTTGGGCAC             1320
```

FIGURE 17BBB (CONT.)

```
AAGTTCTGCA AGGACTTCCC GGGGTTTATC CCCAGCCTGC TCAAGAGGTT ATTGGATGAA    1380
AGGCAAGAAA TAAAAGGAA GATGAAAGCT TCTAAAGACC CAATCGAGAA GAAGATGCTT    1440
GATTACAGGC AACGGGCAAT CAAAATCCTG GCAAACAGCT ATTATGGGTA TTATGGGTAC   1500
GCAAAAGCCC GTTGGTACTG TAAGGAGTGC GCAGAGACG GAAAAGTTCG GGGGAGGGAA    1560
TATATAGAGT TCGTAAGGAA GGAACTGGAG GAAAAGTTCG GGTTCAAAGT CTTATACATA   1620
GACACAGATG GACTCTACGC CACAATTCCT GGGGCAAAAC CCGAGAGAT AAAGAAGAAA    1680
GCCCTAGAGT TCGTAGATTA TATAAACGCC AAGCTCCCAG GGCTGTTGA GCTTGAGTAC    1740
GAGGCTTCT ACGTGAGAGG GTTCTTCGTG ACGAAGAAGA AGTATGCGTT GATAGATGAG    1800
GAAGGAAGA TAATCACTAG GGGGCTTGAA ATAGTCAGGA GGGACTGGAG CGAAATAGCC    1860
AAGAAACCC AAGCAAAAGT CCTAGAGGCT AACTGAAAAG CTGAGCAAGT ATCCTAAAGC    1920
GTAAAGATAG TTAAGGAGGT ACGAGCAGAT CTTCACGAGT ACGAAATACC TCCAGAAAAG   1980
CTAGTTATT ACGAGCAGAT CCAAAAGGTT AGCCGCTAGA GGAGTAAAGG TGAGGCCTGG    2040
GTTGCCGTGG CAAAAAGGTT AGCCGCTAGA GGAGTAAAGG TGAGGCCTGG CATGGTGATA   2100
GGGTACATAG TGCTGAGGGG GACGGGCCA ATAAGCAAGA GGGCTATCCT TGCAGAGGAG   2160
TTCGATCTCA GGAAGCATAA GTATGACGCT GAGTATTACA TAGAAAATCA GGTTTTACCT   2220
GCCGTTCTTA GAATATTAGA GGCCTTTGGG TACAGGAAAG AAGACCTCAG GTGGCAGAAG   2280
ACTAAACAGA CAGGTCTTAC GGCATGGCTT AACATCAAGA AGAAG TAA             2328
```

Figure 17CCC

JDF-3 — Sac7d fusion protein

Nucleotide sequence (SEQ ID NO: 39) // Nucleotide sequence (SEQ ID NO: 69)
Nucleotide sequence (SEQ ID NO: 40) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGACGACTCTGGGTCCATGAAGAAATCAAAAAGATAACCGCGGAGAGGCACGGCAGGTCGTTAAGCGCCGGAAGTTAAGGTTAAGCGCCGGAAGGTGAAGAAAAGTTCCTGG
CAGGTCGTGGAGGTCGGGTCCTCACTTCACGGACXXXCCGGCAATCCGGACAAATAAGGAAGCACCCGGTCATCGACATCTACGAGTACGACATACCC
TTCGCCAAGCGCTACCTCATAGACAAGGGCCTAATCCGATGGAAGGTGAGGAAGAGCTTAAACTCATGTCCTTCGAGATCGAGCGCTCTACCACGAGGAGAAGAGTTTGGAA
CCGGGCGATTCTGATGATAAGCTACGCCGATGAAAGCGAGGCGCGTCTGATAACATCAACGGCGACAACTTCGACTTCGCCTACTGAAGGTACAACTTCAGTCCAGTCGAGAAGGGAAGTGAAG
GCGCTTCTTGAGGGGTCGTTAAGGAGAAGAGAGACCCGGAAGATCGCGATGGGGGACAGTTTGCGGTCGAGGTGAAGGTCAGGTACACTTCAGTCAGTCCACCATAA
ACCCTGCGGACGGGACGGAGCGAGCGAAGATACAGCGCATGGGAAGATACAGCGGTTTTCGCAAGCCCAAGGAGGAGAAGGTCTACGCCCGAGGAGAGATAGCCACCGCCTGGGAGACCGGCGAGGGGCTTGAGAG
ACCTCCCGACCTTACACACCCTTGAGGCTGTATACGAGGCGTTTTCGCAAGCCCAAGGAGGAGAAGGTCTACGCCCGAGGAGAGATAGCCACCGCCTGGGAGACCGGCGAGGGGCTTGAGAG
```

FIGURE 17CCC (CONT.)

```
GGTCGCGCGCTACTCGATGAGGACGCGAGGGTTACCTACGACGCTTGGCAGGAGTTCTTCCCAGGCTCTCATCGGCCAAGGCCTCTGGGACGTTTCC
CGCTCCAGCACCGGCCAACCTCGTCGAGTGGTTCCTCCTAAGGAAGGCCTACGAGAGGAACGAACTCGCTCCGACGAGGGAGCTGGCGAGGAAGGGGGCT
ACgcCGGTTGGCTACGTCAAGGAGCCGGAGCGGGACTGTGGGACATATCGTATCTAGACTTTCGTAGTCTCTACCCTCAATCATAATCACCCACAACGTCTCGCCAGATAC
GCTCAACCGCGAGGGGTGTAGAGCTACGACGTTGCCCCCGAGTCGGTCACAAGTTCTGCAAGGACTTCCCGGCTTCATTCCGAAACCTGCTGGAGAAAGG
CAGAAGATAAAGAGGAAGATGAAGGCAACTCTGCAGGGAGTGCGCCAGAAGCGTTACGCCGAGAAGAATTCTCCTGGAGAGCTTGAGGAAAGTTCGGTTTAAAGTCCT
ATGCCAGGGCAAGATGTACTGCAGGGAGTGCGCCAGAAGCGTTACGACGCGTCGGAGCGACGAACCATTCCTGGAGCGACGTGAAACAGTCAAGAAATGGTCATCAGAGACTTGAGGAAATGTCATCAGAGAGTTCATCAAACTGCCGGCCTTCTC
CTATGCGACACAGACGGTCTCCATGCCACCATTCCTGGAGCGACGTGAAACAGTCAAGAAAAGGCAATGGAGTTCTTAAACTATATCAATCCAAACTGCCGGCCTTCTC
GAACTCGAATACGAGGGCTTCTACGTCAGGGACTTCTTCGTCACGAAGCCGGTCATCGACGAGGGCAAGATAACCACGCGCGGCTTGAGATAGTCAGGCGCG
ACTGAGCGAGATAGCGAAGGAGACGCAGGGAGGGTTTTGGAGGCGATATCGCGAGCTCAAGGACTACAAGGCCACGGGCGATTCCTTCGACGAGTTCGACCCGACGAAGCACAAGTACGATG
GTTAAAATCCGCCCGGAACTGTGATAAGCTACATCGTTCGGCAGTTGAGAGAATCCTCGAGCGAGATAGGCGACAGGGCGATTCCTTCGACGAGTTCGACCCGACGAAGCACAAGTACGATG
CGGACTACTACATCGAGAACCAGGTTCTGCCGGCAGTTCTGAGAGAATCCTCGAGCGCTTCGCGCTACCGCAAGGAAGACCTGCGCTACCAGAGACGAGGCCAGGTCGGGCTTGCGC
GTGGCTGAAGCCGAAGGGGAAGGAAGAAG//
```

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA GAG AGA AGA AAA // TAG

Figure 17DDD

Sac7d - JDF-3 fusion protein

Nucleotide sequence (SEQ ID NO: 69) // Nucleotide sequence (SEQ ID NO: 39)
Nucleotide sequence (SEQ ID NO: 69) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA AGA AAA //

FIGURE 17DDD (CONT.)

```
//ATGATCCTTGACGTTGATTACATCACCGAGAATGAAAGCCCGTCATCAGGGTCTTCAAGAAGGAGAACGGCGAGTTCAGGATTGAATACGACCGGCGAGTTCGAGCCCTACTT
CTACGCGCTCCTCAGGACGACTCTGCCATGCGAAGAAATCAAAAGATAACCGCGAGGCACGGCAGGGTCGTTAAGGTTAAGCGCGGAGAAGGTGAAGAAAAGTTCCTC
GGCAGGTCTGTGAGGTCTGGGTCTCCTCTACTTCACGCACCCGCAGGACXXXCCGCGACACCGGTCATCGACATTCTACGAGTACGACATAC
CCTTCGCCAAGCGGCTACCTCATAGACAAGGGCTAATCCGATGGAAGGTGAGGAAGTCGAGGCGCGTCTTG[GAG]ATC[GAG]ACGCTCTACCACGAGGGAGAAGAGTTTGG
AACCGGGCGATTCTGATGATAAGCTACGCCGATGAAAGCGAGGCGCGTGATAACATACAACGGCGACAACTTCGACCTTCGTTGAGGTTGTCTCCACGAGAAGGAGATGATT
AAGCGCTTCTGAGGGTCGTTAAGGAGAAGGACCCGGCTGCGATGGGGACAGGTTTGCGGTCGAAGGTACACTTCGACCTTTATCAGTCATAAGGCGCACCAT
TTACCCTCGGGAGGGACGGAGCGAAGATACAGCGGTTTTCGGCAAGCCCAAGGAGAAGGTCTACGCCGAGGAGATAGCCACCGCCTGGGAGACCGGCGAGGGCTTGAG
AAACCTCCGACCTACACCCTTGAGGCTGTGTATACGAGGGCGGTGTTCCTACGAGCTTGGCAGGGAGTTCTTCCCGATGGAGGCCCAGCTTTCCAGGCTCATCGCCGGCTCGGGAGCTTT
AGGGTCGCGCAGCACCGGCAACCTCGTCGAGTGGTTCCTCTAAGGAAGGCCTACGAGAGGAACGAACTCGCTCCAAGCCCGACGAGGAGCTGGCGAGGAGAAGGGGGG
CCCGGCTCAACCGGCTACGTCAAGGAGCTGTAGGAGCTACGACGTTGCCCCGGGACTGTGGGGACAATATCGTTATCTAGACTTCGTAGTCTCTA[CCT]CAATCATAATCACCCACAACGTCTCGCCAGAT
CTACgcCGGTGGCTACGTCAAGGGGTGTAGGAGCTACGACGTTGCCCGACCCGCTGAGAGCGAACTCTCGAAGCTTCTGCAAGACTTCTGCAAGGACAGGCAACCGG[GCC]ATCAAGATTCTCGCCAACAGCTACTACGGCTACTACGG
ACGTCAACCGCGAGCTACGCGAGGGGTGTAGGAGCTACGACGTTGCCCGACCCGCTGAGAGCGAACTCTCGAAGCTTCTGCAAGACTTCTGCAAGGACAGGCAACCGGGCCATCAAGATTCTCGCCAACAGCTACTACGGCTACTACGG
GGCAGAGATAAAGAGGAAGATGAAGGCAACTCTGCAGGGAGTGCGCCAGGGAGTGCGAGAGCGTTACGGCAGGGAGTACATCGAAATGCATGGGAAGCAATGGAGTTCATCGAGAGCTTCTTAAACTATATCAATCCCAAACTGCCCGCCTTC
CTCTATGCAGATCAGACAGAGAGGGCTTCATGCGAACGGTCTCCACCATTCCTGAGGGCTTCAGGGGCTTCTCTTCGTCAGGAGCGCATGCTCAGGGAGCGTTCGTCACGAGAAAAGGAAGCAGTACGCGGTCATCGAGCGACGACCGGTGAAGCTCAAGACAGTCAAGGAACAGTACAACCGCGGGCTTGAGATAGTCAGGCG
CGACTGAGCGAGTAGCGAAGGAGAAGCGAAGGAGAGAAGCTGTTATCCACGAGCAGATAAACGGCGAGCTCCGAAGGATAAGCGGCTCCGAAGGATAGGCACAGGCGATTCCTTCGACGAGTTCGACCGAGTTCGACCGAGTTCGACCGAGCTACCGCATAGCGAGcGTTTGCCGCCAGAG
AAGTACGAGGTTCCGCCGCAGAAGCTGGTTATCGACGAGCAGATAAACGGCGAGCTCCGAAGGATAAGCGGCTCCGAAGGATAGGCACAGGCGATTCCTTCGACGAGTTCGACCCGAAGGACACAAGTACGA
GTGTTAAAATCCGGCCCGAACTGTGATAAGCTACATCGTTCTGCCGGCAGTTCTGCCGGCAGTTCTGCGAGAGAATCCTCAGGGCCTTCGGGACGTACCGCTACCCAGGAAGACCTGCGCTACCAAGGAAGACGAGGCAGTCGGCTTGGC
GCCGTGGCTGAAGCCGAAGGGGAAGAAGAAGTGA
```

Figure 17EEE

Synthetic Sso7d gene:

Nucleotide sequence (SEQ ID NO: 71)
Amino acid sequence (SEQ ID NO: 72)

```
A   T   V   K   F   K   Y   K   G   E   E   K   E   V   D   I   S   K
GCA ACC GTA AAG TTC AAG TAC AAA GGC GAA GAA AAA GAG GTA GAC ATC TCC AAG

I   K   K   V   W   R   V   G   K   M   I   S   F   T   Y   D   E   G
ATC AAG AAA GTA TGG CGT GTG GGC AAG ATG ATC TCC TTC ACC TAC GAC GAG GGC

G   G   K   T   G   R   G   A   V   S   E   K   D   A   P   K   E   L
GGT GGC AAG ACC GGC CGT GGT GCG GTA AGC GAA AAG GAC GCG CCG AAG GAG CTG

L   Q   M   L   E   K   Q   K   K
CTG CAG ATG CTG GAG AAG CAG AAA AAG
```

Figure 17FFF

Sso7d-Taq DNA polymerase fusion protein

Nucleotide sequence (SEQ ID NO: 71) // Nucleotide sequence (SEQ ID NO: 65)
Amino acid sequence (SEQ ID NO: 72) // Amino acid sequence (SEQ ID NO: 66)

```
//  A   T   V   K   F   K   Y   K   G   E   E   K   E   V   D   I   S   K
//  GCA ACC GTA AAG TTC AAG TAC AAA GGC GAA GAA AAA GAG GTA GAC ATC TCC AAG

I   K   K   V   W   R   V   G   K   M   I   S   F   T   Y   D   E   G
ATC AAG AAA GTA TGG CGT GTG GGC AAG ATG ATC TCC TTC ACC TAC GAC GAG GGC

G   G   K   T   G   R   G   A   V   S   E   K   D   A   P   K   E   L
GGT GGC AAG ACC GGC CGT GGT GCG GTA AGC GAA AAG GAC GCG CCG AAG GAG CTG

L   Q   M   L   E   K   Q   K   K       //      G   G   G
CTG CAG ATG CTG GAG AAG CAG AAA AAG     //      GGC GGC GGT
```

FIGURE 17FFF (CONT.)

```
V    T    S    G    M    L    P    L    F    E    P    K    G    R    V    L    L    V
GTC  ACT  AGT  GGG  ATG  CTG  CCC  CTC  TTT  GAG  CCC  AAG  GGC  CGG  GTC  CTC  CTG  GTG

D    G    H    L    A    Y    Q    V    H    F    T    F    A    L    G    L    T    T
GAC  GGC  CAC  CTG  GCC  TAC  CAG  GTG  CAC  TTC  CAC  TTC  GCC  CTG  GGC  CTC  ACC  ACC

S    R    G    H    E    P    V    Q    G    Y    I    V    V    F    A    K    L    K
AGC  CGG  GGG  CAC  GAG  CCG  GTG  CAG  GGG  TAC  ATC  GTG  GTC  TTC  GCC  AAG  CTC  AAG

A    L    K    E    D    G    D    Y    A    V    K    Y    A    D    R    V    A    P
GCC  CTC  AAG  GAG  GAC  GGG  GAC  TAC  GCG  GTG  AAG  TAC  GCG  GAC  CGG  GTC  GCC  CCC

S    F    R    H    E    P    Y    G    A    L    E    L    V    D    L    A    T    P
TCC  TTC  CGC  CAC  GAG  CCG  TAC  GGG  GCC  CTC  GAG  CTG  GTG  GAC  CTG  GCC  ACG  CCA

E    D    F    P    R    Q    L    A    Y    I    K    E    A    D    R    L    L    G
GAG  GAC  TTT  CCC  CGG  CAA  CTC  GCC  TAC  ATC  AAG  GAG  GCG  GAC  CGG  CTC  CTG  GGG

L    A    R    L    E    V    P    G    Y    L    R    V    L    T    H    P    S    L
CTG  GCG  CGC  CTC  GAG  GTC  CCG  GGC  TAC  CTC  CGC  GTG  CTG  ACC  CAC  CCC  AGC  CTG

A    K    K    A    E    L    W    E    Y    D    R    I    L    V    G    P    D    K
GCC  AAG  AAG  GCG  GAA  CTC  TGG  GAA  TAC  CGC  CGC  ATC  CTC  GTC  GGC  CCC  GAC  AAA

D    L    I    T    P    W    L    S    D    R    I    H    K    Y    G    E    G    Y
GAC  CTT  ATC  ACC  CCG  TGG  CTT  TCC  GAC  CGC  ATC  CAC  AAG  TAC  GGC  GAG  GGG  TAC

L    I    T    P    R    A    T    L    E    D    S    L    L    L    P    D    W    K
CTC  ATC  ACC  CCG  CGG  GCC  ACG  CTG  GAG  GAC  TCC  CTG  CTT  CTG  CCC  GAC  TGG  AAG

A    D    Y    R    E    T    A    K    L    L    K    P    G    S    L    V    K
GCC  GAC  TAC  CGG  GAG  ACG  GCG  AAG  CTT  CTG  AAG  CCC  GGG  AGC  GTC  AAG

G    I    G    E    K    N    L    D    R    K    A    I    R    B    L    E
GGG  ATC  GGG  GAG  AAG  AAC  CTG  GAC  CGG  AAG  GCC  ATC  CGG  GAG  CTG  GAA

A    L    L    K    N    L    D    P    K    L    R    V    K    I    R    T    L
GCC  CTC  CTC  AAG  AAC  CTG  GAC  CTG  AAG  CTG  CGG  GTC  AAG  ATC  CGG  ACC  CTG

```
S    R    D    Q    L    E    R    V    L    F    D    E    L    G    L    P    A    I
TCC  CGG  GAC  CAG  CTG  GAA  AGG  GTC  CTC  TTT  GAC  GAG  CTA  GGG  CTT  CCC  GCC  ATC

G    T    E    K    T    G    K    V    E    S    A    A    Y    A    V    L    E    A
GGC  ACG  GAG  AAG  ACC  GGC  AAG  GTG  GAG  AGC  GCC  GCC  TAC  GCC  GTC  CTG  GAG  GCC

L    R    E    A    H    T    P    Y    I    L    Q    L    R    E    H    P    L    T
CTC  CGC  GAG  GCC  CAC  ACC  CCC  TAC  ATC  CTG  CAG  CTG  CGC  GAG  CAC  CCC  CTC  ACC

K    L    K    S    T    Y    I    D    P    L    P    D    L    I    H    P    R    T
AAG  CTG  AAG  AGC  ACC  TAC  ATT  GAC  CCG  CTG  CCC  GAC  CTC  ATC  CAC  CCC  AGG  ACG

G    R    L    H    T    R    F    N    Q    T    A    A    T    G    R    L    S    AGT
GGC  CGC  CTC  CAC  CGC  TTC  AAC  CAG  GCC  ACG  GCC  ACG  GGC  AGG  CTA  AGT

S    D    P    N    L    Q    I    A    P    V    R    L    V    A    L    G    Q    R
AGC  GAT  CCC  AAC  CTC  CAG  ATC  GCC  CCG  GTC  CGC  TTG  GTG  GCC  CTT  GGG  CAG  AGG

I    R    A    F    I    R    A    E    G    W    L    T    P    V    A    L    D    Y
ATC  CGG  GCC  TTC  ATC  CGG  GCC  GAG  GGG  TGG  CTA  ACC  CCG  GTG  GCC  CTG  GAC  TAT

S    Q    I    E    L    R    V    L    S    G    H    L    T    P    V    D    E    N    L    I
AGC  CAG  ATA  GAG  CTC  AGG  GTG  CTG  TCC  GGC  CAC  CTC  ACG  CCC  GTG  GAC  GAG  AAC  CTG  ATC

R    V    F    Q    E    R    G    R    T    E    T    A    S    A    W    M    F
CGG  GTC  TTC  CAG  GAG  CGG  GGG  CGG  ACG  GAG  ACC  GCC  AGC  GCC  TGG  ATG  TTC

G    P    R    E    Q    A    V    R    M    H    D    P    L    S    A    A    K    T    I
GGC  CCC  CGG  GAG  CAG  GCG  GTG  CGG  ATG  CAC  GAC  CCC  CTG  TCG  GCC  GCG  AAG  ACC  ATC

N    F    Y    L    Q    A    F    I    E    R    L    Y    F    Q    S    E    L    A
AAC  TTC  TAC  CTC  CAG  GCC  TTC  ATT  GAG  CGG  CTC  TAC  TTT  CAG  AGC  GAG  CTA  GCC

I    P    Y    E    K    I    E    K    T    L    E    G    R    R    R    S    F    P
ATC  CCT  TAC  GAG  ATT  GAG  AAG  ACC  CTG  GAG  GGG  AGG  AGG  CGG  AGC  TTC  CCC

K    V    R    A    W    L    F    G    R    R    R    K    R    R    L    R    G    Y
AAG  GTG  CGG  GCC  TGG  CTC  TTC  GGC  CGC  CGG  CGC  AAG  AGG  CGG  CTG  CGG  GGG  TAC

V    E    T    L    F    G    R    R    Y    V    P    D    L    E    A    R    V
GTG  GAG  ACC  CTC  TTC  GGC  CGC  CGC  TAC  GTG  CCA  GAC  CTA  GAG  GCC  CGG  GTG
```

FIGURE 17FFF (CONT.)

```
K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

L   S   A   K   E   G   I   D   G   R   G   G   G   H   H   H   H   H
CTC TCC GCC AAG GAG GGC ATT GAT GGC CGC GGC GGA GGC CAT CAT CAT CAT CAT

H   H   *
CAT CAT TAA
```

Figure 17GGG

Pfu DNA Polymerase (WT)-Sso7d fusion protein

Nucleotide sequence (SEQ ID NO: 61) // Nucleotide sequence (SEQ ID NO: 71)

```
cctggtcct   gggtccacat   atatgttctt   actcgccttt   atgaagaatc   cccagtcgc
tctaacctgg  gttatagtga   caaatcttcc   tccaccaccg   cccaagaagg   ttatttctat
caactctaca  cctcccctat   tttctctctt   atgagatttt   taagtatagt   tatagagaag
gttttatact  ccaaactgag   ttagtagata   tgtggggagc   ataatgattt   tagatgtgga
//
```

FIGURE 17GGG (CONT.)

```
ttacataact gaagaaggaa aacctgttat taggctattc aaaaaagaga acggaaaatt
taagatagag catgatagaa cttttagacc atacatttac gtccttctca gggatgattc
aaagattgaa gaagtaaga aataacggg ggaaggcat ggaagattg tgagaattgt
tgatgtagag aaggttgaga aaaagtttct cggcaagcct attacgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
aataccaatg gagggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gattctcag gattatcagg gagaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acattcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac
aggtggattc gttaaagagc cagaaaaggg gttgtgggaa aacatagtat acctagattt
tagagcccta tatccctga ttataattac ccacaatgtt tctcccgata ctctaaatct
```

FIGURE 17GGG (CONT.)

```
tgagggatgc aagaactatg atatcgctcc tcaagtaggc cacaagttct gcaaggacat
cctggtttt ataccaagtc tcttgggaca tttgttagag gaaagacaaa agattaagac
aaaatgaag gaaactcaag atcctataga aaaatactc cttgactata gacaaaaagc
gataaaactc ttagcaaatt cttctacgg atattatggc tatgcaaaag caagatggta
ctgtaaggag tgtgctgaga gcgttactgc ctggggaaga aagtacatcg agttagtatg
gaaggagctc gaagaaaagt ttggatttaa agtcctctac attgacactg atggtctcta
tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa acacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagc aggaatggta attggataca tagtacttag
aggcgatggt ccaattagca atagggcaat tctagctgag gaatacgatc ccaaaagca
caagtatgac gcagaatatt acattgaaa ccaggttctt ccagcggtac ttaggatatt
ggagggattt ggatacagaa aggaagacct cagataccaa aagacaagac aagtcggcct
aacttcctgg cttaacatta aaaaatccta gaaagcgat agatatcaac tttattctt
tctaacctt ttctatgaaa gaagaactga gcaggaatta ccagttcttc cgttattta
tgggtaatta aaaacccatg ctcctgggag aatcttcgaa taaaatccct aacttcaggc
```

FIGURE 17GGG (CONT.)

```
tttgctaagt gaatagaata aacaacatca ctcacttcaa acgccttcgt tagaaatggt
ctatctgcat gcttctctgg ctcggaanng gaggattcat aacaacagta tcaacattct
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttcgggagt tttgtattgc tctagccaag gtttgggatt tttgaatcct ttaactctgg
aaagtataat ttcaagctcc ttcttcttca tgacagatga aaaattgttt tgtctctttt
taactttac agaataact gtctcaaatt atgacaactc ttgacatttt tacttcatta
ccagggtaat gtttttaagt atgaaatttt tctttcatag aggagnnnn nngtcctctc
ctcgattcc ttggttgtgc tccatatgat aagcttccaa agtgggtgtt cagactttta
gacactcaaa taccagacga caatggtgtg ctcactcaag cccatatgg gttgagaaaa
gtagaagcgg cactactcag atgcttcccc aggaatgagg ttgtgtagc tcntcccnga
aagattgaga tgttcttgg //

// GCA ACC GTA AAG TTC AAG TAC AAA GGC GAA GAA AAA GAG GTA GAC ATC TCC AAG

ATC AAG AAA GTA TGG CGT GTG GGC AAG ATG ATC TCC TTC ACC TAC GAC GAG GGC

GGT GGC AAG ACC GGC CGT GGT GCG GTA AGC GAC GAA AAG GAC GCG CCG AAG GAG CTG

CTG CAG ATG CTG GAG AAG CAG AAA AAG    // TGA
```

Figure 17HHH

PFU DNA POLYMERASE (V93 R OR E)-Sso7d fusion protein

Nucleotide sequence (SEQ ID NO: 27) // Nucleotide sequence (SEQ ID NO: 71)
Nucleotide sequence (SEQ ID NO: 28) // Nucleotide sequence (SEQ ID NO: 71)

```
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)
ATGATTTTAG ATGTGGATTA CATAACTGAA GAAGGAAAAC CTGTTATTAG GCTATTCAAA     60
AAGAGAACG GAAAATTTAA GATAGAGCAT GATAGAACTT TTAGACCATA CATTTACGCT    120
CTTCTCAGGG ATGATTCAAA GATTGAAGAA GTTAAGAAAA TAACGGGGGA AAGGCATGGA    180
AAGATTGTGA ATGATTGTTA TGTAGAGAAG GTTGAGAAAA AGTTTCTCGG CAAGCCTATT    240
ACCGTGTGGA AACTTTATTT GGAACATCCC CAAGATXXXC CCACTATTAG AGAAAAAGTT    300
AGAGAACATC CAGCAGTTGT GGACATCTTC GAATACGATA TTCCATTTGC AAAGAGATAC    360
CTCATCGACA AAGGCTAAT ACCAATGGAG GGGAAGAAG AGCTAAAGAT TCTTGCCTTC    420
GATATAGAAA CCCTCTATCA CGAAGGAGAA GAGTTTGGAA AAGGCCCAAT TATAATGATT    480
AGTTATGCAG ATGAAAATGA AGCAAAGGTG ATTACTTGGA AAAACATAGA TCTTCCATAC    540
GTTGAGGTTG TATCAAGCGA GAGAGATG ATAAAGAGAT TTCTCAGGAT TATCAGGGAG    600
AAGGATCCTG ACATTATAGT TACTTATAAT GGAGACTCAT TCGATTTCCC ATATTTAGCG    660
AAAAGGGCAG AAAAACTTGG GATTAAATTA ACCATTGGAA GAGATGGAAG CGAGCCCAAG    720
ATGCAGAGAA TAGGCGATAT GACGGCTGTA GAAGTCAAGG GAAGAATACA TTTCGACTTG    780
TATCATGTAA TAACAAGGAC AATAAATCTC CCAACATACA CTAGAGAGGC TGTATATGAA    840
GCAATTTTTG GAAAGCCAAA GGAGAAGGTA TACGCCGACG AGATAGCAAA AGCCTGGGAA    900
AGTGGAGAGA ACCTTGAGAG AGTTGCCAAA TACTCGATGG AAGATGCAAA GGCAACTTAT    960
GAACTCGGGA AAGAATTCCT TCCAATGGAA ATTCAGCTTT CAAGATTAGT TGGACAACCT   1020
TTATGGGATG TTTCAAGGTC AAGCACAGGG AACCTTGTAG AGTGGTTCTT ACTTAGGAAA   1080
GCCTACGAA GAAACGAAGT AGTTCCAAAC AAGCCAAGTG AAGAGGAGTA TCAAAGAAGG   1140
CTCAGGGAGA GCTACACAGG TGGATTCGTT AAAGAGCCAG AAAGGGGTT GTGGAAAC    1200
ATAGTATACC TAGATTTTAG AGCCTATAT CCCTCGATTA TAATTACCCA CAATGTTTCT   1260
CCCGATACTC TAAATCTTGA GGGATGCAAG AACTATGATA TCGCTCCTCA AGTAGGCCAC   1320
AAGTTCTGCA AGGACATCCC TGGTTTTATA CCAAGTCTCT TGGACATTT GTTAGAGGAA   1380
AGACAAAAGA TTAAGACAAA AATGAAGGAA ACTCAAGATC CTATAGAAAA AATACTCCTT   1440
GACTATAGAC AAAAAGCGAT AAAACTCTTA GCAAATTCTT TCTACGGATA TTATGGCTAT   1500
GCAAAAGCAA GATGTACTG TAAGGAGTGT GCTGAGAGCG TTACTGCCTG GGAAGAAAAG   1560
TACATCGAGT TAGTATGGAA GGAGCTCGAA GAAAGTTTG GATTTAAAGT CCTCTACATT   1620
GACACTGATG GTCTCTATGC AACTATCCCA GGAGGAGAAA GTGAGGAAAT AAAGAAAAAG   1680
```

FIGURE 17HHH (CONT.)

```
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACAAAAG ACGGAGATGT TGAAGAAGCT 1920
GTGAGAATAG TAAAGAAGT AATACAAGCA CTTGCCAATT ATGAAATTCC ACCAGAAAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA TCCGCTAAC TTCCTGGCTT AACATTAAAA AATCC 2280
ACAAGACAAG TCGGCTACTA TTCCTGGCTT AACATTAAAA AATCC 2328
// GCA ACC GTA AAG TTC AAG TAC AAA GGC GAA GAA GAG GTA GAC ATC TCC AAG
   ATC AAG AAA GTA TGG GGC CGT GTG GGC AAG ATG ATC TCC TTC ACC TAC GAC GAG GGC
   GGT GGC AAG ACC GGC CGT GGT GCG GTA AGC GAA GAC GCG CCG AAG GAG CTG
   CTG CAG ATG CTG GAG GAG AAG CAG AAA AAG // TGA
```

Figure 17III

PFU DNA POLYMERASE (G387P/V93R OR E) -Sso7d fusion protein

Nucleotide sequence (SEQ ID NO: 29) // Nucleotide sequence (SEQ ID NO: 71)
Nucleotide sequence (SEQ ID NO: 30) // Nucleotide sequence (SEQ ID NO: 71)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAGTT 300
AGAGAACATC CAGCAGTTGT GGATATCTTC GAATACGATA TTCCATTTGC AAAGAGATAC 360
CTCATCGACA AGGGCCTAAT ACCAATGGAG GGGAAGAAG AGTTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGATTTCCC ATATTTAGCG 660
AAAAGGGCAG AAAAACTTGG GATTAAATTA ACCATTGGAA GAGATGGAAG CGAGCCCAAG 720
```

FIGURE 17III (CONT.)

```
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG CGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGAGAG GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGAAGAAAAG 1560
TACATCGAGT GAGGCTCGAA AACTATCCCA GAAAAGTTTG GATTTAAAGT CCCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GATGGTGGAG TGAAATTGCA 1860
AAAGAAACTC AAGCTAGAGT TTTTGAGACA ATACTAAAAC ACGGAGATGT TGAAGAAGCT 1920
GTGAATAAGT TAAAAGAAGT AATACAAAAG CTTGCCAATT AATAAAGCGAT AGGTCCTCAC 1980
CTCGCAATAT ATGAGCAGAT AGCTGCTAAA GGAGTTAAAA TAAAGCCAGG AATGGTAATT 2040
GTAGCTGTTG CAAAGAAACT TACTTAGAGG CGATGGTCCA ATTAGCAATA GGGCAATTCT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC // 2328
```

// GCA ACC GTA AAG TTC GTA AAG TAC AAA GGC GAA GAA AAA GAG GTA GAC TAC ATC TCC AAG
ATC AAG GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TGA

Figure 17JJJ

PFU DNA POLYMERASE (D141A/E143A/V93R OR E)-Sso7d fusion protein

Nucleotide sequence (SEQ ID NO: 31) // Nucleotide sequence (SEQ ID NO: 71)
Nucleotide sequence (SEQ ID NO: 32) // Nucleotide sequence (SEQ ID NO: 71)

FIGURE 17JJJ (CONT.)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACA GTTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
```

FIGURE 17JJJ (CONT.)

```
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC //                  2328

// GCA ACC GTA AAG TTC AAA GGC GAA GAA AAA GAG GTA GAC ATC TCC AAG
   ATC AAG AAA GTA TGG CGT GTG GGC AAG ATG ATC TCC TTC GAC TAC GAG GGC
   GGT GGC AAG ACC GGC CGT GGT GCG GTA AGC GAA AAG GAC GCG GCG AAG GAG CTG
   CTG CAG ATG CTG GAG AAG CAG AAA AAG // TGA
```

Figure 17KKK

KOD DNA POLYMERASE – Sso7d fusion protein

Nucleotide sequence (SEQ ID NO: 33)   // Nucleotide sequence (SEQ ID NO: 71)
Nucleotide sequence (SEQ ID NO: 34)   // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG   60
AAGGAAAACG GCGAGTTTAA GATTGAGTAC GACCGGACTT TTGAACCCTA CTTCTACGCC  120
CTCCTGAAGG ACGATTCTGC CATTGAGGAA GTCAAGAAGA TAACGCCGA GAGGCACGGG  180
ACGGTTGAAG CGGTTAAGCG GTTGAAAAG AGTTCCTCGG GAGACCAGTT              240
GAGGTCTGAA AACTCTACTT TACTCATCCG CAGGACXXXC CAGGAGATAAG GGACAAGATA  300
CGAGAGCATC CAGCAGTTAT TGACAGTACA GAGTACGACA TACCCTTCGC CAAGCGCTAC  360
CTCATAGACA AGGATTAGT GCCAATGGAA GGGCGACGAGG AGCTGAAAAT GCTCGCCTTC  420
GACTCTGAAA CTCTCTACCA TGAGGGCGAG GGCCAGGGTG GAGTTCGCCG CCTTATGATA  480
AGCTACGCCG ACGAGGAAGG GGCCAGGGTG ATAACTTGGA AGAACGTGGA TCTCCCCTAC  540
GTTGACGTCG TCTCGACGGA GAGGGAGATG ATAAAGCGCT TCCTCCGTGT CTATCGGAG   600
AAAGACCCGG ACGTTCTCAT AACCTACAAC GGCGACAACT TCGACTTCGC CTATCTGAAA  660
AAGCGCTGTG AAAAGCTCGG AATAAACTTC GCCCTCGGAA GGGATGGAAG CGAGCCGAAG  720
ATTCAGAGGA TGGGCGACAG GTTTGCCGTC GAAGTGAAGG GACGATACA CTTCGATCTC  780
TATCCTGTGA TAAGACGGAC GATAAACCTG GGAGAAGGTT CGCTTGAGGC CGTTTATGAA  840
GCCGTCTTCG GTCAGCCGAA AGTGCGCCGA AGTCGCCGAA AATAACCAC AGCCTGGGAA  900
ACCGGCGAGA ACCTTGAGAG AGGAGTTCCT TCCGATGGAG GCCCAGCTTT AAGATGCGAA GGTCACATAC  960
GAGCTTTGGA AGGAGTTCCT CTCCCGCTC CAGCACTGGC AACCTCGTTG AGTGGTTCCT CCTCAGGAAG 1020
GCCTATGAGA GGAATGAGCT GGCCCCGAAC AAGCCCGATG AAAAGGAGCT GGCCAGAAGA 1080
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCACAGTT CGGCACCGC  1320
TTCTGCAAGG ACTTCCCAGG ATTTATCCCG AGCTTCCTTG GAGACCTCCT AGAGGAGAGG 1380
```

FIGURE 17KKK (CONT.)

```
CAGAGAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA ACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG AGTTCCGCC GGAGAAGCTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGGCACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT 2325

// GCA ACC GTA AAG TTC AAG TAC AAA GAG GAA AAA GAG GTA GAC GAG ATC TCC AAG
   ATC AAG AAA GTA TGG CGT GTG GGC AAG ATG ATC TCC TTC ACC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG // TGA
```

Figure 17LLL

Ss07d - KOD DNA POLYMERASE fusion protein

Nucleotide sequence (SEQ ID NO: 71) // Nucleotide sequence (SEQ ID NO: 33)
Nucleotide sequence (SEQ ID NO: 71) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC GAG ATC TCC AAG
  ATC AAG AAA GTA TGG CGT GTG GGC AAG ATG ATC TCC TTC ACC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG      //
```

FIGURE 17LLL (CONT.)

```
//ATGATCCTCG ACACTGACTA CATAACCGAG GATGGAAAGC CTGTCATAAG AATTTTCAAG   60
AAGGAAAACG GCGAGTTTAA GATTGAGTAC GACCGGACTT TTGAACCCTA CTTCTACGCC   120
CTTCTGAAGG ACGATTCTGC CATTGAGGAA GTCAAGAAGA TAACCGCCGA GAGGCACGGG   180
ACGTTGTAA CGGTTAAGCG GGTTGAAAAG GTTCAGAAGA AGTTCCTCGG GAGACCAGTT   240
GAGGTCTGGA AACTCTACTT TACTCATCCG CAGGACXXXC CAGCGATAAG GGACAAGATA   300
CGAGAGCATC CAGCAGTTAT TGACATCTAC GAGTACGACA TACCCTTCGC CAAGCGCTAC   360
CTCATAGACA AGGGATTAGT GCCAATGGAA GGCGACGAGG AGCTGAAAAT GCTCGCCTTC   420
GACATTGAAA CTCTCTACCA TGAGGGCGAG GAGTTCGCCCG AGGGGCCAAT CCTTATGATA   480
AGCTACGCCG ACGAGGAAGG GGCCAGGGTG ATAACTTGGA AGAACGTGGA TCTCCCCTAC   540
GTTGACGTCG TCTCGACGGA GAGGGAGATG ATAAAGCGCT TCCTCCGTGT TGTGAAGGAG   600
AAAGACCCGG ACGTTCTCAT AACCTACAAC GGCGACAACT TCGACTTCGC CTATCTGAAA   660
AAGCGCTGTG AAAAGCTCGG AATAAACTTC GCCCTCGGAA GGGATGGAAG CGAGCCGAAG   720
ATTCAGAGGA TGGGCGACAG GTTTGCCGTC GAAGTGAAGG GACGGATACA CTTCGATCTC   780
TATCCTGTGA TAAGACGGAC GATAAACCTG CCCACATACA CGCTTGAGGC CGTTTATGAA   840
GCCGTCTTCG GTCAGCCGAA GGAGAAGGTT TACGCTGAGG AATAACCAC AGCCTGGGAA   900
ACCGGCGAGA ACCTTGAGAG AGTCGCCCGC TACTCGATGG AAGATGCGAA GGTCACATAC   960
GAGCTTGGGA AGGAGTTCCT TCCGATGGAG GCCCAGTTT CTCGCTTAAT CGGCCAGTCC  1020
CTCTGGGACG TCTCCCGCTC CAGCACTGGC AACCTCGTTG AGTGGTTCCT CCTCAGGAAG  1080
GCCTATGAGA GGAATGAGCT GGCCCCGAAC AAGCCGATG AAAAGGAGCT GGCCAGAAGA  1140
CGGCAGAGCT ATGAAGGAGG CTATGTAAAA GAGCCCGAGA GAGGGTTGTG GAGAACATA  1200
GTGTACTTAG ATTTTAGATC CCTGTACCCC TCAATCATCA TCACCCACAA CGTCTCGCCG  1260
GATACGCTCA ACAGAGAAGG ATGCAAGGAA TATGACGTTG CCCCACAGGT CGGCCACCGC  1320
TTCTGCAAGG ACTTCCCAGG ATTTATCCCG AGCCTGCTTG GAGACCTCCT AGAGGAGAGG  1380
CAGAAGATAA AGAAGAAGAT GAAGGCCACG GATCCTGGCA ATTGACCCGA TCGAGAGGAA  1440
TACAGGCAGA GGGCCATCAA GATCCTGGCA AACAGCTACT ACGGTTACTA CGGCTATGCA  1500
AGGGGCGCGT GGTACTCAAGGA GGAGTGTGCA GAGAGCGTAA CGGCCTGGGG AAGGAGTAC  1560
ATAACGATGA CCATCAAGGA GATAGAGGAA AAGTACGGCT TTAAGGTAAT CTACAGCGAC  1620
ACCGACGGAT TTTTGCCCAC AATACCTGGA GCCGATGCTG AAACCGTCAA AAAGAAGGCT  1680
ATGGAGTTCC TCAAGTATAT CAACGCCAAA CTTCCGGGCG CGCTTGAGCT CGAGTACGAG  1740
GGCTTCTACA AACGCGGCTT CTTCGTCACG AAGAAGAAGT ATGCGGTGAT AGACGAGGAA  1800
GGCAAGATAA CAACGCGCGG ACTTGAGATT GTGAGGCGTG ACTGGAGCGA GATAGCGAAA  1860
GAGACGCAGG CGAGGGTTCT TGAAGCTTTG CTAAAGGACG AGGTTCCGCC GAAGGGCCGTG  1920
AGGATAGTCA AAGAGGTTAC CGAAAAGCTG AGCAAAGCTA AAGGACTACA AGGCAACCGG  1980
GTGATCCACG AGCAGATAAC GCGGAGAGGA GTCAAAATAC GCCCTGGAAC TCCCCACGTT  2040
GCCGTTGCCA AGAGGTTGGC CGCGAGAGGA GGCGACAGGG CGATACCGGT GGTGATAAGC  2100
TACATCGTGC TCAAGGGCTC TGGGAGGATA TACTACAATTG AGAACCAGTT CGACGAGTTC  2160
GACCCGACGA AGCACAAGTA CGACGCCGAG CTTCGGTTAC CGAAGGAAG ACCTGCGCTA  2220
GTTGAGAGAA TTCTGAGCGC CTTCGATGC CGGTTACGGC TGGCTGAGTC CCAGAAGACG  2280
AGACAGGTTG GTTTGAGTGC TTGGCTGAAG CCGAAGGGAA CCGAAGGGAA
CT  //TAG 2325
```

Figure 17MMM

Sso7d-Vent DNA POLYMERASE FUSION PROTEIN

Nucleotide sequence (SEQ ID NO: 71)  // Nucleotide sequence (SEQ ID NO: 35)
Nucleotide sequence (SEQ ID NO: 71)  // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC GAG ATC TCC AAG
  ATC AAG AAA GTA TGG CGT GTG GGC AAG ATG ATC TCC TTC ACC TAC GAC GAG GGC
  GGT GGC AAG ACC GGC GGT CGT GGT GCG GTA AGC GAA AAG GAC GCG CCG AAG GAG CTG
  CTG CAG ATG CTG GAG AAG CAG AAA AAG //

ATGATACTGG ACACTGATTA CATAACAAAA GATGGCAAGC CTATAATCCG AATTTTTAAG   60
AAAGAGAACG GGGAGTTTAA AATAGAACTT GACCCTCATT TTCAGCCCTA TATATATGCT  120
CTTCTCAAAG ATGACTCCGC TATTGAGGAG GTCAGAGGCA ATAAAGGCGA GAGACATGGA  180
AAACTGTGA GAGTGCTCGA TGCAGTGAAA GTCAGGAAAA AATTTTTGGG AAGGGAAGTT   240
GAAGTCTGGA AGCTCATTTT CGAGCATCCC CAGCTATGCG GGGCAAAATA             300
AGGGAACATC CAGCTGTGGT TGACATTTAC GAATATGACA TACCCTTTGC CAAGCGTTAT  360
CTCATAGACA AGGGCTTGAT TCCCATGGAG GGAGACGAGG AGCTTAAGCT CCTTGCCTTT  420
GATATTGAAA CGTTTTATCA TGGGGAGAT GAATTTGGAA AGGGCGAGAT AATAATGATT   480
AGTTATGCCG ATGAAGAAGA GGCCAGAGTA ATCACATGGA AAAATATCGA TTTGCCGTAT  540
GTCGATGTTG TGTCCAATGA AAGAGAAATG ATAAAGCGTT TGTTCAAGT TGTTAAAGAA   600
AAAGACCCCG ATGTGATAAT AACTTACAAT GGGGACAATT TTGATTTGCC GTATCTCATA  660
AAACGGGCAG AAAAGCTGGG AGTTCGGCTT GTCTTAGGAA GGGACAAAGA ACATCCCGAA  720
CCCAAGATTC AGAGGATGGG TGATAGTTTT GCTGTGGAAA TCAAGGGTAG AATCCACTTT  780
GATCTTTTCC CAGTTGTGCG AAGGACGATA AACCTCCCAA CGTATACGCT TGAGGCAGTT  840
TATGAAGCAG TTTTAGGAAA ACCAAAAGC AAATTAGGAG CAGAGAAAT TGCCGCTATA   900
TGGGAAAACAG AAGAAAGCAT GAAAAAACTA GCCCAGTACT CAATGGAAGA TGCTAGGGCA  960
ACGTATGAGC TCGGAAAGGA ATTCTTCCCC ATGGAAGCTG TGGAAGCTGC AAA GCTGATAGGT 1020
CAAGTGTAT GGGACGTCTC GAGATCAAGC ACCGGCAACC TCGTGGAGTG GTATCTTTTA  1080
AGGGTGGCAT ACGCGAGGAA TGAACTTGCA CCGAACAAAC CTGAGGGAA AGAGTATAAA   1140
CGGCGCTTAA GAACAACTTA CCTGGGAGGA TATGTAAAAG AGCCAGAAAG AGTTTGTGG   1200
GAAAATATCA TTTATTTGGA TTTCCGCAGT CTGTACCCTT CAATAATAGT TACTCACAAC  1260
GTATCCCCAG ATACCCTTGA AAAAGAGGGC TGTAAGAATT ACGATGTTGC TCCGATAGTA  1320
GGATATAGGT TCTGCAAGGA CTTTCCGGGC TTTATTCCCT CCATACTCGG GGACTTAATT  1380
GCAATGAGGC AAGATATAAA GAAGAAATG AATCCACAA TTGACCCCGAT CGAAAAGAAA   1440
```

FIGURE 17MMM (CONT.)

```
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGATTTAA TTAAAGAGGG AAGTGTTGAA 1920
AAAGCTGTAG AAGTTGTTAG AGATGTTGTA GCAGATTACC AGGGATTTAA CAAAATACAG GGTTCCACTT 1980
GAAAAGCTTG TTATCCATGA GCAGATTACC AGGGATTTAA AGAACTACAA AGCCATTGGC 2040
CCTCATGTCG CGATAGACAA AGACTTCCGC CAAGAGGAGA TAAAAGTGAA ACCGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGA TTTAAGGTAT 2280
CAAAGCTCAA AACAAACCGG CTTAGATGCA TGGCTCAAGA GGTAG 2325
```

Figure 17NNN

Vent DNA POLYMERASE - Sso7d FUSION PROTEIN

Nucleotide sequence (SEQ ID NO: 35) // Nucleotide sequence (SEQ ID NO: 71)
Nucleotide sequence (SEQ ID NO: 36) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAGA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC TCCCATGAGA GGAGACGAGG CCTTGCCTTT 420
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAGA GGCCAGAGTA AAGAGAAATG ATCACATGGA AAAATATGA TTTGCCGTAT 540
GTCGATGTTG TGTCCAATGA AAGAGAAATG ACTTACAAT GGGGACAATT TTGTTCAAGT TGTTAAAGAA 600
AAAGACCCCG ATGTGATAAT ACTTACAAT GGGGACAATT TTGATTTGCC GTATCTCATA 660
AAACGGGCAG AAAAGCTGGG AGTTCGGCTT GTCTTAGGAA GGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA GTATACGCT TGAGGCAGTT 840
```

FIGURE 17NNN (CONT.)

```
TATGAAGCAG TTTTAGAAAA AACCAAAAGC AAATTAGGAG CAGAGGAAAT TGCCGCTATA 900
TGGGAAACAG AAGAAAGCAT GAAAGAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGCTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAAGATAAC CAAGGGGGC AAAGTTTTA TTGGAAGTAG TGGAGTGAG 1860
ATAGCTAAGG AGACTCAGGC AAGTGTTGTA GAGGCTATAC TAAAGAGGG AAGTGTTGAA 1920
AAAGCTGTAG AAGTTGTTAA GCAGATTACC GAGGATTTAA CAAATACAG GGTTCCACTT 1980
GAAAAGCTTG TTATCCATGA CGATAGCAAA AAGACTTACC AGGGATGGGA AGACTACAA ACCGGCCACA 2040
CCTCATCTCG CGATAGCAAA AAGACTTGCC GCAAGAGGGA TAAAAGTGAA AAGAC AAG GAC ACCGGCCACA 2040
ATAATAAGCT ATATCGTTCT CAAAGGGAGC GGAAAGATAA GCGATAGGGT ACTACATAGA AAATTTACTT 2160
ACAGAATACG ATCCTAGAAA ACACAAGTAC GATCGGAGCT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //
```

// GCA ACC GTA AAG TTC AAG TAC AAA GGC GAA GAA AAA GAG GTA GAC ATC TCC AAG
ATC AAG AAA GTA TGG CGT GTG GGT GTG GGT ATC TCC TTC ACC TAC GAC GAG GGC
GGT GGC AAG ACC GGC CGT GGT GCG GTA AGC GAC GAA AAG GCG CCG AAG GAG CTG
CTG CAG ATG CTG GAG AAG CAG AAA AAG // TGA

Figure 17OOO

Deep Vent- Ssod7 DNA polymerase fusion protein

Nucleotide sequence (SEQ ID NO: 37)    // Nucleotide sequence (SEQ ID NO: 71)
Nucleotide sequence (SEQ ID NO: 38)    // Nucleotide sequence (SEQ ID NO: 71)

FIGURE 17OOO (CONT.)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG   60
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220
GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAG            2328
```

FIGURE 17OOO (CONT.)

```
// GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC GAC GAG GAG GGC
GGT GGC AAG ACC GGC CGT GGT GCG GTA AGC GAA GAC GCG CCG AAG GAG CTG
CTG CAG ATG CTG GAG AAG CAG AAA AAG // TGA
```

Figure 17PPP

Ssod7 - Deep Vent DNA polymerase fusion protein

Nucleotide sequence (SEQ ID NO: 71)   // Nucleotide sequence (SEQ ID NO: 37)
Nucleotide sequence (SEQ ID NO: 71)   // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC GAC GAG GAG GGC
GGT GGC AAG ACC GGC CGT GGT GCG GTA AGC GAA GAC GCG CCG AAG GAG CTG
CTG CAG ATG CTG GAG AAG CAG AAA AAG    //

ATGATACTTG ACGCTGACTA CATCACCGAG GATGGGAAGC CGATTATAAG GATTTTCAAG       60
AAGAAAACG  GCGAGTTTAA GGTTGAGTAC GACAGAAACT TTAGACCTTA CATTTACGCT      120
CTCCTCAAAG ATGACTCGCA GATTGATGAG GTTAGGAAGA TAACCGCCGA GAGGCATGGG      180
AAGATAGTGA GAATTATAGA TGCCGAAAAG GTAAGGAAGA AGTTCCTGGG GAGGCCGATT      240
GAGGTGTGGA GGCTGTACTT TGAACACCCT CAGGACXXXC CCGCAATAAG GGATAAGATA      300
AGAGAGCATT CCGCAGTTAT TGACATCTTT GAGTACGACA TTCCGTTCGC GAAGAGGTAC      360
CTAATAGACA AAGGCCTAAT TCCAATGGAA GGCGATGAAG AGCTCAAGTT GCTCGCATTT      420
GACATAGAAA CCCTCTATCA CGAAGGGGAG GAGTTCGCGA AGGGCCCAT  TATAATGATA      480
AGCTATGCTG ATGAGGAAGA AGCCAAAGTC ATAACGTGGA AAAAGATCGA TCTCCCGTAC      540
GTCGAGGTAG TTTCCAGCGA GAGGGAGATG TACCTACAAC GCGATTCTT  TCGACCTTCC      600
AAAGATCCCG ATGTTATAAT GGCGATTCTT TCGACCTTCC CTATCTAGTT                600
AAGAGGGCCG AAAAGCTCGG GATAAAGCTA CCCCTGGAA  GGGACGGTAG TGAGCCAAAG      660
AAGAGGGCCG AAAAGCTCGG GATAAAGCTA CCCCTGGGAA GGGACGGTAG TGAGCCAAAG      720
ATGCAGAGGC TTGGGGATAT GACAGCGGTG GAGATAAAGG GAAGGATACA CTTTGACCTC      780
```

FIGURE 17PPP (CONT.)

```
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGGAGGATG AGAAAGGGCT CGAGAGAAGG  1140
CTAAGGAGA GCTACGCTGG GGATACGTT AAGGAGCGG AGAGGAGTA CGAGAAGGG  1200
TTAGTTTCCC TAGATTTCAG GAGCCTGTAC CCCTCGATAA TAATCACCCA TAACGTCTCA  1260
CCCGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAAGT TCTAAAGACC CAATCGAGAA GAAGATGCTT  1440
GATTACAGGC AACGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAGGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAGGCTAT TCCAGAAAAG  1980
CTAGTTATTT ACGAGCAGAT CACGAGGCCC AGCCGCTAGA GGAGTAAAGG TGCAGAGAGG  2040
GTTCCGTGG CAAAAGGTT AGCCGCTAGA GGAGTAAAGG TGAGGCTGG CATGGTGATA  2100
GGGTACATAG TGCTGAGGGG GACGGGGCCA ATAAGCAAGA TAGTATTACA TGCAGAGAAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA             2328
```

Figure 17QQQ

JDF-3 – Sso7d fusion protein

Nucleotide sequence (SEQ ID NO: 39)    // Nucleotide sequence (SEQ ID NO: 71)
Nucleotide sequence (SEQ ID NO: 40)    // Nucleotide sequence (SEQ ID NO: 71)

V93R MUTANT:  XXX = AGA, AGG, CGA, CGC, CGG, CGT (ALL POSSIBLE CODONS FOR ARGININE)
V93E MUTANT:  XXX = GAA, GAG (ALL CODONS FOR GLUTAMIC ACID)

```
ATGATCCTTGACGTTGATTACATCACCGAGAATGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCGGTCGTTAAGGTTAAGCGCGGAGAAGGTGAAGAAAAGTTCCTCGG
CAGGTCTGTGGAGGTCTGGAGGTCTGGGTCCTCATCACGGAAGGAAGCACCCCGCAATCCGCGACAAATAAGGAAGCACCCCGCGGTCATCGACATCTACGAGTACGACATACCC
```

FIGURE 17QQQ (CONT.)

TTCGCCAAGCGCTACCTCATAGACAAGGGCCTAATCCCGATGAAGTGAGGAAGAGCTTAAACTCATGTCCTTCGACATCGAGACGCTCTACCACGAGGAGGAGAAGAGTTTGAA
CCGGGCCGATTCTGAGGGTCGTTAAGGAGAAGCTACGCCGATGATAAGCGAGGCGGGCGATAACCTGGAAGAAGATGACCTTCGAGTTGTCTCCACGAGAAGAGAGATGATTAA
GCGCTTCTGAGGGTCGTTAAGGAGAAGGACCCGGACGTGCTGATAACATACAACGCGACAACTTCGACTTCGCCTACTCGACTTGAGAAAAGCGTTGGCGTGAGCTTT
ACCCTCGGGAGGGACGGAGCGAGCCATGGGAGATACAGCGCAGGTTTGCGGTGAGGTGAAGAGGCTACACTTCGACCTTTATCCAGTCATAAGGCGCACCATAA
ACCTCCCGACCTACACCCTTGAGGCTGATGGAGGACGCGAGTGGTTACCTACGAGGTTACCGAGCCGTTCTCCGATGGAGGCCAAGGCCTCTGGACGTTTCC
CGTCCAGCACCGGCAACCTCGTCGAGTGGTTCCTCCTAAGGAAGGCCTACGAGGAACCTGCTCGAGAGAACCGACGAGAGGAGCTGGGGAGAAGGGGGGCT
ACgCCGGTGGCTACGTACGTAGGAGACCGGAGCGGGAGTGGGACAATATCGTGGGACACTTTCGTAGTCTCTACGCTCAATCATAATCACCCACAGCGTCTCGCCAGATAC
GCTCAACCTGGCGGAGGGTGTAGGAGCTACGAGTGAAGGCAAGGCACTCTCGACCTTGCCCGAGGAATCTCCTCGATTACAGCCAACGCGATCAAGATTCTCGCCAACAGCTACTACGGCT
CAGAAGATAAAGGCAAGACACAGAATGGTACTCAGGGAGTGCGCGAGGAGCGTTACGGCGACGCTGAAACAGTGCAAGAAATGTCATCAGAGAGCTTCGGTTTAAAGTCCT
ATGCCAGGGCAAGACACAGAGAGATGGTACTCAGGAGTGCGCGAGGAGCGTTACGGCGACGCTGAAACAGTGCAAGAAATGTCATCAGAGAGCTTCGGTTTAAAGTCCT
CTATGCAGACAGACAGAGGGCTTCCATGCACCATTCCTCAGGGCTTTCTTCGTCAGGAGCGTCAGGGCGATATCGCGGCATGAATTGTCAGGGAAGTCACCGAGACGAAAAGCTGAGCAA
GAACTCGAATACGAGGGCGTTGTTATCGAAGCGAGCAGGAGAAGCTGTTCACGAGAAGCGTGTTATCAGGAGCAGATAAGCGGCAGTCCGAGCTCAAGGCCATAGCGACGAGTTCGACGAGTTCACCAGAAGCTGAGCAA
GTTAAATCCGGCCCGGAACTGTATAAGCTACATCGTTCTGAGAGAATCCGCCCAGTTGAGGAGAACTCGGCAAGGAAGACCTGCGCTACCAGAAGAGACCTGCGCTACCAGAAGACGACCAAGTACGATG
CGGACTACTACATCGAGAACGAAGCCAGGTTCTGCGCAGTTGAGGAGGGGAAGAAG//
GTGGCTGAAGCCGAAGGGGAAGAAG//

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC GAC TAC GAC GAG GGC
GGT GGC AAG ACC GGC CGT GGT GCG GTA AGC GAC GCG CCG AAG GAG GAG CTG
CTG CAG ATG CTG GAG AAG CAG AAG AAA AAG  // TAG

Figure 17RRR sso7d - JDP-3 fusion protein

Nucleotide sequence (SEQ ID NO: 71) // Nucleotide sequence (SEQ ID NO: 39)
Nucleotide sequence (SEQ ID NO: 71) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC GAC TAC GAC GAG GGC
GGT GGC AAG ACC GGC CGT GGT GCG GTA AGC GAC GCG CCG AAG GAG GAG CTG
CTG CAG ATG CTG GAG AAG CAG AAA AAG  //

FIGURE 17RRR (CONT.)

```
ATGATCCTTGACGTTGATTACATCACCGAGAATGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGGAGAAGGTGAAGAAAAAGTTCCTCGG
CAGGTCTGTGGAGGTCTGGGTCCTCTACTTCACGCGACACCCGGACAATCCGGCGACAAATAAGGAAGCGGTCATCGACATCTACGAGTACGACATACCC
TTCGCCAAGCGCTACCTCATAGACAAGGGCCTAATCCGATGGAAGGTGAGCGCGTCTAAACTCATGTCCTTCGAGATCGAGTTGAGTTGTCTCCACCGAGGAAGGAGATGATTAA
CGGGCCGATTCTGATGATAAGCTACGCCGGATGAAAGCGAGGCCGGACGTGCTGATAACATAACAACGGCGACAACTTCGACCTTCGCCTACCTGAAAAAGCGTGTGAGAAGCTTGGCGTGAGCTTT
GCCTTCTTGAGGGTCGTTAAGGAGAAGGACCGGAAGCCATGGGGGACCAGGTTTGCGGTCGAGGTGAAGGCCAGGTACACTTCGACCTTTATCCAGTCATAAGGCGCACCATAA
ACCCTCCGGACCTACACCCTTGAGCTGTATACGAGGCGGTTTCGGCAAGCCCAAGGAGAAGGTCTACGCCAAGGACACCGCCTGGGAGACCGGCGAGGGCTTGAGAG
GGTCGCGCTACTGACTCGATGGAGGACGGAGGGTTACTACGACGAGTTCTTCCGATGGAGGCCCAGCTTCTCATCGGAGGCCTCGGGACGTTTCC
CGCTCCAGCACCGCAACCTCGTCGAGTGGTTCCTCCTAAGGAAGGCCTACGAGAGAAGGCCTACGAGAGAACGAACTCGCTCGACAAGCCCGACGAGAGGAGCTGGCGAGGAGAAGGGGGCT
ACgCCGGTGGCTACGTCAAGGAGTCGAGGAGCCGGAGCGGGACGTGGGGACCAATATCGTGTATCTAGACTTTCGTAGTCTCTACCCTTCAATCATAATCACCCACAACGTCTCGCCAGATAC
GCTCAACCGCGAGGGTGTAGGAGTACGACGTTGCCCCGAGTCGGTCACAAGTTCTGCAAGGACTTCTCATTCTGAAGGACTTCTCATTCTGAGGCTACTACGGCT
CAGAAGATAAAGAGGAAGATGAAGGCAACTCTCGACCGCCGAGAGCGTTACGGCATGGGGGAAGGGAGTACAGAAGAGTTCGGTTTTAAAGTCCT
ATGCCAGGGCAAGACACAGACGGTCTCCACCATTCCATGCCAGGGGCTTCTACGTCAGGAGACGCAGGGCTTATCCGAACAGTCAAGAAACAGTACGCGGTCATCGACGAGAGGGCAAGTAACCACGCGCGGGCTTCAGGAAGTCACCGAAAAGCTGAGCAA
CTATGCAGACAGACGGTCTCCATGCCAGGGGCTTCTACGTCAGGAGACGCAGGGCTTATCCGAACAGTCTGTGATAAGCTACATCGTTTCGCGGACCAGTTCGACCCGACGAGTTCGACCCGACGAGTTCGACCCGACGAGTTGTCACCGAAGCTGAGATAGTCAGGCGCG
GAACTCGAATACGAGGGCTTCCACCATTCCATGCCAGGGGCTTCTACGTCAGGAGACGCAGGGCTTATCCGAACAGTCAAGAAACAGTACGCGGTCATCGACGAGAGGGCAAGTAACCACGCGCGGGCTTCAGGAAGTCACCGAAAAGCTGAGCAA
GTACGAGGTTCCGCCGGAGTAGCCGGAGAAGCTGGTTATCCGAGCAGATAACGCGGAGCAGATAACGCCGAGTCAAGGACTACAAGCGCGAGTCCGGAAGGATAGGCGACAGGGCGATTCCCTTCGACGAGTTCGACCCGACGAGTTCGACCCGACGAGTTCGACCCGACGAGTTGTCACCGAAGCTGAGATAGTCAGGCGCG
GTTAAAATCGGCCCGAACTGTATAAGCTACATCGTTTCGCGGACCAGTTCGACCCGACGAGTTCGACCCGACGAGTTGTCACCGAAGCTGAGATAGTCAGGCGCG
CGGACTACTACATCGAGAACGAACCAGGTTCTGCCGGAGAATCCTCAGGGCCTTCGGCTACCCGGGCCTTCGGCTACCCAGGAAGACCTGCGCTACCCAGGAAGACCTGCGCTACCCAGGAAGACCTGCGCTACCCAGGAAGACCTGCGCTACCCAGGAAGACGAGGCAGGTCGGGCTTGGCGC
GTGGCTGAAGCCGAAGGGGAAGAAGAAGTGA
```

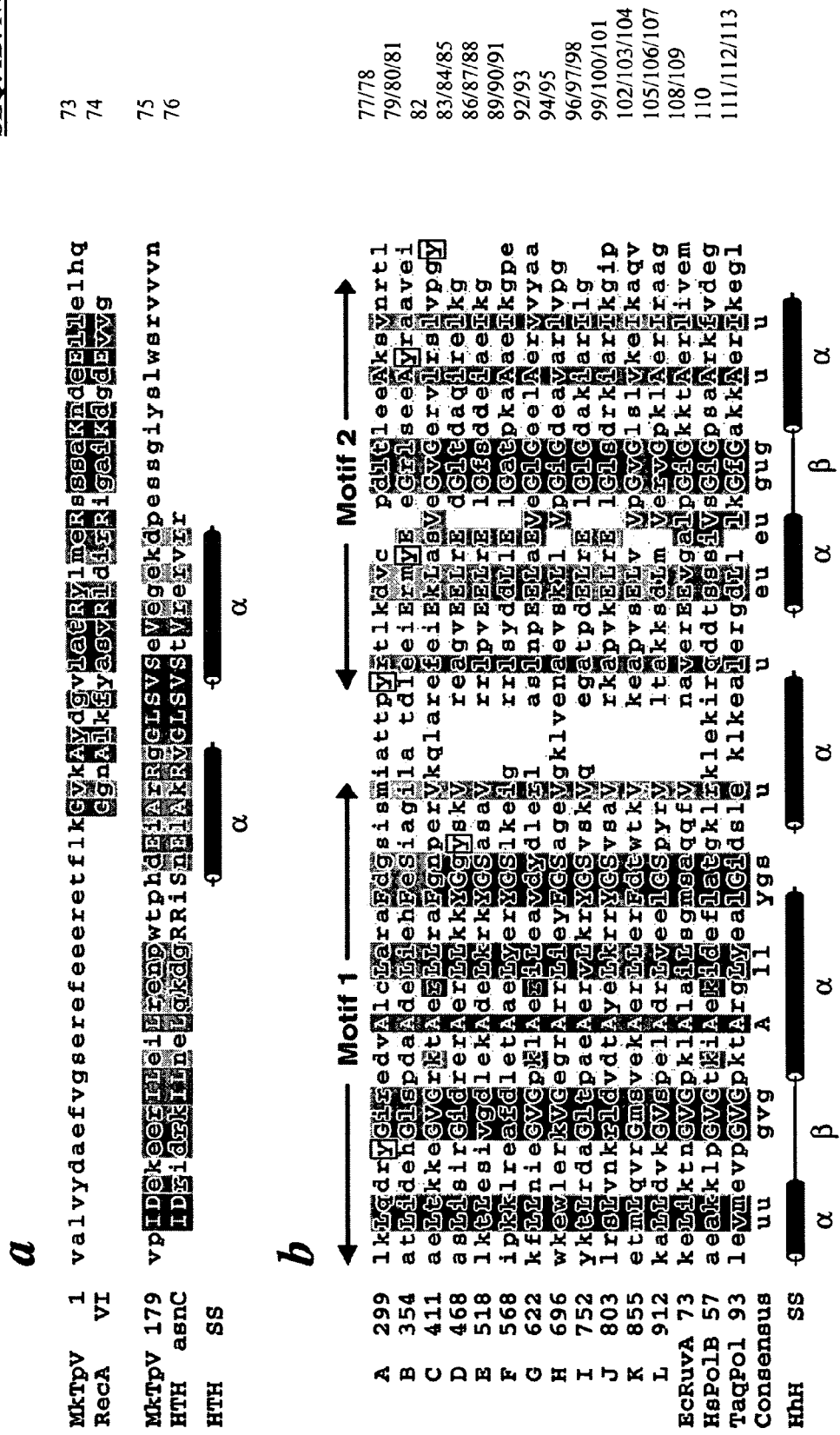
FIGURE 18 (cited from Belova et al. (2001) Proc. Natl. Acad. Sci 98: 6015-6020)

FIGURE 19

SEQ ID NO: 120 Synthetic Sso7d gene

GCAACCGTAAAGTTCAAGTACAAAGGCGAAGAAAAGAGGTAGACATCTCCAA
GATCAAGAAAGTATGGCGTGTGGGCAAGATGATCTCCTTCACCTACGACGAGGG
CGGTGGCAAGACCGGCCGTGGTGCGGTAAGCGAAAAGGACGCGCCGAAGGAGC
TGCTGCAGATGCTGGAGAAG CAGAAAAAG

SEQ ID NO: 121 The amino acid sequence of Sso7d.

ATVKFKYKGEEKEVDISKIKKVWRVGKMISFTYDEGGGKTGRGAVSEKDAPKELLQ
MLEKQKK

SEQ ID NO: 122 The DNA sequence encoding the Sso7d-ΔTaq fusion protein

ATGATTACGAATTCGAGCGCAACCGTAAAGTTCAAGTACAAAGGCGAAGAAAAA
GAGGTAGACATCTCCAAGATCAAGAAAGTATGGCGTGTGGGCAAGATGATCTCC
TTCACCTACGACGAGGGCGGTGGCAAGACCGGCCGTGGTGCGGTAAGCGAAAAG
GACGCGCCGAAGGAGCTGCTGCAGATGCTGGAGAAGCAGAAAAAGGGCGGCGG
TGTCACTAGTCCCAAGGCcCTGGAGGAGGCCCCCTGGCCCCCGCCGGAAGGGGCC
TTCGTGGGCTTTGTGCTTTCCCGCAAGGAGCCCATGTGGGCCGATCTTCTGGCCCT
GGCCGCCGCCAGGGGGGGCCGGGTCCACCGGGCCCCCGAGCCTTATAAAGCCCT
CAGGGACCTGAAGGAGGCGCGGGGGCTTCTCGCCAAAGACCTGAGCGTTCTGGC
CCTGAGGGAAGGCCTTGGCCTCCCGCCCGGCGACGACCCCATGCTCCTCGCCTAC
CTCCTGGACCCTTCCAACACCACCCCCGAGGGGGTGGCCCGGCGCTACGGCGGG
GAGTGGACGGAGGAGGCGGGGGAGCGGGCCGCCCTTTCCGAGAGGCTCTTCGCC
AACCTGTGGGGGAGGCTTGAGGGGGAGGAGAGGCTCCTTTGGCTTTACCGGGAG
GTGGAGAGGCCCCTTTCCGCTGTCCTGGCCCACATGGAGGCCACGGGGGTGCGC
CTGGACGTGGCCTATCTCAGGGCCTTGTCCCTGGAGGTGGCCGAGGAGATCGCCC
GCCTCGAGGCCGAGGTCTTCCGCCTGGCCGGCCACCCCTTCAACCTCAACTCCCG
GGACCAGCTGGAAAGGGTCCTCTTTGACGAGCTAGGGCTTCCCGCCATCGGCAA
GACGGAGAAGACCGGCAAGCGCTCCACCAGCGCCGCCGTCCTGGAGGCCCTCCG
CGAGGCCCACCCCATCGTGGAGAAGATCCTGCAGTACCGGGAGCTCACCAAGCT
GAAGAGCACCTACATTGACCCCTTGCCGGACCTCATCCACCCCAGGACGGGCCG
CCTCCACACCCGCTTCAACCAGACGGCCACGGCCACGGGCAGGCTAAGTAGCTC
CGATCCCAACCTCCAGAACATCCCCGTCCGCACCCCGCTTGGGCAGAGGATCCGC
CGGGCCTTCATCGCCGAGGAGGGGTGGCTATTGGTGGCCCTGGACTATAGCCAG
ATAGAGCTCAGGGTGCTGGCCCACCTCTCCGGCGACGAGAACCTGATCCGGGTCT
TCCAGGAGGGGCGGGACATCCACACGGAGACCGCCAGCTGGATGTTCGGCGTCC
CCCGGGAGGCCGTGGACCCCCTGATGCGCCGGGCGGCCAAGACCATCAACTTCG
GGGTCCTCTACGGCATGTCGGCCCACCGCCTCTCCCAGGAGCTAGCCATCCCTTA
CGAGGAGGCCCAGGCCTTCATTGAGCGCTACTTTCAGAGCTTCCCCAAGGTGCGG
GCCTGGATTGAGAAGACCCTGGAGGAGGGCAGGAGGCGGGGGTACGTGGAGAC
CCTCTTCGGCCGCCGCCGCTACGTGCCAGACCTAGAGGCCCGGGTGAAGAGCGT
GCGGGAGGCGGCCGAGCGCATGGCCTTCAACATGCCCGTCCAGGGCACCGCCGC
CGACCTCATGAAGCTGGCTATGGTGAAGCTCTTCCCCAGGCTGGAGGAAATGGG
GGCCAGGATGCTCCTTCAGGTCCACGACGAGCTGGTCCTCGAGGCCCCAAAAGA
GAGGGCGGAGGCCGTGGCCCGGCTGGCCAAGGAGGTCATGGAGGGGGTGTATCC
CCTGGCCGTGCCCCTGGAGGTGGAGGTGGGGATAGGGGAGGACTGGCTCTCCGC
CAAGGAGGGCATTGATGGCCGCGGCGGAGGCGGGCATCATCATCATCATTA A

SEQ ID NO: 123 The amino acid sequence of Sso7d-ΔTaq fusion protein

MITNSSATVKFKYKGEEKEVDISKIKKVWRVGKMISFTYDEGGGKTGRGAVSEKDA
PKELLQMLEKQKKGGGVTSPKALEEAPWPPPEGAFVGFVLSRKEPMWADLLALAA

FIGURE 19 (CONT.)

ARGGRVHRAPEPYKALRDLKEARGLLAKDLSVLALREGLGLPPGDDPMLLAYLLDP
SNTTPEGVARRYGGEWTEEAGERAALSERLFANLWGRLEGEERLLWLYREVERPLS
AVLAHMEATGVRLDVAYLRALSLEVAEEIARLEAEVFRLAGHPFNLNSRDQLERVLF
DELGLPAIGKTEKTGKRSTSAAVLEALREAHPIVEKILQYRELTKLKSTYIDPLPDLIH
PRTGRLHTRFNQTATATGRLSSSDPNLQNIPVRTPLGQRIRRAFIAEEGWLLVALDYS
QIELRVLAHLSGDENLIRVFQEGRDIHTETASWMFGVPREAVDPLMRRAAKTINFGV
LYGMSAHRLSQELAIPYEEAQAFIERYFQSFPKVRAWIEKTLEEGRRRGYVETLFGRR
RYVPDLEARVKSVREAAERMAFNMPVQGTAADLMKLAMVKLFPRLEEMGARMLL
QVHDELVLEAPKERAEAVARLAKEVMEGVYPLAVPLEVEVGIGEDWLSAKEGIDGR
GGGGHHHHHH

SEQ ID NO: 124 The DNA sequence encoding the Sso7d-Taq fusion protein

ATGATTACGAATTCGAGCGCAACCGTAAAGTTCAAGTACAAAGGCGAAGAAAAA
GAGGTAGACATCTCCAAGATCAAGAAAGTATGGCGTGTGGGCAAGATGATCTCC
TTCACCTACGACGAGGGCGGTGGCAAGACCGGCCGTGGTGCGGTAAGCGAAAAG
GACGCGCCGAAGGAGCTGCTGCAGATGCTGGAGAAGCAGAAAAAGGGCGGCGG
TGTCACTAGTGGGATGCTGCCCCTCTTTGAGCCCAAGGGCCGGGTCCTCCTGGTG
GACGGCCACCACCTGGCCTACCGCACCTTCCACGCCCTGAAGGGCCTCACCACCA
GCCGGGGGGAGCCGGTGCAGGCGGTCTACGGCTTCGCCAAGAGCCTCCTCAAGG
CCCTCAAGGAGGACGGGGACGCGGTGATCGTGGTCTTTGACGCCAAGGCCCCCT
CCTTCCGCCACGAGGCCTACGGGGGGTACAAGGCGGGCCGGGCCCCCACGCCAG
AGGACTTTCCCCGGCAACTCGCCCTCATCAAGGAGCTGGTGGACCTCCTGGGGCT
GGCGCGCCTCGAGGTCCCGGGCTACGAGGCGGACGACGTCCTGGCCAGCCTGGC
CAAGAAGGCGGAAAAGGAGGGCTACGAGGTCCGCATCCTCACCGCCGACAAAG
ACCTTTACCAGCTCCTTTCCGACCGCATCCACGTCCTCCACCCCGAGGGGTACCT
CATCACCCCGGCCTGGCTTTGGGAAAAGTACGGCCTGAGGCCCGACCAGTGGGC
CGACTACCGGGCCCTGACCGGGGACGAGTCCGACAACCTTCCCGGGGTCAAGGG
CATCGGGGAGAAGACGGCGAGGAAGCTTCTGGAGGAGTGGGGGAGCCTGGAAG
CCCTCCTCAAGAACCTGGACCGGCTGAAGCCCGCCATCCGGGAGAAGATCCTGG
CCCACATGGACGATCTGAAGCTCTCCTGGGACCTGGCCAAGGTGCGCACCGACCT
GCCCCTGGAGGTGGACTTCGCCAAAAGGCGGGAGCCCGACCGGGAGAGGCTTAG
GGCCTTTCTGGAGAGGCTTGAGTTTGGCAGCCTCCTCCACGAGTTCGGCCTTCTG
GAAAGCCCCAAGGCcCTGGAGGAGGCCCCCTGGCCCCCGCCGGAAGGGGCCTTC
GTGGGCTTTGTGCTTTCCCGCAAGGAGCCCATGTGGGCCGATCTTCTGGCCCTGG
CCGCCGCCAGGGGGGGCCGGGTCCACCGGGCCCCCGAGCCTTATAAAGCCCTCA
GGGACCTGAAGGAGGCGCGGGGCTTCTCGCCAAAGACCTGAGCGTTCTGGCCC
TGAGGGAAGGCCTTGGCCTCCCGCCCGGCGACGACCCCATGCTCCTCGCCTACCT
CCTGGACCCTTCCAACACCACCCCCGAGGGGGTGGCCCGGCGCTACGGCGGGGA
GTGGACGGAGGAGGCGGGGGAGCGGGCCGCCCTTTCCGAGAGGCTCTTCGCCAA
CCTGTGGGGGAGGCTTGAGGGGGAGGAGAGGCTCCTTTGGCTTTACCGGGAGGT
GGAGAGGCCCCTTTCCGCTGTCCTGGCCCACATGGAGGCCACGGGGGTGCGCCT
GGACGTGGCCTATCTCAGGGCCTTGTCCCTGGAGGTGGCCGAGGAGATCGCCCG
CCTCGAGGCCGAGGTCTTCCGCCTGGCCGGCCACCCCTTCAACCTCAACTCCCGG
GACCAGCTGGAAAGGGTCCTCTTTGACGAGCTAGGGCTTCCCGCCATCGGCAAG
ACGGAGAAGACCGGCAAGCGCTCCACCAGCGCCGCCGTCCTGGAGGCCCTCCGC
GAGGCCCACCCCATCGTGGAGAAGATCCTGCAGTACCGGGAGCTCACCAAGCTG
AAGAGCACCTACATTGACCCCTTGCCGGACCTCATCCACCCCAGGACGGGCCGCC
TCCACACCCGCTTCAACCAGACGGCCACGGCCACGGGCAGGCTAAGTAGCTCCG
ATCCCAACCTCCAGA. ACATCCCCGTCCGCACCCCGCTTGGGCAGAGGATCCGCCG
GGCCTTCATCGCCGAGGAGGGGTGGCTATTGGTGGCCCTGGACTATAGCCAGAT
AGAGCTCAGGGTGCTGGCCCACCTCTCCGGCGACGAGAACCTGATCCGGGTCTTC
CAGGAGGGGCGGGACATCCACACGGAGACCGCCAGCTGGATGTTCGGCGTCCCC
CGGGAGGCCGTGGACCCCCTGATGCGCCGGGCGGCCAAGACCATCAACTTCGGG
GTCCTCTACGGCATGTCGGCCCACCGCCTCTCCCAGGAGCTAGCCATCCCTTACG
AGGAGGCCCAGGCCTTCATTGAGCGCTACTTTCAGAGCTTCCCCAAGGTGCGGGC

FIGURE 19 (CONT.)

CTGGATTGAGAAGACCCTGGAGGAGGGCAGGAGGCGGGGGTACGTGGAGACCC
TCTTCGGCCGCCGCCGCTACGTGCCAGACCTAGAGGCCCGGGTGAAGAGCGTGC
GGGAGGCGGCCGAGCGCATGGCCTTCAACATGCCCGTCCAGGGCACCGCCGCCG
ACCTCATGAAGCTGGCTATGGTGAAGCTCTTCCCCAGGCTGGAGGAAATGGGGG
CCAGGATGCTCCTTCAGGTCCACGACGAGCTGGTCCTCGAGGCCCCAAAAGAGA
GGGCGGAGGCCGTGGCCCGGCTGGCCAAGGAGGTCATGGAGGGGGTGTATCCCC
TGGCCGTGCCCCTGGAGGTGGAGGTGGGGATAGGGGAGGACTGGCTCTCCGCCA
AGGAGGGCATTGATGGCCGCGGCGGAGGCGGGCATCATCATCATCATCATTAA

SEQ ID NO: 125 The amino acid sequence of Sso7d-Taq fusion protein.

MITNSSATVKFKYKGEEKEVDISKIKKVWRVGKMISFTYDEGGGKTGRGAVSEKDA
PKELLQMLEKQKKGGGVTSGMLPLFEPKGRVLLVDGHHLAYRTFHALKGLTTSRGE
PVQAVYGFAKSLLKALKEDGDAVIVVFDAKAPSFRHEAYGGYKAGRAPTPEDFPRQ
LALIKELVDLLGLARLEVPGYEADDVLASLAKKAEKEGYEVRILTADKDLYQLLSDR
IHVLHPEGYLITPAWLWEKYGLR. PDQWADYRALTGDESDNLPGVKGIGEKTARKLL
EEWGSLEALLKNLDRLKPAIREKILAHMDDLKLSWDLAKVRTDLPLEVDFAKRREP
DRERLRAFLERLEFGSLLHEFGLLESPKALEEAPWPPPEGAFVGFVLSRKEPMWADL
LALAAARGGRVHRAPEPYKALRDLKEARGLLAKDLSVLALREGLGLPPGDDPMLLA
YLLDPSNTTPEGVARRYGGEWTEEAGERAALSERLFANLWGRLEGEERLLWLYREV
ERPLSAVLAHMEATGVRLDVAYLRALSLEVAEEIARLEAEVFRLAGHPFNLNSRDQL
ERVLFDELGLPAIGKTEKTGKRSTSAAVLEALREAHPIVEKILQYRELTKLKSTYIDPL
PDLIHPRTGRLHTRFNQTATATGRLSSSDPNLQNIPVRTPLGQIRJRRAFIAEEGWLLVA
LDYSQIELRVLAHLSGDENLIRVFQEGRDIHTETASWMFGVPREAVDPLMRRAAKTI
NFGVLYGMSAHRLSQELAIPYEEAQAFIERYFQSFPKVRAWIEKTLEEGRRRGYVETL
FGRRRYVPDLEARVKSVREAAERMAFNMPVQGTAADLMKLAMVKLFPRLEEMGA
RMLLQVHDELVLEAPKERAEAVARLAKEVMEGVYPLAVPLEVEVGIGEDWLSAKE
GIDGRGGGGHHHHHH

SEQ ID NO: 126 The DNA sequence encoding the Pfu-Sso7d fusion protein

ATGATTTTAGATGTGGATTACATAACTGAAGAAGGAAAACCTGTTATTAGGCTAT
TCAAAAAAGAGAACGGAAAATTTAAGATAGAGCATGATAGAACTTTTAGACCAT
ACATTTACGCTCTTCTCAGGGATGATTCAAAGATTGAAGAAGTTAAGAAAATAAC
GGGGGAAAGGCATGGAAAGATTGTGAGAATTGTTGATGTAGAGAAGGTTGAGAA
AAAGTTTCTCGGCAAGCCTATTACCGTGTGGAAACTTTATTTGGAACATCCCCAA
GATGTTCCCACTATTAGAGAAAAAGTTAGAGAACATCCAGCAGTTGTGGACATCT
TCGAATACGATATTCCATTTGCAAAGAGATACCTCATCGACAAAGGCCTAATACC
AATGGAGGGGGAAGAAGAGCTAAAGATTCTTGCCTTCGATATAGAAACCCTCTA
TCACGAAGGAGAAGAGTTTGGAAAAGGCCCAATTATAATGATTAGTTATGCAGA
TGAAAATGAAGCAAAGGTGATTACTTGGAAAAACATAGATCTTCCATACGTTGA
GGTTGTATCAAGCGAGAGAGAGATGATAAAGAGATTTCTCAGGATTATCAGGGA
GAAGGATCCTGACATTATAGTTACTTATAATGGAGACTCATTCGACTTCCCATAT
TTAGCGAAAAGGGCAGAAAAACTTGGGATTAAATTAACCATTGGAAGAGATGGA
AGCGAGCCCAAGATGCAGAGAATAGGCGATATGACGGCTGTAGAAGTCAAGGG
AAGAATACATTTCGACTTGTATCATGTAATAACAAGGACAATAAATCTCCCAACA
TACACACTAGAGGCTGTATATGAAGCAATTTTTGGAAAGCCAAAGGAGAAGGTA
TACGCCGACGAGATAGCAAAAGCCTGGGAAAGTGGAGAGAACCTTGAGAGAGTT
GCCAAATACTCGATGGAAGATGCAAAGGCAACTTATGAACTCGGGAAAGAATTC
CTTCCAATGGAAATTCAGCTTTCAAGATTAGTTGGACAACCTTTATGGGATGTTT
CAAGGTCAAGCACAGGGAACCTTGTAGAGTGGTTCTTACTTAGGAAAGCCTACG
AAAGAAACGAAGTAGCTCCAAACAAGCCAAGTGAAGAGGAGTATCAAAGAAGG
CTCAGGGAGAGCTACACAGGTGGATTCGTTAAAGAGCCAGAAAAGGGGTTGTGG
GAAAACATAGTATACCTAGATTTTAGAGCCCTATATCCCTCGATTATAATTACCC
ACAATGTTTCTCCCGATACTCTAAATCTTGAGGGATGCAAGAACTATGATATCGC
TCCTCAAGTAGGCCACAAGTTCTGCAAGGACATCCCTGGTTTTATACCAAGTCTC

FIGURE 19 (CONT.)

TTGGGACATTTGTTAGAGGAAAGACAAAAGATTAAGACAAAAATGAAGGAAACT
TTAGCAAATTCTTTCTACGGATATTATGGCTATGCAAAAGCAAGATGGTACTGTA
AGGAGTGTGCTGAGAGCGTTACTGCCTGGGGAAGAAAGTACATCGAGTTAGTAT
GGAAGGAGCTCGAAGAAAAGTTTGGATTTAAAGTCCTCTACATTGACACTGATG
GTCTCTATGCAACTATCCCAGGAGGAGAAAGTGAGGAAATAAAGAAAAAGGCTC
TAGAATTTGTAAAATACATAAATTCAAAGCTCCCTGGACTGCTAGAGCTTGAATA
TGAAGGGTTTTATAAGAGGGGATTCTTCGTTACGAAGAAGAGGTATGCAGTAAT
AGATGAAGAAGGAAAAGTCATTACTCGTGGTTTAGAGATAGTTAGGAGAGATTG
GAGTGAAATTGCAAAAGAAACTCAAGCTAGAGTTTTGGAGACAATACTAAAACA
CGGAGATGTTGAAGAAGCTGTGAGAATAGTAAAAGAAGTAATACAAAAGCTTGC
CAATTATGAAATTCCACCAGAGAAGCTCGCAATATATGAGCAGATAACAAGACC
ATTACATGAGTATAAGGCGATAGGTCCTCACGTAGCTGTTGCAAAGAAACTAGCT
GCTAAAGGAGTTAAAATAAAGCCAGGAATGGTAATTGGATACATAGTACTTAGA
GGCGATGGTCCAATTAGCAATAGGGCAATTCTAGCTGAGGAATACGATCCCAAA
AAGCACAAGTATGACGCAGAATATTACATTGAGAACCAGGTTCTTCCAGCGGTA
CTTAGGATATTGGAGGGATTTGGATACAGAAAGGAAGACCTCAGATACCAAAAG
ACAAGACAAGTCGGCCTAACTTCCTGGCTTAACATTAAAAAATCCGGTACCGGC
GGTGGCGGTGCAACCGTAAAGTTCAAGTACAAAGGCGAAGAAAAAGAGGTAGA
CATCTCCAAGATCAAGAAAGTATGGCGTGTGGGCAAGATGATCTCCTTCACCTAC
GACGAGGGCGGTGGCAAGACCGGCCGTGGTGCGGTAAGCGAAAAGGACGCGCC
GAAGGAGCTGCTGCAGATGCTGGAGAAGCAGAAAAAGTGA

SEQ ID NO: 127  The amino acid sequence of the Pfu-Sso7d fusion protein

MILDVDYITEEGKPVIRLFKKENGKFKIEHDRTFRPYIYALLRDDSKIEEVKKITGERH
GKIVRIVDVEKVEKKFLGKPITVWKLYLEHPQDVPTIREKVREHPAVVDIFEYDIPFA
KRYLIDKGLIPMEGEEELKILAFDIETLYHEGEEFGKGPIIMISYADENEAKVITWKNID
LPYVEVVSSEREMIKRFLRIIREKDPDIIVTYNGDSFDFPYLAKRAEKLGIKLTIGRDGS
EPKMQRIGDMTAVEVKGRIHFDLYHVITRTINLPTYTLEAVYEAIFGKPKEKVYADEI
AKAWESGENLERVAKYSMEDAKATYELGKEFLPMEIQLSRLVGQPLWDVSRSSTGN
LVEWFLLRKAYERNEVAPNKPSEEEYQRRLRESYTGGFVKEPEKGLWENIVYLDFR
ALYPSIIITHNVSPDTLNLEGCKNYDIAPQVGHKFCKDIPGFIPSLLGHLLEERQKIKTK
MKETQDPIEKILLDYRQKAIKLLANSFYGYYGYAKARWYCKECAESVTAWGRKYIE
LVWKELEEKFGFKVLYIDTDGLYATIPGGESEEIKKKALEFVKYINSKLPGLLELEYE
GFYKRGFFVTKKRYAVIDEEGKVITRGLEIVRRDWSEIAKETQARVLETILKHGDVEE
AVRIVKEVIQKLANYEIPPEKLAIYEQITRPLHEYKAIGPHVAVAKKLAAKGVKIKPG
MVIGYTVLRGDGPISNRAILAEEYDPKKHKYDAEYYIENQVLPAVLRILEGFGYRKED
LRYQKTRQVGLTSWLNIKKSGTGGGGATVKFKYKGEEKEVDISKIKKVWRVGKMIS
FTYDEGGGKTGRGAVSEKDAPKELLQMLEKQKK

SEQ ID NO: 128  The DNA sequence encoding the Sac7d-ΔTaq fusion protein

```
atgattacga attcgacggt gaaggtaaag ttcaagtata agggtgaaga gaaagaagta
gacacttcaa agataaagaa ggtttggaga gtaggcaaaa tggtgtcctt tacctatgac
gacaatggta agacaggtag aggagctgta agcgagaaag atgctccaaa agaattatta
gacatgttag caagagcaga aagagagaag aaagcggcg gtgtcactag ccccaaggcc
ctggaggagg cccctggcc cccgccggaa ggggccttcg tgggctttgt gctttcccgc
aaggagccca tgtgggccga tcttctggcc ctggccgccg caggggggg ccgggtccac
cgggccccg agccttataa agccctcagg gacctgaagg aggcgcgggg gcttctcgcc
aaagacctga gcgttctggc cctgagggaa ggccttggcc tcccgcccgg cgacgacccc
atgctcctcg cctacctcct ggacccttcc aacaccaccc ccgaggggt ggcccggcgc
tacggcgggg agtggacgga ggaggcgggg gagcgggccg cccttccga gaggctcttc
gccaacctgt gggggaggct tgagggggag gagaggctcc tttggcttta ccggagggtg
gagaggcccc tttccgctgt cctggcccac atggaggcca cgggggtgcg cctggacgtg
gcctatctca gggccttgtc cctggaggtg gccgaggaga tcgcccgcct cgaggccgag
gtcttccgcc tggccggcca ccccttcaac ctcaactccc gggaccagct ggaaagggtc
ctctttgacg agctagggct tcccgccatc ggcaagacgt agaagaccgg caagcgctcc
accagcgccg ccgtcctgga ggcctccgc gaggcccacc ccatcgtgga agatctg
cagtaccggg agctcaccaa gctgaagagc cctacattg accccttgcc ggacctcatc
```

FIGURE 19 (CONT.)

```
cacccccagga cgggccgcct ccacacccgc ttcaaccaga cggccacggc cacgggcagg
ctaagtagct ccgatcccaa cctccagaac atcccgtcc gcaccccgct tgggcagagg
atccgccggg ccttcatcgc cgaggagggg tggctattgg tggccctgga ctatagccag
atagagctca gggtgctggc ccacctctcc ggcgacgaga acctgatccg ggtcttccag
gaggggcggg acatccacac ggagaccgcc agctggatgt tcggcgtccc ccgggaggcc
gtggaccccc tgatgcgccg ggcggccaag accatcaact tcggggtcct ctacggcatg
tcggcccacc gcctctccca ggagctagcc atcccttacg aggaggccca ggcctttcatt
gagcgctact ttcagagctt ccccaaggtg cgggcctgga ttgagaagac cctggaggag
ggcaggaggc gggggtacgt ggagaccctc ttcggccgcc gccgctacgt gccagaccta
gaggcccggg tgaagagcgt gcgggaggcg gccgagcgca tggccttcaa catgcccgtc
cagggcaccg ccgccgacct catgaagctg gctatggtga agctcttccc caggctggag
gaaatggggg ccaggatgct ccttcaggtc cacgacgagc tggtcctcga ggccccaaaa
gagagggcgg aggccgtggc ccggctggcc aaggaggtca tggagggggt gtatcccctg
gccgtgcccc tggaggtgga ggtggggata ggggaggact ggctctccgc caaggagggc
attgatggcc gcggcggagg cgggcatcat catcatcatc attaa
```

SEQ ID NO: 129 The amino acid sequence of the Sac7d-ΔTaq fusion protein

MITNSTVKVKFKYKGEEKEVDTSKIKKVWRVGKMVSFTYDDNGKTGRGAVSEKDA
PKELLDMLARAEREKKGGGVTSPKALEEAPWPPPEGAFVGFVLSRKEPMWADLLAL
AAARGGRVHRAPEPYKALRDLKEARGLLAKDLSVLALREGLGLPPGDDPMLLAYLL
DPSNTTPEGVARRYGGEWTEEAGERAALSERLFANLWGRLEGEERLLWLYREVERP
LSAVLAHMEATGVRLDVAYLRALSLEVAEEIARLEAEVFRLAGHPFNLNSRDQLERV
LFDELGLPAIGKTEKTGKRSTSAAVLEALREAHPIVEKILQYRELTKLKSTYIDPLPDLI
HPRTGRLHTRFNQTATATGRLSSSDPNLQNIPVRTPLGQRIRRAFIAEEGWLLVALDY
SQIELRVLAHLSGDENLIRVFQEGRDIHTETASWMFGVPREAVDPLMRRAAKTINFG
VLYGMSAHRLSQELAIPYEEAQAFIERYFQSFPKVRAWIEKTLEEGRRRGYVETLFGR
RRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKEGIDG
RGGGGHHHHHH

SEQ ID NO: 130 The DNA sequence encoding the PL-ΔTaq fusion protein

ATGATTACGAATTCGAAGAAAAAGAAAAAGAAAAAGCGTAAGAAACGCAAAAA
GAAAAAGAAAGGCGGCGGTGTCACTAGTGGCGCAACCGTAAAGTTCAAGTACAA
AGGCGAAGAAAAAGAGGTAGACATCTCCAAGATCAAGAAAGTATGGCGTGTGG
GCAAGATGATCTCCTTCACCTACGACGAGGGCGGTGGCAAGACCGGCCGTGGTG
CGGTAAGCGAAAAGGACGCGCCGAAGGAGCTGCTGCAGATGCTGGAGAAGCAG
AAAAAGGGCGGCGGTGTCACCAGTCCCAAGGCCCTGGAGGAGGCCCCCTGGCCC
CCGCCGGAAGGGGCCTTCGTGGGCTTTGTGCTTTCCCGCAAGGAGCCCATGTGGG
CCGATCTTCTGGCCCTGGCCGCCGCCAGGGGGGGCCGGGTCCACCGGGCCCCCG
AGCCTTATAAAGCCCTCAGGGACCTGAAGGAGGCGCGGGGGCTTCTCGCCAAAG
ACCTGAGCGTTCTGGCCCTGAGGGAAGGCCTTGGCCTCCCGCCCGGCGACGACCC
CATGCTCCTCGCCTACCTCCTGGACCCTTCCAACACCACCCCGAGGGGGTGGCC
CGGCGCTACGGCGGGGAGTGGACGGAGGAGGCGGGGGAGCGGGCCGCCCTTTCC
GAGAGGCTCTTCGCCAACCTGTGGGGGAGGCTTGAGGGGGAGGAGAGGCTCCTT
TGGCTTTACCGGGAGGTGGAGAGGCCCCTTTCCGCTGTCCTGGCCCACATGGAGG
CCACGGGGGTGCGCCTGGACGTGGCCTATCTCAGGGCCTTGTCCCTGGAGGTGGC
CGAGGAGATCGCCCGCCTCGAGGCCGAGGTCTTCCGCCTGGCCGGCCACCCCTTC
AACCTCAACTCCCGGGACCAGCTGGAAAGGGTCCTCTTTGACGAGCTAGGGCTTC
CCGCCATCGGCAAGACGGAGAAGACCGGCAAGCGCTCCACCAGCGCCGCCGTCC
TGGAGGCCCTCCGCGAGGCCCACCCCATCGTGGAGAAGATCCTGCAGTACCGGG
AGCTCACCAAGCTGAAGAGCACCTACATTGACCCCTTGCCGGACCTCATCCACCC
CAGGACGGGCCGCCTCCACACCCGCTTCAACCAGACGGCCACGGCCACGGGCAG
GCTAAGTAGCTCCGATCCCAACCTCCAGAACATCCCCGTCCGCACCCCGCTTGGG
CAGAGGATCCGCCGGGCCTTCATCGCCGAGGAGGGGTGGCTATTGGTGGCCCTG
GACTATAGCCAGATAGAGCTCAGGGTGCTGGCCCACCTCTCCGGCGACGAGAAC
CTGATCCGGGTCTTCCAGGAGGGGCGGGACATCCACACGGAGACCGCCAGCTGG
```

FIGURE 19 (CONT.)

```
ATGTTCGGCGTCCCCCGGGAGGCCGTGGACCCCCTGATGCGCCGGGCGGCCAAG
ACCATCAACTTCGGGGTCCTCTACGGCATGTCGGCCCACCGCCTCTCCCAGGAGC
TAGCCATCCCTTACGAGGAGGCCCAGGCCTTCATTGAGCGCTACTTTCAGAGCTT
CCCCAAGGTGCGGGCCTGGATTGAGAAGACCCTGGAGGAGGGCAGGAGGCGGG
GGTACGTGGAGACCCTCTTCGGCCGCCGCCGCTACGTGCCAGACCTAGAGGCCC
GGGTGAAGAGCGTGCGGGAGGCGGCCGAGCGCATGGCCTTCAACATGCCCGTCC
AGGGCACCGCCGCCGACCTCATGAAGCTGGCTATGGTGAAGCTCTTCCCCAGGCT
GGAGGAAATGGGGGCCAGGATGCTCCTTCAGGTCCACGACGAGCTGGTCCTCGA
GGCCCCAAAAGAGAGGGCGGAGGCCGTGGCCCGGCTGGCCAAGGAGGTCATGG
AGGGGGTGTATCCCCTGGCCGTGCCCCTGGAGGTGGAGGTGGGGATAGGGGAGG
ACTGGCTCTCCGCCAAGGAGGGCATTGATGGCCGCGGCGGAGGCGGGCATCATC
ATCATCATCATTAA
```

SEQ ID NO: 131 The amino acid sequence of PL- ΔTaq fusion protein

```
MITNSKKKKKKKRKKRKKKKKGGGVTSGATVKFKYKGEEKEVDISKIKKVWRVGK
MISFTYDEGGGKTGRGAVSEKDAPKELLQMLEKQKKGGGVTSPKALEEAPWPPPEG
AFVGFVLSRKEPMWADLLALAAARGGRVHRAPEPYKALRDLKEARGLLAKDLSVL
ALREGLGLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAEEIARLE
AEVFRLAGHPFNLNSRDQLERVLFDELGLPAIGKTEKTGKRSTSAAVLEALREAHPIV
EKILQYRELTKLKSTYIDPLPDLIHPRTGRLHTRFNQTATATGRLSSSDPNLQNIPVRTP
LGQRIRRAFIAEEGWLLVALDYSQIELRVLAHLSGDENLIRVFQEGRDIHTETASWMF
GVPREAVDPLMRRAAKTINFGVLYGMSAHRLSQELAIPYEEAQAFIERYFQSFPKVR
AWIEKTLEEGRRRGYVETLFGRRRYVPDLEARVKSVREAAERMAFNMPVQGTAAD
LMKLAMVKLFPRLEEMGARMLLQVHDELVLEAPKERAEAVARLAKEVMEGVYPL
AVPLEVEVGIGEDWLSAKEGIDGRGGGGHHHHHH
```

SEQ ID NO: 132 PRIMER L71F 5'-CCTGCTCTGCCGCTTCACGC-3'

SEQIDNO: 133 PRIMER L71R 5'-GCACAGCGGCTGGCTGAGGA-3'

SEQ ID NO: 134 PRIMER L18015F 15 5'-TGACGGAGGATAACGCCAGCAG-3'

SEQ ID NO: 135 PRIMER L23474R 5'-GAAAGACGA TGGGTCGCTAATACGC-3'

SEQ ID NO: 136 PRIMER L18015F 5'-TGACGGAGGATAAC GCCAGCAG-3'

SEQ ID NO: 137 PRIMER L29930R 5'-GGGGTTGGAGGTCAATGGGTTC-3'

SEQ ID NO: 138 PRIMER L30350F 5'-CCTGCTCTGCCGCTTCACGC-3'

SEQ ID NO: 139 PRIMER L35121R 30 5'- CACATGGTACAGCAAGCCTGGC-3'

SEQ ID NO: 140 PRIMER L2089F 5'-CCCGTATCTGCTGGGA TACTGGC-3'

SEQ IUD NO: 141 PRIMER L7112R 5'-CAGCGGTGCTGACTGAATCATGG-3'

SEQ ID NO: 142 PRIMER L30350F 5 5'-CCTGCCTGCCGCTTCACGC-3'

SEQ ID NO: 143 PRIMER L40547R 5'-CCAATACCCGTTTCA TCGCGGC-3'

SEQ ID NO: 144 PRIMER H-Amelo-Y 5'-CCACCTCATCCTGG GCACC-3'

SEQ ID NO: 145 PRIMER H-Amelo-YR 5'-GCTTGAGGCCAACCATCAGAGC-3'

FIGURE 19 (CONT.)

SEQ ID NO: 146 Human beta-globin primer 536F 5'-GGTTGGCCAATCTACTCCCAGG-3'

SEQ ID NO: 147 Human beta-globin primer 536R 5'-GCTCACTCAGTGTGGCAAAG-3'

SEQ ID NO: 148 Human beta-globin primer 1408R 5'-GATTAGCAAAAGGGCCTAGCTTGG- 3'

Figure 20

PURIFIED THERMOSTABLE PYROCOCCUS FURIOSUS DNA POLYMERASE I

AMINO ACID SEQUENCE (SEQ ID NO: 62)

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
            50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Asp Ile Glu Thr
            130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
            260                 265                 270
```

FIGURE 20 (CONT.)

```
Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575
```

FIGURE 20 (CONT.)

```
Glu Leu Glu Tyr Glu Gly Phe Tyr Lys Arg Gly Phe Phe Val Thr Lys
        580             585             590
Lys Arg Tyr Ala Val Ile Asp Glu Gly Lys Val Ile Thr Arg Gly
        595             600             605
Leu Glu Ile Val Arg Arg Asp Trp Ser Glu Ile Ala Lys Glu Thr Gln
610             615             620
Ala Arg Val Leu Glu Thr Ile Leu Lys His Gly Asp Val Glu Glu Ala
625             630             635             640
Val Arg Ile Val Lys Glu Val Ile Gln Lys Leu Ala Asn Tyr Glu Ile
            645             650             655
Pro Pro Glu Lys Leu Ala Ile Tyr Glu Gln Ile Thr Arg Pro Leu His
            660             665             670
Glu Tyr Lys Ala Ile Gly Pro His Val Ala Val Ala Lys Lys Leu Ala
        675             680             685
Ala Lys Gly Val Lys Ile Lys Pro Gly Met Val Ile Gly Tyr Ile Val
        690             695             700
Leu Arg Gly Asp Gly Pro Ile Ser Asn Arg Ala Ile Leu Ala Glu Glu
705             710             715             720
Tyr Asp Pro Lys Lys His Lys Tyr Asp Ala Glu Tyr Tyr Ile Glu Asn
                725             730             735
Gln Val Leu Pro Ala Val Leu Arg Ile Leu Glu Gly Phe Gly Tyr Arg
            740             745             750
Lys Glu Asp Leu Arg Tyr Gln Lys Thr Arg Gln Val Gly Leu Thr Ser
        755             760             765
Trp Leu Asn Ile Lys Lys Ser
        770             775
```

PURIFIED THERMOSTABLE PYROCOCCUS FURIOSUS DNA POLYMERASE I

NUCLEOTIDE SEQUENCE (SEQ ID NO: 61)

| | | | | | |
|---|---|---|---|---|---|
| ccctggtcct | gggtccacat | atatgttctt | actcgccttt | atgaagaatc | ccccagtcgc | 60 |
| tctaacctgg | gttatagtga | caaatcttcc | tccaccaccg | cccaagaagg | ttatttctat | 120 |
| caactctaca | cctcccctat | tttctctctt | atgagatttt | taagtatagt | tatagagaag | 180 |
| gttttatact | ccaaactgag | ttagtagata | tgtggggagc | ataatgattt | tagatgtgga | 240 |
| ttacataact | gaagaaggaa | aacctgttat | taggctattc | aaaaaagaga | acggaaaatt | 300 |
| taagatagag | catgatagaa | cttttagacc | atacatttac | gctcttctca | gggatgattc | 360 |
| aaagattgaa | gaagttaaga | aaataacggg | ggaaaggcat | ggaaagattg | tgagaattgt | 420 |

FIGURE 20 (CONT.)

```
tgatgtagag aaggttgaga aaaagtttct cggcaagcct attaccgtgt ggaaacttta    480
tttggaacat ccccaagatg ttcccactat tagagaaaaa gttagagaac atccagcagt    540
tgtggacatc ttcgaatacg atattccatt tgcaaagaga tacctcatcg acaaaggcct    600
aataccaatg gagggggaag aagagctaaa gattcttgcc ttcgatatag aaaccctcta    660
tcacgaagga gaagagtttg gaaaaggccc aattataatg attagttatg cagatgaaaa    720
tgaagcaaag gtgattactt ggaaaaacat agatcttcca tacgttgagg ttgtatcaag    780
cgagagagag atgataaaga gatttctcag gattatcagg gagaaggatc ctgacattat    840
agttacttat aatggagact cattcgactt cccatattta gcgaaaaggg cagaaaaact    900
tgggattaaa ttaaccattg gaagagatgg aagcgagccc aagatgcaga gaataggcga    960
tatgacggct gtagaagtca agggaagaat acatttcgac ttgtatcatg taataacaag   1020
gacaataaat ctcccaacat acacactaga ggctgtatat gaagcaattt ttggaaagcc   1080
aaggagaag gtatacgccg acgagatagc aaaagcctgg gaaagtggag agaaccttga   1140
gagagttgcc aaatactcga tggaagatgc aaaggcaact tatgaactcg ggaaagaatt   1200
ccttccaatg gaaattcagc tttcaagatt agttggacaa cctttatggg atgtttcaag   1260
gtcaagcaca gggaaccttg tagagtggtt cttacttagg aaagcctacg aaagaaacga   1320
agtagctcca aacaagccaa gtgaagagga gtatcaaaga aggctcaggg agagctacac   1380
aggtggattc gttaaagagc cagaaaaggg gttgtgggaa acatagtat acctagattt   1440
tagagcccta tatccctcga ttataattac ccacaatgtt tctcccgata ctctaaatct   1500
tgagggatgc aagaactatg atatcgctcc tcaagtaggc cacaagttct gcaaggacat   1560
ccctggtttt ataccaagtc tcttgggaca tttgttagag gaaagacaaa agattaagac   1620
aaaaatgaag gaaactcaag atcctataga aaaaatactc cttgactata gacaaaaagc   1680
gataaaactc ttagcaaatt ctttctacgg atattatggc tatgcaaaag caagatggta   1740
ctgtaaggag tgtgctgaga gcgttactgc ctggggaaga aagtacatcg agttagtatg   1800
gaaggagctc gaagaaaagt ttggatttaa agtcctctac attgacactg atggtctcta   1860
tgcaactatc ccaggaggag aaagtgagga aataaagaaa aaggctctag aatttgtaaa   1920
atacataaat tcaaagctcc ctggactgct agagcttgaa tatgaagggt tttataagag   1980
gggattcttc gttacgaaga agaggtatgc agtaatagat gaagaaggaa aagtcattac   2040
tcgtggttta gagatagtta ggagagattg gagtgaaatt gcaaaagaaa ctcaagctag   2100
agttttggag acaatactaa aacacggaga tgttgaagaa gctgtgagaa tagtaaaaga   2160
```

FIGURE 20 (CONT.)

```
agtaatacaa aagcttgcca attatgaaat tccaccagag aagctcgcaa tatatgagca     2220
gataacaaga ccattacatg agtataaggc gataggtcct cacgtagctg ttgcaaagaa     2280
actagctgct aaaggagtta aaataaagcc aggaatggta attggataca tagtacttag     2340
aggcgatggt ccaattagca atagggcaat tctagctgag gaatacgatc ccaaaaagca     2400
caagtatgac gcagaatatt acattgagaa ccaggttctt ccagcggtac ttaggatatt     2460
ggagggattt ggatacagaa aggaagacct cagataccaa aagacaagac aagtcggcct     2520
aacttcctgg cttaacatta aaaaatccta gaaaagcgat agatatcaac ttttattctt     2580
tctaaccttt ttctatgaaa gaagaactga gcaggaatta ccagttcttc cgttatttta     2640
tgggtaatta aaaacccatg ctcttgggag aatcttcgaa taaaatccct aacttcaggc     2700
tttgctaagt gaatagaata acaacatca ctcacttcaa acgccttcgt tagaaatggt      2760
ctatctgcat gcttctctgg ctcggaanng gaggattcat aacaacagta tcaacattct     2820
cagagaattg agaaacatca gaaactttga cttctacaac atttctaact ttgcaactct     2880
tcaagatttt ctaaaagaat tttaacggcc tcctcgtcaa tttcgacgac gtagatcttt     2940
tttgctccaa gcagagccgc tccaatggat aacacccctg ttcccgcacc caagtccgct     3000
acaatttttt ccttgtatct cctaatgtat aagcaagcca aggagagta gatgctacct      3060 ttccgggagt tttgtattgc tctagccaag gtttgggatt tttgaatcct ttaactctgg     3120
aaagtataat ttcaagctcc ttcttcttca tgacagatga aaaattgttt tgtctctttt     3180
taacttttac agaaataact gtctcaaatt atgacaactc ttgacatttt tacttcatta     3240
ccagggtaat gttttttaagt atgaaatttt tctttcatag aggaggnnnn nngtcctctc    3300
ctcgatttcc ttggttgtgc tccatatgat aagcttccaa agtgggtgtt cagactttta    3360
gacactcaaa taccagacga caatggtgtg ctcactcaag ccccatatgg gttgagaaaa    3420
gtagaagcgg cactactcag atgcttcccc aggaatgagg ttgttgtagc tcntcccnga    3480
aagattgaga tgttcttgg                                                  3499
```

DNA POLYMERASE FUSIONS AND USES THEREOF

RELATED APPLICATIONS

This application claims the benefit of U.S. Provisional Application No. 60/457,426, filed Mar. 25, 2003. The entire teachings of the above application are incorporated herein by reference.

FIELD OF THE INVENTION

The present invention relates to blends of chimeric and non chimeric DNA polymerases, methods for their synthesis, and methods for their use. The DNA polymerase blends disclosed herein are useful for many recombinant DNA techniques, especially nucleic acid sequencing, nucleic acid amplification by the polymerase chain reaction (PCR) or mutagenesis.

BACKGROUND

Thermostable DNA polymerases which catalyze the template-directed polymerization of deoxyribonucleoside triphosphates (dNTPs) to form DNA, are used in a variety of in vitro DNA synthesis applications, such as DNA sequencing, DNA amplification and mutagenesis. However, thermostable DNA polymerases and their associated activities (reviewed in Abramson, 1995, in PCR Strategies, (Innis et al. ed., Academic Press, Inc.)) are not always optimal for a given application (reviewed in WO 01/61015, hereby incorporated by reference in its entirety). Because of the diversity of properties and characteristics potentially exhibited by nucleic acid polymerases generally, practitioners in the art have sought to modify, to alter, or to recombine various features of nucleic acid polymerases in an effort to develop new and useful variants of the enzyme.

One approach has been directed to the discovery and isolation of new thermophilic nucleic acid polymerases, which may possess a unique and/or improved collection of catalytic properties. As a result, thermostable nucleic acid polymerases have been isolated from a variety of biological sources, including, but not limited to, species of the *taxonomic genera, Thermus, Thermococcus, Thermotoga, Pyrococcus*, and *Sulfolobus*.

Some of these naturally occurring thermostable DNA polymerases possess enzymatically active 3'-5'exonuclease domains, providing a natural proofreading capability and, thus, exhibiting higher fidelity than Taq DNA polymerase. However, these DNA polymerases also show slower DNA extension rates and an overall lower processivity when compared to Taq DNA polymerase, thus rendering these naturally occurring thermostable DNA polymerases less desirable for PCR, despite their higher fidelity.

In an effort to compensate for the deficiencies of individual thermostable polymerases, a second approach has been to develop multiple enzyme assemblages, combining, for example, Taq polymerase and a proofreading enzyme, such as Pfu polymerase or *Thermococcus litoralis*-derived VENT® DNA polymerase. These multiple-enzyme mixtures exhibit higher PCR efficiency and reduced error rates when compared to Taq polymerase alone (Barnes, Proc. Natl. Acad. Sci USA 91:2216-2220 (1994).).

Another approach has been to develop new and useful variants of Taq polymerase through deletion/truncation techniques. The Stoffel fragment, for example, is a 544 amino acid C-terminal truncation of Taq DNA polymerase, possessing an enzymatically active 5' 3' polymerase domain but lacking 3'-5'exonuclease and 5-3' exonuclease activity. Other commercially available thermostable polymerase deletions include *Thermococcus litoralis*-derived VENT (exo-) and Deep Vent$_R$™(exo-) (New England Biolabs, Beverly, Mass.). Deletion mutations serve only to remove functional domains of a nucleic acid polymerase, however, and do not add any novel features or enzymatic properties.

Polymerase mutagenesis is yet another approach that has been attempted to develop new and useful nucleic acid polymerase variants. For example, naturally occurring DNA polymerases strongly discriminate against the incorporation of nucleotide analogues. This property contributes to the fidelity of DNA replication and repair. However, the incorporation of nucleotide analogues is useful for many DNA synthesis applications, especially DNA sequencing. Hence, a DNA polymerase that lacks associated exonucleolytic activity, either 5'-nuclease activity or 3' to 5' exonuclease activity, is preferred for DNA sequencing. In order to generate thermostable DNA polymerases with reduced nucleotide discrimination, site-directed mutagenesis studies were initiated and resulted in the identification of mutant forms of a number of thermostable DNA polymerases with the requisite activities suitable for DNA sequencing (U.S. Pat. No. 5,466,591, incorporated herein by reference).

Yet another approach to modifying the property of a DNA polymerase is to generate DNA polymerase fusions in which one or more protein domains having the requisite activity are combined with a DNA polymerase. DNA polymerase has been fused in frame to the helix-hairpin-helix DNA binding motifs from DNA topoisomerase V and shown to increase processivity, salt resistance and thermostability of the chimeric DNA polymerase as described in Pavlov et al., 2002, Proc. Natl. Acad. Sci USA, 99:13510-13515. Fusion of the thioredoxin binding domain to T7 DNA polymerase enhances the processivity of the DNA polymerase fusion in the presence of thioredoxin as described in WO 97/29209, U.S. Pat. No. 5,972,603 and Bedford et al. Proc. Natl. Acad. Sci. USA 94: 479-484 (1997). Fusion of the archaeal PCNA binding domain to Taq DNA polymerase results in a DNA polymerase fusion that has enhanced processivity and produces higher yields of PCR amplified DNA in the presence of PCNA (Motz, M., et al., J. Biol. Chem. May 3, 2002; 277 (18); 16179-88). Also, fusion of the sequence non-specific DNA binding protein Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1 which is hereby incorporated by reference in its entirety. Domain substitution of all or a portion of a DNA polymerase with the corresponding domain of a different DNA polymerase have also been described (U.S. 2002/0119461).

Despite these intense research efforts, there remains a need in the art to develop conditions, which are more suitable for supporting the nucleic acid synthesis, sequencing, and amplification activity of DNA polymerases.

SUMMARY OF THE INVENTION

The invention relates to methods of using a DNA polymerase fusion at high pH for DNA synthesis, DNA sequencing, cloning of a DNA synthesis product or linear or exponential PCR amplification.

One of skill in the art will understand that the DNA polymerase fusions useful according to the invention possess one or more DNA polymerase functions which are active at high pH. DNA polymerase functions are well known in the art (Ausubel et. al. *Short Protocols in Molecular Biology* (1995)

3rd Ed. John Wiley & Sons, Inc.; (Sambrook et al., (1989) in: Molecular Cloning, A Laboratory Manual (2nd Ed.), Cold Spring Harbor Laboratory Press, Cold Spring Harbor, N.Y.); Stratagene Catalog). Thus, the invention specifically encompasses a method of using the DNA polymerase fusions of the invention at high pH for a DNA polymerase fusion that is now known or becomes available in the art.

As used herein, "DNA polymerase function" refers to the activity of a DNA polymerase, described herein. Activities of the DNA polymerase include, but are not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, as defined hereinbelow. DNA polymerase activities are well known in the art (Ausubel et. al. *Short Protocols in Molecular Biology* (1995) 3rd Ed. John Wiley & Sons, Inc.; (Sambrook et al., (1989) in: Molecular Cloning, A Laboratory Manual (2nd Ed.), Cold Spring Harbor Laboratory Press, Cold Spring Harbor, N.Y., see additional references incorporated by reference in their entirety herein); Stratagene Catalog). Thus, the invention specifically encompasses a method of using a DNA polymerase fusions according to the invention at high pH for a DNA polymerase activity that is now known or becomes available in the art.

DNA polymerase "function" also includes an activity of a "mutant" DNA polymerase, as defined herein. The invention encompasses but is not limited to the following activities of a "mutant" according to the invention: base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity, efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein. In one embodiment, the "mutant" polymerase of the invention refers to a DNA polymerase containing one or more mutations that reduce one or more base analog detection activities of the DNA polymerase. In one embodiment, a "mutant" refers to a polymerase that has a mutation that confers an improved polymerization rate or fidelity on the polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. In another preferred embodiment, the "mutant" polymerase of the invention has a reduced DNA polymerization activity. Any of the "mutants", for example, a mutant with reduced uracil activity, may also possess improved polymerization rate and/or fidelity, as compared to a wild-type polymerase.

The invention provides for a method for DNA synthesis at high pH, comprising: a) providing a DNA polymerase fusion; and b) contacting the fusion with a nucleic acid template, wherein the fusion permits DNA synthesis.

The invention also provides for a method for cloning of a DNA synthesis product at high pH comprising: a) providing a DNA polymerase fusion; b) contacting the fusion with a nucleic acid template, wherein the fusion permits DNA synthesis to generate a synthesized DNA product; and c) inserting the synthesized DNA product into a cloning vector.

The invention also provides for a method for sequencing DNA at high pH, comprising the steps of: (a) contacting a template DNA strand with a sequencing DNA primer; (b) contacting the DNA of step (a) with a DNA polymerase fusion, deoxyribonucleoside triphosphates, and a chain-terminating nucleotide analog; (c) incubating the mixture of step (b) under conditions sufficient to synthesize a random population of DNA molecules complementary to the first DNA molecule, wherein the synthesized DNA molecules are shorter in length than the first DNA molecule and wherein the synthesized DNA molecules comprise a terminator nucleotide at their 5' termini; and (d) separating the synthesized DNA molecules by size so that at least a part of the nucleotide sequence of the first DNA molecule can be determined.

The invention also provides a method of linear or exponential PCR amplification at high pH for site-directed or random mutagenesis comprising the steps of: incubating a reaction mixture comprising a nucleic acid template, at least two PCR primers, and a DNA polymerase fusion under conditions which permit amplification of the nucleic acid template by the fusion to produce a mutated amplified product.

The invention also provides a method of reverse transcriptase PCR at high pH comprising the steps of incubating a reaction mixture comprising a nucleic acid template, at least one PCR primer, and a DNA polymerase fusion under conditions which permit amplification of the nucleic acid template by said fusion to produce an amplified product.

The invention provides for a composition for any one of DNA synthesis, cloning of a DNA synthesis product at high pH, sequencing DNA, linear or exponential PCR amplification for site directed or random mutagenesis, wherein the composition comprises a DNA polymerase fusion and a high pH buffer. In addition to the high pH buffer and polymerase fusion, the other components of a reaction mix may be present in the composition, e.g., template, primer, nucleotides, labels, labeled nucleotides, etc.

The invention provides for a composition for DNA synthesis, wherein the composition comprises a DNA polymerase fusion and a high pH DNA synthesis buffer. The invention contemplates a high pH DNA synthesis buffer, wherein the composition of the DNA synthesis buffer is that of a DNA synthesis buffer known in the art and described herein in the section entitled, "Applications of the Subject Invention", and wherein the DNA synthesis buffer is a "high pH" buffer, as defined herein.

The invention provides for a composition for cloning of a DNA synthesis product, wherein the composition comprises a DNA polymerase fusion and a high pH DNA cloning buffer. The invention contemplates a high pH DNA cloning buffer, wherein the composition of the DNA cloning buffer is that of a DNA cloning buffer known in the art and described herein in the section entitled, "Applications of the Subject Invention", and wherein the DNA cloning buffer is a "high pH" buffer, as defined herein.

The invention provides for a composition for sequencing DNA, wherein the composition comprises a DNA polymerase fusion and a high pH DNA sequencing buffer. The invention contemplates a high pH DNA sequencing buffer, wherein the composition of the DNA sequencing buffer is that of a DNA sequencing buffer known in the art and described herein in the section entitled, "Applications of the Subject Invention", and wherein the DNA sequencing buffer is a "high pH" buffer, as defined herein.

The invention provides for a composition for linear or exponential PCR amplification for site directed or random mutagenesis, wherein the composition comprises a DNA polymerase fusion and a high pH PCR reaction buffer. The invention contemplates a high pH PCR reaction buffer, wherein the composition of the PCR reaction buffer is that of a PCR reaction buffer known in the art and described herein in the section entitled, "Applications of the Subject Invention", and wherein the PCR reaction buffer is a "high pH" buffer, as defined herein.

In one embodiment, the methods and compositions of the invention further comprise a PCR enhancing factor and/or an additive.

In another embodiment, the DNA polymerase fusion used in the methods of the invention has reduced DNA polymerization activity.

In another embodiment, the DNA polymerase fusion comprises a Glycine to Proline substitution at amino acid position 387 (G387P) and has reduced DNA polymerization activity.

In another embodiment, the DNA polymerase fusion comprises reduced base analog detection activity.

In another embodiment, the DNA polymerase fusion comprises reduced base analog detection activity and a mutation at position V93, wherein the mutation is a Valine to Arginine substitution, a Valine to Glutamic acid substitution, a Valine to Lysine substitution, a Valine to Aspartic acid substitution or a Valine to Asparagine substitution.

In another embodiment, the DNA polymerase fusion has reduced base analog detection activity.

In another embodiment, the DNA polymerase fusion comprises reduced base analog detection activity.

In another embodiment, the DNA polymerase fusion further comprises a mutation at position V93, wherein the mutation is a Valine to Arginine substitution, a Valine to Glutamic acid substitution, a Valine to Lysine substitution, a Valine to Aspartic acid substitution or a Valine to Asparagine substitution that confers a reduced base analog detection activity phenotype to the chimeric DNA polymerase.

In another embodiment, the DNA polymerase fusion further comprises a reduced DNA polymerization activity.

In another embodiment, the DNA polymerase fusion further comprises a Glycine to Proline substitution at amino acid position 387 (G387P) that confers a reduced DNA polymerization phenotype to said chimeric DNA polymerase.

In another embodiment, the DNA polymerase fusion further comprises an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

In another embodiment, the DNA polymerase fusion with reduced base analog detection activity further comprises an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

In another embodiment, the DNA polymerase fusion comprises a wild type, mutant or chemically modified DNA polymerase.

In another embodiment, the DNA polymerase fusion is a proofreading polymerase.

In another embodiment, the proofreading polymerase is selected from the group consisting of Pfu, KOD, Tgo, *Thermococcus litoralis*-derived VENT®(exo-) and Deep Vent$_R$™ (exo-) (New England Biolabs, Beverly, Mass.).

In another embodiment, the DNA polymerase fusion further comprises a polypeptide with an increase in an activity selected from the group consisting of: processivity, proofreading, fidelity, DNA binding activity, strand displacement activity, polymerase activity, nucleotide binding and recognition, efficiency, template length amplification capability, GC-rich target amplification efficiency, specificity, thermostability, intrinsic hot start capability, or salt resistance.

In another embodiment, the DNA polymerase fusion further comprises a polypeptide with a reduced activity selected from the group consisting of: DNA polymerase activity at room temperature, amplification slippage on templates with tri-nucleotide repeat stretches, extension time in a PCR reaction or amplification cycles in a PCR reaction.

In another embodiment, the DNA polymerase fusion consists of a protein domain selected from the group of: thioredoxin processivity factor binding domain of bacteriophage T7, archaeal PCNA binding domain, PCNA, the helix-hairpin-helix DNA binding motifs from DNA topoisomerase V or the DNA binding protein Sso7d or Sac7d.

The invention also provides for a kit for performing at high pH a method selected from the group consisting of: DNA synthesis; cloning of a DNA synthesis product; sequencing DNA; and linear or exponential PCR amplification, or any additional polymerase function encompassed herein, comprising a DNA polymerase fusion and packaging materials.

The kit of the invention may further comprise a high pH buffer, or a PCR enhancing factor and/or an additive.

DEFINITIONS

A "fusion" as defined herein, is a first amino acid sequence (protein) comprising a wild type or mutant DNA polymerase of the invention, joined to a second amino acid sequence defining a polypeptide that modulates one or more activities of the DNA polymerase including, but not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, wherein the first and second amino acids are not found in the same relationship in nature. A "fusion" according to the invention contains two or more amino acid sequences (for example a sequence encoding a wild type or mutant DNA polymerase and a polypeptide that increases processivity and/or salt resistance) from unrelated proteins, joined to form a new functional protein. In one embodiment a "fusion" according to the invention comprises a first amino acid sequence derived from a first polymerase species (e.g. Pfu N-terminus) and a second amino acid sequence derived from a second polymerase species (e.g. KOD C-terminus. In one embodiment, a "fusion" of the invention comprises a first amino acid sequence derived from a first polymerase and a second amino acid sequence derived from a polypeptide that is not a polymerase. In one embodiment, the amino acid sequence derived from a polypeptide that is not a polymerase is not enzymatically active.

As used herein, "enzymatically active" means catalyzing a specific enzymatic reaction.

A fusion of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses fusions wherein the polypeptide that increases processivity and/or salt resistance is joined N-terminally or C-terminally to, or is inserted at any internal position of a wild-type DNA polymerase or any of the mutant DNA polymerases described herein or known in the art.

In one embodiment, the fusion of the invention is a fusion DNA polymerase comprising a wild type or mutated thermostable DNA polymerase with or without 3'-5' exonuclease activity including but not limited to Pfu or Taq. The chimeric component added to the Pfu or Taq DNA polymerase is a basic or non-basic, protein or protein domain fused to the Pfu or Taq DNA polymerase at the N- or C-terminus or at any internal position such that the chimeric component and the polymerase are in a relationship that does not exist in nature. The chimeric contribution to the activity of the Pfu or Taq DNA polymerase increases or enhances processivity, DNA binding, strand displacement activity, polymerase activity, nucleotide binding and recognition, proofreading, fidelity, and salt resistance and/or decrease DNA polymerase activity at room temperature.

A DNA polymerase fusion of the invention has a >10% increase in one or more of the following activities (using the assays described hereinbelow) as compared to a DNA polymerase that is not a fusion using a genomic and/or plasmid template: processivity, efficiency, template length amplification capability, GC-rich target amplification efficiency, specificity, thermostability; intrinsic hot start capability, proofreading activity, fidelity, DNA binding activity, strand displacement activity, nucleotide binding and recognition, and salt resistance. A DNA polymerase fusion of the invention will also have a >10% decrease as compared to a DNA polymerase that is not a fusion using a genomic and/or plasmid template in one or more of the following activities (assayed as described hereinbelow): amplification slippage on templates with tri-nucleotide repeat stretches or DNA polymerase activity at room temperature. In one embodiment, a "fusion" of the invention has an extension time in a PCR reaction that is decreased by 5 sec, preferably 15 sec and more preferably 45 sec or more, as compared to the extension time observed in the presence of a DNA polymerase that is not a fusion alone. In another embodiment, a "fusion" of the invention has a decrease in the number of amplification cycles for PCR of 1, 1-5 or 5 or more cycles, as compared to a DNA polymerase that is not a fusion alone. In another embodiment, fewer units (0.001, 0.01, 1 or 1 or more) of a "fusion" of the invention are useful in an application of the invention as compared to a DNA polymerase that is not a fusion. In all cases where the activity of a "fusion" is compared to the activity of a DNA polymerase that is not a fusion, the DNA polymerase that is not a fusion is identical to the polymerase domain of the fusion, and only differs from the fusion by the absence of the second amino acid sequence of the fusion, as defined herein.

As used herein, a "genomic template" means a template comprising the nucleic acid material constituting the genome of a cell or an organism.

As used herein, "fused" or "joined" refers to any method known in the art for functionally connecting polypeptide domains, including without limitation recombinant fusion with or without intervening domains, intein-mediated fusion, non-covalent association, and covalent bonding, including disulfide bonding, hydrogen bonding, electrostatic bonding, and conformational bonding.

"Domain" refers to a unit of a protein or protein complex, comprising a polypeptide subsequence, a complete polypeptide sequence, or a plurality of peptide sequences.

As used herein, the term "modulate" refers to an increase or decrease of 2 fold, preferably 5 fold, preferably 20 fold, preferably 100 fold, more preferably 500 fold or more in an activity of a DNA polymerase fusion of the invention as compared to a DNA polymerase that is not a fusion. In one embodiment, the DNA polymerase domain of the fusion comprises one or more mutations, as described herein. In this embodiment, the term "modulate" refers to an increase or decrease of 2 fold, preferably 5 fold, preferably 20 fold, preferably 100 fold, more preferably 500 fold or more in an activity of a DNA polymerase fusion of the invention as compared to a DNA polymerase that is not a fusion, wherein the DNA polymerase that is not a fusion is identical to the mutant DNA polymerase domain of the fusion but lacks the second amino acid sequence of the fusion as described herein.

A DNA polymerase fusion be used in combination with a PCR enhancing factor and/or an additive, as described herein.

As used herein, "high pH" refers to a pH that is greater than 9. A "high pH" is preferably 10 or more, for example 10, 11, 12, 13 or 14. A "high pH" includes any pH greater than 9 and up to a pH of 14, for example a pH of 9.1, 9.5, 9.8, 10, 10.5, 11, 11.5, 12, 12.5, 13, 13.5, or 14 is a "high pH" according to the invention.

As used herein, "polypeptide that increases processivity and/or salt resistance" refers to a domain that is a protein or a region of a protein or a protein complex, comprising a polypeptide sequence, or a plurality of peptide sequences wherein that region increases processivity, as defined herein, or increases salt resistance, as defined herein. A "polypeptide that increases processivity and/or salt resistance useful according to the invention includes but is not limited to any of the domains included in Pavlov et al., supra or WO 01/92501, for example Sso7d, Sac7d, HMF-like proteins, PCNA homologs, helix-hairpin-helix domains, for example derived from Topoisomerase V, or the thioredoxin binding domain of T7 DNA polymerase as described in WO 97/29209, U.S. Pat. No. 5,972,603 and Bedford et al. Proc. Natl. Acad. Sci. USA 94: 479-484 (1997).

As used herein, "processivity" refers to the ability of a nucleic acid modifying enzyme, for example a polymerase, to remain attached to the template or substrate and perform multiple modification reactions. "Modification reactions" include but are not limited to polymerization, and exonucleolytic cleavage. "Processivity" also refers to the ability of a nucleic acid modifying enzyme, for example a polymerase, to modify relatively long (for example 0.5-1 kb, 1-5 kb or 5 kb or more) tracts of nucleotides. "Processivity" also refers to the ability of a nucleic acid modifying enzyme, for example a DNA polymerase, to perform a sequence of polymerization steps without intervening dissociation of the enzyme from the growing DNA chains. "Processivity" can depend on the nature of the polymerase, the sequence of a DNA template, and reaction conditions, for example, salt concentration, temperature or the presence of specific proteins.

As used herein, "increased processivity" refers to an increase of 5-10%, preferably 10-50%, more preferably 50-100% or more, as compared to a wild type or mutant archael DNA polymerase that lacks a polypeptide that increases processivity and/or salt resistance as defined herein. Processivity and increased processivity can be measured according to the methods defined herein and in Pavlov et al., supra and WO 01/92501 A1. A polymerase with increased processivity that is a chimera comprising a polypeptide that increases processivity, as defined herein, is described in Pavlov et al. supra and WO 01/92501 A1.

As used herein, "increased salt resistance" refers to a polymerase that exhibits >50% activity at a salt concentration that is know to be greater than the maximum salt concentration at which the wild-type polymerase is active. The maximum salt concentration differs for each polymerase and is known in the art, or can be experimentally determined according to methods in the art. For example, Pfu is inhibited at 30 mM salt (in a PCR reaction) so a Pfu enzyme with increased salt resistance would have significant activity (>50%) at salt concentrations above 30 mM. A polymerase with increased salt resistance that is a fusion comprising a polypeptide that increases salt resistance, as defined herein, is described in Pavlov et al. supra and WO 01/92501 A1.

As used herein, "fidelity" refers to the accuracy of polymerization, or the ability of the polymerase to discriminate correct from incorrect substrates, (e.g., nucleotides) when synthesizing nucleic acid molecules (e.g. RNA or DNA) which are complementary to a template. The higher the fidelity of a polymerase, the less the polymerase misincorporates nucleotides in the growing strand during nucleic acid synthesis; that is, an increase or enhancement in fidelity results in a more faithful polymerase having a decreased error rate (decreased misincorporation rate).

The term "fidelity" as used herein also refers to the accuracy of DNA polymerization by a template-dependent DNA polymerase. The fidelity of a DNA polymerase is measured by the error rate (the frequency of incorporating an inaccurate nucleotide, i.e., a nucleotide that is not incorporated in a template-dependent manner). The accuracy or fidelity of DNA polymerization is maintained by both the polymerase activity and the 3'-5' exonuclease activity of a DNA polymerase. The term "high fidelity" refers to an error rate of $5 \times 10^{-6}$ per base pair or lower. The fidelity or error rate of a DNA polymerase may be measured using assays known in the art. For example, the error rates of DNA polymerase mutants can be tested using the lacI PCR fidelity assay described in Cline, J., Braman, J. C., and Hogrefe, H. H. (96) NAR 24:3546-3551. Briefly, a 1.9 kb fragment encoding the lacIOlacZα target gene is amplified from pPRIAZ plasmid DNA using 2.5 U DNA polymerase (i.e. amount of enzyme necessary to incorporate 25 nmoles of total dNTPs in 30 min. at 72° C.) in the appropriate PCR buffer. The lacI-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per bp per duplication (MF/bp/d), where bp is the number of detectable sites in the lacI gene sequence (349) and d is the number of effective target doublings. For each DNA polymerase mutant, at least two independent PCR amplifications are performed.

A DNA polymerase having increased/enhanced/higher fidelity is defined as a polymerase having about 2 to about 10,000 fold, about 2 to about 5,000 fold, or about 2 to about 2,000 fold (preferably greater than about 5 fold, more preferably greater than about 10 fold, still more preferably greater than about 50 fold, still more preferably greater than about 100 fold, still more preferably greater than about 500 fold and most preferably greater than about 1000 fold) reduction in the number of misincorporated nucleotides during synthesis of any given nucleic acid molecule of a given length. For example, a mutated polymerase may misincorporate one nucleotide in the synthesis of 1000 bases compared to an unmutated polymerase misincorporating 10 nucleotides. Such a mutant polymerase would be said to have an increase of fidelity of 10 fold.

A DNA polymerase having reduced misincorporation is defined herein as either a mutated or modified DNA polymerase that has about or less than 50%, or preferably about or less than 25%, more preferably about or less than 10% and most preferably about or less than 1% of relative misincorporation compared to the corresponding unmutated, unmodified or wild type enzyme. A DNA polymerase of lower fidelity may also initiate DNA synthesis with an incorrect nucleotide incorporation (Perrion & Loeb, 1989, J. Biol. Chem. 264:2898-2905).

The fidelity or misincorporation rate of a polymerase can be determined in a sequencing reaction by other methods known in the art (Eckert & Kunkel, Nucl. Acids Res. 3739-3744(1990)). In one example, the sequence of a DNA molecule synthesized by the unmutated and mutated polymerase can be compared to the expected (known) sequence. In this way, the number of errors (misincorporation) can be determined for each enzyme and compared.

DNA binding and assays for detecting DNA binding are described in: PCT/US01/7492.

Strand displacement refers to the activity described in Hogrefe et al Methods of Enzymology (2001) 334:91-116 and Kong et al (93) J. Biol. Chem. 268:1965. Assays for measuring strand displacement activity are described in Hogrefe et al Methods of Enzymology (2001) 334:91-116 and Kong et al (93) J. Biol. Chem. 268:1965.

DNA polymerase activity at room temperature is as described in The Methods of Enzymology (2001) 334:91-116. Assays for measuring DNA polymerase activity at room temperature are described in The Methods of Enzymology (2001) 334:91-116 and in Nielson et al (1997) Strategies 10:40-43 Newsletter articles.

As used herein, "GC-rich target amplification efficiency" refers to the amplification efficiency of DNA templates that have greater than 50% GC content and are more difficult to melt during PCR. These targets frequently form secondary structure when the temperature cycles to the annealing temperature making PCR amplification difficult. "GC-rich target amplification" is assayed by performing PCR amplification on a target with greater than 50% GC content and comparing the yield of amplicon generated on a gel (see Biotechniques April 2002; 32(4):866, 868, 870-2, 874).

A polymerase with "intrinsic hot start capability" refers to a thermostable DNA polymerase that has very low (<25°) DNA polymerase activity at non-stringent primer annealing temperatures (≦45°). These polymerases and assays for their detection are described in Nielson et al (1997) Strategies 10:40-43.

"DNA slippage" or "amplification slippage on templates with tri-nucleotide repeat stretches" and assays for detection of this activity is as described in J Mol Biol Sep. 14, 2001; 312(2):323-33, J Biol Chem Sep. 24, 1999; 274(39):27481-90, EMBO J May 15, 2001; 20(10):2587-95, Biochemistry Jan. 23, 1996; 35(3):1046-53.

A DNA polymerase fusion that exhibits decreased DNA polymerase activity at room temperature preferably exhibits a shift in the activity vs. temperature profile such that reduced polymerase activity is observed at a suboptimal temperature (for example a non-specific primer annealing/extension temperature) and wild type polymerase activity is observed at stringent primer annealing/extension temperature. Such fusions are expected to exhibit improved specificity in PCR.

Methods of measuring the efficiency of a DNA polymerase are described in PCR Primer: A Laboratory Manual, 1995, CSHL Press, Cha and Thilly, pp. 37-51.

Methods of measuring template length amplification capability are described in Proc Natl. Acad. Sci USA, 2002, 99:596-601 and J. Biotechnol., 2001, 88:141-149.

Methods of measuring specificity of a DNA polymerase are described in J. Biochem. (Tokyo), 1999, 126:762-8.

Methods of measuring thermostability of a DNA polymerase are described in FEMS Microbiol. Lett, 2002, 217:89-94.

Methods of measuring nucleotide binding and recognition are described in J. Mol. Biol., 2002, 322:719-729 and Nucleic Acids Res., 2002, 30:605-13.

A "domain" useful according to the invention includes any double stranded or single stranded DNA binding domain known in the art or that becomes known in the art.

As used herein, "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides. In a preferred embodiment, the DNA polymerase according to the invention is thermostable. In another preferred embodiment, the DNA polymerase according to the invention is an archaeal DNA polymerase.

As used herein in reference to a DNA polymerase, the term DNA polymerase includes a "functional fragment thereof". A "functional fragment thereof" refers to any portion of a wild-type or mutant DNA polymerase that encompasses less than the entire amino acid sequence of the polymerase and which retains the ability, under at least one set of conditions, to catalyze the polymerization of a polynucleotide. Such a functional fragment may exist as a separate entity, or it may be a constituent of a larger polypeptide, such as a fusion protein.

The nucleic acid polymerases used in the present invention may be mesophilic or thermophilic, and are preferably thermophilic. Preferred mesophilic DNA polymerases include T7 DNA polymerase, T5 DNA polymerase, T4 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, *Thermococcus litoralis*-derived VENT® (exo-) and Deep Vent$_R$™ (exo-) (New England Biolabs, Beverly, Mass.) DNA polymerases, KOD, Tgo, JDF3, and mutants, variants and derivatives thereof (U.S. Pat. No. 5,436,149; U.S. Pat. No. 4,889,818; U.S. Pat. No. 4,965,18S; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nuc. Acids Res. 22(15):3259-3260 (1994)). For amplification of long nucleic acid molecules (e.g., nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Frames, W. M., Gene 112:29-35 (1992); and copending U.S. patent application Ser. No. 09/741,664, filed Dec. 21, 2000, the disclosures of which are incorporated herein in their entireties. Examples of DNA polymerases substantially lacking in 3' exonuclease activity include, but are not limited to, Taq, Tne(exo-), Tma(exo-), Pfu(exo-), Pwo(exo-), exo-KOD and Tth DNA polymerases, and mutants, variants and derivatives thereof.

As used herein, "archaeal" DNA polymerase refers to DNA polymerases that belong to either the Family B/polI-type group (e.g., Pfu, KOD, Pfx, Vent, Deep Vent, Tgo, Pwo) or the pol II group (e.g., *Pyrococcus furiosus* DP1/DP22-subunit DNA polymerase). In one embodiment, "archaeal" DNA polymerase refers to thermostable archaeal DNA polymerases (PCR-able) and include, but are not limited to, DNA polymerases isolated from *Pyrococcus* species (furiosus, species GB-D, woesii, abysii, horikoshii), *Thermococcus* species (kodakaraensis KOD1, litoralis, species 9 degrees North-7, species JDF-3, gorgonarius), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), *Thermococcus litoralis*-derived VENT® (New England BioLabs), and Deep Vent$_R$™(exo-) (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995.

As used herein, "mutant" polymerase refers to a DNA polymerase, as defined herein, comprising one or more mutations that modulate, as defined herein, one or more activities of the DNA polymerase including, but not limited to, base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity, efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein. In one embodiment, the "mutant" polymerase of the invention refers to a DNA polymerase containing one or more mutations that reduce one or more base analog detection activities of the DNA polymerase. In one embodiment, a "mutant" refers to a polymerase that has a mutation that confers an improved polymerization rate or fidelity on the polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. In another preferred embodiment, the "mutant" polymerase of the invention has a reduced DNA polymerization activity. Any of the "mutants" for example a mutant with reduced uracil activity, may also possess improved polymerization rate and/or fidelity, as compared to a wild-type polymerase. A "mutant" polymerase as defined herein, includes a polymerase comprising one or more amino acid substitutions, one or more amino acid insertions, a truncation or an internal deletion. A "mutant" polymerase as defined herein includes non-fusion and fusion polymerases as defined herein.

A "mutant" polymerase as defined herein also includes a fusion polymerase wherein any of the single, double or triple mutant DNA polymerases described herein, any mutant DNA polymerase comprising an insertion, described herein, or any of the truncated, or deleted mutant DNA polymerases described herein, occur in combination with a polypeptide that modulates one or more activities of the DNA polymerase including, but not limited to, DNA polymerization activity, base analog detection activities, DNA polymerization activity, reverse transcriptase activity, processivity, salt resistance, DNA binding, strand displacement activity, nucleotide or nucleotide analog binding and recognition, sensitivity to uracil, 3'-5' or 5'-3' exonuclease activities, proofreading, fidelity efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein, thereby forming a fusion, as defined herein. For example, a polypeptide that increases processivity and or salt resistance is described in WO 01/92501 A1 and Pavlov et al., 2002, Proc. Natl. Acad. Sci. USA, 99:13510-13515, herein incorporated by reference in their entirety. Other specific examples of commercially useful mutations include, but are not limited to, V93R,K,E,D in Pfu, which confer uracil insensitivity and D141A/E143A in Pfu, which eliminates 3'-5' exonuclease activity. A commercially useful truncation includes, but is not limited to the N-terminal truncation in Taq (KlenTaq) which eliminates 5'-3' exonulease activity.

As used herein, "mutation" refers to a change introduced into a parental or wild type DNA sequence that changes the amino acid sequence encoded by the DNA, including, but not limited to, substitutions, insertions, deletions or truncations. The consequences of a mutation include, but are not limited to, the creation of a new character, property, function, or trait not found in the protein encoded by the parental DNA, including, but not limited to, N terminal truncation, C terminal truncation or chemical modification. A "mutant" DNA polymerase as used herein, refers to a DNA polymerase comprising a mutation as defined herein. A "mutant" DNA polymerase of the invention can encompass a DNA polymerase "fusion" of the invention.

As used herein, a DNA polymerase with a "reduced DNA polymerization activity" is a DNA polymerase mutant comprising a DNA polymerization activity which is lower than that of the wild-type enzyme, e.g., comprising less than 10% DNA (e.g., 19.9%, 9%, 8%, 6%, 4%, 2% or less than 1%) polymerization activity of that of the wild-type enzyme or less than that of a DNA polymerase that is not a fusion. Methods used to generate and characterize Pfu DNA polymerases with reduced DNA polymerization activity are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety. The invention contemplates a DNA polymerase fusion with reduced DNA polymerization activity.

As used herein, "proofreading" activity refers to 3' to 5' exonuclease activity of a DNA polymerase.

A "non-proofreading" enyzme refers to a DNA polymerase that is "3' to 5' exonuclease deficient" or "3' to 5' exo-".

As used herein, "3' to 5' exonuclease deficient" or "3' to 5' exo-" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, for example, 0.03%, 0.05%, 0.1%, 1%, 5%, 10%, 20% or even up to 50% of the exonuclease activity relative to the parental enzyme. Methods used to generate and characterize 3'-5' exonuclease DNA polymerases including the D141A and E143A mutations as well as other mutations that reduce or eliminate 3'-5' exonuclease activity are disclosed in the pending U.S. patent application Ser. No. 09/698,341 (Sorge et al; filed Oct. 27, 2000). Additional mutations that reduce or eliminate 3' to 5' exonuclease activity are known in the art and contemplated herein.

As used herein, "synthesis" refers to any in vitro method for making a new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

"DNA synthesis", according to the invention, includes, but is not limited to, PCR, the labelling of polynucleotide (i.e., for probes and oligonucleotide primers), and polynucleotide sequencing. The invention contemplates mutant DNA polymerases, and fusions thereof, that exhibit reduced base analog detection (for example, reduced detection of a particular base analog such as uracil or inosine or reduced detection of at least two base analogs).

As used herein, "base analogs" refer to bases that have undergone a chemical modification as a result of the elevated temperatures required for PCR reactions. In a preferred embodiment, "base analog" refers to uracil that is generated by deamination of cytosine. In another preferred embodiment, "base analog" refers to inosine that is generated by deamination of adenine.

As used herein, "thermostable" refers to an enzyme which is stable and active at temperatures as great as preferably between about 90-100° C. and more preferably between about 70-980 C to heat as compared, for example, to a non-thermostable form of an enzyme with a similar activity. For example, a thermostable nucleic acid polymerase derived from thermophilic organisms such as *P. furiosus, M jannaschii, A. fulgidus* or *P. horikoshii* are more stable and active at elevated temperatures as compared to a nucleic acid polymerase from *E. coli*. A representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases are preferred in a thermocycling process wherein double stranded nucleic acids are denatured by exposure to a high temperature (about 95° C.) during the PCR cycle.

As used herein, the term "template DNA molecule" refers to that strand of a nucleic acid from which a complementary nucleic acid strand is synthesized by a DNA polymerase, for example, in a primer extension reaction.

As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

As used herein, an "amplified product" refers to the double stranded polynucleotide population at the end of a PCR amplification reaction. The amplified product contains the original polynucleotide template and polynucleotide synthesized by DNA polymerase using the polynucleotide template during the PCR reaction.

As used herein, "polynucleotide template" or "target polynucleotide template" or "template" refers to a polynucleotide containing an amplified region. The "amplified region," as used herein, is a region of a polynucleotide that is to be, for example, synthesized by polymerase chain reaction (PCR). For example, an amplified region of a polynucleotide template resides between two sequences, to which two PCR primers are complementary.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein, "reduced base analog detection" refers to a DNA polymerase, with a reduced ability to recognize a base analog, for example, uracil or inosine, present in a DNA template. In this context, mutant DNA polymerase with "reduced" base analog detection activity is a DNA polymerase mutant having a base analog detection activity which is lower than that of the wild-type enzyme. In the case of a mutant DNA polymerase fusion the activity of a mutant DNA polymerase may be compared to the corresponding non-fusion DNA polymerase, i.e., having less than 10% (e.g., 9.9%, 9%, 8%, 6%, 4%, 2% or less than 1%) of the base analog detection activity of that of the wild-type enzyme. Base analog detection activity may be determined according to the assays similar to those described for the detection of DNA polymerases having a reduced uracil detection activity as described in Greagg et al. (1999) Proc. Natl. Acad. Sci. 96, 9045-9050. Alternatively, "reduced" base analog detection refers to a mutant DNA polymerase with a reduced ability to recognize a base analog, the "reduced" recognition of a base analog being evident by an increase in the amount of >10 Kb PCR of at least 10%, preferably 50%, more preferably 90%, most preferably 99% or more, as compared to a wild type DNA polymerase without a reduced base analog detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, "reduced uracil detection" refers to a DNA polymerase with a reduced ability to recognize a uracil base present in a DNA template. In this context, mutant DNA polymerase with "reduced" uracil detection activity is a DNA polymerase mutant having a uracil detection activity which is lower than that of the wild-type enzyme, i.e., having less than 10% (e.g., 9.9% 1.9%, 8%, 6%, 4%, 2% or less than 1%) of the uracil detection activity of that of the wild-type enzyme. Uracil detection activity may be determined according to the assays described in Greagg et al. (1999) Proc. Natl. Acad. Sci. 96, 9045-9050. Alternatively, "reduced" uracil detection refers to a mutant DNA polymerase with a reduced ability to recognize uracil, the "reduced" recognition of uracil being evident by an increase in the amount of >10 Kb PCR of at least 10%, preferably 50%, more preferably 90%, most preferably 99% or more, as compared to a wild type DNA polymerase without a reduced uracil detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImagerrm (Amersham Biosciences, catalogue #63-0007-79).

As used herein, "chemically modified" refers to a nucleic acid that is chemically or biochemically modified or contains non-natural or derivatized nucleotide bases. Such modifications include, for example, labels, methylation, substitution of one or more of the naturally occurring nucleotides with an analog, intemucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

As used herein, a "PCR enhancing factor" or a "Polymerase Enhancing Factor" (PEF) refers to a complex or protein possessing polynucleotide polymerase enhancing activity including, but not limited to, PEF, dUTPase, ssbPCNA, RFC, helicases etc (Hogrefe et al., 1997, Strategies 10:93-96; and U.S. Pat. No. 6,183,997, both of which are hereby incorporated by reference). A "PCR enhancing factor" also includes non-protein factors, for example DMSO and betaine.

The invention also contemplates mutant archael DNA polymerases in combination with accessory factors, for example as described in U.S. Pat. No. 6,333,158, and WO 01/09347 A2, hereby incorporated by reference in their entirety.

As used herein, "additive" refers to a PCR enhancing additive, including but not limited to, Pfu dUTPase (PEF), PCNA, RPA, ssb, antibodies, DMSO, betaine, or 3'-5' exonuclease (e.g., Pfu G387P).

The invention also provides for kits for performing at high pH a method selected from the group consisting of: DNA synthesis; cloning of a DNA synthesis product; sequencing DNA; and linear or exponential PCR amplification comprising a DNA polymerase fusion and packaging materials therefore. The kits of the invention may include a high pH buffer and/or a PCR enhancing factor and/or an additive.

As used herein, a high pH buffer refers to a buffer that has a pH greater than 9. As used herein, "high pH" refers to a pH that is greater than 9. A "high pH" is preferably 10 or more, for example 11, 12, 13 or 14. A "high pH" includes any pH greater than 9 and up to a pH of 14, for example a pH of 9.1, 9.5, 9.8, 10, 10.5, 11, 11.5, 12, 12.5, 13, 13.5, or 14 is a "high pH" according to the invention.

In a preferred embodiment the high pH buffer is a standard PCR reaction buffer, for example cloned Pfu reaction buffer described in Example 3, but wherein the buffering component is at a high pH (i.e., 9.1-14). For example, a buffering component of the invention is 30 mM Tris [Tris(hydroxymethyl) aminomethane] at a pH of 10.0 or 11.8. The pH of the buffering component in standard PCR reaction buffers is from 8.3-8.8. The buffering component is used at a concentration from 1 mM to 1M in the final PCR reaction and is at a pH from 9.1-14. The highly alkaline buffer for PCR reactions is used with the fusion DNA polymerases or fusion DNA polymerase blends of the invention. A buffering component of the present invention includes, but is not limited to, Tris, Tricine, bicine, Bis-Tris, CAPS, EPPS, HEPES, MES, MOPS, PIPES, TAPS and TES.

As used herein "FEN-1 nuclease" refers to thermostable FEN-1 endonucleases useful according to the invention and includes, but is not limited to, FEN-1 endonuclease purified from the "hyperthermophiles", e.g., from *M. jannaschii*, *P. furiosus* and *P. woesei*. See U.S. Pat. No. 5,843,669, hereby incorporated by reference.

According to the methods of the present invention, the addition of FEN-1 in the amplification reaction dramatically increases the efficiency of the multi-site mutagenesis. 400 ng to 4000 ng of FEN-1 may be used in each amplification reaction. Preferably 400-1000 ng, more preferably, 400-600 ng of FEN-1 is used in the amplification reaction. In a preferred embodiment of the invention, 400 ng FEN-1 is used.

As used herein, "*Thermus* DNA ligase" refers to a thermostable DNA ligase that is used in the multi-site mutagenesis amplification reaction to ligate the mutant fragments synthesized by extending each mutagenic primer so as to form a circular mutant strand. Tth and Taq DNA ligase require NAD as a cofactor.

Preferably, 1-20 U DNA ligase is used in each amplification reaction, more preferably, 2-15 U DNA ligase is used in each amplification reaction.

In a preferred embodiment, 15 U Taq DNA ligase is used in an amplification reaction. Taq DNA ligase cofactor NAD is used at a concentration of 0-1 mM, preferably between 0.02-0.2 mM, more preferably at 0.1 mM.

As used herein, a "blend" refers to a combination of two or more DNA polymerases comprising at least one DNA polymerase fusion and at least one non-fusion DNA polymerase (see Example 2). The invention contemplates a "blend" wherein at least one of said fusion or non-fusion DNA polymerase is thermostable, is an archael or eubacterial DNA polymerase and/or is a Pfu DNA polymerase. The ratio of DNA polymerase enzymes in a "blend" comprising one fusion and one non-fusion polymerase is in the range of 1:1-1:5-5:1, or 1:1-1:10-10:1, or 1:1-1:25-25:1 or 1:1-1:100-100:1. For embodiments wherein a "blend" comprises one fusion DNA polymerase and two non-fusion polymerases the ratio of the first non-fusion DNA polymerase to the second non-fusion DNA polymerase is in the range of 1:1-1:5-5:1, or 1:1-1:10-10:1, or 1:1-1:25-25:1 or 1:1-1:100-100:1. A "blend" invention has a >10% increase in one or more of the following activities (using the assays described hereinbelow) as compared to the non-fusion component of the blend using a genomic and/or plasmid template.: processivity, efficiency, template length amplification capability, GC-rich target amplification efficiency, specificity, thermostability; intrinsic hot start capability, proofreading activity, fidelity, DNA binding activity, strand displacement activity, nucleotide binding and recognition, and salt resistance. A blend of the invention will also have a >10% decrease as compared to the non-fusion blends using genomic and/or plasmid template in one or more of the following activities (assayed as described hereinbelow): amplification slippage on templates with tri-nucleotide repeat stretches or DNA polymerase activity at room temperature. In one embodiment, a "blend" of the invention has an extension time in a PCR reaction that is decreased by 5 sec, preferably 15 sec and more preferably 45 sec or more, as compared to the extension time observed in the presence of the non-fusion component of the blend alone. In another embodiment, a "blend" of the invention has a decrease in the number of amplification cycles for PCR of 1, 1-5 or 5 or more cycles, as compared to the non-chimeric component of the blend alone. In another embodiment, fewer units (0.001, 0.01, 0.1 or 1 or more) of a "blend" of the invention are useful in an application of the invention as compared to the non-fusion component of the blend.

A blend may also include a PCR enhancing factor and/or an additive, as described herein.

The invention also relates to compositions made for carrying out the methods of the invention and compositions made while carrying out the methods of the invention. Such compositions may comprise one or more components selected from the group consisting of one or more polymerases of the invention, one or more nucleotides, one or more templates, one or more reaction buffers or buffering salts, one or more primers, one or more nucleic acid products made by the methods of the invention and the like.

BRIEF DESCRIPTION OF THE DRAWINGS

FIG. 10: Oligonucleotide Primers for QuickChange Mutagenesis (SEQ ID Nos: 6-14)

FIG. 11: (a) dUTP incorporation of V93E and V93R mutants compared to wild type Pfu DNA polymerase.
(b) PCR Amplification of Pfu V93R mutant extract in the presence of 100% dUTP.

FIG. 13: 13A. DNA sequence of mutant archeael DNA polymerases
13B. Amino acid sequence of mutant archeael DNA polymerases
FIG. 14: DNA and Amino acid sequence of mutant Tgo DNA polymerase DNA
FIG. 16: DNA polymerase activity of N-terminal Pfu DNA polymerase truncation mutants.

FIG. 17: shows the sequence of
A. HMf-like protein
B. HMf-like protein-Taq fusion
C. HMf-like protein-Taq fusion
D. Pfu WT-HMf like protein fusion
E. Pfu WT-HMf like protein fusion
F. Pfu-V93 R or E-HMf-like protein fusion
G. Pfu-V93 R or E-HMf-like protein fusion
H. Pfu-G387P/V93 R or E-HMf-like protein fusion
I. Pfu-G387P/V93 R or E-HMf-like protein fusion
J. Pfu-D141A/E143A/V93 R or E-HMf-like protein fusion
K. Pfu-D141A/E143A/V93 R or E-HMf-like protein fusion
L. KOD-HMf-like protein fusion
M. KOD-HMf-like protein fusion
N. HMf-like protein-*Thermococcus litoralis*-derived VENT® (New England BioLabs) fusion
O. HMf-like protein-*Thermococcus litoralis*-derived VENT® (New England BioLabs) fusion
P. HMf-like protein-Deep Vent$_R$™(exo-) (New England BioLabs) fusion
Q. HMf-like protein-Deep Vent$_R$™(exo-) (New England BioLabs) fusion
R. HMf-like protein-JDF3 fusion
S. HMf-like protein-JDF3 fusion
T. PCNA
U. PCNA-Taq fusion
V. PCNA-Taq fusion
W. PCNA-PfuWT fusion
X. PCNA-PfuWT fusion
Y. Pfu-V93 R or E-PCNA fusion
Z. Pfu-V93 R or E-PCNA fusion
AA. Pfu-G387P/V93 R or E-PCNA fusion
BB. Pfu-G387P/V93 R or E-PCNA fusion
CC. Pfu-D141A/E143A/V93 R or E-PCNA fusion
DD. Pfu-D141A/E143A/V93 R or E-PCNA fusion
EE. KOD-PCNA fusion
FF. KOD-PCNA protein fusion
GG. PCNA-*Thermococcus litoralis*-derived VENT (New England BioLabs) fusion
HH. PCNA-*Thermococcus litoralis*-derived VENT (New England BioLabs) fusion II. PCNA-Deep Vent$_R$™(exo-) (New England BioLabs) fusion
JJ. PCNA-Deep Vent$_R$™(exo-) (New England BioLabs) fusion
KK. PCNA-JDF3 fusion
LL. PCNA-JDF3 fusion
MM. Sac7d
NN. Sac7d-Taq fusion
OO. Sac7d-Taq fusion
PP. Sac7d-PfuWT fusion
QQ. Sac7d-PfuWT fusion
RR. Pfu-V93 R or E-Sac7d-like protein fusion
SS. Pfu-V93 R or E-Sac7d fusion
TT. Pfu-G387P/V93 R or E-Sac7d fusion
UU. Pfu-G387P/V93 R or E-Sac7d fusion
VV. Pfu-D141A/E143A/V93 R or E-Sac7d fusion
WW. KOD-Sac7d fusion
XX. KOD-Sac7d protein fusion
YY. Sac7d-*Thermococcus litoralis*-derived VENT (New England BioLabs) fusion
ZZ. Sac7d-*Thermococcus litoralis*-derived VENT® (New England BioLabs) fusion
AAA. Sac7d-Deep Vent$_R$™(exo-) (New England BioLabs) fusion
BBB. Sac7d-Deep Vent$_R$™(exo-) (New England BioLabs) fusion
CCC. Sac7d-JDF3 fusion
DDD. Sac7d-JDF3 fusion
EEE. Sso7D
FFF. Sso7D-Taq fusion
GGG. Sso7D-PfuWT fusion
HHH. Pfu-G387P/V93 R or E-Sso7D fusion
III. Pfu-G387P/V93 R or E-Sso7D fusion
JJJ. Pfu-D141A/E143A/V93 R or E-Sso7D fusion
KKK. KOD-Sso7D fusion
LLL. KOD-Sso7D fusion
MMM. Sso7D-*Thermococcus litoralis*-derived VENT (New England BioLabs) fusion
NNN. Sso7D-*Thermococcus litoralis*-derived VENT (New England BioLabs) fusion
OOO. Sso7D-Deep Vent$_R$™(exo-) (New England BioLabs) fusion
PPP. Sso7D-Deep Vent$_R$™(exo-) (New England BioLabs) fusion
QQQ. Sso7D-JDF3 fusion
RRR. Sso7D-JDF3 fusion FIG. 18: HhH motif Sequences (a) Motifs conserved between topo V, RecA, and leucine-responsive regulator signature sequences. Topo V amino acid region 236-298 made no hits in databases and is not shown. A short region between positions 677-695 connecting repeats G and H and the 19-aa residues at the end of the sequence is not shown for simplicity. Invariant residues are shown on blue backgrounds with white lettering. Conservative positions are highlighted on the yellow background. (b) Structure of topo V HhH motifs. Backgrounds of Lys-68 and Lys-72 of -pol and corresponding positions in C and G repeats of topo V are colored cyan and magenta, respectively. Secondary structures in a and b were predicted by using JPRED. Cylinders represent-helices, and lines between them (b) represent-hairpins. MkTpV, M. kandleri topo V; HTH asnC, the three-element fingerprint that provides a signature for the HTH motif of the asnC bacterial regulatory proteins; HTH SS, secondary structure of the HTH motif; A-L, topo V's HhH repeats; EcRuvA, *E. coli* RuvA protein, HsPolB, human polymerase; TaqPol, T. aquaticus polymerase I; HhH SS, secondary structure of HhH motifs. ALSCRIPT (Pargellis et al. (1988) J. Biol. Chem. 263, 7678-7685) was used to illustrate the alignments. Cited from Belova et al., 2001, Proc. Natl. Acad. Sci. USA, 98:6015).

FIG. 19: Additional sequences of the invention

FIG. 20: DNA and Amino acid sequence of wild type Pfu DNA polymerase

DETAILED DESCRIPTION

Figure 1:
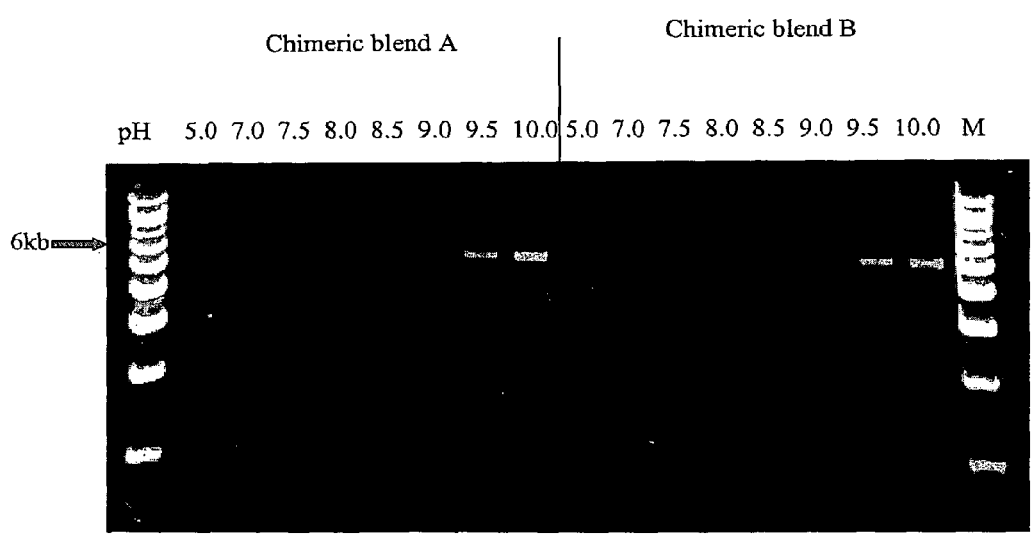
FIG. 1: 6 kb human βeta globin genomic DNA target amplified with a 15 second per kb extension time (1 minute 30 second total extension time). The PCR reaction buffer consisted of 1× cloned Pfu buffer using a 30 mM Tris pH gradient from 5.0 to 10.0. The chimeric DNA polymerase blend was composed of A; 0.25 U chimeric Pfu DNA polymerase and 2.5 U Pfu Turbo for a total of 2.75 U/reaction and B; 0.25 U chimeric Pfu DNA polymerase and 5.0 U Pfu Turbo for a total of 5.25 U/reaction. M is 1 kb DNA marker (Stratagene).

The present invention discloses DNA polymerase fusions for use in PCR, DNA sequencing and mutagenesis protocols at high pH. The invention allows for PCR reactions with shorter extension times that will facilitate PCR amplification of genomic DNA templates and improve the efficacy of long PCR.

I. DNA Polymerases According to the Invention

The invention provides for a DNA polymerase fusion. The DNA polymerase fusions, useful according to the invention, can be with or without 3'-5' exonuclease activity, i.e., proof-reading or non-proofreading, and are preferably thermostable. The invention provides for DNA polymerase fusions that harbor one or more mutations that modify one or more activities normally found in the wild-type DNA polymerase that is not a fusion, as defined herein.

Additional nucleic acid polymerases useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea: 1. Family B/pol I type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol I or pol II) can be derived from archaea with optimal growth temperatures that are similar to the desired assay temperatures.

Thermostable archaeal DNA polymerases are isolated from *Pyrococcus* species (furiosus, species GB-D, woesii, abysii, horikoshii), *Thermococcus* species (kodakaraensis KOD1, litoralis, species 9 degrees North-7, species JDF-3, gorgonarius), Pyrodictium occultum, and Archaeoglobus fulgidus. It is estimated that suitable archaea would exhibit maximal growth temperatures of >80-85° C. or optimal growth temperatures of >70-80° C. Appropriate PCR enzymes from the archaeal poll DNA polymerase group are commercially available, including Pfu (Stratagene), KOD (Toyobo), Pfx (Life Technologies, Inc.), *Thermococcus litoralis*-derived VENT® (New England BioLabs), Deep Vent$_R$™(exo-)(New England BioLabs), Tgo (Roche), and Pwo (Roche).

Additional archaea DNA polymerases related to those listed above are described in the following references: Archaea: A Laboratory Manual (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

The invention therefore provides for thermostable archaeal DNA polymerases of either Family B/pol I type or pol II type as well as mutants or derivatives thereof.

TABLE 1

| ACCESSION INFORMATION FOR CLONED FAMILY B POLYMERASES | |
|---|---|
| Vent *Thermococcus litoralis* | |
| ACCESSION | AAA72101 |
| PID | g348689 |
| VERSION | AAA72101.1 GI: 348689 |
| DBSOURCE | locus THCVDPE accession M74198.1 |
| THEST *THERMOCOCCUS* SP. (STRAIN TY) | |
| ACCESSION | O33845 |
| PID | g3913524 |
| VERSION | O33845 GI: 3913524 |
| DBSOURCE | swissprot: locus DPOL__THEST, accession O33845 |
| Pab *Pyrococcus abyssi* | |
| ACCESSION | P77916 |
| PID | g3913529 |
| VERSION | P77916 GI: 3913529 |
| DBSOURCE | swissprot: locus DPOL__PYRAB, accession P77916 |
| PYRHO *Pyrococcus horikoshii* | |
| ACCESSION | O59610 |
| PID | g3913526 |
| VERSION | O59610 GI: 3913526 |
| DBSOURCE | swissprot: locus DPOL__PYRHO, accession O59610 |
| PYRSE *PYROCOCCUS* SP. (STRAIN GE23) | |
| ACCESSION | P77932 |
| PID | g3913530 |
| VERSION | P77932 GI: 3913530 |
| DBSOURCE | swissprot: locus DPOL__PYRSE, accession P77932 |
| DeepVent *Pyrococcus* sp. | |
| ACCESSION | AAA67131 |
| PID | g436495 |
| VERSION | AAA67131.1 GI: 436495 |
| DBSOURCE | locus PSU00707 accession U00707.1 |
| Pfu *Pyrococcus furiosus* | |
| ACCESSION | P80061 |
| PID | g399403 |
| VERSION | P80061 GI: 399403 |
| DBSOURCE | swissprot: locus DPOL__PYRFU, accession P80061 |
| JDF-3 *Thermococcus* sp. | |
| Unpublished | |
| Baross gi|2097756|pat|US|5602011|12 Sequence 12 from patent U.S. Pat. No. 5602011 | |
| 9degN *THERMOCOCCUS* SP. (STRAIN 9ON-7). | |
| ACCESSION | Q56366 |
| PID | g3913540 |
| VERSION | Q56366 GI: 3913540 |
| DBSOURCE | swissprot: locus DPOL__THES9, accession Q56366 |
| KOD *Pyrococcus* sp. | |
| ACCESSION | BAA06142 |
| PID | g1620911 |
| VERSION | BAA06142.1 GI: 1620911 |
| DBSOURCE | locus PYWKODPOL accession D29671.1 |
| Tgo *Thermococcus gorgonarius*. | |
| ACCESSION | 4699806 |
| PID | g4699806 |
| VERSION | GI: 4699806 |
| DBSOURCE | pdb: chain 65, release Feb. 23, 1999 |
| THEFM *Thermococcus fumicolans* | |
| ACCESSION | P74918 |
| PID | g3913528 |

TABLE 1-continued

| ACCESSION INFORMATION FOR CLONED FAMILY B POLYMERASES | |
|---|---|
| VERSION | P74918 GI: 3913528 |
| DBSOURCE | swissprot: locus DPOL__THEFM, accession P74918 |
| METTH *Methanobacterium thermoautotrophicum* | |
| ACCESSION | O27276 |
| PID | g3913522 |
| VERSION | O27276 GI: 3913522 |
| DBSOURCE | swissprot: locus DPOL__METTH, accession O27276 |
| Metja *Methanococcus jannaschii* | |
| ACCESSION | Q58295 |
| PID | g3915679 |
| VERSION | Q58295 GI: 3915679 |
| DBSOURCE | swissprot: locus DPOL__METJA, accession Q58295 |
| POC *Pyrodictium occultum* | |
| ACCESSION | B56277 |
| PID | g1363344 |
| VERSION | B56277 GI: 1363344 |
| DBSOURCE | pir: locus B56277 |
| ApeI *Aeropyrum pernix* | |
| ACCESSION | BAA81109 |
| PID | g5105797 |
| VERSION | BAA81109.1 GI: 5105797 |
| DBSOURCE | locus AP000063 accession AP000063.1 |
| ARCFU *Archaeoglobus fulgidus* | |
| ACCESSION | O29753 |
| PID | g3122019 |
| VERSION | O29753 GI: 3122019 |
| DBSOURCE | swissprot: locus DPOL__ARCFU, accession O29753 |
| *Desulfurococcus* sp. Tok. | |
| ACCESSION | 6435708 |
| PID | g64357089 |
| VERSION | GT: 6435708 |
| DBSOURCE | pdb. chain 65, release Jun. 2, 1999 |

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity.

Suitable thermostable pol I DNA polymerases can be isolated from a variety of thermophilic eubacteria, including *Thermus* species and *Thermotoga maritima* such as *Thermus aquaticus* (Taq), *Thermus thermophilus* (Tth) and *Thermotoga maritima* (Tma UlTma).

Additional eubacteria related to those listed above are described in *Thermophilic Bacteria* (Kristjansson, J. K., ed.) CRC Press, Inc., Boca Raton, Fla., 1992.

The invention further provides for chimeric or non-chimeric DNA polymerases that are chemically modified according to methods disclosed in U.S. Pat. Nos. 5,677,152, 6,479,264 and 6,183,998, the contents of which are hereby incorporated by reference in their entirety.

II. Preparing Mutant DNA Polymerases

According to the invention, DNA polymerases can be generated from any DNA polymerase either wild-type or modified to contain one or more mutations, including but not limited to, one or more point mutations, N- and/or C-truncations, internal deletion or insertion that would cause the DNA polymerase to behave differently than the wild-type polymerase. DNA polymerase mutations useful to the invention include, but are not limited to, mutations that confer base analog or uracil insensitivity, increase fidelity, eliminate 3'-5' exonuclease activity or eliminate 5'-3' exonuclease activity or reduce polymerase activity. Specific examples of useful mutations or truncations include but are not limited to, V93R, K,E,D in Pfu DNA polymerase, which confer uracil insensitivity, D141A/E143A in Pfu DNA polymerase, which eliminates 3'-5' exonuclease activity, and the N-terminal truncation of Taq DNA polymerase to eliminate 5'-3' exonuclease activity(KlenTaq). Methods for generating DNA polymerase mutants are described below and other methods are known in the art.

Genetic Modification—Mutagenesis

Direct comparison of DNA polymerases from diverse organisms indicates that the domain structure of these enzymes is highly conserved and in many instances, it is possible to assign a particular function to a well-defined domain of the enzyme. For example, the six most conserved C-terminal regions, spanning approximately 340 amino acids, are located in the same linear arrangement and contain highly conserved motifs that form the metal and dNTP binding sites and the cleft for holding the DNA template and are therefore essential for the polymerization function. In another example, the three amino acid regions containing the critical residues in the E. coli DNA polymerase I involved in metal binding, single-stranded DNA binding, and catalysis of the 3'-5' exonuclease reaction are located in the amino-terminal half and in the same linear arrangement in several prokaryotic and eukaryotic DNA polymerases. The location of these conserved regions provides a useful model to direct genetic modifications for preparing mutant DNA polymerase with modified activities whilst conserving essential functions e.g. DNA polymerization and proofreading activity.

For example, a mutant DNA polymerase can be generated by genetic modification (e.g., by modifying the DNA sequence of a wild-type DNA polymerase). A number of methods are known in the art that permit the random as well as targeted mutation of DNA sequences (see for example, Ausubel et. al. *Short Protocols in Molecular Biology* (1995) $3^{rd}$ Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition mutant DNA polymerases may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of non-chimeric mutant DNA polymerases is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 µM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of I min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis, which will result in a panel of mutants bearing one or more randomly situated mutations, exist in the art. Such a panel of mutants may then be screened for improved activity such as those exhibiting properties including but not limited to reduced DNA polymerization activity, 3'-5' exonuclease deficiency, and/or reduced uracil detection activity relative to the wild-type polymerase (e.g., by measuring the incorporation of 10 nmoles of dNTPs into polymeric form in 30 minutes in the presence of 200 µM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the invention provides for blends of two or more DNA polymerases comprising one or more DNA polymerase fusions of the invention with or without an additive as described herein.

In a preferred embodiment, the invention provides for blends of two or more DNA polymerases comprising one or more DNA polymerase fusions and one or more mutant DNA polymerases, at least one of which is derived from Pfu DNA polymerase.

In another preferred embodiment, the invention provides for blends of two or more DNA polymerases comprising one or more DNA polymerase fusions and one or more non-chimeric DNA polymerases, at least one of which is derived from TaqDNA polymerase.

In another preferred embodiment, the invention provides for a high pH buffer used in PCR amplification reactions with a fusion DNA polymerase or with a blend of a fusion DNA polymerase and a wild type, mutant, or chemically modified DNA polymerase and/or a wild type, mutant, or chemically modified DNA polymerase formulation (see Example 2). As used herein, a "DNA polymerase" formulation is a blend of two or more DNA polymerases, for example, 2,3,4,5 or more, with or without an additive as defined herein.

A person of average skill in the art having the benefit of this disclosure will recognize that DNA polymerases derived from other exo+ DNA polymerases including *Thermococcus litoralis*-derived VENT® (New England BioLabs) DNA polymerase, JDF-3 DNA polymerase, Tgo DNA polymerase, KOD DNA polymerase and the like may be suitably used in the subject compositions.

The amino acid and DNA coding sequence of a wild-type Pfu DNA polymerase are shown in FIG. 20 (Genbank Accession #P80061). A detailed description of the structure and function of Pfu DNA polymerase can be found, among other places in U.S. Pat. Nos. 5,948,663; 5,866,395; 5,545,552; 5,556,772, all of which are hereby incorporated in their entirety by reference.

The enzyme of the subject composition may comprise DNA polymerases that have not yet been isolated.

The invention provides for blends of two or more DNA polymerases comprising one or more DNA polymerase fusion and one or more mutant or wild type DNA polymerase that is not a fusion.

The invention provides for blends of two or more DNA polymerases comprising one or more DNA polymerase fusions and one or more non-fusion mutant Pfu DNA polymerases containing one or more mutations that reduce base analog detection activity as disclosed in the pending U.S. patent application Ser. No. 10/280,962 (Sorge et al.; filed: Oct. 25, 2002) and the pending U.S. patent application Ser. No. 10/298,680 (Sorge et al.; filed Nov. 18, 2002), the contents of which are hereby incorporated in their entirety.

In a preferred embodiment, the blend of two or more DNA polymerases comprises one or more DNA polymerase fusion and one or more non-fusion mutant Pfu DNA polymerase of the invention containing a Valine to Arginine, Valine to Glutamic acid, Valine to Lysine, Valine to Aspartic Acid or Valine to Asparagine substitution at amino acid position 93.

The invention further provides for a blend of two or more DNA polymerases comprising one or more DNA polymerase fusions and one or more non-fusion mutant archaeal DNA polymerases with reduced base analog detection activity that contain a Valine to Arginine, Valine to Glutamic acid, Valine to Lysine, Valine to Aspartic Acid or Valine to Asparagine substitution at amino acid position 93.

A Pfu DNA polymerase mutant with Reduced Uracil Detection can be prepared as follows. Mutations are introduced into Pfu DNA polymerase that are likely to reduce uracil detection, while having minimal effects on polymerase or proofreading activity. The DNA template used for mutagenesis contains the Pfu pol gene, cloned into pBluescript (pF72 clone described in U.S. Pat. No. 5,489,523). Point mutations are introduced using the QuikChange or the QuikChange Multi Site-Directed Mutagenesis Kit (Stratagene). With the QuikChange kit, point mutations are introduced using a pair of mutagenic primers (V93E, H, K, R, and N). With the QuikChange Multi kit, specific point mutations are introduced by incorporating one phosphorylated mutagenic primer or by selecting random mutants from a library of Pfu V93 variants, created by incorporating a degenerate codon (V93G and L). Clones are sequenced to identify the incorporated mutations.

Valine 93 in Pfu DNA polymerase was substituted with Glycine (G), asparagine (N), arginine [R], glutamic acid (E), histidine (H), and leucine (L) using the QuikChange primer sequences listed in FIG. 10.

Assessment of the activity of a mutant chimeric or non-chimeric Pfu DNA polymerase is determined as follows.

Partially-purified Pfu mutant preparations (heat-treated bacterial extracts) were assayed for dUTP incorporation during PCR. In this example, a 2.3 kb fragment containing the Pfu poi gene was from plasmid DNA using PCR primers: (FPfuLIC) 5'-gACgACgACAAgATgATTTTAgATgTggAT-3' (SEQ ID NO: 1) and (RPfuLIC) 5'-ggAACAAgAC- CCgTCTAggATTTTTTAATg-3' (SEQ ID NO: 2). Amplification reactions consisted of 1× cloned Pfu PCR buffer, 7 ng plasmid DNA, 100 ng of each primer, 2.5 U of Pfu mutant (or wild type Pfu), and 200 μM each dGTP, dCTP, and dATP. To assess relative dUTP incorporation, various amounts of dUTP (0-400 μM) and/or TTP (0-200 μM) were added to the PCR reaction cocktail. The amplification reactions were cycled as described in example 6.

polymerases with reduced uracil detection activity that contain one or mutations that reduce DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110

| Target size (kb) | Target gene | Cycling Parameters |
|---|---|---|
| 0.9 | Hα1AT | (1 cycle) 95° C. 2 min<br>(30 cycles) 95° C. 5 sec, 58° C. 5 sec, 72° C. 5 sec.<br>(1 cycle) 72° C. 2 min |
| 2.6 | Hα1AT | (1 cycle) 95° C. 2 min<br>(30 cycles) 95° C. 20 sec, 58° C. 20 sec, 72° C. 5 sec<br>or 1 min 30 sec. (1 cycle) 72° C. 3 min |
| 6 | β globin | (1 cycle) 95° C. 2 min<br>(30 cycles)95° C. 30 sec, 58° C. 30 sec, 72° C. 1 min<br>or 1 min 30 sec. (1 cycle) 72° C. 5 min |
| 19 | β globin | (one cycle) 92° C. 2 min<br>(10 cycles) 92° C. 10 sec, 63° C. 30 sec, 68° C. 9.5 min<br>(20 cycles) 92° C. 10 sec, 63° C. 30 sec, 68° C. 9.5 min<br>(plus 10 sec/cycle) (one cycle) 68° C. 7 min |

| Primer size (bp) | Target | Primer sequence |
|---|---|---|
| 30 | Hα1AT 0.9 kb | F-5'-AGA.GCT.TGA.GGA.GAG.CAG.GAA.AGG.TGG.AAC-3' (SEQ ID NO. 3) |
| 30 | Hα1AT 0.9 kb | R-5'-GGG.AGG.GGA.GGT.ACA.GGG.TTG.AGG.CTA.GTG-3' (SEQ ID NO. 4) |
| 30 | Hα1AT 2.6 kb | F-5'-AGA.GCT.TGA.GGA.GAG.CAG.GAA.AGG.TGG.AAC-3' (SEQ ID NO. 114) |
| 24 | Hα1AT 2.6 kb | R-5'-TGC.AGA.GCG.ATT.ATT.CAG.GAA.TGC-3' (SEQ ID NO. 115) |
| 30 | β globin 6.0 kb | F-5'-ACA.AGG.GCT.ACT.GGT.TGC.CGA.TTT.TTA.TTG-3' (SEQ ID NO. 116) |
| 27 | β globin 6.0 kb | R-5'-GGG.ACT.GGC.CTC.AGA.GGA.AAC.TTC.AGG-3' (SEQ ID NO. 117) |
| 30 | β globin 19 kb | F-5'-ACA.AGG.GCT.ACT.GGT.TGC.CGA.TTT.TTA.TTG-3' (SEQ ID NO. 118) |
| 28 | β globin 19 kb | R-5'-CCT.GCA.TTT.GTG.GGG.TGA.ATT.CCT.TGC.C-3' (SEQ ID NO. 119) |

The invention further provides for a blend of two or more DNA polymerases comprising one or more DNA polymerase fusion and one or more non-fusion mutant archaeal DNA polymerases with a G387P mutant archaeal DNA polymerase with reduced DNA polymerization activity.

The invention further provides for a blend of two or more DNA polymerases comprising one or more DNA polymerase fusions and one or more non-fusion V93 mutant Pfu DNA polymerases with reduced uracil detection activity that contain one or more additional mutations that modulates one or more additional activities of V93 Pfu DNA polymerases, e.g., DNA polymerization activity or 3'-5' exonuclease activity. In one embodiment, the non-fusion V93 mutant Pfu DNA polymerase according to the invention contains one or more mutations that renders the DNA polymerase 3'-5' exonuclease deficient. In another embodiment, the non-fusion V93 mutant Pfu DNA polymerase according to the invention contains one or more mutations that reduce the DNA polymerization activity of the non-fusion V93 Pfu DNA polymerase.

The invention further provides for a blend of two or more DNA polymerases comprising one or more DNA polymerase fusions and one or more non-fusion V93 mutant Pfu DNA (Hogrefe et al.; filed Aug. 23, 2002), the contents of which are hereby incorporated in their entirety.

In one embodiment, the invention provides for a V93R/G387P, V93E/G387P, V93D/G387P, V93K/G387P or V93N/G387P double mutant Pfu DNA polymerase with reduced DNA polymerization activity and reduced uracil detection activity.

The invention further provides for V93R, V93E, V93D, V93K or V93N mutant Pfu DNA polymerases with reduced uracil detection activity containing one or more mutations that reduce or eliminate 3'-5' exonuclease activity as disclosed in the pending U.S. patent application Ser. No. 09/698,341 (Sorge et al; filed Oct. 27, 2000).

In one embodiment, the invention provides for a non-fusion V93R/D141A/E143A triple mutant Pfu DNA polymerase with reduced 3'-5' exonuclease activity and reduced uracil detection activity.

The invention further provides for one or more Pfu DNA polymerases of the invention comprising any combination of one or more mutations that may increase or eliminate base analog detection activity of an archaeal DNA polymerase.

DNA polymerases containing additional mutations are generated by site directed mutagenesis using the DNA polymerases of the invention as a template DNA molecule, for example, the Pfu DNA polymerase or Pfu V93R cDNA, according to methods that are well known in the art and are described herein.

The invention contemplates DNA polymerase fusions wherein the DNA polymerase domain of the fusion comprises any of the mutations described herein and known in the art.

Methods used to generate Pfu DNA polymerases with reduced DNA polymerization activity of the invention are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002); and the pending U.S. patent application Ser. No. 10/324,846 (Borns et al.; filed Dec. 20, 2002), the contents of which are hereby incorporated in their entirety.

Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000). A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into a DNA polymerase of the invention including for example, the non-chimeric V93 Pfu DNA polymerase cDNA, as disclosed in the pending U.S. patent application Ser. No. 09/698,341, using established site-directed mutagenesis methodology.

Three 3' to 5' exonuclease motifs have been identified, and mutations in these regions have also been shown to abolish 3' to 5' exonuclease activity in Klenow, φ29, T4, T7, and *Thermococcus litoralis*-derived VENT® (New England BioLabs) DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ *Thermococcus litoralis*-derived VENT® (New England BioLabs), exo⁻ Deep Vent$_R$™(exo-) (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the non chimeric DNA polymerase component in the blend of the invention disclosed herein.

In accordance with the invention, in addition to the mutations described above, one or more additional mutations or modifications (or combinations thereof) may be made to the polymerases of interest. Mutations or modifications of particular interest include those modifications of mutations which (1) eliminate or reduce 5' to 3' exonuclease activity; and (2) reduce discrimination of dideoxynucleotides (that is, increase incorporation of dideoxynucleotides). The 5'-3' exonuclease activity of the polymerases can be reduced or eliminated by mutating the polymerase gene or by deleting the 5' to 3' exonuclease domain. Such mutations include point mutations, frame shift mutations, deletions, and insertions. Preferably, the region of the gene encoding an DNA polymerase activity is deleted using techniques well known in the art. For example, any one of six conserved amino acids that are associated with the 5'-3' exonuclease activity can be mutated. Examples of these conserved amino acids with respect to Taq DNA polymerase include $Asp^{18}$, $Glu^{117}$, $Asp^{119}$, $Asp^{120}$, $Asp^{142}$, and $Asp^{144}$.

Polymerase mutants can also be made to render the polymerase non-discriminating against non-natural nucleotides such as dideoxynucleotides (see U.S. Pat. No. 5,614,365). Changes within the O-helix, such as other point mutations, deletions, and insertions, can be made to render the polymerase non-discriminating. By way of example, one Tne DNA polymerase mutant having this property substitutes a non-natural amino acid such as Tyr for Phe730 in the O-helix.

Typically, the 5'-3' exonuclease activity, 3' to 5' exonuclease activity, discriminatory activity and fidelity can be affected by substitution of amino acids typically which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged). Glu may be changed to Asp, Ala, Val Leu, Ile, Pro, Met, Phe, Trp, Gly, Ser, Thr, Cys, Tyr, Asn or Gln.

Preferably, oligonucleotide directed mutagenesis is used to create the mutant polymerases which allows for all possible classes of base pair changes at any determined site along the encoding DNA molecule. In general, this technique involves annealing a oligonucleotide complementary (except for one or more mismatches) to a single stranded nucleotide sequence coding for the DNA polymerase of interest. The mismatched oligonucleotide is then extended by DNA polymerase, generating a double stranded DNA molecule which contains the desired change in sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

In one embodiment, the non-chimeric mutant Pfu DNA polymerases are expressed and purified as described in U.S. Pat. No. 5,489,523, hereby incorporated by reference in its entirety.

III. Preparing DNA Polymerase Fusions

The DNA polymerase fusion of the invention has at least two polypeptides covalently linked, in which one polypeptide comes from one protein sequence or domain and the other polypeptide comes from another protein sequence or domain. According to the invention, at least one of the domains of the DNA polymerase fusion originates from a wild type or mutant DNA polymerase of the invention. The polypeptides can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a DNA polymerase of the invention. The polypeptides of the fusion protein can be in any order. The term "fusion polypeptide" or "chimera" also refers to conservatively modified variants, polymorphic variants, alleles, mutant, subsequences and interspecies homologues of the polypeptides that make up the fusion protein. Fusion proteins may be produced by covalently linking a chain of amino acids from one protein sequence to a chain of amino acids from another protein sequence, e.g., by preparing a recombinant polynucleotide contiguously encoding the fusion protein. Fusion proteins can comprise 2, 3, 4 or more different chains of amino acids from the same or different species. The different chains of amino acids in-a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In a preferred embodiment, the DNA polymerase fusion, useful according to the invention, is a thermostable DNA polymerase with reduced DNA polymerization activity or with reduced uracil detection activity. In addition, the DNA polymerase fusion of the invention may or may not have 3'-5' exonuclease activity.

In one embodiment, the component fused to the DNA polymerase is any non-native protein or protein domain fused to the DNA polymerase at the N- or C-terminus or at any internal position. The contribution to the activity of the DNA polymerase from the DNA polymerase fusion partner (that is the second amino acid sequence of the fusion as described herein) includes, but is not limited to, an increase in one or more of the following DNA polymerase activities: processivity, DNA binding, strand displacement activity, polymerase activity, nucleotide binding and recognition, proofreading, fidelity, and salt resistance and/or decreased DNA polymerase activity at room temperature.

A DNA polymerase fusion can be prepared by molecular biology techniques for preparing fusion proteins well known in the art.

Using techniques well known in the art (Sambrook et al., (1989) in: Molecular Cloning, A Laboratory Manual (2nd Ed.), Cold Spring Harbor Laboratory Press, Cold Spring Harbor, N.Y.), a protein domain of a DNA polymerase can be substituted with a domain from another polymerase which has the desired activity. Methods of preparing a DNA polymerase fusions of the invention are also described in WO 01/92501 Al and Pavlov et al., 2002, Proc. Natl. Acad. Sci. USA, 99:13510-13515, which are herein incorporated in its entirety.

In one embodiment, the DNA polymerase fusion of the invention comprises a protein domain of one wild type DNA polymerase of the invention that is fused to a protein domain of a different DNA polymerase of the invention containing one or more mutations.

In another preferred embodiment, the DNA polymerase fusion of the invention comprises all of or a part of Pfu or Taq DNA polymerase.

In one embodiment, the DNA polymerase fusion of the invention comprises a Pfu DNA polymerase, or part thereof, having reduced DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated by reference in their entirety.

In one embodiment, the DNA polymerase fusion of the invention comprises a Pfu DNA polymerase, or part thereof, having one or mutations that reduce base analog detection activity as disclosed in the pending U.S. patent application Ser. No. 10/280,962 (Hogrefe, et al.; filed: Oct. 25, 2002) and the pending U.S. patent application Ser. No. 10/298,680 (Hogrefe et al.; filed Nov. 18, 2002) and the pending U.S. patent application Ser. No. 10/324,846 (Borns et al.; filed Dec. 20, 2002), the contents of which are hereby incorporated by reference in their entirety.

In one embodiment, the DNA polymerase fusion of the invention comprises a protein domain of one mutant DNA polymerase of the invention that is fused to a protein domain of a different DNA polymerase of the invention containing one or more mutations.

In one embodiment, the DNA polymerase fusion of the invention comprises a protein domain of one DNA polymerase that replaces an analogous protein domain within another DNA polymerase of the invention. As used herein, two protein domains are said to be "analogous" if they share in common a domain that confers at least one DNA polymerase activity such as processivity, DNA binding, strand displacement activity, nucleotide binding and recognition, proofreading, e.g. 3'-5' exonuclease activity, fidelity, e.g. 5'-3' exonuclease activity, or salt resistance.

In one embodiment, the DNA polymerase fusion of the invention comprises the helix-hairpin-helix DNA binding motifs from DNA topoisomerase V that increases processivity, salt resistance and thermostability as described in Pavlov et al., 2002, Proc. Natl. Acad. Sci USA, 99:13510-13515.

In another embodiment, the DNA polymerase fusion of the invention comprises the thioredoxin binding domain that enhances the processivity of the DNA polymerase fusion as described in WO 97/29209.

In another embodiment, the DNA polymerase fusion of the invention comprises the archaeal PCNA binding domain fused to Taq DNA polymerase or a related eubacterial DNA polymerase. Addition of PCNA to the PCR reaction containing the PCNA binding domain-Taq DNA polymerase chimera results in enhanced processivity of the DNA polymerase fusion and higher yields of PCR amplified DNA (Motz, M., et al., J. Biol. Chem. May 3, 2002; 277 (18); 16179-88).

In another embodiment, the DNA polymerase fusion of the invention comprises the sequence non-specific DNA binding protein Sso7d or Sac7d from (for example, from *Sulfolobus sulfataricus* fused to a DNA polymerase of the invention. The fusion of the DNA binding protein Sso7d or Sac7d to DNA polymerase fusions of the invention, such as Pfu or Taq DNA polymerase, greatly enhances the processivity of these DNA polymerases as disclosed in WO 01/92501 A1 which is hereby incorporated by reference in its entirety.

The invention contemplates DNA polymerase fusions wherein any of the HhH domains known in the art (see Belova et al., 2001, Proc. Natl. Acad. Sci. USA, 98:6015 and FIG. 18) are fused to any of the wildtype or mutant DNA polymerases included herein. The HhH can be fused directly to the N or C terminus or at any internal site of any of the wildtype or mutant DNA polymerases included herein. One of more (for example the H-L or E-L) HhH domains can be used to create a DNA polymerase fusion.

In another embodiment, the DNA polymerase fusion of the invention comprises a Pfu DNA polymerase, or part thereof, having reduced 3'-5' exonuclease activity. Methods used to generate 3'-5' exonuclease deficient JDF-3 DNA polymerases including the D141 A and E143A mutations are disclosed in the pending U.S. patent application Ser. No. 09/698,341 (Sorge et al; filed Oct. 27, 2000), the contents of which are hereby incorporated by reference in their entirety. A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into any one of the DNA polymerase fusions of the invention i.e. a DNA polymerase fusion with reduced base analog detection activity or reduced DNA polymerization activity as disclosed herein.

In another embodiment, the DNA polymerase fusion of the invention comprises a DNA polymerase, or part thereof, that lacks both 5' to 3' and 3' to 5, exonuclease activities including, but not limited to, Sequenase (exo$^{31}$ T7; USB), Pfu exo$^-$ (Stratagene), exo$^-$ Vent (New England BioLabs), exo$^-$ Deep Vent$_R$™(exo-) (New England BioLabs), exo$^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the chimeric DNA polymerase fusion of the invention disclosed herein.

In another embodiment, the DNA polymerase fusion of the invention comprises a thermostable DNA polymerase, or part thereof, that has enhanced 3' to 5' exonuclease activity that confers enhanced fidelity to the DNA polymerase fusion of the invention as disclosed in U.S. Pat. No. 5,795,762, the contents of which are hereby incorporated by reference in their entirety.

IV. Expression of Wild-Type or Mutant Enzymes According to the Invention

Methods known in the art may be applied to express and isolate DNA polymerases of the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, E. coli strain BL-21 is commonly used for expression of exogenous proteins since it is protease deficient relative to other strains of E. coli. BL-21 strains bearing an inducible T7 RNA polymerase gene include WJ56 and ER2566 (Gardner & Jack, 1999, supra). For situations in which codon usage for the particular polymerase gene differs from that normally seen in E. coli genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a DNA polymerase of the invention. For example, the method of Lawyer et al. (1993, PCR Meth. & App. 2: 275) is well suited for the isolation of DNA polymerases expressed in E. coli, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerases may be isolated by an ammonium sulfate fractionation, followed by Q Sepharose and DNA cellulose columns, or by adsorption of contaminants on a HiTrap Q column, followed by gradient elution from a HiTrap heparin column.

V. Blends of Fusion and Non-Fusion DNA Polymerases

A DNA polymerase fusion blend formulation, according to the invention, can include at least one DNA polymerase fusion and: (1) a proofreading or a non-proofreading non-chimeric DNA polymerase; or (2) a proofreading plus non-proofreading, non-proofreading plus non-proofreading or a proofreading plus proofreading non-fusion DNA polymerase blend, e.g., Pfu, Taq, Pfu/Taq, Pfu/exo-Pfu, Taq/exo-Pfu, Pfu/JDF3, or any of these combinations with pol-Pfu (Pfu G387P). The ratio of DNA polymerase enzymes in a "blend" comprising one fusion and one non-fusion polymerase is in the range of 1:1-1:5-5:1, or 1:1-1:10-10:1, or 1:1-1:25-25:1 or 1:1-1:100-100:1. For embodiments wherein a "blend" comprises one DNA polymerase fusion and two non-fusion polymerases the ratio of the first non-fusion DNA polymerase to the second non-fusion DNA polymerase is in the range of 1:1-1:5-5:1, or 1:1-1:10-10:1, or 1:1-1:25-25:1 or 1:1-1:100-100:1. The formulation of the invention has no limitations on the ratios of the individual components.

In one embodiment, the blend formulation of the invention is 2.5 U Pfu/0.25 U chimeric Pfu.

The wild type DNA polymerase that is blended with the DNA polymerase fusion can be any native or cloned DNA polymerase having native levels of polymerase activity and proofreading activity and preferably is thermostable such as Pfu or Taq. The DNA polymerase fusion and wild type DNA polymerase are blended in the ratio range described above and can be mixed with any replication accessory factor or PCR enhancing additives, e.g., Pfu dUTPase (PEF), PCNA, RPA, ssb, antibodies, DMSO, betaine, or 3'-5' exonuclease (e.g., Pfu G387P).

The mutant DNA polymerase that is blended with the DNA polymerase fusion of the invention is any DNA polymerase having introduced mutations and/or truncations that generates a DNA polymerase with an activity that is distinct from a wild type DNA polymerase. The mutant could have any amount of polymerase and/or proofreading activity. Specific examples of useful mutations or truncations include, but are not limited to, V93R,K,E, or D in Pfu DNA polymerase, which confer uracil insensitivity, D141A/E143A in Pfu DNA polymerase, which eliminates 3'-5' exonuclease activity, and the N-terminal truncation of Taq that eliminates 5'-3' exonuclease activity (KlenTaq).

The invention further provides for mutant V93R, V93E, V93D, V93K or V93N non-fusion Pfu DNA polymerases that contain one or more additional mutations with improved reverse transcriptase activity.

The invention provides for a blend wherein the ratio of DNA polymerase fusion to non-fusion DNA polymerase is in the ratio range of 1:1-1:5-5:1, or 1:1-1:10-10:1, or 1:1-1:25-25:1 or 1:1-1:100-100:1. The invention contemplates a blend comprising a mixture of a DNA polymerase fusion and more than one non-fusion DNA polymerase. For a blend comprising a DNA polymerase fusion in combination with two non-fusion DNA polymerases, the ratio range of the first non-fusion DNA polymerases to the second non-fusion DNA polymerase is 1:1-1:5-5:1, or 1:1-1:10-10:1, or 1:1-1:25-25:1 or 1:1-1:100-100:1.

VI. Applications of the Subject Invention

The invention provides for methods of using polymerase fusions of the invention at high pH as defined herein.

A high pH buffer useful according to the invention includes but is not limited to a standard PCR reaction buffer like cloned Pfu reaction buffer (described in Example 3) wherein the buffering component is at a high pH (i.e. 9.3-14). The buffering component used in the following examples is 30 mM Tris [Tris(hydroxymethyl)aminomethane] at a pH of 10.0 or 11.8. The pH of the buffering component in standard PCR reaction buffers is from 8.3-8.8. The buffering component is used at a concentration from 1 mM to 1M in the final PCR reaction and may be any pH from 9.5-14. The buffering component of the present invention includes, but is not limited to, Tris, Tricine, bicine, Bis-Tris, CAPS, EPPS, HEPES, MES, MOPS, PIPES, TAPS and TES.

In one aspect, the invention provides a method for DNA synthesis using the compositions of the subject invention. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application on Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

The enzymes provided herein are also useful for dUTP/UNG cleanup methods that require PCR enzymes that incorporate dUTP (Longo et al., Supra).

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported that PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increase non-specific annealing and produce undesirable PCR products (gives multiple bands in gel). When non-specific amplification occurs, the $Mg^{2+}$ concentration may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication 2<sup>nd</sup> edition,* supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 μM to 2 mM each is suitable, and 100-600 μM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 μM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 μM) may therefore reduce error rate. PCR reaction for amplifying larger size template may need more dNTPs.

The PCR reaction buffer is a standard PCR reaction buffer like cloned Pfu reaction buffer but with a buffering component at a high pH (i.e. 9.1-14). One suitable buffering component is 30 mM Tris [Tris(hydroxymethyl)aminomethane] at a pH of 10.0 or 11.8. The pH of the buffering component in standard PCR reaction buffers is from 8.3-8.8. The buffering component is used at a concentration from 1 mM to 1M in the final PCR reaction at a pH from 9.1-14. A buffering component useful in this invention includes, but is not limited to, Tris, Tricine, bicine, Bis-Tris, CAPS, EPPS, HEPES, MES, MOPS, PIPES, TAPS and TES.

PCR is a very powerful tool for DNA amplification and therefore very little template DNA is needed. However, in some embodiments, to reduce the likelihood of error, a higher DNA concentration may be used, though too many templates may increase the amount of contaminants and reduce efficiency.

Usually, up to 3 μM of primers may be used, but high primer to template ratio can result in non-specific amplification and primer-dimer formation. Therefore it is usually necessary to check primer sequences to avoid primer-dimer formation.

The invention provides for Pfu V93R, V93E, V93K, V93D, or V93N fusion or non-fusion DNA polymerases with reduced uracil detection activity that enhance PCR of GC rich DNA templates by minimizing the effect of cytosine deamination in the template and by allowing the use of higher denaturation times and denaturation temperatures.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycles can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10::93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reactions. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO)

may also be used. Test PCR reactions may be performed to determine optimum concentrations of each additive mentioned above.

The invention provides for additives including, but not limited to antibodies (for hot start PCR) and ssb (single strand DNA binding protein; higher specificity). The invention also contemplates mutant archael DNA polymerases in combination with accessory factors, for example as described in U.S. Pat. No. 6,333,158, and WO 01/09347 A2, hereby incorporated by reference in its entirety.

Various specific PCR amplification applications are available in the art (for reviews, see for example, Erlich, 1999, *Rev Immunogenet.*, 1:127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications including, but not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) PCR for amplification of regions flanking a known sequence; (in this method, DNA is digested, the desired fragment is circularized by ligation, then PCR using primer complementary to the known sequence extending outwards; v) AP-PCR (arbitrary primed)/RAPD (random amplified polymorphic DNA); these methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cell. It may also be used to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be used as a control to verify the quality of PCR; x) Q/C-PCR (Quantitative comparative) which uses an internal control DNA sequence (but of a different size) which competes with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention.

B. Application in Direct Cloning of PCR Amplified Product

It is understood that the amplified product produced using the subject enzyme can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) disclose methods for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without a need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directly ligated into vectors containing single 3'dT overhangs. Pfu DNA polymerase, on the other hand, lacks terminal transferase activity, and thus produces blunt-ended PCR products that are efficiently cloned into blunt-ended vectors. The invention also encompasses an Easy A composition that contains of a blend of Taq (5 U/ul), recombinant PEF (4 U/ul), and Pfu G387P(40 ng/ul) as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety. With cloned archaeal DNA polymerase with reduced base analog detection activity at 2.5 U/ul i.e. ~20-50 ng per ul, the ratio of Taq:Pfu is preferably 1:1 or more preferably 2:1 or more.

In one embodiment, the invention provides for a PCR product, generated in the presence of a DNA polymerase fusion at high pH, that is subsequently incubated with Taq DNA polymerase in the presence of dATP at 72° C. for 15-30 minutes. Addition of 3'-dAMP to the ends of the amplified DNA product then permits cloning into TA cloning vectors according to methods that are well known to a person skilled in the art.

C. Application in DNA Sequencing

The invention further provides for dideoxynucleotide DNA sequencing methods using thermostable DNA polymerase fusions to catalyze the primer extension reactions at high pH. Methods for dideoxynucleotide DNA sequencing are well known in the art and are disclosed in U.S. Pat. Nos. 5,075,216, 4,795,699 and 5,885,813, the contents of which are hereby incorporated in their entirety. The invention encompasses DNA polymerase fusions comprising exo-Pfu (for example D141A/E143A double mutant) or the JDF3 P410L/A485T mutant with reduced ddNTP discrimination.

D. Application in Mutagenesis

The DNA polymerase fusions of the invention also provide enhanced efficacy for PCR-based or linear amplification-based mutagenesis. The invention therefore provides for DNA polymerase fusions for site-directed mutagenesis at high pH and their incorporation into commercially available kits, for example, QuikChange Site-directed Mutagenesis, QuikChange Multi-Site-Directed Mutagenesis (Stratagene). Site-directed mutagenesis methods and reagents are disclosed in the pending U.S. patent application Ser. No. 10/198, 449 (Hogrefe et al.; filed Jul. 18, 2002), the contents of which are hereby incorporated in its entirety. The invention also encompasses Mutazyme (exo⁻Pfu in combination with PEF, GeneMorph Kit). The GeneMorph kits are disclosed in the pending U.S. patent application Ser. No. 10/154,206 (filed May 23, 2002), the contents of which are hereby incorporated in its entirety.

The DNA polymerase fusions described herein are used in the same way as conventional DNA polymerase/DNA polymerase formulations and can be used at high pH in any primer extension application, including PCR, to produce high product yields with shortened extension times. Amplification of genomic targets, in particular, which typically require extension times of 1-2 min./kb and take hours to amplify, is greatly facilitated by the disclosed invention because extension times are reduced to 5-30 sec./kb, or shorter, with the DNA polymerase fusions described herein (see Example 3).

Other applications of the present invention include RT-PCR, site-directed mutagenesis and random mutagenesis. The DNA polymerase fusions of the invention used in all of these applications increase length capability, shorten reaction times and greatly improve overall performance in all standard protocols (see Example 3).

A DNA polymerase fusion with proofreading activity (3'-5' exonuclease activity) is useful for high fidelity PCR: A DNA polymerase fusion that is useful for high fidelity PCR will demonstrate an increase of $\geq 10\%$ 3'-5' exonuclease activity and PCR fidelity, and accuracy of incorporation as compared to a corresponding non-fusion polymerase (with 3'-5' exonuclease activity) alone using a complex genomic and/or plasmid template.

A DNA polymerase fusion with higher misinsertion and/or mispair extension frequency is useful for PCR random mutagenesis. A DNA polymerase fusion that is useful for PCR random mutagenesis preferably demonstrates an increase of $\geq 10\%$ of the mutagenic properties or changes in mutational spectra as compared to a corresponding non-fusion polymerase for plasmid template.

By "mutagenic properties" is meant mutation rate and the overall number of mutation instances per kb of amplicon.

By "mutational spectra" is meant the number of transition and transversion mutations. "Mutational spectra" also encompasses the ratio of transitions to transversions. Preferably the ratio of transitions to transversion is 1:1.

All of the DNA polymerase fusions contemplated herein are useful for PCR and RT-PCR:

DNA polymerase fusions with proofreading activity that are used for PCR amplification and linear amplification are useful for Site Directed Mutagenesis.

DNA polymerase fusions that lack 3'-5' exonuclease activity are useful for sequencing applications. A DNA polymerase fusion useful for sequencing will demonstrate one or more of shorter extension times, higher efficiency, higher specificity, higher fidelity (more accurate incorporation), and higher processivity (an increase of $\geq 10\%$ above the non-chimeric component of the blend for sequencing template). DNA polymerase fusions that lack 3'-5' exonuclease activity are also useful for random mutagenesis.

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers (preferably a high pH buffer), instructions, and controls. Kits may include containers of reagents mixed together in suitable proportions for performing the methods in accordance with the invention. Reagent containers preferably contain reagents in unit quantities that obviate measuring steps when performing the subject methods.

The invention contemplates a kit comprising a DNA polymerase fusion and a high pH buffer according to the invention, PCR enhancing reagents and reagents for PCR amplification, DNA sequencing or mutagenesis.

A kit for sequencing DNA will comprise a number of container means. A first container means may, for example, comprise a substantially purified sample of the polymerases of the invention. A second container means may comprise one or a number of types of nucleotides needed to synthesize a DNA molecule complementary to DNA template. A third container means may comprise one or a number of different types of terminators (such as dideoxynucleoside triphosphates). A fourth container means may comprise pyrophosphatase. In addition to the above container means, additional container means may be included in the kit which comprise one or a number of primers and/or a suitable sequencing buffer, preferably a high pH buffer.

A kit used for amplifying or synthesis of nucleic acids will comprise, for example, a first container means comprising a substantially pure polymerase fusion of the invention and one or a number of additional container means which comprise a single type of nucleotide or mixtures of nucleotides, and/or a high pH buffer.

Various primers may be included in a kit as well as a suitable amplification or synthesis buffers.

When desired, the kit of the present invention may also include container means which comprise detectably labeled nucleotides which may be used during the synthesis or sequencing of a nucleic acid molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLES

Example 1

Construction of DNA Polymerase Fusions

A chimera is made by combining the domains of different DNA polymerases, for example, the insertion of the thioredoxin processivity factor binding domain of bacteriophage T7 DNA polymerase into the homologous site in *E. coli* DNA polymerase I. This facilitates a substantial increase in the processivity of the chimeric *E. coli* DNA polymerase I in the presence of thioredoxin. (Bedford, E., et al., PNAS, USA vol. 94, pp. 479-484, January 1997 Biochem.). Another illustration of this strategy is the addition of an archaeal PCNA binding domain to Taq DNA polymerase. PCNA is then added to the PCR reaction with the Taq chimera to enhance processivity and generate higher yields (Motz, M., et al., J. Biol. Chem. 2002 May 3; 277 (18); 16179-88).

A chimeric DNA polymerase is also generated by combining elements (protein or domain) of a double stranded DNA binding protein with a DNA polymerase. The helix-hairpin-helix DNA binding motifs from DNA topoisomerase V have been added to the NH(2) terminus or COOH terminus of Taq DNA polymerase, Stoffel fragment of Taq DNA polymerase or Pfu DNA polymerase. The resulting chimeras have increased processivity, salt tolerance, and thermostability (Pavlov, A.R., et al. PNAS USA, Oct. 15, 2002; 99 (21); 13510-5). Another example is the fusion of DNA polymerase with the sequence non-specific DNA binding protein Sso7d or Sac7d from *Sulfolobus sulfataricus*, or an archaeal PCNA DNA binding domain. This strategy is used to enhance the processivity of Pfu or Taq DNA polymerase (WO 01/92501 A1).

DNA polymerases of the invention including but not limited to Pfu fusion proteins are purified as described in PCT/US01 17492 or Pavlov et al., supra.

Example 2

Chimeric DNA Polymerase Blend Formulations

A chimeric DNA polymerase blend formulation is comprised of a chimeric DNA polymerase and: (1) a proofreading or a non-proofreading DNA polymerase; or (2) a proofreading plus non-proofreading, non-proofreading plus non-proofreading or a proofreading plus proofreading DNA polymerase blend, e.g., Pfu, Taq, Pfu/Taq, Pfu/exo-Pfu, Taq/exo-Pfu, Pfu/JDF3, or any of these combinations with pol-Pfu (Pfu G387P). A specific non limiting example of a blend formulation is 2.5 U Pfu/0.25 U chimeric Pfu. A chimeric DNA blend comprises a chimeric DNA polymerase in combination with at least one wild type and/or at least one mutant DNA polymerase (as defined herein).

The wild type DNA polymerase that is blended with the DNA polymerase chimera is any native or cloned DNA polymerase having native levels of polymerase activity, proofreading activity and is preferably thermostable like Pfu or Taq. The chimeric DNA polymerase and wt DNA polymerase are blended (for example in any ratio described herein) and mixed with any replication accessory factor (a protein that enhances DNA synthesis) or PCR enhancing additives, e.g., Pfu dUTPase (PEF), PCNA, RPA, ssb, antibodies, DMSO, betaine, or 3'-5' exonuclease (e.g., Pfu G387P). Specific non-limiting examples of commercially useful mutations or truncations are V93R,K,E,D in Pfu, which confer uracil insensitivity, D141A/E143A in Pfu, which eliminates 3'-5' exonuclease activity, and the N-terminal truncation of Taq to eliminate 5'-3' exonuclease activity(KlenTaq). The chimeric DNA polymerase and mutant DNA polymerase are blended in any ratio and mixed with any replication accessory factor or PCR additives. The DNA polymerase formulation is any mixture of wt, wt and mutant, mutant and mutant DNA polymerases. The chimeric DNA polymerase and DNA polymerase formulation are blended in any ratio and mixed with any replication accessory factor or PCR additives.

High pH PCR Reaction Buffer.

A high pH PCR reaction buffer is formulated at a 10× concentration and used in PCR reactions at a final 1× concentration, which is standard for most commercially produced PCR reaction buffers. A 10× buffer formulation useful according to the invention is: 300 mM Tris pH 10.0 or pH 11.8; 100 mM KCl; 100 mM Ammonium Sulfate; 20 mM Magnesium Sulfate; 1% Triton X-100; 1 mg/ml nuclease-free bovine serum albumin (BSA). This formulation is in no way a limitation of the components or concentrations of components used for the invention. The components of the buffer, other than the buffering component, are varied depending on the requirements for the maximal activity of a specific DNA polymerase or DNA polymerase blend.

Example 3

PCR Amplification with a Chimeric Pfu DNA Polymerase or with DNA Polymerase Blends Containing a Chimeric Pfu DNA Polymerase PCR Reaction Conditions PCR reactions were conducted under standard conditions in 1× cloned Pfu PCR buffer (10 mM KCl, 10 mM $(NH_4)_2SO_4$, 2 mM $MgSO_4$, 0.1% Triton X-100, and 100 µg/ml BSA) except that 1). The Tris component was at pH 10.0 or 11.8 and at a final concentration of 30 mM and 2). The mixture contained 0.25-1.3 U Pfu-Sso7d chimeric DNA polymerase (sequence provided herein and 10 01/92501, incorporated by reference in its entirety) or chimeric DNA polymerase blends composed of 0.25 U Pfu-Sso7d and either 2.5 U or 5.0 U Pfu DNA polymerase. All PCR reactions contained 2 U/50 µl cloned *Pyrococcus furiosus* dUTPase (PEF). For all genomic targets 0.9-6.0 kb in length, PCR reactions contained 100 ng of human genomic DNA, 300 µM each dNTP, and 100 ng of each primer. For the 19 kb genomic target, PCR reactions contained 250 ng of human genomic DNA, 500 µM each dNTP, and 200 ng of each primer.

Cycling Conditions and Primer Sequences:

| Target size (kb) | Target gene | Cycling Parameters |
|---|---|---|
| 0.9 | HαlAT | (1 cycle) 95° C. 2 min |
|  |  | (30 cycles) 95° C. 5 sec, |
|  |  | 58° C. 5 sec, 72° C. 1 sec |
|  |  | or 5 sec. |
|  |  | (1 cycle) 72° C. 2 min |
| 2.6 | HαlAT | (1 cycle) 95° C. 2 min |
|  |  | (30 cycles) 95° C. 20 sec, |
|  |  | 58° C. 20 sec, 72° C. 5 |
|  |  | sec or 1 min 30 sec. |
|  |  | (1 cycle) 72° C. 3 min |
| 6 | β globin | (1 cycle) 95° C. 2 min |
|  |  | (30 cycles) 95° C. 30 sec, |
|  |  | 58° C. 30 sec, 72° C. 1 |
|  |  | min or 1 min 30 sec. |
|  |  | (1 cycle) 72° C. 5 min |

-continued

| Target size (kb) | Target gene | Cycling Parameters |
|---|---|---|
| 19 | β globin | (one cycle) 92° C. 2 min |
| | | (10 cycles) 92° C. 10 sec, 63° C. 30 sec, 68° C. 9.5 min |
| | | (20 cycles) 92° C. 10 sec, 63° C. 30 sec, 68° C. 9.5 min (plus 10 sec/cycle) |
| | | (one cycle) 68° C. 7 min |

| Primer size (bp) | Target | Primer sequence |
|---|---|---|
| 30 | HαlAT 0.9 kb | F-5'-AGA.GCT.TGA.GGA.GAG.CAG.GAA.AGG.TGG.AAC-3' |
| 30 | HαlAT 0.9 kb | R-5'-GGG.AGG.GGA.GGT.ACA.GGG.TTG.AGG.CTA.GTG-3' |
| 30 | HαlAT 2.6 kb | F-5'-AGA.GCT.TGA.GGA.GAG.CAG.GAA.AGG.TGG.AAC-3' |
| 24 | HαlAT 2.6 kb | R-5'-TGC.AGA.GCG.ATT.ATT.CAG.GAA.TGC-3' |
| 30 | β globin 6.0 kb | F-5'-ACA.AGG.GCT.ACT.GGT.TGC.CGA.TTT.TTA.TTG-3' |
| 27 | β globin 6.0 kb | R-5'-GGG.ACT.GGC.CTC.AGA.GGA.AAC.TTC.AGG-3' |
| 30 | β globin 19 kb | F-5'-ACA.AGG.GCT.ACT.GGT.TGC.CGA.TTT.TTA.TTG-3' |
| 28 | β globin 19 kb | R-5'-CCT.GCA.TTT.GTG.GGG.TGA.ATT.CCT.TGC.C-3' |

Effect of Buffer pH on PCR Amplification

Figure 2:
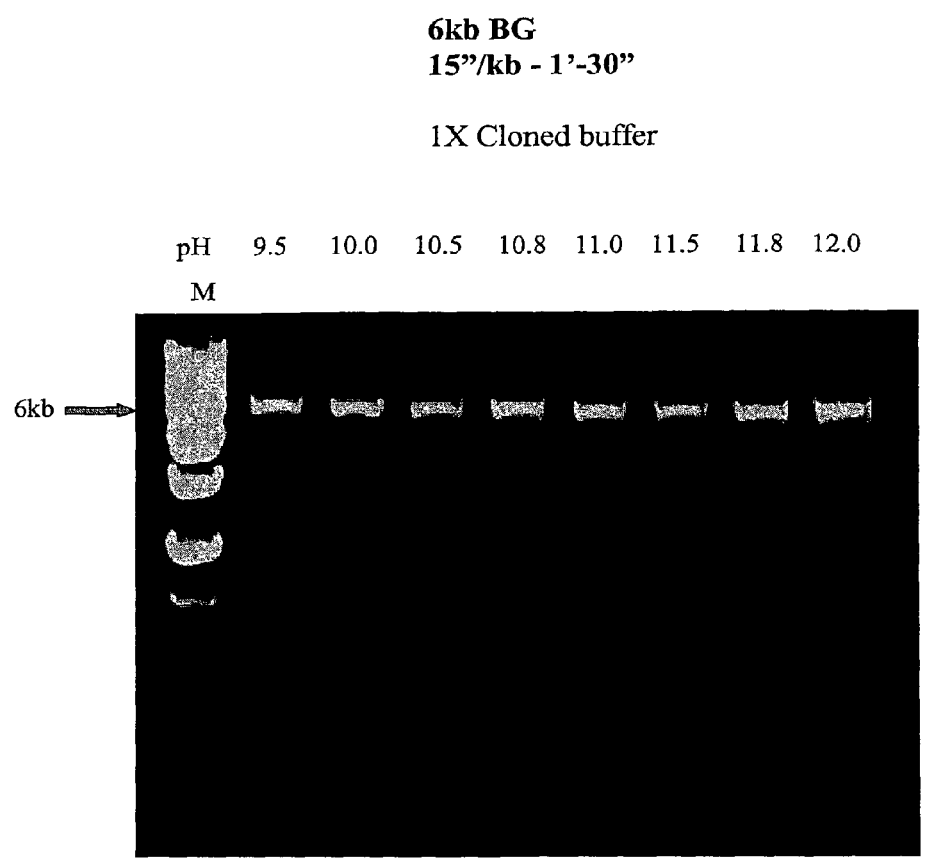
FIG. 2: 6 kb human Beta globin genomic DNA target amplified with a 15 second per kb extension time (1 minute 30 second total extension time). The PCR reaction buffer consisted of 1× cloned Pfu buffer using a 30 mM Tris pH gradient from 9.5 to 12.0. The chimeric DNA polymerase blend was composed of 0.25 U chimeric Pfu DNA polymerase and 2.5 U Pfu Turbo for a total of 2.75 U/reaction. M is 1 kb DNA marker (Stratagene).

To demonstrate the effect of pH on PCR reactions with chimeric Pfu-Sso7d DNA polymerase, PCR reactions were prepared using 1× Pfu reaction buffer wherein the pH of the Tris component was titrated from pH 5.0-12.0 (FIGS. 1 & 2). Pfu-Sso7d/Pfu Turbo blends (0.25 U Pfu-Sso7d+2.5 U or 5.0 U Pfu Turbo) were used to amplify a 6 kb human beta globin genomic target with an extension time of 15 seconds per kb. Pfu Turbo alone cannot amplify this target at 15 seconds per kb. Amplification is only achieved with the contribution of the more processive Pfu-Sso7d. Amplification appears at pH 8.5 and is strongest between pH 10.0-12.0, demonstrating the enhancing effect of high pH on the chimeric Pfu-Sso7d DNA polymerase (FIGS. 1 & 2).

Figure 3:
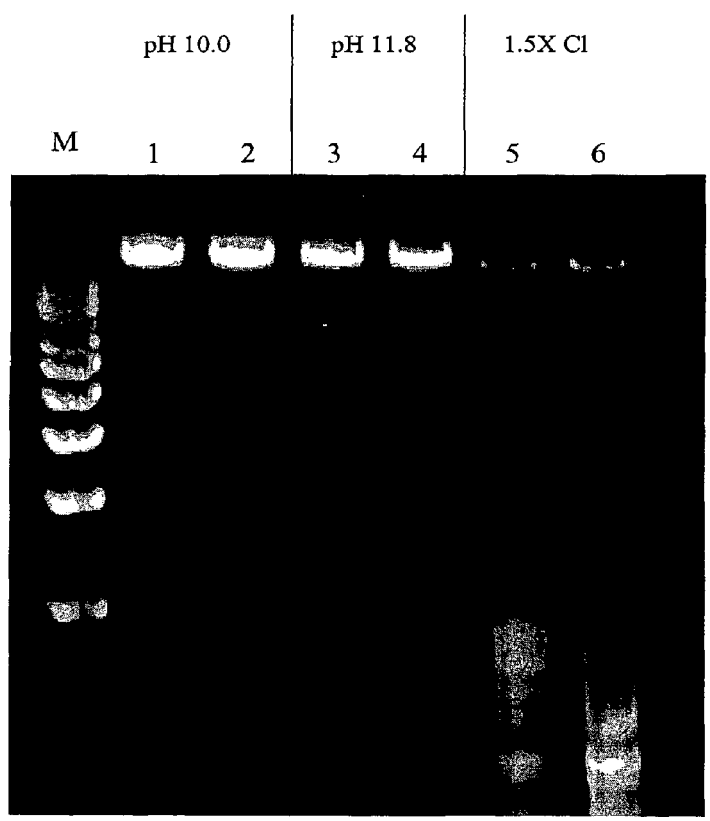
FIG. 3: Comparison of high pH reaction buffers and 1.5× cloned Pfu reaction buffer for the 19 kb beta globin genomic target. Lanes 1 and 2 are with the pH 10 buffer. Lanes 3 and 4 are with the pH 11 buffer. Lanes 5 and 6 are with 1.5× cloned Pfu reaction buffer. Lanes 1, 3 and 5 were amplified with the chimeric DNA polymerase blend that was composed of 0.25 U chimeric Pfu DNA polymerase and 2.5 U Pfu Turbo for a total of 2.75 U/reaction. Lanes 2, 4, & 6 were amplified with the chimeric DNA polymerase blend that was composed of 0.25 U chimeric Pfu DNA polymerase and 5.0 U Pfu Turbo for a total of 5.25 U/reaction. M is 1 kb DNA marker (Stratagene). A 30 second per kb extension time was used.

To demonstrate the enhancing effect of a high pH PCR reaction buffer for the PCR amplification of long genomic targets, a 19 kb fragment of human beta globin was amplified using Pfu-Sso7d/Pfu Turbo blend with an extension time of 30 seconds per kb. Amplification of this target with an extension time of 30 seconds per kb can only be achieved with the contribution of the more processive Pfu-Sso7d chimeric DNA polymerase component of the blend. PCR amplification in the pH 10.0 and pH 11.8 reaction buffers was compared to amplification in 1.5× cloned Pfu reaction buffer, which is the optimal PCR reaction buffer condition for Pfu Turbo (Strategies: Vol. 12, #4; "High fidelity PCR of genomic targets up to 19 kb"). PCR reactions using the high pH 10.0 and 11.8 reaction buffers were dramatically superior to the 1.5× cloned Pfu buffer, further demonstrating the enhancing effects of high pH for PCR amplification with Pfu-Sso7d (FIG. 3).

Figure 4:
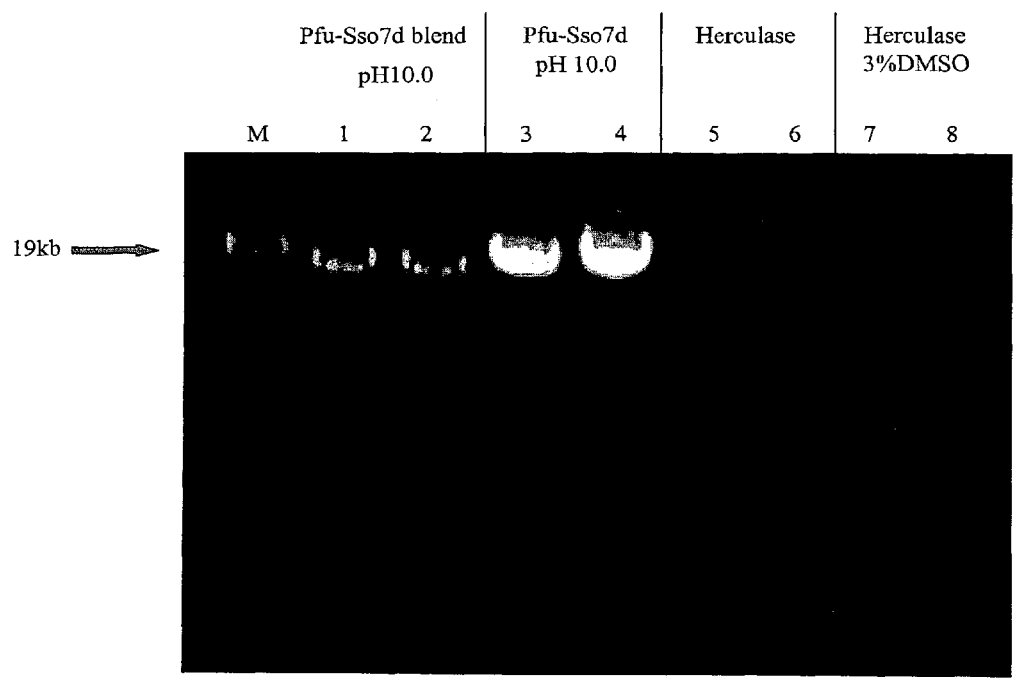
FIG. 4: Comparison of the chimeric Pfu DNA polymerase/Pfu Turbo DNA polymerase blend and the chimeric Pfu DNA polymerase in the high pH PCR reaction buffer and Herculase DNA polymerase in Herculase PCR reaction buffer for the PCR amplification of the 19 kb beta globin genomic target. Lanes 1 to 4 used the pH 10 PCR reaction buffer. Lanes 5 to 8 used Herculase PCR reaction buffer. Lane 1 was amplified with the chimeric DNA polymerase blend that was composed of 0.25 U chimeric Pfu DNA polymerase and 2.5 U Pfu Turbo for a total of 2.75 U/reaction. Lane 2 was amplified with the chimeric DNA polymerase blend that was composed of 0.25 U chimeric Pfu DNA polymerase and 5.0 U Pfu Turbo for a total of 5.25 U/reaction. Lane 3 was amplified with 0.83 U of the Pfu chimeric DNA polymerase. Lane 4 was amplified with 1.3 U of the chimeric DNA polymerase. Lanes 5 and 6 were amplified with 5.0 U of Herculase DNA polymerase with out DMSO. Lanes 7 and 8 were amplified with 5.0 U of Herculase DNA polymerase with 3% DMSO. A 30 second per kb extension time was used. M is the Lambda/Hind III DNA marker (Stratagene).

To further demonstrate the enhancing effects of high pH on PCR amplification with the chimeric Pfu-Sso7d DNA polymerase, amplification of the 19 kb human beta globin genomic target was compared using the Pfu-Sso7d/Pfu Turbo blends (0.25 U Pfu-Sso7d+2.5 U or 5.0 U Pfu Turbo) and 0.83 U and 1.3 U of Pfu-Sso7d in the pH 10.0 PCR reaction buffer with a 30 second per kb extension time (FIG. 4). The significant difference between these PCR reactions, since they all use the pH 10.0 buffer, is the amounts of Pfu-Sso7d in each reaction (i.e. 0.25 U Pfu-Sso7d for the blends and 0.83 U and 1.3 U Pfu-Sso7d for the non-blend reactions). The reactions which have 0.83 U and 1.3 U Pfu-Sso7d without any cloned Pfu DNA polymerase (#3 and #4 FIG. 4) generated dramatically higher yields than the blend reactions (#1 and #2 FIG. 4) which only had 0.25 U Pfu-Sso7d even though the total units of DNA polymerase were higher for the blend reactions (2.75 U #1, 5.25 U #2 for the blends and 0.83 U #3 and 1.3 U #4 for the Pfu-Sso7d reactions—FIG. 4).

PCR Performance Using a Reaction Buffer at pH 10.0.

Figure 5:
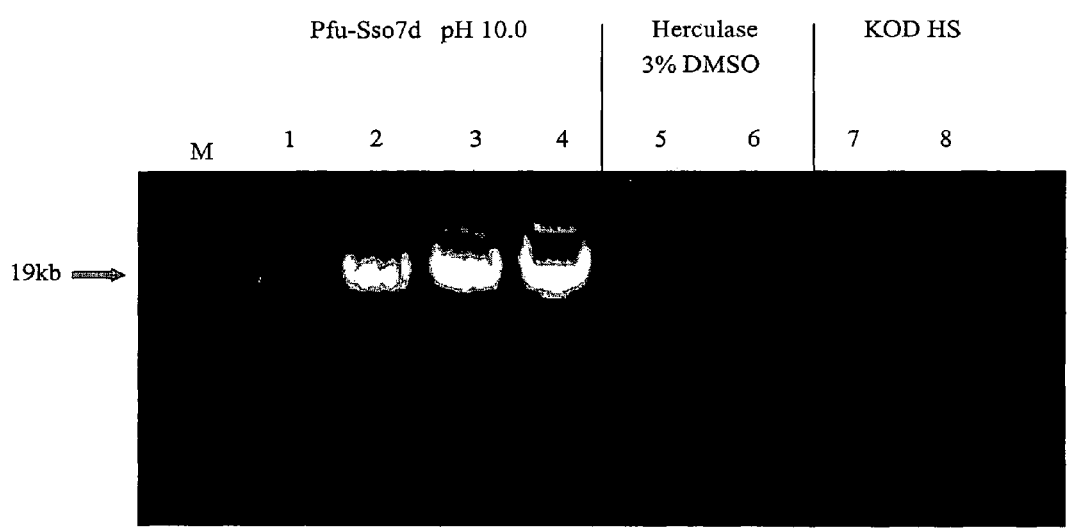
FIG. 5: Unit titration of chimeric Pfu DNA polymerase in high pH PCR reaction buffer and performance comparison to Herculase DNA polymerase and KOD hot start for the amplification of the 19 kb human beta globin with an extension time of 30 seconds per kb. #1-4, chimeric Pfu-Sso7d DNA polymerase in pH 10.0 PCR reaction buffer. #1-0.25 U; #2-0.5 U; #3-0.83 U; #4-1.3 U. #5-6, 5.0 U of Herculase DNA polymerase in 1× Herculase PCR reaction buffer and 3% DMSO. #7-8, KOD hot start DNA polymerase in KOD hot start DNA polymerase PCR reaction buffer. #7-1.25 U; #8-2.5 U. M is the Lambda/Hind III DNA marker (Stratagene).

The amplification efficiency of the 19 kb human beta globin target with Herculase DNA polymerase, KOD hot start DNA polymerase and a unit titration of the Pfu-Sso7d chimeric DNA polymerase was compared (FIG. 5). All enzymes were used in their optimal reaction buffers. The pH 10.0 buffer was used for Pfu-Sso7d, KOD hot start buffer for KOD hot start, and Herculase buffer for Herculase. 3% DMSO was added to the Herculase reactions which is optimal for the amplification of genomic targets over 10 kb in length. A 30 second per kb extension time was used. Most PCR enzymes require an extension time of 1-2 minutes per kb for a target of this length. All unit amounts (0.25-1.3 U) of Pfu-Sso7d in the pH 10 buffer generated PCR product. The Herculase and KOD hot start reactions did not generate any PCR product at this extension time.

Figure 6:
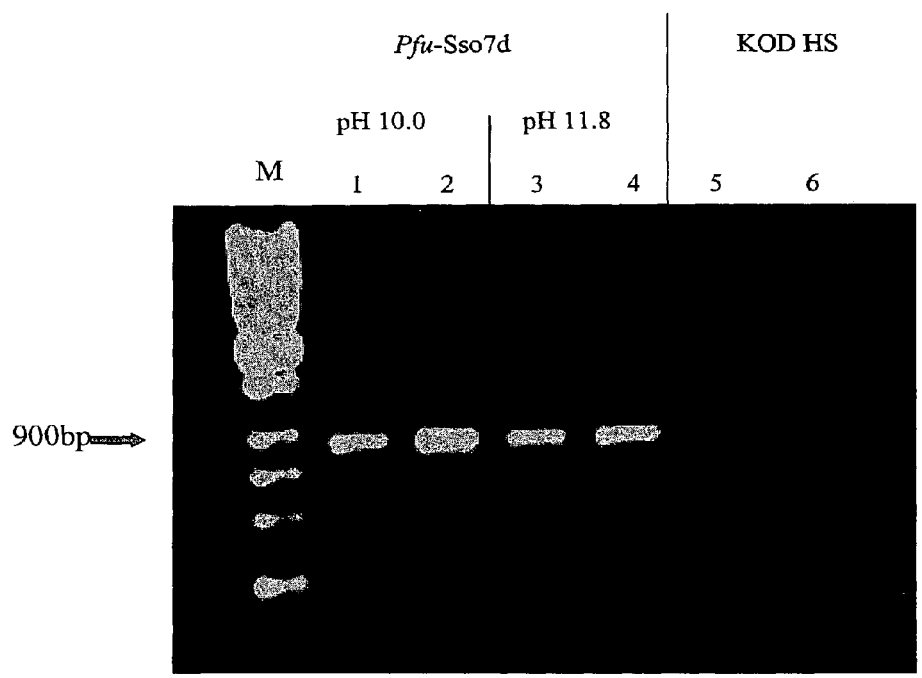
FIG. 6: Performance comparison of chimeric Pfu DNA polymerase in the pH 10.0 PCR reaction buffer and KOD hot start in KOD hot start PCR reaction buffer for the amplification of 900 bp Human alpha-1 antitrypsin (Hα1AT) with a 1 second total extension time. #1-2, chimeric Pfu-Sso7d DNA polymerase in pH 10.0 PCR reaction buffer. #3-4, Pfu-Sso7d DNA polymerase in pH 11.8 PCR reaction buffer. #5-6, 1.0 U KOD hot start in KOD hot start PCR reaction buffer. #1-0.5 U; #2-0.83 U; #3-0.5 U; #4-0.83 U. M-1 kb DNA marker (Stratagene).
Figure 7:
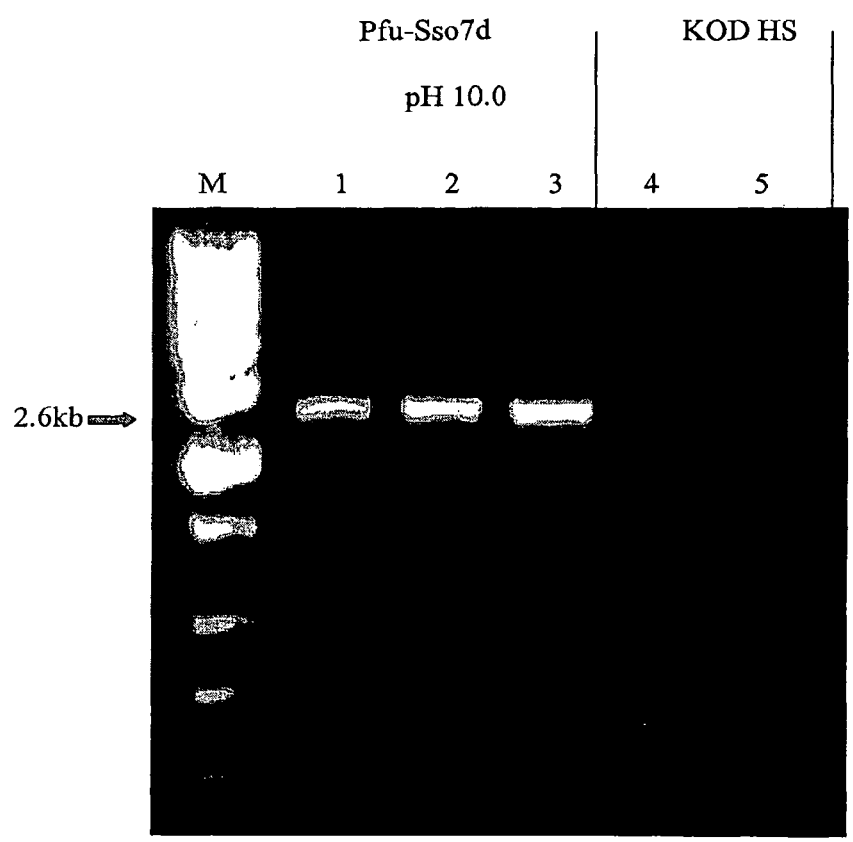
FIG. 7: PCR performance comparison of chimeric Pfu-Sso7d DNA polymerase in pH 10.0 PCR reaction buffer and KOD hot start DNA polymerase in KOD hot start PCR reaction buffer for the amplification of 2.6 kb Human alpha-1 antitrypsin (Hα1AT) with an extension time of 2 seconds per kb (5 second total extension time). #1-3, Pfu-Sso7d DNA polymerase in pH 10.0 PCR reaction buffer. #4-5, KOD hot start DNA polymerase in KOD hot start PCR reaction buffer. #1-0.5 U; #2-0.83 U; #3-1.3 U; #4-1.25 U; #5-2.5 U. M-1 kb DNA ladder (Stratagene).
Figure 8:
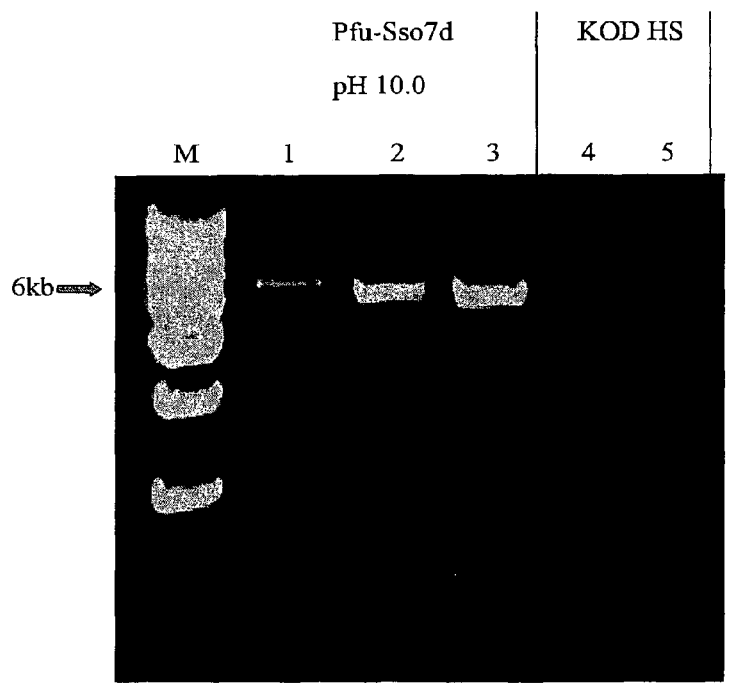
FIG. 8: PCR performance comparison of chimeric Pfu-Sso7d DNA polymerase in pH 10.0 PCR reaction buffer and KOD hot start in KOD hot start PCR reaction buffer for the amplification of 6 kb human beta globin with an extension time of 10 seconds per kb. #1-3, chimeric Pfu-Sso7d DNA polymerase in pH 10.0 PCR reaction buffer. #4-5. KOD hot start DNA polymerase in KOD hot start PCR reaction buffer. #1-0.5 U; #2-0.83 U; #3-1.3 U; #4-1.25 U; #5-2.5 U. M-1 kb DNA ladder (Stratagene).
Figure 9:
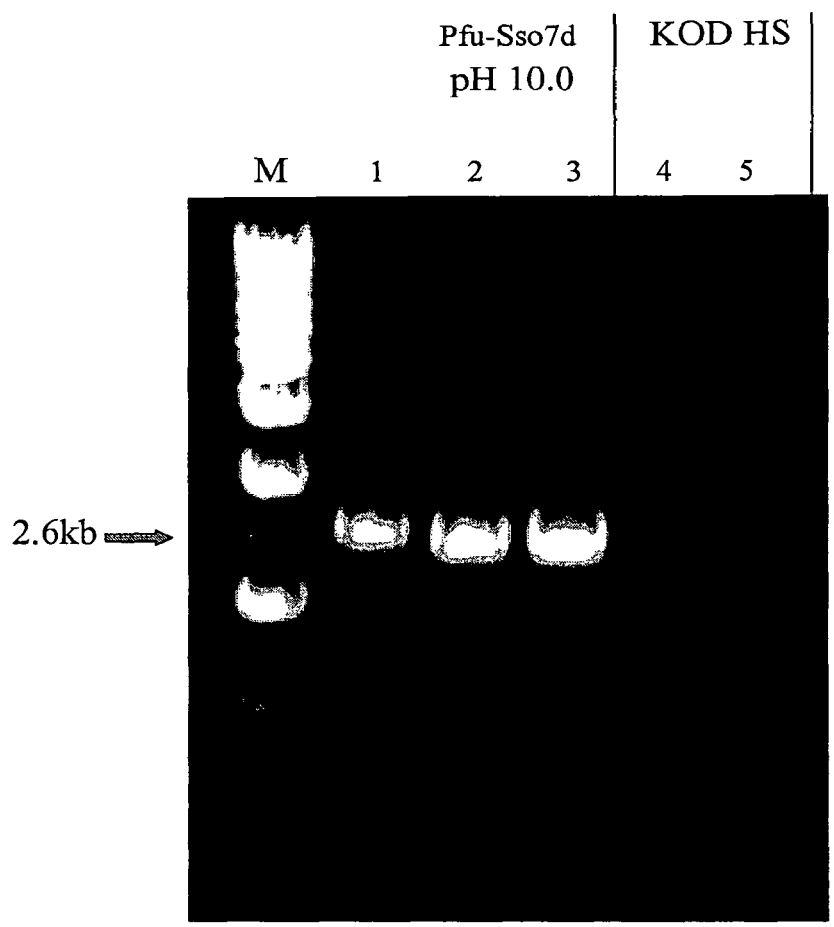
FIG. 9: PCR performance comparison of chimeric Pfu-Sso7d DNA polymerase in pH 10.0 PCR reaction buffer and KOD hot start in KOD hot start PCR reaction buffer for the amplification of 2.6 kb Hα1AT with an extension of 30 seconds per kb (1 minute 18 seconds total extension time). #1-3, Pfu-Sso7d DNA polymerase. #4-5, KOD hot start DNA polymerase. #1-0.5 U; #2-0.83 U; #3-1.3 U; #4-1.25 U; #5-2.5 U. M-1 kb ladder (Stratagene).
Figure 12:
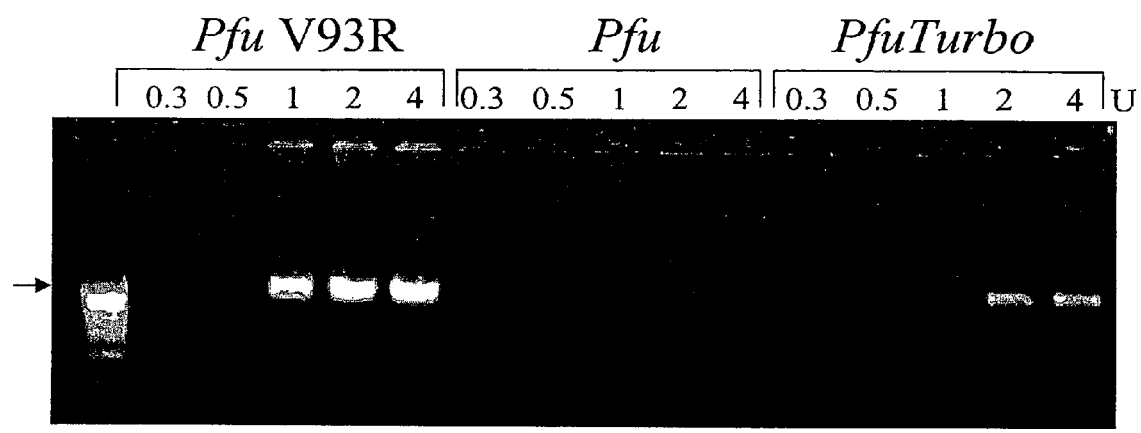
FIG. 12: Comparison of the efficacy of "long" PCR amplification of Pfu DNA polymerase mutants and wt enzyme.
Figure 15A:
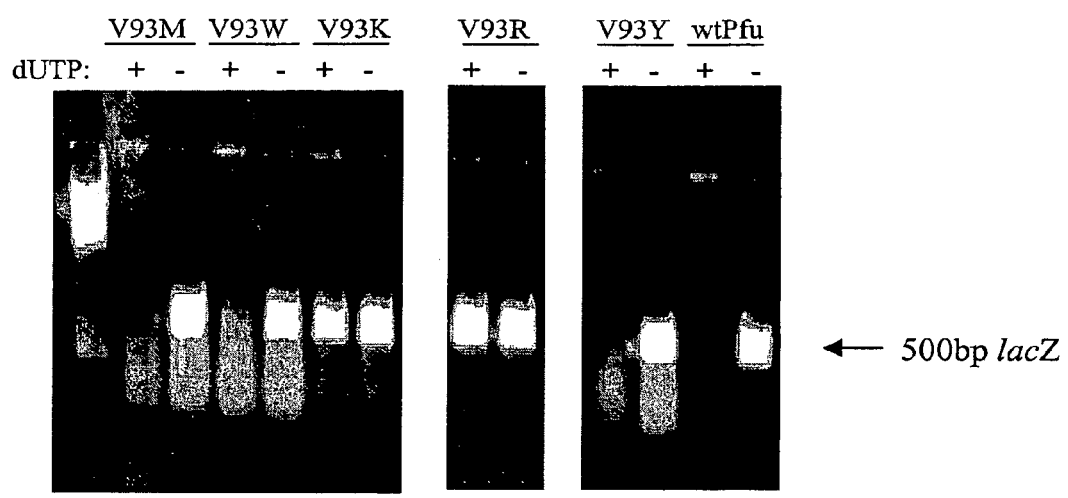
FIG. 15: dUTP incorporation of Pfu mutants compared to wild type Pfu DNA polymerase
15A. dUTP incorporation of Pfu mutants V93W, V93Y, V93M, V93K and V93R compared to wild type Pfu DNA polymerase
15B. dUTP incorporation of the Pfu V93D and V93R mutants compared to wild type Pfu DNA polymerase.
15C. dUTP incorporation of the Pfu V93N and V93G mutant compared to wild type Pfu DNA polymerase
Figure 15B:
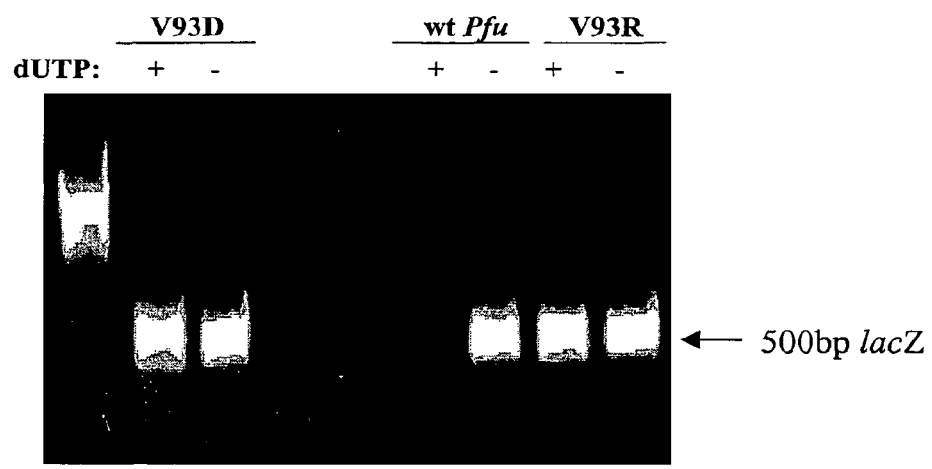
Figure 15C:
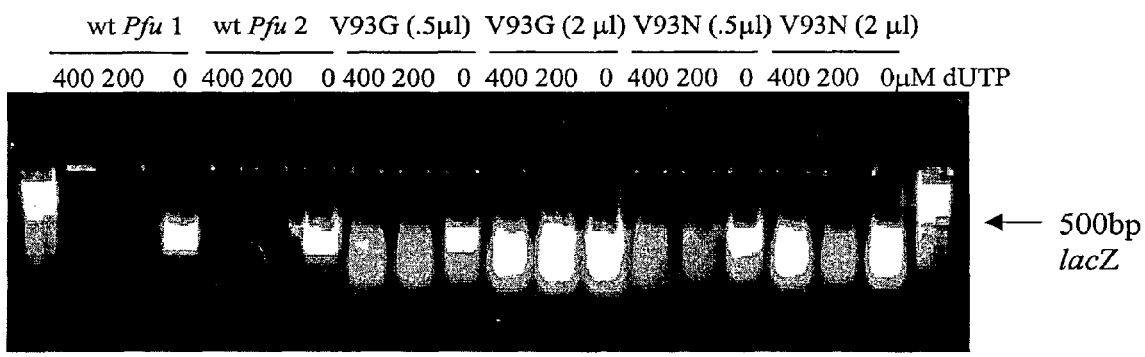

The amplification of smaller genomic targets was also compared using the Pfu-Sso7d chimeric DNA polymerase in the high pH 10.0 PCR reaction buffer and KOD hot start DNA polymerase in KOD hot start PCR reaction buffer. A 900 bp fragment of human alpha-1 anti trypsin (HαlAT) was amplified with a 1 second total extension time using 1) 0.5 U or 0.83 U of Pfu-Sso7d in pH 10.0 or pH 11.8 PCR reaction buffers, and 2) 1 U of KOD hot start in KOD hot start PCR reaction buffer (FIG. 6). A 2.6 kb fragment of HαlAT was amplified with a 2 second per kb extension time (5 second total extension time) (FIG. 7) and a 30 second per kb extension time (1 minute 18 second total extension time) (FIG. 9) using 0.5 U, 0.83 U and 1.3 U of Pfu-Sso7d in the pH 10.0 PCR reaction buffer and 1.25 U and 2.5 U of KOD hot start in KOD hot start PCR reaction buffer. A 6 kb fragment of human beta globin was amplified with a 10 second per kb extension time (1 minute total extension time) (FIG. 8) using 0.5 U, 0.83 U and 1.3 U of Pfu-Sso7d in the pH 10.0 PCR reaction buffer and 1.25 U and 2.5 U of KOD hot start in KOD hot start PCR reaction buffer. The extension times for all targets were shorter than the standard time for most PCR enzymes. 30 seconds to 2 minutes per kb is standard for most PCR enzymes. For all targets, the chimeric Pfu-Sso7d DNA polymerase in the high pH PCR reaction buffers displayed vastly superior performance at all unit amounts (0.25-1.3 U per reaction).

By the use of a high pH PCR reaction buffer with a processive chimeric Pfu DNA polymerase (in the presence of PEF/dUTPase), PCR extension times were substantially reduced for the amplification of genomic targets. For genomic targets between 1-6 kb an extension time of 1 min/kb for a non-chimeric DNA polymerase/DNA polymerase formulation was reduced to 1-10 seconds per kb. For genomic targets between 17-19 kb an extension time of 2 min/kb for a non-chimeric DNA polymerase/polymerase formulation was reduced to 30 sec/kb. The high pH reaction buffer/chimeric DNA polymerase/chimeric DNA polymerase blend combination is used in the same way as a conventional PCR reaction buffer/DNA polymerase/DNA polymerase blend combination and can be used in any primer extension application, including PCR, to produce high product yields with shortened extension times. The main application would be for the amplification of genomic targets, which typically require extension times of 1-2 minutes per kb and can take hours to amplify. Extension times could be reduced to 1-30 seconds per kb, or shorter, with the high pH buffer and chimeric DNA polymerase. Amplification times could be dramatically reduced, substantially improving PCR applications. Other applications include RT-PCR, site-directed mutagensis and random mutagenesis. A high pH reaction buffer/chimera combination used in all of these applications would increase length capability and shorten reaction times and highly increase overall performance in all standard protocols.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); (Harlow, E. and Lane, D.) Using Antibodies: A Laboratory Manual (1999) Cold Spring Harbor Laboratory Press; and a series, *Methods in Enzymology* (Academic Press, Inc.); *Short Protocols In Molecular Biology*, (Ausubel et al., ed., 1995).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for DNA synthesis at high pH, comprising: a) contacting a DNA polymerase fusion with a nucleic acid template under conditions of high pH, and b) effecting template dependent synthesis of DNA, wherein said high pH ranges from 9.3 to 12, and wherein said DNA polymerase fusion comprises wild type *Pyrococcus furiosus* polymerase I fused to *Sulfolobus solfataricus* SSso7d protein, wherein said DNA polymerase fusion functions as a DNA polymerase.

2. The method of claim 1, further comprising contacting a PCR enhancing factor and/or an additive with said DNA polymerase fusion and said nucleic acid template.

3. The method of claim 1, wherein said high pH ranges from 9.5 to 12.

4. The method of claim 3, wherein the DNA polymerase fusion is part of a blend comprising a second DNA polymerase.

5. The method of claim 4, wherein the second DNA polymerase is Pfu.

6. A method for the cloning of a DNA synthesis product, at high pH, wherein said high pH ranges from 9.3 to 12, comprising:
   a) providing a DNA polymerase fusion comprising wild-type *Pyrococcus furiosus* polymerase I fused to *Sulfolobus solfataricus* SSso7d protein, wherein said DNA polymerase fusion functions as a DNA polymerase;
   b) contacting said DNA polymerase fusion with a nucleic acid template under conditions of said high pH so as to effect the template dependent synthesis of a DNA synthesis product, and
   c) inserting said synthesized DNA product into a cloning vector, thereby cloning said synthesized DNA product.

7. The method of claim 6, further comprising contacting a PCR enhancing factor and/or an additive with said DNA polymerase fusion and said nucleic acid template in step (b).

8. The method of claim 6, wherein said high pH ranges from 9.5 to 12.

9. A method for sequencing DNA at high pH, wherein said high pH ranges from 9.3 to 12, comprising the steps of:
   (a) contacting a template DNA strand with a sequencing DNA primer;
   (b) contacting said DNA of step (a) with a DNA polymerase fusion comprising wild-type *Pyrococcus furiosus* polymerase I fused to *Sulfolobus solfataricus* SSso7d protein, wherein said DNA polymerase fusion functions as a DNA polymerase, deoxyribonucleoside triphosphates, and a chain-terminating nucleotide analog;
   (c) incubating the mixture of step (b) under conditions sufficient to synthesize at said high pH a random population of DNA molecules complementary to said DNA molecule, wherein said synthesized DNA molecules are shorter in length than said first DNA molecule and wherein said synthesized DNA molecules comprise a terminator nucleotide at their 5' termini; and
   (d) separating said synthesized DNA molecules by size so that at least a part of the nucleotide sequence of said first DNA molecule can be determined.

10. The method of claim 9, further comprising a PCR enhancing factor and/or an additive.

11. The method of claim 9, wherein said high pH ranges from 9.5 to 12.

12. A method of linear or exponential PCR amplification at high pH, wherein said high pH ranges from 9.3 to 12, for site-directed or random mutagenesis comprising the step of: incubating a reaction mixture comprising a nucleic acid template, at least one PCR primers, and a DNA polymerase fusion comprising wild-type *Pyrococcus furiosus* polymerase I fused to *Sulfolobus solfataricus* SSso7d protein, wherein said DNA polymerase fusion functions as a DNA polymerase, under conditions which permit amplification of said nucleic acid template at said high pH by said fusion to produce a mutated amplified product.

13. The method of claim 12, further comprising a PCR enhancing factor and/or an additive.

14. The method of claim 12, wherein said high pH ranges from 9.5 to 12.

15. A method of reverse transcriptase PCR at high pH, wherein said high pH ranges from 9.3 to 12, comprising the step of incubating a reaction mixture comprising a nucleic acid template, at least one PCR primer, and a DNA polymerase fusion comprising wild-type *Pyrococcus furiosus* polymerase I fused to *Sulfolobus solfataricus* SSso7d protein, wherein said DNA polymerase fusion functions as a DNA polymerase, under reaction conditions which permit amplification of said nucleic acid template at said high pH by said fusion to produce an amplified product.

16. The method of claim 15, further comprising a PCR enhancing factor and/or an additive.

17. The method of claim 15, wherein said high pH ranges from 9.5 to 12.

18. The method of claim 1, 6, 9, 12 or 15, wherein said DNA polymerase fusion comprises reduced base analog detection activity relative to wild-type *Pyrococcus furiosus* polymerase I under identical reaction conditions.

19. The method of claim 1, 6, 9, 12 or 15, wherein said DNA polymerase fusion comprises a wild type, mutant or chemically modified DNA polymerase.

20. The method of claim 1, 6, 9, 12, or 15, wherein said DNA polymerase fusion is a proofreading polymerase.

21. The method of claim 20, wherein said proofreading polymerase comprises wild-type *Pyrococcus furiosus* polymerase I.

22. The method of claim 1, 6, 9, 12, or 15, wherein said DNA polymerase fusion comprises an increase, as compared to said wild type *Pyrococcus furiosus* polymerase I, in at least one activity selected from the group consisting of: processivity, proofreading, fidelity, DNA binding activity, strand displacement activity, polymerase activity, nucleotide binding and recognition, efficiency, template length amplification capability, GC-rich target amplification efficiency, specificity, thermostability, intrinsic hot start capability, or salt resistance.

23. The method of claim 1, 6, 9, 12 or 15, wherein said DNA polymerase fusion comprises a reduction, as compared to said wild type *Pyrococcus furiosus* polymerase I, in at least one activity selected from the group consisting of: amplification slippage on templates with tri-nucleotide repeat stretches, extension time in a PCR reaction or amplification cycles in a PCR reaction.

24. The method of claim 23, wherein the activity is extension time in a PCR reaction.

25. The method of claim 24, wherein the extension time is decreased by at least 15 seconds as compared to the extension time observed under the same conditions with the wild type Pfu polymerase.

26. The method of claim 25, wherein the extension time is decreased by at least 45 seconds as compared to the extension time observed under the same conditions with the wild type Pfu polymerase.

27. The method of claim 26, wherein said high pH ranges from 9.5 to 12.

28. The method of claim 25, wherein said high pH ranges from 9.5 to 12.

29. The method of any one of claims 1, 6, 9, 12, and 15, wherein said DNA polymerase fusion is encoded by SEQ ID NO: 126 and has an amino acid sequence of SEQ ID NO:127.

* * * * *

UNITED STATES PATENT AND TRADEMARK OFFICE
CERTIFICATE OF CORRECTION

PATENT NO. : 7,704,712 B2  Page 1 of 1
APPLICATION NO. : 10/805650
DATED : April 27, 2010
INVENTOR(S) : Michael Borns It is certified that error appears in the above-identified patent and that said Letters Patent is hereby corrected as shown below:

On the Title page, in field (56), under "Other Publications", in column 1, line 5-6, delete "Tihe Journal op Biology" and insert -- The Journal of Biological --, therefor.

On the Title page, in field (56), under "Other Publications", in column 2, line 22, delete "Wahsington," and insert -- Washington, --, therefor.

On the Title page, in field (56), under "Other Publications", in column 2, line 38, delete "mutuations" and insert -- mutations --, therefor.

On the Title page, in field (56), under "Other Publications", in column 2, line 41, delete "recognitioin" and insert -- recognition --, therefor.

On the Title page, in field (56), under "Other Publications", in column 2, line 44, delete "Determinanats" and insert -- Determinants --, therefor.

Signed and Sealed this

Twentieth Day of July, 2010

David J. Kappos
*Director of the United States Patent and Trademark Office*

SEQUENCE LISTING

```
<160> NUMBER OF SEQ ID NOS: 148

<210> SEQ ID NO 1
<211> LENGTH: 30
<212> TYPE: DNA
<213> ORGANISM: Artificial sequence
<220> FEATURE:
<223> OTHER INFORMATION: primer

<400> SEQUENCE: 1
gacgacgaca agatgatttt agatgtggat                                    30

<210> SEQ ID NO 2
<211> LENGTH: 30
<212> TYPE: DNA
<213> ORGANISM: Artificial sequence
<220> FEATURE:
<223> OTHER INFORMATION: primer

<400> SEQUENCE: 2
ggaacaagac ccgtctagga tttttaatg                                     30

<210> SEQ ID NO 3
<211> LENGTH: 30
<212> TYPE: DNA
<213> ORGANISM: Artificial sequence
<220> FEATURE:
<223> OTHER INFORMATION: primer

<400> SEQUENCE: 3
agagcttgag gagagcagga aaggtggaac                                    30

<210> SEQ ID NO 4
<211> LENGTH: 30
```

-continued

<212> TYPE: DNA
<213> ORGANISM: Artificial sequence
<220> FEATURE:
<223> OTHER INFORMATION: primer

<400> SEQUENCE: 4
gggaggggag gtacagggtt gaggctagtg 30

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
gaacatcccc aagatgaacc cactattaga gaaaaag 37

<210> SEQ ID NO 6
<211> LENGTH: 37
<212> TYPE: DNA
<213> ORGANISM: Artificial sequence
<220> FEATURE:
<223> OTHER INFORMATION: primer

<400> SEQUENCE: 6
ctttttctct aatagtgggt tcatcttggg gatgttc 37

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
gaacatcccc aagatagacc cactattaga gaaaaag 37

<210> SEQ ID NO 8
<211> LENGTH: 37
<212> TYPE: DNA
<213> ORGANISM: Artificial sequence
<220> FEATURE:
<223> OTHER INFORMATION: primer
<400> SEQUENCE: 8
ctttttctct aatagtgggt ctatcttggg gatgttc 37

<210> SEQ ID NO 9
<211> LENGTH: 37
<212> TYPE: DNA
<213> ORGANISM: Artificial sequence
<220> FEATURE:
<223> OTHER INFORMATION: primer

<400> SEQUENCE: 9
gaacatcccc aagataaccc cactattaga gaaaaag 37

<210> SEQ ID NO 10
<211> LENGTH: 37
<212> TYPE: DNA
<213> ORGANISM: Artificial sequence
<220> FEATURE:
<223> OTHER INFORMATION: primer

<400> SEQUENCE: 10 cttttctct aatagtgggg ttatcttggg gatgttc                                37

<210> SEQ ID NO 11
<211> LENGTH: 37
<212> TYPE: DNA
<213> ORGANISM: Artificial sequence
<220> FEATURE:
<223> OTHER INFORMATION: primer

<400> SEQUENCE: 11
gaacatcccc aagatcaccc cactattaga gaaaaag                                37

<210> SEQ ID NO 12
<211> LENGTH: 37
<212> TYPE: DNA
<213> ORGANISM: Artificial sequence
<220> FEATURE:
<223> OTHER INFORMATION: primer

<400> SEQUENCE: 12 cttttctct aatagtgggg tgatcttggg gatgttc                                37

<210> SEQ ID NO 13
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate
<220> FEATURE:
<221> NAME/KEY: misc_feature
<222> LOCATION: (16)..(18)
<223> OTHER INFORMATION: NNK where N=any nucleotide

<400> SEQUENCE: 13
gaacatcccc aagatnnkcc cactattaga gaaaaag                                37

<210> SEQ ID NO 14
<211> LENGTH: 31
<212> TYPE: DNA
<213> ORGANISM: Artificial sequence
<220> FEATURE:
<223> OTHER INFORMATION: primer

<400> SEQUENCE: 14
gaacatcccc aagataaacc cactattaga g                                      31

<210> SEQ ID NO 15
<211> LENGTH: 31
<212> TYPE: DNA
<213> ORGANISM: Artificial sequence
<220> FEATURE:
<223> OTHER INFORMATION: primer

<400> SEQUENCE: 15
ctctaatagt gggtttatct tggggatgtt c                                      31

<210> SEQ ID NO 16
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature

```
<222> LOCATION: (1)..(1)
<223> OTHER INFORMATION: 5'-phosphate

<400> SEQUENCE: 16
gaacatcccc aagatgcacc cactattaga gaaaaag                                37

<210> SEQ ID NO 17
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 17
gaacatcccc aagatgaccc cactattaga gaaaaag                                37

<210> SEQ ID NO 18
<211> LENGTH: 38
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 18
gaacatcccc aagattgccc ccactattag agaaaaag                               38

<210> SEQ ID NO 19
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 19
gaacatcccc aagatatacc cactattaga gaaaaag                                37

<210> SEQ ID NO 20
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 20
gaacatcccc aagatatgcc cactattaga gaaaaag                                37

<210> SEQ ID NO 21
<211> LENGTH: 37
<212> TYPE: DNA
<213> ORGANISM: Artificial sequence
<220> FEATURE:
<223> OTHER INFORMATION: primer
<220> FEATURE:
```

```
<221> NAME/KEY: misc_feature
<222> LOCATION: (1)..(1)
<223> OTHER INFORMATION: 5'-phosphate

<400> SEQUENCE: 21
gaacatcccc aagatttccc cactattaga gaaaaag                                37

<210> SEQ ID NO 22
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 22
gaacatcccc aagatcctcc cactattaga gaaaaag                                37

<210> SEQ ID NO 23
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 23
gaacatcccc aagatagccc cactattaga gaaaaag                                37

<210> SEQ ID NO 24
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 24
gaacatcccc aagatacacc cactattaga gaaaaag                                37

<210> SEQ ID NO 25
<211> LENGTH: 37
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(1)
<223> OTHER INFORMATION: 5'-phosphate

<400> SEQUENCE: 25
gaacatcccc aagattaccc cactattaga gaaaaag                                37

<210> SEQ ID NO 26
<211> LENGTH: 37
<212> TYPE: DNA
<213> ORGANISM: Artificial sequence
<220> FEATURE:
<223> OTHER INFORMATION: primer
```

```
<220> FEATURE:
<221> NAME/KEY: misc_feature
<222> LOCATION: (1)..(1)
<223> OTHER INFORMATION: 5'-phosphate

<400> SEQUENCE: 26
gaacatcccc aagattggcc cactattaga gaaaaag                                37

<210> SEQ ID NO 27
<211> LENGTH: 2328
<212> TYPE: DNA
<213> ORGANISM: Pyrococcus furiosus
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 27
atgattttag atgtggatta cataactgaa gaaggaaaac ctgttattag gctattcaaa      60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa agtttctcgg caagcctatt    240
accgtgtgga aactttattt ggaacatccc caagatnnnc ccactattag agaaaagtt     300 agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca gtaggccac    1320 aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggaagaaag    1560 tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaaattca aagctccctg gactgctaga gcttgaatat   1740
```

```
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag               2328
```

<210> SEQ ID NO 28
<211> LENGTH: 2328
<212> TYPE: DNA
<213> ORGANISM: Pyrococcus furiosus
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 28

```
atgattttag atgtggatta cataactgaa gaaggaaaac ctgttattag gctattcaaa     60
aaagagaacg gaaaatttaa gatagagcat gatagaactt ttagaccata catttacgct    120
cttctcaggg atgattcaaa gattgaagaa gttaagaaaa taacggggga aaggcatgga    180
aagattgtga gaattgttga tgtagagaag gttgagaaaa gtttctcgg caagcctatt     240 accgtgtgga aactttattt ggaacatccc caagatnnnc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aagcccaat tataatgatt     480 agttatgcag atgaaaatga agcaaggtg attacttgga aaaacataga tcttccatac    540 gttgaggtt tatcaagcga gagagagatg ataaagagat ttctcaggat tatcagggag    600
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat acggctgta gaagtcaagg gaagaataca tttcgacttg     780
tatcatgtaa taacaaggac aataaatctc ccaacataca cactagaggc tgtatatgaa    840 gcaattttg gaaagccaaa ggagaaggta tacgccgacg atagcaaa agcctgggaa       900 agtggagaga accttgagag agttgccaaa tactcgatgg aagatgcaaa ggcaacttat    960
gaactcggga agaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaagggggtt gtgggaaaac   1200 atagtatacc tagattttag agccctatat ccctcgatta taattaccca caatgtttct   1260
cccgatactc taaatcttga gggatgcaag aactatgata tcgctcctca agtaggccac    1320
aagttctgca aggacatccc tggttttata ccaagtctct tgggacattt gttagaggaa   1380
```

-continued

```
agacaaaaga ttaagacaaa aatgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                2328
```

```
<210> SEQ ID NO 29
<211> LENGTH: 2328
<212> TYPE: DNA
<213> ORGANISM: Pyrococcus furiosus
<220> FEATURE:
<221> NAME/KEY: misc_feature
<222> LOCATION: (1161)..(1161)
<223> OTHER INFORMATION: N = C, G, A, or T
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 29
```

```
atgattttag atgtggatta cataactgaa gaaggaaaac ctgttattag gctattcaaa      60
aaagagaacg gaaatttaa gatagagcat gatagaactt ttagaccata catttacgct     120
cttctcaggg atgattcaaa gattgaagaa gttaagaaaa taacgggga aaggcatgga     180 aagattgtga gaattgttga tgtagagaag gttgagaaaa gtttctcgg caagcctatt     240 accgtgtgga aactttattt ggaacatccc caagatnnnc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaggtg attacttgga aaaacataga tcttccatac     540
gttgaggttg tatcaagcga gagagagatg ataaagagat ttctcaggat tatcagggag     600
aaggatcctg acattatagt tactataat ggagactcat tcgcattccc atatttagcg     660
aaaagggcag aaaacttgg gattaaatta ccattggaa gagatggaag cgagcccaag     720
atgcagagaa taggcgatat gacggctgta gaagtcaagg gaagaataca tttcgacttg     780
tatcatgtaa taacaaggac aataaatctc ccaacataca cactgaggc tgtatatgaa     840 gcaatttttg gaaagccaaa ggagaaggta tacgccgacg agatagcaaa agcctgggaa     900
```

```
agtggagaga accttgagag agttgccaaa tactcgatgg aagatgcaaa ggcaacttat      960
gaactcggga agaattcct tccaatggaa attcagcttt caagattagt tggacaacct     1020
ttatgggatg tttcaaggtc aagcacaggg aaccttgtag agtggttctt acttaggaaa     1080
gcctacgaaa gaaacgaagt agctccaaac aagccaagtg aagaggagta tcaaagaagg     1140
ctcagggaga gctacacacc nggattcgtt aaagagccag aaaagggggtt gtgggaaaac    1200
atagtatacc tagattttag agccctatat ccctcgatta taattaccca caatgtttct     1260
cccgatactc taaatcttga gggatgcaag aactatgata tcgctcctca agtaggccac     1320
aagttctgca aggacatccc tggttttata ccaagtctct tgggacattt gttagaggaa     1380
agacaaaaga ttaagacaaa aatgaaggaa actcaagatc ctatagaaaa aatactcctt     1440
gactatagac aaaaagcgat aaaactctta gcaaattctt tctacggata ttatggctat     1500
gcaaaagcaa gatggtactg taaggagtgt gctgagagcg ttactgcctg gggaagaaag     1560
tacatcgagt tagtatggaa ggagctcgaa gaaaagtttg gatttaaagt cctctacatt     1620
gacactgatg gtctctatgc aactatccca ggaggagaaa gtgaggaaat aaagaaaaag    1680
gctctagaat ttgtaaaata cataaaattca aagctccctg gactgctaga gcttgaatat    1740
gaagggtttt ataagagggg attcttcgtt acgaagaaga ggtatgcagt aatagatgaa     1800
gaaggaaaag tcattactcg tggtttagag atagttagga gagattggag tgaaattgca     1860
aaagaaactc aagctagagt tttggagaca atactaaaac acggagatgt tgaagaagct    1920
gtgagaatag taaagaagt aatacaaaag cttgccaatt atgaaattcc accagagaag     1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                 2328
```

<210> SEQ ID NO 30
<211> LENGTH: 2328
<212> TYPE: DNA
<213> ORGANISM: Pyrococcus furiosus
<220> FEATURE:
<221> NAME/KEY: misc_feature
<222> LOCATION: (1161)..(1161)
<223> OTHER INFORMATION: N= A,T,C or G
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 30

```
atgattttag atgtggatta cataactgaa gaaggaaaac ctgttattag gctattcaaa       60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa agtttctcgg caagcctatt     240
accgtgtgga aactttattt ggaacatccc caagatnnnc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc    420
gatatagaaa ccctctatca cgaaggagaa gagtttggaa aaggcccaat tataatgatt     480
```

```
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840 gcaattttg  gaaagccaaa ggagaaggta tacgccgacg atagcaaaa agcctgggaa     900 agtggagaga accttgagag agttgccaaa tactcgatgg aagatgcaaa ggcaacttat    960
gaactcggga agaattcct  tccaatcgaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacacc nggattcgtt aaagagccag aaagggggtt gtgggaaaac   1200
atagtatacc tagattttag agccctatat ccctcgatta taattaccca caatgttttct  1260 cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag              2328
```

<210> SEQ ID NO 31
<211> LENGTH: 2328
<212> TYPE: DNA
<213> ORGANISM: Pyrococcus furiosus
<220> FEATURE:
<221> NAME/KEY: misc_feature
<222> LOCATION: (423)..(423)
<223> OTHER INFORMATION: N = C, G, A, or T
<220> FEATURE:
<221> NAME/KEY: misc_feature
<222> LOCATION: (429)..(429)
<223> OTHER INFORMATION: N = C, G, A, or T
<220> FEATURE:
<221> NAME/KEY: misc_feature
<222> LOCATION: (277)..(279)

<223> OTHER INFORMATION: NNN = AGA, AGG, CGA, CGC, CGG, CGT (ALL POSSIBLE CODONS FOR ARGININE)

<400> SEQUENCE: 31

| | |
|---|---|
| atgattttag atgtggatta cataactgaa gaaggaaaac ctgttattag gctattcaaa | 60 |
| aaagagaacg gaaaatttaa gatagagcat gatagaactt ttagaccata catttacgct | 120 |
| cttctcaggg atgattcaaa gattgaagaa gttaagaaaa taacgggga aaggcatgga | 180 |
| aagattgtga gaattgttga tgtagagaag gttgagaaaa agtttctcgg caagcctatt | 240 |
| accgtgtgga aactttattt ggaacatccc caagatnnnc ccactattag agaaaaagtt | 300 |
| agagaacatc cagcagttgt ggacatcttc gaatacgata ttccatttgc aaagagatac | 360 |
| ctcatcgaca aaggcctaat accaatggag ggggaagaag agctaaagat tcttgccttc | 420 |
| gcnatagcna ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat ttctcaggat tatcagggag | 600 |
| aaggatcctg acattatagt tacttataat ggagactcat tcgcattccc atatttagcg | 660 |
| aaaagggcag aaaaacttgg gattaaatta accattggaa gagatggaag cgagcccaag | 720 |
| atgcagagaa taggcgatat gacggctgta gaagtcaagg gaagaataca tttcgacttg | 780 |
| tatcatgtaa taacaaggac aataaatctc ccaacataca cactagaggc tgtatatgaa | 840 |
| gcaattttg aaagccaaa ggagaaggta tacgccgacg agatagcaaa agcctgggaa | 900 |
| agtggagaga accttgagag agttgccaaa tactcgatgg aagatgcaaa ggcaacttat | 960 |
| gaactcggga agaattcct tccaatggaa attcagcttt caagattagt tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aaagagccag aaaagggggtt gtgggaaaac | 1200 |
| atagtatacc tagattttag agccctatat ccctcgatta taattaccca caatgtttct | 1260 |
| cccgatactc taaatcttga gggatgcaag aactatgata tcgctcctca gtaggccac | 1320 |
| aagttctgca aggacatccc tggttttata ccaagtctct tgggacattt gttagaggaa | 1380 |
| agacaaaaga ttaagacaaa aatgaaggaa actcaagatc ctatagaaaa atactccttt | 1440 |
| gactatagac aaaaagcgat aaaactctta gcaaattctt tctacggata ttatggctat | 1500 |
| gcaaaagcaa gatggtactg taaggagtgt gctgagagcg ttactgcctg gggaagaaag | 1560 |
| tacatcgagt tagtatggaa ggagctcgaa gaaaagtttg gatttaaagt cctctacatt | 1620 |
| gacactgatg gtctctatgc aactatccca ggaggagaaa gtgaggaaat aaagaaaaag | 1680 |
| gctctagaat ttgtaaaata cataaattca aagctccctg gactgctaga gcttgaatat | 1740 |
| gaagggtttt ataagagggg attcttcgtt acgaagaaga ggtatgcagt aatagatgaa | 1800 |
| gaaggaaaag tcattactcg tggtttagag atagttagga gagattggag tgaaattgca | 1860 |
| aaagaaactc aagctagagt tttggagaca atactaaaac acggagatgt tgaagaagct | 1920 |
| gtgagaatag taaagaagt aatacaaaag cttgccaatt atgaaattcc accagagaag | 1980 |
| ctcgcaatat atgagcagat aacaagacca ttacatgagt ataaggcgat aggtcctcac | 2040 |
| gtagctgttg caaagaaact agctgctaaa ggagttaaaa taaagccagg aatggtaatt | 2100 |
| ggatacatag tacttagagg cgatggtcca attagcaata gggcaattct agctgaggaa | 2160 |
| tacgatccca aaaagcacaa gtatgacgca gaatattaca tggagaacca ggttcttcca | 2220 |

-continued

```
gcggtactta ggatattgga gggatttgga tacagaaagg aagacctcag ataccaaaag      2280
acaagacaag tcggcctaac ttcctggctt aacattaaaa aatcctag                  2328
```

<210> SEQ ID NO 32
<211> LENGTH: 2328
<212> TYPE: DNA
<213> ORGANISM: Pyrococcus furiosus
<220> FEATURE:
<221> NAME/KEY: misc_feature
<222> LOCATION: (423)..(423)
<223> OTHER INFORMATION: N = C, G, A, or T
<220> FEATURE:
<221> NAME/KEY: misc_feature
<222> LOCATION: (429)..(429)
<223> OTHER INFORMATION: N = C, G, A, or T
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 32

```
atgattttag atgtggatta cataactgaa gaaggaaaac ctgttattag gctattcaaa       60
aaagagaacg gaaaatttaa gatagagcat gatagaactt ttagaccata catttacgct      120
cttctcaggg atgattcaaa gattgaagaa gttaagaaaa taacggggga aaggcatgga      180
aagattgtga gaattgttga tgtagagaag gttgagaaaa agtttctcgg caagcctatt      240
accgtgtgga aactttattt ggaacatccc caagatnnnc ccactattag agaaaaagtt      300
agagaacatc cagcagttgt ggacatcttc gaatacgata ttccatttgc aaagagatac      360
ctcatcgaca aaggcctaat accaatggag ggggaagaag agctaaagat tcttgccttc      420
gcnatagcna ccctctatca cgaaggagaa gagtttggaa aaggcccaat tataatgatt      480
agttatgcag atgaaaatga agcaaaggtg attacttgga aaaacataga tcttccatac      540
gttgaggttg tatcaagcga gagagagatg ataaagagat ttctcaggat tatcagggag      600
aaggatcctg acattatagt tacttataat ggagactcat tcgcattccc atatttagcg      660 aaaaggggcag aaaaacttgg gattaaatta accattggaa gagatggaag cgagcccaag      720
atgcagagaa taggcgatat gacggctgta gaagtcaagg gaagaataca tttcgacttg      780
tatcatgtaa taacaaggac aataaatctc caacataca cactagaggc tgtatatgaa      840 gcaattttg gaaagccaaa ggagaaggta tacgccgacg agatagcaaa agcctgggaa      900
agtggagaga accttgagag agttgccaaa tactcgatgg aagatgcaaa ggcaacttat      960
gaactcggga agaattcct tccaatggaa attcagcttt caagattagt tggacaacct     1020
ttatgggatg tttcaaggtc aagcacaggg aaccttgtag agtggttctt acttaggaaa     1080
gcctacgaaa gaaacgaagt agctccaaac aagccaagtg aagaggagta tcaaagaagg     1140
ctcagggaga gctacacagg tggattcgtt aaagagccag aaaagggggtt gtgggaaaac     1200 atagtatacc tagattttag agccctatat ccctcgatta taattccca caatgttttct     1260 cccgatactc taaatcttga gggatgcaag aactatgata tcgctcctca agtaggccac     1320
aagttctgca aggacatccc tggttttata ccaagtctct tgggacattt gttagaggaa     1380
agacaaaaga ttaagacaaa aatgaaggaa actcaagatc ctatagaaaa aatactcctt     1440
gactatagac aaaaagcgat aaaactctta gcaaattctt tctacggata ttatggctat     1500
gcaaaagcaa gatggtactg taaggagtgt gctgagagcg ttactgcctg gggaagaaag     1560
tacatcgagt tagtatggaa ggagctcgaa gaaaagtttg gatttaaagt cctctacatt     1620
gacactgatg gtctctatgc aactatccca ggaggagaaa gtgaggaaat aaagaaaaag     1680
```

-continued

```
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca tggagaacca ggttcttcca    2220
gcggtactta ggatattgga gggatttgga tacagaaagg aagacctcag ataccaaaag    2280
acaagacaag tcggcctaac ttcctggctt aacattaaaa aatcctag                2328
```

<210> SEQ ID NO 33
<211> LENGTH: 2325
<212> TYPE: DNA
<213> ORGANISM: Thermococcus kodakaraensis
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 33

```
atgatcctcg acactgacta cataaccgag gatggaaagc ctgtcataag aattttcaag      60
aaggaaaacg gcgagtttaa gattgagtac gaccggactt tgaaccccta cttctacgcc     120
ctcctgaagg acgattctgc cattgaggaa gtcaagaaga taaccgccga gaggcacggg     180
acggttgtaa cggttaagcg ggttgaaaag gttcagaaga agttcctcgg agaccagtt     240
gaggtctgga aactctactt tactcatccg caggacnnnc cagcgataag ggacaagata     300
cgagagcatc cagcagttat tgacatctac gagtacgaca tacccttcgc caagcgctac     360
ctcatagaca agggattagt gccaatggaa ggcgacgagg agctgaaaat gctcgccttc     420
gacattgaaa ctctctacca tgagggcgag gagttcgccg aggggccaat ccttatgata     480
agctacgccg acgaggaagg ggccagggtg ataacttgga gaacgtgga tctcccctac     540
gttgacgtcg tctcgacgga gagggagatg ataaagcgct cctccgtgt tgtgaaggag     600
aaagacccgg acgttctcat aacctacaac ggcgacaact tcgacttcgc ctatctgaaa     660
aagcgctgtg aaaagctcgg aataaacttc gccctcggaa gggatggaag cgagccgaag     720
attcagagga tgggcgacag gtttgccgtc gaagtgaagg gacggataca cttcgatctc     780
tatcctgtga taagacggac gataaacctg cccacataca cgcttgaggc cgtttatgaa     840
gccgtcttcg gtcagccgaa ggagaaggtt acgctgagg aaataaccac agcctgggaa     900
accggcgaga accttgagag agtcgcccgc tactcgatgg aagatgcgaa ggtcacatac     960
gagcttggga aggagttcct tccgatggag gcccagcttt tcgcttaat cggccagtcc    1020
ctctgggacg tctcccgctc cagcactggc aacctcgttg agtggttcct cctcaggaag    1080
gcctatgaga ggaatgagct ggccccgaac aagcccgatg aaaaggagct ggccagaaga    1140
cggcagagct atgaaggagg ctatgtaaaa gagcccgaga gagggttgtg ggagaacata    1200
gtgtacctag attttagatc cctgtacccc tcaatcatca tcacccacaa cgtctcgccg    1260
gatacgctca acagagaagg atgcaaggaa tatgacgttg ccccacaggt cggccaccgc    1320
```

-continued

```
ttctgcaagg acttcccagg atttatcccg agcctgcttg gagacctcct agaggagagg    1380
cagaagataa agaagaagat gaaggccacg attgacccga tcgagaggaa gctcctcgat    1440
tacaggcaga gggccatcaa gatcctggca aacagctact acggttacta cggctatgca    1500
agggcgcgct ggtactgcaa ggagtgtgca gagagcgtaa cggcctgggg aagggagtac    1560
ataacgatga ccatcaagga gatagaggaa aagtacggtt taaggtaat ctacagcgac     1620 accgacggat tttttgccac aatacctgga gccgatgctg aaaccgtcaa aagaaggct     1680 atggagttcc tcaagtatat caacgccaaa cttccgggcg cgcttgagct cgagtacgag    1740
ggcttctaca acgcggctt cttcgtcacg aagaagaagt atgcggtgat agacgaggaa     1800
ggcaagataa caacgcgcgg acttgagatt gtgaggcgtg actggagcga gatagcgaaa    1860
gagacgcagg cgagggttct gaagctttg ctaaggacg gtgacgtcga aaggccgtg      1920 aggatagtca agaagttac cgaaaagctg agcaagtacg aggttccgcc ggagaagctg    1980
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaagggaa cttga                    2325
```

<210> SEQ ID NO 34
<211> LENGTH: 2325
<212> TYPE: DNA
<213> ORGANISM: Thermococcus kodakaraensis
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 34

```
atgatcctcg acactgacta cataaccgag gatggaaagc ctgtcataag aattttcaag     60
aaggaaaacg gcgagtttaa gattgagtac gaccggactt tgaacccta cttctacgcc     120 ctcctgaagg acgattctgc cattgaggaa gtcaagaaga taaccgccga gaggcacggg    180
acggttgtaa cggttaagcg ggttgaaaag gttcagaaga agttcctcgg agaccagtt     240 gaggtctgga aactctactt tactcatccg caggacnnnc cagcgataag ggacaagata    300
cgagagcatc cagcagttat tgacatctac gagtacgaca taccctttcgc caagcgctac    360 ctcatagaca agggattagt gccaatggaa ggcgacgagg agctgaaaat gctcgccttc    420
gacattgaaa ctctctacca tgagggcgag gagttcgccg agggccaat ccttatgata     480 agctacgccg acgaggaagg ggccagggtg ataacttgga gaacgtgga tctcccctac    540 gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg gacggataca cttcgatctc    780
tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
```

```
gagcttggga aggagttcct tccgatggag gcccagcttt ctcgcttaat cggccagtcc   1020
ctctgggacg tctcccgctc cagcactggc aacctcgttg agtggttcct cctcaggaag   1080
gcctatgaga ggaatgagct ggccccgaac aagcccgatg aaaaggagct ggccagaaga   1140
cggcagagct atgaaggagg ctatgtaaaa gagcccgaga gagggttgtg ggagaacata   1200
gtgtacctag attttagatc cctgtacccc tcaatcatca tcacccacaa cgtctcgccg   1260
gatacgctca acagagaagg atgcaaggaa tatgacgttg ccccacaggt cggccaccgc   1320
ttctgcaagg acttcccagg atttatcccg agcctgcttg agacctcct agaggagagg    1380 cagaagataa agaagaagat gaaggccacg attgacccga tcgagaggaa gctcctcgat   1440
tacaggcaga gggccatcaa gatcctggca acagctact acggttacta cggctatgca    1500
agggcgcgct ggtactgcaa ggagtgtgca gagagcgtaa cggcctgggg aagggagtac   1560
ataacgatga ccatcaagga gatagaggaa aagtacggct ttaaggtaat ctacagcgac   1620
accgacggat tttttgccac aatacctgga gccgatgctg aaaccgtcaa aaagaaggct   1680
atggagttcc tcaagtatat caacgccaaa cttccgggcg cgcttgagct cgagtacgag   1740
ggcttctaca acgcggctt cttcgtcacg aagaagaagt atgcggtgat agacgaggaa    1800
ggcaagataa caacgcgcgg acttgagatt gtgaggcgtg actggagcga gatagcgaaa   1860
gagacgcagg cgagggttct tgaagctttg ctaaaggacg tgacgtcga gaaggccgtg    1920 aggatagtca agaagttac cgaaaagctg agcaagtacg aggttccgcc ggagaagctg    1980
gtgatccacg agcagataac gagggattta aaggactaca aggcaaccgg tccccacgtt   2040
gccgttgcca agaggttggc cgcgagagga gtcaaaatac gccctggaac ggtgataagc   2100
tacatcgtgc tcaagggctc tgggaggata ggcgacaggg cgataccgtt cgacgagttc   2160
gacccgacga agcacaagta cgacgccgag tactacattg agaaccaggt tctcccagcc   2220
gttgagagaa ttctgagagc cttcggttac cgcaaggaag acctgcgcta ccagaagacg   2280
agacaggttg gtttgagtgc ttggctgaag ccgaagggaa cttga                   2325
```

<210> SEQ ID NO 35
<211> LENGTH: 2325
<212> TYPE: DNA
<213> ORGANISM: Thermococcus litoralis
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 35

```
atgatactgg acactgatta cataacaaaa gatggcaagc ctataatccg aattttttaag   60 aaagagaacg gggagtttaa aatagaactt gaccctcatt ttcagcccta tatatatgct   120
cttctcaaag atgactccgc tattgaggag ataaaggcaa taaagggcga gagacatgga   180
aaaactgtga gagtgctcga tgcagtgaaa gtcaggaaaa aattttttggg aagggaagtt   240 gaagtctgga agctcatttt cgagcatccc aagacnnnc cagctatgcg ggcaaaata    300 agggaacatc cagctgtggt tgacatttac gaatatgaca tacccttgc caagcgttat    360 ctcatagaca agggcttgat tcccatggag ggagacgagg agcttaagct ccttgccttt   420
gatattgaaa cgttttatca tgagggagat gaatttggaa agggcgagat aataatgatt   480
agttatgccg atgaagaaga ggccagagta atcacatgga aaaatatcga tttgccgtat   540
gtcgatgttg tgtccaatga agagaaatg ataaagcgtt ttgttcaagt tgttaaagaa    600
```

```
aaagaccccg atgtgataat aacttacaat ggggacaatt ttgatttgcc gtatctcata      660
aaacgggcag aaaagctggg agttcggctt gtcttaggaa gggacaaaga acatcccgaa      720
cccaagattc agaggatggg tgatagtttt gctgtggaaa tcaagggtag aatccacttt      780
gatcttttcc cagttgtgcg aaggacgata aacctcccaa cgtatacgct tgaggcagtt      840
tatgaagcag ttttaggaaa aaccaaaagc aaattaggag cagaggaaat tgccgctata      900
tgggaaacag aagaaagcat gaaaaaacta gcccagtact caatgaaaga tgctagggca      960
acgtatgagc tcgggaagga attcttcccc atggaagctg agctggcaaa gctgataggt     1020
caaagtgtat gggacgtctc gagatcaagc accggcaacc tcgtggagtg gtatctttta     1080
agggtggcat acgcgaggaa tgaacttgca ccgaacaaac ctgatgagga agagtataaa     1140
cggcgcttaa gaacaactta cctggggaga tatgtaaaag agccagaaaa aggtttgtgg     1200
gaaaatatca tttatttgga tttccgcagt ctgtacccct caataatagt tactcacaac     1260
gtatccccag atacccttga aaagagggc tgtaagaatt acgatgttgc tccgatagta     1320
ggatataggt tctgcaagga cttttccgggc tttattccct ccatactcgg ggacttaatt     1380
gcaatgaggc aagatataaa gaagaaaatg aaatccacaa ttgacccgat cgaaaagaaa     1440
atgctcgatt ataggcaaag ggctattaaa ttgcttgcaa acagctatta cggctatatg     1500
gggtatccta aggcaagatg gtactcgaag gaatgtgctg aaagcgttac cgcatggggg     1560
agacactaca tagagatgac gataagagaa atagaggaaa agttcggctt taaggttctt     1620
tatgcggaca ctgacggctt ttatgccaca atacccgggg aaaagcctga actcattaaa     1680
aagaaagcca aggaattcct aaactacata aactccaaac ttccaggtct gcttgagctt     1740
gagtatgagg gcttttactt gagaggattc tttgttacaa aaaagcgcta tgcagtcata     1800
gatgaagagg gcaggataac aacaaggggc ttggaagtag taaggagaga ttggagtgag     1860
atagctaagg agactcaggc aaaggtttta gaggctatac ttaaagaggg aagtgttgaa     1920
aaagctgtag aagttgttag agatgttgta gagaaaatag caaaatacag ggttccactt     1980
gaaaagcttg ttatccatga gcagattacc agggatttaa aggactacaa agccattggc     2040
cctcatgtcg cgatagcaaa aagacttgcc gcaagaggga taaaagtgaa accgggcaca     2100
ataataagct atatcgttct caagggagc ggaaagataa gcgatagggt aattttactt     2160
acagaatacg atcctagaaa acacaagtac gatccggact actacataga aaaccaagtt     2220
ttgccggcag tacttaggat actcgaagcg tttggataca gaaggagga tttaaggtat     2280 caaagctcaa aacaaccgg cttagatgca tggctcaaga ggtag                       2325
```

<210> SEQ ID NO 36
<211> LENGTH: 2325
<212> TYPE: DNA
<213> ORGANISM: Thermococcus litoralis
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 36

```
atgatactgg acactgatta cataacaaaa gatggcaagc ctataatccg aattttaag       60 aaagagaacg gggagtttaa aatagaactt gaccctcatt ttcagcccta tatatatgct      120
cttctcaaag atgactccgc tattgaggag ataaaggcaa taagggcga gagacatgga      180 aaaactgtga gagtgctcga tgcagtgaaa gtcaggaaaa aattttttggg aagggaagtt      240 gaagtctgga agctcatttt cgagcatccc caagacnnnc cagctatgcg gggcaaaata      300
```

```
agggaacatc cagctgtggt tgacatttac gaatatgaca tacccttttgc caagcgttat      360 ctcatagaca agggcttgat tcccatggag ggagacgagg agcttaagct ccttgccttt      420
gatattgaaa cgttttatca tgagggagat gaatttggaa agggcgagat aataatgatt      480
agttatgccg atgaagaaga ggccagagta atcacatgga aaaatatcga tttgccgtat      540
gtcgatgttg tgtccaatga agagaaatg ataaagcgtt ttgttcaagt tgttaaagaa       600
aaagaccccg atgtgataat aacttacaat ggggacaatt ttgatttgcc gtatctcata      660
aaacgggcag aaaagctggg agttcggctt gtcttaggaa gggacaaaga acatcccgaa      720
cccaagattc agaggatggg tgatagtttt gctgtggaaa tcaagggtag aatccacttt      780
gatcttttcc cagttgtgcg aaggacgata aacctcccaa cgtatacgct tgaggcagtt      840
tatgaagcag ttttaggaaa aaccaaaagc aaattaggag cagaggaaat tgccgctata      900
tgggaaacag aagaaagcat gaaaaaacta gcccagtact caatggaaga tgctagggca      960
acgtatgagc tcgggaagga attcttcccc atggaagctg agctggcaaa gctgataggt     1020
caaagtgtat gggacgtctc gagatcaagc accggcaacc tcgtggagtg gtatctttta     1080
agggtggcat acgcgaggaa tgaacttgca ccgaacaaac ctgatgagga agagtataaa     1140
cggcgcttaa gaacaactta cctgggagga tatgtaaaag agccagaaaa aggtttgtgg     1200
gaaaatatca tttatttgga tttccgcagt ctgtaccctt caataatagt tactcacaac     1260
gtatccccag ataccctgta aaaagagggc tgtaagaatt acgatgttgc tccgatagta     1320
ggatataggt tctgcaagga cttccgggc tttattccct ccatactcgg ggacttaatt      1380
gcaatgaggc aagatataaa gaagaaaatg aaatccacaa ttgacccgat cgaaaagaaa     1440
atgctcgatt ataggcaaag ggctattaaa ttgcttgcaa acagctatta cggctatatg     1500
gggtatccta aggcaagatg gtactcgaag gaatgtgctg aaagcgttac cgcatggggg     1560
agacactaca tagagatgac gataagagaa atagaggaaa agttcggctt taaggttctt     1620
tatgcggaca ctgacggctt ttatgccaca atacccgggg aaaagcctga actcattaaa     1680
aagaaagcca aggaattcct aaactacata aactccaaac ttccaggtct gcttgagctt     1740
gagtatgagg gcttttactt gagaggattc tttgttacaa aaaagcgcta tgcagtcata     1800
gatgaagagg gcaggataac aacaaggggc ttggaagtag taaggagaga ttggagtgag     1860
atagctaagg agactcaggc aaaggtttta gaggctatac ttaaagaggg aagtgttgaa     1920
aaagctgtag aagttgttag agatgttgta gagaaaatag caaaatacag ggttccacttt    1980 gaaaagcttg ttatccatga gcagattacc agggattaa aggactacaa agccattggc     2040
cctcatgtcg cgatagcaaa aagacttgcc gcaagaggga taaagtgaa accgggcaca    2100 ataataagct atatcgttct caaagggagc ggaaagataa gcgatagggt aattttactt     2160
acagaatacg atcctagaaa acacaagtac gatccggact actacataga aaaccaagtt     2220
ttgccggcag tacttaggat actcgaagcg tttggataca gaaaggagga tttaaggtat     2280
caaagctcaa acaaaccgg cttagatgca tggctcaaga ggtag                       2325
```

<210> SEQ ID NO 37
<211> LENGTH: 2328
<212> TYPE: DNA
<213> ORGANISM: Pyrococcus GB-D
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 37

```
atgatacttg acgctgacta catcaccgag gatgggaagc cgattataag gattttcaag      60
aaagaaaacg gcgagtttaa ggttgagtac gacagaaact ttagacctta catttacgct    120
ctcctcaaag atgactcgca gattgatgag gttaggaaga taaccgccga gaggcatggg    180
aagatagtga gaattataga tgccgaaaag gtaaggaaga agttcctggg gaggccgatt    240
gaggtatgga ggctgtactt tgaacaccct caggacnnnc ccgcaataag ggataagata    300
agagagcatt ccgcagttat tgacatcttt gagtacgaca ttccgttcgc gaagaggtac    360
ctaatagaca aaggcctaat tccaatggaa ggcgatgaag agctcaagtt gctcgcattt    420
gacatagaaa ccctctatca cgaagggag gagttcgcga aggggcccat tataatgata    480
agctatgctg atgaggaaga agccaaagtc ataacgtgga aaaagatcga tctcccgtac    540
gtcgaggtag tttccagcga gagggagatg ataaagcggt tcctcaaggt gataagggag    600
aaagatcccg atgttataat tacctacaac ggcgattctt tcgaccttcc ctatctagtt    660
aagagggccg aaaagctcgg gataaagcta cccctgggaa gggacggtag tgagccaaag    720
atgcagaggc ttggggatat gacagcggtg gagataaagg gaaggataca ctttgacctc    780
taccacgtga ttaggagaac gataaacctc ccaacataca ccctcgaggc agtttatgag    840
gcaatcttcg gaaagccaaa ggagaaagtt tacgctcacg agatagctga ggcctgggag    900
actggaaagg gactggagag agttgcaaag tattcaatgg aggatgcaaa ggtaacgtac    960
gagctcggta gggagttctt cccaatggag gcccagcttt caaggttagt cggccagccc   1020
ctgtgggatg tttctaggtc ttcaactggc aacttggtgg agtggtacct cctcaggaag   1080
gcctacgaga ggaatgaatt ggctccaaac aagccggatg agagggagta cgagagaagg   1140
ctaagggaga gctacgctgg gggatacgtt aaggagccgg agaaagggct ctgggagggg   1200
ttagtttccc tagatttcag gagcctgtac ccctcgataa taatcaccca taacgtctca   1260
ccggatacgc tgaacaggga agggtgtagg gaatacgatg tcgccccaga ggttgggcac   1320
aagttctgca aggacttccc gggggtttatc cccagcctgc tcaagaggtt attggatgaa   1380
aggcaagaaa taaaaggaa gatgaaagct tctaaagacc caatcgagaa gaagatgctt   1440
gattacaggc aacgggcaat caaaatcctg gcaaacagct attatgggta ttatgggtac   1500
gcaaaagccc gttggtactg taaggagtgc gcagagagcg ttacggcctg ggggagggaa   1560
tatatagagt tcgtaaggaa ggaactggag gaaaagttcg ggttcaaagt cttatacata   1620
gacacagatg gactctacgc cacaattcct ggggcaaaac ccgaggagat aaagaagaaa   1680
gccctagagt tcgtagatta tataaacgcc aagctcccag ggctgttgga gcttgagtac   1740
gagggcttct acgtgagagg gttcttcgtg acgaagaaga agtatgcgtt gatagatgag   1800
gaagggaaga taatcactag ggggcttgaa atagtcagga gggactggag cgaaatagcc   1860
aaagaaaccc aagcaaaagt cctagaggct atcctaaagc atggcaacgt tgaggaggca   1920
gtaaagatag ttaaggaggt aactgaaaag ctgagcaagt acgaaatacc tccagaaaag   1980
ctagttattt acgagcagat cacgaggccc cttcacgagt acaaggctat aggtccgcac   2040
gttgccgtgg caaaaaggtt agccgctaga ggagtaaagg tgaggcctgg catggtgata   2100
gggtacatag tgctgagggg agacgggcca ataagcaaga gggctatcct tgcagaggag   2160
ttcgatctca ggaagcataa gtatgacgct gagtattaca tagaaaatca ggttttacct   2220
gccgttctta gaatattaga ggcctttggg tacaggaaag aagacctcag gtggcagaag   2280
```

```
actaaacaga caggtcttac ggcatggctt aacatcaaga agaagtaa           2328
```

<210> SEQ ID NO 38
<211> LENGTH: 2328
<212> TYPE: DNA
<213> ORGANISM: Pyrococcus GB-D
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 38

```
atgatacttg acgctgacta catcaccgag gatgggaagc cgattataag gattttcaag    60
aaagaaaacg gcgagtttaa ggttgagtac gacagaaact ttagacctta catttacgct   120
ctcctcaaag atgactcgca gattgatgag gttaggaaga taaccgccga gaggcatggg   180
aagatagtga gaattataga tgccgaaaag gtaaggaaga agttcctggg gaggccgatt   240
gaggtatgga ggctgtactt tgaacaccct caggacnnnc ccgcaataag ggataagata   300
agagagcatt ccgcagttat tgacatcttt gagtacgaca ttccgttcgc gaagaggtac   360
ctaatagaca aaggcctaat tccaatggaa ggcgatgaag agctcaagtt gctcgcattt   420
gacatagaaa ccctctatca cgaaggggag gagttcgcga aggggcccat tataatgata   480
agctatgctg atgaggaaga agccaaagtc ataacgtgga aaaagatcga tctcccgtac   540
gtcgaggtag tttccagcga gagggagatg ataaagcggt tcctcaaggt gataagggag   600
aaagatcccg atgttataat tacctacaac ggcgattctt tcgaccttcc ctatctagtt   660
aagagggccg aaaagctcgg gataaagcta ccccctgggaa gggacggtag tgagccaaag   720
atgcagaggc ttggggatat gacagcggtg gagataaagg gaaggataca ctttgacctc   780
taccacgtga ttaggagaac gataaacctc ccaacataca ccctcgaggc agtttatgag   840
gcaatcttcg gaaagccaaa ggagaaagtt tacgctcacg agatagctga ggcctgggag   900
actggaaagg gactggagag agttgcaaag tattcaatgg aggatgcaaa ggtaacgtac   960
gagctcggta gggagttctt cccaatggag gcccagcttt caaggttagt cggccagccc   1020
ctgtgggatg tttctaggtc ttcaactggc aacttggtgg agtggtacct cctcaggaag  1080
gcctacgaga ggaatgaatt ggctccaaac aagccggatg agagggagta cgagagaagg  1140
ctaagggaga gctacgctgg gggatacgtt aaggagccgg agaaagggct ctgggagggg  1200
ttagtttccc tagatttcag gagcctgtac ccctcgataa taatcaccca taacgtctca  1260
ccggatacgc tgaacaggga agggtgtagg gaatacgatg tcgccccaga ggttgggcac  1320
aagttctgca aggacttccc cgggtttatc cccagcctgc tcaagaggtt attggatgaa  1380
aggcaagaaa taaaaggaa gatgaaagct tctaaagacc caatcgagaa gagatgcttc  1440
gattacaggc aacgggcaat caaaatcctg gcaaacagct attatgggta ttatgggtac  1500
gcaaaagccc gttggtactg taaggagtgc gcagagagcg ttacggcctg ggggagggaa  1560
tatatagagt tcgtaaggaa ggaactggag gaaaagttcg ggttcaaagt cttatacata  1620
gacacagatg gactctacgc cacaattcct ggggcaaaac ccgaggagat aaagaagaaa  1680
gccctagagt tcgtagatta tataaacgcc aagctcccag ggctgttgga gcttgagtac  1740
gagggcttct acgtgagagg gttcttcgtg acgaagaaga gtatgcgtt gatagatgag  1800
gaagggaaga taatcactag ggggcttgaa atagtcagga gggactggag cgaaatagcc  1860
aaagaaaccc aagcaaaagt cctagaggct atcctaaagc atggcaacgt tgaggaggca  1920
gtaaagatag ttaaggaggt aactgaaaag ctgagcaagt acgaaatacc tccagaaaag  1980
```

```
ctagttattt acgagcagat cacgaggccc cttcacgagt acaaggctat aggtccgcac    2040
gttgccgtgg caaaaaggtt agccgctaga ggagtaaagg tgaggcctgg catggtgata    2100
gggtacatag tgctgagggg agacgggcca ataagcaaga gggctatcct tgcagaggag    2160
ttcgatctca ggaagcataa gtatgacgct gagtattaca tagaaaatca ggttttacct    2220
gccgttctta gaatattaga ggcctttggg tacaggaaag aagacctcag gtggcagaag    2280
actaaacaga caggtcttac ggcatggctt aacatcaaga agaagtaa                 2328

<210> SEQ ID NO 39
<211> LENGTH: 2331
<212> TYPE: DNA
<213> ORGANISM: Thermococcus sp.
<220> FEATURE:
<221> NAME/KEY: misc_feature
<222> LOCATION: (277)..(279)
<223> OTHER INFORMATION: NNN = AGA, AGG, CGA, CGC, CGG, CGT (ALL
      POSSIBLE CODONS FOR ARGININE)

<400> SEQUENCE: 39
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacnnnc cggcaatccg cgacaaaata     300
aggaagcacc ccgcggtcat cgacatctac gagtacgaca tacccttcgc caagcgctac     360
ctcatagaca agggcctaat cccgatggaa ggtgaggaag agcttaaact catgtccttc     420
gacatcgaga cgctctacca cgagggagaa gagtttggaa ccgggccgat tctgatgata     480
agctacgccg atgaaagcga ggcgcgcgtg ataacctgga gaagatcga ccttccttac      540 gttgaggttg tctccaccga aaggagatg attaagcgct tcttgagggt cgttaaggag      600
aaggacccgg acgtgctgat aacatacaac ggcgacaact tcgacttcgc ctacctgaaa     660
aagcgctgtg agaagcttgg cgtgagcttt acccctcggga gggacgggag cgagccgaag     720
atacagcgca tgggggacag gtttgcggtc gaggtgaagg gcagggtaca cttcgacctt     780
tatccagtca taaggcgcac cataaacctc ccgacctaca cccttgaggc tgtatacgag     840
gcggttttcg gcaagcccaa ggagaaggtc tacgccgagg agatagccac cgcctgggag     900 accgcgagg ggcttgagag ggtcgcgcgc tactcgatgg aggacgcgag ggttacctac     960
gagcttggca gggagttctt cccgatggag gcccagcttt ccaggctcat cggccaaggc    1020
ctctgggacg tttcccgctc cagcaccggc aacctcgtcg agtggttcct cctaaggaag    1080
gcctacgaga ggaacgaact cgctcccaac aagcccgacg agagggagct ggcgaggaga    1140 aggggggggct acgccggtgg ctacgtcaag gagccggagc ggggactgtg gacaatatc    1200 gtgtatctag actttcgtag tctctaccct tcaatcataa tcacccacaa cgtctcgcca    1260
gatacgctca accgcgaggg tgtaggagc tacgacgttg cccccgaggt cggtcacaag    1320
ttctgcaagg acttccccgg cttcattccg agcctgctcg gaaacctgct ggaggaaagg    1380
cagaagataa agaggaagat gaaggcaact ctcgacccgc tggagaagaa tctcctcgat    1440
tacaggcaac gcgccatcaa gattctcgcc aacagctact acggctacta cggctatgcc    1500
agggcaagat ggtactgcag ggagtgcgcc gagagcgtta cggcatgggg aagggagtac    1560
atcgaaatgg tcatcagaga gcttgaggaa aagttcggtt ttaaagtcct ctatgcagac    1620
```

```
acagacggtc tccatgccac cattcctgga gcggacgctg aaacagtcaa gaaaaaggca   1680
atggagttct taaactatat caatcccaaa ctgcccggcc ttctcgaact cgaatacgag   1740
ggcttctacg tcagggcgtt cttcgtcacg aagaaaaagt acgcggtcat cgacgaggag   1800
ggcaagataa ccacgcgcgg gcttgagata gtcaggcgcg actggagcga gatagcgaag   1860
gagacgcagg cgagggtttt ggaggcgata ctcaggcacg gtgacgttga agaggccgtc   1920
agaattgtca gggaagtcac cgaaaagctg agcaagtacg aggttccgcc ggagaagctg   1980
gttatccacg agcagataac gcgcgagctc aaggactaca aggccaccgg cccgcacgta   2040
gccatagcga agcgtttggc cgccagaggt gttaaaatcc ggcccggaac tgtgataagc   2100
tacatcgttc tgaagggctc cggaaggata ggcgacaggg cgattcccct cgacgagttc   2160
gacccgacga agcacaagta cgatgcggac tactacatcg agaaccaggt tctgccggca   2220
gttgagagaa tcctcagggc cttcggctac cgcaaggaag acctgcgcta ccagaagacg   2280
aggcaggtcg ggcttggcgc gtggctgaag ccgaagggga agaagaagtg a             2331
```

<210> SEQ ID NO 40
<211> LENGTH: 2331
<212> TYPE: DNA
<213> ORGANISM: Thermococcus sp.
<220> FEATURE:
<221> NAME/KEY: misc_feature
<222> LOCATION: (277)..(279)
<223> OTHER INFORMATION: NNN = GAA, GAG (ALL CODONS FOR GLUTAMIC ACID)

<400> SEQUENCE: 40

```
atgatccttg acgttgatta catcaccgag aatggaaagc ccgtcatcag ggtcttcaag     60
aaggagaacg cgagttcag gattgaatac gaccgcgagt tcgagcccta cttctacgcg    120
ctcctcaggg acgactctgc catcgaagaa atcaaaaaga taaccgcgga gaggcacggc    180
agggtcgtta aggttaagcg cgcggagaag gtgaagaaaa agttcctcgg caggtctgtg    240
gaggtctggg tcctctactt cacgcacccg caggacnnnc cggcaatccg cgacaaaata    300
aggaagcacc ccgcggtcat cgacatctac gagtacgaca taccccttcgc caagcgctac    360 ctcatagaca agggcctaat cccgatggaa ggtgaggaag agcttaaact catgtccttc    420
gacatcgaga cgctctacca cgagggagaa gagtttggaa ccggggccgat tctgatgata    480 agctacgccg atgaaagcga ggcgcgcgtg ataacctgga gaagatcga ccttccttac    540 gttgaggttg tctccaccga gaaggagatg attaagcgct tcttgagggt cgttaaggag    600
aaggacccgg acgtgctgat aacatacaac ggcgacaact tcgacttcgc ctacctgaaa    660
aagcgctgtg agaagcttgg cgtgagcttt accctcggga gggacgggag cgagccgaag    720
atacagcgca tggggacag gtttgcggtc gaggtgaagg gcagggtaca cttcgacctt    780
tatccagtca taaggcgcac cataaacctc ccgacctaca cccttgaggc tgtatacgag    840
gcggttttcg gcaagcccaa ggagaaggtc tacgccgagg agatagccac cgcctgggag    900
accggcgagg ggcttgagag ggtcgcgcgc tactcgatgg aggacgcgag ggttacctac    960
gagcttggca gggagttctt cccgatggag gcccagcttt ccaggctcat cggccaaggc   1020
ctctgggacg tttcccgctc cagcaccggc aacctcgtcg agtggttcct cctaaggaag   1080
gcctacgaga ggaacgaact cgctcccaac aagcccgacg agggagct ggcgaggaga    1140 aggggggggct acgccggtgg ctacgtcaag gagccggagc ggggactgtg ggacaatatc    1200
gtgtatctag actttcgtag tctctaccct tcaatcataa tcacccacaa cgtctccgca   1260
```

-continued

```
gatacgctca accgcgaggg gtgtaggagc tacgacgttg cccccgaggt cggtcacaag    1320
ttctgcaagg acttccccgg cttcattccg agcctgctcg gaaacctgct ggaggaaagg    1380
cagaagataa agaggaagat gaaggcaact ctcgacccgc tggagaagaa tctcctcgat    1440
tacaggcaac gcgccatcaa gattctcgcc aacagctact acggctacta cggctatgcc    1500
agggcaagat ggtactgcag ggagtgcgcc gagagcgtta cggcatgggg aagggagtac    1560
atcgaaatgg tcatcagaga gcttgaggaa aagttcggtt ttaaagtcct ctatgcagac    1620
acagacggtc tccatgccac cattcctgga gcggacgctg aaacagtcaa gaaaaaggca    1680
atggagttct taaactatat caatcccaaa ctgcccggcc ttctcgaact cgaatacgag    1740
ggcttctacg tcagggctt cttcgtcacg aagaaaaagt acgcggtcat cgacgaggag    1800
ggcaagataa ccacgcgcgg gcttgagata gtcaggcgcg actggagcga gatagcgaag    1860
gagacgcagg cgagggtttt ggaggcgata ctcaggcacg gtgacgttga agaggccgtc    1920
agaattgtca gggaagtcac cgaaaagctg agcaagtacg aggttccgcc ggagaagctg    1980
gttatccacg agcagataac gcgcgagctc aaggactaca aggccaccgg cccgcacgta    2040
gccatagcga agcgtttggc cgccagaggt gttaaaatcc ggcccggaac tgtgataagc    2100
tacatcgttc tgaagggctc cggaaggata ggcgacaggg cgattcccct cgacgagttc    2160
gacccgacga agcacaagta cgatgcggac tactacatcg agaaccaggt tctgccggca    2220
gttgagagaa tcctcagggc cttcggctac cgcaaggaag acctgcgcta ccagaagacg    2280
aggcaggtcg ggcttggcgc gtggctgaag ccgaagggga agaagaagtg a             2331
```

<210> SEQ ID NO 41
<211> LENGTH: 775
<212> TYPE: PRT
<213> ORGANISM: Pyrococcus furiosus

<400> SEQUENCE: 41

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190
```

-continued

```
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
            275                 280                 285
Lys Val Tyr Ala Asp Glu Ile Ala Lys Ala Trp Glu Ser Gly Glu Asn
            290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
            325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
            355                 360                 365
Pro Asn Lys Pro Ser Glu Glu Tyr Gln Arg Arg Leu Arg Glu Ser
            370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
            405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
            450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
            530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
            565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
            595                 600                 605
```

-continued

```
Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 42
<211> LENGTH: 775
<212> TYPE: PRT
<213> ORGANISM: Pyrococcus furiosus

<400> SEQUENCE: 42

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Glu Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205
```

-continued

```
Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620
```

```
Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
770                 775

<210> SEQ ID NO 43
<211> LENGTH: 775
<212> TYPE: PRT
<213> ORGANISM: Pyrococcus furiosus

<400> SEQUENCE: 43

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220
```

-continued

```
Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Val Ala
    355                 360                 365

Pro Asn Lys Pro Ser Glu Glu Glu Tyr Gln Arg Arg Leu Arg Glu Ser
370                 375                 380

Tyr Thr Pro Gly Phe Val Lys Glu Pro Leu Lys Gly Leu Trp Glu Asn
385                 390                 395                 400

Ile Val Tyr Leu Asp Phe Arg Ala Leu Tyr Pro Ser Ile Ile Ile Thr
            405                 410                 415

His Asn Val Ser Pro Asp Thr Leu Asn Leu Glu Gly Cys Lys Asn Tyr
        420                 425                 430

Asp Ile Ala Pro Gln Val Gly His Lys Phe Cys Lys Asp Ile Pro Gly
    435                 440                 445

Phe Ile Pro Ser Leu Leu Gly His Leu Leu Glu Glu Arg Gln Lys Ile
450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
            565                 570                 575

Glu Leu Glu Tyr Glu Gly Phe Tyr Lys Arg Gly Phe Phe Val Thr Lys
        580                 585                 590

Lys Arg Tyr Ala Val Ile Asp Glu Glu Gly Lys Val Ile Thr Arg Gly
    595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640
```

```
Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Lys Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
        740                 745                 750

Lys Glu Asp Leu Arg Tyr Gln Lys Thr Arg Gln Val Gly Leu Thr Ser
    755                 760                 765

Trp Leu Asn Ile Lys Lys Ser
770                 775

<210> SEQ ID NO 44
<211> LENGTH: 775
<212> TYPE: PRT
<213> ORGANISM: Pyrococcus furiosus

<400> SEQUENCE: 44

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
            85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Val Ser Ser Glu Arg Glu Met Ile Lys
        180                 185                 190

Arg Phe Leu Arg Ile Ile Arg Glu Lys Asp Pro Asp Ile Ile Val Thr
    195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240
```

-continued

```
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
            580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
    610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
```

-continued

```
Pro Pro Glu Lys Leu Ala Ile Tyr Glu Gln Ile Thr Arg Pro Leu His
        660                 665                 670

Glu Tyr Lys Ala Ile Gly Pro His Val Ala Val Ala Lys Lys Leu Ala
    675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 45
<211> LENGTH: 775
<212> TYPE: PRT
<213> ORGANISM: Pyrococcus furiosus

<400> SEQUENCE: 45

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Glu Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255
```

-continued

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
        370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

```
Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
                755                 760                 765

Trp Leu Asn Ile Lys Lys Ser
        770                 775

<210> SEQ ID NO 46
<211> LENGTH: 775
<212> TYPE: PRT
<213> ORGANISM: Pyrococcus furiosus

<400> SEQUENCE: 46

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
        50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Ile Leu Ala Phe Ala Ile Ala Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270
```

-continued

Tyr Thr Leu Glu Ala Val Tyr Glu Ala Ile Phe Gly Lys Pro Lys Glu
         275                 280                 285

Lys Val Tyr Ala Asp Glu Ile Ala Lys Ala Trp Glu Ser Gly Glu Asn
         290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

```
Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 47
<211> LENGTH: 775
<212> TYPE: PRT
<213> ORGANISM: Thermococcus sp.

<400> SEQUENCE: 47

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Arg Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285
```

```
Lys Val Tyr Ala His Glu Ile Ala Glu Ala Trp Glu Thr Gly Lys Gly
    290                 295                 300
Leu Glu Arg Val Ala Lys Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Val Gly Gln Pro Leu Trp Asp Val Ser Arg Ser Thr Gly Asn Leu
            340                 345                 350
Val Glu Trp Tyr Leu Leu Arg Lys Ala Tyr Glu Arg Asn Glu Leu Ala
        355                 360                 365
Pro Asn Lys Pro Asp Glu Arg Glu Tyr Glu Arg Arg Leu Arg Glu Ser
    370                 375                 380
Tyr Ala Gly Gly Tyr Val Lys Glu Pro Glu Lys Gly Leu Trp Glu Gly
385                 390                 395                 400
Leu Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Arg Glu Tyr
            420                 425                 430
Asp Val Ala Pro Glu Val Gly His Lys Phe Cys Lys Asp Phe Pro Gly
        435                 440                 445
Phe Ile Pro Ser Leu Leu Lys Arg Leu Leu Asp Glu Arg Gln Glu Ile
    450                 455                 460
Lys Arg Lys Met Lys Ala Ser Lys Asp Pro Ile Glu Lys Lys Met Leu
465                 470                 475                 480
Asp Tyr Arg Gln Arg Ala Ile Lys Ile Leu Ala Asn Ser Tyr Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Glu Tyr Ile Glu Phe Val Arg Lys Glu
        515                 520                 525
Leu Glu Glu Lys Phe Gly Phe Lys Val Leu Tyr Ile Asp Thr Asp Gly
530                 535                 540
Leu Tyr Ala Thr Ile Pro Gly Ala Lys Pro Glu Glu Ile Lys Lys Lys
545                 550                 555                 560
Ala Leu Glu Phe Val Asp Tyr Ile Asn Ala Lys Leu Pro Gly Leu Leu
                565                 570                 575
Glu Leu Glu Tyr Glu Gly Phe Tyr Val Arg Gly Phe Phe Val Thr Lys
            580                 585                 590
Lys Lys Tyr Ala Leu Ile Asp Glu Glu Gly Lys Ile Ile Thr Arg Gly
        595                 600                 605
Leu Glu Ile Val Arg Arg Asp Trp Ser Glu Ile Ala Lys Glu Thr Gln
    610                 615                 620
Ala Lys Val Leu Glu Ala Ile Leu Lys His Gly Asn Val Glu Glu Ala
625                 630                 635                 640
Val Lys Ile Val Lys Glu Val Thr Glu Lys Leu Ser Lys Tyr Glu Ile
                645                 650                 655
Pro Pro Glu Lys Leu Val Ile Tyr Glu Gln Ile Thr Arg Pro Leu His
            660                 665                 670
Glu Tyr Lys Ala Ile Gly Pro His Val Ala Val Ala Lys Arg Leu Ala
        675                 680                 685
Ala Arg Gly Val Lys Val Arg Pro Gly Met Val Ile Gly Tyr Ile Val
    690                 695                 700
```

```
Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Ile Glu Asn
            725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
            755                 760                 765

Trp Leu Asn Ile Lys Lys Lys
            770             775

<210> SEQ ID NO 48
<211> LENGTH: 775
<212> TYPE: PRT
<213> ORGANISM: Thermococcus sp.

<400> SEQUENCE: 48

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Lys Lys Phe Leu Gly Arg Pro Ile
65                  70                  75                  80

Glu Val Trp Arg Leu Tyr Phe Glu His Pro Gln Asp Glu Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300
```

-continued

```
Leu Glu Arg Val Ala Lys Tyr Ser Met Glu Asp Ala Lys Val Thr Tyr
305                 310                 315                 320

Glu Leu Gly Arg Glu Phe Pro Met Glu Ala Gln Leu Ser Arg Leu
            325                 330                 335

Val Gly Gln Pro Leu Trp Asp Val Ser Arg Ser Thr Gly Asn Leu
            340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
            450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
            675                 680                 685

Ala Arg Gly Val Lys Val Arg Pro Gly Met Val Ile Gly Tyr Ile Val
            690                 695                 700

Leu Arg Gly Asp Gly Pro Ile Ser Lys Arg Ala Ile Leu Ala Glu Glu
705                 710                 715                 720
```

```
Phe Asp Leu Arg Lys His Lys Tyr Asp Ala Glu Tyr Tyr Ile Glu Asn
            725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
            755                 760                 765

Trp Leu Asn Ile Lys Lys Lys
            770             775

<210> SEQ ID NO 49
<211> LENGTH: 773
<212> TYPE: PRT
<213> ORGANISM: Thermococcus gorgonarius

<400> SEQUENCE: 49

Met Ile Leu Asp Thr Asp Tyr Ile Thr Glu Asp Gly Lys Pro Val Ile
 1               5                  10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Arg Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320
```

-continued

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Thr Gly Asn Leu
            340                 345                 350

Val Glu Trp Phe Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
            435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
    515                 520                 525

Glu Glu Lys Phe Gly Phe Lys Val Leu Tyr Ala Asp Thr Asp Gly Phe
                530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
    595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

```
Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
            755                 760                 765

Leu Lys Pro Lys Thr
        770

<210> SEQ ID NO 50
<211> LENGTH: 773
<212> TYPE: PRT
<213> ORGANISM: Thermococcus gorgonarius

<400> SEQUENCE: 50

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Glu Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335
```

```
Val Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
                355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
                435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Gln Tyr Ile Glu Thr Thr Ile Arg Glu Ile
                515                 520                 525

Glu Glu Lys Phe Gly Phe Lys Val Leu Tyr Ala Asp Thr Asp Gly Phe
                530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
                690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750
```

<210> SEQ ID NO 51
<211> LENGTH: 774
<212> TYPE: PRT
<213> ORGANISM: Thermococcus kodakaraensis

<400> SEQUENCE: 51

```
Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
50                  55                  60
Val Lys Arg Val Glu Lys Val Gln Lys Lys Phe Leu Gly Arg Pro Val
65                  70                  75                  80
Glu Val Trp Lys Leu Tyr Phe Thr His Pro Gln Asp Arg Pro Ala Ile
                85                  90                  95
Arg Asp Lys Ile Arg Glu His Gly Ala Val Ile Asp Ile Tyr Glu Tyr
            100                 105                 110
Asp Ile Pro Phe Ala Lys Arg Tyr Leu Ile Asp Lys Gly Leu Val Pro
        115                 120                 125
Met Glu Gly Asp Glu Glu Leu Lys Met Leu Ala Phe Asp Ile Gln Thr
130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Pro Ala Trp Glu Thr Gly Glu Asn
290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
```

Glu Asp Leu Arg Tyr Gln Lys Thr Arg Gln Val Gly Leu Gly Ala Trp
                755                 760                 765
Leu Lys Pro Lys Thr
            770

-continued

```
Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765
```

Leu Lys Pro Lys Gly Thr
      770

<210> SEQ ID NO 52
<211> LENGTH: 774
<212> TYPE: PRT
<213> ORGANISM: Thermococcus kodakaraensis

<400> SEQUENCE: 52

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Glu Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

-continued

```
Pro Asn Lys Pro Asp Glu Lys Glu Leu Ala Arg Arg Arg Gln Ser Tyr
    370                 375                 380
Glu Gly Gly Tyr Val Lys Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
    530                 535                 540
Phe Ala Thr Ile Pro Gly Ala Asp Ala Glu Thr Val Lys Lys Lys Ala
545                 550                 555                 560
Met Glu Phe Leu Asn Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Ser Ala Trp
        755                 760                 765
Leu Lys Pro Lys Gly Thr
    770
```

<210> SEQ ID NO 53
<211> LENGTH: 774
<212> TYPE: PRT
<213> ORGANISM: Thermococcus litoralis

<400> SEQUENCE: 53

```
Met Ile Leu Asp Thr Asp Tyr Ile Thr Lys Asp Gly Lys Pro Ile Ile
 1               5                  10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Arg Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
    370                 375                 380
```

```
Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
                500                 505                 510

Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
                580                 585                 590

Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
        610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
                660                 665                 670

Leu Lys Asp Tyr Lys Ala Ile Gly Pro His Val Ala Ile Ala Lys Arg
            675                 680                 685

Leu Ala Ala Arg Gly Ile Lys Val Lys Pro Gly Thr Ile Ile Ser Tyr
        690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770
```

<210> SEQ ID NO 54
<211> LENGTH: 774

<212> TYPE: PRT
<213> ORGANISM: Thermococcus litoralis

<400> SEQUENCE: 54

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Glu Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400

```
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Asp Ile Lys Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
            660                 665                 670
Leu Lys Asp Tyr Lys Ala Ile Gly Pro His Val Ala Ile Ala Lys Arg
        675                 680                 685
Leu Ala Ala Arg Gly Ile Lys Val Lys Pro Gly Thr Ile Ile Ser Tyr
    690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Arg Tyr Gln Ser Ser Lys Gln Thr Gly Leu
        755                 760                 765
Asp Ala Trp Leu Lys Arg
    770

<210> SEQ ID NO 55
<211> LENGTH: 776
<212> TYPE: PRT
<213> ORGANISM: Pyrococcus GB-D
```

<400> SEQUENCE: 55

```
Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Arg Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Leu Met Ser Phe Asp Ile Glu Thr
130                 135                 140

Leu Tyr His Glu Gly Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415
```

Asn Val Ser Pro Asp Thr Leu Asn Arg Glu Gly Cys Arg Ser Tyr Asp
            420                 425                 430
Val Ala Pro Glu Val Gly His Lys Phe Cys Lys Asp Phe Pro Gly Phe
        435                 440                 445
Ile Pro Ser Leu Leu Gly Asn Leu Leu Glu Glu Arg Gln Lys Ile Lys
    450                 455                 460
Arg Lys Met Lys Ala Thr Leu Asp Pro Leu Glu Lys Asn Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Arg Glu Cys Ala Glu Ser
            500                 505                 510
Val Thr Ala Trp Gly Arg Glu Tyr Ile Glu Met Val Ile Arg Glu Leu
        515                 520                 525
Glu Glu Lys Phe Gly Phe Lys Val Leu Tyr Ala Asp Thr Asp Gly Leu
    530                 535                 540
His Ala Thr Ile Pro Gly Ala Asp Ala Glu Thr Val Lys Lys Lys Ala
545                 550                 555                 560
Met Glu Phe Leu Asn Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Arg His Gly Asp Val Glu Glu Ala Val
625                 630                 635                 640
Arg Ile Val Arg Glu Val Thr Glu Lys Leu Ser Lys Tyr Glu Val Pro
                645                 650                 655
Pro Glu Lys Leu Val Ile His Glu Gln Ile Thr Arg Glu Leu Lys Asp
            660                 665                 670
Tyr Lys Ala Thr Gly Pro His Val Ala Ile Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Asp Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Gly Ala Trp
        755                 760                 765
Leu Lys Pro Lys Gly Lys Lys Lys
    770                 775

<210> SEQ ID NO 56
<211> LENGTH: 776
<212> TYPE: PRT
<213> ORGANISM: Pyrococcus GB-D

<400> SEQUENCE: 56

Met Ile Leu Asp Val Asp Tyr Ile Thr Glu Asn Gly Lys Pro Val Ile

-continued

```
1               5               10              15
Arg Val Phe Lys Lys Glu Asn Gly Glu Phe Arg Ile Glu Tyr Asp Arg
                20              25              30
Glu Phe Glu Pro Tyr Phe Tyr Ala Leu Leu Arg Asp Asp Ser Ala Ile
                35              40              45
Glu Glu Ile Lys Lys Ile Thr Ala Glu Arg His Gly Arg Val Val Lys
                50              55              60
Val Lys Arg Ala Glu Lys Val Lys Lys Phe Leu Gly Arg Ser Val
65                  70              75              80
Glu Val Trp Val Leu Tyr Phe Thr His Pro Gln Asp Glu Pro Ala Ile
                85              90              95
Arg Asp Lys Ile Arg Lys His Pro Ala Val Ile Asp Ile Tyr Glu Tyr
                100             105             110
Asp Ile Pro Phe Ala Lys Arg Tyr Leu Ile Asp Lys Gly Leu Ile Pro
                115             120             125
Met Glu Gly Glu Glu Leu Lys Leu Met Ser Phe Asp Ile Glu Thr
                130             135             140
Leu Tyr His Glu Gly Glu Glu Phe Gly Thr Gly Pro Ile Leu Met Ile
145             150             155             160
Ser Tyr Ala Asp Glu Ser Glu Ala Arg Val Ile Thr Trp Lys Lys Ile
                165             170             175
Asp Leu Pro Tyr Val Glu Val Val Ser Thr Glu Lys Glu Met Ile Lys
                180             185             190
Arg Phe Leu Arg Val Val Lys Glu Lys Asp Pro Asp Val Leu Ile Thr
                195             200             205
Tyr Asn Gly Asp Asn Phe Asp Phe Ala Tyr Leu Lys Lys Arg Cys Glu
                210             215             220
Lys Leu Gly Val Ser Phe Thr Leu Gly Arg Asp Gly Ser Glu Pro Lys
225             230             235             240
Ile Gln Arg Met Gly Asp Arg Phe Ala Val Glu Val Lys Gly Arg Val
                245             250             255
His Phe Asp Leu Tyr Pro Val Ile Arg Arg Thr Ile Asn Leu Pro Thr
                260             265             270
Tyr Thr Leu Glu Ala Val Tyr Glu Ala Val Phe Gly Lys Pro Lys Glu
                275             280             285
Lys Val Tyr Ala Glu Glu Ile Ala Thr Ala Trp Glu Thr Gly Glu Gly
                290             295             300
Leu Glu Arg Val Ala Arg Tyr Ser Met Glu Asp Ala Arg Val Thr Tyr
305             310             315             320
Glu Leu Gly Arg Glu Phe Phe Pro Met Glu Ala Gln Leu Ser Arg Leu
                325             330             335
Ile Gly Gln Gly Leu Trp Asp Val Ser Arg Ser Ser Thr Gly Asn Leu
                340             345             350
Val Glu Trp Phe Leu Leu Arg Lys Ala Tyr Glu Arg Asn Glu Leu Ala
                355             360             365
Pro Asn Lys Pro Asp Glu Arg Glu Leu Ala Arg Arg Gly Gly Tyr
                370             375             380
Ala Gly Gly Tyr Val Lys Glu Pro Glu Arg Gly Leu Trp Asp Asn Ile
385             390             395             400
Val Tyr Leu Asp Phe Arg Ser Leu Tyr Pro Ser Ile Ile Ile Thr His
                405             410             415
Asn Val Ser Pro Asp Thr Leu Asn Arg Glu Gly Cys Arg Ser Tyr Asp
                420             425             430
```

```
Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
        450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
        485                 490                 495

Tyr Gly Tyr Ala Arg Ala Arg Trp Tyr Cys Arg Glu Cys Ala Glu Ser
        500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
        565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
        645                 650                 655

Pro Glu Lys Leu Val Ile His Glu Gln Ile Thr Arg Glu Leu Lys Asp
        660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
        725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
        770                 775

<210> SEQ ID NO 57
<211> LENGTH: 2322
<212> TYPE: DNA
<213> ORGANISM: Thermococcus gorgonarius
<220> FEATURE:
<221> NAME/KEY: misc_feature
<222> LOCATION: (277)..(279)
<223> OTHER INFORMATION: NNN = AGA, AGG, CGA, CGC, CGG, CGT
<220> FEATURE:
<221> NAME/KEY: CDS
<222> LOCATION: (1)..(2322)
```

<223> OTHER INFORMATION:

<400> SEQUENCE: 57

```
atg atc ctc gat aca gac tac ata act gag gat gga aag ccc gtc atc      48
Met Ile Leu Asp Thr Asp Tyr Ile Thr Glu Asp Gly Lys Pro Val Ile
1               5                   10                  15 agg atc ttc aag aag gag aac ggc gag ttc aaa ata gac tac gac aga      96
Arg Ile Phe Lys Lys Glu Asn Gly Glu Phe Lys Ile Asp Tyr Asp Arg
            20                  25                  30 aac ttt gag cca tac atc tac gcg ctc ttg aag gac gac tct gcg att     144
Asn Phe Glu Pro Tyr Ile Tyr Ala Leu Leu Lys Asp Asp Ser Ala Ile
        35                  40                  45 gag gac gtc aag aag ata act gcc gag agg cac ggc act acc gtt agg     192
Glu Asp Val Lys Lys Ile Thr Ala Glu Arg His Gly Thr Thr Val Arg
    50                  55                  60 gtt gtc agg gcc gag aaa gtg aag aag aag ttc cta ggc agg ccg ata     240
Val Val Arg Ala Glu Lys Val Lys Lys Lys Phe Leu Gly Arg Pro Ile
65                  70                  75                  80 gag gtc tgg aag ctc tac ttc act cac ccc cag gac nnn ccc gca atc     288
Glu Val Trp Lys Leu Tyr Phe Thr His Pro Gln Asp Xaa Pro Ala Ile
                85                  90                  95 agg gac aag ata aag gag cat cct gcc gtt gtg gac atc tac gag tac     336
Arg Asp Lys Ile Lys Glu His Pro Ala Val Val Asp Ile Tyr Glu Tyr
            100                 105                 110 gac atc ccc ttc gcg aag cgc tac ctc ata gac aaa ggc tta atc ccg     384
Asp Ile Pro Phe Ala Lys Arg Tyr Leu Ile Asp Lys Gly Leu Ile Pro
        115                 120                 125 atg gag ggc gac gag gaa ctt aag atg ctc gcc ttc gac atc gag acg     432
Met Glu Gly Asp Glu Glu Leu Lys Met Leu Ala Phe Asp Ile Glu Thr
    130                 135                 140 ctc tat cac gag ggc gag gag ttc gcc gaa ggg cct atc ctg atg ata     480
Leu Tyr His Glu Gly Glu Glu Phe Ala Glu Gly Pro Ile Leu Met Ile
145                 150                 155                 160 agc tac gcc gac gag gaa ggg gcg cgc gtt att acc tgg aag aat atc     528
Ser Tyr Ala Asp Glu Glu Gly Ala Arg Val Ile Thr Trp Lys Asn Ile
                165                 170                 175 gac ctt ccc tat gtc gac gtc gtt tcc acc gag aag gag atg ata aag     576
Asp Leu Pro Tyr Val Asp Val Val Ser Thr Glu Lys Glu Met Ile Lys
            180                 185                 190 cgc ttc ctc aag gtc gtc aag gaa aag gat ccc gac gtc ctc ata acc     624
Arg Phe Leu Lys Val Val Lys Glu Lys Asp Pro Asp Val Leu Ile Thr
        195                 200                 205 tac aac ggc gac aac ttc gac ttc gcc tac ctc aag aag cgc tcc gag     672
Tyr Asn Gly Asp Asn Phe Asp Phe Ala Tyr Leu Lys Lys Arg Ser Glu
    210                 215                 220 aag ctc gga gtc aag ttc atc ctc gga agg gaa ggg agc gag ccg aaa     720
Lys Leu Gly Val Lys Phe Ile Leu Gly Arg Glu Gly Ser Glu Pro Lys
225                 230                 235                 240 atc cag cgc atg ggc gat cgc ttt gcg gtg gag gtc aag gga agg att     768
Ile Gln Arg Met Gly Asp Arg Phe Ala Val Glu Val Lys Gly Arg Ile
                245                 250                 255 cac ttc gac ctc tac ccc gtc att agg aga acg att aac ctc ccc act     816
His Phe Asp Leu Tyr Pro Val Ile Arg Arg Thr Ile Asn Leu Pro Thr
            260                 265                 270 tac acc ctt gag gca gta tat gaa gcc atc ttt gga cag ccg aag gag     864
Tyr Thr Leu Glu Ala Val Tyr Glu Ala Ile Phe Gly Gln Pro Lys Glu
        275                 280                 285 aag gtc tac gct gag gag ata gcg cag gcc tgg gaa acg ggc gag gga     912
Lys Val Tyr Ala Glu Glu Ile Ala Gln Ala Trp Glu Thr Gly Glu Gly
    290                 295                 300
```

|   |   |   |   |   |   |   |   |   |   |   |   |   |   |   |   |
|---|---|---|---|---|---|---|---|---|---|---|---|---|---|---|---|
| tta | gaa | agg | gtg | gcc | cgc | tac | tcg | atg | gag | gac | gca | aag | gta | acc | tat | 960 |
| Leu | Glu | Arg | Val | Ala | Arg | Tyr | Ser | Met | Glu | Asp | Ala | Lys | Val | Thr | Tyr |
| 305 |  |  |  |  | 310 |  |  |  |  | 315 |  |  |  |  | 320 |

```
gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                    325                 330                 335 gta ggc cag agc ctc tgg gat gta tct cgc tcg agt acc gga aac ctc     1056
Val Gly Gln Ser Leu Trp Asp Val Ser Arg Ser Ser Thr Gly Asn Leu
                340                 345                 350 gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
            355                 360                 365 cca aac aag ccg gac gag agg gag ctg gca aga aga agg gag agc tac     1152
Pro Asn Lys Pro Asp Glu Arg Glu Leu Ala Arg Arg Arg Glu Ser Tyr
370                 375                 380 gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400 gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                    405                 410                 415 aac gtc tcc cct gat aca ctc aac agg gag ggt tgt gag gag tac gac     1296
Asn Val Ser Pro Asp Thr Leu Asn Arg Glu Gly Cys Glu Glu Tyr Asp
                420                 425                 430 gtg gct cct cag gta ggc cat aag ttc tgc aag gac ttc ccc ggc ttc     1344
Val Ala Pro Gln Val Gly His Lys Phe Cys Lys Asp Phe Pro Gly Phe
            435                 440                 445 atc cca agc ctc ctc gga gac ctc ttg gag gag aga cag aag gta aag     1392
Ile Pro Ser Leu Leu Gly Asp Leu Leu Glu Glu Arg Gln Lys Val Lys
450                 455                 460 aag aag atg aag gcc act ata gac cca atc gag aag aaa ctc ctc gat     1440
Lys Lys Met Lys Ala Thr Ile Asp Pro Ile Glu Lys Lys Leu Leu Asp
465                 470                 475                 480 tac agg caa cga gca atc aaa atc ctt gct aat agc ttc tac ggt tac     1488
Tyr Arg Gln Arg Ala Ile Lys Ile Leu Ala Asn Ser Phe Tyr Gly Tyr
                    485                 490                 495 tac ggc tat gca aag gcc cgc tgg tac tgc aag gag tgc gcc gag agc     1536
Tyr Gly Tyr Ala Lys Ala Arg Trp Tyr Cys Lys Glu Cys Ala Glu Ser
                500                 505                 510 gtt acc gct tgg ggc agg cag tac atc gag acc acg ata agg gaa ata     1584
Val Thr Ala Trp Gly Arg Gln Tyr Ile Glu Thr Thr Ile Arg Glu Ile
            515                 520                 525 gag gag aaa ttt ggc ttt aaa gtc ctc tac gcg gac aca gat gga ttt     1632
Glu Glu Lys Phe Gly Phe Lys Val Leu Tyr Ala Asp Thr Asp Gly Phe
530                 535                 540 ttc gca aca ata cct gga gcg gac gcc gaa acc gtc aaa aag aag gca     1680
Phe Ala Thr Ile Pro Gly Ala Asp Ala Glu Thr Val Lys Lys Lys Ala
545                 550                 555                 560 aag gag ttc ctg gac tac atc aac gcc aaa ctg ccc ggc ctg ctc gaa     1728
Lys Glu Phe Leu Asp Tyr Ile Asn Ala Lys Leu Pro Gly Leu Leu Glu
                    565                 570                 575 ctc gaa tac gag ggc ttc tac aag cgc ggc ttc ttc gtg acg aag aag     1776
Leu Glu Tyr Glu Gly Phe Tyr Lys Arg Gly Phe Phe Val Thr Lys Lys
                580                 585                 590 aag tac gcg gtt ata gac gag gag gac aag ata acg acg cgc ggg ctt     1824
Lys Tyr Ala Val Ile Asp Glu Glu Asp Lys Ile Thr Thr Arg Gly Leu
            595                 600                 605 gaa ata gtt agg cgt gac tgg agc gag ata gcg aag gag acg cag gcg     1872
Glu Ile Val Arg Arg Asp Trp Ser Glu Ile Ala Lys Glu Thr Gln Ala
```

-continued

| | | | | | | | | | | | | | | |
|---|---|---|---|---|---|---|---|---|---|---|---|---|---|---|
| | 610 | | | | 615 | | | | | 620 | | | | |
| agg | gtt | ctt | gag | gcg | ata | cta | aag | cac | ggt | gac | gtt | gaa | gaa | gcg | gta | 1920 |
| Arg | Val | Leu | Glu | Ala | Ile | Leu | Lys | His | Gly | Asp | Val | Glu | Glu | Ala | Val |
| 625 | | | | | 630 | | | | | 635 | | | | | 640 |

| agg | att | gtc | aaa | gag | gtt | acg | gag | aag | ctg | agc | aag | tac | gag | gtt | cca | 1968 |
|---|---|---|---|---|---|---|---|---|---|---|---|---|---|---|---|---|
| Arg | Ile | Val | Lys | Glu | Val | Thr | Glu | Lys | Leu | Ser | Lys | Tyr | Glu | Val | Pro |
| | | | | 645 | | | | | 650 | | | | | 655 | |

| ccg | gag | aag | ctg | gtc | atc | tac | gag | cag | ata | acc | cgc | gac | ctg | aag | gac | 2016 |
|---|---|---|---|---|---|---|---|---|---|---|---|---|---|---|---|---|
| Pro | Glu | Lys | Leu | Val | Ile | Tyr | Glu | Gln | Ile | Thr | Arg | Asp | Leu | Lys | Asp |
| | | 660 | | | | | 665 | | | | | 670 | | | |

| tac | aag | gcc | acc | ggg | ccg | cat | gtg | gct | gtt | gca | aaa | cgc | ctc | gcc | gca | 2064 |
|---|---|---|---|---|---|---|---|---|---|---|---|---|---|---|---|---|
| Tyr | Lys | Ala | Thr | Gly | Pro | His | Val | Ala | Val | Ala | Lys | Arg | Leu | Ala | Ala |
| | | | 675 | | | | | 680 | | | | | 685 | | |

| agg | ggg | ata | aaa | atc | cgg | ccc | gga | acg | gtc | ata | agc | tac | atc | gtg | ctc | 2112 |
|---|---|---|---|---|---|---|---|---|---|---|---|---|---|---|---|---|
| Arg | Gly | Ile | Lys | Ile | Arg | Pro | Gly | Thr | Val | Ile | Ser | Tyr | Ile | Val | Leu |
| | 690 | | | | | 695 | | | | | 700 | | | | |

| aaa | ggc | tcg | gga | agg | att | ggg | gac | agg | gct | ata | ccc | ttt | gac | gaa | ttt | 2160 |
|---|---|---|---|---|---|---|---|---|---|---|---|---|---|---|---|---|
| Lys | Gly | Ser | Gly | Arg | Ile | Gly | Asp | Arg | Ala | Ile | Pro | Phe | Asp | Glu | Phe |
| 705 | | | | | 710 | | | | | 715 | | | | | 720 |

| gac | ccg | gca | aag | cac | aag | tac | gat | gca | gaa | tac | tac | atc | gag | aac | cag | 2208 |
|---|---|---|---|---|---|---|---|---|---|---|---|---|---|---|---|---|
| Asp | Pro | Ala | Lys | His | Lys | Tyr | Asp | Ala | Glu | Tyr | Tyr | Ile | Glu | Asn | Gln |
| | | | | 725 | | | | | 730 | | | | | 735 | |

| gtt | ctt | cca | gct | gtg | gag | agg | att | ctg | agg | gcc | ttt | ggt | tac | cgt | aaa | 2256 |
|---|---|---|---|---|---|---|---|---|---|---|---|---|---|---|---|---|
| Val | Leu | Pro | Ala | Val | Glu | Arg | Ile | Leu | Arg | Ala | Phe | Gly | Tyr | Arg | Lys |
| | | | 740 | | | | | 745 | | | | | 750 | | |

| gaa | gat | tta | agg | tat | cag | aaa | acg | cgg | cag | gtt | ggc | ttg | ggg | gcg | tgg | 2304 |
|---|---|---|---|---|---|---|---|---|---|---|---|---|---|---|---|---|
| Glu | Asp | Leu | Arg | Tyr | Gln | Lys | Thr | Arg | Gln | Val | Gly | Leu | Gly | Ala | Trp |
| | | 755 | | | | | 760 | | | | | 765 | | | |

| cta | aaa | cct | aag | aca | tga | | | | | | | | | | | 2322 |
|---|---|---|---|---|---|---|---|---|---|---|---|---|---|---|---|---|
| Leu | Lys | Pro | Lys | Thr | | | | | | | | | | | |
| | 770 | | | | | | | | | | | | | | |

<210> SEQ ID NO 58
<211> LENGTH: 773
<212> TYPE: PRT
<213> ORGANISM: Thermococcus gorgonarius
<220> FEATURE:
<221> NAME/KEY: misc_feature
<222> LOCATION: (93)..(93)
<223> OTHER INFORMATION: The 'Xaa' at location 93 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 58

| Met | Ile | Leu | Asp | Thr | Asp | Tyr | Ile | Thr | Glu | Asp | Gly | Lys | Pro | Val | Ile |
|---|---|---|---|---|---|---|---|---|---|---|---|---|---|---|---|
| 1 | | | | 5 | | | | | 10 | | | | | 15 | |

| Arg | Ile | Phe | Lys | Lys | Glu | Asn | Gly | Glu | Phe | Lys | Ile | Asp | Tyr | Asp | Arg |
|---|---|---|---|---|---|---|---|---|---|---|---|---|---|---|---|
| | | | 20 | | | | | 25 | | | | | 30 | | |

| Asn | Phe | Glu | Pro | Tyr | Ile | Tyr | Ala | Leu | Leu | Lys | Asp | Asp | Ser | Ala | Ile |
|---|---|---|---|---|---|---|---|---|---|---|---|---|---|---|---|
| | | | 35 | | | | | 40 | | | | | 45 | | |

| Glu | Asp | Val | Lys | Lys | Ile | Thr | Ala | Glu | Arg | His | Gly | Thr | Thr | Val | Arg |
|---|---|---|---|---|---|---|---|---|---|---|---|---|---|---|---|
| | 50 | | | | | 55 | | | | | 60 | | | | |

| Val | Val | Arg | Ala | Glu | Lys | Val | Lys | Lys | Phe | Leu | Gly | Arg | Pro | Ile |
|---|---|---|---|---|---|---|---|---|---|---|---|---|---|---|
| 65 | | | | | 70 | | | | | 75 | | | | | 80 |

| Glu | Val | Trp | Lys | Leu | Tyr | Phe | Thr | His | Pro | Gln | Asp | Xaa | Pro | Ala | Ile |
|---|---|---|---|---|---|---|---|---|---|---|---|---|---|---|---|
| | | | | 85 | | | | | 90 | | | | | 95 | |

| Arg | Asp | Lys | Ile | Lys | Glu | His | Pro | Ala | Val | Val | Asp | Ile | Tyr | Glu | Tyr |
|---|---|---|---|---|---|---|---|---|---|---|---|---|---|---|---|
| | | | 100 | | | | | 105 | | | | | 110 | | |

| Asp | Ile | Pro | Phe | Ala | Lys | Arg | Tyr | Leu | Ile | Asp | Lys | Gly | Leu | Ile | Pro |
|---|---|---|---|---|---|---|---|---|---|---|---|---|---|---|---|
| | | | 115 | | | | | 120 | | | | | 125 | | |

```
Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Ser Thr Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
    275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
    355                 360                 365

Pro Asn Lys Pro Asp Glu Arg Glu Leu Ala Arg Arg Arg Glu Ser Tyr
370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
    435                 440                 445

Ile Pro Ser Leu Leu Gly Asp Leu Leu Glu Glu Arg Gln Lys Val Lys
450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
    515                 520                 525

Glu Glu Lys Phe Gly Phe Lys Val Leu Tyr Ala Asp Thr Asp Gly Phe
530                 535                 540
```

```
Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
                660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
            755                 760                 765

Leu Lys Pro Lys Thr
    770

<210> SEQ ID NO 59
<211> LENGTH: 2322
<212> TYPE: DNA
<213> ORGANISM: Thermococcus gorgonarius
<220> FEATURE:
<221> NAME/KEY: CDS
<222> LOCATION: (1)..(2322)
<223> OTHER INFORMATION:
<220> FEATURE:
<221> NAME/KEY: misc_feature
<222> LOCATION: (277)..(279)
<223> OTHER INFORMATION: NNN = GAA, GAG

<400> SEQUENCE: 59 atg atc ctc gat aca gac tac ata act gag gat gga aag ccc gtc atc      48
Met Ile Leu Asp Thr Asp Tyr Ile Thr Glu Asp Gly Lys Pro Val Ile
1               5                   10                  15 agg atc ttc aag aag gag aac ggc gag ttc aaa ata gac tac gac aga      96
Arg Ile Phe Lys Lys Glu Asn Gly Glu Phe Lys Ile Asp Tyr Asp Arg
                20                  25                  30 aac ttt gag cca tac atc tac gcg ctc ttg aag gac gac tct gcg att     144
Asn Phe Glu Pro Tyr Ile Tyr Ala Leu Leu Lys Asp Asp Ser Ala Ile
            35                  40                  45 gag gac gtc aag aag ata act gcc gag agg cac ggc act acc gtt agg     192
Glu Asp Val Lys Lys Ile Thr Ala Glu Arg His Gly Thr Thr Val Arg
        50                  55                  60 gtt gtc agg gcc gag aaa gtg aag aag aag ttc cta ggc agg ccg ata     240
Val Val Arg Ala Glu Lys Val Lys Lys Lys Phe Leu Gly Arg Pro Ile
```

-continued

| | | | | | | | | | | | | | | | |
|---|---|---|---|---|---|---|---|---|---|---|---|---|---|---|---|
| 65 | | | | | 70 | | | | | 75 | | | | | 80 |

```
gag gtc tgg aag ctc tac ttc act cac ccc cag gac nnn ccc gca atc     288
Glu Val Trp Lys Leu Tyr Phe Thr His Pro Gln Asp Xaa Pro Ala Ile
                85                  90                  95 agg gac aag ata aag gag cat cct gcc gtt gtg gac atc tac gag tac     336
Arg Asp Lys Ile Lys Glu His Pro Ala Val Val Asp Ile Tyr Glu Tyr
            100                 105                 110 gac atc ccc ttc gcg aag cgc tac ctc ata gac aaa ggc tta atc ccg     384
Asp Ile Pro Phe Ala Lys Arg Tyr Leu Ile Asp Lys Gly Leu Ile Pro
        115                 120                 125 atg gag ggc gac gag gaa ctt aag atg ctc gcc ttc gac atc gag acg     432
Met Glu Gly Asp Glu Glu Leu Lys Met Leu Ala Phe Asp Ile Glu Thr
    130                 135                 140 ctc tat cac gag ggc gag gag ttc gcc gaa ggg cct atc ctg atg ata     480
Leu Tyr His Glu Gly Glu Glu Phe Ala Glu Gly Pro Ile Leu Met Ile
145                 150                 155                 160 agc tac gcc gac gag gaa ggg gcg cgc gtt att acc tgg aag aat atc     528
Ser Tyr Ala Asp Glu Glu Gly Ala Arg Val Ile Thr Trp Lys Asn Ile
                165                 170                 175 gac ctt ccc tat gtc gac gtc gtt tcc acc gag aag gag atg ata aag     576
Asp Leu Pro Tyr Val Asp Val Val Ser Thr Glu Lys Glu Met Ile Lys
            180                 185                 190 cgc ttc ctc aag gtc gtc aag gaa aag gat ccc gac gtc ctc ata acc     624
Arg Phe Leu Lys Val Val Lys Glu Lys Asp Pro Asp Val Leu Ile Thr
        195                 200                 205 tac aac ggc gac aac ttc gac ttc gcc tac ctc aag aag cgc tcc gag     672
Tyr Asn Gly Asp Asn Phe Asp Phe Ala Tyr Leu Lys Lys Arg Ser Glu
    210                 215                 220 aag ctc gga gtc aag ttc atc ctc gga agg gaa ggg agc gag ccg aaa     720
Lys Leu Gly Val Lys Phe Ile Leu Gly Arg Glu Gly Ser Glu Pro Lys
225                 230                 235                 240 atc cag cgc atg ggc gat cgc ttt gcg gtg gag gtc aag gga agg att     768
Ile Gln Arg Met Gly Asp Arg Phe Ala Val Glu Val Lys Gly Arg Ile
                245                 250                 255 cac ttc gac ctc tac ccc gtc att agg aga acg att aac ctc ccc act     816
His Phe Asp Leu Tyr Pro Val Ile Arg Arg Thr Ile Asn Leu Pro Thr
            260                 265                 270 tac acc ctt gag gca gta tat gaa gcc atc ttt gga cag ccg aag gag     864
Tyr Thr Leu Glu Ala Val Tyr Glu Ala Ile Phe Gly Gln Pro Lys Glu
        275                 280                 285 aag gtc tac gct gag gag ata gcg cag gcc tgg gaa acg ggc gag gga     912
Lys Val Tyr Ala Glu Glu Ile Ala Gln Ala Trp Glu Thr Gly Glu Gly
    290                 295                 300 tta gaa agg gtg gcc cgc tac tcg atg gag gac gca aag gta acc tat     960
Leu Glu Arg Val Ala Arg Tyr Ser Met Glu Asp Ala Lys Val Thr Tyr
305                 310                 315                 320 gaa ctc gga aaa gag ttc ttc cct atg gaa gcc cag ctc tcg cgc ctc    1008
Glu Leu Gly Lys Glu Phe Phe Pro Met Glu Ala Gln Leu Ser Arg Leu
                325                 330                 335 gta ggc cag agc ctc tgg gat gta tct cgc tcg agt acc gga aac ctc    1056
Val Gly Gln Ser Leu Trp Asp Val Ser Arg Ser Ser Thr Gly Asn Leu
            340                 345                 350 gtc gag tgg ttt ttg ctg agg aag gcc tac gag agg aat gaa ctt gca    1104
Val Glu Trp Phe Leu Leu Arg Lys Ala Tyr Glu Arg Asn Glu Leu Ala
        355                 360                 365 cca aac aag ccg gac gag agg gag ctg gca aga aga agg gag agc tac    1152
Pro Asn Lys Pro Asp Glu Arg Glu Leu Ala Arg Arg Arg Glu Ser Tyr
    370                 375                 380 gcg ggt gga tac gtc aag gag ccc gaa agg gga ctg tgg gag aac atc    1200
Ala Gly Gly Tyr Val Lys Glu Pro Glu Arg Gly Leu Trp Glu Asn Ile
```

```
Ala Gly Gly Tyr Val Lys Glu Pro Glu Arg Gly Leu Trp Glu Asn Ile
385                 390                 395                 400 gtg tat ctg gac ttc cgc tcc ctg tat cct tcg ata ata atc acc cat    1248
Val Tyr Leu Asp Phe Arg Ser Leu Tyr Pro Ser Ile Ile Ile Thr His
                    405                 410                 415 aac gtc tcc cct gat aca ctc aac agg gag ggt tgt gag gag tac gac    1296
Asn Val Ser Pro Asp Thr Leu Asn Arg Glu Gly Cys Glu Glu Tyr Asp
                420                 425                 430 gtg gct cct cag gta ggc cat aag ttc tgc aag gac ttc ccc ggc ttc    1344
Val Ala Pro Gln Val Gly His Lys Phe Cys Lys Asp Phe Pro Gly Phe
            435                 440                 445 atc cca agc ctc ctc gga gac ctc ttg gag gag aga cag aag gta aag    1392
Ile Pro Ser Leu Leu Gly Asp Leu Leu Glu Glu Arg Gln Lys Val Lys
        450                 455                 460 aag aag atg aag gcc act ata gac cca atc gag aag aaa ctc ctc gat    1440
Lys Lys Met Lys Ala Thr Ile Asp Pro Ile Glu Lys Lys Leu Leu Asp
465                 470                 475                 480 tac agg caa cga gca atc aaa atc ctt gct aat agc ttc tac ggt tac    1488
Tyr Arg Gln Arg Ala Ile Lys Ile Leu Ala Asn Ser Phe Tyr Gly Tyr
                    485                 490                 495 tac ggc tat gca aag gcc cgc tgg tac tgc aag gag tgc gcc gag agc    1536
Tyr Gly Tyr Ala Lys Ala Arg Trp Tyr Cys Lys Glu Cys Ala Glu Ser
                500                 505                 510 gtt acc gct tgg ggc agg cag tac atc gag acc acg ata agg gaa ata    1584
Val Thr Ala Trp Gly Arg Gln Tyr Ile Glu Thr Thr Ile Arg Glu Ile
            515                 520                 525 gag gag aaa ttt ggc ttt aaa gtc ctc tac gcg gac aca gat gga ttt    1632
Glu Glu Lys Phe Gly Phe Lys Val Leu Tyr Ala Asp Thr Asp Gly Phe
        530                 535                 540 ttc gca aca ata cct gga gcg gac gcc gaa acc gtc aaa aag aag gca    1680
Phe Ala Thr Ile Pro Gly Ala Asp Ala Glu Thr Val Lys Lys Lys Ala
545                 550                 555                 560 aag gag ttc ctg gac tac atc aac gcc aaa ctg ccc ggc ctg ctc gaa    1728
Lys Glu Phe Leu Asp Tyr Ile Asn Ala Lys Leu Pro Gly Leu Leu Glu
                    565                 570                 575 ctc gaa tac gag ggc ttc tac aag cgc ggc ttc ttc gtg acg aag aag    1776
Leu Glu Tyr Glu Gly Phe Tyr Lys Arg Gly Phe Phe Val Thr Lys Lys
                580                 585                 590 aag tac gcg gtt ata gac gag gag gac aag ata acg acg cgc ggg ctt    1824
Lys Tyr Ala Val Ile Asp Glu Glu Asp Lys Ile Thr Thr Arg Gly Leu
            595                 600                 605 gaa ata gtt agg cgt gac tgg agc gag ata gcg aag gag acg cag gcg    1872
Glu Ile Val Arg Arg Asp Trp Ser Glu Ile Ala Lys Glu Thr Gln Ala
        610                 615                 620 agg gtt ctt gag gcg ata cta aag cac ggt gac gtt gaa gaa gcg gta    1920
Arg Val Leu Glu Ala Ile Leu Lys His Gly Asp Val Glu Glu Ala Val
625                 630                 635                 640 agg att gtc aaa gag gtt acg gag aag ctg agc aag tac gag gtt cca    1968
Arg Ile Val Lys Glu Val Thr Glu Lys Leu Ser Lys Tyr Glu Val Pro
                    645                 650                 655 ccg gag aag ctg gtc atc tac gag cag ata acc cgc gac ctg aag gac    2016
Pro Glu Lys Leu Val Ile Tyr Glu Gln Ile Thr Arg Asp Leu Lys Asp
                660                 665                 670 tac aag gcc acc ggg ccg cat gtg gct gtt gca aaa cgc ctc gcc gca    2064
Tyr Lys Ala Thr Gly Pro His Val Ala Val Ala Lys Arg Leu Ala Ala
            675                 680                 685 agg ggg ata aaa atc cgg ccc gga acg gtc ata agc tac atc gtg ctc    2112
Arg Gly Ile Lys Ile Arg Pro Gly Thr Val Ile Ser Tyr Ile Val Leu
        690                 695                 700
```

```
aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                 710                 715                 720 gac ccg gca aag cac aag tac gat gca gaa tac tac atc gag aac cag      2208
Asp Pro Ala Lys His Lys Tyr Asp Ala Glu Tyr Tyr Ile Glu Asn Gln
                725                 730                 735 gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                 745                 750 gaa gat tta agg tat cag aaa acg cgg cag gtt ggc ttg ggg gcg tgg      2304
Glu Asp Leu Arg Tyr Gln Lys Thr Arg Gln Val Gly Leu Gly Ala Trp
        755                 760                 765 cta aaa cct aag aca tga                                              2322
Leu Lys Pro Lys Thr
    770
```

<210> SEQ ID NO 60
<211> LENGTH: 773
<212> TYPE: PRT
<213> ORGANISM: Thermococcus gorgonarius
<220> FEATURE:
<221> NAME/KEY: misc_feature
<222> LOCATION: (93)..(93)
<223> OTHER INFORMATION: The 'Xaa' at location 93 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 60

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240
```

-continued

```
Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
```

-continued

```
            660                 665                 670
Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
        690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
        770

<210> SEQ ID NO 61
<211> LENGTH: 3499
<212> TYPE: DNA
<213> ORGANISM: Pyrococcus furiosus
<220> FEATURE:
<221> NAME/KEY: misc_feature
<222> LOCATION: (1)..(3499)
<223> OTHER INFORMATION: n = A, T, G or C
<220> FEATURE:
<221> NAME/KEY: CDS
<222> LOCATION: (224)..(2551)
<223> OTHER INFORMATION:

<400> SEQUENCE: 61
ccctggtcct gggtccacat atatgttctt actcgccttt atgaagaatc ccccagtcgc      60
tctaacctgg gttatagtga caaatcttcc tccaccaccg cccaagaagg ttatttctat     120
caactctaca cctcccctat tttctctctt atgagatttt aagtatagt tatagagaag     180 gttttatact ccaaactgag ttagtagata tgtggggagc ata atg att tta gat     235
                                                 Met Ile Leu Asp
                                                   1 gtg gat tac ata act gaa gaa gga aaa cct gtt att agg cta ttc aaa     283
Val Asp Tyr Ile Thr Glu Glu Gly Lys Pro Val Ile Arg Leu Phe Lys
  5              10                  15                  20 aaa gag aac gga aaa ttt aag ata gag cat gat aga act ttt aga cca     331
Lys Glu Asn Gly Lys Phe Lys Ile Glu His Asp Arg Thr Phe Arg Pro
              25                  30                  35 tac att tac gct ctt ctc agg gat gat tca aag att gaa gaa gtt aag     379
Tyr Ile Tyr Ala Leu Leu Arg Asp Asp Ser Lys Ile Glu Glu Val Lys
          40                  45                  50 aaa ata acg ggg gaa agg cat gga aag att gtg aga att gtt gat gta     427
Lys Ile Thr Gly Glu Arg His Gly Lys Ile Val Arg Ile Val Asp Val
              55                  60                  65 gag aag gtt gag aaa aag ttt ctc ggc aag cct att acc gtg tgg aaa     475
Glu Lys Val Glu Lys Lys Phe Leu Gly Lys Pro Ile Thr Val Trp Lys
 70                  75                  80 ctt tat ttg gaa cat ccc caa gat gtt ccc act att aga gaa aaa gtt     523
Leu Tyr Leu Glu His Pro Gln Asp Val Pro Thr Ile Arg Glu Lys Val
 85                  90                  95                 100 aga gaa cat cca gca gtt gtg gac atc ttc gaa tac gat att cca ttt     571
Arg Glu His Pro Ala Val Val Asp Ile Phe Glu Tyr Asp Ile Pro Phe
                105                 110                 115 gca aag aga tac ctc atc gac aaa ggc cta ata cca atg gag ggg gaa     619
Ala Lys Arg Tyr Leu Ile Asp Lys Gly Leu Ile Pro Met Glu Gly Glu
```

-continued

```
                  120                 125                 130
gaa gag cta aag att ctt gcc ttc gat ata gaa acc ctc tat cac gaa      667
Glu Glu Leu Lys Ile Leu Ala Phe Asp Ile Glu Thr Leu Tyr His Glu
        135                 140                 145 gga gaa gag ttt gga aaa ggc cca att ata atg att agt tat gca gat      715
Gly Glu Glu Phe Gly Lys Gly Pro Ile Ile Met Ile Ser Tyr Ala Asp
150                 155                 160 gaa aat gaa gca aag gtg att act tgg aaa aac ata gat ctt cca tac      763
Glu Asn Glu Ala Lys Val Ile Thr Trp Lys Asn Ile Asp Leu Pro Tyr
165                 170                 175                 180 gtt gag gtt gta tca agc gag aga gag atg ata aag aga ttt ctc agg      811
Val Glu Val Val Ser Ser Glu Arg Glu Met Ile Lys Arg Phe Leu Arg
                185                 190                 195 att atc agg gag aag gat cct gac att ata gtt act tat aat gga gac      859
Ile Ile Arg Glu Lys Asp Pro Asp Ile Ile Val Thr Tyr Asn Gly Asp
            200                 205                 210 tca ttc gac ttc cca tat tta gcg aaa agg gca gaa aaa ctt ggg att      907
Ser Phe Asp Phe Pro Tyr Leu Ala Lys Arg Ala Glu Lys Leu Gly Ile
        215                 220                 225 aaa tta acc att gga aga gat gga agc gag ccc aag atg cag aga ata      955
Lys Leu Thr Ile Gly Arg Asp Gly Ser Glu Pro Lys Met Gln Arg Ile
230                 235                 240 ggc gat atg acg gct gta gaa gtc aag gga aga ata cat ttc gac ttg     1003
Gly Asp Met Thr Ala Val Glu Val Lys Gly Arg Ile His Phe Asp Leu
245                 250                 255                 260 tat cat gta ata aca agg aca ata aat ctc cca aca tac aca cta gag     1051
Tyr His Val Ile Thr Arg Thr Ile Asn Leu Pro Thr Tyr Thr Leu Glu
                265                 270                 275 gct gta tat gaa gca att ttt gga aag cca aag gag aag gta tac gcc     1099
Ala Val Tyr Glu Ala Ile Phe Gly Lys Pro Lys Glu Lys Val Tyr Ala
            280                 285                 290 gac gag ata gca aaa gcc tgg gaa agt gga gag aac ctt gag aga gtt     1147
Asp Glu Ile Ala Lys Ala Trp Glu Ser Gly Glu Asn Leu Glu Arg Val
        295                 300                 305 gcc aaa tac tcg atg gaa gat gca aag gca act tat gaa ctc ggg aaa     1195
Ala Lys Tyr Ser Met Glu Asp Ala Lys Ala Thr Tyr Glu Leu Gly Lys
310                 315                 320 gaa ttc ctt cca atg gaa att cag ctt tca aga tta gtt gga caa cct     1243
Glu Phe Leu Pro Met Glu Ile Gln Leu Ser Arg Leu Val Gly Gln Pro
325                 330                 335                 340 tta tgg gat gtt tca agg tca agc aca ggg aac ctt gta gag tgg ttc     1291
Leu Trp Asp Val Ser Arg Ser Ser Thr Gly Asn Leu Val Glu Trp Phe
                345                 350                 355 tta ctt agg aaa gcc tac gaa aga aac gaa gta gct cca aac aag cca     1339
Leu Leu Arg Lys Ala Tyr Glu Arg Asn Glu Val Ala Pro Asn Lys Pro
            360                 365                 370 agt gaa gag gag tat caa aga agg ctc agg gag agc tac aca ggt gga     1387
Ser Glu Glu Glu Tyr Gln Arg Arg Leu Arg Glu Ser Tyr Thr Gly Gly
        375                 380                 385 ttc gtt aaa gag cca gaa aag ggg ttg tgg gaa aac ata gta tac cta     1435
Phe Val Lys Glu Pro Glu Lys Gly Leu Trp Glu Asn Ile Val Tyr Leu
390                 395                 400 gat ttt aga gcc cta tat ccc tcg att ata att acc cac aat gtt tct     1483
Asp Phe Arg Ala Leu Tyr Pro Ser Ile Ile Ile Thr His Asn Val Ser
405                 410                 415                 420 ccc gat act cta aat ctt gag gga tgc aag aac tat gat atc gct cct     1531
Pro Asp Thr Leu Asn Leu Glu Gly Cys Lys Asn Tyr Asp Ile Ala Pro
                425                 430                 435 caa gta ggc cac aag ttc tgc aag gac atc cct ggt ttt ata cca agt     1579
```

-continued

```
Gln Val Gly His Lys Phe Cys Lys Asp Ile Pro Gly Phe Ile Pro Ser
        440                 445                 450 ctc ttg gga cat ttg tta gag gaa aga caa aag att aag aca aaa atg       1627
Leu Leu Gly His Leu Leu Glu Glu Arg Gln Lys Ile Lys Thr Lys Met
            455                 460                 465 aag gaa act caa gat cct ata gaa aaa ata ctc ctt gac tat aga caa       1675
Lys Glu Thr Gln Asp Pro Ile Glu Lys Ile Leu Leu Asp Tyr Arg Gln
        470                 475                 480 aaa gcg ata aaa ctc tta gca aat tct ttc tac gga tat tat ggc tat       1723
Lys Ala Ile Lys Leu Leu Ala Asn Ser Phe Tyr Gly Tyr Tyr Gly Tyr
485                 490                 495                 500 gca aaa gca aga tgg tac tgt aag gag tgt gct gag agc gtt act gcc       1771
Ala Lys Ala Arg Trp Tyr Cys Lys Glu Cys Ala Glu Ser Val Thr Ala
            505                 510                 515 tgg gga aga aag tac atc gag tta gta tgg aag gag ctc gaa gaa aag       1819
Trp Gly Arg Lys Tyr Ile Glu Leu Val Trp Lys Glu Leu Glu Glu Lys
        520                 525                 530 ttt gga ttt aaa gtc ctc tac att gac act gat ggt ctc tat gca act       1867
Phe Gly Phe Lys Val Leu Tyr Ile Asp Thr Asp Gly Leu Tyr Ala Thr
            535                 540                 545 atc cca gga gga gaa agt gag gaa ata aag aaa aag gct cta gaa ttt       1915
Ile Pro Gly Gly Glu Ser Glu Glu Ile Lys Lys Lys Ala Leu Glu Phe
        550                 555                 560 gta aaa tac ata aat tca aag ctc cct gga ctg cta gag ctt gaa tat       1963
Val Lys Tyr Ile Asn Ser Lys Leu Pro Gly Leu Leu Glu Leu Glu Tyr
565                 570                 575                 580 gaa ggg ttt tat aag agg gga ttc ttc gtt acg aag aag agg tat gca       2011
Glu Gly Phe Tyr Lys Arg Gly Phe Phe Val Thr Lys Lys Arg Tyr Ala
            585                 590                 595 gta ata gat gaa gaa gga aaa gtc att act cgt ggt tta gag ata gtt       2059
Val Ile Asp Glu Glu Gly Lys Val Ile Thr Arg Gly Leu Glu Ile Val
        600                 605                 610 agg aga gat tgg agt gaa att gca aaa gaa act caa gct aga gtt ttg       2107
Arg Arg Asp Trp Ser Glu Ile Ala Lys Glu Thr Gln Ala Arg Val Leu
            615                 620                 625 gag aca ata cta aaa cac gga gat gtt gaa gaa gct gtg aga ata gta       2155
Glu Thr Ile Leu Lys His Gly Asp Val Glu Glu Ala Val Arg Ile Val
        630                 635                 640 aaa gaa gta ata caa aag ctt gcc aat tat gaa att cca cca gag aag       2203
Lys Glu Val Ile Gln Lys Leu Ala Asn Tyr Glu Ile Pro Pro Glu Lys
645                 650                 655                 660 ctc gca ata tat gag cag ata aca aga cca tta cat gag tat aag gcg       2251
Leu Ala Ile Tyr Glu Gln Ile Thr Arg Pro Leu His Glu Tyr Lys Ala
            665                 670                 675 ata ggt cct cac gta gct gtt gca aag aaa cta gct gct aaa gga gtt       2299
Ile Gly Pro His Val Ala Val Ala Lys Lys Leu Ala Ala Lys Gly Val
        680                 685                 690 aaa ata aag cca gga atg gta att gga tac ata gta ctt aga ggc gat       2347
Lys Ile Lys Pro Gly Met Val Ile Gly Tyr Ile Val Leu Arg Gly Asp
            695                 700                 705 ggt cca att agc aat agg gca att cta gct gag gaa tac gat ccc aaa       2395
Gly Pro Ile Ser Asn Arg Ala Ile Leu Ala Glu Glu Tyr Asp Pro Lys
        710                 715                 720 aag cac aag tat gac gca gaa tat tac att gag aac cag gtt ctt cca       2443
Lys His Lys Tyr Asp Ala Glu Tyr Tyr Ile Glu Asn Gln Val Leu Pro
725                 730                 735                 740 gcg gta ctt agg ata ttg gag gga ttt gga tac aga aag gaa gac ctc       2491
Ala Val Leu Arg Ile Leu Glu Gly Phe Gly Tyr Arg Lys Glu Asp Leu
            745                 750                 755
```

-continued

```
aga tac caa aag aca aga caa gtc ggc cta act tcc tgg ctt aac att    2539
Arg Tyr Gln Lys Thr Arg Gln Val Gly Leu Thr Ser Trp Leu Asn Ile
            760                 765                 770 aaa aaa tcc tag aaaagcgata gatatcaact tttattcttt ctaaccttttt       2591
Lys Lys Ser
        775 tctatgaaag aagaactgag caggaattac cagttcttcc gttatttat gggtaattaa   2651 aaacccatgc tcttgggaga atcttcgaat aaaatccta acttcaggct ttgctaagtg   2711 aatagaataa acaacatcac tcacttcaaa cgccttcgtt agaaatggtc tatctgcatg  2771 cttctctggc tcggaanngg aggattcata acaacagtat caacattctc agagaattga  2831 gaaacatcag aaactttgac ttctacaaca tttctaactt gcaactctt caagattttc   2891 taaaagaatt ttaacggcct cctcgtcaat ttcgacgacg tagatctttt ttgctccaag  2951 cagagccgct ccaatggata acaccctgt tcccgcaccc aagtccgcta caatttttc    3011 cttgtatctc ctaatgtata agcaagccaa aggagagtag atgctacctt tccgggagtt  3071 ttgtattgct ctagccaagg tttgggattt ttgaatcctt taactctgga agtataatt   3131 tcaagctcct tcttcttcat gacagatgaa aaattgtttt gtctctttt aacttttaca   3191 gaaataactg tctcaaatta tgacaactct tgacattttt acttcattac cagggtaatg  3251 ttttaagta tgaaattttt ctttcataga ggaggnnnnn ngtcctctcc tcgatttcct   3311 tggttgtgct ccatatgata agcttccaaa gtgggtgttc agacttttag acactcaaat  3371 accagacgac aatggtgtgc tcactcaagc cccatatggg ttgagaaaag tagaagcggc  3431 actactcaga tgcttcccca ggaatgaggt tgttgtagct cntcccngaa agattgagat  3491 gttcttgg                                                          3499
```

<210> SEQ ID NO 62
<211> LENGTH: 775
<212> TYPE: PRT
<213> ORGANISM: Pyrococcus furiosus

<400> SEQUENCE: 62

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
```

-continued

```
                165                 170                 175
Asp Leu Pro Tyr Val Glu Val Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
        260                 265                 270
Tyr Thr Leu Glu Ala Val Tyr Glu Ala Ile Phe Gly Lys Pro Lys Glu
    275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
            325                 330                 335
Val Gly Gln Pro Leu Trp Asp Val Ser Arg Ser Ser Thr Gly Asn Leu
        340                 345                 350
Val Glu Trp Phe Leu Leu Arg Lys Ala Tyr Glu Arg Asn Glu Val Ala
    355                 360                 365
Pro Asn Lys Pro Ser Glu Glu Glu Tyr Gln Arg Arg Leu Arg Glu Ser
370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
            405                 410                 415
His Asn Val Ser Pro Asp Thr Leu Asn Leu Glu Gly Cys Lys Asn Tyr
        420                 425                 430
Asp Ile Ala Pro Gln Val Gly His Lys Phe Cys Lys Asp Ile Pro Gly
    435                 440                 445
Phe Ile Pro Ser Leu Leu Gly His Leu Leu Glu Glu Arg Gln Lys Ile
450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
            485                 490                 495
Tyr Tyr Gly Tyr Ala Lys Ala Arg Trp Tyr Cys Lys Glu Cys Ala Glu
        500                 505                 510
Ser Val Thr Ala Trp Gly Arg Lys Tyr Ile Glu Leu Val Trp Lys Glu
    515                 520                 525
Leu Glu Glu Lys Phe Gly Phe Lys Val Leu Tyr Ile Asp Thr Asp Gly
530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
            565                 570                 575
Glu Leu Glu Tyr Glu Gly Phe Tyr Lys Arg Gly Phe Phe Val Thr Lys
        580                 585                 590
```

```
Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 63
<211> LENGTH: 207
<212> TYPE: DNA
<213> ORGANISM: Pyrococcus furiosus
<220> FEATURE:
<221> NAME/KEY: CDS
<222> LOCATION: (1)..(207)
<223> OTHER INFORMATION:

<400> SEQUENCE: 63 atg atg gga gaa tta cca att gcc cca gtt gac aga ctt ata aga aag      48
Met Met Gly Glu Leu Pro Ile Ala Pro Val Asp Arg Leu Ile Arg Lys
1               5                   10                  15 gct ggt gct cag aga gtt agc gag caa gca gct aag gta ctt gca gag      96
Ala Gly Ala Gln Arg Val Ser Glu Gln Ala Ala Lys Val Leu Ala Glu
            20                  25                  30 cac ctt gag gaa aaa gct att gag atc gca aaa aag gca gta gat ctt     144
His Leu Glu Glu Lys Ala Ile Glu Ile Ala Lys Lys Ala Val Asp Leu
        35                  40                  45 gca aag cac gca ggt aga aag acc gtt aag gtc gaa gac att aag ctc     192
Ala Lys His Ala Gly Arg Lys Thr Val Lys Val Glu Asp Ile Lys Leu
    50                  55                  60 gca att aag agc tga                                                  207
Ala Ile Lys Ser
65

<210> SEQ ID NO 64
<211> LENGTH: 68
<212> TYPE: PRT
<213> ORGANISM: Pyrococcus furiosus

<400> SEQUENCE: 64

Met Met Gly Glu Leu Pro Ile Ala Pro Val Asp Arg Leu Ile Arg Lys
1               5                   10                  15
```

```
Ala Gly Ala Gln Arg Val Ser Glu Gln Ala Ala Lys Val Leu Ala Glu
             20                  25                  30

His Leu Glu Glu Lys Ala Ile Glu Ile Ala Lys Lys Ala Val Asp Leu
         35                  40                  45

Ala Lys His Ala Gly Arg Lys Thr Val Lys Val Glu Asp Ile Lys Leu
 50                  55                  60

Ala Ile Lys Ser
 65

<210> SEQ ID NO 65
<211> LENGTH: 2556
<212> TYPE: DNA
<213> ORGANISM: Thermus aquaticus
<220> FEATURE:
<221> NAME/KEY: CDS
<222> LOCATION: (1)..(2556)
<223> OTHER INFORMATION:

<400> SEQUENCE: 65 ggc ggc ggt gtc act agt ggg atg ctg ccc ctc ttt gag ccc aag ggc      48
Gly Gly Gly Val Thr Ser Gly Met Leu Pro Leu Phe Glu Pro Lys Gly
 1               5                  10                  15 cgg gtc ctc ctg gtg gac ggc cac cac ctg gcc tac cgc acc ttc cac      96
Arg Val Leu Leu Val Asp Gly His His Leu Ala Tyr Arg Thr Phe His
             20                  25                  30 gcc ctg aag ggc ctc acc acc agc cgg ggg gag ccg gtg cag gcg gtc     144
Ala Leu Lys Gly Leu Thr Thr Ser Arg Gly Glu Pro Val Gln Ala Val
         35                  40                  45 tac ggc ttc gcc aag agc ctc ctc aag gcc ctc aag gag gac ggg gac     192
Tyr Gly Phe Ala Lys Ser Leu Leu Lys Ala Leu Lys Glu Asp Gly Asp
 50                  55                  60 gcg gtg atc gtg gtc ttt gac gcc aag gcc ccc tcc ttc cgc cac gag     240
Ala Val Ile Val Val Phe Asp Ala Lys Ala Pro Ser Phe Arg His Glu
 65                  70                  75                  80 gcc tac ggg ggg tac aag gcg ggc cgg gcc ccc acg cca gag gac ttt     288
Ala Tyr Gly Gly Tyr Lys Ala Gly Arg Ala Pro Thr Pro Glu Asp Phe
                 85                  90                  95 ccc cgg caa ctc gcc ctc atc aag gag ctg gtg gac ctc ctg ggg ctg     336
Pro Arg Gln Leu Ala Leu Ile Lys Glu Leu Val Asp Leu Leu Gly Leu
            100                 105                 110 gcg cgc ctc gag gtc ccg ggc tac gag gcg gac gac gtc ctg gcc agc     384
Ala Arg Leu Glu Val Pro Gly Tyr Glu Ala Asp Asp Val Leu Ala Ser
        115                 120                 125 ctg gcc aag aag gcg gaa aag gag ggc tac gag gtc cgc atc ctc acc     432
Leu Ala Lys Lys Ala Glu Lys Glu Gly Tyr Glu Val Arg Ile Leu Thr
    130                 135                 140 gcc gac aaa gac ctt tac cag ctc ctt tcc gac cgc atc cac gtc ctc     480
Ala Asp Lys Asp Leu Tyr Gln Leu Leu Ser Asp Arg Ile His Val Leu
145                 150                 155                 160 cac ccc gag ggg tac ctc atc acc ccg gcc tgg ctt tgg gaa aag tac     528
His Pro Glu Gly Tyr Leu Ile Thr Pro Ala Trp Leu Trp Glu Lys Tyr
                165                 170                 175 ggc ctg agg ccc gac cag tgg gcc gac tac cgg gcc ctg acc ggg gac     576
Gly Leu Arg Pro Asp Gln Trp Ala Asp Tyr Arg Ala Leu Thr Gly Asp
            180                 185                 190 gag tcc gac aac ctt ccc ggg gtc aag ggc atc ggg gag aag acg gcg     624
Glu Ser Asp Asn Leu Pro Gly Val Lys Gly Ile Gly Glu Lys Thr Ala
        195                 200                 205 agg aag ctt ctg gag gag tgg ggg agc ctg gaa gcc ctc ctc aag aac     672
Arg Lys Leu Leu Glu Glu Trp Gly Ser Leu Glu Ala Leu Leu Lys Asn
```

```
                      210                 215                 220
ctg gac cgg ctg aag ccc gcc atc cgg gag aag atc ctg gcc cac atg       720
Leu Asp Arg Leu Lys Pro Ala Ile Arg Glu Lys Ile Leu Ala His Met
225                 230                 235                 240 gac gat ctg aag ctc tcc tgg gac ctg gcc aag gtg cgc acc gac ctg       768
Asp Asp Leu Lys Leu Ser Trp Asp Leu Ala Lys Val Arg Thr Asp Leu
                245                 250                 255 ccc ctg gag gtg gac ttc gcc aaa agg cgg gag ccc gac cgg gag agg       816
Pro Leu Glu Val Asp Phe Ala Lys Arg Arg Glu Pro Asp Arg Glu Arg
            260                 265                 270 ctt agg gcc ttt ctg gag agg ctt gag ttt ggc agc ctc ctc cac gag       864
Leu Arg Ala Phe Leu Glu Arg Leu Glu Phe Gly Ser Leu Leu His Glu
        275                 280                 285 ttc ggc ctt ctg gaa agc ccc aag gcc ctg gag gag gcc ccc tgg ccc       912
Phe Gly Leu Leu Glu Ser Pro Lys Ala Leu Glu Glu Ala Pro Trp Pro
    290                 295                 300 ccg ccg gaa ggg gcc ttc gtg ggc ttt gtg ctt tcc cgc aag gag ccc       960
Pro Pro Glu Gly Ala Phe Val Gly Phe Val Leu Ser Arg Lys Glu Pro
305                 310                 315                 320 atg tgg gcc gat ctt ctg gcc ctg gcc gcc gcc agg ggg ggc cgg gtc      1008
Met Trp Ala Asp Leu Leu Ala Leu Ala Ala Ala Arg Gly Gly Arg Val
                325                 330                 335 cac cgg gcc ccc gag cct tat aaa gcc ctc agg gac ctg aag gag gcg      1056
His Arg Ala Pro Glu Pro Tyr Lys Ala Leu Arg Asp Leu Lys Glu Ala
            340                 345                 350 cgg ggg ctt ctc gcc aaa gac ctg agc gtt ctg gcc ctg agg gaa ggc      1104
Arg Gly Leu Leu Ala Lys Asp Leu Ser Val Leu Ala Leu Arg Glu Gly
        355                 360                 365 ctt ggc ctc ccg ccc ggc gac gac ccc atg ctc ctc gcc tac ctc ctg      1152
Leu Gly Leu Pro Pro Gly Asp Asp Pro Met Leu Leu Ala Tyr Leu Leu
    370                 375                 380 gac cct tcc aac acc acc ccc gag ggg gtg gcc cgg cgc tac ggc ggg      1200
Asp Pro Ser Asn Thr Thr Pro Glu Gly Val Ala Arg Arg Tyr Gly Gly
385                 390                 395                 400 gag tgg acg gag gag gcg ggg gag cgg gcc gcc ctt tcc gag agg ctc      1248
Glu Trp Thr Glu Glu Ala Gly Glu Arg Ala Ala Leu Ser Glu Arg Leu
                405                 410                 415 ttc gcc aac ctg tgg ggg agg ctt gag ggg gag gag agg ctc ctt tgg      1296
Phe Ala Asn Leu Trp Gly Arg Leu Glu Gly Glu Glu Arg Leu Leu Trp
            420                 425                 430 ctt tac cgg gag gtg gag agg ccc ctt tcc gct gtc ctg gcc cac atg      1344
Leu Tyr Arg Glu Val Glu Arg Pro Leu Ser Ala Val Leu Ala His Met
        435                 440                 445 gag gcc acg ggg gtg cgc ctg gac gtg gcc tat ctc agg gcc ttg tcc      1392
Glu Ala Thr Gly Val Arg Leu Asp Val Ala Tyr Leu Arg Ala Leu Ser
    450                 455                 460 ctg gag gtg gcc gag gag atc gcc cgc ctc gag gcc gag gtc ttc cgc      1440
Leu Glu Val Ala Glu Glu Ile Ala Arg Leu Glu Ala Glu Val Phe Arg
465                 470                 475                 480 ctg gcc ggc cac ccc ttc aac ctc aac tcc cgg gac cag ctg gaa agg      1488
Leu Ala Gly His Pro Phe Asn Leu Asn Ser Arg Asp Gln Leu Glu Arg
                485                 490                 495 gtc ctc ttt gac gag cta ggg ctt ccc gcc atc ggc aag acg gag aag      1536
Val Leu Phe Asp Glu Leu Gly Leu Pro Ala Ile Gly Lys Thr Glu Lys
            500                 505                 510 acc ggc aag cgc tcc acc agc gcc gcc gtc ctg gag gcc ctc cgc gag      1584
Thr Gly Lys Arg Ser Thr Ser Ala Ala Val Leu Glu Ala Leu Arg Glu
        515                 520                 525 gcc cac ccc atc gtg gag aag atc ctg cag tac cgg gag ctc acc aag      1632
```

```
                  -continued

Ala His Pro Ile Val Glu Lys Ile Leu Gln Tyr Arg Glu Leu Thr Lys
    530                 535                 540 ctg aag agc acc tac att gac ccc ttg ccg gac ctc atc cac ccc agg    1680
Leu Lys Ser Thr Tyr Ile Asp Pro Leu Pro Asp Leu Ile His Pro Arg
545                 550                 555                 560 acg ggc cgc ctc cac acc cgc ttc aac cag acg gcc acg gcc acg ggc    1728
Thr Gly Arg Leu His Thr Arg Phe Asn Gln Thr Ala Thr Ala Thr Gly
                    565                 570                 575 agg cta agt agc tcc gat ccc aac ctc cag aac atc ccc gtc cgc acc    1776
Arg Leu Ser Ser Ser Asp Pro Asn Leu Gln Asn Ile Pro Val Arg Thr
                580                 585                 590 ccg ctt ggg cag agg atc cgc cgg gcc ttc atc gcc gag gag ggg tgg    1824
Pro Leu Gly Gln Arg Ile Arg Arg Ala Phe Ile Ala Glu Glu Gly Trp
            595                 600                 605 cta ttg gtg gcc ctg gac tat agc cag ata gag ctc agg gtg ctg gcc    1872
Leu Leu Val Ala Leu Asp Tyr Ser Gln Ile Glu Leu Arg Val Leu Ala
        610                 615                 620 cac ctc tcc ggc gac gag aac ctg atc cgg gtc ttc cag gag ggg cgg    1920
His Leu Ser Gly Asp Glu Asn Leu Ile Arg Val Phe Gln Glu Gly Arg
625                 630                 635                 640 gac atc cac acg gag acc gcc agc tgg atg ttc ggc gtc ccc cgg gag    1968
Asp Ile His Thr Glu Thr Ala Ser Trp Met Phe Gly Val Pro Arg Glu
                    645                 650                 655 gcc gtg gac ccc ctg atg cgc cgg gcg gcc aag acc atc aac ttc ggg    2016
Ala Val Asp Pro Leu Met Arg Arg Ala Ala Lys Thr Ile Asn Phe Gly
                660                 665                 670 gtc ctc tac ggc atg tcg gcc cac cgc ctc tcc cag gag cta gcc atc    2064
Val Leu Tyr Gly Met Ser Ala His Arg Leu Ser Gln Glu Leu Ala Ile
            675                 680                 685 cct tac gag gag gcc cag gcc ttc att gag cgc tac ttt cag agc ttc    2112
Pro Tyr Glu Glu Ala Gln Ala Phe Ile Glu Arg Tyr Phe Gln Ser Phe
        690                 695                 700 ccc aag gtg cgg gcc tgg att gag aag acc ctg gag gag ggc agg agg    2160
Pro Lys Val Arg Ala Trp Ile Glu Lys Thr Leu Glu Glu Gly Arg Arg
705                 710                 715                 720 cgg ggg tac gtg gag acc ctc ttc ggc cgc cgc cgc tac gtg cca gac    2208
Arg Gly Tyr Val Glu Thr Leu Phe Gly Arg Arg Arg Tyr Val Pro Asp
                    725                 730                 735 cta gag gcc cgg gtg aag agc gtg cgg gag gcg gcc gag cgc atg gcc    2256
Leu Glu Ala Arg Val Lys Ser Val Arg Glu Ala Ala Glu Arg Met Ala
                740                 745                 750 ttc aac atg ccc gtc cag ggc acc gcc gcc gac ctc atg aag ctg gct    2304
Phe Asn Met Pro Val Gln Gly Thr Ala Ala Asp Leu Met Lys Leu Ala
            755                 760                 765 atg gtg aag ctc ttc ccc agg ctg gag gaa atg ggg gcc agg atg ctc    2352
Met Val Lys Leu Phe Pro Arg Leu Glu Glu Met Gly Ala Arg Met Leu
        770                 775                 780 ctt cag gtc cac gac gag ctg gtc ctc gag gcc cca aaa gag agg gcg    2400
Leu Gln Val His Asp Glu Leu Val Leu Glu Ala Pro Lys Glu Arg Ala
785                 790                 795                 800 gag gcc gtg gcc cgg ctg gcc aag gag gtc atg gag ggg gtg tat ccc    2448
Glu Ala Val Ala Arg Leu Ala Lys Glu Val Met Glu Gly Val Tyr Pro
                    805                 810                 815 ctg gcc gtg ccc ctg gag gtg gag gtg ggg ata ggg gag gac tgg ctc    2496
Leu Ala Val Pro Leu Glu Val Glu Val Gly Ile Gly Glu Asp Trp Leu
                820                 825                 830 tcc gcc aag gag ggc att gat ggc cgc ggc gga ggc ggg cat cat cat    2544
Ser Ala Lys Glu Gly Ile Asp Gly Arg Gly Gly Gly Gly His His His
            835                 840                 845
```

```
cat cat cat taa                                              2556
His His His
    850
```

<210> SEQ ID NO 66
<211> LENGTH: 851
<212> TYPE: PRT
<213> ORGANISM: Thermus aquaticus

<400> SEQUENCE: 66

```
Gly Gly Gly Val Thr Ser Gly Met Leu Pro Leu Phe Glu Pro Lys Gly
1               5                   10                  15

Arg Val Leu Val Asp Gly His His Leu Ala Tyr Arg Thr Phe His
            20                  25                  30

Ala Leu Lys Gly Leu Thr Thr Ser Arg Gly Glu Pro Val Gln Ala Val
            35                  40                  45

Tyr Gly Phe Ala Lys Ser Leu Leu Lys Ala Leu Lys Glu Asp Gly Asp
    50                  55                  60

Ala Val Ile Val Val Phe Asp Ala Lys Ala Pro Ser Phe Arg His Glu
65                  70                  75                  80

Ala Tyr Gly Gly Tyr Lys Ala Gly Arg Ala Pro Thr Pro Glu Asp Phe
                85                  90                  95

Pro Arg Gln Leu Ala Leu Ile Lys Glu Leu Val Asp Leu Leu Gly Leu
            100                 105                 110

Ala Arg Leu Glu Val Pro Gly Tyr Glu Ala Asp Asp Val Leu Ala Ser
            115                 120                 125

Leu Ala Lys Lys Ala Glu Lys Glu Gly Tyr Glu Val Arg Ile Leu Thr
130                 135                 140

Ala Asp Lys Asp Leu Tyr Gln Leu Leu Ser Asp Arg Ile His Val Leu
145                 150                 155                 160

His Pro Glu Gly Tyr Leu Ile Thr Pro Ala Trp Leu Trp Glu Lys Tyr
                165                 170                 175

Gly Leu Arg Pro Asp Gln Trp Ala Asp Tyr Arg Ala Leu Thr Gly Asp
            180                 185                 190

Glu Ser Asp Asn Leu Pro Gly Val Lys Gly Ile Gly Glu Lys Thr Ala
            195                 200                 205

Arg Lys Leu Leu Glu Glu Trp Gly Ser Leu Glu Ala Leu Leu Lys Asn
        210                 215                 220

Leu Asp Arg Leu Lys Pro Ala Ile Arg Glu Lys Ile Leu Ala His Met
225                 230                 235                 240

Asp Asp Leu Lys Leu Ser Trp Asp Leu Ala Lys Val Arg Thr Asp Leu
                245                 250                 255

Pro Leu Glu Val Asp Phe Ala Lys Arg Arg Glu Pro Asp Arg Glu Arg
            260                 265                 270

Leu Arg Ala Phe Leu Glu Arg Leu Glu Phe Gly Ser Leu Leu His Glu
        275                 280                 285

Phe Gly Leu Leu Glu Ser Pro Lys Ala Leu Glu Glu Ala Pro Trp Pro
    290                 295                 300

Pro Pro Glu Gly Ala Phe Val Gly Phe Val Leu Ser Arg Lys Glu Pro
305                 310                 315                 320

Met Trp Ala Asp Leu Leu Ala Leu Ala Ala Ala Arg Gly Gly Arg Val
                325                 330                 335

His Arg Ala Pro Glu Pro Tyr Lys Ala Leu Arg Asp Leu Lys Glu Ala
            340                 345                 350

Arg Gly Leu Leu Ala Lys Asp Leu Ser Val Leu Ala Leu Arg Glu Gly
```

-continued

```
              355                 360                 365
Leu Gly Leu Pro Pro Gly Asp Asp Pro Met Leu Leu Ala Tyr Leu Leu
    370                 375                 380
Asp Pro Ser Asn Thr Thr Pro Glu Gly Val Ala Arg Arg Tyr Gly Gly
385                 390                 395                 400
Glu Trp Thr Glu Glu Ala Gly Glu Arg Ala Ala Leu Ser Glu Arg Leu
                405                 410                 415
Phe Ala Asn Leu Trp Gly Arg Leu Gly Glu Arg Leu Leu Trp
            420                 425                 430
Leu Tyr Arg Glu Val Glu Arg Pro Leu Ser Ala Val Leu Ala His Met
        435                 440                 445
Glu Ala Thr Gly Val Arg Leu Asp Val Ala Tyr Leu Arg Ala Leu Ser
    450                 455                 460
Leu Glu Val Ala Glu Glu Ile Ala Arg Leu Glu Ala Glu Val Phe Arg
465                 470                 475                 480
Leu Ala Gly His Pro Phe Asn Leu Asn Ser Arg Asp Gln Leu Glu Arg
                485                 490                 495
Val Leu Phe Asp Glu Leu Gly Leu Pro Ala Ile Gly Lys Thr Glu Lys
            500                 505                 510
Thr Gly Lys Arg Ser Thr Ser Ala Ala Val Leu Glu Ala Leu Arg Glu
        515                 520                 525
Ala His Pro Ile Val Glu Lys Ile Leu Gln Tyr Arg Glu Leu Thr Lys
    530                 535                 540
Leu Lys Ser Thr Tyr Ile Asp Pro Leu Pro Asp Leu Ile His Pro Arg
545                 550                 555                 560
Thr Gly Arg Leu His Thr Arg Phe Asn Gln Thr Ala Thr Ala Thr Gly
                565                 570                 575
Arg Leu Ser Ser Ser Asp Pro Asn Leu Gln Asn Ile Pro Val Arg Thr
            580                 585                 590
Pro Leu Gly Gln Arg Ile Arg Arg Ala Phe Ile Ala Glu Glu Gly Trp
        595                 600                 605
Leu Leu Val Ala Leu Asp Tyr Ser Gln Ile Glu Leu Arg Val Leu Ala
    610                 615                 620
His Leu Ser Gly Asp Glu Asn Leu Ile Arg Val Phe Gln Glu Gly Arg
625                 630                 635                 640
Asp Ile His Thr Glu Thr Ala Ser Trp Met Phe Gly Val Pro Arg Glu
                645                 650                 655
Ala Val Asp Pro Leu Met Arg Arg Ala Lys Thr Ile Asn Phe Gly
            660                 665                 670
Val Leu Tyr Gly Met Ser Ala His Arg Leu Ser Gln Glu Leu Ala Ile
        675                 680                 685
Pro Tyr Glu Glu Ala Gln Ala Phe Ile Glu Arg Tyr Phe Gln Ser Phe
    690                 695                 700
Pro Lys Val Arg Ala Trp Ile Glu Lys Thr Leu Glu Glu Gly Arg Arg
705                 710                 715                 720
Arg Gly Tyr Val Glu Thr Leu Phe Gly Arg Arg Arg Tyr Val Pro Asp
                725                 730                 735
Leu Glu Ala Arg Val Lys Ser Val Arg Glu Ala Ala Glu Arg Met Ala
            740                 745                 750
Phe Asn Met Pro Val Gln Gly Thr Ala Ala Asp Leu Met Lys Leu Ala
        755                 760                 765
Met Val Lys Leu Phe Pro Arg Leu Glu Glu Met Gly Ala Arg Met Leu
    770                 775                 780
```

```
Leu Gln Val His Asp Glu Leu Val Leu Glu Ala Pro Lys Glu Arg Ala
785                 790                 795                 800

Glu Ala Val Ala Arg Leu Ala Lys Glu Val Met Glu Gly Val Tyr Pro
                805                 810                 815

Leu Ala Val Pro Leu Glu Val Glu Val Gly Ile Gly Glu Asp Trp Leu
                820                 825                 830

Ser Ala Lys Glu Gly Ile Asp Gly Arg Gly Gly Gly His His His
            835                 840                 845

His His His
    850

<210> SEQ ID NO 67
<211> LENGTH: 750
<212> TYPE: DNA
<213> ORGANISM: Pyrococcus furiosus
<220> FEATURE:
<221> NAME/KEY: CDS
<222> LOCATION: (1)..(750)
<223> OTHER INFORMATION:

<400> SEQUENCE: 67 atg cca ttt gaa atc gta ttt gaa ggt gca aaa gag ttt gcc caa ctt      48
Met Pro Phe Glu Ile Val Phe Glu Gly Ala Lys Glu Phe Ala Gln Leu
1               5                   10                  15 ata gac acc gca agt aag tta ata gat gag gcc gcg ttt aaa gtt aca      96
Ile Asp Thr Ala Ser Lys Leu Ile Asp Glu Ala Ala Phe Lys Val Thr
            20                  25                  30 gaa gat ggg ata agc atg agg gcc atg gat cca agt aga gtt gtc ctg     144
Glu Asp Gly Ile Ser Met Arg Ala Met Asp Pro Ser Arg Val Val Leu
        35                  40                  45 att gac cta aat ctc ccg tca agc ata ttt agc aaa tat gaa gtt gtt     192
Ile Asp Leu Asn Leu Pro Ser Ser Ile Phe Ser Lys Tyr Glu Val Val
    50                  55                  60 gaa cca gaa aca att gga gtt aac atg gac cac cta aag aag atc cta     240
Glu Pro Glu Thr Ile Gly Val Asn Met Asp His Leu Lys Lys Ile Leu
65                  70                  75                  80 aag aga ggt aaa gca aag gac acc tta ata ctc aag aaa gga gag gaa     288
Lys Arg Gly Lys Ala Lys Asp Thr Leu Ile Leu Lys Lys Gly Glu Glu
                85                  90                  95 aac ttc tta gag ata aca att caa gga act gca aca aga aca ttt aga     336
Asn Phe Leu Glu Ile Thr Ile Gln Gly Thr Ala Thr Arg Thr Phe Arg
            100                 105                 110 gtt ccc cta ata gat gta gaa gag atg gaa gtt gac ctc cca gaa ctt     384
Val Pro Leu Ile Asp Val Glu Glu Met Glu Val Asp Leu Pro Glu Leu
        115                 120                 125 cca ttc act gca aag gtt gta gtt ctt gga gaa gtc cta aaa gat gct     432
Pro Phe Thr Ala Lys Val Val Val Leu Gly Glu Val Leu Lys Asp Ala
    130                 135                 140 gtt aaa gat gcc tct cta gtg agt gac agc ata aaa ttt att gcc agg     480
Val Lys Asp Ala Ser Leu Val Ser Asp Ser Ile Lys Phe Ile Ala Arg
145                 150                 155                 160 gaa aat gaa ttt ata atg aag gca gag gga gaa acc cag gaa gtt gag     528
Glu Asn Glu Phe Ile Met Lys Ala Glu Gly Glu Thr Gln Glu Val Glu
                165                 170                 175 ata aag cta act ctt gaa gat gag gga tta ttg gac atc gag gtt caa     576
Ile Lys Leu Thr Leu Glu Asp Glu Gly Leu Leu Asp Ile Glu Val Gln
            180                 185                 190 gag gag aca aag agc gca tat gga gtc agc tat ctc tcc gac atg gtt     624
Glu Glu Thr Lys Ser Ala Tyr Gly Val Ser Tyr Leu Ser Asp Met Val
        195                 200                 205
```

```
aaa gga ctt gga aag gcc gat gaa gtt aca ata aag ttt gga aat gaa    672
Lys Gly Leu Gly Lys Ala Asp Glu Val Thr Ile Lys Phe Gly Asn Glu
    210                 215                 220 atg ccc atg caa atg gag tat tac att aga gat gaa gga aga ctt aca    720
Met Pro Met Gln Met Glu Tyr Tyr Ile Arg Asp Glu Gly Arg Leu Thr
225                 230                 235                 240 ttc cta ctg gct cca aga gtt gaa gag tga                            750
Phe Leu Leu Ala Pro Arg Val Glu Glu
                245
```

<210> SEQ ID NO 68
<211> LENGTH: 249
<212> TYPE: PRT
<213> ORGANISM: Pyrococcus furiosus

<400> SEQUENCE: 68

```
Met Pro Phe Glu Ile Val Phe Glu Gly Ala Lys Glu Phe Ala Gln Leu
1               5                   10                  15

Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Met Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160

Glu Asn Glu Phe Ile Met Lys Ala Glu Gly Glu Thr Gln Glu Val Glu
                165                 170                 175

Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
        195                 200                 205

Lys Gly Leu Gly Lys Ala Asp Glu Val Thr Ile Lys Phe Gly Asn Glu
    210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245
```

<210> SEQ ID NO 69
<211> LENGTH: 201
<212> TYPE: DNA
<213> ORGANISM: Sulfolobus acidocaldarius
<220> FEATURE:
<221> NAME/KEY: CDS
<222> LOCATION: (1)..(201)
<223> OTHER INFORMATION:

-continued

```
<400> SEQUENCE: 69 atg gtg aag gta aag ttc aag tat aag ggt gaa gag aaa gaa gta gac    48
Met Val Lys Val Lys Phe Lys Tyr Lys Gly Glu Glu Lys Glu Val Asp
1               5                   10                  15 act tca aag ata aag aag gtt tgg aga gta ggc aaa atg gtg tcc ttt    96
Thr Ser Lys Ile Lys Lys Val Trp Arg Val Gly Lys Met Val Ser Phe
            20                  25                  30 acc tat gac gac aat ggt aag aca ggt aga gga gct gta agc gag aaa    144
Thr Tyr Asp Asp Asn Gly Lys Thr Gly Arg Gly Ala Val Ser Glu Lys
        35                  40                  45 gat gct cca aaa gaa tta tta gac atg tta gca aga gca gaa aga gag    192
Asp Ala Pro Lys Glu Leu Leu Asp Met Leu Ala Arg Ala Glu Arg Glu
    50                  55                  60 aag aaa taa                                                        201
Lys Lys
65

<210> SEQ ID NO 70
<211> LENGTH: 66
<212> TYPE: PRT
<213> ORGANISM: Sulfolobus acidocaldarius

<400> SEQUENCE: 70

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 71
<211> LENGTH: 189
<212> TYPE: DNA
<213> ORGANISM: Sulfolobus solfactaricus
<220> FEATURE:
<221> NAME/KEY: CDS
<222> LOCATION: (1)..(189)
<223> OTHER INFORMATION:

<400> SEQUENCE: 71 gca acc gta aag ttc aag tac aaa ggc gaa gaa aaa gag gta gac atc    48
Ala Thr Val Lys Phe Lys Tyr Lys Gly Glu Glu Lys Glu Val Asp Ile
1               5                   10                  15 tcc aag atc aag aaa gta tgg cgt gtg ggc aag atg atc tcc ttc acc    96
Ser Lys Ile Lys Lys Val Trp Arg Val Gly Lys Met Ile Ser Phe Thr
            20                  25                  30 tac gac gag ggc ggt ggc aag acc ggc cgt ggt gcg gta agc gaa aag    144
Tyr Asp Glu Gly Gly Gly Lys Thr Gly Arg Gly Ala Val Ser Glu Lys
        35                  40                  45 gac gcg ccg aag gag ctg ctg cag atg ctg gag aag cag aaa aag        189
Asp Ala Pro Lys Glu Leu Leu Gln Met Leu Glu Lys Gln Lys Lys
    50                  55                  60

<210> SEQ ID NO 72
<211> LENGTH: 63
<212> TYPE: PRT
<213> ORGANISM: Sulfolobus solfactaricus
```

<400> SEQUENCE: 72

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 73
<211> LENGTH: 57
<212> TYPE: PRT
<213> ORGANISM: Methanopyrus kandleri

<400> SEQUENCE: 73

Val Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30

Val Leu Ala Thr Arg Tyr Leu Met Glu Arg Ser Ser Ala Lys Asn
        35                  40                  45

Asp Glu Glu Leu Leu Glu Leu His Gln
    50                  55

<210> SEQ ID NO 74
<211> LENGTH: 29
<212> TYPE: PRT
<213> ORGANISM: Escherichia coli

<400> SEQUENCE: 74

Gly Gly Asn Ala Leu Lys Phe Tyr Ala Ser Val Arg Leu Asp Ile Arg
1               5                   10                  15

Arg Ile Gly Ala Ile Lys Asp Gly Asp Glu Val Val Gly
            20                  25

<210> SEQ ID NO 75
<211> LENGTH: 57
<212> TYPE: PRT
<213> ORGANISM: Methanopyrus kandleri

<400> SEQUENCE: 75

Val Pro Ile Asp Glu Lys Glu Glu Arg Ile Leu Glu Ile Leu Arg Glu
1               5                   10                  15

Asn Pro Trp Thr Pro His Asp Glu Ile Ala Arg Arg Gly Gly Leu Ser
            20                  25                  30

Val Ser Glu Val Glu Gly Glu Lys Asp Pro Glu Ser Ser Gly Ile Tyr
        35                  40                  45

Ser Leu Trp Ser Arg Val Val Val Asn
    50                  55

<210> SEQ ID NO 76
<211> LENGTH: 40
<212> TYPE: PRT
<213> ORGANISM: Escherichia coli

<400> SEQUENCE: 76

Ile Asp Arg Ile Asp Arg Lys Ile Leu Asn Glu Leu Gln Lys Asp Gly
1               5                   10                  15

-continued

Arg Arg Ile Ser Asn Glu Leu Ala Lys Arg Val Gly Leu Ser Val Ser
            20                  25                  30

Thr Val Arg Glu Arg Val Arg Arg
            35                  40

<210> SEQ ID NO 77
<211> LENGTH: 40
<212> TYPE: PRT
<213> ORGANISM: Methanopyrus kandleri

<400> SEQUENCE: 77

Leu Lys Leu Gln Asp Arg Tyr Gly Ile Arg Glu Asp Val Ala Leu Cys
1               5                   10                  15

Leu Ala Arg Ala Phe Asp Gly Ser Ile Ser Met Ile Ala Thr Thr Pro
            20                  25                  30

Tyr Arg Thr Leu Lys Asp Val Cys
            35                  40

<210> SEQ ID NO 78
<211> LENGTH: 15
<212> TYPE: PRT
<213> ORGANISM: Methanopyrus kandleri

<400> SEQUENCE: 78

Pro Asp Leu Thr Leu Glu Glu Ala Lys Ser Val Asn Arg Thr Leu
1               5                   10                  15

<210> SEQ ID NO 79
<211> LENGTH: 30
<212> TYPE: PRT
<213> ORGANISM: Methanopyrus kandleri

<400> SEQUENCE: 79

Ala Thr Leu Ile Asp Glu His Gly Leu Ser Pro Ala Asp Ala Ala Asp
1               5                   10                  15

Glu Leu Ile Glu His Phe Glu Ser Ile Ala Gly Ile Leu Ala
            20                  25                  30

<210> SEQ ID NO 80
<211> LENGTH: 11
<212> TYPE: PRT
<213> ORGANISM: Methanopyrus kandleri

<400> SEQUENCE: 80

Thr Asp Leu Glu Glu Ile Glu Arg Met Tyr Glu
1               5                   10

<210> SEQ ID NO 81
<211> LENGTH: 15
<212> TYPE: PRT
<213> ORGANISM: Methanopyrus kandleri

<400> SEQUENCE: 81

Glu Gly Arg Leu Ser Glu Glu Ala Tyr Arg Ala Ala Val Glu Ile
1               5                   10                  15

<210> SEQ ID NO 82
<211> LENGTH: 57
<212> TYPE: PRT
<213> ORGANISM: Thermococcus kodakaraensis

<400> SEQUENCE: 82

Ala Glu Leu Thr Lys Lys Glu Gly Val Gly Arg Lys Thr Ala Glu Arg

-continued

```
                1               5                  10                 15
Leu Leu Arg Ala Phe Gly Asn Pro Glu Arg Val Lys Gln Leu Ala Arg
                    20                  25                  30
Glu Phe Glu Ile Glu Lys Leu Ala Ser Val Glu Gly Val Gly Glu Arg
        35                  40                  45
Val Leu Arg Ser Leu Val Pro Gly Tyr
    50                  55
```

<210> SEQ ID NO 83
<211> LENGTH: 27
<212> TYPE: PRT
<213> ORGANISM: Methanopyrus kandleri

<400> SEQUENCE: 83

```
Ala Ser Leu Ile Ser Ile Arg Gly Ile Asp Arg Glu Arg Ala Glu Arg
1               5                   10                  15
Leu Leu Lys Lys Tyr Gly Gly Tyr Ser Lys Val
                20                  25
```

<210> SEQ ID NO 84
<211> LENGTH: 10
<212> TYPE: PRT
<213> ORGANISM: Methanopyrus kandleri

<400> SEQUENCE: 84

```
Arg Glu Ala Gly Val Glu Glu Leu Arg Glu
1               5                   10
```

<210> SEQ ID NO 85
<211> LENGTH: 13
<212> TYPE: PRT
<213> ORGANISM: Methanopyrus kandleri

<400> SEQUENCE: 85

```
Asp Gly Leu Thr Asp Ala Gln Ile Arg Glu Leu Lys Gly
1               5                   10
```

<210> SEQ ID NO 86
<211> LENGTH: 27
<212> TYPE: PRT
<213> ORGANISM: Methanopyrus kandleri

<400> SEQUENCE: 86

```
Leu Lys Thr Leu Glu Ser Ile Val Gly Asp Leu Glu Lys Ala Asp Glu
1               5                   10                  15
Leu Lys Arg Lys Tyr Gly Ser Ala Ser Ala Val
                20                  25
```

<210> SEQ ID NO 87
<211> LENGTH: 10
<212> TYPE: PRT
<213> ORGANISM: Methanopyrus kandleri

<400> SEQUENCE: 87

```
Arg Arg Leu Pro Val Glu Glu Leu Arg Glu
1               5                   10
```

<210> SEQ ID NO 88
<211> LENGTH: 13
<212> TYPE: PRT
<213> ORGANISM: Methanopyrus kandleri

<400> SEQUENCE: 88

Leu Gly Phe Ser Asp Asp Glu Ile Ala Glu Ile Lys Gly
1               5                   10

<210> SEQ ID NO 89
<211> LENGTH: 28
<212> TYPE: PRT
<213> ORGANISM: Methanopyrus kandleri

<400> SEQUENCE: 89

Ile Pro Lys Lys Leu Arg Glu Ala Phe Asp Leu Glu Thr Ala Ala Glu
1               5                   10                  15

Leu Tyr Glu Arg Tyr Gly Ser Leu Lys Glu Ile Gly
            20                  25

<210> SEQ ID NO 90
<211> LENGTH: 10
<212> TYPE: PRT
<213> ORGANISM: Methanopyrus kandleri

<400> SEQUENCE: 90

Arg Arg Leu Ser Tyr Asp Asp Leu Leu Glu
1               5                   10

<210> SEQ ID NO 91
<211> LENGTH: 15
<212> TYPE: PRT
<213> ORGANISM: Methanopyrus kandleri

<400> SEQUENCE: 91

Leu Gly Ala Thr Pro Lys Ala Ala Ala Glu Ile Lys Gly Pro Glu
1               5                   10                  15

<210> SEQ ID NO 92
<211> LENGTH: 28
<212> TYPE: PRT
<213> ORGANISM: Methanopyrus kandleri

<400> SEQUENCE: 92

Lys Phe Leu Leu Asn Ile Glu Gly Val Gly Pro Lys Leu Ala Glu Arg
1               5                   10                  15

Ile Leu Glu Ala Val Asp Tyr Asp Leu Glu Arg Leu
            20                  25

<210> SEQ ID NO 93
<211> LENGTH: 26
<212> TYPE: PRT
<213> ORGANISM: Methanopyrus kandleri

<400> SEQUENCE: 93

Ala Ser Leu Asn Pro Glu Glu Leu Ala Glu Val Glu Gly Leu Gly Glu
1               5                   10                  15

Glu Leu Ala Glu Arg Val Val Tyr Ala Ala
            20                  25

<210> SEQ ID NO 94
<211> LENGTH: 40
<212> TYPE: PRT
<213> ORGANISM: Methanopyrus kandleri

<400> SEQUENCE: 94

Trp Lys Glu Trp Leu Glu Arg Lys Val Gly Glu Gly Arg Ala Arg Arg
1               5                   10                  15

```
Leu Ile Glu Tyr Phe Gly Ser Ala Gly Glu Val Gly Lys Leu Val Glu
        20                  25                  30

Asn Ala Glu Val Ser Lys Leu Leu
        35                  40
```

<210> SEQ ID NO 95
<211> LENGTH: 15
<212> TYPE: PRT
<213> ORGANISM: Methanopyrus kandleri

<400> SEQUENCE: 95

```
Val Pro Gly Ile Gly Asp Glu Ala Val Ala Arg Leu Val Pro Gly
1               5                   10                  15
```

<210> SEQ ID NO 96
<211> LENGTH: 28
<212> TYPE: PRT
<213> ORGANISM: Methanopyrus kandleri

<400> SEQUENCE: 96

```
Tyr Lys Thr Leu Arg Asp Ala Gly Leu Thr Pro Ala Glu Ala Glu Arg
1               5                   10                  15

Val Leu Lys Arg Tyr Gly Ser Val Ser Lys Val Gln
            20                  25
```

<210> SEQ ID NO 97
<211> LENGTH: 10
<212> TYPE: PRT
<213> ORGANISM: Methanopyrus kandleri

<400> SEQUENCE: 97

```
Glu Gly Ala Thr Pro Asp Glu Leu Arg Glu
1               5                   10
```

<210> SEQ ID NO 98
<211> LENGTH: 13
<212> TYPE: PRT
<213> ORGANISM: Methanopyrus kandleri

<400> SEQUENCE: 98

```
Leu Gly Leu Gly Asp Ala Lys Ile Ala Arg Ile Leu Gly
1               5                   10
```

<210> SEQ ID NO 99
<211> LENGTH: 27
<212> TYPE: PRT
<213> ORGANISM: Methanopyrus kandleri

<400> SEQUENCE: 99

```
Leu Arg Ser Leu Val Asn Lys Arg Leu Asp Val Asp Thr Ala Tyr Glu
1               5                   10                  15

Leu Lys Arg Arg Tyr Gly Ser Val Ser Ala Val
            20                  25
```

<210> SEQ ID NO 100
<211> LENGTH: 10
<212> TYPE: PRT
<213> ORGANISM: Methanopyrus kandleri

<400> SEQUENCE: 100

```
Arg Lys Ala Pro Val Lys Glu Leu Arg Glu
1               5                   10
```

```
<210> SEQ ID NO 101
<211> LENGTH: 15
<212> TYPE: PRT
<213> ORGANISM: Methanopyrus kandleri

<400> SEQUENCE: 101

Leu Gly Leu Ser Asp Arg Lys Ile Ala Arg Ile Lys Gly Ile Pro
1               5                   10                  15

<210> SEQ ID NO 102
<211> LENGTH: 27
<212> TYPE: PRT
<213> ORGANISM: Methanopyrus kandleri

<400> SEQUENCE: 102

Glu Thr Met Leu Gln Val Arg Gly Met Ser Val Glu Lys Ala Glu Arg
1               5                   10                  15

Leu Leu Glu Arg Phe Asp Thr Trp Thr Lys Val
            20                  25

<210> SEQ ID NO 103
<211> LENGTH: 9
<212> TYPE: PRT
<213> ORGANISM: Methanopyrus kandleri

<400> SEQUENCE: 103

Lys Glu Ala Pro Val Ser Glu Leu Val
1               5

<210> SEQ ID NO 104
<211> LENGTH: 16
<212> TYPE: PRT
<213> ORGANISM: Methanopyrus kandleri

<400> SEQUENCE: 104

Val Pro Gly Val Gly Leu Ser Leu Val Lys Glu Ile Lys Ala Gln Val
1               5                   10                  15

<210> SEQ ID NO 105
<211> LENGTH: 27
<212> TYPE: PRT
<213> ORGANISM: Methanopyrus kandleri

<400> SEQUENCE: 105

Lys Ala Leu Leu Asp Val Lys Gly Val Ser Pro Glu Leu Ala Asp Arg
1               5                   10                  15

Leu Val Glu Glu Leu Gly Ser Pro Tyr Arg Val
            20                  25

<210> SEQ ID NO 106
<211> LENGTH: 9
<212> TYPE: PRT
<213> ORGANISM: Methanopyrus kandleri

<400> SEQUENCE: 106

Leu Thr Ala Lys Lys Ser Asp Leu Met
1               5

<210> SEQ ID NO 107
<211> LENGTH: 16
<212> TYPE: PRT
<213> ORGANISM: Methanopyrus kandleri

<400> SEQUENCE: 107
```

```
Val Glu Arg Val Gly Pro Lys Leu Ala Glu Arg Ile Arg Ala Ala Gly
1               5                   10                  15
```

<210> SEQ ID NO 108
<211> LENGTH: 27
<212> TYPE: PRT
<213> ORGANISM: Escherichia coli

<400> SEQUENCE: 108

```
Lys Glu Leu Ile Lys Thr Asn Gly Val Gly Pro Lys Leu Ala Leu Ala
1               5                   10                  15

Ile Leu Ser Gly Met Ser Ala Gln Gln Phe Val
            20                  25
```

<210> SEQ ID NO 109
<211> LENGTH: 26
<212> TYPE: PRT
<213> ORGANISM: Escherichia coli

<400> SEQUENCE: 109

```
Asn Ala Val Glu Arg Glu Val Gly Ala Leu Pro Gly Ile Gly Lys
1               5                   10                  15

Lys Thr Ala Glu Arg Leu Ile Val Glu Met
            20                  25
```

<210> SEQ ID NO 110
<211> LENGTH: 57
<212> TYPE: PRT
<213> ORGANISM: Homo sapiens

<400> SEQUENCE: 110

```
Ala Glu Ala Lys Lys Leu Pro Gly Val Gly Thr Lys Ile Ala Glu Lys
1               5                   10                  15

Ile Asp Glu Phe Leu Ala Thr Gly Lys Leu Arg Lys Leu Glu Lys Ile
            20                  25                  30

Arg Gln Asp Asp Thr Ser Ser Ser Ile Val Ser Gly Ile Gly Pro Ser
        35                  40                  45

Ala Ala Arg Lys Phe Val Asp Glu Gly
        50                  55
```

<210> SEQ ID NO 111
<211> LENGTH: 27
<212> TYPE: PRT
<213> ORGANISM: Escherichia coli

<400> SEQUENCE: 111

```
Leu Glu Val Met Glu Val Pro Gly Val Gly Pro Lys Thr Ala Arg Gly
1               5                   10                  15

Leu Tyr Glu Ala Leu Gly Ile Asp Ser Leu Glu
            20                  25
```

<210> SEQ ID NO 112
<211> LENGTH: 12
<212> TYPE: PRT
<213> ORGANISM: Escherichia coli

<400> SEQUENCE: 112

```
Lys Leu Lys Glu Ala Leu Glu Arg Gly Asp Leu Leu
1               5                   10
```

<210> SEQ ID NO 113
<211> LENGTH: 16

```
<212> TYPE: PRT
<213> ORGANISM: Escherichia coli

<400> SEQUENCE: 113

Leu Lys Gly Phe Gly Ala Lys Lys Ala Glu Arg Ile Lys Glu Gly Leu
1               5                   10                  15

<210> SEQ ID NO 114
<211> LENGTH: 30
<212> TYPE: DNA
<213> ORGANISM: artificial sequence
<220> FEATURE:
<223> OTHER INFORMATION: primer

<400> SEQUENCE: 114
agagcttgag gagagcagga aaggtggaac                                    30

<210> SEQ ID NO 115
<211> LENGTH: 24
<212> TYPE: DNA
<213> ORGANISM: artificial sequence
<220> FEATURE:
<223> OTHER INFORMATION: primer

<400> SEQUENCE: 115
tgcagagcga ttattcagga atgc                                          24

<210> SEQ ID NO 116
<211> LENGTH: 30
<212> TYPE: DNA
<213> ORGANISM: artificial sequence
<220> FEATURE:
<223> OTHER INFORMATION: primer

<400> SEQUENCE: 116
acaagggcta ctggttgccg attttttattg                                   30

<210> SEQ ID NO 117
<211> LENGTH: 27
<212> TYPE: DNA
<213> ORGANISM: artificial sequence
<220> FEATURE:
<223> OTHER INFORMATION: primer

<400> SEQUENCE: 117
gggactggcc tcagaggaaa cttcagg                                       27

<210> SEQ ID NO 118
<211> LENGTH: 30
<212> TYPE: DNA
<213> ORGANISM: artificial sequence
<220> FEATURE:
<223> OTHER INFORMATION: primer

<400> SEQUENCE: 118
acaagggcta ctggttgccg attttttattg                                   30

<210> SEQ ID NO 119
<211> LENGTH: 28
<212> TYPE: DNA
<213> ORGANISM: artificial sequence
<220> FEATURE:
<223> OTHER INFORMATION: primer

<400> SEQUENCE: 119
cctgcatttg tggggtgaat tccttgcc                                      28
```

<210> SEQ ID NO 120
<211> LENGTH: 189
<212> TYPE: DNA
<213> ORGANISM: artificial sequence
<220> FEATURE:
<223> OTHER INFORMATION: Synthetic Sso7d gene
<220> FEATURE:
<221> NAME/KEY: CDS
<222> LOCATION: (1)..(189)
<223> OTHER INFORMATION:

<400> SEQUENCE: 120

```
gca acc gta aag ttc aag tac aaa ggc gaa gaa aaa gag gta gac atc      48
Ala Thr Val Lys Phe Lys Tyr Lys Gly Glu Glu Lys Glu Val Asp Ile
1               5                   10                  15 tcc aag atc aag aaa gta tgg cgt gtg ggc aag atg atc tcc ttc acc      96
Ser Lys Ile Lys Lys Val Trp Arg Val Gly Lys Met Ile Ser Phe Thr
            20                  25                  30 tac gac gag ggc ggt ggc aag acc ggc cgt ggt gcg gta agc gaa aag    144
Tyr Asp Glu Gly Gly Gly Lys Thr Gly Arg Gly Ala Val Ser Glu Lys
        35                  40                  45 gac gcg ccg aag gag ctg ctg cag atg ctg gag aag cag aaa aag         189
Asp Ala Pro Lys Glu Leu Leu Gln Met Leu Glu Lys Gln Lys Lys
    50                  55                  60
```

<210> SEQ ID NO 121
<211> LENGTH: 63
<212> TYPE: PRT
<213> ORGANISM: artificial sequence
<220> FEATURE:
<223> OTHER INFORMATION: Synthetic Sso7d gene

<400> SEQUENCE: 121

```
Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60
```

<210> SEQ ID NO 122
<211> LENGTH: 1899
<212> TYPE: DNA
<213> ORGANISM: artificial sequence
<220> FEATURE:
<223> OTHER INFORMATION: The DNA sequence encoding the Sso7d-ATaq fusion
      protein
<220> FEATURE:
<221> NAME/KEY: CDS
<222> LOCATION: (1)..(1899)
<223> OTHER INFORMATION:

<400> SEQUENCE: 122

```
atg att acg aat tcg agc gca acc gta aag ttc aag tac aaa ggc gaa      48
Met Ile Thr Asn Ser Ser Ala Thr Val Lys Phe Lys Tyr Lys Gly Glu
1               5                   10                  15 gaa aaa gag gta gac atc tcc aag atc aag aaa gta tgg cgt gtg ggc      96
Glu Lys Glu Val Asp Ile Ser Lys Ile Lys Lys Val Trp Arg Val Gly
            20                  25                  30 aag atg atc tcc ttc acc tac gac gag ggc ggt ggc aag acc ggc cgt    144
Lys Met Ile Ser Phe Thr Tyr Asp Glu Gly Gly Gly Lys Thr Gly Arg
        35                  40                  45
```

-continued

| | | |
|---|---|---|
| ggt gcg gta agc gaa aag gac gcg ccg aag gag ctg ctg cag atg ctg<br>Gly Ala Val Ser Glu Lys Asp Ala Pro Lys Glu Leu Leu Gln Met Leu<br>50                       55                      60 | 192 |
| gag aag cag aaa aag ggc ggt gtc act agt ccc aag gcc ctg gag<br>Glu Lys Gln Lys Lys Gly Gly Val Thr Ser Pro Lys Ala Leu Glu<br>65                    70                   75                80 | 240 |
| gag gcc ccc tgg ccc ccg ccg gaa ggg gcc ttc gtg ggc ttt gtg ctt<br>Glu Ala Pro Trp Pro Pro Pro Glu Gly Ala Phe Val Gly Phe Val Leu<br>                   85                       90                   95 | 288 |
| tcc cgc aag gag ccc atg tgg gcc gat ctt ctg gcc ctg gcc gcc gcc<br>Ser Arg Lys Glu Pro Met Trp Ala Asp Leu Leu Ala Leu Ala Ala Ala<br>             100                    105                  110 | 336 |
| agg ggg ggc cgg gtc cac cgg gcc ccc gag cct tat aaa gcc ctc agg<br>Arg Gly Gly Arg Val His Arg Ala Pro Glu Pro Tyr Lys Ala Leu Arg<br>115                   120                  125 | 384 |
| gac ctg aag gag gcg cgg ggg ctt ctc gcc aaa gac ctg agc gtt ctg<br>Asp Leu Lys Glu Ala Arg Gly Leu Leu Ala Lys Asp Leu Ser Val Leu<br>130                   135                  140 | 432 |
| gcc ctg agg gaa ggc ctt ggc ctc ccg ccc ggc gac gac ccc atg ctc<br>Ala Leu Arg Glu Gly Leu Gly Leu Pro Pro Gly Asp Asp Pro Met Leu<br>145                   150                  155               160 | 480 |
| ctc gcc tac ctc ctg gac cct tcc aac acc acc ccc gag ggg gtg gcc<br>Leu Ala Tyr Leu Leu Asp Pro Ser Asn Thr Thr Pro Glu Gly Val Ala<br>                  165                  170                175 | 528 |
| cgg cgc tac ggc ggg gag tgg acg gag gag gcg ggg gag cgg gcc gcc<br>Arg Arg Tyr Gly Gly Glu Trp Thr Glu Glu Ala Gly Glu Arg Ala Ala<br>                  180                  185                190 | 576 |
| ctt tcc gag agg ctc ttc gcc aac ctg tgg ggg agg ctt gag ggg gag<br>Leu Ser Glu Arg Leu Phe Ala Asn Leu Trp Gly Arg Leu Glu Gly Glu<br>                  195                  200                205 | 624 |
| gag agg ctc ctt tgg ctt tac cgg gag gtg gag agg ccc ctt tcc gct<br>Glu Arg Leu Leu Trp Leu Tyr Arg Glu Val Glu Arg Pro Leu Ser Ala<br>        210                  215                  220 | 672 |
| gtc ctg gcc cac atg gag gcc acg ggg gtg cgc ctg gac gtg gcc tat<br>Val Leu Ala His Met Glu Ala Thr Gly Val Arg Leu Asp Val Ala Tyr<br>225                   230                  235               240 | 720 |
| ctc agg gcc ttg tcc ctg gag gtg gcc gag gag atc gcc cgc ctc gag<br>Leu Arg Ala Leu Ser Leu Glu Val Ala Glu Glu Ile Ala Arg Leu Glu<br>                  245                  250                255 | 768 |
| gcc gag gtc ttc cgc ctg gcc ggc cac ccc ttc aac ctc aac tcc cgg<br>Ala Glu Val Phe Arg Leu Ala Gly His Pro Phe Asn Leu Asn Ser Arg<br>             260                    265                  270 | 816 |
| gac cag ctg gaa agg gtc ctc ttt gac gag cta ggg ctt ccc gcc atc<br>Asp Gln Leu Glu Arg Val Leu Phe Asp Glu Leu Gly Leu Pro Ala Ile<br>             275                    280                  285 | 864 |
| ggc aag acg gag aag acc ggc aag cgc tcc acc agc gcc gcc gtc ctg<br>Gly Lys Thr Glu Lys Thr Gly Lys Arg Ser Thr Ser Ala Ala Val Leu<br>290                   295                  300 | 912 |
| gag gcc ctc cgc gag gcc cac ccc atc gtg gag aag atc ctg cag tac<br>Glu Ala Leu Arg Glu Ala His Pro Ile Val Glu Lys Ile Leu Gln Tyr<br>305                   310                  315               320 | 960 |
| cgg gag ctc acc aag ctg aag agc acc tac att gac ccc ttg ccg gac<br>Arg Glu Leu Thr Lys Leu Lys Ser Thr Tyr Ile Asp Pro Leu Pro Asp<br>                  325                  330                335 | 1008 |
| ctc atc cac ccc agg acg ggc cgc ctc cac acc cgc ttc aac cag acg<br>Leu Ile His Pro Arg Thr Gly Arg Leu His Thr Arg Phe Asn Gln Thr<br>             340                    345                  350 | 1056 |
| gcc acg gcc acg ggc agg cta agt agc tcc gat ccc aac ctc cag aac<br>Ala Thr Ala Thr Gly Arg Leu Ser Ser Ser Asp Pro Asn Leu Gln Asn | 1104 |

-continued

```
                 355                 360                 365
atc ccc gtc cgc acc ccg ctt ggg cag agg atc cgc cgg gcc ttc atc    1152
Ile Pro Val Arg Thr Pro Leu Gly Gln Arg Ile Arg Arg Ala Phe Ile
    370                 375                 380 gcc gag gag ggg tgg cta ttg gtg gcc ctg gac tat agc cag ata gag    1200
Ala Glu Glu Gly Trp Leu Leu Val Ala Leu Asp Tyr Ser Gln Ile Glu
385                 390                 395                 400 ctc agg gtg ctg gcc cac ctc tcc ggc gac gag aac ctg atc cgg gtc    1248
Leu Arg Val Leu Ala His Leu Ser Gly Asp Glu Asn Leu Ile Arg Val
                405                 410                 415 ttc cag gag ggg cgg gac atc cac acg gag acc gcc agc tgg atg ttc    1296
Phe Gln Glu Gly Arg Asp Ile His Thr Glu Thr Ala Ser Trp Met Phe
            420                 425                 430 ggc gtc ccc cgg gag gcc gtg gac ccc ctg atg cgc cgg gcg gcc aag    1344
Gly Val Pro Arg Glu Ala Val Asp Pro Leu Met Arg Arg Ala Ala Lys
        435                 440                 445 acc atc aac ttc ggg gtc ctc tac ggc atg tcg gcc cac cgc ctc tcc    1392
Thr Ile Asn Phe Gly Val Leu Tyr Gly Met Ser Ala His Arg Leu Ser
    450                 455                 460 cag gag cta gcc atc cct tac gag gag gcc cag gcc ttc att gag cgc    1440
Gln Glu Leu Ala Ile Pro Tyr Glu Glu Ala Gln Ala Phe Ile Glu Arg
465                 470                 475                 480 tac ttt cag agc ttc ccc aag gtg cgg gcc tgg att gag aag acc ctg    1488
Tyr Phe Gln Ser Phe Pro Lys Val Arg Ala Trp Ile Glu Lys Thr Leu
                485                 490                 495 gag gag ggc agg agg cgg ggg tac gtg gag acc ctc ttc ggc cgc cgc    1536
Glu Glu Gly Arg Arg Arg Gly Tyr Val Glu Thr Leu Phe Gly Arg Arg
            500                 505                 510 cgc tac gtg cca gac cta gag gcc cgg gtg aag agc gtg cgg gag gcg    1584
Arg Tyr Val Pro Asp Leu Glu Ala Arg Val Lys Ser Val Arg Glu Ala
        515                 520                 525 gcc gag cgc atg gcc ttc aac atg ccc gtc cag ggc acc gcc gcc gac    1632
Ala Glu Arg Met Ala Phe Asn Met Pro Val Gln Gly Thr Ala Ala Asp
    530                 535                 540 ctc atg aag ctg gct atg gtg aag ctc ttc ccc agg ctg gag gaa atg    1680
Leu Met Lys Leu Ala Met Val Lys Leu Phe Pro Arg Leu Glu Glu Met
545                 550                 555                 560 ggg gcc agg atg ctc ctt cag gtc cac gac gag ctg gtc ctc gag gcc    1728
Gly Ala Arg Met Leu Leu Gln Val His Asp Glu Leu Val Leu Glu Ala
                565                 570                 575 cca aaa gag agg gcg gag gcc gtg gcc cgg ctg gcc aag gag gtc atg    1776
Pro Lys Glu Arg Ala Glu Ala Val Ala Arg Leu Ala Lys Glu Val Met
            580                 585                 590 gag ggg gtg tat ccc ctg gcc gtg ccc ctg gag gtg gag gtg ggg ata    1824
Glu Gly Val Tyr Pro Leu Ala Val Pro Leu Glu Val Glu Val Gly Ile
        595                 600                 605 ggg gag gac tgg ctc tcc gcc aag gag ggc att gat ggc cgc ggc gga    1872
Gly Glu Asp Trp Leu Ser Ala Lys Glu Gly Ile Asp Gly Arg Gly Gly
    610                 615                 620 ggc ggg cat cat cat cat cat cat taa                                1899
Gly Gly His His His His His His
625                 630
```

<210> SEQ ID NO 123
<211> LENGTH: 632
<212> TYPE: PRT
<213> ORGANISM: artificial sequence
<220> FEATURE:
<223> OTHER INFORMATION: The DNA sequence encoding the Sso7d-ATaq fusion protein

<400> SEQUENCE: 123

```
Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Lys Thr Gly Arg
        35                  40                  45

Gly Ala Val Ser Glu Lys Asp Ala Pro Lys Glu Leu Leu Gln Met Leu
50                  55                  60

Glu Lys Gln Lys Lys Gly Gly Val Thr Ser Pro Lys Ala Leu Glu
65                  70                  75                  80

Glu Ala Pro Trp Pro Pro Glu Gly Ala Phe Val Gly Phe Val Leu
                85                  90                  95

Ser Arg Lys Glu Pro Met Trp Ala Asp Leu Leu Ala Leu Ala Ala Ala
                100                 105                 110

Arg Gly Gly Arg Val His Arg Ala Pro Glu Pro Tyr Lys Ala Leu Arg
            115                 120                 125

Asp Leu Lys Glu Ala Arg Gly Leu Leu Ala Lys Asp Leu Ser Val Leu
130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
            180                 185                 190

Leu Ser Glu Arg Leu Phe Ala Asn Leu Trp Gly Arg Leu Glu Gly Glu
        195                 200                 205

Glu Arg Leu Leu Trp Leu Tyr Arg Glu Val Glu Arg Pro Leu Ser Ala
210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
            260                 265                 270

Asp Gln Leu Glu Arg Val Leu Phe Asp Glu Leu Gly Leu Pro Ala Ile
        275                 280                 285

Gly Lys Thr Glu Lys Thr Gly Lys Arg Ser Thr Ser Ala Ala Val Leu
290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
            340                 345                 350

Ala Thr Ala Thr Gly Arg Leu Ser Ser Asp Pro Asn Leu Gln Asn
        355                 360                 365

Ile Pro Val Arg Thr Pro Leu Gly Gln Arg Ile Arg Arg Ala Phe Ile
370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415
```

```
Phe Gln Glu Gly Arg Asp Ile His Thr Glu Thr Ala Ser Trp Met Phe
            420                 425                 430
Gly Val Pro Arg Glu Ala Val Asp Pro Leu Met Arg Arg Ala Ala Lys
            435                 440                 445
Thr Ile Asn Phe Gly Val Leu Tyr Gly Met Ser Ala His Arg Leu Ser
            450                 455                 460
Gln Glu Leu Ala Ile Pro Tyr Glu Glu Ala Gln Ala Phe Ile Glu Arg
465                 470                 475                 480
Tyr Phe Gln Ser Phe Pro Lys Val Arg Ala Trp Ile Glu Lys Thr Leu
                485                 490                 495
Glu Glu Gly Arg Arg Arg Gly Tyr Val Glu Thr Leu Phe Gly Arg Arg
                500                 505                 510
Arg Tyr Val Pro Asp Leu Glu Ala Arg Val Lys Ser Val Arg Glu Ala
            515                 520                 525
Ala Glu Arg Met Ala Phe Asn Met Pro Val Gln Gly Thr Ala Ala Asp
            530                 535                 540
Leu Met Lys Leu Ala Met Val Lys Leu Phe Pro Arg Leu Glu Glu Met
545                 550                 555                 560
Gly Ala Arg Met Leu Leu Gln Val His Asp Glu Leu Val Leu Glu Ala
                565                 570                 575
Pro Lys Glu Arg Ala Glu Ala Val Ala Arg Leu Ala Lys Glu Val Met
                580                 585                 590
Glu Gly Val Tyr Pro Leu Ala Val Pro Leu Glu Val Glu Val Gly Ile
            595                 600                 605
Gly Glu Asp Trp Leu Ser Ala Lys Glu Gly Ile Asp Gly Arg Gly Gly
            610                 615                 620
Gly Gly His His His His His His
625                 630

<210> SEQ ID NO 124
<211> LENGTH: 2763
<212> TYPE: DNA
<213> ORGANISM: artificial sequence
<220> FEATURE:
<223> OTHER INFORMATION: The DNA sequence encoding the Sso7d-Taq fusion
      protein
<220> FEATURE:
<221> NAME/KEY: CDS
<222> LOCATION: (1)..(2763)
<223> OTHER INFORMATION:

<400> SEQUENCE: 124 atg att acg aat tcg agc gca acc gta aag ttc aag tac aaa ggc gaa      48
Met Ile Thr Asn Ser Ser Ala Thr Val Lys Phe Lys Tyr Lys Gly Glu
1               5                   10                  15 gaa aaa gag gta gac atc tcc aag atc aag aaa gta tgg cgt gtg ggc      96
Glu Lys Glu Val Asp Ile Ser Lys Ile Lys Lys Val Trp Arg Val Gly
                20                  25                  30 aag atg atc tcc ttc acc tac gac gag ggc ggt ggc aag acc ggc cgt     144
Lys Met Ile Ser Phe Thr Tyr Asp Glu Gly Gly Gly Lys Thr Gly Arg
            35                  40                  45 ggt gcg gta agc gaa aag gac gcg ccg aag gag ctg ctg cag atg ctg     192
Gly Ala Val Ser Glu Lys Asp Ala Pro Lys Glu Leu Leu Gln Met Leu
        50                  55                  60 gag aag cag aaa aag ggc ggt ggt gtc act agt ggg atg ctg ccc ctc     240
Glu Lys Gln Lys Lys Gly Gly Gly Val Thr Ser Gly Met Leu Pro Leu
65                  70                  75                  80 ttt gag ccc aag ggc cgg gtc ctc ctg gtg gac ggc cac cac ctg gcc     288
```

|  |  |
|---|---|
| Phe Glu Pro Lys Gly Arg Val Leu Leu Val Asp Gly His His Leu Ala<br>              85                   90                 95 |  |
| tac cgc acc ttc cac gcc ctg aag ggc ctc acc acc agc cgg ggg gag<br>Tyr Arg Thr Phe His Ala Leu Lys Gly Leu Thr Thr Ser Arg Gly Glu<br>            100                 105              110 | 336 |
| ccg gtg cag gcg gtc tac ggc ttc gcc aag agc ctc ctc aag gcc ctc<br>Pro Val Gln Ala Val Tyr Gly Phe Ala Lys Ser Leu Leu Lys Ala Leu<br>       115                 120               125 | 384 |
| aag gag gac ggg gac gcg gtg atc gtg gtc ttt gac gcc aag gcc ccc<br>Lys Glu Asp Gly Asp Ala Val Ile Val Val Phe Asp Ala Lys Ala Pro<br>    130                 135               140 | 432 |
| tcc ttc cgc cac gag gcc tac ggg ggg tac aag gcg ggc cgg gcc ccc<br>Ser Phe Arg His Glu Ala Tyr Gly Gly Tyr Lys Ala Gly Arg Ala Pro<br>145                 150               155               160 | 480 |
| acg cca gag gac ttt ccc cgg caa ctc gcc ctc atc aag gag ctg gtg<br>Thr Pro Glu Asp Phe Pro Arg Gln Leu Ala Leu Ile Lys Glu Leu Val<br>                  165               170               175 | 528 |
| gac ctc ctg ggg ctg gcg cgc ctc gag gtc ccg ggc tac gag gcg gac<br>Asp Leu Leu Gly Leu Ala Arg Leu Glu Val Pro Gly Tyr Glu Ala Asp<br>            180                 185               190 | 576 |
| gac gtc ctg gcc agc ctg gcc aag aag gcg gaa aag gag ggc tac gag<br>Asp Val Leu Ala Ser Leu Ala Lys Lys Ala Glu Lys Glu Gly Tyr Glu<br>       195                 200               205 | 624 |
| gtc cgc atc ctc acc gcc gac aaa gac ctt tac cag ctc ctt tcc gac<br>Val Arg Ile Leu Thr Ala Asp Lys Asp Leu Tyr Gln Leu Leu Ser Asp<br>210                 215               220 | 672 |
| cgc atc cac gtc ctc cac ccc gag ggg tac ctc atc acc ccg gcc tgg<br>Arg Ile His Val Leu His Pro Glu Gly Tyr Leu Ile Thr Pro Ala Trp<br>225                 230               235               240 | 720 |
| ctt tgg gaa aag tac ggc ctg agg ccc gac cag tgg gcc gac tac cgg<br>Leu Trp Glu Lys Tyr Gly Leu Arg Pro Asp Gln Trp Ala Asp Tyr Arg<br>                  245               250               255 | 768 |
| gcc ctg acc ggg gac gag tcc gac aac ctt ccc ggg gtc aag ggc atc<br>Ala Leu Thr Gly Asp Glu Ser Asp Asn Leu Pro Gly Val Lys Gly Ile<br>            260                 265               270 | 816 |
| ggg gag aag acg gcg agg aag ctt ctg gag gag tgg ggg agc ctg gaa<br>Gly Glu Lys Thr Ala Arg Lys Leu Leu Glu Glu Trp Gly Ser Leu Glu<br>       275                 280               285 | 864 |
| gcc ctc ctc aag aac ctg gac cgg ctg aag ccc gcc atc cgg gag aag<br>Ala Leu Leu Lys Asn Leu Asp Arg Leu Lys Pro Ala Ile Arg Glu Lys<br>    290                 295               300 | 912 |
| atc ctg gcc cac atg gac gat ctg aag ctc tcc tgg gac ctg gcc aag<br>Ile Leu Ala His Met Asp Asp Leu Lys Leu Ser Trp Asp Leu Ala Lys<br>305                 310               315               320 | 960 |
| gtg cgc acc gac ctg ccc ctg gag gtg gac ttc gcc aaa agg cgg gag<br>Val Arg Thr Asp Leu Pro Leu Glu Val Asp Phe Ala Lys Arg Arg Glu<br>                  325               330               335 | 1008 |
| ccc gac cgg gag agg ctt agg gcc ttt ctg gag agg ctt gag ttt ggc<br>Pro Asp Arg Glu Arg Leu Arg Ala Phe Leu Glu Arg Leu Glu Phe Gly<br>            340                 345               350 | 1056 |
| agc ctc ctc cac gag ttc ggc ctt ctg gaa agc ccc aag gcc ctg gag<br>Ser Leu Leu His Glu Phe Gly Leu Leu Glu Ser Pro Lys Ala Leu Glu<br>       355                 360               365 | 1104 |
| gag gcc ccc tgg ccc ccg ccg gaa ggg gcc ttc gtg ggc ttt gtg ctt<br>Glu Ala Pro Trp Pro Pro Pro Glu Gly Ala Phe Val Gly Phe Val Leu<br>370                 375               380 | 1152 |
| tcc cgc aag gag ccc atg tgg gcc gat ctt ctg gcc ctg gcc gcc gcc<br>Ser Arg Lys Glu Pro Met Trp Ala Asp Leu Leu Ala Leu Ala Ala Ala<br>385                 390               395               400 | 1200 |

```
                                                        -continued agg ggg ggc cgg gtc cac cgg gcc ccc gag cct tat aaa gcc ctc agg    1248
Arg Gly Gly Arg Val His Arg Ala Pro Glu Pro Tyr Lys Ala Leu Arg
                405                 410                 415 gac ctg aag gag gcg cgg ggg ctt ctc gcc aaa gac ctg agc gtt ctg    1296
Asp Leu Lys Glu Ala Arg Gly Leu Leu Ala Lys Asp Leu Ser Val Leu
            420                 425                 430 gcc ctg agg gaa ggc ctt ggc ctc ccg ccc ggc gac gac ccc atg ctc    1344
Ala Leu Arg Glu Gly Leu Gly Leu Pro Pro Gly Asp Asp Pro Met Leu
        435                 440                 445 ctc gcc tac ctc ctg gac cct tcc aac acc acc ccc gag ggg gtg gcc    1392
Leu Ala Tyr Leu Leu Asp Pro Ser Asn Thr Thr Pro Glu Gly Val Ala
    450                 455                 460 cgg cgc tac ggc ggg gag tgg acg gag gag gcg ggg gag cgg gcc gcc    1440
Arg Arg Tyr Gly Gly Glu Trp Thr Glu Glu Ala Gly Glu Arg Ala Ala
465                 470                 475                 480 ctt tcc gag agg ctc ttc gcc aac ctg tgg ggg agg ctt gag ggg gag    1488
Leu Ser Glu Arg Leu Phe Ala Asn Leu Trp Gly Arg Leu Glu Gly Glu
                485                 490                 495 gag agg ctc ctt tgg ctt tac cgg gag gtg gag agg ccc ctt tcc gct    1536
Glu Arg Leu Leu Trp Leu Tyr Arg Glu Val Glu Arg Pro Leu Ser Ala
            500                 505                 510 gtc ctg gcc cac atg gag gcc acg ggg gtg cgc ctg gac gtg gcc tat    1584
Val Leu Ala His Met Glu Ala Thr Gly Val Arg Leu Asp Val Ala Tyr
        515                 520                 525 ctc agg gcc ttg tcc ctg gag gtg gcc gag gag atc gcc cgc ctc gag    1632
Leu Arg Ala Leu Ser Leu Glu Val Ala Glu Glu Ile Ala Arg Leu Glu
    530                 535                 540 gcc gag gtc ttc cgc ctg gcc ggc cac ccc ttc aac ctc aac tcc cgg    1680
Ala Glu Val Phe Arg Leu Ala Gly His Pro Phe Asn Leu Asn Ser Arg
545                 550                 555                 560 gac cag ctg gaa agg gtc ctc ttt gac gag cta ggg ctt ccc gcc atc    1728
Asp Gln Leu Glu Arg Val Leu Phe Asp Glu Leu Gly Leu Pro Ala Ile
                565                 570                 575 ggc aag acg gag aag acc ggc aag cgc tcc acc agc gcc gcc gtc ctg    1776
Gly Lys Thr Glu Lys Thr Gly Lys Arg Ser Thr Ser Ala Ala Val Leu
            580                 585                 590 gag gcc ctc cgc gag gcc cac ccc atc gtg gag aag atc ctg cag tac    1824
Glu Ala Leu Arg Glu Ala His Pro Ile Val Glu Lys Ile Leu Gln Tyr
        595                 600                 605 cgg gag ctc acc aag ctg aag agc acc tac att gac ccc ttg ccg gac    1872
Arg Glu Leu Thr Lys Leu Lys Ser Thr Tyr Ile Asp Pro Leu Pro Asp
    610                 615                 620 ctc atc cac ccc agg acg ggc cgc ctc cac acc cgc ttc aac cag acg    1920
Leu Ile His Pro Arg Thr Gly Arg Leu His Thr Arg Phe Asn Gln Thr
625                 630                 635                 640 gcc acg gcc acg ggc agg cta agt agc tcc gat ccc aac ctc cag aac    1968
Ala Thr Ala Thr Gly Arg Leu Ser Ser Ser Asp Pro Asn Leu Gln Asn
                645                 650                 655 atc ccc gtc cgc acc ccg ctt ggg cag agg atc gcc cgg gcc ttc atc    2016
Ile Pro Val Arg Thr Pro Leu Gly Gln Arg Ile Arg Arg Ala Phe Ile
            660                 665                 670 gcc gag gag ggg tgg cta ttg gtg gcc ctg gac tat agc cag ata gag    2064
Ala Glu Glu Gly Trp Leu Leu Val Ala Leu Asp Tyr Ser Gln Ile Glu
        675                 680                 685 ctc agg gtg ctg gcc cac ctc tcc ggc gac gag aac ctg atc cgg gtc    2112
Leu Arg Val Leu Ala His Leu Ser Gly Asp Glu Asn Leu Ile Arg Val
    690                 695                 700 ttc cag gag ggg cgg gac atc cac acg gag acc gcc agc tgg atg ttc    2160
Phe Gln Glu Gly Arg Asp Ile His Thr Glu Thr Ala Ser Trp Met Phe
705                 710                 715                 720
```

```
ggc gtc ccc cgg gag gcc gtg gac ccc ctg atg cgc cgg gcg gcc aag    2208
Gly Val Pro Arg Glu Ala Val Asp Pro Leu Met Arg Arg Ala Ala Lys
            725                 730                 735 acc atc aac ttc ggg gtc ctc tac ggc atg tcg gcc cac cgc ctc tcc    2256
Thr Ile Asn Phe Gly Val Leu Tyr Gly Met Ser Ala His Arg Leu Ser
            740                 745                 750 cag gag cta gcc atc cct tac gag gag gcc cag gcc ttc att gag cgc    2304
Gln Glu Leu Ala Ile Pro Tyr Glu Glu Ala Gln Ala Phe Ile Glu Arg
            755                 760                 765 tac ttt cag agc ttc ccc aag gtg cgg gcc tgg att gag aag acc ctg    2352
Tyr Phe Gln Ser Phe Pro Lys Val Arg Ala Trp Ile Glu Lys Thr Leu
            770                 775                 780 gag gag ggc agg agg cgg ggg tac gtg gag acc ctc ttc ggc cgc cgc    2400
Glu Glu Gly Arg Arg Arg Gly Tyr Val Glu Thr Leu Phe Gly Arg Arg
785                 790                 795                 800 cgc tac gtg cca gac cta gag gcc cgg gtg aag agc gtg cgg gag gcg    2448
Arg Tyr Val Pro Asp Leu Glu Ala Arg Val Lys Ser Val Arg Glu Ala
                805                 810                 815 gcc gag cgc atg gcc ttc aac atg ccc gtc cag ggc acc gcc gcc gac    2496
Ala Glu Arg Met Ala Phe Asn Met Pro Val Gln Gly Thr Ala Ala Asp
            820                 825                 830 ctc atg aag ctg gct atg gtg aag ctc ttc ccc agg ctg gag gaa atg    2544
Leu Met Lys Leu Ala Met Val Lys Leu Phe Pro Arg Leu Glu Glu Met
            835                 840                 845 ggg gcc agg atg ctc ctt cag gtc cac gac gag ctg gtc ctc gag gcc    2592
Gly Ala Arg Met Leu Leu Gln Val His Asp Glu Leu Val Leu Glu Ala
            850                 855                 860 cca aaa gag agg gcg gag gcc gtg gcc cgg ctg gcc aag gag gtc atg    2640
Pro Lys Glu Arg Ala Glu Ala Val Ala Arg Leu Ala Lys Glu Val Met
865                 870                 875                 880 gag ggg gtg tat ccc ctg gcc gtg ccc ctg gag gtg gag gtg ggg ata    2688
Glu Gly Val Tyr Pro Leu Ala Val Pro Leu Glu Val Glu Val Gly Ile
                885                 890                 895 ggg gag gac tgg ctc tcc gcc aag gag ggc att gat ggc cgc ggc gga    2736
Gly Glu Asp Trp Leu Ser Ala Lys Glu Gly Ile Asp Gly Arg Gly Gly
            900                 905                 910 ggc ggg cat cat cat cat cat cat taa                                2763
Gly Gly His His His His His His
            915                 920

<210> SEQ ID NO 125
<211> LENGTH: 920
<212> TYPE: PRT
<213> ORGANISM: artificial sequence
<220> FEATURE:
<223> OTHER INFORMATION: The DNA sequence encoding the Sso7d-Taq fusion
      protein

<400> SEQUENCE: 125

Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Lys Thr Gly Arg
        35                  40                  45

Gly Ala Val Ser Glu Lys Asp Ala Pro Lys Glu Leu Leu Gln Met Leu
    50                  55                  60

Glu Lys Gln Lys Lys Gly Gly Val Thr Ser Gly Met Leu Pro Leu
65                  70                  75                  80
```

```
Phe Glu Pro Lys Gly Arg Val Leu Leu Val Asp Gly His His Leu Ala
            85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
            115                 120                 125

Lys Glu Asp Gly Asp Ala Val Ile Val Val Phe Asp Ala Lys Ala Pro
            130                 135                 140

Ser Phe Arg His Glu Ala Tyr Gly Gly Tyr Lys Ala Gly Arg Ala Pro
145                 150                 155                 160

Thr Pro Glu Asp Phe Pro Arg Gln Leu Ala Leu Ile Lys Glu Leu Val
            165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
            195                 200                 205

Val Arg Ile Leu Thr Ala Asp Lys Asp Leu Tyr Gln Leu Leu Ser Asp
            210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
            245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
            275                 280                 285

Ala Leu Leu Lys Asn Leu Asp Arg Leu Lys Pro Ala Ile Arg Glu Lys
            290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
            325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
            355                 360                 365

Glu Ala Pro Trp Pro Pro Pro Glu Gly Ala Phe Val Gly Phe Val Leu
            370                 375                 380

Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
            405                 410                 415

Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
            435                 440                 445

Leu Ala Tyr Leu Leu Asp Pro Ser Asn Thr Thr Pro Glu Gly Val Ala
            450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu
            485                 490                 495

Glu Arg Leu Leu Trp Leu Tyr Arg Glu Val Glu Arg Pro Leu Ser Ala
```

-continued

```
                500             505             510
Val Leu Ala His Met Glu Ala Thr Gly Val Arg Leu Asp Val Ala Tyr
            515                 520                 525

Leu Arg Ala Leu Ser Leu Glu Val Ala Glu Ile Ala Arg Leu Glu
            530                 535                 540

Ala Glu Val Phe Arg Leu Ala Gly His Pro Phe Asn Leu Asn Ser Arg
545                 550                 555                 560

Asp Gln Leu Glu Arg Val Leu Phe Asp Glu Leu Gly Leu Pro Ala Ile
                565                 570                 575

Gly Lys Thr Glu Lys Thr Gly Lys Arg Ser Thr Ser Ala Ala Val Leu
            580                 585                 590

Glu Ala Leu Arg Glu Ala His Pro Ile Val Glu Lys Ile Leu Gln Tyr
            595                 600                 605

Arg Glu Leu Thr Lys Leu Lys Ser Thr Tyr Ile Asp Pro Leu Pro Asp
            610                 615                 620

Leu Ile His Pro Arg Thr Gly Arg Leu His Thr Arg Phe Asn Gln Thr
625                 630                 635                 640

Ala Thr Ala Thr Gly Arg Leu Ser Ser Ser Asp Pro Asn Leu Gln Asn
                645                 650                 655

Ile Pro Val Arg Thr Pro Leu Gly Gln Arg Ile Arg Arg Ala Phe Ile
            660                 665                 670

Ala Glu Glu Gly Trp Leu Leu Val Ala Leu Asp Tyr Ser Gln Ile Glu
            675                 680                 685

Leu Arg Val Leu Ala His Leu Ser Gly Asp Glu Asn Leu Ile Arg Val
            690                 695                 700

Phe Gln Glu Gly Arg Asp Ile His Thr Glu Thr Ala Ser Trp Met Phe
705                 710                 715                 720

Gly Val Pro Arg Glu Ala Val Asp Pro Leu Met Arg Arg Ala Ala Lys
                725                 730                 735

Thr Ile Asn Phe Gly Val Leu Tyr Gly Met Ser Ala His Arg Leu Ser
            740                 745                 750

Gln Glu Leu Ala Ile Pro Tyr Glu Glu Ala Gln Ala Phe Ile Glu Arg
            755                 760                 765

Tyr Phe Gln Ser Phe Pro Lys Val Arg Ala Trp Ile Glu Lys Thr Leu
770                 775                 780

Glu Glu Gly Arg Arg Arg Gly Tyr Val Glu Thr Leu Phe Gly Arg Arg
785                 790                 795                 800

Arg Tyr Val Pro Asp Leu Glu Ala Arg Val Lys Ser Val Arg Glu Ala
                805                 810                 815

Ala Glu Arg Met Ala Phe Asn Met Pro Val Gln Gly Thr Ala Ala Asp
            820                 825                 830

Leu Met Lys Leu Ala Met Val Lys Leu Phe Pro Arg Leu Glu Glu Met
            835                 840                 845

Gly Ala Arg Met Leu Leu Gln Val His Asp Glu Leu Val Leu Glu Ala
            850                 855                 860

Pro Lys Glu Arg Ala Glu Ala Val Ala Arg Leu Ala Lys Glu Val Met
865                 870                 875                 880

Glu Gly Val Tyr Pro Leu Ala Val Pro Leu Glu Val Glu Val Gly Ile
                885                 890                 895

Gly Glu Asp Trp Leu Ser Ala Lys Glu Gly Ile Asp Gly Arg Gly Gly
            900                 905                 910

Gly Gly His His His His His His
            915                 920
```

<210> SEQ ID NO 126
<211> LENGTH: 2481
<212> TYPE: DNA
<213> ORGANISM: artificial sequence
<220> FEATURE:
<223> OTHER INFORMATION: The DNA sequence encoding the Pfu-Sso7d fusion protein
<220> FEATURE:
<221> NAME/KEY: CDS
<222> LOCATION: (1)..(2481)
<223> OTHER INFORMATION:

<400> SEQUENCE: 126

```
atg att tta gat gtg gat tac ata act gaa gaa gga aaa cct gtt att      48
Met Ile Leu Asp Val Asp Tyr Ile Thr Glu Glu Gly Lys Pro Val Ile
1               5                   10                  15 agg cta ttc aaa aaa gag aac gga aaa ttt aag ata gag cat gat aga      96
Arg Leu Phe Lys Lys Glu Asn Gly Lys Phe Lys Ile Glu His Asp Arg
                20                  25                  30 act ttt aga cca tac att tac gct ctt ctc agg gat gat tca aag att     144
Thr Phe Arg Pro Tyr Ile Tyr Ala Leu Leu Arg Asp Asp Ser Lys Ile
            35                  40                  45 gaa gaa gtt aag aaa ata acg ggg gaa agg cat gga aag att gtg aga     192
Glu Glu Val Lys Lys Ile Thr Gly Glu Arg His Gly Lys Ile Val Arg
        50                  55                  60 att gtt gat gta gag aag gtt gag aaa aag ttt ctc ggc aag cct att     240
Ile Val Asp Val Glu Lys Val Glu Lys Lys Phe Leu Gly Lys Pro Ile
65                  70                  75                  80 acc gtg tgg aaa ctt tat ttg gaa cat ccc caa gat gtt ccc act att     288
Thr Val Trp Lys Leu Tyr Leu Glu His Pro Gln Asp Val Pro Thr Ile
                85                  90                  95 aga gaa aaa gtt aga gaa cat cca gca gtt gtg gac atc ttc gaa tac     336
Arg Glu Lys Val Arg Glu His Pro Ala Val Val Asp Ile Phe Glu Tyr
            100                 105                 110 gat att cca ttt gca aag aga tac ctc atc gac aaa ggc cta ata cca     384
Asp Ile Pro Phe Ala Lys Arg Tyr Leu Ile Asp Lys Gly Leu Ile Pro
        115                 120                 125 atg gag ggg gaa gaa gag cta aag att ctt gcc ttc gat ata gaa acc     432
Met Glu Gly Glu Glu Glu Leu Lys Ile Leu Ala Phe Asp Ile Glu Thr
    130                 135                 140 ctc tat cac gaa gga gaa gag ttt gga aaa ggc cca att ata atg att     480
Leu Tyr His Glu Gly Glu Glu Phe Gly Lys Gly Pro Ile Ile Met Ile
145                 150                 155                 160 agt tat gca gat gaa aat gaa gca aag gtg att act tgg aaa aac ata     528
Ser Tyr Ala Asp Glu Asn Glu Ala Lys Val Ile Thr Trp Lys Asn Ile
                165                 170                 175 gat ctt cca tac gtt gag gtt gta tca agc gag aga gag atg ata aag     576
Asp Leu Pro Tyr Val Glu Val Val Ser Ser Glu Arg Glu Met Ile Lys
            180                 185                 190 aga ttt ctc agg att atc agg gag aag gat cct gac att ata gtt act     624
Arg Phe Leu Arg Ile Ile Arg Glu Lys Asp Pro Asp Ile Ile Val Thr
        195                 200                 205 tat aat gga gac tca ttc gac ttc cca tat tta gcg aaa agg gca gaa     672
Tyr Asn Gly Asp Ser Phe Asp Phe Pro Tyr Leu Ala Lys Arg Ala Glu
    210                 215                 220 aaa ctt ggg att aaa tta acc att gga aga gat gga agc gag ccc aag     720
Lys Leu Gly Ile Lys Leu Thr Ile Gly Arg Asp Gly Ser Glu Pro Lys
225                 230                 235                 240 atg cag aga ata ggc gat atg acg gct gta gaa gtc aag gga aga ata     768
Met Gln Arg Ile Gly Asp Met Thr Ala Val Glu Val Lys Gly Arg Ile
                245                 250                 255
```

```
                                                         -continued
cat ttc gac ttg tat cat gta ata aca agg aca ata aat ctc cca aca       816
His Phe Asp Leu Tyr His Val Ile Thr Arg Thr Ile Asn Leu Pro Thr
            260                 265                 270 tac aca cta gag gct gta tat gaa gca att ttt gga aag cca aag gag       864
Tyr Thr Leu Glu Ala Val Tyr Glu Ala Ile Phe Gly Lys Pro Lys Glu
            275                 280                 285 aag gta tac gcc gac gag ata gca aaa gcc tgg gaa agt gga gag aac       912
Lys Val Tyr Ala Asp Glu Ile Ala Lys Ala Trp Glu Ser Gly Glu Asn
            290                 295                 300 ctt gag aga gtt gcc aaa tac tcg atg gaa gat gca aag gca act tat       960
Leu Glu Arg Val Ala Lys Tyr Ser Met Glu Asp Ala Lys Ala Thr Tyr
305                 310                 315                 320 gaa ctc ggg aaa gaa ttc ctt cca atg gaa att cag ctt tca aga tta      1008
Glu Leu Gly Lys Glu Phe Leu Pro Met Glu Ile Gln Leu Ser Arg Leu
                325                 330                 335 gtt gga caa cct tta tgg gat gtt tca agg tca agc aca ggg aac ctt      1056
Val Gly Gln Pro Leu Trp Asp Val Ser Arg Ser Ser Thr Gly Asn Leu
            340                 345                 350 gta gag tgg ttc tta ctt agg aaa gcc tac gaa aga aac gaa gta gct      1104
Val Glu Trp Phe Leu Leu Arg Lys Ala Tyr Glu Arg Asn Glu Val Ala
            355                 360                 365 cca aac aag cca agt gaa gag gag tat caa aga agg ctc agg gag agc      1152
Pro Asn Lys Pro Ser Glu Glu Glu Tyr Gln Arg Arg Leu Arg Glu Ser
            370                 375                 380 tac aca ggt gga ttc gtt aaa gag cca gaa aag ggg ttg tgg gaa aac      1200
Tyr Thr Gly Gly Phe Val Lys Glu Pro Glu Lys Gly Leu Trp Glu Asn
385                 390                 395                 400 ata gta tac cta gat ttt aga gcc cta tat ccc tcg att ata att acc      1248
Ile Val Tyr Leu Asp Phe Arg Ala Leu Tyr Pro Ser Ile Ile Ile Thr
                405                 410                 415 cac aat gtt tct ccc gat act cta aat ctt gag gga tgc aag aac tat      1296
His Asn Val Ser Pro Asp Thr Leu Asn Leu Glu Gly Cys Lys Asn Tyr
            420                 425                 430 gat atc gct cct caa gta ggc cac aag ttc tgc aag gac atc cct ggt      1344
Asp Ile Ala Pro Gln Val Gly His Lys Phe Cys Lys Asp Ile Pro Gly
            435                 440                 445 ttt ata cca agt ctc ttg gga cat ttg tta gag gaa aga caa aag att      1392
Phe Ile Pro Ser Leu Leu Gly His Leu Leu Glu Glu Arg Gln Lys Ile
450                 455                 460 aag aca aaa atg aag gaa act tta gca aat tct ttc tac gga tat tat      1440
Lys Thr Lys Met Lys Glu Thr Leu Ala Asn Ser Phe Tyr Gly Tyr Tyr
465                 470                 475                 480 ggc tat gca aaa gca aga tgg tac tgt aag gag tgt gct gag agc gtt      1488
Gly Tyr Ala Lys Ala Arg Trp Tyr Cys Lys Glu Cys Ala Glu Ser Val
                485                 490                 495 act gcc tgg gga aga aag tac atc gag tta gta tgg aag gag ctc gaa      1536
Thr Ala Trp Gly Arg Lys Tyr Ile Glu Leu Val Trp Lys Glu Leu Glu
            500                 505                 510 gaa aag ttt gga ttt aaa gtc ctc tac att gac act gat ggt ctc tat      1584
Glu Lys Phe Gly Phe Lys Val Leu Tyr Ile Asp Thr Asp Gly Leu Tyr
            515                 520                 525 gca act atc cca gga gga gaa agt gag gaa ata aag aaa aag gct cta      1632
Ala Thr Ile Pro Gly Gly Glu Ser Glu Glu Ile Lys Lys Lys Ala Leu
            530                 535                 540 gaa ttt gta aaa tac ata aat tca aag ctc cct gga ctg cta gag ctt      1680
Glu Phe Val Lys Tyr Ile Asn Ser Lys Leu Pro Gly Leu Leu Glu Leu
545                 550                 555                 560 gaa tat gaa ggg ttt tat aag agg gga ttc ttc gtt acg aag aag agg      1728
Glu Tyr Glu Gly Phe Tyr Lys Arg Gly Phe Phe Val Thr Lys Lys Arg
```

```
                 565                 570                 575
tat gca gta ata gat gaa gaa gga aaa gtc att act cgt ggt tta gag      1776
Tyr Ala Val Ile Asp Glu Glu Gly Lys Val Ile Thr Arg Gly Leu Glu
            580                 585                 590 ata gtt agg aga gat tgg agt gaa att gca aaa gaa act caa gct aga      1824
Ile Val Arg Arg Asp Trp Ser Glu Ile Ala Lys Glu Thr Gln Ala Arg
        595                 600                 605 gtt ttg gag aca ata cta aaa cac gga gat gtt gaa gaa gct gtg aga      1872
Val Leu Glu Thr Ile Leu Lys His Gly Asp Val Glu Glu Ala Val Arg
    610                 615                 620 ata gta aaa gaa gta ata caa aag ctt gcc aat tat gaa att cca cca      1920
Ile Val Lys Glu Val Ile Gln Lys Leu Ala Asn Tyr Glu Ile Pro Pro
625                 630                 635                 640 gag aag ctc gca ata tat gag cag ata aca aga cca tta cat gag tat      1968
Glu Lys Leu Ala Ile Tyr Glu Gln Ile Thr Arg Pro Leu His Glu Tyr
                645                 650                 655 aag gcg ata ggt cct cac gta gct gtt gca aag aaa cta gct gct aaa      2016
Lys Ala Ile Gly Pro His Val Ala Val Ala Lys Lys Leu Ala Ala Lys
            660                 665                 670 gga gtt aaa ata aag cca gga atg gta att gga tac ata gta ctt aga      2064
Gly Val Lys Ile Lys Pro Gly Met Val Ile Gly Tyr Ile Val Leu Arg
        675                 680                 685 ggc gat ggt cca att agc aat agg gca att cta gct gag gaa tac gat      2112
Gly Asp Gly Pro Ile Ser Asn Arg Ala Ile Leu Ala Glu Glu Tyr Asp
    690                 695                 700 ccc aaa aag cac aag tat gac gca gaa tat tac att gag aac cag gtt      2160
Pro Lys Lys His Lys Tyr Asp Ala Glu Tyr Tyr Ile Glu Asn Gln Val
705                 710                 715                 720 ctt cca gcg gta ctt agg ata ttg gag gga ttt gga tac aga aag gaa      2208
Leu Pro Ala Val Leu Arg Ile Leu Glu Gly Phe Gly Tyr Arg Lys Glu
                725                 730                 735 gac ctc aga tac caa aag aca aga caa gtc ggc cta act tcc tgg ctt      2256
Asp Leu Arg Tyr Gln Lys Thr Arg Gln Val Gly Leu Thr Ser Trp Leu
            740                 745                 750 aac att aaa aaa tcc ggt acc ggc ggt ggc ggt gca acc gta aag ttc      2304
Asn Ile Lys Lys Ser Gly Thr Gly Gly Gly Gly Ala Thr Val Lys Phe
        755                 760                 765 aag tac aaa ggc gaa gaa aaa gag gta gac atc tcc aag atc aag aaa      2352
Lys Tyr Lys Gly Glu Glu Lys Glu Val Asp Ile Ser Lys Ile Lys Lys
    770                 775                 780 gta tgg cgt gtg ggc aag atg atc tcc ttc acc tac gac gag ggc ggt      2400
Val Trp Arg Val Gly Lys Met Ile Ser Phe Thr Tyr Asp Glu Gly Gly
785                 790                 795                 800 ggc aag acc ggc cgt ggt gcg gta agc gaa aag gac gcg ccg aag gag      2448
Gly Lys Thr Gly Arg Gly Ala Val Ser Glu Lys Asp Ala Pro Lys Glu
                805                 810                 815 ctg ctg cag atg ctg gag aag cag aaa aag tga                          2481
Leu Leu Gln Met Leu Glu Lys Gln Lys Lys
            820                 825
```

<210> SEQ ID NO 127
<211> LENGTH: 826
<212> TYPE: PRT
<213> ORGANISM: artificial sequence
<220> FEATURE:
<223> OTHER INFORMATION: The DNA sequence encoding the Pfu-Sso7d fusion
      protein

<400> SEQUENCE: 127

Met Ile Leu Asp Val Asp Tyr Ile Thr Glu Glu Gly Lys Pro Val Ile
1               5                   10                  15

-continued

```
Arg Leu Phe Lys Lys Glu Asn Gly Lys Phe Lys Ile Glu His Asp Arg
             20                  25                  30
Thr Phe Arg Pro Tyr Ile Tyr Ala Leu Leu Arg Asp Asp Ser Lys Ile
         35                  40                  45
Glu Glu Val Lys Lys Ile Thr Gly Glu Arg His Gly Lys Ile Val Arg
     50                  55                  60
Ile Val Asp Val Glu Lys Val Glu Lys Phe Leu Gly Lys Pro Ile
 65                  70                  75                  80
Thr Val Trp Lys Leu Tyr Leu Glu His Pro Gln Asp Val Pro Thr Ile
             85                  90                  95
Arg Glu Lys Val Arg Glu His Pro Ala Val Val Asp Ile Phe Glu Tyr
            100                 105                 110
Asp Ile Pro Phe Ala Lys Arg Tyr Leu Ile Asp Lys Gly Leu Ile Pro
            115                 120                 125
Met Glu Gly Glu Glu Glu Leu Lys Ile Leu Ala Phe Asp Ile Glu Thr
        130                 135                 140
Leu Tyr His Glu Gly Glu Glu Phe Gly Lys Gly Pro Ile Ile Met Ile
145                 150                 155                 160
Ser Tyr Ala Asp Glu Asn Glu Ala Lys Val Ile Thr Trp Lys Asn Ile
                165                 170                 175
Asp Leu Pro Tyr Val Glu Val Val Ser Ser Arg Glu Met Ile Lys
            180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
        290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
        370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Asp Thr Leu Asn Leu Glu Gly Cys Lys Asn Tyr
            420                 425                 430
```

```
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
        450                 455                 460
Lys Thr Lys Met Lys Glu Thr Leu Ala Asn Ser Phe Tyr Gly Tyr Tyr
465                 470                 475                 480
Gly Tyr Ala Lys Ala Arg Trp Tyr Cys Lys Glu Cys Ala Glu Ser Val
                485                 490                 495
Thr Ala Trp Gly Arg Lys Tyr Ile Glu Leu Val Trp Lys Glu Leu Glu
            500                 505                 510
Glu Lys Phe Gly Phe Lys Val Leu Tyr Ile Asp Thr Asp Gly Leu Tyr
        515                 520                 525
Ala Thr Ile Pro Gly Gly Glu Ser Glu Glu Ile Lys Lys Lys Ala Leu
    530                 535                 540
Glu Phe Val Lys Tyr Ile Asn Ser Lys Leu Pro Gly Leu Leu Glu Leu
545                 550                 555                 560
Glu Tyr Glu Gly Phe Tyr Lys Arg Gly Phe Phe Val Thr Lys Lys Arg
                565                 570                 575
Tyr Ala Val Ile Asp Glu Glu Gly Lys Val Ile Thr Arg Gly Leu Glu
            580                 585                 590
Ile Val Arg Arg Asp Trp Ser Glu Ile Ala Lys Glu Thr Gln Ala Arg
        595                 600                 605
Val Leu Glu Thr Ile Leu Lys His Gly Asp Val Glu Glu Ala Val Arg
    610                 615                 620
Ile Val Lys Glu Val Ile Gln Lys Leu Ala Asn Tyr Glu Ile Pro Pro
625                 630                 635                 640
Glu Lys Leu Ala Ile Tyr Glu Gln Ile Thr Arg Pro Leu His Glu Tyr
                645                 650                 655
Lys Ala Ile Gly Pro His Val Ala Val Ala Lys Lys Leu Ala Ala Lys
            660                 665                 670
Gly Val Lys Ile Lys Pro Gly Met Val Ile Gly Tyr Ile Val Leu Arg
        675                 680                 685
Gly Asp Gly Pro Ile Ser Asn Arg Ala Ile Leu Ala Glu Glu Tyr Asp
    690                 695                 700
Pro Lys Lys His Lys Tyr Asp Ala Glu Tyr Tyr Ile Glu Asn Gln Val
705                 710                 715                 720
Leu Pro Ala Val Leu Arg Ile Leu Glu Gly Phe Gly Tyr Arg Lys Glu
                725                 730                 735
Asp Leu Arg Tyr Gln Lys Thr Arg Gln Val Gly Leu Thr Ser Trp Leu
            740                 745                 750
Asn Ile Lys Lys Ser Gly Thr Gly Gly Gly Ala Thr Val Lys Phe
        755                 760                 765
Lys Tyr Lys Gly Glu Glu Lys Glu Val Asp Ile Ser Lys Ile Lys Lys
    770                 775                 780
Val Trp Arg Val Gly Lys Met Ile Ser Phe Thr Tyr Asp Glu Gly Gly
785                 790                 795                 800
Gly Lys Thr Gly Arg Gly Ala Val Ser Glu Lys Asp Ala Pro Lys Glu
                805                 810                 815
Leu Leu Gln Met Leu Glu Lys Gln Lys Lys
            820                 825

<210> SEQ ID NO 128
<211> LENGTH: 1905
<212> TYPE: DNA
```

<213> ORGANISM: artificial sequence
<220> FEATURE:
<223> OTHER INFORMATION: The DNA sequence encoding the Sac7d-ATaq fusion protein

<400> SEQUENCE: 128

```
atgattacga attcgacggt gaaggtaaag ttcaagtata agggtgaaga gaagaagta      60
gacacttcaa agataaagaa ggtttggaga gtaggcaaaa tggtgtcctt tacctatgac    120
gacaatggta agacaggtag aggagctgta agcgagaaag atgctccaaa agaattatta   180
gacatgttag caagagcaga aagagagaag aaaggcggcg tgtgtcactag ccccaaggcc   240
ctggaggagg ccccctggcc cccgccggaa ggggccttcg tgggctttgt gctttcccgc   300
aaggagccca tgtgggccga tcttctggcc ctggccgccg caggggggg ccgggtccac    360
cgggccccg agccttataa agccctcagg gacctgaagg aggcgcgggg gcttctcgcc    420
aaagacctga gcgttctggc cctgagggaa ggccttggcc tcccgcccgg cgacgacccc   480
atgctcctcg cctacctcct ggacccttcc aacaccaccc ccgagggggt ggcccggcgc   540
tacggcgggg agtggacgga ggaggcgggg agcggggccg ccctttccga gaggctcttc   600
gccaacctgt gggggaggct tgaggggag gagaggctcc tttggcttta ccgggaggtg    660
gagaggcccc tttccgctgt cctggcccac atggaggcca cggggggtgcg cctggacgtg   720
gcctatctca gggccttgtc cctggaggtg gccgaggaga tcgcccgcct cgaggccgag   780
gtcttccgcc tggccggcca cccccttcaac ctcaactccc gggaccagct ggaaagggtc   840
ctctttgacg agctagggct tcccgccatc ggcaagacgg agaagaccgg caagcgctcc   900
accagcgccg ccgtcctgga ggccctccgc gaggccacc ccatcgtgga aagatcctg    960
cagtaccggg agctcaccaa gctgaagagc acctacattg accccttgcc ggacctcatc  1020
caccccagga cgggccgcct ccacacccgc ttcaaccaga cggccacggc cacgggcagg  1080
ctaagtagct ccgatcccaa cctccagaac atccccgtcc gcaccccgct ggggcagagg  1140
atccgccggg ccttcatcgc cgaggagggg tggctattgg tggccctgga ctatagccag  1200
atagagctca gggtgctggc ccacctctcc ggcgacgaga acctgatccg ggtcttccag  1260
gaggggcggg acatccacac ggagaccgcc agctggatgt tcggcgtccc ccgggaggcc  1320
gtgaccccc tgatgcgccg ggcggccaag accatcaact cgggggtcct ctacggcatg  1380
tcggcccacc gcctctccca ggagctagcc atcccttacg aggaggccca ggccttcatt  1440
gagcgctact ttcagagctt ccccaaggtg cgggcctgga ttgagaagac cctggaggag  1500
ggcaggaggc gggggtacgt ggagaccctc ttcggccgcc gccgctacgt gccagaccta  1560
gaggcccggg tgaagagcgt gcgggaggcg gccgagcgca tggccttcaa catgcccgtc  1620
cagggcaccg ccgccgacct catgaagctg gctatggtga agctcttccc caggctggag  1680
gaaatggggg ccaggatgct ccttcaggtc cacgacgagc tggtcctcga ggccccaaaa  1740
gagagggcgg aggccgtggc ccggctggcc aaggaggtca tggagggggt gtatccctg    1800
gccgtgcccc tggaggtgga ggtggggata ggggaggact ggctctccgc caaggagggc  1860
attgatggcc gcggcggagg cgggcatcat catcatcatc attaa                    1905
```

<210> SEQ ID NO 129
<211> LENGTH: 634
<212> TYPE: PRT
<213> ORGANISM: artificial sequence
<220> FEATURE:
<223> OTHER INFORMATION: The amino acid sequence of the Sac7d-ATaq fusion protein

<400> SEQUENCE: 129

```
Met Ile Thr Asn Ser Thr Val Lys Val Lys Phe Lys Tyr Lys Gly Glu
1               5                   10                  15
Glu Lys Glu Val Asp Thr Ser Lys Ile Lys Lys Val Trp Arg Val Gly
            20                  25                  30
Lys Met Val Ser Phe Thr Tyr Asp Asp Asn Gly Lys Thr Gly Arg Gly
        35                  40                  45
Ala Val Ser Glu Lys Asp Ala Pro Lys Glu Leu Leu Asp Met Leu Ala
    50                  55                  60
Arg Ala Glu Arg Glu Lys Gly Gly Val Thr Ser Pro Lys Ala
65                  70                  75                  80
Leu Glu Glu Ala Pro Trp Pro Pro Glu Gly Ala Phe Val Gly Phe
                85                  90                  95
Val Leu Ser Arg Lys Glu Pro Met Trp Ala Asp Leu Leu Ala Leu Ala
            100                 105                 110
Ala Ala Arg Gly Gly Arg Val His Arg Ala Pro Glu Pro Tyr Lys Ala
        115                 120                 125
Leu Arg Asp Leu Lys Glu Ala Arg Gly Leu Leu Ala Lys Asp Leu Ser
    130                 135                 140
Val Leu Ala Leu Arg Glu Gly Leu Gly Leu Pro Pro Gly Asp Pro
145                 150                 155                 160
Met Leu Leu Ala Tyr Leu Leu Asp Pro Ser Asn Thr Thr Pro Glu Gly
                165                 170                 175
Val Ala Arg Arg Tyr Gly Gly Glu Trp Thr Glu Ala Gly Glu Arg
            180                 185                 190
Ala Ala Leu Ser Glu Arg Leu Phe Ala Asn Leu Trp Gly Arg Leu Glu
        195                 200                 205
Gly Glu Glu Arg Leu Leu Trp Leu Tyr Arg Glu Val Glu Arg Pro Leu
    210                 215                 220
Ser Ala Val Leu Ala His Met Glu Ala Thr Gly Val Arg Leu Asp Val
225                 230                 235                 240
Ala Tyr Leu Arg Ala Leu Ser Leu Glu Val Ala Glu Glu Ile Ala Arg
                245                 250                 255
Leu Glu Ala Glu Val Phe Arg Leu Ala Gly His Pro Phe Asn Leu Asn
            260                 265                 270
Ser Arg Asp Gln Leu Glu Arg Val Leu Phe Asp Glu Leu Gly Leu Pro
        275                 280                 285
Ala Ile Gly Lys Thr Glu Lys Thr Gly Lys Arg Ser Thr Ser Ala Ala
    290                 295                 300
Val Leu Glu Ala Leu Arg Glu Ala His Pro Ile Val Glu Lys Ile Leu
305                 310                 315                 320
Gln Tyr Arg Glu Leu Thr Lys Leu Lys Ser Thr Tyr Ile Asp Pro Leu
                325                 330                 335
Pro Asp Leu Ile His Pro Arg Thr Gly Arg Leu His Thr Arg Phe Asn
            340                 345                 350
Gln Thr Ala Thr Ala Thr Gly Arg Leu Ser Ser Asp Pro Asn Leu
        355                 360                 365
Gln Asn Ile Pro Val Arg Thr Pro Leu Gly Gln Arg Ile Arg Arg Ala
    370                 375                 380
Phe Ile Ala Glu Glu Gly Trp Leu Leu Val Ala Leu Asp Tyr Ser Gln
385                 390                 395                 400
Ile Glu Leu Arg Val Leu Ala His Leu Ser Gly Asp Glu Asn Leu Ile
```

```
                    405                 410                 415
Arg Val Phe Gln Glu Gly Arg Asp Ile His Thr Glu Thr Ala Ser Trp
                420                 425                 430

Met Phe Gly Val Pro Arg Glu Ala Val Asp Pro Leu Met Arg Arg Ala
            435                 440                 445

Ala Lys Thr Ile Asn Phe Gly Val Leu Tyr Gly Met Ser Ala His Arg
        450                 455                 460

Leu Ser Gln Glu Leu Ala Ile Pro Tyr Glu Glu Ala Gln Ala Phe Ile
465                 470                 475                 480

Glu Arg Tyr Phe Gln Ser Phe Pro Lys Val Arg Ala Trp Ile Glu Lys
                485                 490                 495

Thr Leu Glu Glu Gly Arg Arg Gly Tyr Val Glu Thr Leu Phe Gly
            500                 505                 510

Arg Arg Arg Tyr Val Pro Asp Leu Glu Ala Arg Val Lys Ser Val Arg
        515                 520                 525

Glu Ala Ala Glu Arg Met Ala Phe Asn Met Pro Val Gln Gly Thr Ala
    530                 535                 540

Ala Asp Leu Met Lys Leu Ala Met Val Lys Leu Phe Pro Arg Leu Glu
545                 550                 555                 560

Glu Met Gly Ala Arg Met Leu Leu Gln Val His Asp Glu Leu Val Leu
                565                 570                 575

Glu Ala Pro Lys Glu Arg Ala Glu Ala Val Ala Arg Leu Ala Lys Glu
            580                 585                 590

Val Met Glu Gly Val Tyr Pro Leu Ala Val Pro Leu Glu Val Glu Val
        595                 600                 605

Gly Ile Gly Glu Asp Trp Leu Ser Ala Lys Glu Gly Ile Asp Gly Arg
    610                 615                 620

Gly Gly Gly Gly His His His His His
625                 630

<210> SEQ ID NO 130
<211> LENGTH: 1965
<212> TYPE: DNA
<213> ORGANISM: artificial sequence
<220> FEATURE:
<223> OTHER INFORMATION: The DNA sequence encoding the PL-delta Taq
      fusion protein

<400> SEQUENCE: 130
atgattacga attcgaagaa aaagaaaaag aaaagcgta agaaacgcaa aaagaaaaag      60
aaaggcggcg gtgtcactag tggcgcaacc gtaaagttca agtacaaagg cgaagaaaaa     120
gaggtagaca tctccaagat caagaaagta tggcgtgtgg gcaagatgat ctccttcacc    180
tacgacgagg gcggtggcaa gaccggccgt ggtgcggtaa gcgaaaagga cgcgccgaag    240
gagctgctgc agatgctgga gaagcagaaa aagggcggcg tgtcaccagt cccaaggcc     300 ctggaggagg ccccctggcc cccgccggaa ggggccttcg tgggctttgt gctttcccgc    360
aaggagccca tgtgggccga tcttctggcc ctggccgccg ccaggggggg ccgggtccac    420
cgggcccccg agccttataa agccctcagg gacctgaagg aggcgcgggg gcttctcgcc    480
aaagacctga gcgttctggc cctgagggaa ggccttggcc tcccgcccgg cgacgacccc    540
atgctcctcg cctacctcct ggacccttcc aacaccaccc ccgaggggt ggcccggcgc     600 tacggcgggg agtggacgga ggaggcgggg gagcgggccg cccttccga gaggctcttc     660 gccaacctgt gggggaggct tgaggggag gagaggctcc tttggcttta ccgggaggtg    720
```

```
gagaggcccc tttccgctgt cctggcccac atggaggcca cggggtgcg cctggacgtg    780
gcctatctca gggccttgtc cctggaggtg gccgaggaga tcgcccgcct cgaggccgag    840
gtcttccgcc tggccggcca cccttcaac ctcaactccc gggaccagct ggaaagggtc    900
ctctttgacg agctagggct tcccgccatc ggcaagacgg agaagaccgg caagcgctcc    960
accagcgccg ccgtcctgga ggccctccgc gaggcccacc ccatcgtgga aagatcctg    1020
cagtaccggg agctcaccaa gctgaagagc acctacattg accccttgcc ggacctcatc    1080
caccccagga cgggccgcct ccacacccgc ttcaaccaga cggccacggc cacgggcagg    1140
ctaagtagct ccgatcccaa cctccagaac atccccgtcc gcaccccgct gggcagagg     1200
atccgccggg ccttcatcgc cgaggagggg tggctattgg tggccctgga ctatagccag    1260
atagagctca gggtgctggc ccacctctcc ggcgacgaga acctgatccg ggtcttccag    1320
gaggggcggg acatccacac ggagaccgcc agctggatgt tcggcgtccc ccggagggcc    1380
gtggaccccc tgatgcgccg gcggccaag accatcaact tcgggtcct ctacggcatg    1440
tcggcccacc gcctctccca ggagctagcc atcccttacg aggaggccca ggccttcatt    1500
gagcgctact ttcagagctt ccccaaggtg cgggcctgga ttgagaagac cctggaggag    1560
ggcaggaggc gggggtacgt ggagaccctc ttcggccgcc gccgctacgt gccagaccta    1620
gaggcccggg tgaagagcgt gcgggaggcg gccgagcgca tggccttcaa catgcccgtc    1680
cagggcaccg ccgccgacct catgaagctg gctatggtga agctcttccc caggctggag    1740
gaaatggggg ccaggatgct ccttcaggtc acgacgagc tggtcctcga ggccccaaaa    1800
gagagggcgg aggccgtggc ccggctggcc aaggaggtca tggaggggt gtatcccctg    1860
gccgtgcccc tggaggtgga ggtggggata ggggaggact ggctctccgc caaggagggc    1920
attgatggcc gcggcggagg cgggcatcat catcatcatc attaa                     1965
```

<210> SEQ ID NO 131
<211> LENGTH: 654
<212> TYPE: PRT
<213> ORGANISM: artificial sequence
<220> FEATURE:
<223> OTHER INFORMATION: The amino acid sequence of PL- delta Taq fusion protein

<400> SEQUENCE: 131

```
Met Ile Thr Asn Ser Lys Lys Lys Lys Lys Lys Arg Lys Lys Arg
1               5                   10                  15

Lys Lys Lys Lys Lys Gly Gly Gly Val Thr Ser Gly Ala Thr Val Lys
            20                  25                  30

Phe Lys Tyr Lys Gly Glu Glu Lys Glu Val Asp Ile Ser Lys Ile Lys
        35                  40                  45

Lys Val Trp Arg Val Gly Lys Met Ile Ser Phe Thr Tyr Asp Glu Gly
    50                  55                  60

Gly Gly Lys Thr Gly Arg Gly Ala Val Ser Glu Lys Asp Ala Pro Lys
65                  70                  75                  80

Glu Leu Leu Gln Met Leu Glu Lys Gln Lys Lys Gly Gly Gly Val Thr
                85                  90                  95

Ser Pro Lys Ala Leu Glu Glu Ala Pro Trp Pro Pro Glu Gly Ala
            100                 105                 110

Phe Val Gly Phe Val Leu Ser Arg Lys Glu Pro Met Trp Ala Asp Leu
        115                 120                 125

Leu Ala Leu Ala Ala Ala Arg Gly Gly Arg Val His Arg Ala Pro Glu
    130                 135                 140
```

-continued

```
Pro Tyr Lys Ala Leu Arg Asp Leu Lys Glu Ala Arg Gly Leu Leu Ala
145                 150                 155                 160

Lys Asp Leu Ser Val Leu Ala Leu Arg Glu Gly Leu Gly Leu Pro Pro
                165                 170                 175

Gly Asp Pro Met Leu Leu Ala Tyr Leu Leu Asp Pro Ser Asn Thr
            180                 185                 190

Thr Pro Glu Gly Val Ala Arg Arg Tyr Gly Gly Glu Trp Thr Glu Glu
                195                 200                 205

Ala Gly Glu Arg Ala Ala Leu Ser Glu Arg Leu Phe Ala Asn Leu Trp
210                 215                 220

Gly Arg Leu Glu Gly Glu Arg Leu Leu Trp Leu Tyr Arg Glu Val
225                 230                 235                 240

Glu Arg Pro Leu Ser Ala Val Leu Ala His Met Glu Ala Thr Gly Val
                245                 250                 255

Arg Leu Asp Val Ala Tyr Leu Arg Ala Leu Ser Leu Glu Val Ala Glu
                260                 265                 270

Glu Ile Ala Arg Leu Glu Ala Glu Val Phe Arg Leu Ala Gly His Pro
                275                 280                 285

Phe Asn Leu Asn Ser Arg Asp Gln Leu Glu Arg Val Leu Phe Asp Glu
                290                 295                 300

Leu Gly Leu Pro Ala Ile Gly Lys Thr Glu Lys Thr Gly Lys Arg Ser
305                 310                 315                 320

Thr Ser Ala Ala Val Leu Glu Ala Leu Arg Glu Ala His Pro Ile Val
                325                 330                 335

Glu Lys Ile Leu Gln Tyr Arg Glu Leu Thr Lys Leu Lys Ser Thr Tyr
                340                 345                 350

Ile Asp Pro Leu Pro Asp Leu Ile His Pro Arg Thr Gly Arg Leu His
                355                 360                 365

Thr Arg Phe Asn Gln Thr Ala Thr Ala Thr Gly Arg Leu Ser Ser Ser
                370                 375                 380

Asp Pro Asn Leu Gln Asn Ile Pro Val Arg Thr Pro Leu Gly Gln Arg
385                 390                 395                 400

Ile Arg Arg Ala Phe Ile Ala Glu Glu Gly Trp Leu Leu Val Ala Leu
                405                 410                 415

Asp Tyr Ser Gln Ile Glu Leu Arg Val Leu Ala His Leu Ser Gly Asp
                420                 425                 430

Glu Asn Leu Ile Arg Val Phe Gln Glu Gly Arg Asp Ile His Thr Glu
                435                 440                 445

Thr Ala Ser Trp Met Phe Gly Val Pro Arg Glu Ala Val Asp Pro Leu
450                 455                 460

Met Arg Arg Ala Ala Lys Thr Ile Asn Phe Gly Val Leu Tyr Gly Met
465                 470                 475                 480

Ser Ala His Arg Leu Ser Gln Glu Leu Ala Ile Pro Tyr Glu Glu Ala
                485                 490                 495

Gln Ala Phe Ile Glu Arg Tyr Phe Gln Ser Phe Pro Lys Val Arg Ala
                500                 505                 510

Trp Ile Glu Lys Thr Leu Glu Glu Gly Arg Arg Gly Tyr Val Glu
                515                 520                 525

Thr Leu Phe Gly Arg Arg Arg Tyr Val Pro Asp Leu Glu Ala Arg Val
                530                 535                 540

Lys Ser Val Arg Glu Ala Ala Glu Arg Met Ala Phe Asn Met Pro Val
545                 550                 555                 560
```

```
Gln Gly Thr Ala Ala Asp Leu Met Lys Leu Ala Met Val Lys Leu Phe
            565                 570                 575

Pro Arg Leu Glu Glu Met Gly Ala Arg Met Leu Leu Gln Val His Asp
        580                 585                 590

Glu Leu Val Leu Glu Ala Pro Lys Glu Arg Ala Glu Ala Val Ala Arg
    595                 600                 605

Leu Ala Lys Glu Val Met Glu Gly Val Tyr Pro Leu Ala Val Pro Leu
610                 615                 620

Glu Val Glu Val Gly Ile Gly Glu Asp Trp Leu Ser Ala Lys Glu Gly
625                 630                 635                 640

Ile Asp Gly Arg Gly Gly Gly His His His His His His
            645                 650
```

<210> SEQ ID NO 132
<211> LENGTH: 20
<212> TYPE: DNA
<213> ORGANISM: artificial sequence
<220> FEATURE:
<223> OTHER INFORMATION: primer

<400> SEQUENCE: 132
cctgctctgc cgcttcacgc                                           20

<210> SEQ ID NO 133
<211> LENGTH: 20
<212> TYPE: DNA
<213> ORGANISM: artificial sequence
<220> FEATURE:
<223> OTHER INFORMATION: primer

<400> SEQUENCE: 133
gcacagcggc tggctgagga                                           20

<210> SEQ ID NO 134
<211> LENGTH: 22
<212> TYPE: DNA
<213> ORGANISM: artificial sequence
<220> FEATURE:
<223> OTHER INFORMATION: primer

<400> SEQUENCE: 134
tgacggagga taacgccagc ag                                        22

<210> SEQ ID NO 135
<211> LENGTH: 25
<212> TYPE: DNA
<213> ORGANISM: artificial sequence
<220> FEATURE:
<223> OTHER INFORMATION: primer

<400> SEQUENCE: 135
gaaagacgat gggtcgctaa tacgc                                     25

<210> SEQ ID NO 136
<211> LENGTH: 22
<212> TYPE: DNA
<213> ORGANISM: artificial sequence
<220> FEATURE:
<223> OTHER INFORMATION: primer

<400> SEQUENCE: 136
tgacggagga taacgccagc ag                                        22

```
<210> SEQ ID NO 137
<211> LENGTH: 22
<212> TYPE: DNA
<213> ORGANISM: artificial sequence
<220> FEATURE:
<223> OTHER INFORMATION: primer

<400> SEQUENCE: 137
ggggttggag gtcaatgggt tc                                     22

<210> SEQ ID NO 138
<211> LENGTH: 20
<212> TYPE: DNA
<213> ORGANISM: artificial sequence
<220> FEATURE:
<223> OTHER INFORMATION: primer

<400> SEQUENCE: 138
cctgctctgc cgcttcacgc                                        20

<210> SEQ ID NO 139
<211> LENGTH: 22
<212> TYPE: DNA
<213> ORGANISM: artificial sequence
<220> FEATURE:
<223> OTHER INFORMATION: primer

<400> SEQUENCE: 139
cacatggtac agcaagcctg gc                                     22

<210> SEQ ID NO 140
<211> LENGTH: 23
<212> TYPE: DNA
<213> ORGANISM: artificial sequence
<220> FEATURE:
<223> OTHER INFORMATION: primer

<400> SEQUENCE: 140
cccgtatctg ctgggatact ggc                                    23

<210> SEQ ID NO 141
<211> LENGTH: 23
<212> TYPE: DNA
<213> ORGANISM: artificial sequence
<220> FEATURE:
<223> OTHER INFORMATION: primer

<400> SEQUENCE: 141
cagcggtgct gactgaatca tgg                                    23

<210> SEQ ID NO 142
<211> LENGTH: 19
<212> TYPE: DNA
<213> ORGANISM: artificial sequence
<220> FEATURE:
<223> OTHER INFORMATION: primer

<400> SEQUENCE: 142
cctgcctgcc gcttcacgc                                         19

<210> SEQ ID NO 143
<211> LENGTH: 22
<212> TYPE: DNA
<213> ORGANISM: artificial sequence
<220> FEATURE:
<223> OTHER INFORMATION: primer
```

```
<400> SEQUENCE: 143 ccaataccccg tttcatcgcg gc                                          22

<210> SEQ ID NO 144
<211> LENGTH: 19
<212> TYPE: DNA
<213> ORGANISM: artificial sequence
<220> FEATURE:
<223> OTHER INFORMATION: primer

<400> SEQUENCE: 144
ccacctcatc ctgggcacc                                               19

<210> SEQ ID NO 145
<211> LENGTH: 22
<212> TYPE: DNA
<213> ORGANISM: artificial sequence
<220> FEATURE:
<223> OTHER INFORMATION: primer

<400> SEQUENCE: 145
gcttgaggcc aaccatcaga gc                                           22

<210> SEQ ID NO 146
<211> LENGTH: 22
<212> TYPE: DNA
<213> ORGANISM: artificial sequence
<220> FEATURE:
<223> OTHER INFORMATION: prmer

<400> SEQUENCE: 146
ggttggccaa tctactccca gg                                           22

<210> SEQ ID NO 147
<211> LENGTH: 20
<212> TYPE: DNA
<213> ORGANISM: artificial sequence
<220> FEATURE:
<223> OTHER INFORMATION: primer

<400> SEQUENCE: 147
gctcactcag tgtggcaaag                                              20

<210> SEQ ID NO 148
<211> LENGTH: 24
<212> TYPE: DNA
<213> ORGANISM: artificial sequence
<220> FEATURE:
<223> OTHER INFORMATION: primer

<400> SEQUENCE: 148
gattagcaaa agggcctagc ttgg                                         24
```